(12) United States Patent
Quattropani et al.

(10) Patent No.: US 9,505,769 B2
(45) Date of Patent: Nov. 29, 2016

(54) TETRAAZA-CYCLOPENTA[A]INDENYL DERIVATIVES

(71) Applicant: ASCENEURON SA, Lausanne (CH)

(72) Inventors: Anna Quattropani, Rolle (CH); Santosh S. Kulkarni, Bangalore (IN); Kathiravan Murugesan, Bangalore (IN); Joydeep Banerjee, Bangalore (IN)

(73) Assignee: Asceneuron SA, Lausanne (CH)

( * ) Notice: Subject to any disclaimer, the term of this patent is extended or adjusted under 35 U.S.C. 154(b) by 0 days.

(21) Appl. No.: 14/896,757

(22) PCT Filed: Jun. 12, 2014

(86) PCT No.: PCT/EP2014/062192
§ 371 (c)(1),
(2) Date: Dec. 8, 2015

(87) PCT Pub. No.: WO2014/198808
PCT Pub. Date: Dec. 18, 2014

(65) Prior Publication Data
US 2016/0137648 A1    May 19, 2016

(30) Foreign Application Priority Data
Jun. 14, 2013   (IN) .......................... 2027/MUM/2013

(51) Int. Cl.
| | | |
|---|---|---|
| *C07D 487/04* | (2006.01) | |
| *A61K 31/519* | (2006.01) | |
| *A61K 31/5377* | (2006.01) | |
| *C07D 519/00* | (2006.01) | |
| *C07D 487/12* | (2006.01) | |

(52) U.S. Cl.
CPC .......... *C07D 487/04* (2013.01); *A61K 31/519* (2013.01); *A61K 31/5377* (2013.01); *C07D 487/12* (2013.01); *C07D 519/00* (2013.01)

(58) Field of Classification Search
None
See application file for complete search history.

(56) References Cited

FOREIGN PATENT DOCUMENTS

| | | |
|---|---|---|
| EP | 2607364 A1 | 6/2013 |
| WO | WO2010/123716 A1 | 10/2010 |
| WO | WO2011/049731 A1 | 4/2011 |
| WO | WO2013/091773 A1 | 6/2013 |

OTHER PUBLICATIONS

PCT International Search Report dated Aug. 25, 2014 for International Application No. PCT/EP2014/062192.

*Primary Examiner* — Brian J Davis
(74) *Attorney, Agent, or Firm* — Saul Ewing LLP; Kathryn Doyle; Domingos J. Silva

(57) ABSTRACT

The present invention provides compounds of Formula (I) as M1 receptor positive allosteric modulators for the treatment of diseases mediated by the muscarinic M1 mediator.

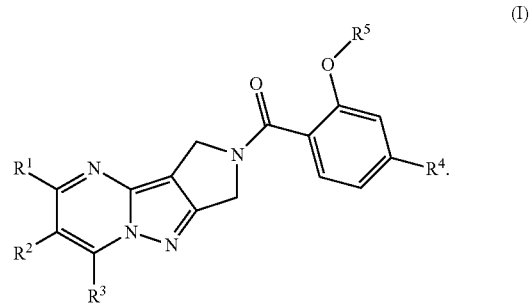

14 Claims, No Drawings

TETRAAZA-CYCLOPENTA[A]INDENYL DERIVATIVES

CROSS-REFERENCE TO RELATED APPLICATIONS

The present application is a 35 U.S.C. §371 national phase application of International Application No. PCT/EP2014/062192, filed Jun. 12, 2014, and published under PCT Article 21(2) in English, which claims priority to Indian Application No. 2027/MUM/2013, filed Jun. 14, 2013, all of which applications are incorporated herein by reference in their entireties.

The invention is directed to a class of tetraaza-cyclopenta[a]indenyl compounds, their salts, pharmaceutical compositions comprising them and their use in therapy of the human body. In particular, the invention is directed to a class of tetraaza-cyclopenta[a]indenyl compounds, which are muscarinic M1 receptor positive allosteric modulators, and hence are useful in the treatment of Alzheimer's disease, schizophrenia and other diseases associated with an impairment of cognitive function or cholinergic dysfunction.

BACKGROUND OF THE INVENTION

Alzheimer's disease is a common neurodegenerative disease affecting the elderly, resulting in progressive memory impairment, loss of language and visuospatial skills, and behavior deficits. Characteristics of the disease include degeneration of cholinergic neurons in the cerebral cortex, hippocampus, basal forebrain, and other regions of the brain, neurofibrillary tangles, and accumulation of the amyloid β peptide Aβ is a 39-43 amino acid produced in the brain by processing of the beta-amyloid precursor protein (APP) by the beta-amyloid protein cleaving enzyme ("beta secretase" or "BACE") and gamma-secretase). The processing leads to accumulation of Aβ in the brain.

The cholinergic pathway is involved in a variety of Central Nervous System (CNS) functions like information processing, attention, learning and memory, nociception, regulation of sleep-wake cycles, motor control. Agents that regulate cholinergic transmission are used to treat various CNS disorders including chronic and neuropathic pain, sleep disorders, epilepsy, schizophrenia. Alzheimer's disease, Parkinson's disease, and other movement disorders and memory disorders (Jeffrey Conn et al. Trends in Pharmacological Sciences Vol 30, N° 30, p148, 2009, Gregory Digby et al. Mol Biosystems 2010, 6, 1345-1354).

Activation of muscarinic receptors is a way to counteract cholinergic hypofunction. Muscarinic receptors are prevalent throughout the body. Five distinct muscarinic receptors (M1-M5) have been identified in mammals. In the central nervous system, muscarinic receptors are involved in cognitive, behavior, sensory, motor and autonomic functions like cardiovascular functions, renal and gastrointestinal functions. The muscarinic M1 receptor, which is prevalent in the cerebral cortex, hippocampus and striatum, has been found to have a major role in cognitive processing and in the pathophysiology of Alzheimer's disease (Eglen et al, TRENDS in Pharmacological Sciences, 2001, 22:8, 409-414).

M1 agonists have the potential to treat the underlying disease mechanism of Alzheimer's disease. The cholinergic hypothesis of Alzheimer's disease is linked to both β-amyloid and hyperphosphorylated tau protein. Formation of β-amyloid may impair the coupling of the muscarinic receptor with G-proteins. Stimulation of the M1 muscarinic receptor has been shown to increase formation of the neuroprotective aAPPs fragment, thereby preventing the formation of the Aβ peptide. Thus, M1 agonists may alter APP processing and enhance aAPPs secretion (Fisher, Jpn J Pharmacol, 2000, 84:101-112). Non selective muscarinic ligands which have been developed and studied for Alzheimer's disease have produced side effects, such as sweating, nausea and diarrhea (Spalding et al, Mol Pharmacol, 2002, 61:6, 1297-1302).

The muscarinic receptors are known to contain one or more allosteric sites, which may alter the affinity with which muscarinic ligands bind to the primary binding or orthosteric sites (S. Lazareno et al, Mol Pharmacol, 2002, 62:6, 1491-1505: S. Lazareno et al, Mol Pharmacol, 2000, 58, 194-207).

Positive allosteric modulation has several advantages in the treatment of CNS disorders. In particular, it mimics neurotransmission under physiological conditions, with greater subtype selectivity. Also, the maximum effect reached by an allosteric modulator is not exceeded by increasing the dose (Jan Jakubik, Pharmaceuticals, 2010, 3, 2838).

Furthermore, the antipsychotic potential of M1 allosteric modulation provides a promising way of treating schizophrenia, dementia, and related disorders like hallucination, delusions, paranoia and other disorganized behaviors (Thomas Bridge et al. Drug News & Perspectives 2010, 23, 229).

From the above, it is clear that a need exists for further modulators of muscarinic receptors. The present invention addresses this need.

Thus the compounds of the present invention, which are muscarinic M1 receptor positive allosteric modulators, are useful in the treatment of CNS disorders including Alzheimer's disease and other degenerative diseases of nervous system, Parkinson's disease, schizophrenia, other diseases which are associated with an impairment or decline in cognitive function or cholinergic dysfunction like movement disorders and memory disorders, chronic and neuropathic pain, sleep disorders, epilepsy, other degenerative diseases of basal ganglia, dementia in Alzheimer's disease, vascular dementia, dementia in other diseases, unspecified dementia, organic amnesic syndrome not induced by alcohol and other psychoactive substances, other mental disorders due to brain damage and dysfunction and to physical disease, personality and behavioral disorders due to brain disease, damage and dysfunction, schizophrenia, schizotypal disorder, schizoaffective disorders.

The present invention also provides a method of synthesis o he compounds of Formula (I) as well as pharmaceutical formulations containing them.

More particularly the compounds of the present invention are compounds of Formula (I)

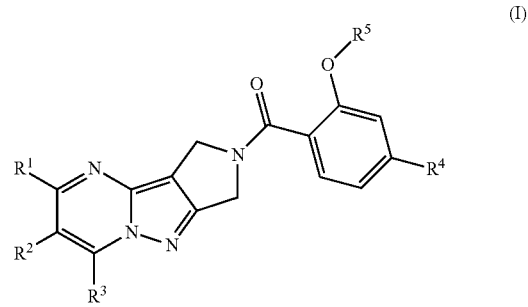

Wherein

R¹, R³ are independently from each other selected from H and linear or branched $C_1$-$C_6$-alkyl, and preferably both R¹ and R³ are simultaneously either H or methyl, R² is selected from chloro and linear or branched $C_1$-$C_6$-alkyl or $C_3$-$C_7$ cycloalkyl, preferably chloro, R⁴ is F or H, preferably F and R⁵ is A or $CH_2CH_2R^7$, wherein A is selected from the following groups:

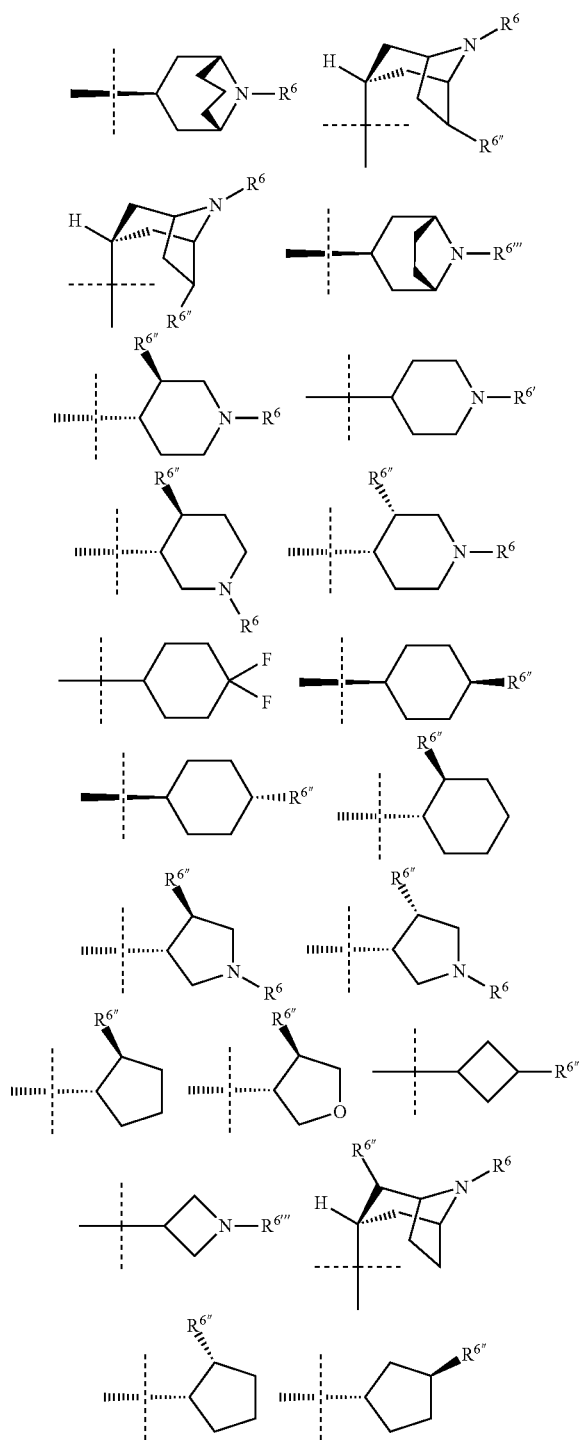

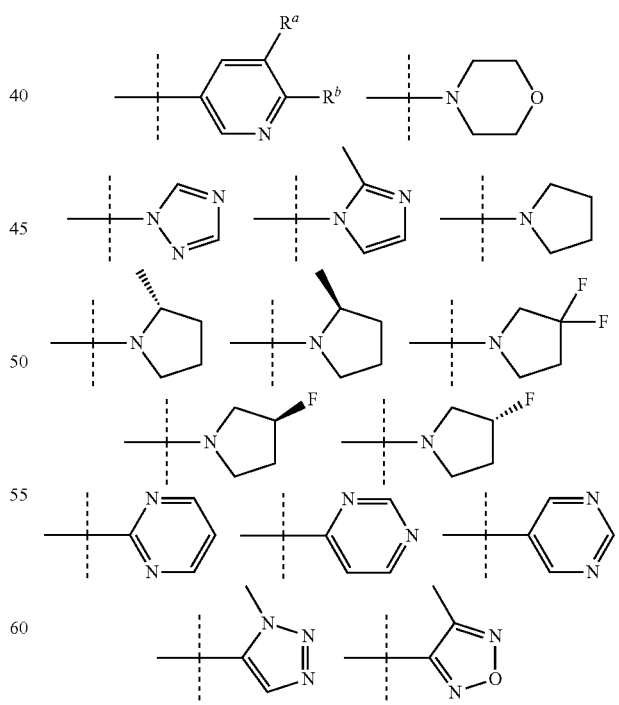

wherein

R⁶ is H, $CH_3$, $CH_2CH_2R$ or $CH(CH_2R)_2$, $CH_2CR_3$, $CH_2$-cyclopropyl, $CH_2CN$, $CH_2CHF_2$, R⁶' is $CH_2CH_2R'$ or $CH(CH_2R')_2$, $CH_2CR_3$, $CH_2CO_2R^1$.

R⁶'' is F, OH, $OCH_3$, $NH_2$, $N(CH_3)_2$, $N(R^1)_2$, $CO_2R^1$.

R⁶''' is $CH_2CH_2R$ or $CH(CH_2R)_2$, $CH_2CR_3$, $CH_2$-cyclopropyl, $CH_2CN$, $CH_2CHF_2$ R is H, CN, OH, $OCH_3$, Cl, F, $CHF_2$, $CH_3$, $CF_3$, $CH_2CH_3$ or cyclopropyl, R' is CN, OH, $OCH_3$, Cl, $CHF_2$, $CH_3$, $CF_3$ or cyclopropyl, and R⁷ is selected from the following groups:

wherein $R^a$ and $R^b$ are each independently H, F, $CH_3$, $OCH_3$, OH or 1-pyrrolidinyl and at least one of $R^a$ and $R^b$ denotes F, $CH_3$, $OCH_3$, OH or 1-pyrrolidinyl, and/or tautomers, salts, solvates, stereoisomers, diastereomers and enantiomers thereof.
$R^6$ is preferably $R^{6'}$ and more preferably $CH_2CH_2R'$ or $CH(CH_2R')_2$.
In a preferred embodiment $R^6$ is preferably $R^{6''''}$ are a group $CH_2CH_2F$ or $CH_2CH_2OH$.
In a preferred embodiment, $R^5$ is selected from the following groups:
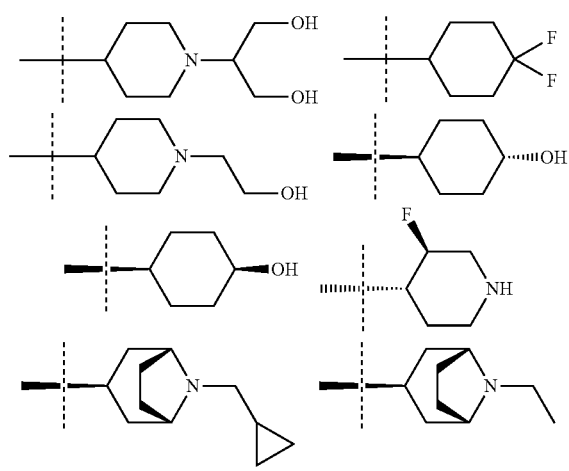
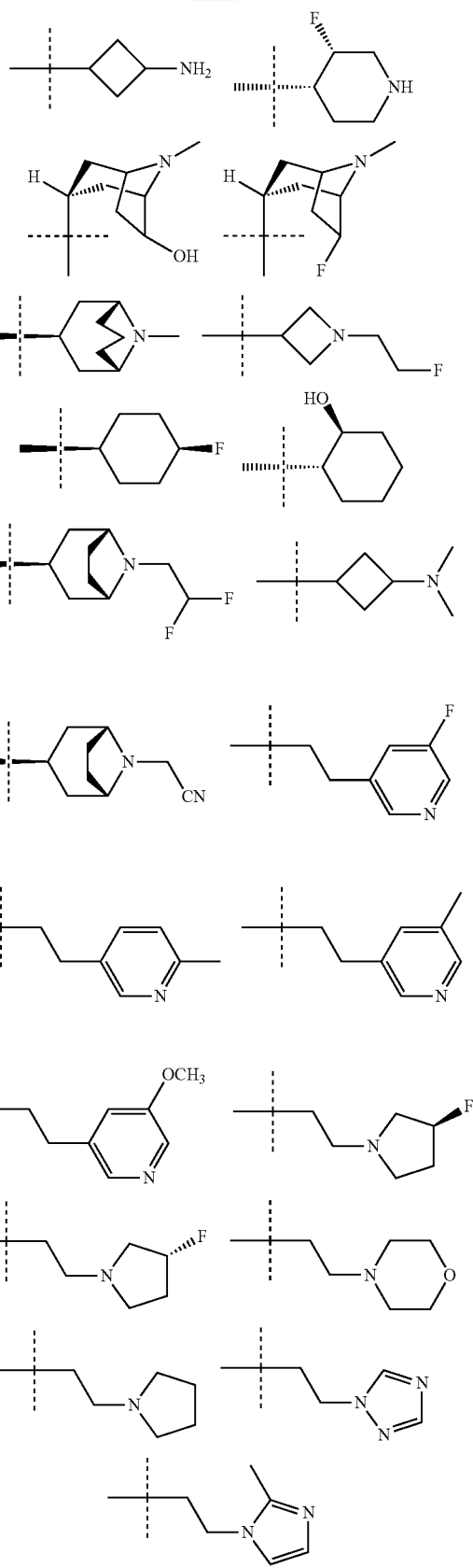
$R^5$ is preferably A.

Preferred compounds provided by the present invention are the following:

| Ex | Structure |
|----|-----------|
| 1 | 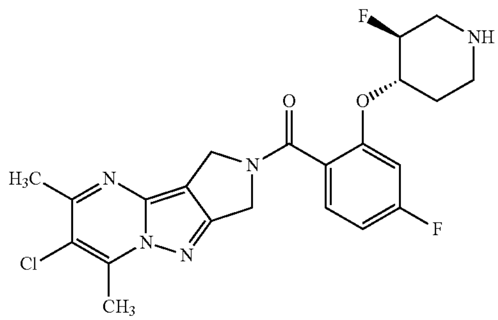 [SMILES: Cc1nc2c3c(nn2c(C)c1Cl)CN(C(=O)c1ccc(F)cc1O[C@H]1CCNC[C@@H]1F)C3] |
| 2 | 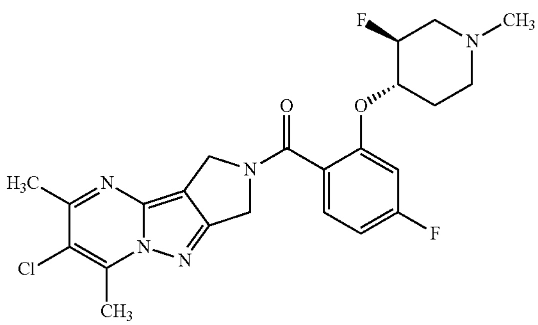 |
| 3 | 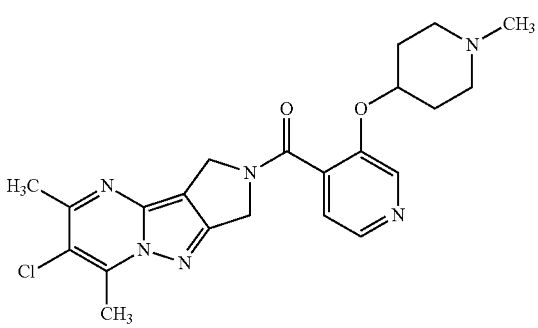 |
| 4 | 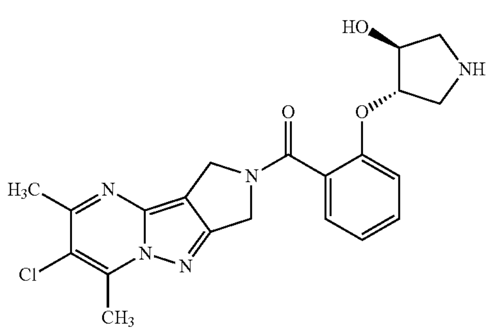 [SMILES: Cc1nc2c3c(nn2c(C)c1Cl)CN(C(=O)c1ccccc1O[C@H]1CNC[C@@H]1O)C3] |

-continued

| Ex | Structure |
|---|---|
| 5 | 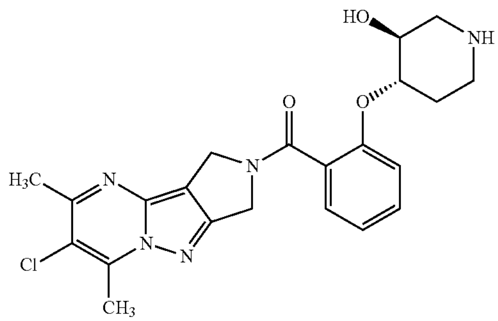 [SMILES: Cc1nc2c3c(nn2c(C)c1Cl)CN(C(=O)c1ccccc1O[C@H]1CCNC[C@@H]1O)C3] |
| 6 | 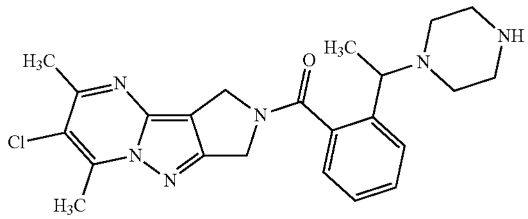 [SMILES: Cc1nc2c3c(nn2c(C)c1Cl)CN(C(=O)c1ccccc1C(C)N1CCNCC1)C3] |
| 7 | 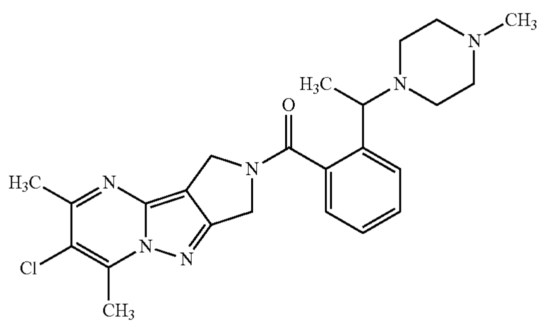 |
| 8 | 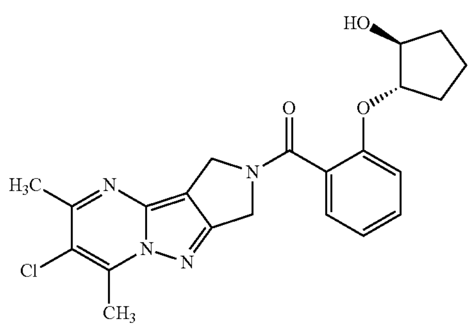 [SMILES: Cc1nc2c3c(nn2c(C)c1Cl)CN(C(=O)c1ccccc1O[C@H]1CCC[C@@H]1O)C3] |
| 9a | 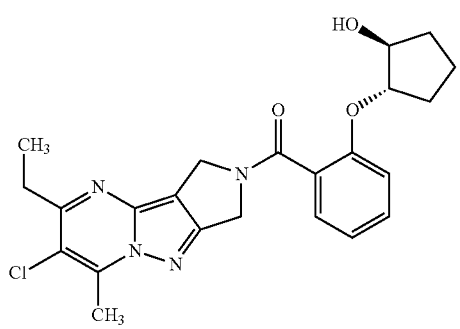 [SMILES: CCc1nc2c3c(nn2c(C)c1Cl)CN(C(=O)c1ccccc1O[C@H]1CCC[C@@H]1O)C3] |

-continued
| Ex | Structure |
|---|---|
| 9b | 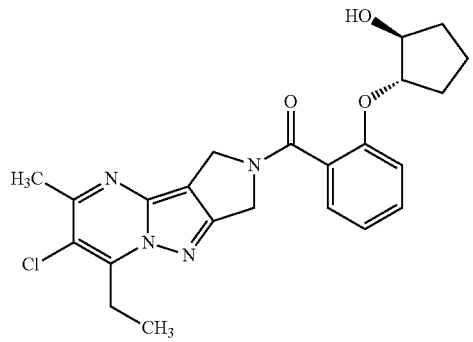 [SMILES: CCc1c(Cl)c(C)nc2c3c(nn12)CN(C(=O)c1ccccc1O[C@H]1CCC[C@@H]1O)C3] |
| 10a | 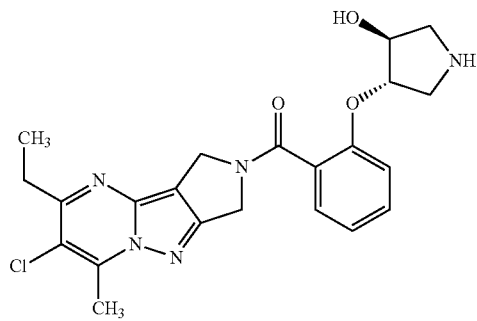 [SMILES: CCc1nc2c3c(nn2c(C)c1Cl)CN(C(=O)c1ccccc1O[C@H]1CNC[C@@H]1O)C3] |
| 10b | 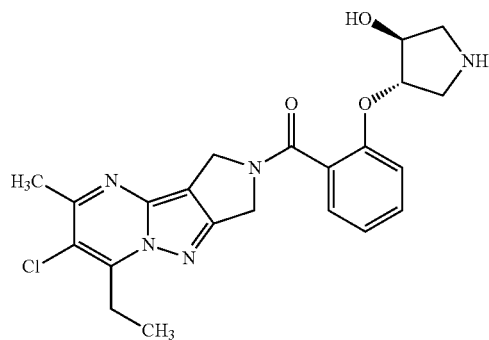 [SMILES: CCc1c(Cl)c(C)nc2c3c(nn12)CN(C(=O)c1ccccc1O[C@H]1CNC[C@@H]1O)C3] |
| 11 | 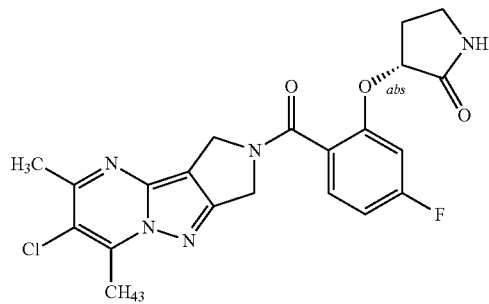 |

-continued
| Ex | Structure |
|---|---|
| 12 | 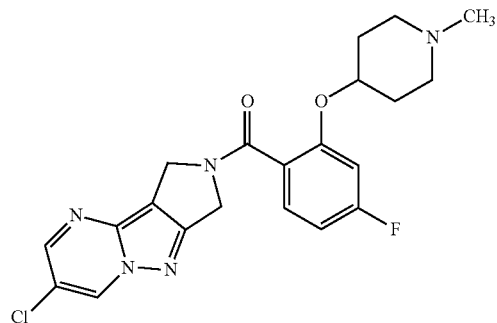 [SMILES: CN1CCC(Oc2cc(F)ccc2C(=O)N2Cc3nn4cc(Cl)cnc4c3C2)CC1] |
| 13 | 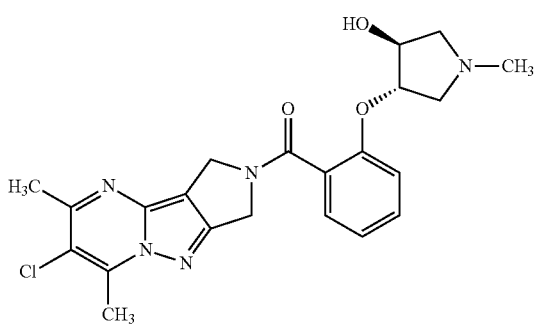 |
| 14 | 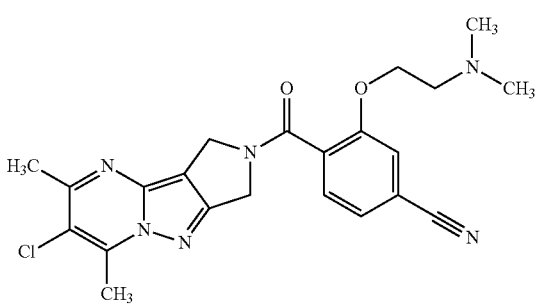 |
| 15 | 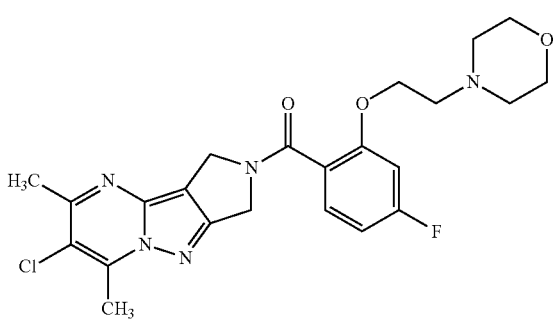 [SMILES: Cc1nc2c3c(nn2c(C)c1Cl)CN(C(=O)c1ccc(F)cc1OCCN1CCOCC1)C3] |

-continued
| Ex | Structure |
|---|---|
| 16 | 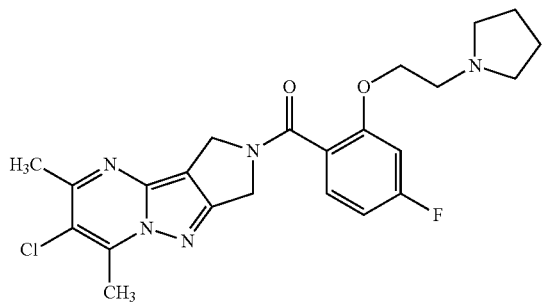 |
| 17 | 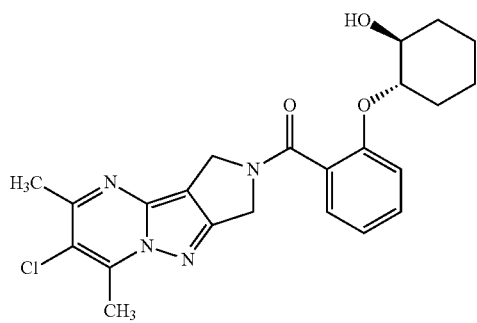 [SMILES: Cc1nc2c3c(nn2c(C)c1Cl)CN(C(=O)c1ccccc1O[C@H]1CCCC[C@@H]1O)C3] |
| 18 | 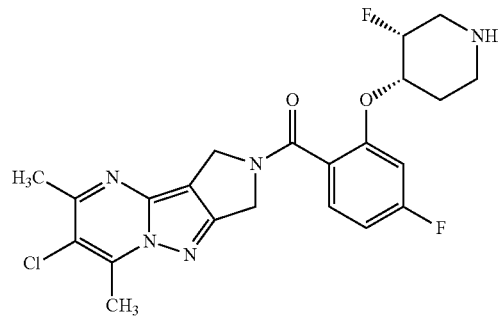 |
| 19 | 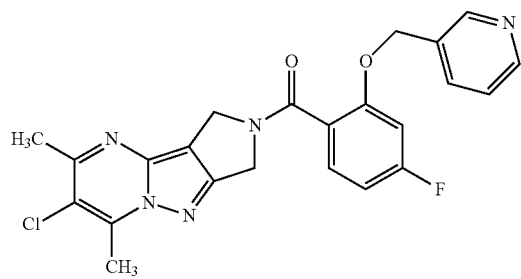 [SMILES: Cc1nc2c3c(nn2c(C)c1Cl)CN(C(=O)c1ccc(F)cc1OCc1cccnc1)C3] |
| 20 | 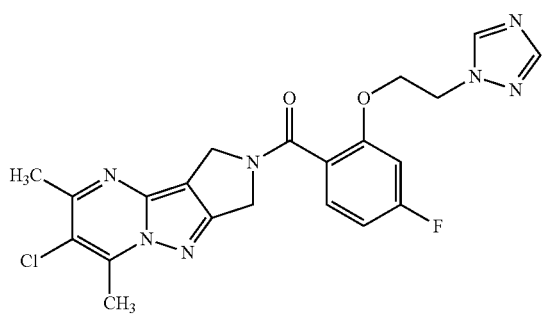 [SMILES: Cc1nc2c3c(nn2c(C)c1Cl)CN(C(=O)c1ccc(F)cc1OCCn1cncn1)C3] |

-continued
| Ex | Structure |
|---|---|
| 21 | 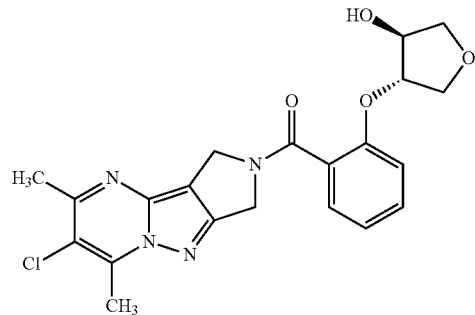 |
| 22a | 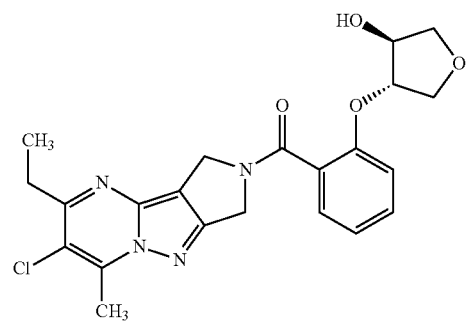 [SMILES: CCc1nc2c3c(nn2c(C)c1Cl)CN(C(=O)c1ccccc1O[C@H]1COC[C@@H]1O)C3] |
| 22b | 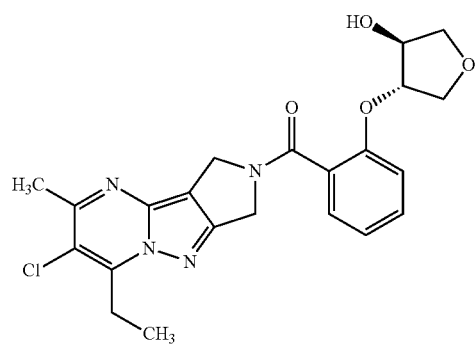 [SMILES: CCc1c(Cl)c(C)nc2c3c(nn12)CN(C(=O)c1ccccc1O[C@H]1COC[C@@H]1O)C3] |
| 23 | 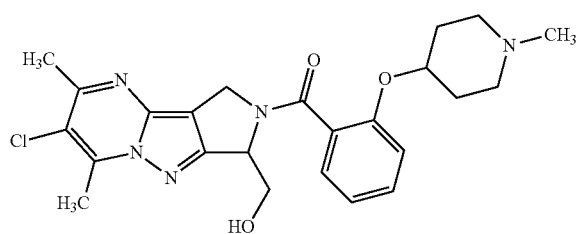 [SMILES: Cc1nc2c3c(nn2c(C)c1Cl)C(CO)N(C(=O)c1ccccc1OC1CCN(C)CC1)C3] |

-continued
| Ex | Structure |
|---|---|
| 24 | 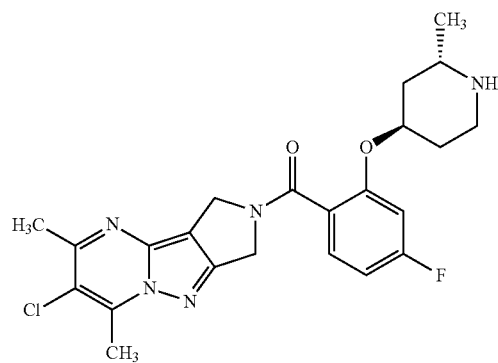 [SMILES: Cc1nc2c3c(nn2c(C)c1Cl)CN(C(=O)c1ccc(F)cc1O[C@@H]1CCN[C@@H](C)C1)C3] |
| 25 | 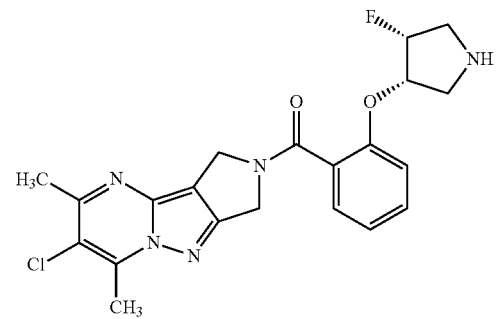 [SMILES: Cc1nc2c3c(nn2c(C)c1Cl)CN(C(=O)c1ccccc1O[C@H]1CNC[C@H]1F)C3] |
| 26 | 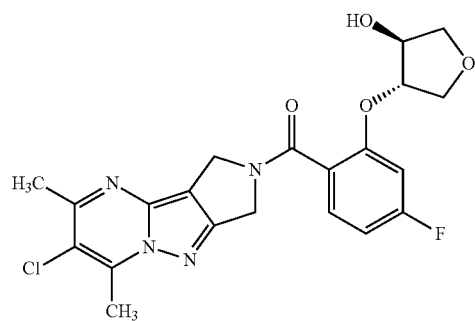 |
| 27 | 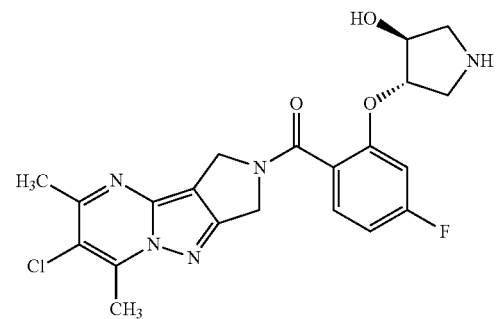 |

-continued
| Ex | Structure |
|---|---|
| 28 | 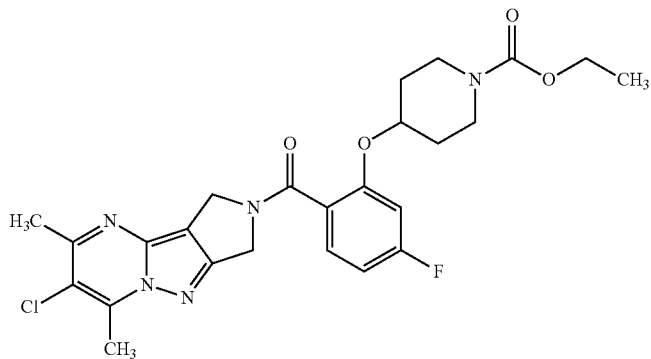 [SMILES: CCOC(=O)N1CCC(Oc2cc(F)ccc2C(=O)N2Cc3nn4c(C)c(Cl)c(C)nc4c3C2)CC1] |
| 29 | 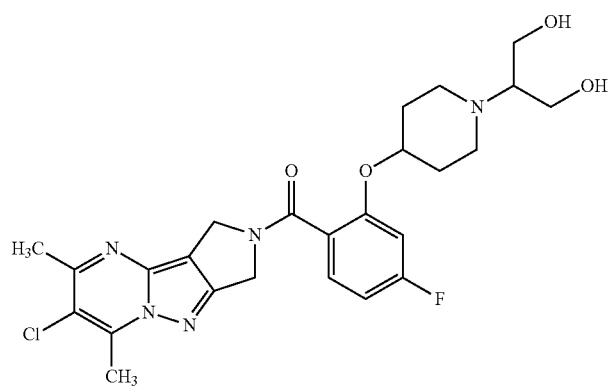 [SMILES: Cc1nc2c3c(nn2c(C)c1Cl)CN(C(=O)c1ccc(F)cc1OC1CCN(C(CO)CO)CC1)C3] |
| 30 | 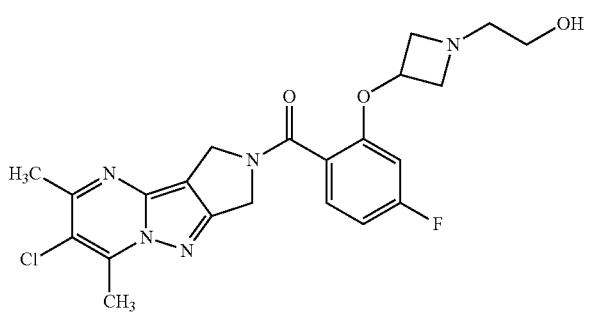 [SMILES: Cc1nc2c3c(nn2c(C)c1Cl)CN(C(=O)c1ccc(F)cc1OC1CN(CCO)C1)C3] |
| 31 | 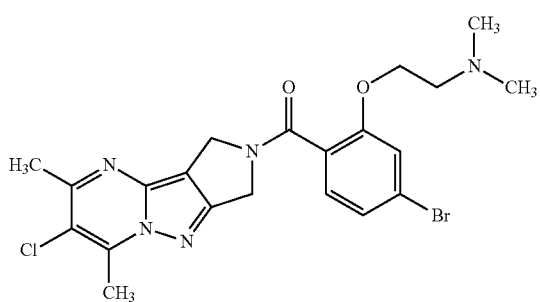 |

-continued
| Ex | Structure |
|---|---|
| 32 | 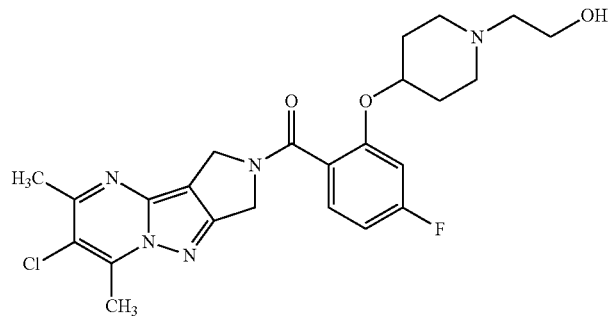 [SMILES: Cc1nc2c3c(nn2c(C)c1Cl)CN(C(=O)c1ccc(F)cc1OC1CCN(CCO)CC1)C3] |
| 33 | 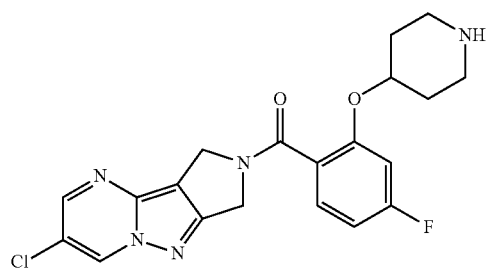 [SMILES: O=C(c1ccc(F)cc1OC1CCNCC1)N1Cc2nn3cc(Cl)cnc3c2C1] |
| 34 | 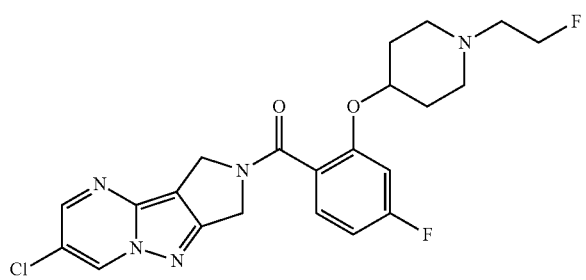 [SMILES: O=C(c1ccc(F)cc1OC1CCN(CCF)CC1)N1Cc2nn3cc(Cl)cnc3c2C1] |
| 35 | 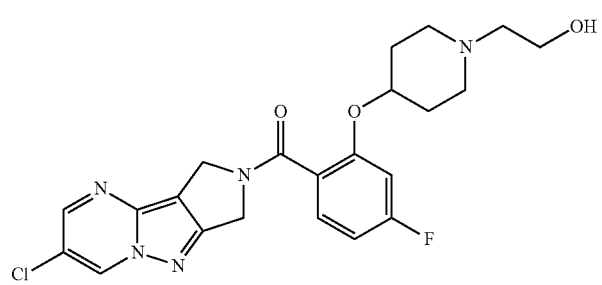 [SMILES: O=C(c1ccc(F)cc1OC1CCN(CCO)CC1)N1Cc2nn3cc(Cl)cnc3c2C1] |
| 36 | 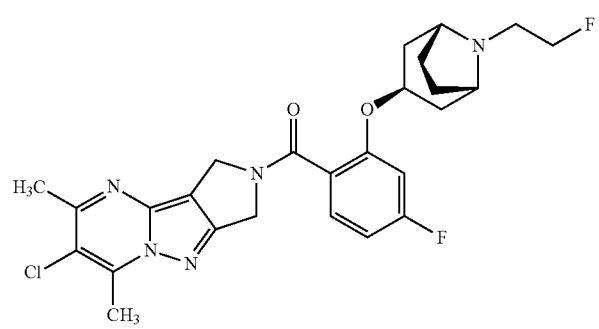 |

-continued
| Ex | Structure |
|---|---|
| 37 | 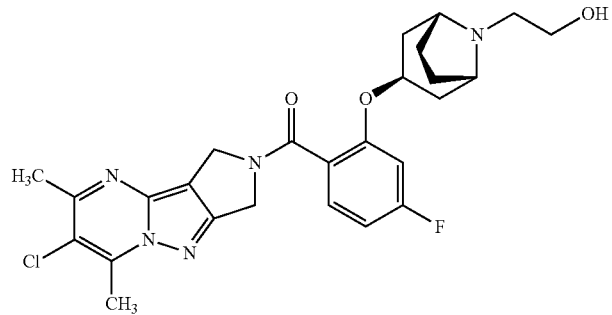 |
| 38 | 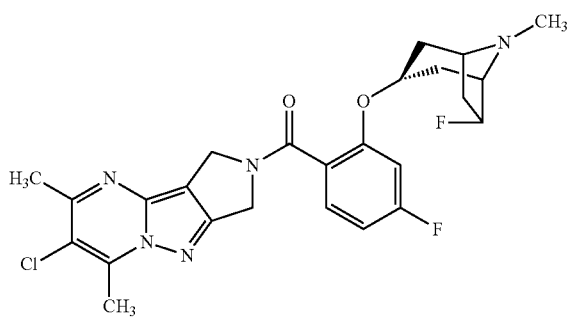 |
| 39 | 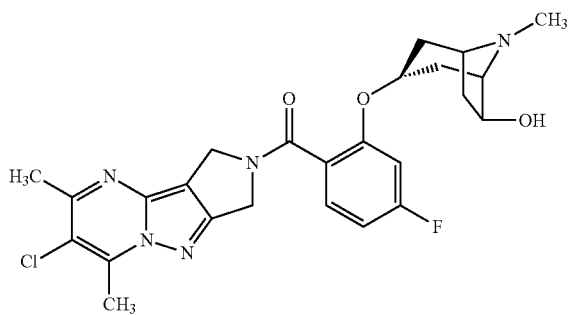 |
| 40 | 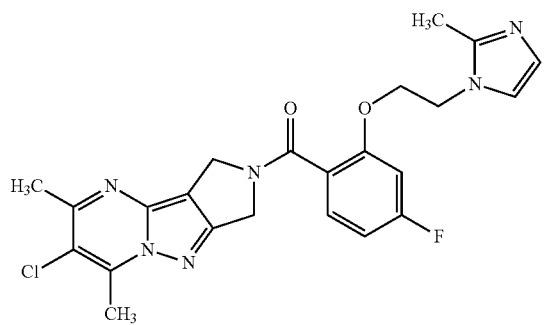 [SMILES: Cc1nc2c3c(nn2c(C)c1Cl)CN(C(=O)c1ccc(F)cc1OCCn1ccnc1C)C3] |

-continued
| Ex | Structure |
|---|---|
| 41 | 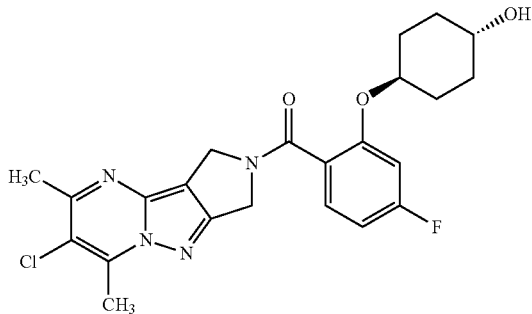 [SMILES: Cc1nc2c3c(nn2c(C)c1Cl)CN(C(=O)c1ccc(F)cc1O[C@H]1CC[C@H](O)CC1)C3] |
| 42 | 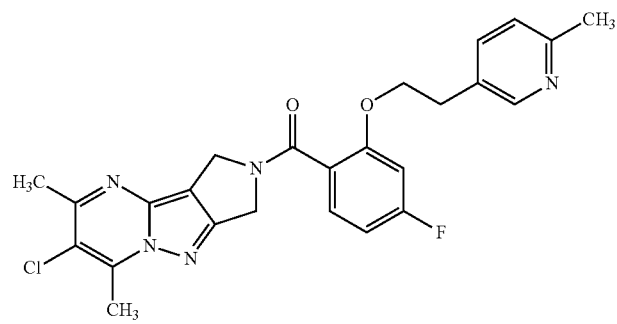 [SMILES: Cc1ccc(CCOc2cc(F)ccc2C(=O)N2Cc3nn4c(C)c(Cl)c(C)nc4c3C2)cn1] |
| 43 | 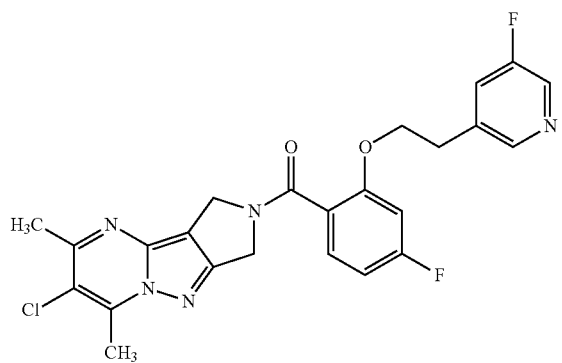 |
| 44 | 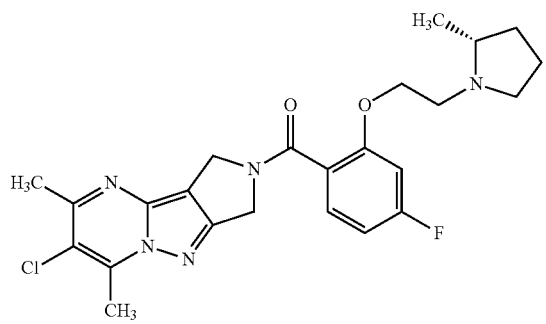 |

| Ex | Structure |
|---|---|
| 45 | 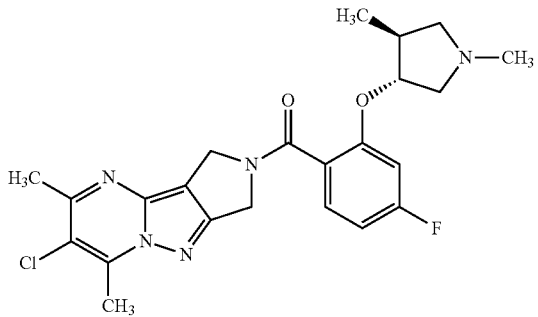 |
| 46 | 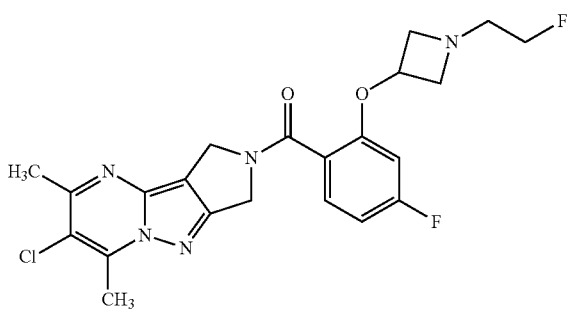 [SMILES: Cc1nc2c3c(nn2c(C)c1Cl)CN(C(=O)c1ccc(F)cc1OC1CN(CCF)C1)C3] |
| 47 | 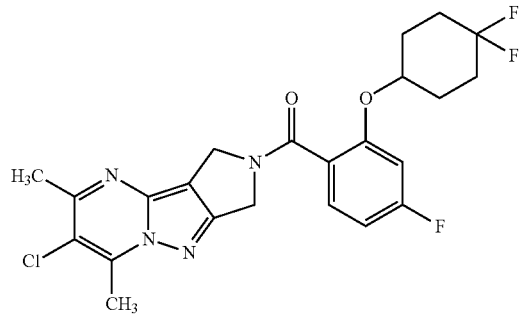 |
| 48 | 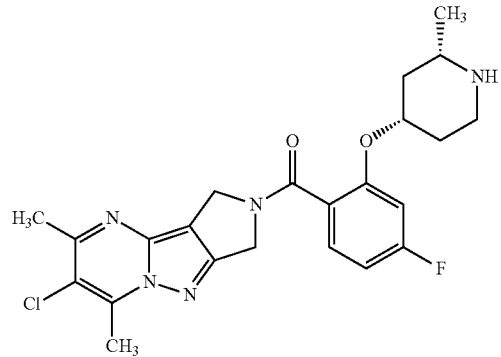 [SMILES: Cc1nc2c3c(nn2c(C)c1Cl)CN(C(=O)c1ccc(F)cc1O[C@H]1CCN[C@@H](C)C1)C3] |

-continued
| Ex | Structure |
|---|---|
| 49 | 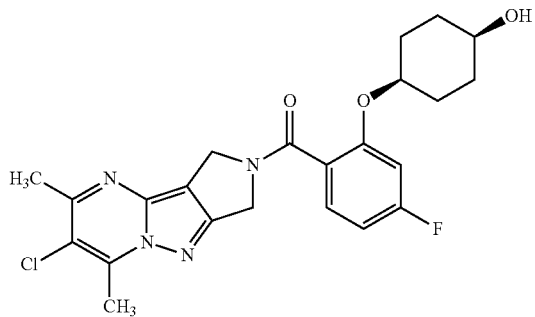 |
| 50 | 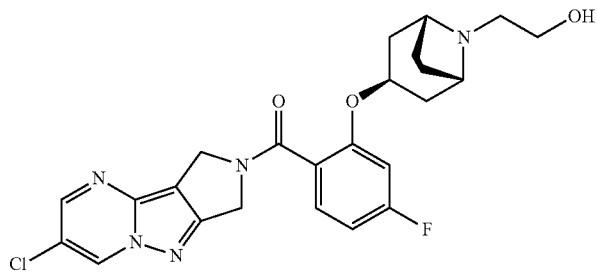 |
| 51 | 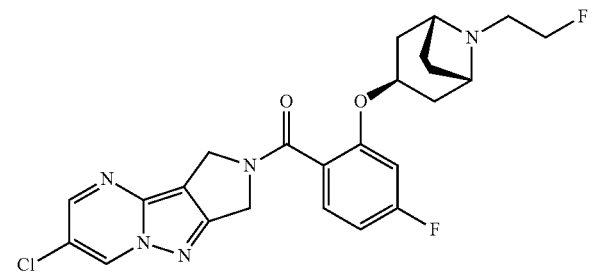 |
| 52 | 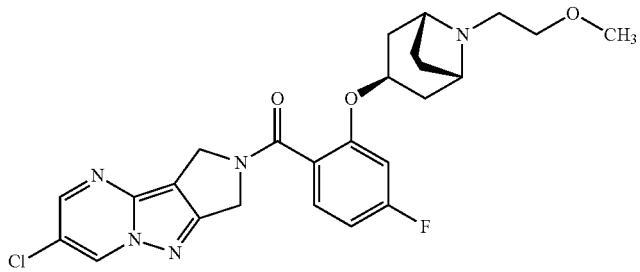 |
| 53 | 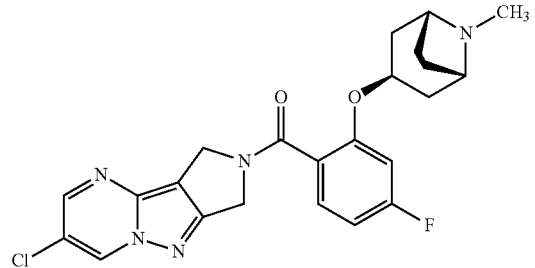 |

| Ex | Structure |
|---|---|
| 54a | 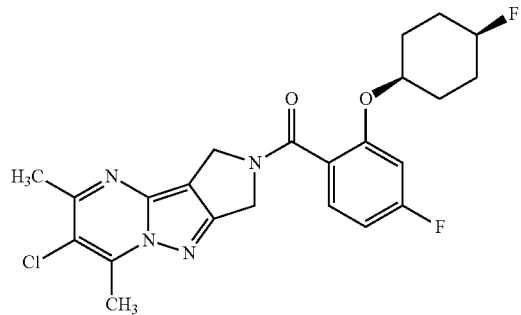 [SMILES: Cc1nc2c3c(nn2c(C)c1Cl)CN(C(=O)c1ccc(F)cc1O[C@H]1CC[C@@H](F)CC1)C3] |
| 54b | 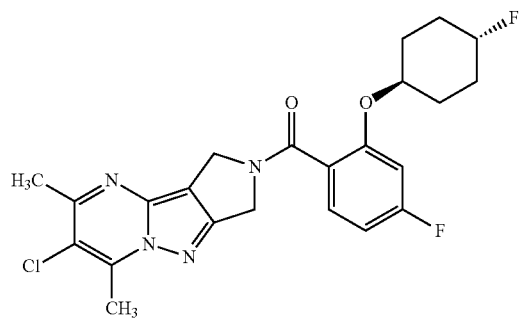 |
| 55 | 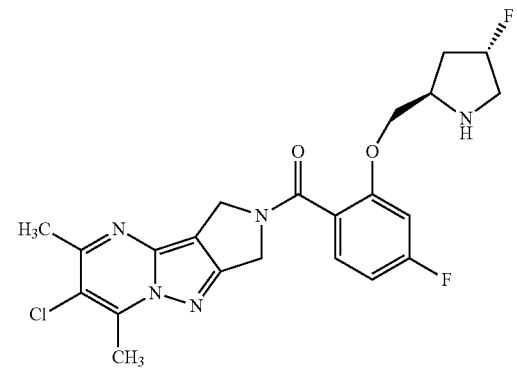 [SMILES: Cc1nc2c3c(nn2c(C)c1Cl)CN(C(=O)c1ccc(F)cc1OC[C@H]1C[C@H](F)CN1)C3] |
| 56 | 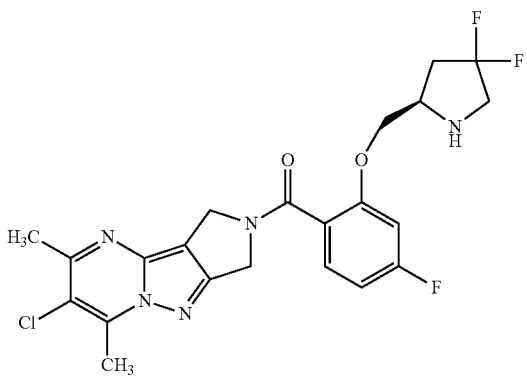 [SMILES: Cc1nc2c3c(nn2c(C)c1Cl)CN(C(=O)c1ccc(F)cc1OC[C@H]1CC(F)(F)CN1)C3] |

| Ex | Structure |
|---|---|
| 58 | 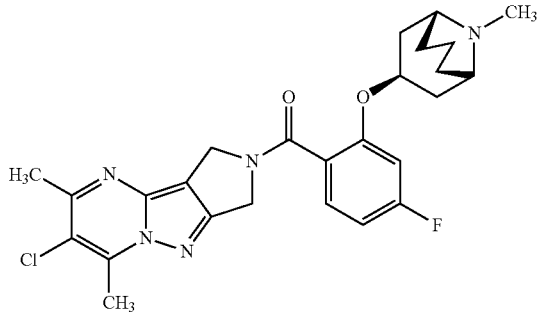 |
| 59 | 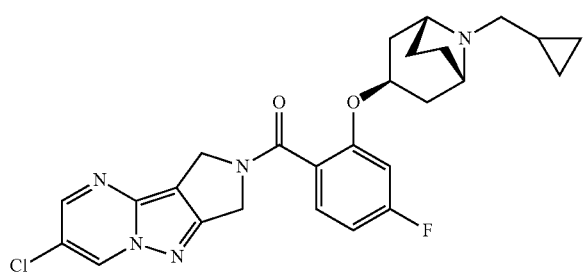 [SMILES: O=C(c1ccc(F)cc1O[C@H]1C[C@H]2CC[C@@H](C1)N2CC1CC1)N1Cc2nn3cc(Cl)cnc3c2C1] |
| 60 | 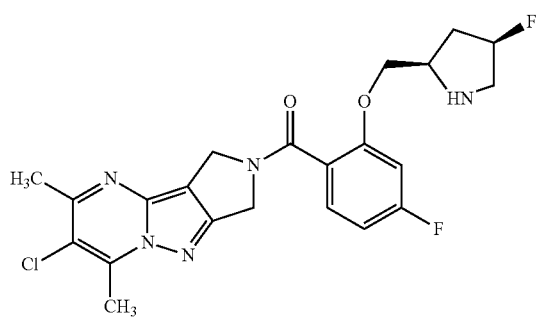 [SMILES: Cc1nc2c3c(nn2c(C)c1Cl)CN(C(=O)c1ccc(F)cc1OC[C@H]1C[C@@H](F)CN1)C3] |
| 61 | 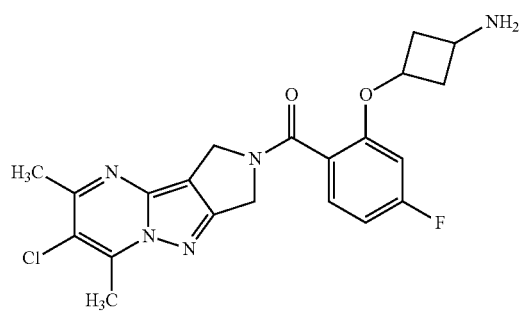 [SMILES: Cc1nc2c3c(nn2c(C)c1Cl)CN(C(=O)c1ccc(F)cc1OC1CC(N)C1)C3] |

-continued
| Ex | Structure |
|---|---|
| 62 | 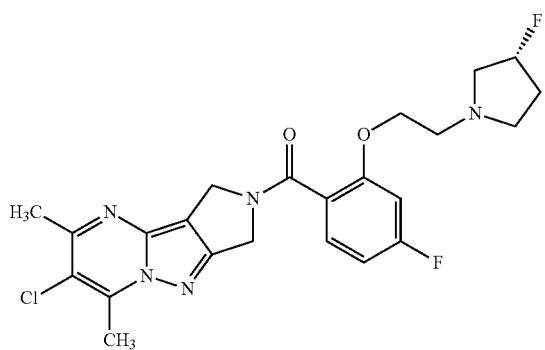 |
| 63 | 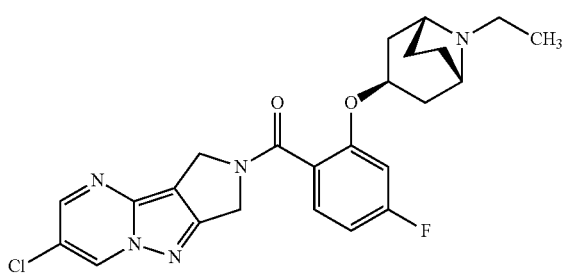 [SMILES: CCN1[C@@H]2CC[C@H]1C[C@@H](Oc1cc(F)ccc1C(=O)N1Cc3nn4cc(Cl)cnc4c3C1)C2] |
| 64 | 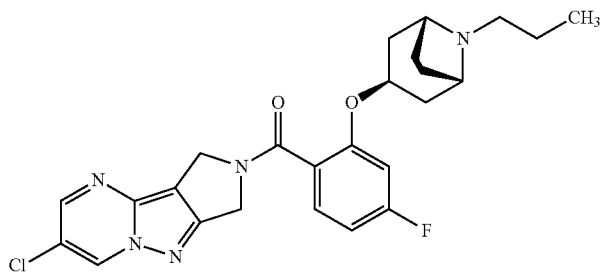 |
| 65 | 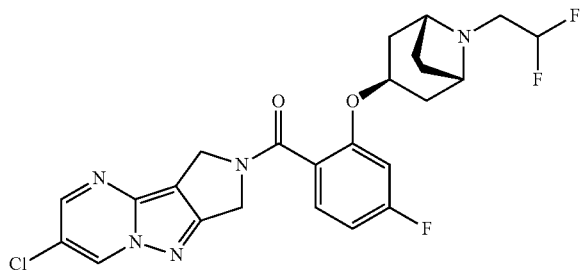 |
| 66 | 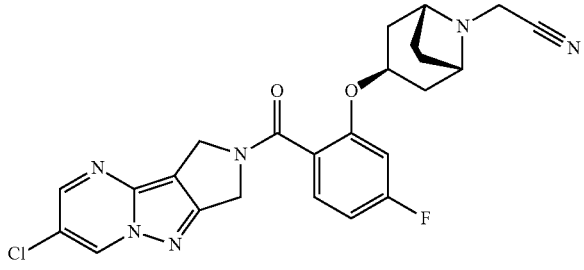 |

-continued
| Ex | Structure |
|---|---|
| 67 | 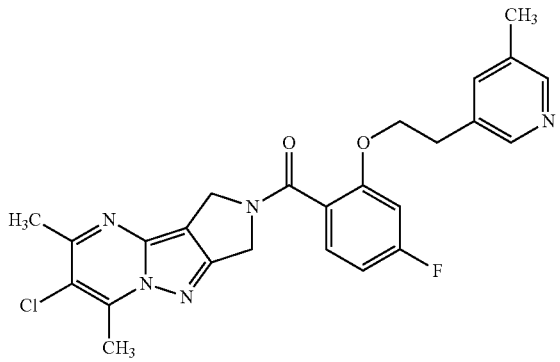 |
| 68 | 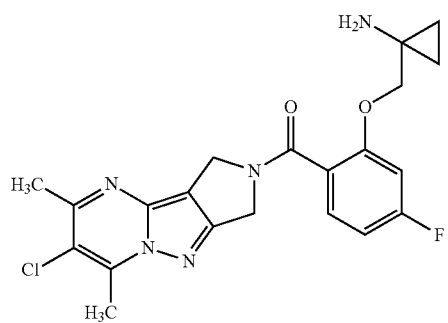 [SMILES: Cc1nc2c3c(nn2c(C)c1Cl)CN(C(=O)c1ccc(F)cc1OCC1(N)CC1)C3] |
| 69 | 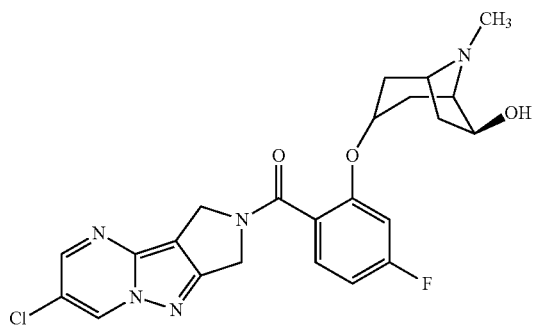 [SMILES: CN1C2CC(Oc3cc(F)ccc3C(=O)N3Cc4nn5cc(Cl)cnc5c4C3)CC1[C@@H](O)C2] |
| 70a | 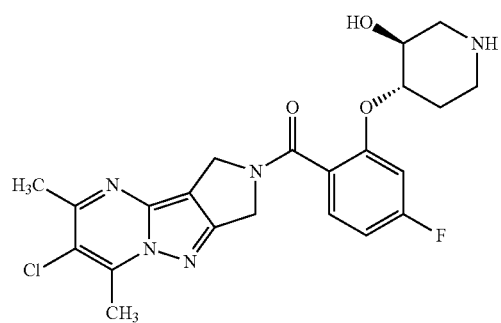 |

-continued
| Ex | Structure |
|---|---|
| 70b | 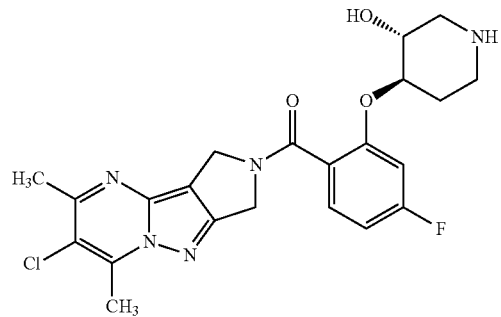 [SMILES: Cc1nc2c3c(nn2c(C)c1Cl)CN(C(=O)c1ccc(F)cc1O[C@@H]1CCNC[C@H]1O)C3] |
| 71 | 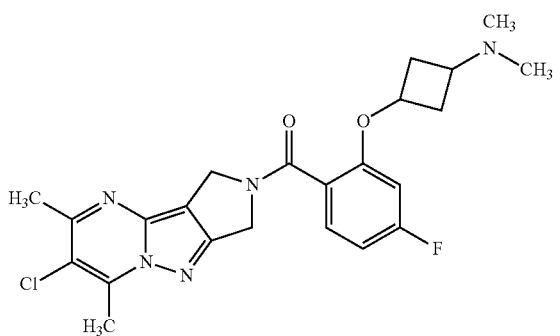 |
| 72 | 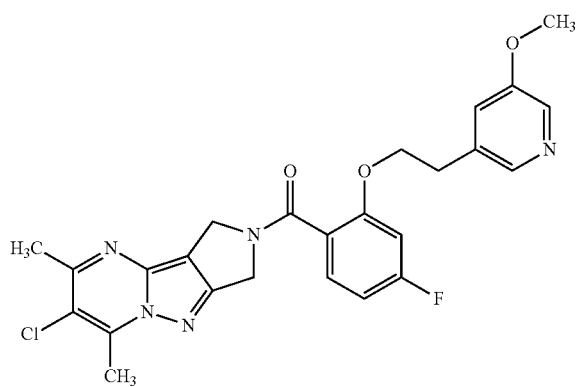 [SMILES: COc1cncc(CCOc2cc(F)ccc2C(=O)N2Cc3nn4c(C)c(Cl)c(C)nc4c3C2)c1] |
| 73 | 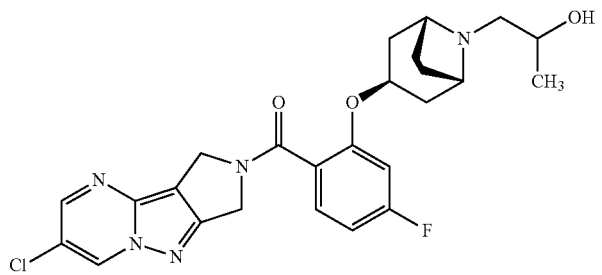 |

| Ex | Structure |
|---|---|
| 74 | 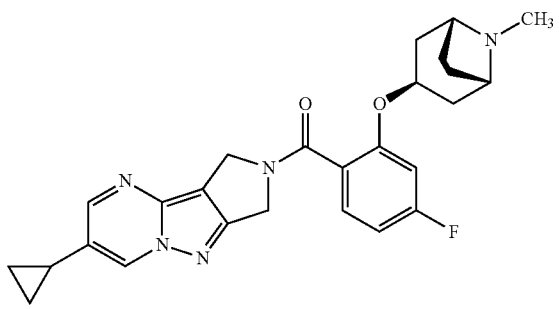 |
| 75 | 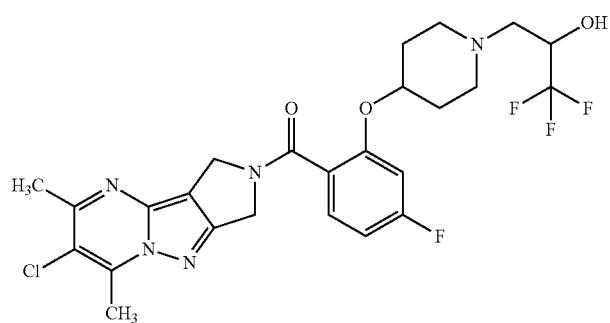 [SMILES: Cc1nc2c3c(nn2c(C)c1Cl)CN(C(=O)c1ccc(F)cc1OC1CCN(CC(O)C(F)(F)F)CC1)C3] |
| 76 | 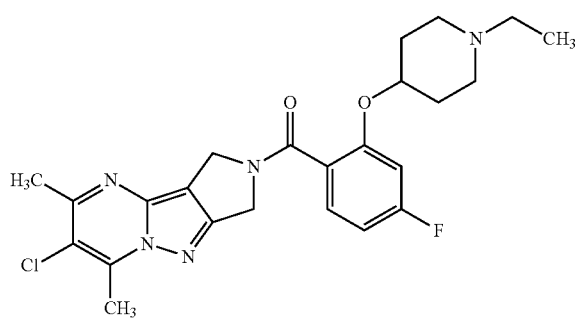 [SMILES: CCN1CCC(Oc2cc(F)ccc2C(=O)N2Cc3nn4c(C)c(Cl)c(C)nc4c3C2)CC1] |
| 77 | 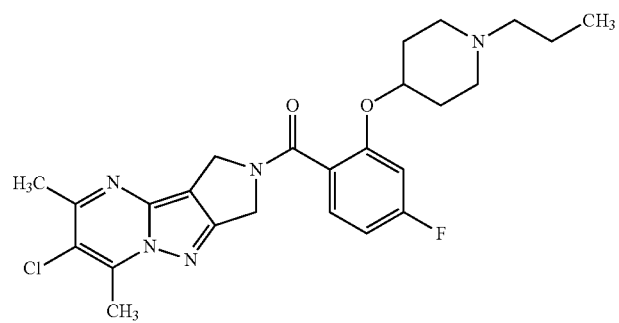 [SMILES: CCCN1CCC(Oc2cc(F)ccc2C(=O)N2Cc3nn4c(C)c(Cl)c(C)nc4c3C2)CC1] |

| Ex | Structure |
|---|---|
| 78a | 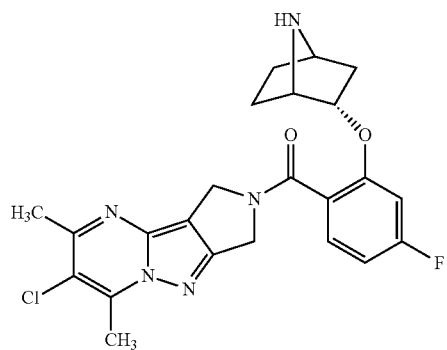 [SMILES: Cc1nc2c3c(nn2c(C)c1Cl)CN(C(=O)c1ccc(F)cc1O[C@H]1CC2CCC1N2)C3] |
| 78b | 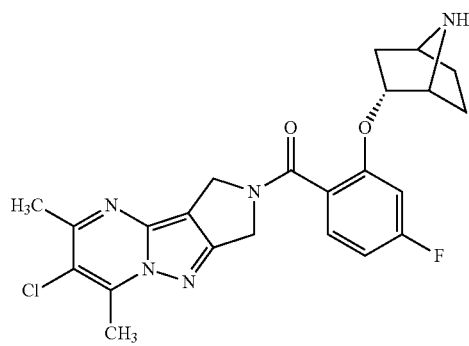 [SMILES: Cc1nc2c3c(nn2c(C)c1Cl)CN(C(=O)c1ccc(F)cc1O[C@@H]1CC2CCC1N2)C3] |
| 79 | 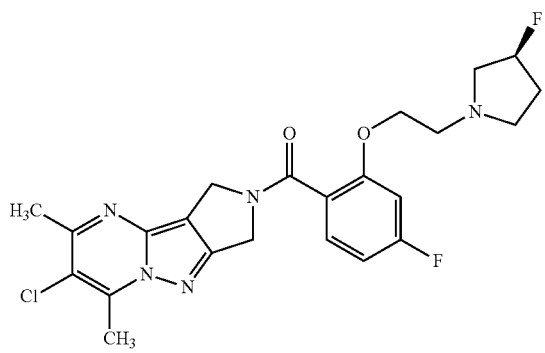 |
| 80 | 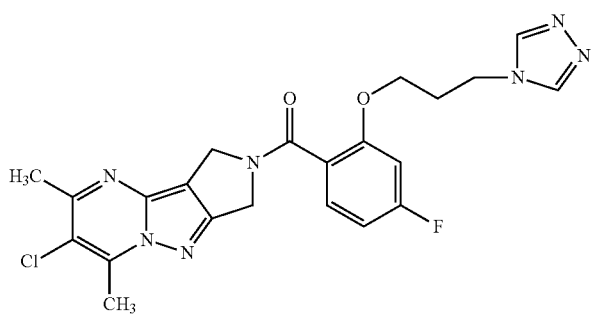 [SMILES: Cc1nc2c3c(nn2c(C)c1Cl)CN(C(=O)c1ccc(F)cc1OCCCn1cnnc1)C3] |

-continued
| Ex | Structure |
|---|---|
| 81 | 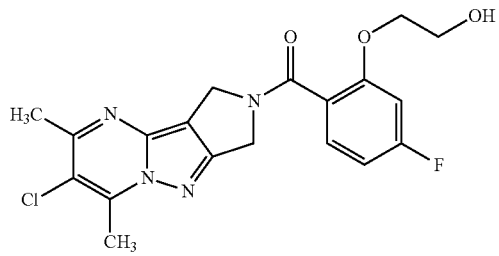 [SMILES: Cc1nc2c3c(nn2c(C)c1Cl)CN(C(=O)c1ccc(F)cc1OCCO)C3] |
| 82 | 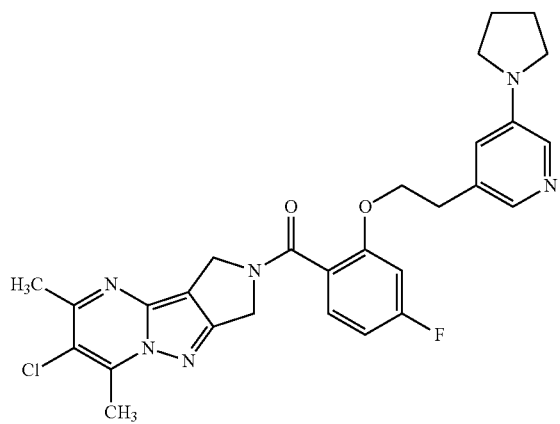 [SMILES: Cc1nc2c3c(nn2c(C)c1Cl)CN(C(=O)c1ccc(F)cc1OCCc1cncc(N2CCCC2)c1)C3] |
| 83 | 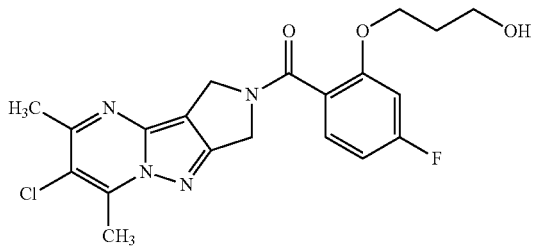 [SMILES: Cc1nc2c3c(nn2c(C)c1Cl)CN(C(=O)c1ccc(F)cc1OCCCO)C3] |
| 84a | 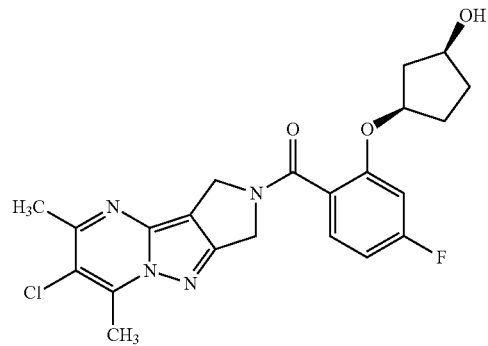 [SMILES: Cc1nc2c3c(nn2c(C)c1Cl)CN(C(=O)c1ccc(F)cc1O[C@@H]1CC[C@H](O)C1)C3] |

| Ex | Structure |
|---|---|
| 84b | 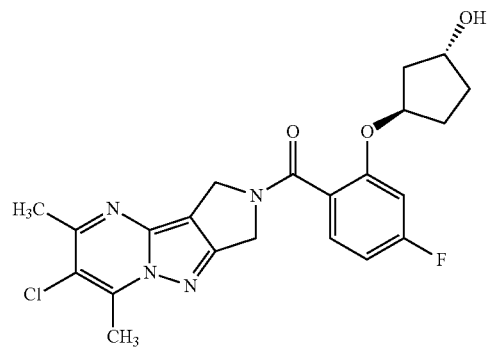 [SMILES: Cc1nc2c3c(nn2c(C)c1Cl)CN(C(=O)c1ccc(F)cc1O[C@@H]1CC[C@@H](O)C1)C3] |
| 85 | 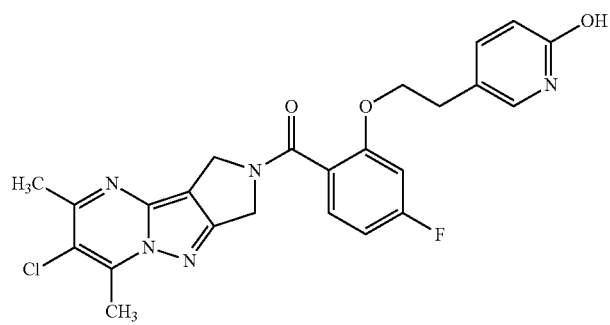 [SMILES: Cc1nc2c3c(nn2c(C)c1Cl)CN(C(=O)c1ccc(F)cc1OCCc1ccc(O)nc1)C3] |
| 86a | 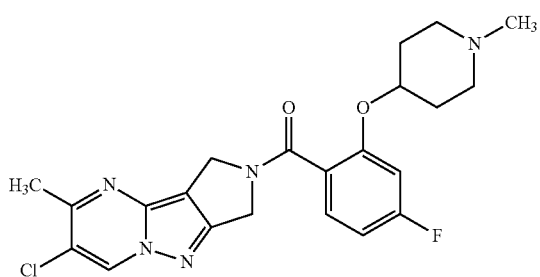 [SMILES: Cc1nc2c3c(nn2cc1Cl)CN(C(=O)c1ccc(F)cc1OC1CCN(C)CC1)C3] |
| 86b | 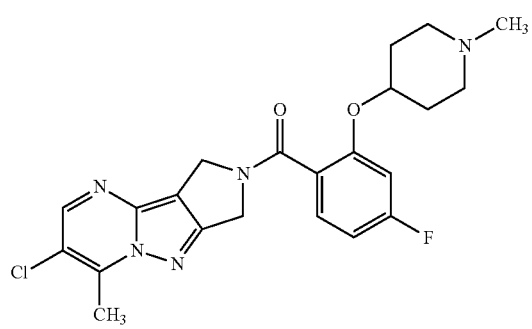 [SMILES: Cc1c(Cl)cnc2c3c(nn12)CN(C(=O)c1ccc(F)cc1OC1CCN(C)CC1)C3] |

-continued
| Ex | Structure |
|---|---|
| 87 | 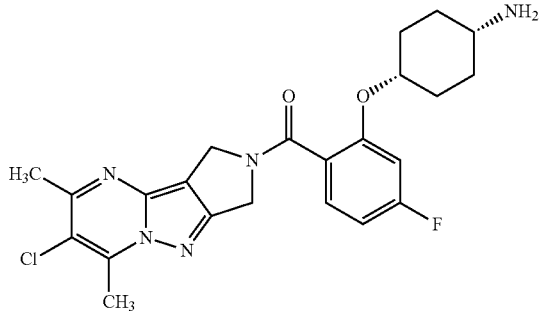 [SMILES: Cc1nc2c3c(nn2c(C)c1Cl)CN(C(=O)c1ccc(F)cc1O[C@H]1CC[C@@H](N)CC1)C3] |
| 88 | 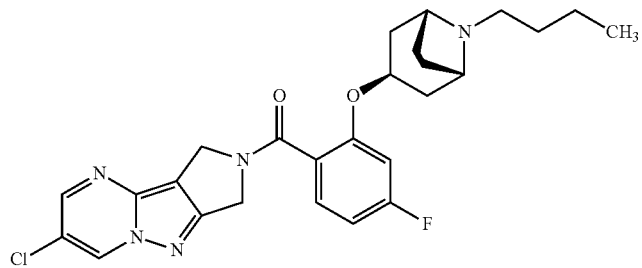 |
| 89 | 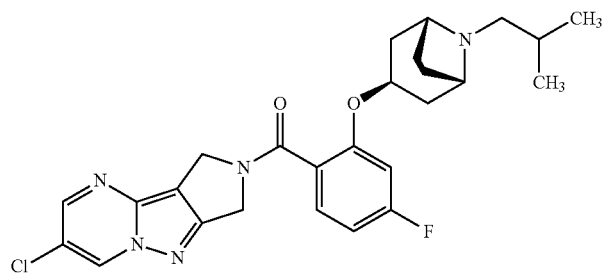 |
| 90a | 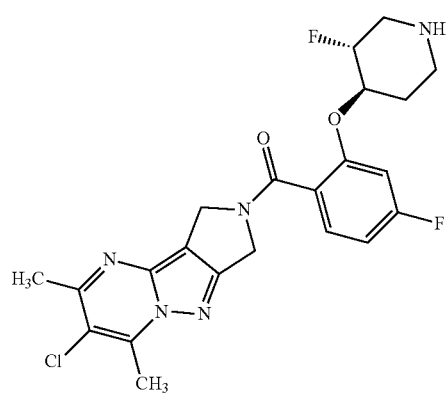 [SMILES: Cc1nc2c3c(nn2c(C)c1Cl)CN(C(=O)c1ccc(F)cc1O[C@@H]1CCNC[C@H]1F)C3] |

-continued

| Ex | Structure |
|---|---|
| 90b | 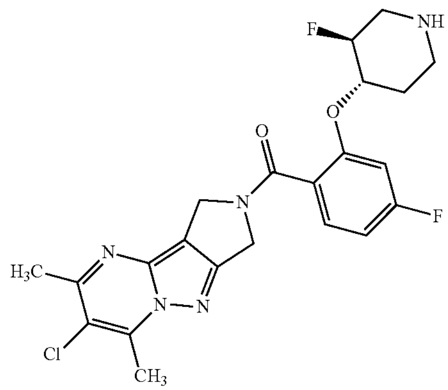 [SMILES: Cc1nc2c3c(nn2c(C)c1Cl)CN(C(=O)c1ccc(F)cc1O[C@H]1CCNC[C@@H]1F)C3] |
| 91a | 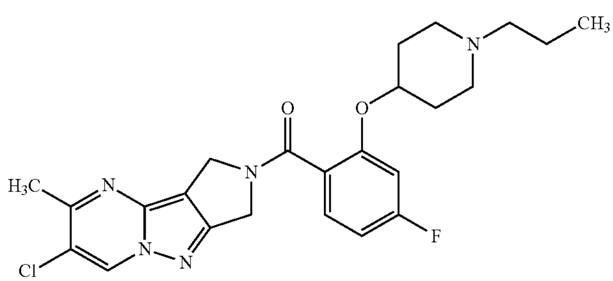 [SMILES: CCCN1CCC(Oc2cc(F)ccc2C(=O)N2Cc3nn4cc(Cl)c(C)nc4c3C2)CC1] |
| 91b | 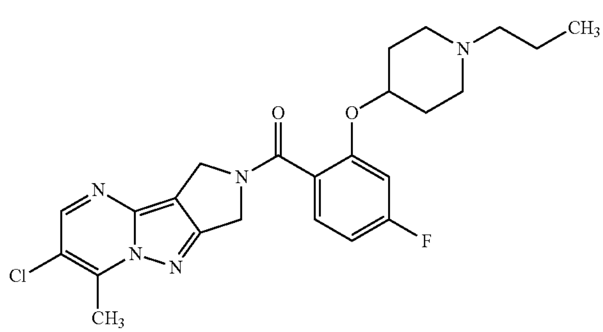 [SMILES: CCCN1CCC(Oc2cc(F)ccc2C(=O)N2Cc3nn4c(C)c(Cl)cnc4c3C2)CC1] |
| 92 | 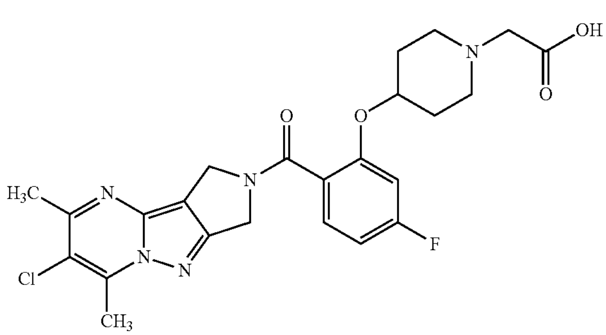 [SMILES: Cc1nc2c3c(nn2c(C)c1Cl)CN(C(=O)c1ccc(F)cc1OC1CCN(CC(=O)O)CC1)C3] |

| Ex | Structure |
|---|---|
| 93a | 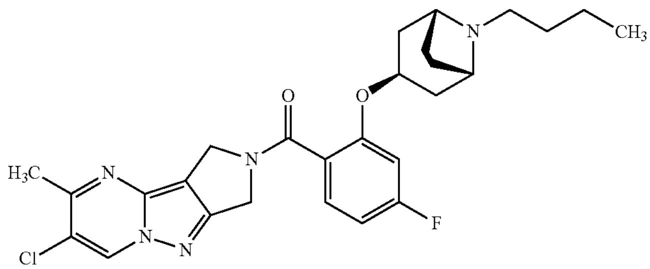 |
| 93b | 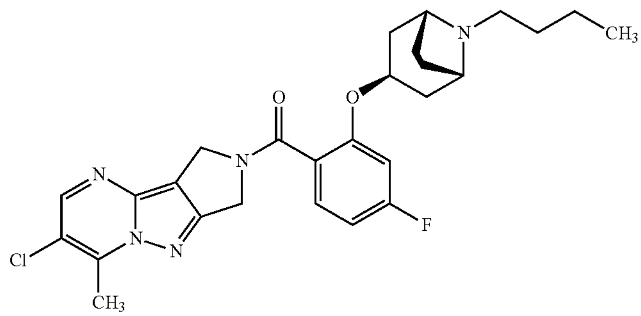 |
| 94a | 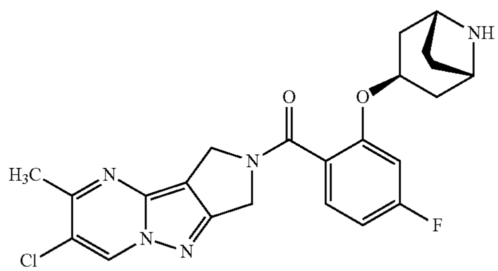 |
| 94b | 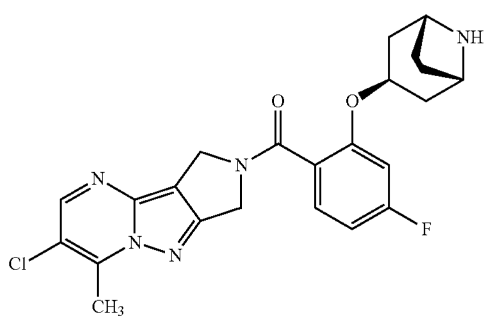 |
| 95 | 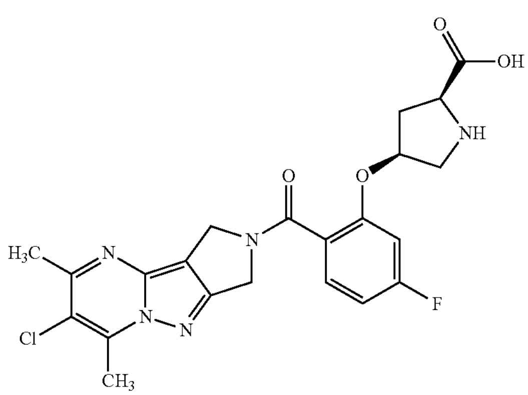 [SMILES: Cc1nc2c3c(nn2c(C)c1Cl)CN(C(=O)c1ccc(F)cc1O[C@@H]1CN[C@H](C(=O)O)C1)C3] |

| Ex | Structure |
|---|---|
| 96 | 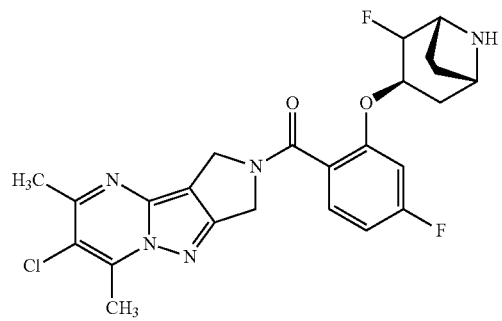 |
| 97 | 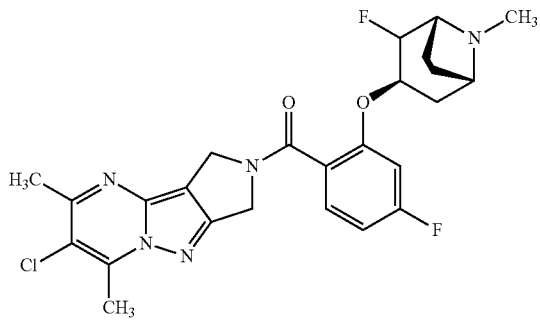 |
| 98 | 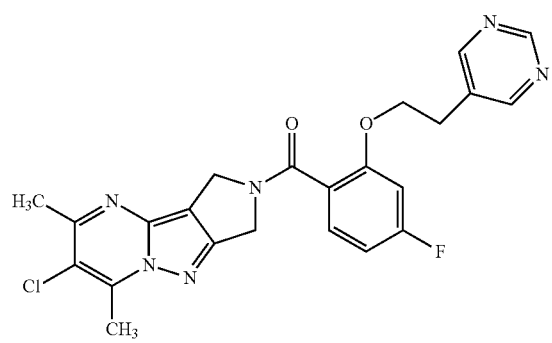 [SMILES: Cc1nc2c3c(nn2c(C)c1Cl)CN(C(=O)c1ccc(F)cc1OCCc1cncnc1)C3] |
| 99 | 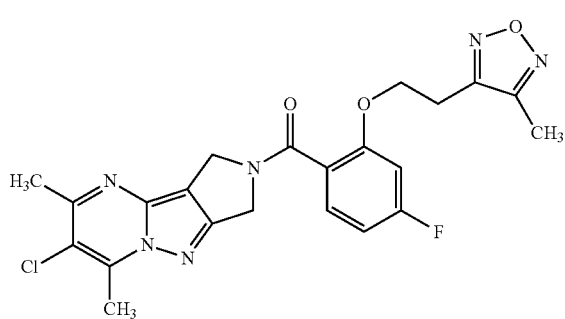 [SMILES: Cc1nonc1CCOc1cc(F)ccc1C(=O)N1Cc2nn3c(C)c(Cl)c(C)nc3c2C1] |

| Ex | Structure |
|---|---|
| 100 | 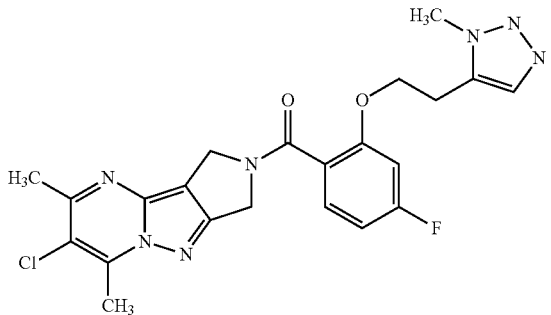 [SMILES: Cc1nc2c3c(nn2c(C)c1Cl)CN(C(=O)c1ccc(F)cc1OCCC1=CNNN1C)C3] |
| 101 | 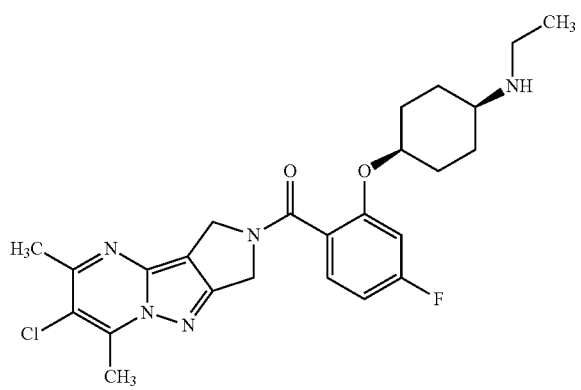 [SMILES: CCN[C@H]1CC[C@@H](Oc2cc(F)ccc2C(=O)N2Cc3nn4c(C)c(Cl)c(C)nc4c3C2)CC1] |
| 102 | 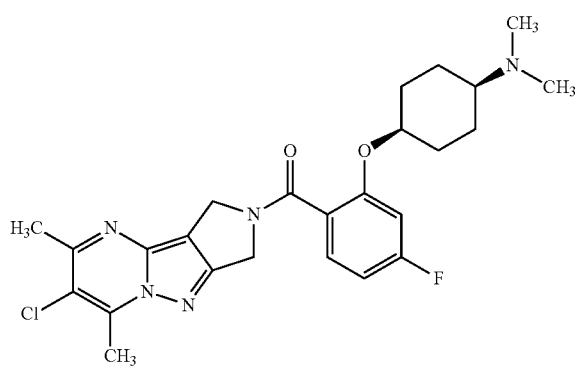 |
| 103 | 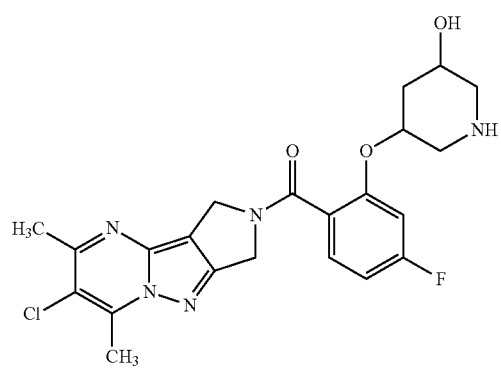 |

-continued
| Ex | Structure |
|---|---|
| 104 | 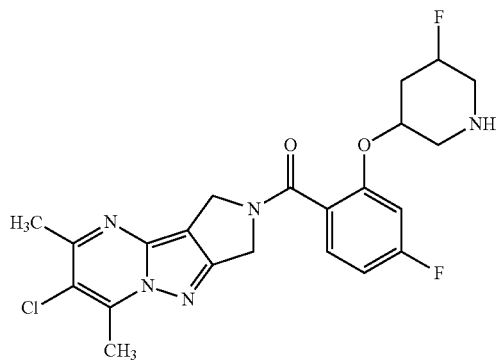 [SMILES: Cc1nc2c3c(nn2c(C)c1Cl)CN(C(=O)c1ccc(F)cc1OC1CNCC(F)C1)C3] |
| 105 | 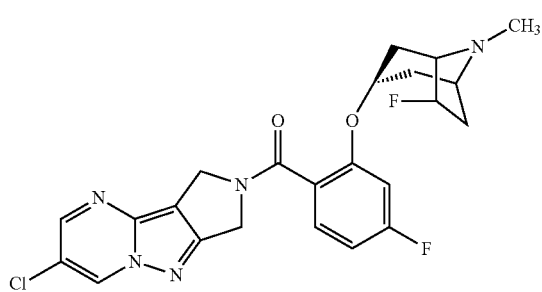 [SMILES: CN1C2CC(F)C1C[C@H](Oc1cc(F)ccc1C(=O)N1Cc3nn4cc(Cl)cnc4c3C1)C2] |
| 106 | 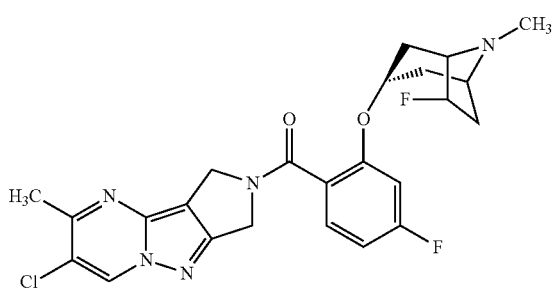 [SMILES: Cc1nc2c3c(nn2cc1Cl)CN(C(=O)c1ccc(F)cc1O[C@@H]1CC2CC(F)C(C1)N2C)C3] |
| 107 | 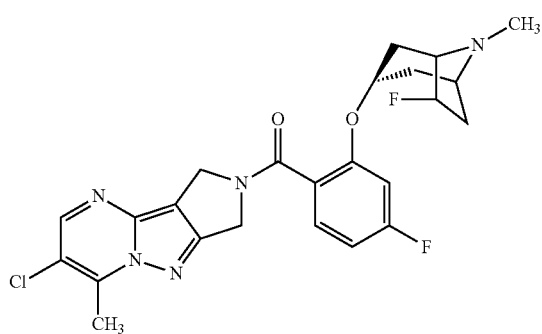 [SMILES: Cc1c(Cl)cnc2c3c(nn12)CN(C(=O)c1ccc(F)cc1O[C@@H]1CC2CC(F)C(C1)N2C)C3] |

| Ex | Structure |
|---|---|
| 108 | 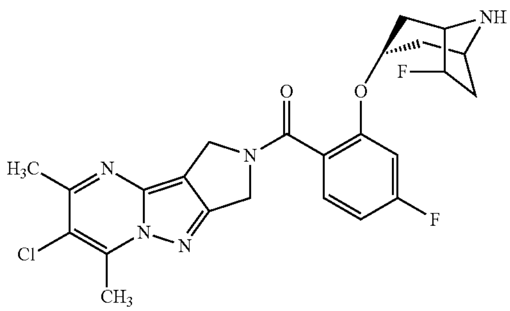 [SMILES: Cc1nc2c3c(nn2c(C)c1Cl)CN(C(=O)c1ccc(F)cc1O[C@@H]1CC2CC(F)C(C1)N2)C3] |
| 109 | 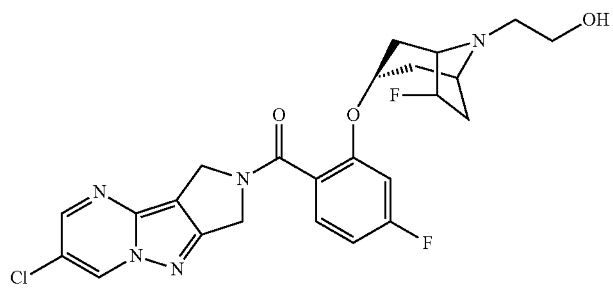 [SMILES: O=C(c1ccc(F)cc1O[C@@H]1CC2CC(F)C(C1)N2CCO)N1Cc2nn3cc(Cl)cnc3c2C1] |
| 110 | 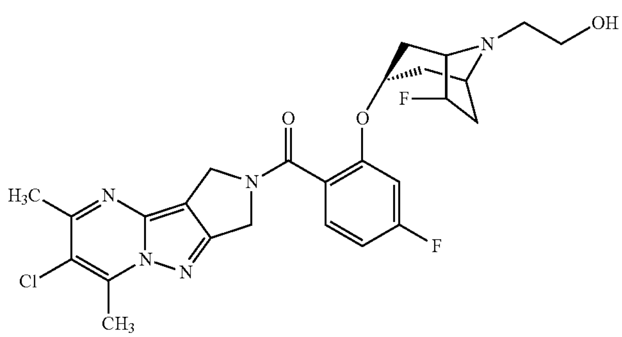 [SMILES: Cc1nc2c3c(nn2c(C)c1Cl)CN(C(=O)c1ccc(F)cc1O[C@@H]1CC2CC(F)C(C1)N2CCO)C3] |
| 111 | 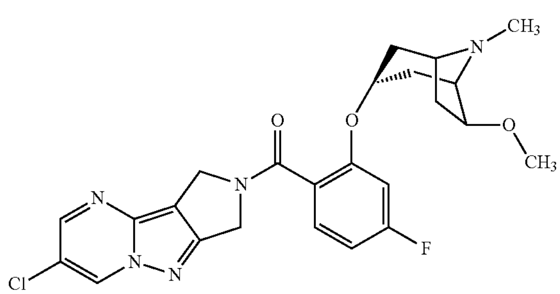 [SMILES: COC1CC2C[C@H](Oc3cc(F)ccc3C(=O)N3Cc4nn5cc(Cl)cnc5c4C3)CC1N2C] |
| 112 | 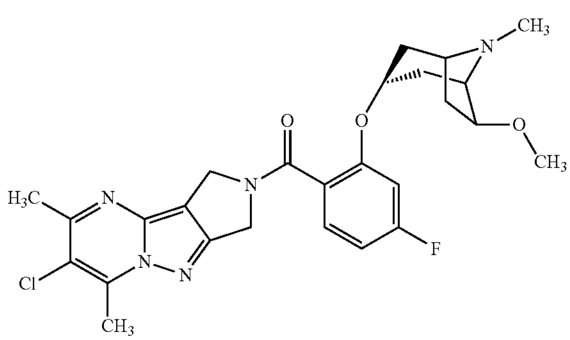 [SMILES: COC1CC2C[C@H](Oc3cc(F)ccc3C(=O)N3Cc4nn5c(C)c(Cl)c(C)nc5c4C3)CC1N2C] |

| Ex | Structure |
|---|---|
| 113 | 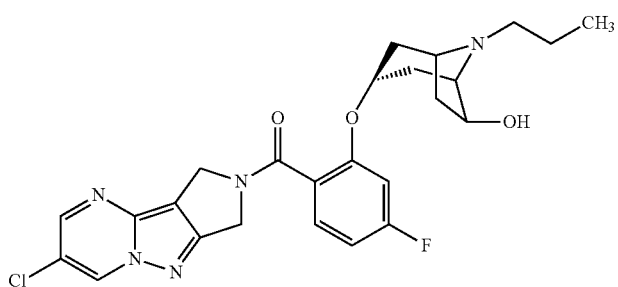 [SMILES: CCCN1C2CC(O)C1C[C@@H](Oc1cc(F)ccc1C(=O)N1Cc3nn4cc(Cl)cnc4c3C1)C2] |
| 114 | 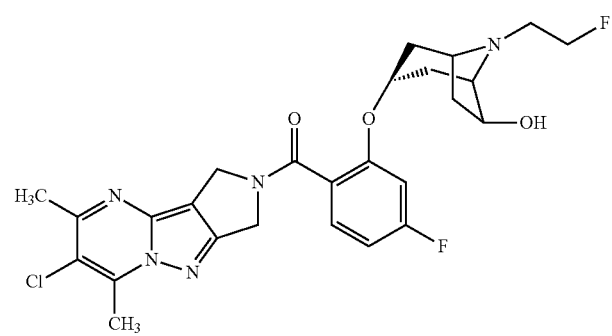 [SMILES: Cc1nc2c3c(nn2c(C)c1Cl)CN(C(=O)c1ccc(F)cc1O[C@H]1CC2CC(O)C(C1)N2CCF)C3] |
| 115 | 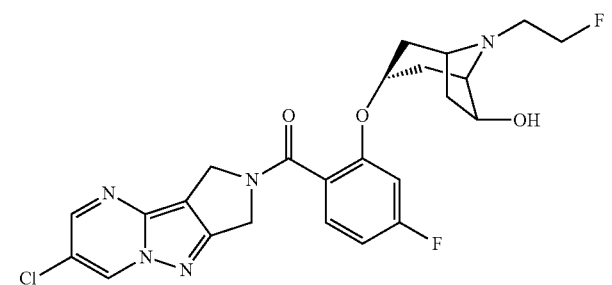 [SMILES: O=C(c1ccc(F)cc1O[C@H]1CC2CC(O)C(C1)N2CCF)N1Cc2nn3cc(Cl)cnc3c2C1] |
| 116 | 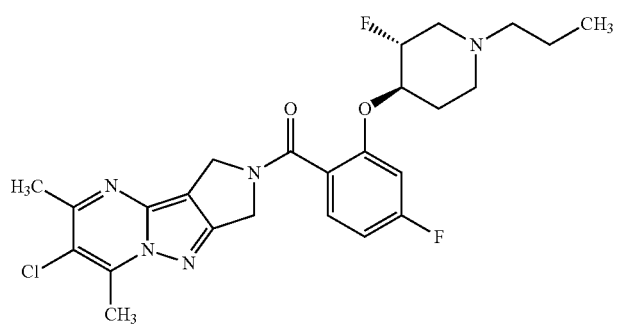 [SMILES: CCCN1CC[C@@H](Oc2cc(F)ccc2C(=O)N2Cc3nn4c(C)c(Cl)c(C)nc4c3C2)[C@H](F)C1] |

| Ex | Structure |
|---|---|
| 117 | (structure) |
| 118 | (structure) |
| 119 | (structure) |
| 120 | (structure) |
| 121 | (structure) |

-continued

| Ex | Structure |
|---|---|
| 122 | 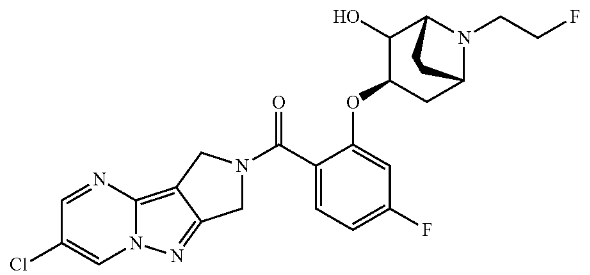 |
| 123 | 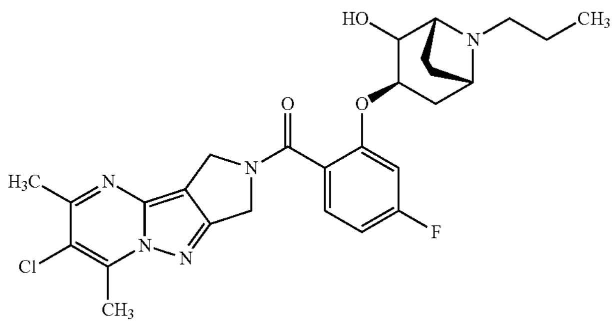 |
| 124 | 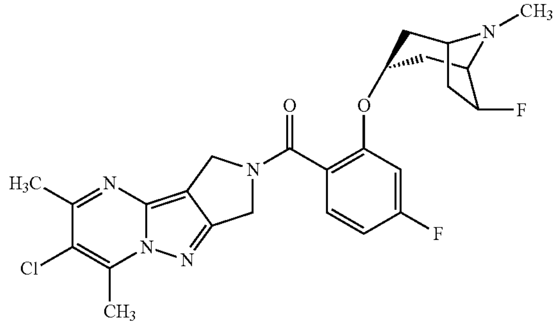 [SMILES: Cc1nc2c3c(nn2c(C)c1Cl)CN(C(=O)c1ccc(F)cc1O[C@H]1CC2CC(F)C(C1)N2C)C3] |
| 125 | 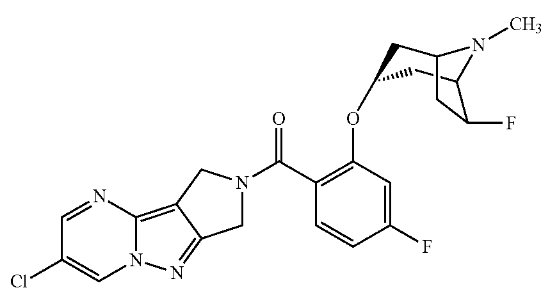 [SMILES: CN1C2CC(F)C1C[C@@H](Oc1cc(F)ccc1C(=O)N1Cc3nn4cc(Cl)cnc4c3C1)C2] |
| 126 | 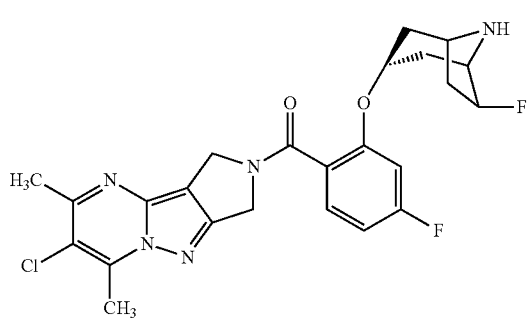 [SMILES: Cc1nc2c3c(nn2c(C)c1Cl)CN(C(=O)c1ccc(F)cc1O[C@H]1CC2CC(F)C(C1)N2)C3] |

| Ex | Structure |
|---|---|
| 127 | 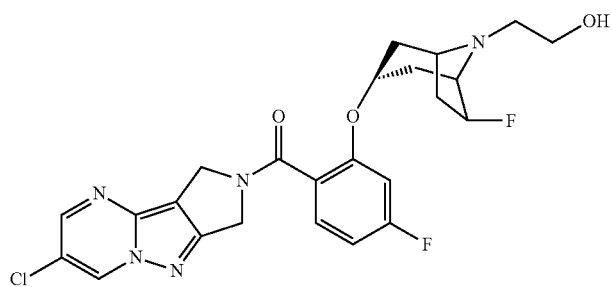 [SMILES: O=C(c1ccc(F)cc1O[C@H]1CC2CC(F)C(C1)N2CCO)N1Cc2nn3cc(Cl)cnc3c2C1] |
| 128 | 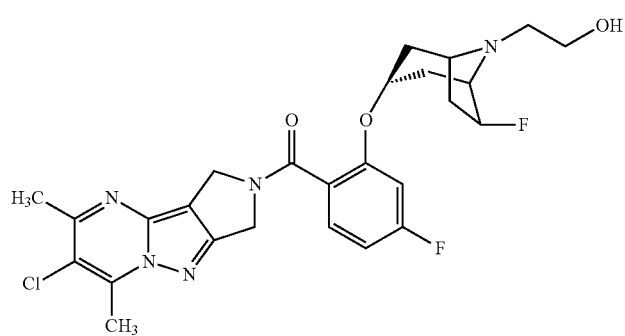 [SMILES: Cc1nc2c3c(nn2c(C)c1Cl)CN(C(=O)c1ccc(F)cc1O[C@H]1CC2CC(F)C(C1)N2CCO)C3] |
| 129 | 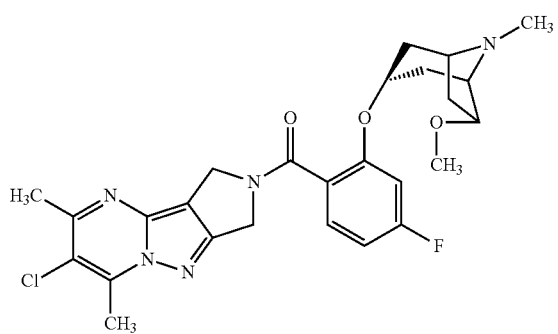 [SMILES: COC1CC2C[C@H](Oc3cc(F)ccc3C(=O)N3Cc4nn5c(C)c(Cl)c(C)nc5c4C3)CC1N2C] |
| 130 | 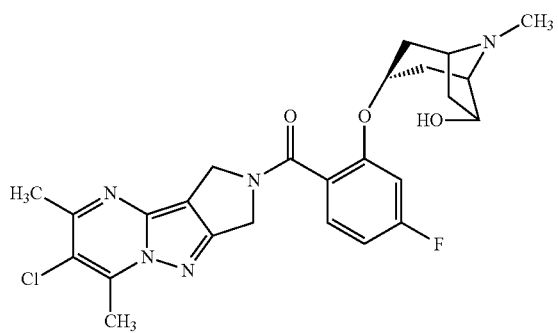 [SMILES: Cc1nc2c3c(nn2c(C)c1Cl)CN(C(=O)c1ccc(F)cc1O[C@H]1CC2CC(O)C(C1)N2C)C3] |

| Ex | Structure |
|---|---|
| 131 | (structure) |
| 132 | (structure) |
| 133 | (structure) |
| 134 | (structure) |
| 135 and | (structure) |

-continued

| Ex | Structure |
|---|---|
| 136 | 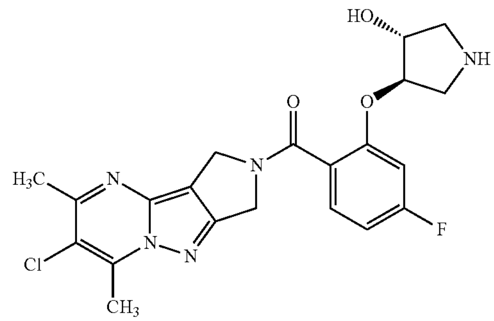 [SMILES: Cc1nc2c3c(nn2c(C)c1Cl)CN(C(=O)c1ccc(F)cc1O[C@@H]1CNC[C@H]1O)C3] |
| 137 and | 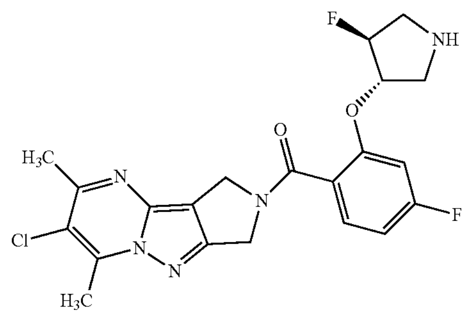 [SMILES: Cc1nc2c3c(nn2c(C)c1Cl)CN(C(=O)c1ccc(F)cc1O[C@H]1CNC[C@@H]1F)C3] |
| 138 | 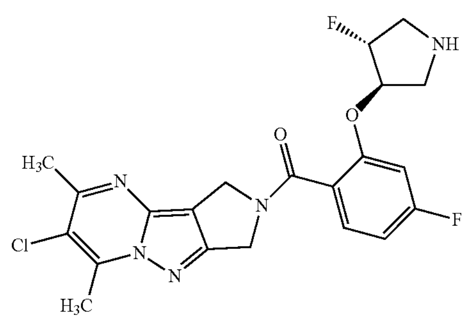 [SMILES: Cc1nc2c3c(nn2c(C)c1Cl)CN(C(=O)c1ccc(F)cc1O[C@@H]1CNC[C@H]1F)C3] |
| 139 | 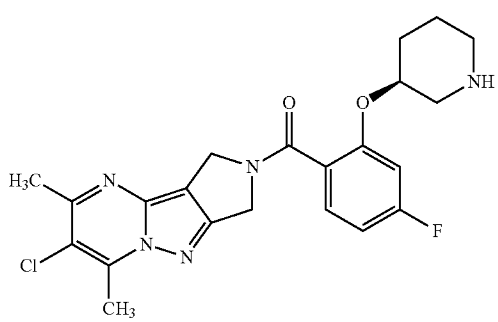 [SMILES: Cc1nc2c3c(nn2c(C)c1Cl)CN(C(=O)c1ccc(F)cc1O[C@H]1CCCNC1)C3] |
| 140 | 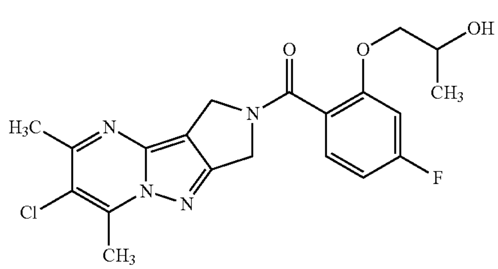 [SMILES: Cc1nc2c3c(nn2c(C)c1Cl)CN(C(=O)c1ccc(F)cc1OCC(C)O)C3] |

-continued
| Ex | Structure |
|---|---|
| 141 | 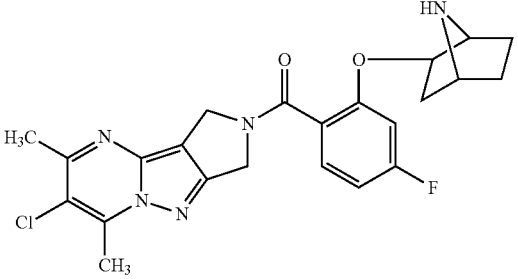 [SMILES: Cc1nc2c3c(nn2c(C)c1Cl)CN(C(=O)c1ccc(F)cc1OC1CC2CCC1N2)C3] |
| 142 | 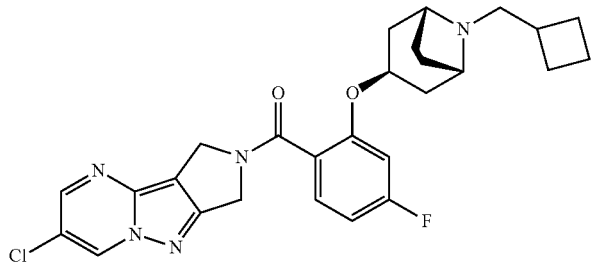 |
| 144a | 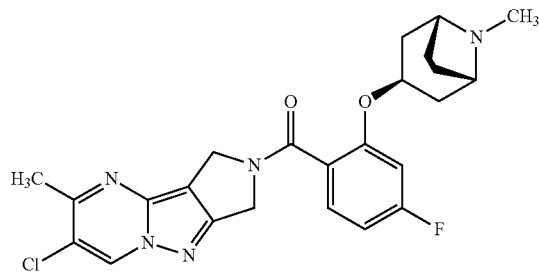 |
| 144b | 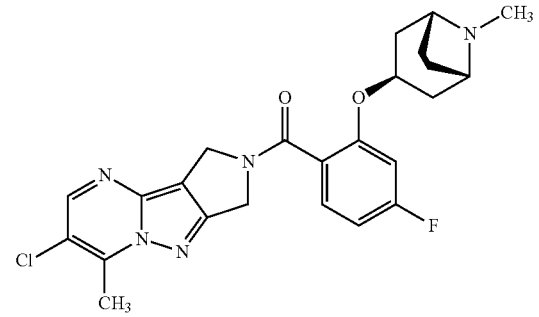 |
| 145a | 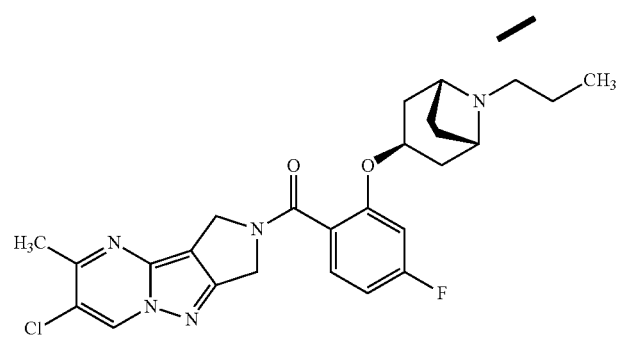 |

-continued

| Ex | Structure |
|---|---|
| 145b | (structure) |
| 146a | (structure) |
| 146b | (structure) |
| 147 | (structure) |
| 148 | (structure) |

| Ex | Structure |
|---|---|
| 150 | 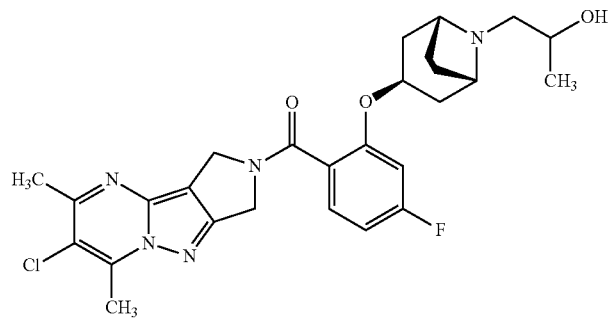 |
| 151 | 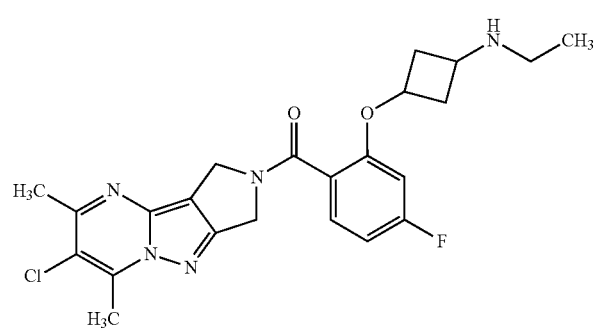 [SMILES: CCNC1CC(Oc2cc(F)ccc2C(=O)N2Cc3nn4c(C)c(Cl)c(C)nc4c3C2)C1] |
| 152 | 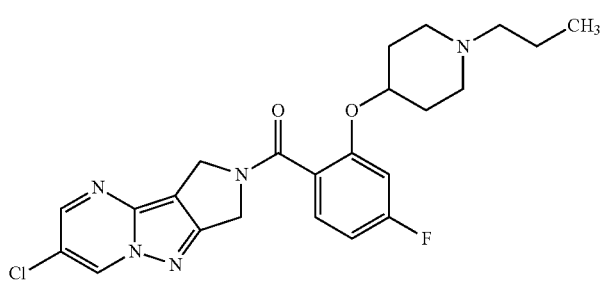 [SMILES: CCCN1CCC(Oc2cc(F)ccc2C(=O)N2Cc3nn4cc(Cl)cnc4c3C2)CC1] |
| 153 | 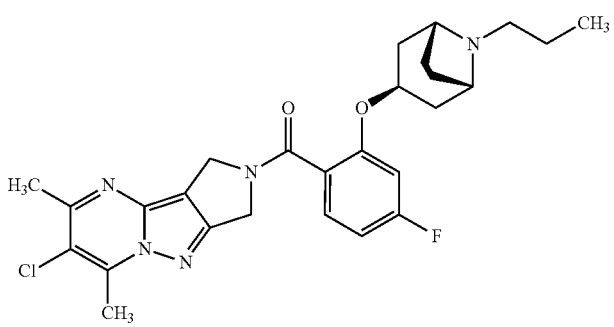 |
| 154 | 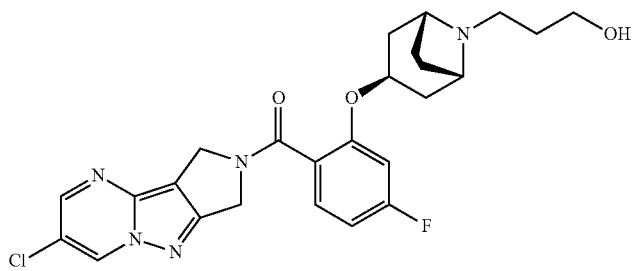 |

| Ex | Structure |
|---|---|
| 155 | 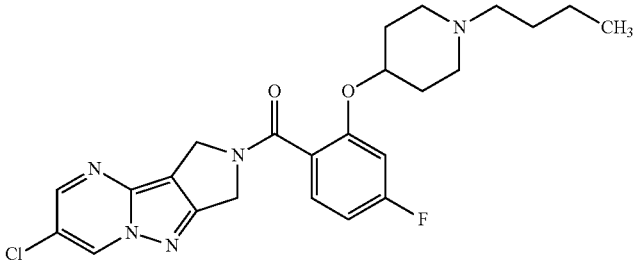 [SMILES: CCCCN1CCC(Oc2cc(F)ccc2C(=O)N2Cc3nn4cc(Cl)cnc4c3C2)CC1] |
| 156 | 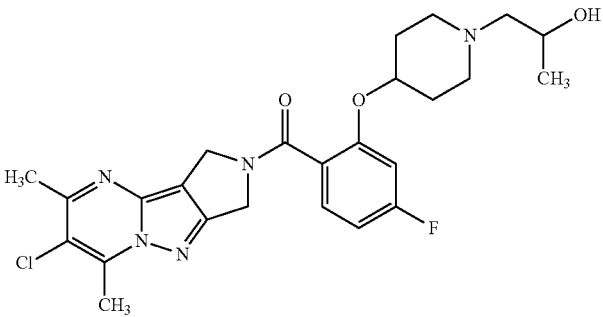 [SMILES: Cc1nc2c3c(nn2c(C)c1Cl)CN(C(=O)c1ccc(F)cc1OC1CCN(CC(C)O)CC1)C3] |
| 157a | 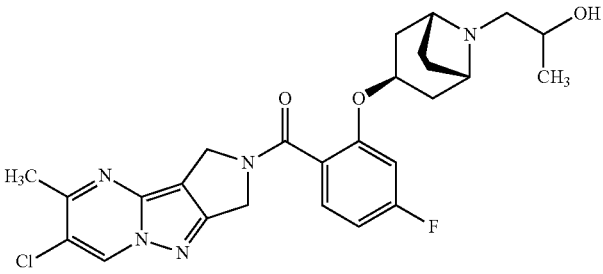 |
| 157b | 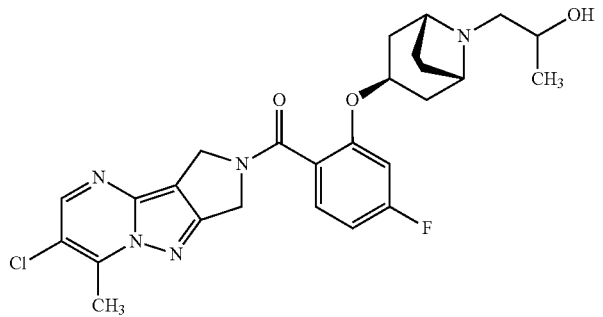 |
| 158 | 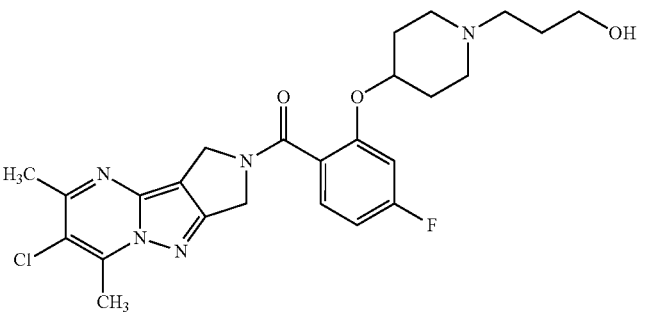 [SMILES: Cc1nc2c3c(nn2c(C)c1Cl)CN(C(=O)c1ccc(F)cc1OC1CCN(CCCO)CC1)C3] |

| Ex | Structure |
|---|---|
| 159a | 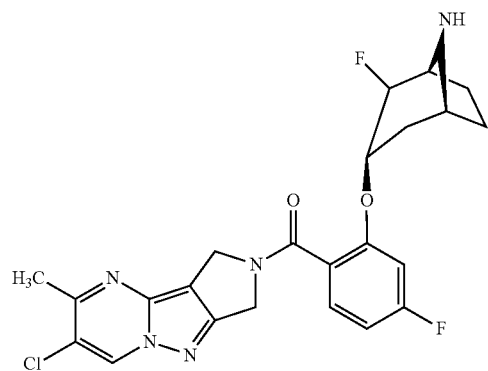 |
| 159b | 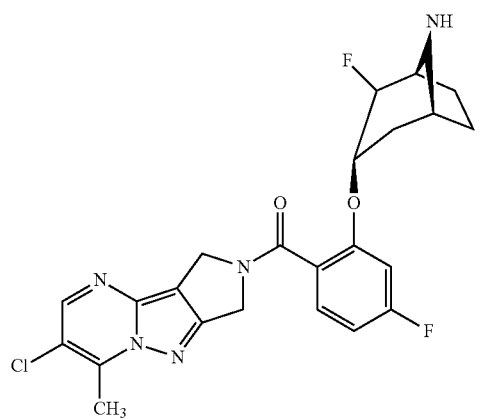 |
| 160 | 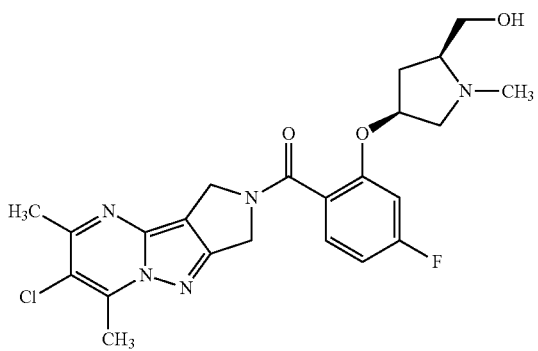 [SMILES: Cc1nc2c3c(nn2c(C)c1Cl)CN(C(=O)c1ccc(F)cc1O[C@H]1C[C@@H](CO)N(C)C1)C3] |
| 161 | 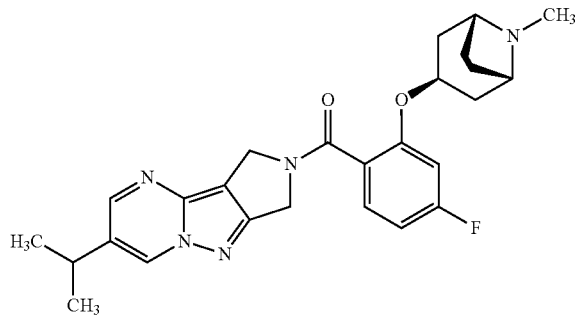 |

| Ex | Structure |
|---|---|
| 162 | 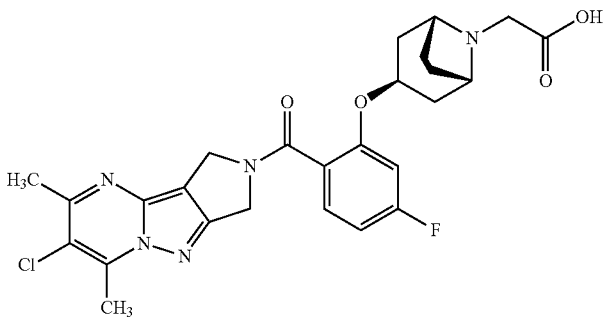 |
| 163 | 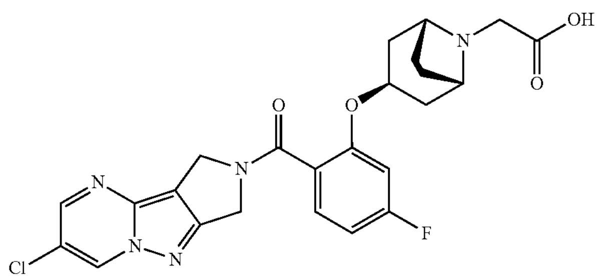 |
| 164 | 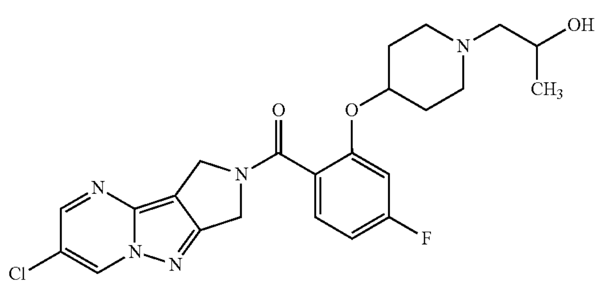 [SMILES: CC(O)CN1CCC(Oc2cc(F)ccc2C(=O)N2Cc3nn4cc(Cl)cnc4c3C2)CC1] |
| 165 | 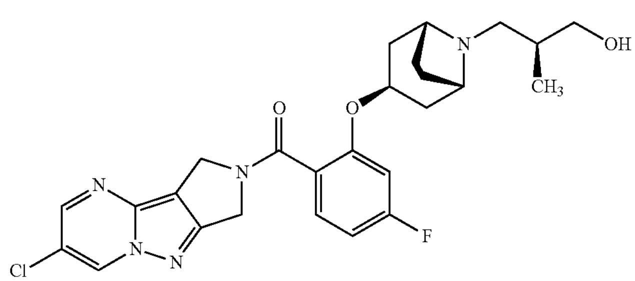 |
| 166 | 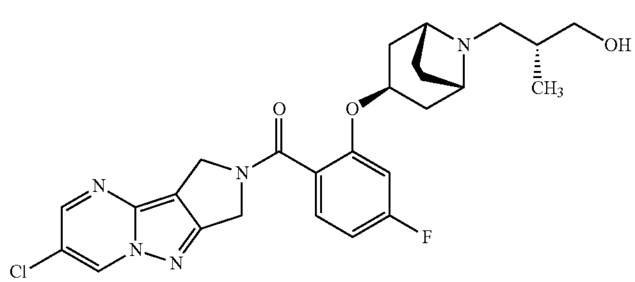 |

| Ex | Structure |
|---|---|
| 167 and | 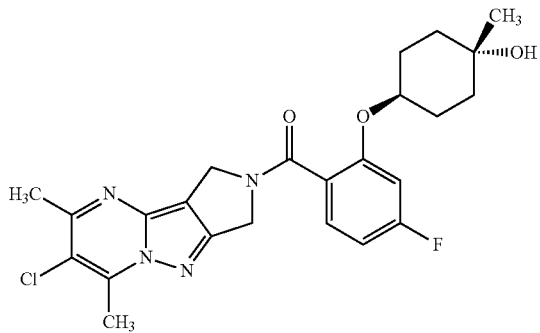 [SMILES: Cc1nc2c3c(nn2c(C)c1Cl)CN(C(=O)c1ccc(F)cc1O[C@H]1CC[C@](C)(O)CC1)C3] |
| 168 | 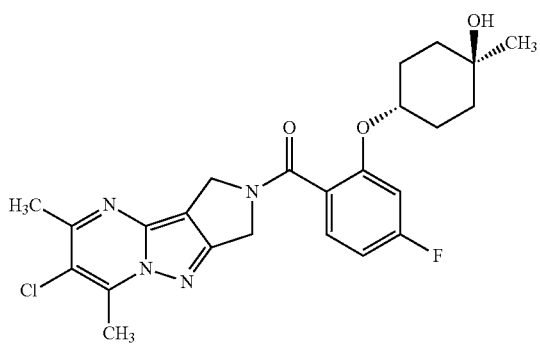 [SMILES: Cc1nc2c3c(nn2c(C)c1Cl)CN(C(=O)c1ccc(F)cc1O[C@H]1CC[C@](C)(O)CC1)C3] |
| 169 | 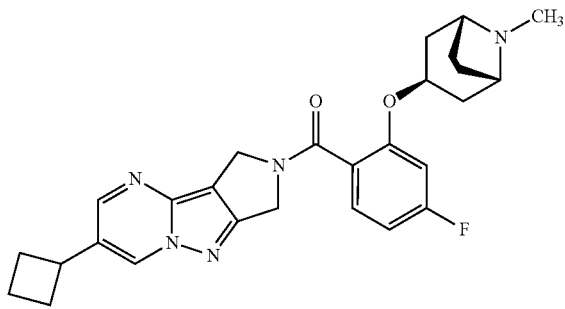 |
| 170 | 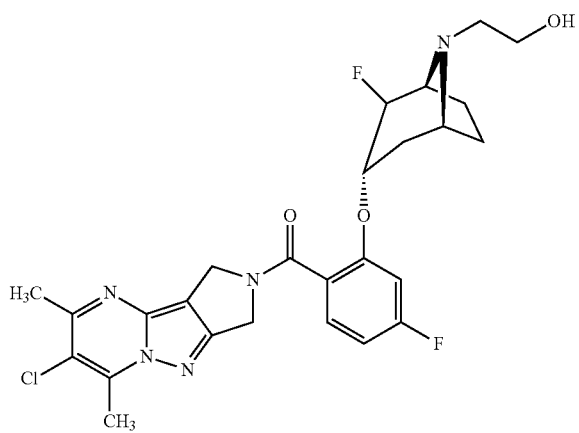 [SMILES: Cc1nc2c3c(nn2c(C)c1Cl)CN(C(=O)c1ccc(F)cc1O[C@H]1C[C@@H]2CC[C@@H](C1F)N2CCO)C3] |

| Ex | Structure |
|---|---|
| 171a | 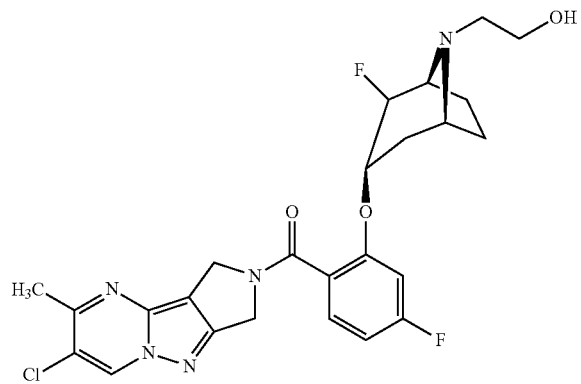 [SMILES: Cc1nc2c3c(nn2cc1Cl)CN(C(=O)c1ccc(F)cc1O[C@@H]1C[C@@H]2CC[C@@H](C1F)N2CCO)C3] |
| 171b | 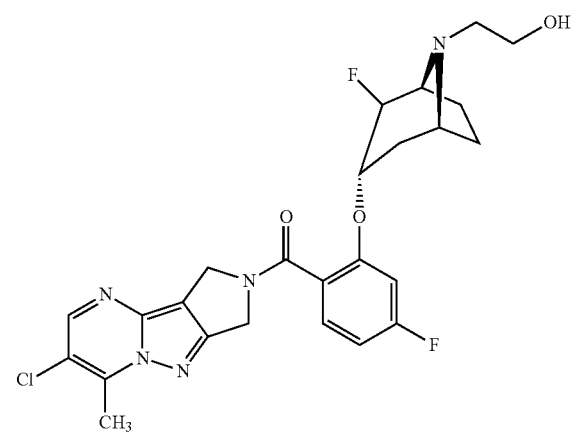 [SMILES: Cc1c(Cl)cnc2c3c(nn12)CN(C(=O)c1ccc(F)cc1O[C@H]1C[C@@H]2CC[C@@H](C1F)N2CCO)C3] |
| 172a | 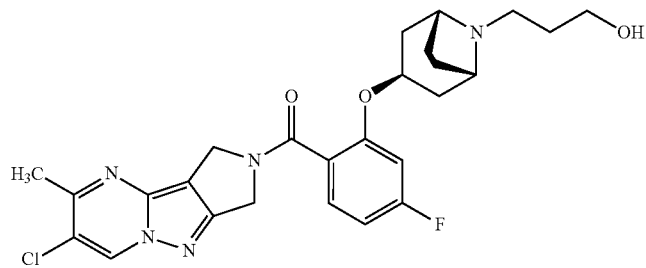 |
| 172b | 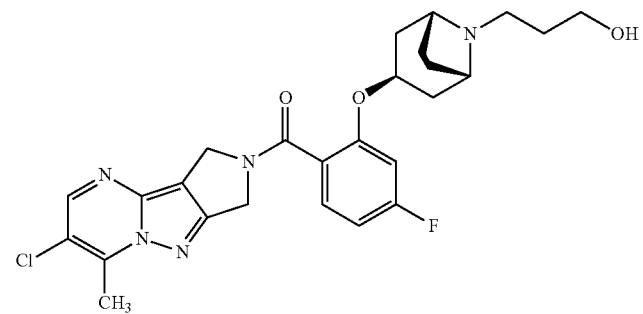 |

| Ex | Structure |
|---|---|
| 173 | 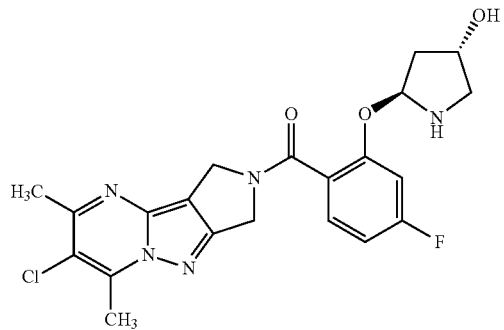 [SMILES: Cc1nc2c3c(nn2c(C)c1Cl)CN(C(=O)c1ccc(F)cc1O[C@H]1C[C@H](O)CN1)C3] |
| 174 | 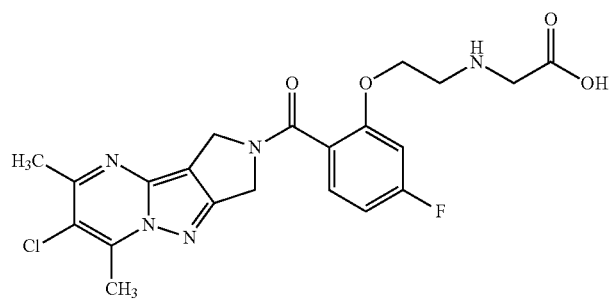 [SMILES: Cc1nc2c3c(nn2c(C)c1Cl)CN(C(=O)c1ccc(F)cc1OCCNCC(=O)O)C3] |
| 175 | 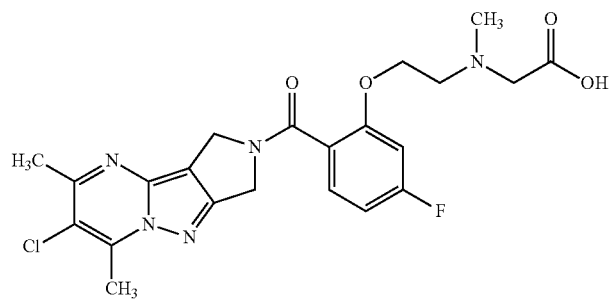 [SMILES: Cc1nc2c3c(nn2c(C)c1Cl)CN(C(=O)c1ccc(F)cc1OCCN(C)CC(=O)O)C3] |
| 176 | 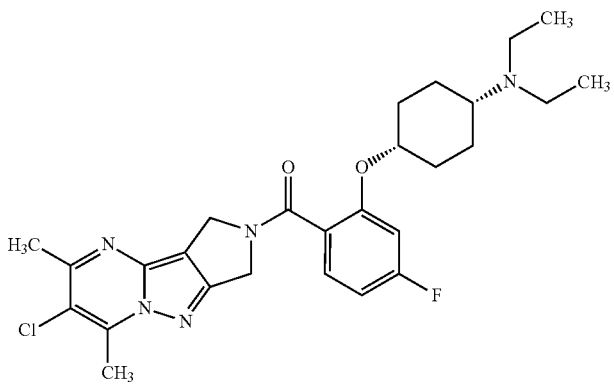 [SMILES: CCN(CC)[C@H]1CC[C@@H](Oc2cc(F)ccc2C(=O)N2Cc3nn4c(C)c(Cl)c(C)nc4c3C2)CC1] |

| Ex | Structure |
|---|---|
| 177 | 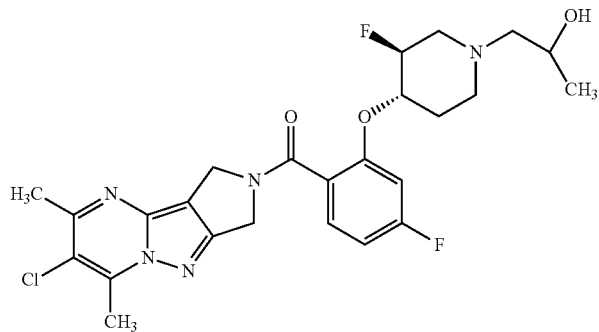 [SMILES: Cc1nc2c3c(nn2c(C)c1Cl)CN(C(=O)c1ccc(F)cc1O[C@H]1CCN(CC(C)O)C[C@@H]1F)C3] |
| 178 | 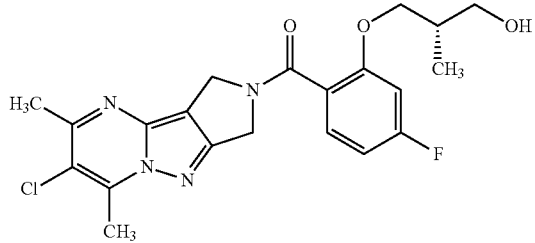 [SMILES: Cc1nc2c3c(nn2c(C)c1Cl)CN(C(=O)c1ccc(F)cc1OC[C@@H](C)CO)C3] |
| 179 | 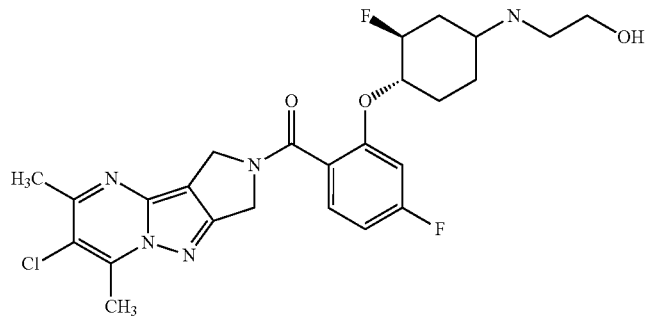 [SMILES: Cc1nc2c3c(nn2c(C)c1Cl)CN(C(=O)c1ccc(F)cc1O[C@H]1CCC(NCCO)C[C@@H]1F)C3] |
| 180 | 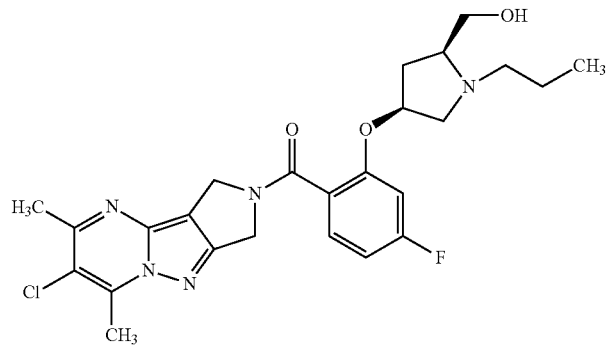 [SMILES: CCCN1C[C@@H](Oc2cc(F)ccc2C(=O)N2Cc3nn4c(C)c(Cl)c(C)nc4c3C2)C[C@H]1CO] |

-continued
| Ex | Structure |
|---|---|
| 181 | 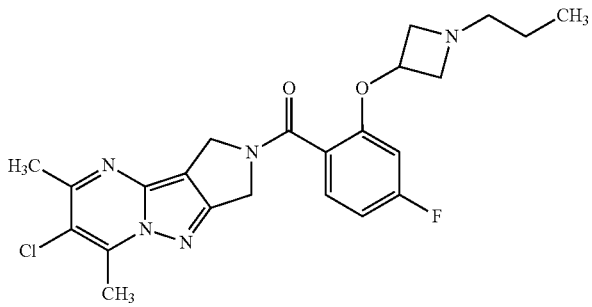 [SMILES: CCCN1CC(Oc2cc(F)ccc2C(=O)N2Cc3nn4c(C)c(Cl)c(C)nc4c3C2)C1] |
| 182 | 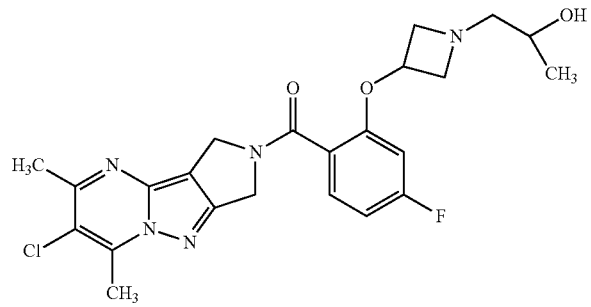 |
| 183 | 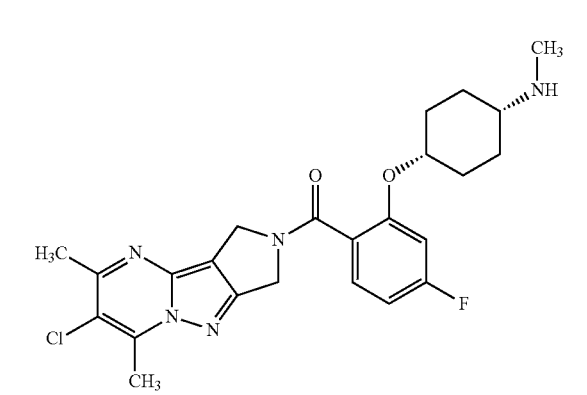 [SMILES: CN[C@H]1CC[C@@H](Oc2cc(F)ccc2C(=O)N2Cc3nn4c(C)c(Cl)c(C)nc4c3C2)CC1] |
| 184 | 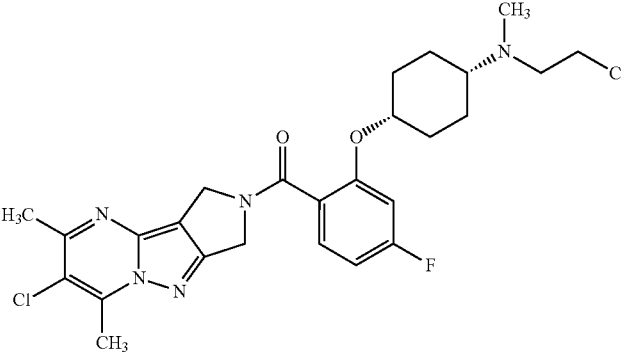 |

-continued
| Ex | Structure |
|---|---|
| 185 | 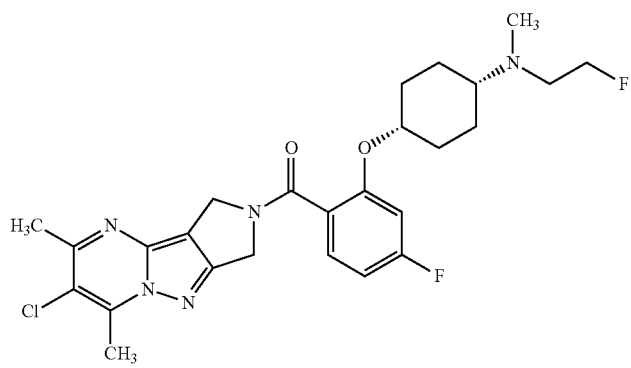 [SMILES: Cc1nc2c3c(nn2c(C)c1Cl)CN(C(=O)c1ccc(F)cc1O[C@H]1CC[C@@H](N(C)CCF)CC1)C3] |
| 186 | 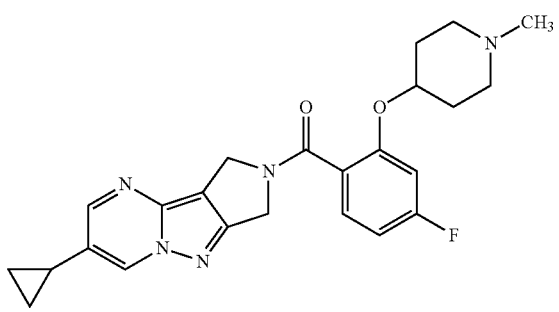 [SMILES: CN1CCC(Oc2cc(F)ccc2C(=O)N2Cc3nn4cc(C5CC5)cnc4c3C2)CC1] |
| 187 | 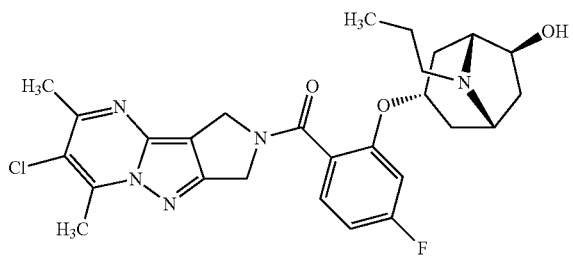 [SMILES: CCCN1[C@H]2C[C@H](Oc3cc(F)ccc3C(=O)N3Cc4nn5c(C)c(Cl)c(C)nc5c4C3)C[C@@H]1[C@@H](O)C2] |
| 188 | 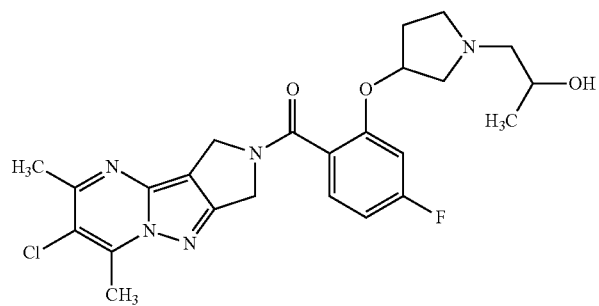 [SMILES: Cc1nc2c3c(nn2c(C)c1Cl)CN(C(=O)c1ccc(F)cc1OC1CCN(CC(C)O)C1)C3] |

-continued
| Ex | Structure |
|---|---|
| 189 | 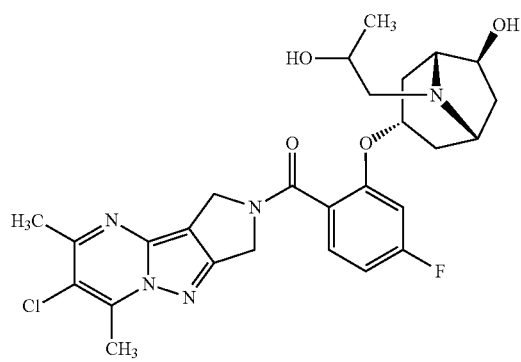 [SMILES: Cc1nc2c3c(nn2c(C)c1Cl)CN(C(=O)c1ccc(F)cc1O[C@H]1C[C@H]2C[C@H](O)[C@@H](C1)N2CC(C)O)C3] |
| 190 | 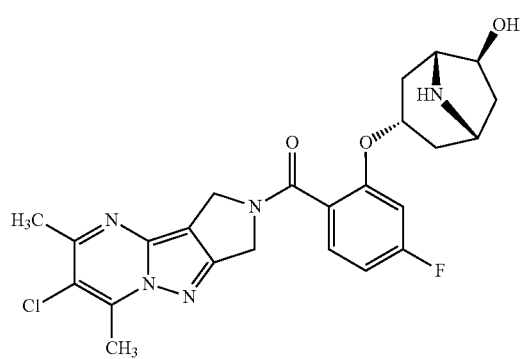 [SMILES: Cc1nc2c3c(nn2c(C)c1Cl)CN(C(=O)c1ccc(F)cc1O[C@H]1C[C@H]2C[C@H](O)[C@@H](C1)N2)C3] |
| 191 | 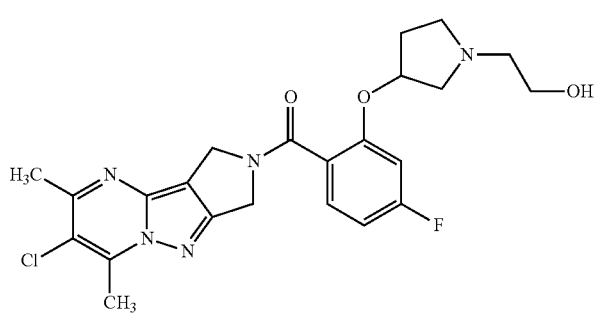 [SMILES: Cc1nc2c3c(nn2c(C)c1Cl)CN(C(=O)c1ccc(F)cc1OC1CCN(CCO)C1)C3] |
| 192 | 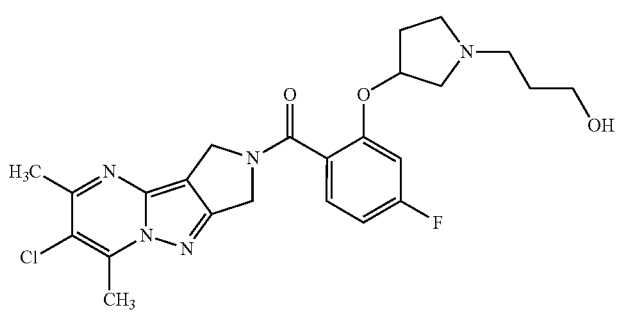 [SMILES: Cc1nc2c3c(nn2c(C)c1Cl)CN(C(=O)c1ccc(F)cc1OC1CCN(CCCO)C1)C3] |

| Ex | Structure |
|---|---|
| 193 | 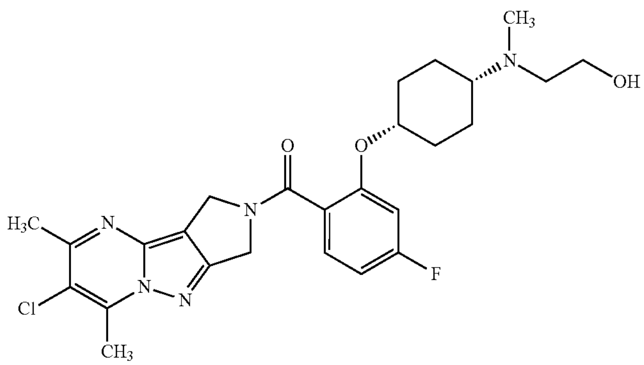 [SMILES: Cc1nc2c3c(nn2c(C)c1Cl)CN(C(=O)c1ccc(F)cc1O[C@H]1CC[C@@H](N(C)CCO)CC1)C3] |
| 194 | 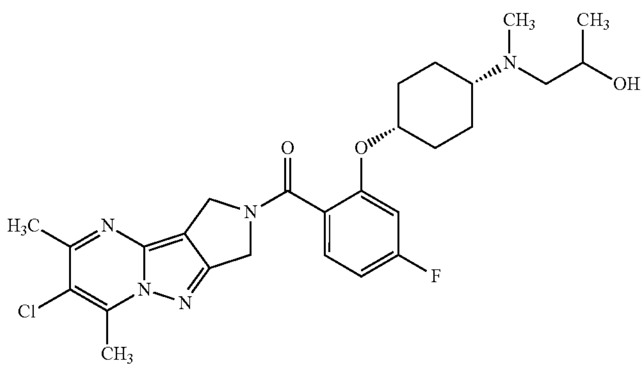 [SMILES: Cc1nc2c3c(nn2c(C)c1Cl)CN(C(=O)c1ccc(F)cc1O[C@H]1CC[C@@H](N(C)CC(C)O)CC1)C3] |
| 195 | 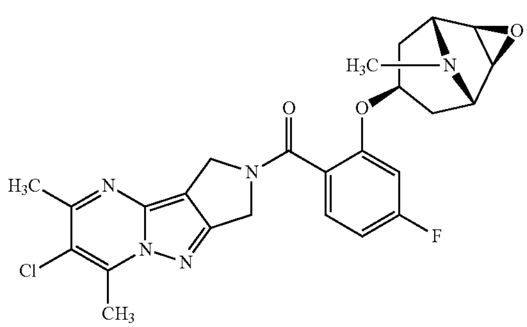 [SMILES: Cc1nc2c3c(nn2c(C)c1Cl)CN(C(=O)c1ccc(F)cc1O[C@H]1C[C@@H]2[C@H]4O[C@H]4[C@H](C1)N2C)C3] |
| 196a | 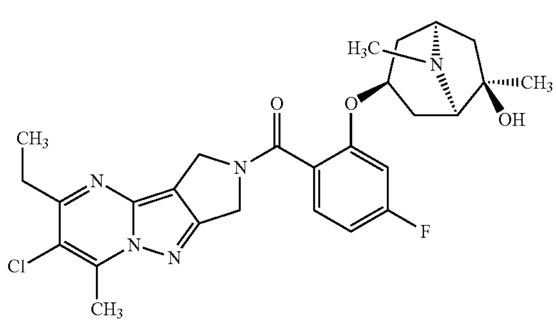 [SMILES: CCc1nc2c3c(nn2c(C)c1Cl)CN(C(=O)c1ccc(F)cc1O[C@H]1C[C@H]2C[C@@](C)(O)[C@@H](C1)N2C)C3] |

-continued
| Ex | Structure |
|---|---|
| 196b | 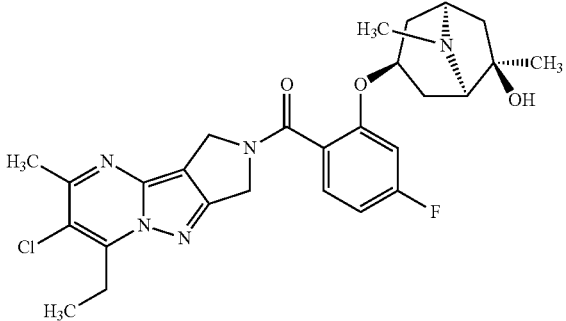 |
| 197 | 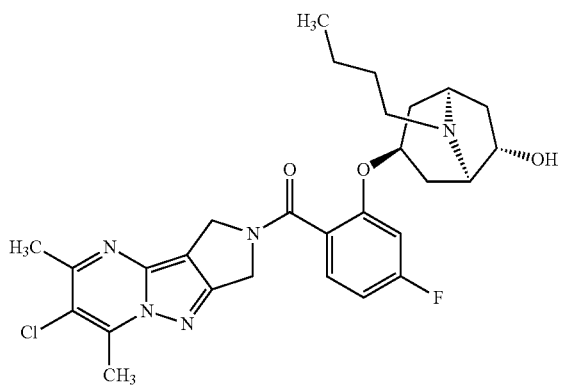 [SMILES: CCCCN1[C@H]2C[C@H](Oc3cc(F)ccc3C(=O)N3Cc4nn5c(C)c(Cl)c(C)nc5c4C3)C[C@@H]1[C@@H](O)C2] |
| 198 | 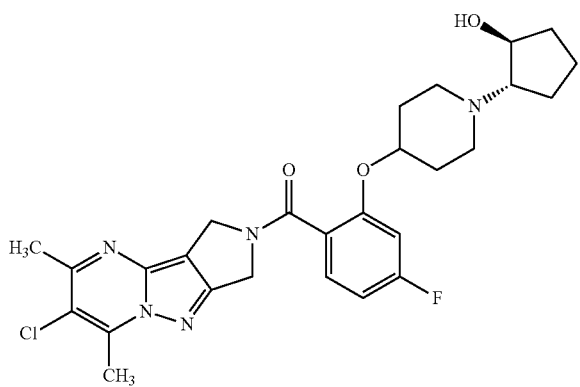 [SMILES: Cc1nc2c3c(nn2c(C)c1Cl)CN(C(=O)c1ccc(F)cc1OC1CCN([C@H]2CCC[C@@H]2O)CC1)C3] |
| 199 | 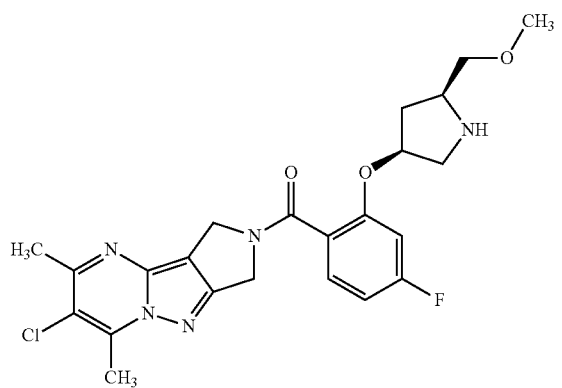 |

-continued
| Ex | Structure |
|---|---|
| 200 | 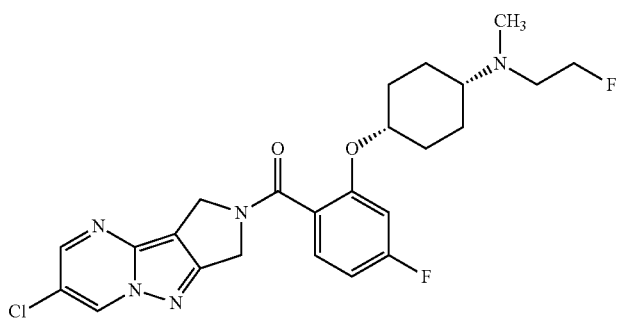 [SMILES: CN(CCF)[C@H]1CC[C@@H](Oc2cc(F)ccc2C(=O)N2Cc3nn4cc(Cl)cnc4c3C2)CC1] |
| 201 | 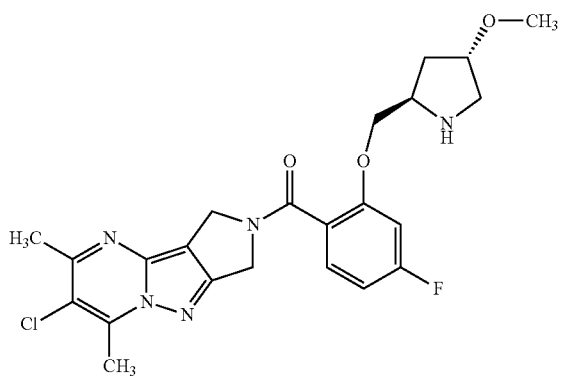 |
| 202 | 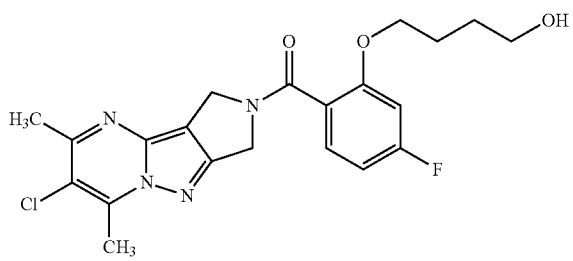 [SMILES: Cc1nc2c3c(nn2c(C)c1Cl)CN(C(=O)c1ccc(F)cc1OCCCCO)C3] |
| 203 | 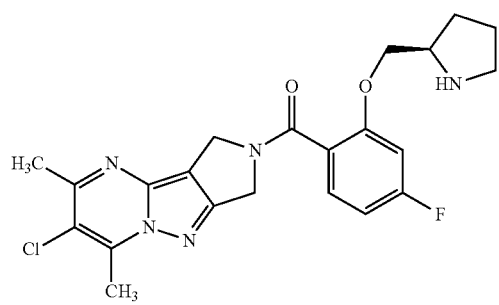 [SMILES: Cc1nc2c3c(nn2c(C)c1Cl)CN(C(=O)c1ccc(F)cc1OC[C@H]1CCCN1)C3] |
| 204 | 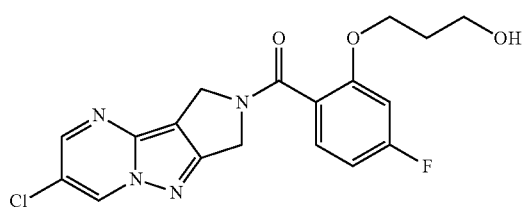 [SMILES: O=C(c1ccc(F)cc1OCCCO)N1Cc2nn3cc(Cl)cnc3c2C1] |

| Ex | Structure |
|---|---|
| 205 | 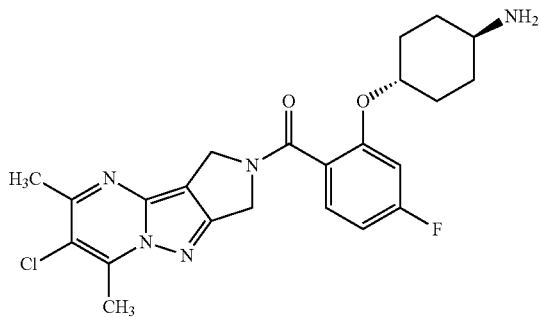 [SMILES: Cc1nc2c3c(nn2c(C)c1Cl)CN(C(=O)c1ccc(F)cc1O[C@H]1CC[C@H](N)CC1)C3] |
| 206 | 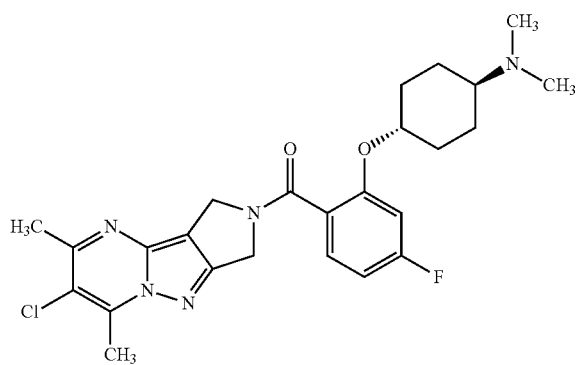 |
| 207 | 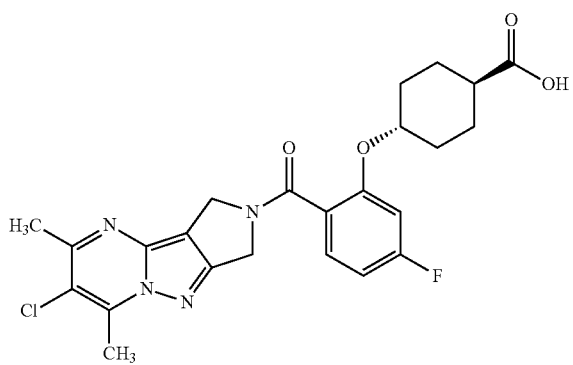 [SMILES: Cc1nc2c3c(nn2c(C)c1Cl)CN(C(=O)c1ccc(F)cc1O[C@H]1CC[C@H](C(=O)O)CC1)C3] |
| 208 | 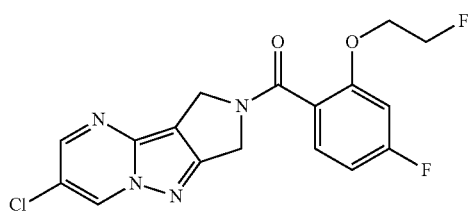 [SMILES: O=C(c1ccc(F)cc1OCCF)N1Cc2nn3cc(Cl)cnc3c2C1] |
| 209 | 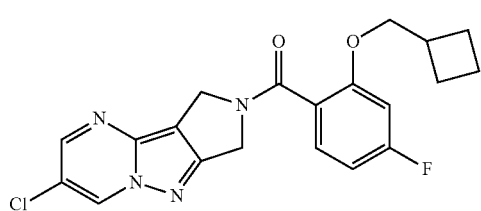 [SMILES: O=C(c1ccc(F)cc1OCC1CCC1)N1Cc2nn3cc(Cl)cnc3c2C1] |

| Ex | Structure |
|---|---|
| 210 | 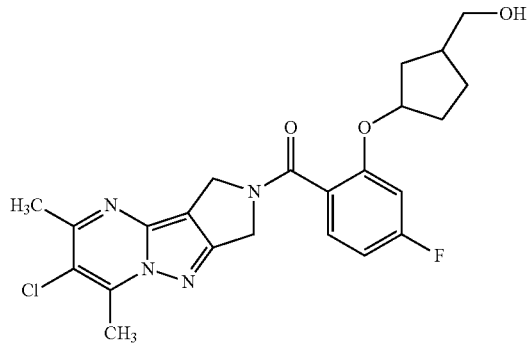 [SMILES: Cc1nc2c3c(nn2c(C)c1Cl)CN(C(=O)c1ccc(F)cc1OC1CCC(CO)C1)C3] |
| 211 | 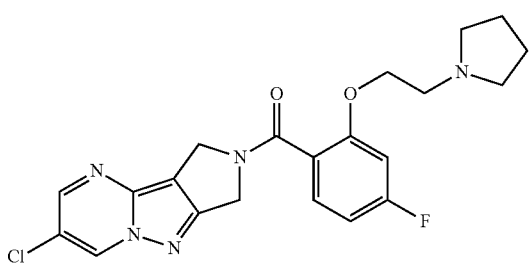 [SMILES: O=C(c1ccc(F)cc1OCCN1CCCC1)N1Cc2nn3cc(Cl)cnc3c2C1] |
| 212 | 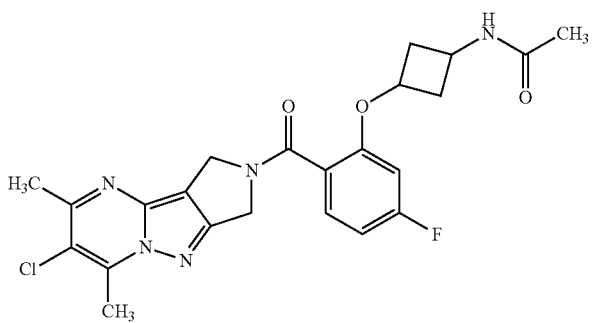 |
| 213 | 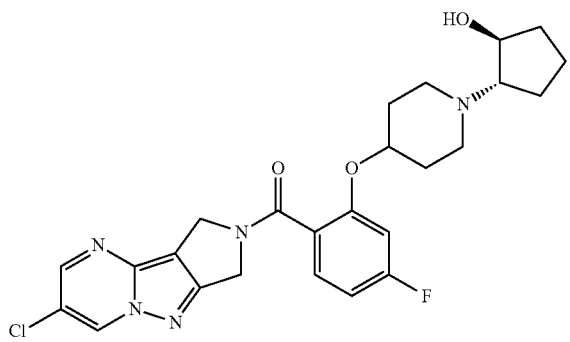 [SMILES: O=C(c1ccc(F)cc1OC1CCN([C@H]2CCC[C@@H]2O)CC1)N1Cc2nn3cc(Cl)cnc3c2C1] |

-continued
| Ex | Structure |
|---|---|
| 214 | 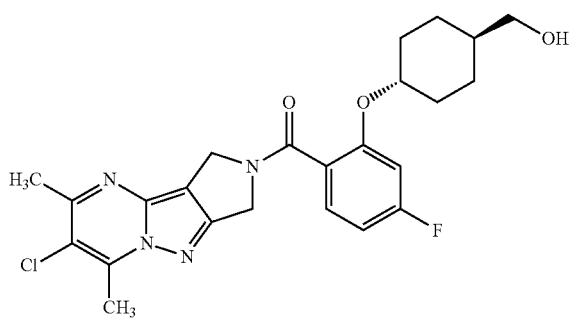 [SMILES: Cc1nc2c3c(nn2c(C)c1Cl)CN(C(=O)c1ccc(F)cc1O[C@H]1CC[C@H](CO)CC1)C3] |
| 215 | 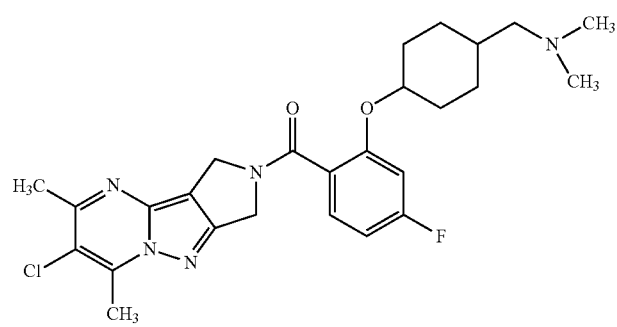 [SMILES: Cc1nc2c3c(nn2c(C)c1Cl)CN(C(=O)c1ccc(F)cc1OC1CCC(CN(C)C)CC1)C3] |
| 216 | 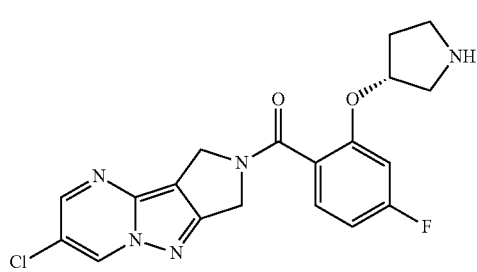 [SMILES: O=C(c1ccc(F)cc1O[C@@H]1CCNC1)N1Cc2nn3cc(Cl)cnc3c2C1] |
| 217 | 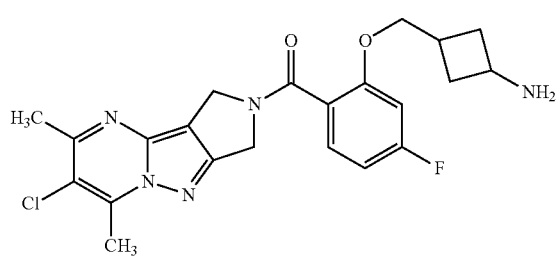 [SMILES: Cc1nc2c3c(nn2c(C)c1Cl)CN(C(=O)c1ccc(F)cc1OCC1CC(N)C1)C3] |
| 218 | 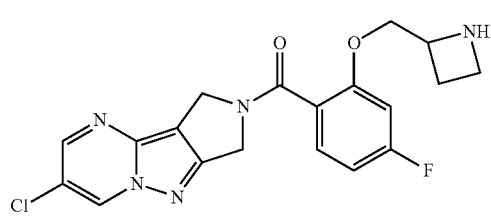 [SMILES: O=C(c1ccc(F)cc1OCC1CCN1)N1Cc2nn3cc(Cl)cnc3c2C1] |

| Ex | Structure |
|---|---|
| 219 | 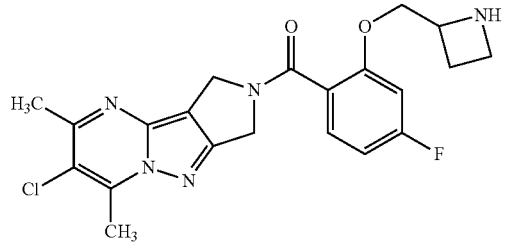 |
| 220 | 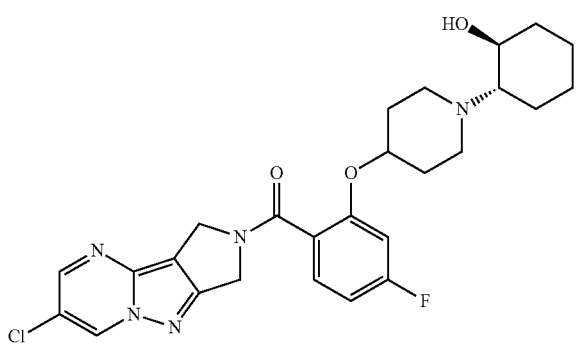 [SMILES: O=C(c1ccc(F)cc1OC1CCN([C@H]2CCCC[C@@H]2O)CC1)N1Cc2nn3cc(Cl)cnc3c2C1] |
| 221 | 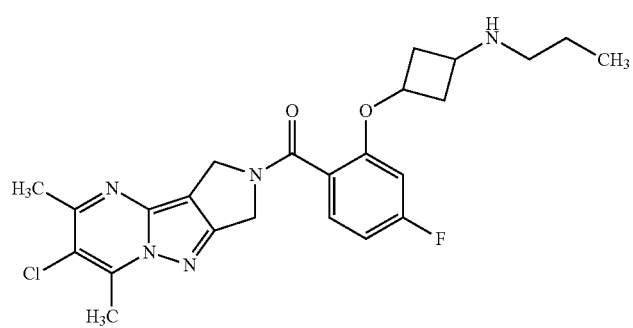 [SMILES: CCCNC1CC(Oc2cc(F)ccc2C(=O)N2Cc3nn4c(C)c(Cl)c(C)nc4c3C2)C1] |
| 222 and | 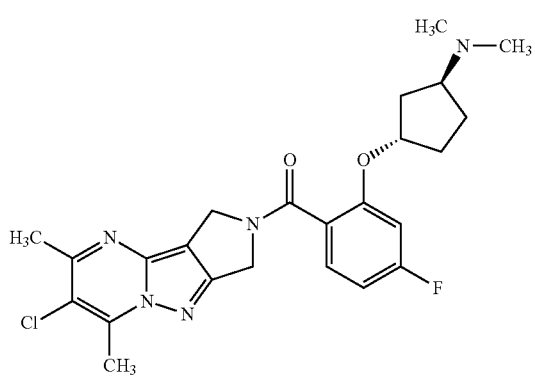 |

| Ex | Structure |
|---|---|
| 223 | 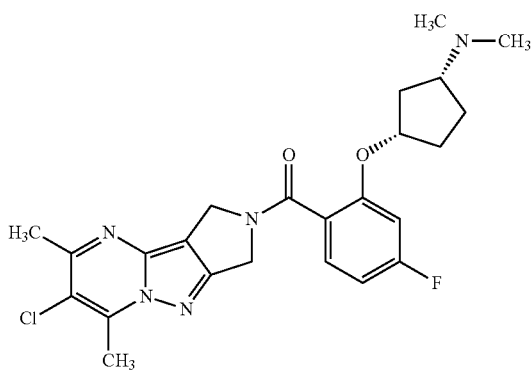 |
| 224 | 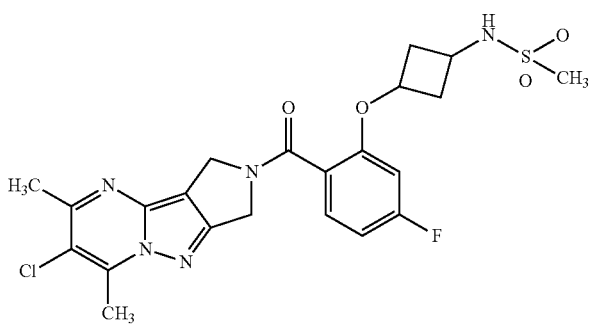 |
| 225 and | 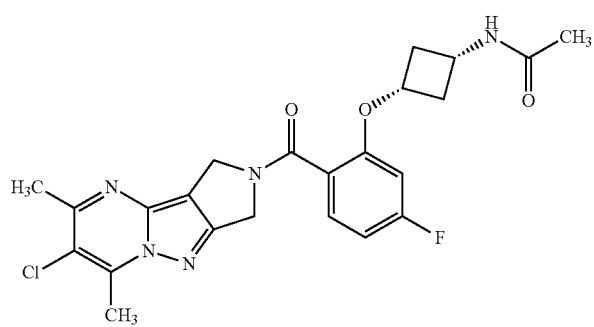 [SMILES: CC(=O)N[C@H]1C[C@@H](Oc2cc(F)ccc2C(=O)N2Cc3nn4c(C)c(Cl)c(C)nc4c3C2)C1] |
| 226 | 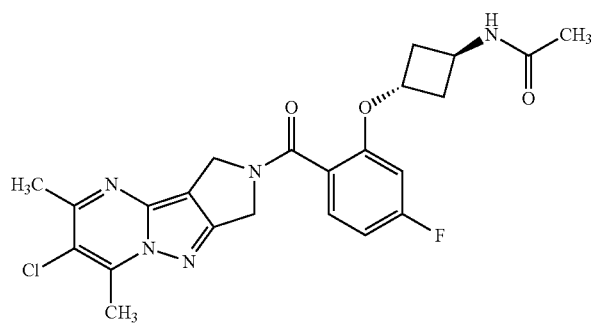 [SMILES: CC(=O)N[C@H]1C[C@H](Oc2cc(F)ccc2C(=O)N2Cc3nn4c(C)c(Cl)c(C)nc4c3C2)C1] |

| Ex | Structure |
|---|---|
| 227 | 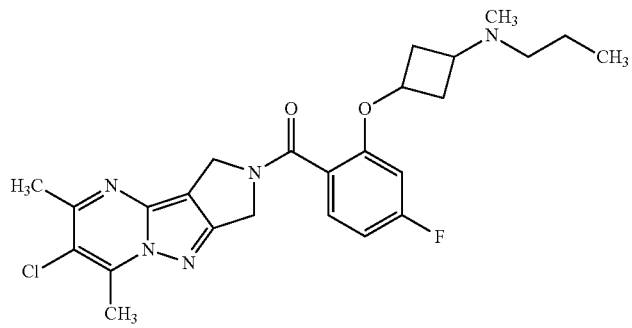 |
| 228 | 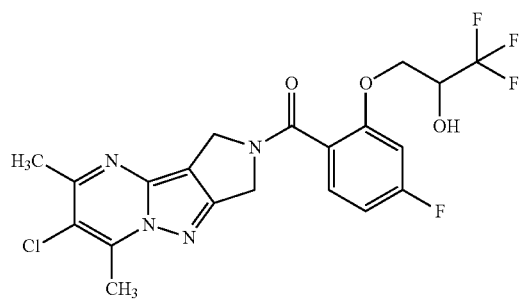 [SMILES: Cc1nc2c3c(nn2c(C)c1Cl)CN(C(=O)c1ccc(F)cc1OCC(O)C(F)(F)F)C3] |
| 229 and | 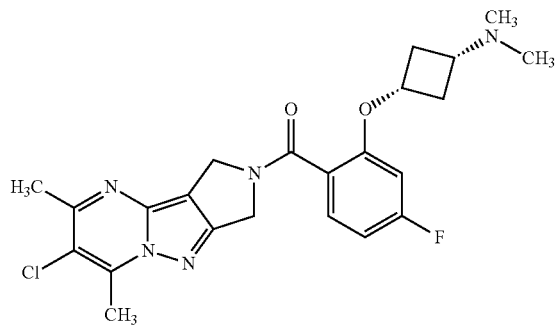 |
| 230 | 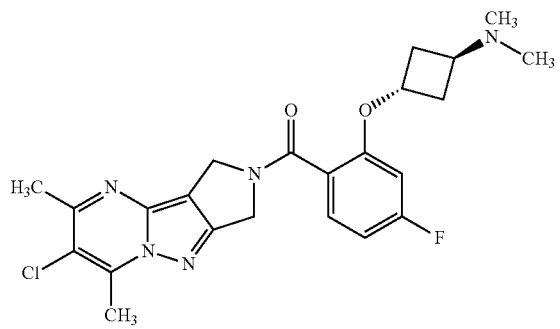 |

| Ex | Structure |
|---|---|
| 231 | 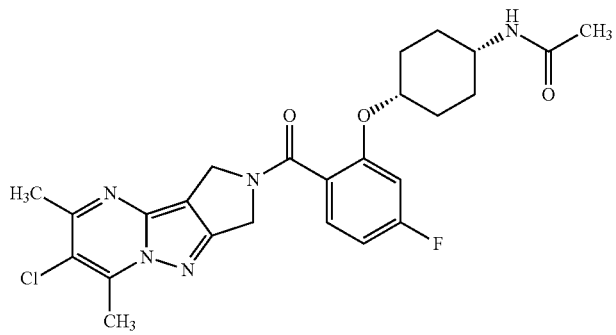 [SMILES: CC(=O)N[C@H]1CC[C@@H](Oc2cc(F)ccc2C(=O)N2Cc3nn4c(C)c(Cl)c(C)nc4c3C2)CC1] |
| 232a | 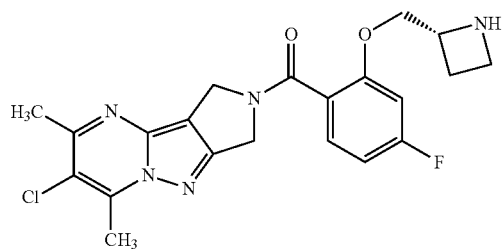 [SMILES: Cc1nc2c3c(nn2c(C)c1Cl)CN(C(=O)c1ccc(F)cc1OC[C@H]1CCN1)C3] |
| 232b | 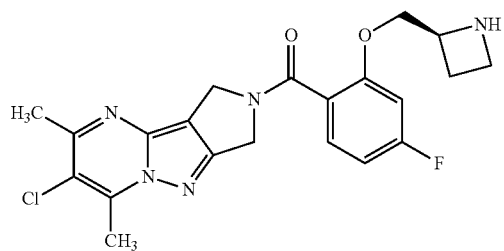 [SMILES: Cc1nc2c3c(nn2c(C)c1Cl)CN(C(=O)c1ccc(F)cc1OC[C@@H]1CCN1)C3] |
| 233 | 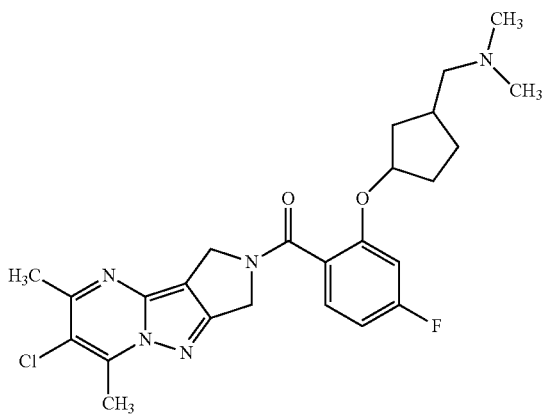 [SMILES: Cc1nc2c3c(nn2c(C)c1Cl)CN(C(=O)c1ccc(F)cc1OC1CCC(CN(C)C)C1)C3] |

| Ex | Structure |
|---|---|
| 234 | 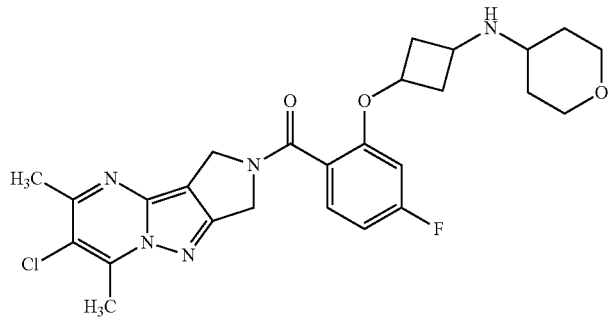 [SMILES: Cc1nc2c3c(nn2c(C)c1Cl)CN(C(=O)c1ccc(F)cc1OC1CC(NC2CCOCC2)C1)C3] |
| 235 | 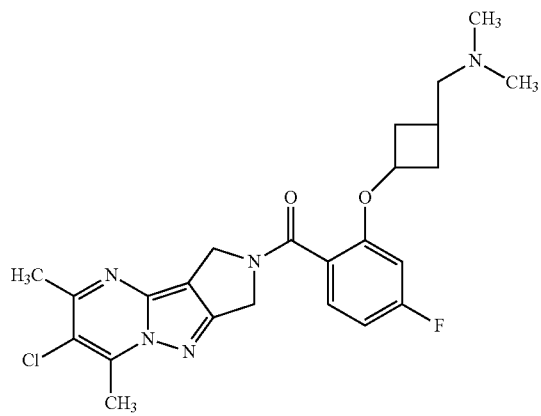 [SMILES: Cc1nc2c3c(nn2c(C)c1Cl)CN(C(=O)c1ccc(F)cc1OC1CC(CN(C)C)C1)C3] |
| 236 | 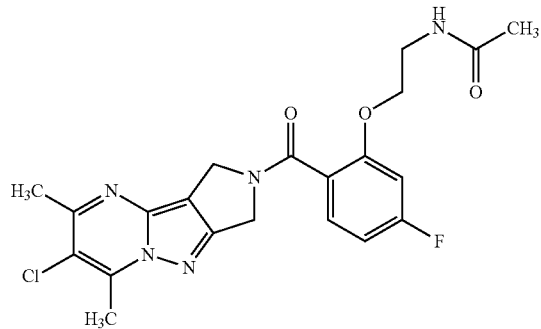 [SMILES: CC(=O)NCCOc1cc(F)ccc1C(=O)N1Cc2nn3c(C)c(Cl)c(C)nc3c2C1] |
| 237 | 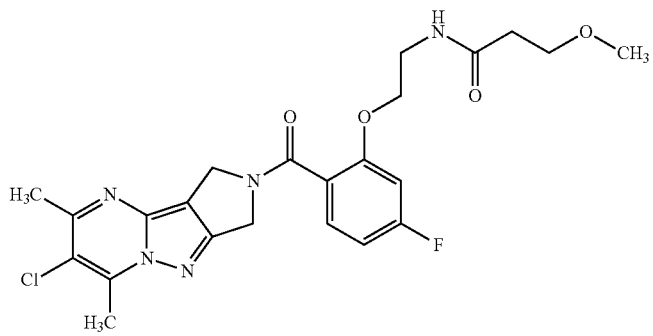 [SMILES: COCCC(=O)NCCOc1cc(F)ccc1C(=O)N1Cc2nn3c(C)c(Cl)c(C)nc3c2C1] |

| Ex | Structure |
|---|---|
| 238 | 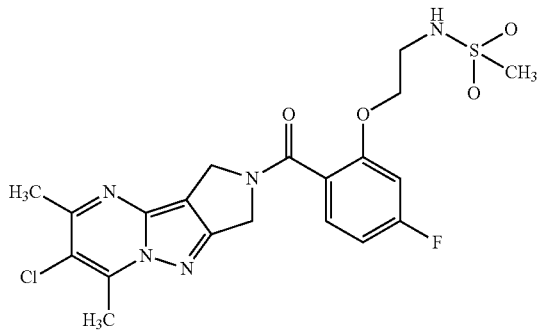 [SMILES: Cc1nc2c3c(nn2c(C)c1Cl)CN(C(=O)c1ccc(F)cc1OCCNS(C)(O)O)C3] |
| 239 | 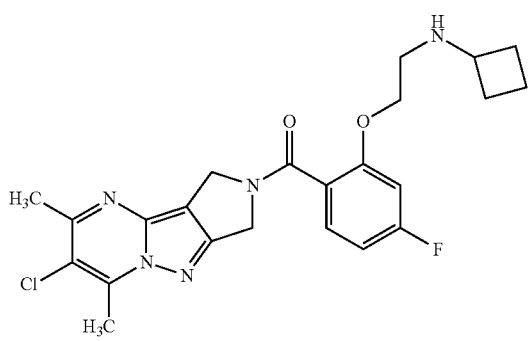 [SMILES: Cc1nc2c3c(nn2c(C)c1Cl)CN(C(=O)c1ccc(F)cc1OCCNC1CCC1)C3] |
| 240 | 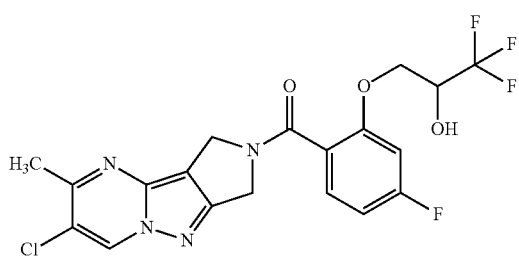 [SMILES: Cc1nc2c3c(nn2cc1Cl)CN(C(=O)c1ccc(F)cc1OCC(O)C(F)(F)F)C3] |
| 241 | 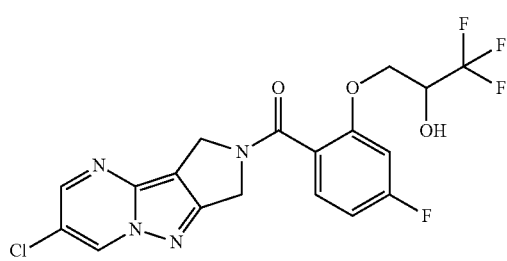 [SMILES: O=C(c1ccc(F)cc1OCC(O)C(F)(F)F)N1Cc2nn3cc(Cl)cnc3c2C1] |
| 242 and | 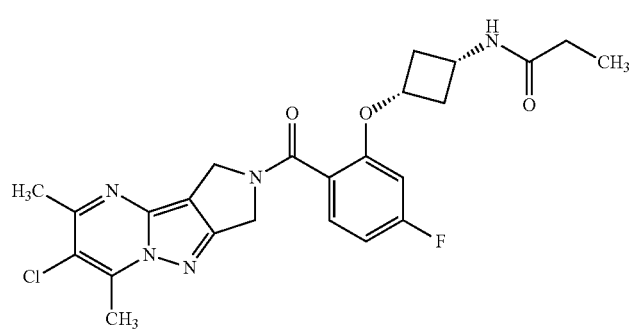 [SMILES: CCC(=O)N[C@H]1C[C@@H](Oc2cc(F)ccc2C(=O)N2Cc3nn4c(C)c(Cl)c(C)nc4c3C2)C1] |

| Ex | Structure |
|---|---|
| 243 | 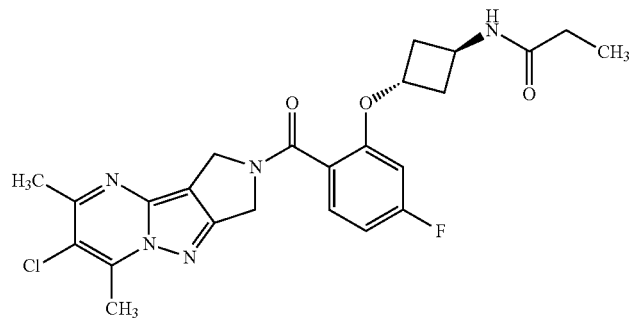 [SMILES: CCC(=O)N[C@H]1C[C@H](Oc2cc(F)ccc2C(=O)N2Cc3nn4c(C)c(Cl)c(C)nc4c3C2)C1] |
| 244 | 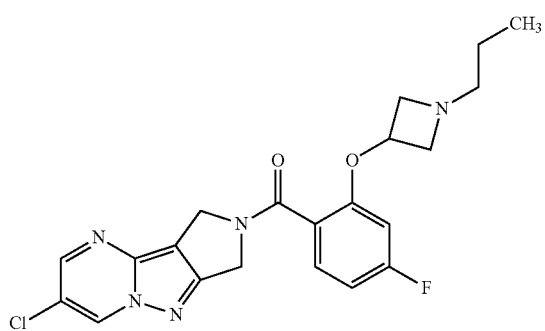 [SMILES: CCCN1CC(Oc2cc(F)ccc2C(=O)N2Cc3nn4cc(Cl)cnc4c3C2)C1] |
| 245 | 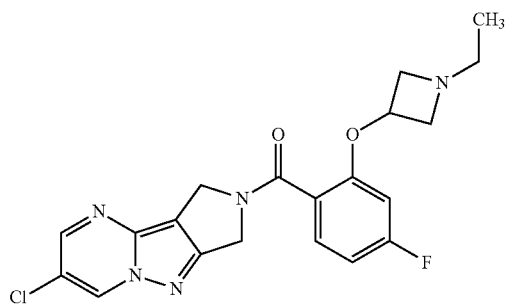 [SMILES: CCN1CC(Oc2cc(F)ccc2C(=O)N2Cc3nn4cc(Cl)cnc4c3C2)C1] |
| 246 | 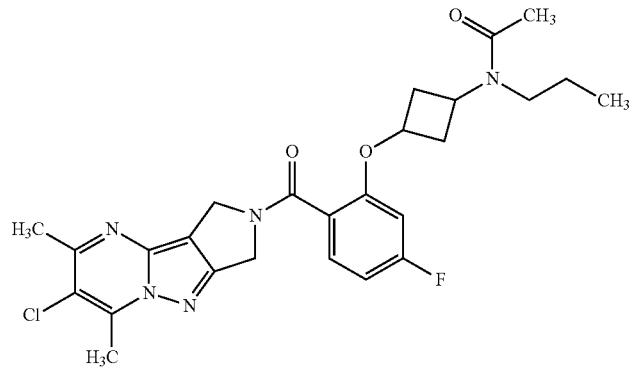 [SMILES: CCCN(C(C)=O)C1CC(Oc2cc(F)ccc2C(=O)N2Cc3nn4c(C)c(Cl)c(C)nc4c3C2)C1] |

| Ex | Structure |
|---|---|
| 247a | 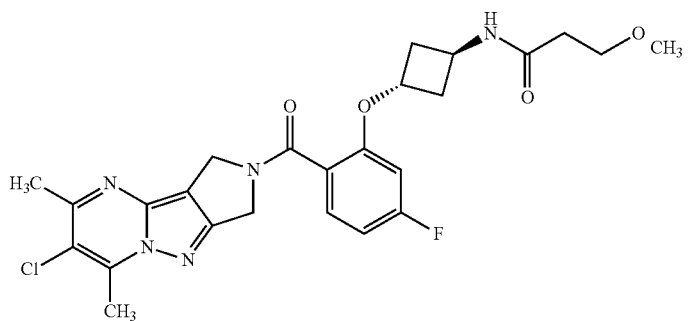 |
| 247b | 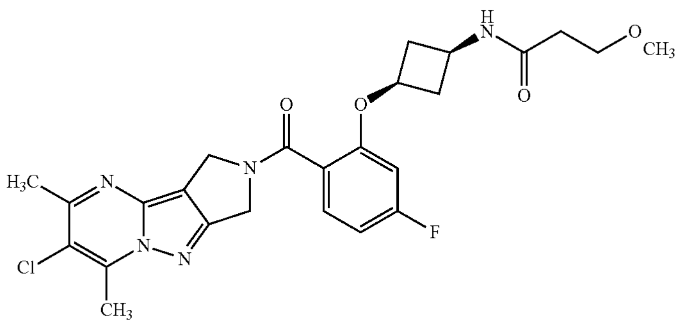 |
| 248a | 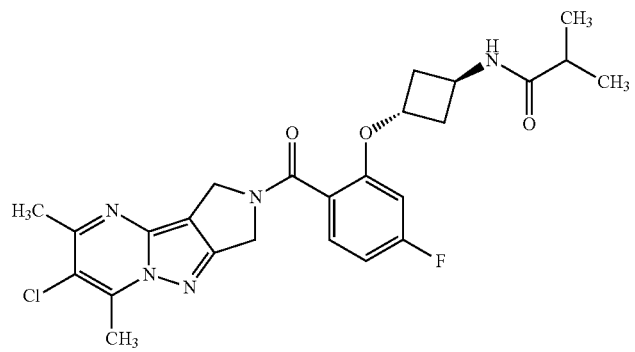 [SMILES: Cc1nc2c3c(nn2c(C)c1Cl)CN(C(=O)c1ccc(F)cc1O[C@H]1C[C@H](NC(=O)C(C)C)C1)C3] |
| 248b | 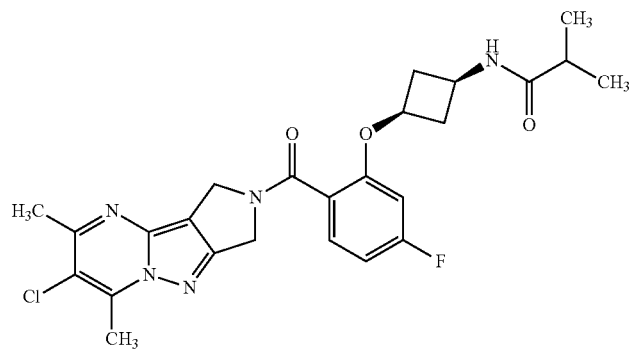 [SMILES: Cc1nc2c3c(nn2c(C)c1Cl)CN(C(=O)c1ccc(F)cc1O[C@H]1C[C@@H](NC(=O)C(C)C)C1)C3] |

| Ex | Structure |
|---|---|
| 249a | 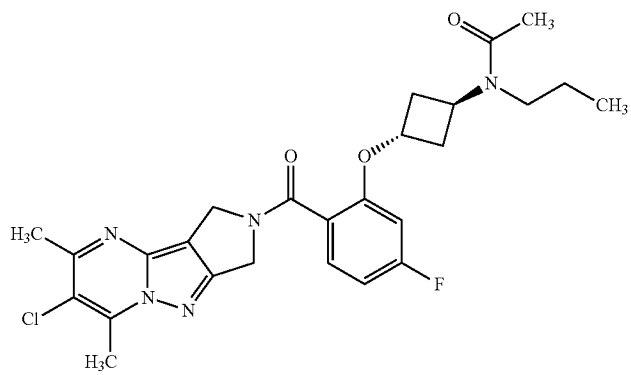 [SMILES: CCCN(C(C)=O)[C@H]1C[C@H](Oc2cc(F)ccc2C(=O)N2Cc3nn4c(C)c(Cl)c(C)nc4c3C2)C1] |
| 249b | 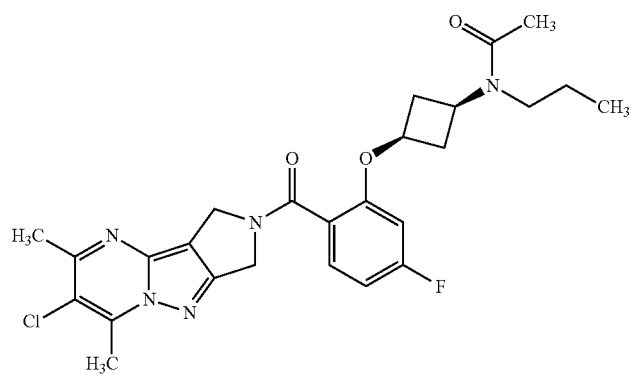 [SMILES: CCCN(C(C)=O)[C@H]1C[C@@H](Oc2cc(F)ccc2C(=O)N2Cc3nn4c(C)c(Cl)c(C)nc4c3C2)C1] |
| 250 | 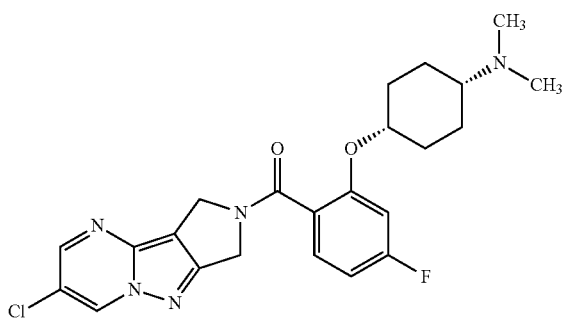 [SMILES: CN(C)[C@H]1CC[C@@H](Oc2cc(F)ccc2C(=O)N2Cc3nn4cc(Cl)cnc4c3C2)CC1] |
| 251 | 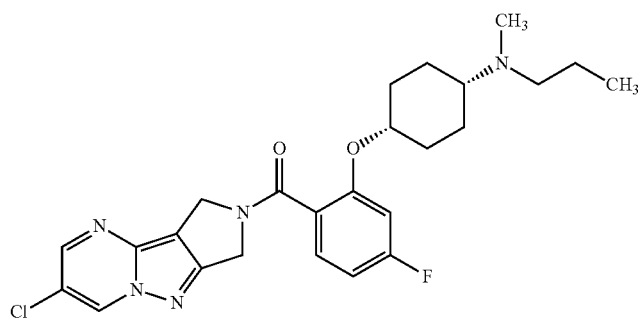 [SMILES: CCCN(C)[C@H]1CC[C@@H](Oc2cc(F)ccc2C(=O)N2Cc3nn4cc(Cl)cnc4c3C2)CC1] |

| Ex | Structure |
|---|---|
| 252 and | 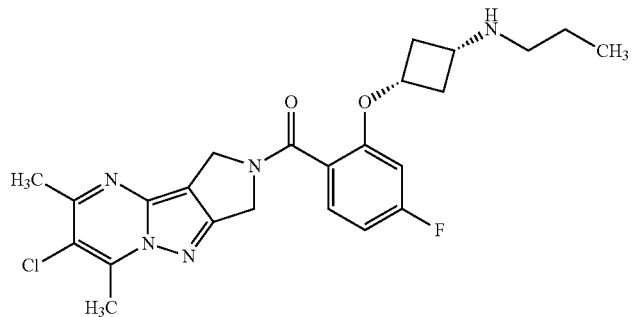 |
| 253 | 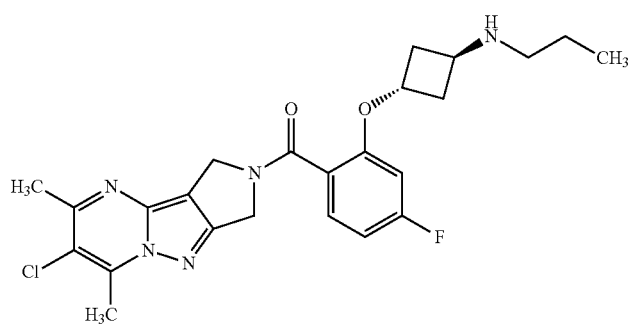 [SMILES: CCCN[C@H]1C[C@H](Oc2cc(F)ccc2C(=O)N2Cc3nn4c(C)c(Cl)c(C)nc4c3C2)C1] |
| 254 | 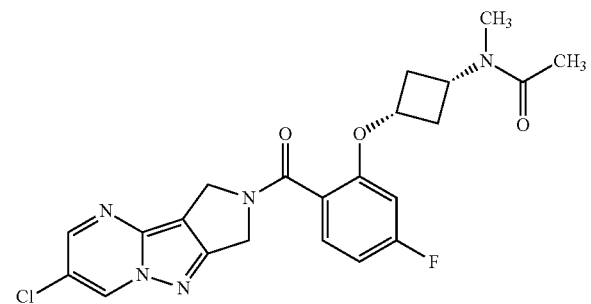 [SMILES: CC(=O)N(C)[C@H]1C[C@@H](Oc2cc(F)ccc2C(=O)N2Cc3nn4cc(Cl)cnc4c3C2)C1] |
| 255 | 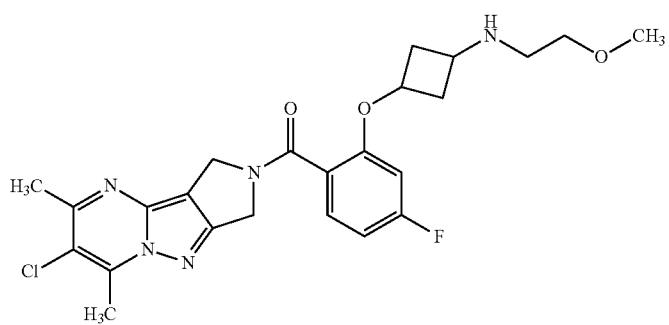 [SMILES: COCCNC1CC(Oc2cc(F)ccc2C(=O)N2Cc3nn4c(C)c(Cl)c(C)nc4c3C2)C1] |

| Ex | Structure |
|---|---|
| 256 | 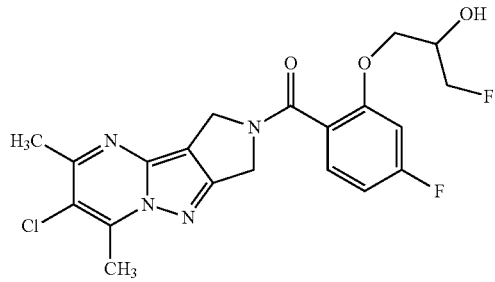 [SMILES: Cc1nc2c3c(nn2c(C)c1Cl)CN(C(=O)c1ccc(F)cc1OCC(O)CF)C3] |
| 257 | 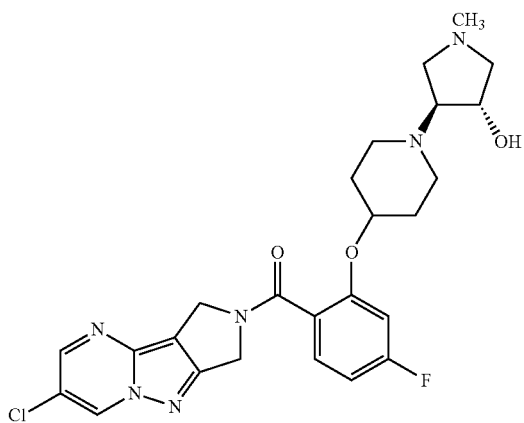 |
| 258 | 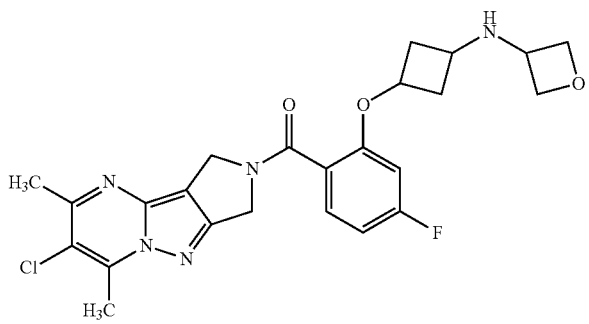 [SMILES: Cc1nc2c3c(nn2c(C)c1Cl)CN(C(=O)c1ccc(F)cc1OC1CC(NC2COC2)C1)C3] |
| 259 | 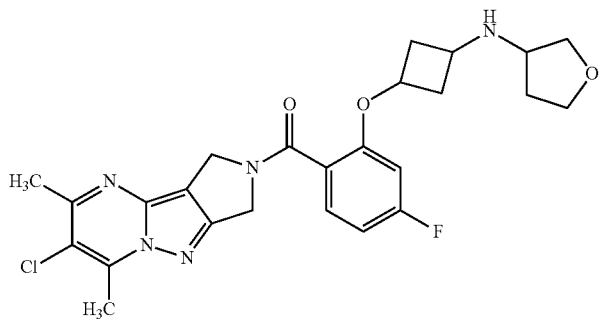 [SMILES: Cc1nc2c3c(nn2c(C)c1Cl)CN(C(=O)c1ccc(F)cc1OC1CC(NC2CCOC2)C1)C3] |

| Ex | Structure |
|---|---|
| 260 | 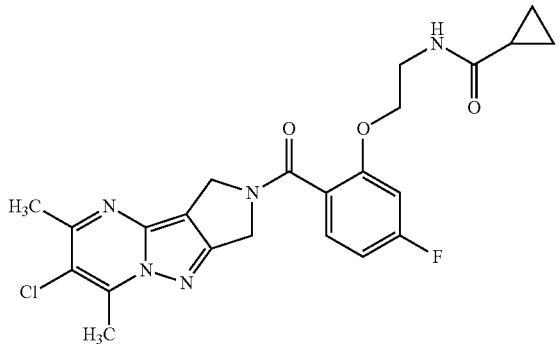 [SMILES: Cc1nc2c3c(nn2c(C)c1Cl)CN(C(=O)c1ccc(F)cc1OCCNC(=O)C1CC1)C3] |
| 261 | 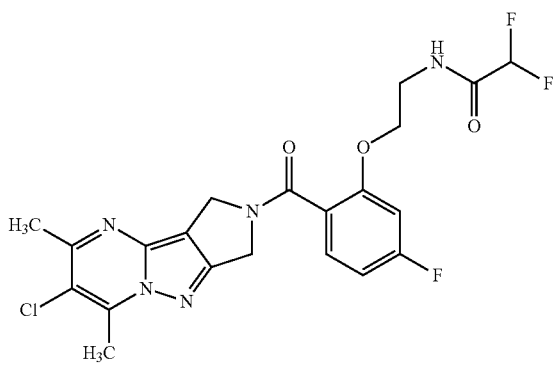 [SMILES: Cc1nc2c3c(nn2c(C)c1Cl)CN(C(=O)c1ccc(F)cc1OCCNC(=O)C(F)F)C3] |
| 262 and | 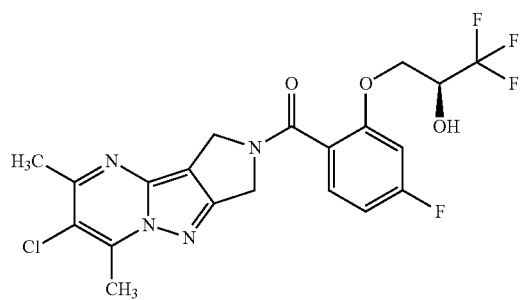 [SMILES: Cc1nc2c3c(nn2c(C)c1Cl)CN(C(=O)c1ccc(F)cc1OC[C@H](O)C(F)(F)F)C3] |
| 263 | 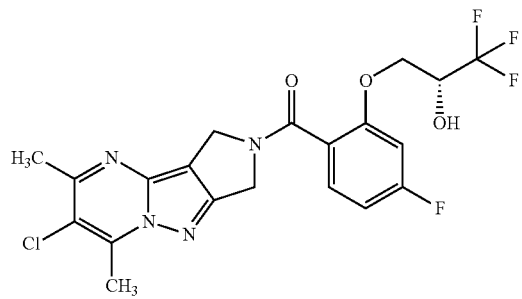 |

| Ex | Structure |
|---|---|
| 264 | 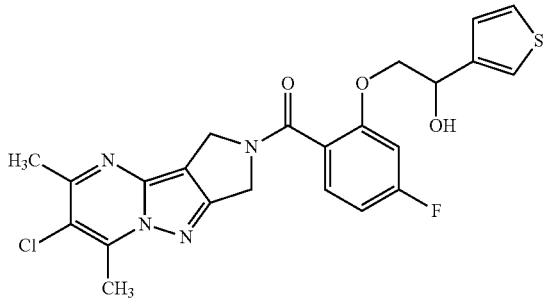 [SMILES: Cc1nc2c3c(nn2c(C)c1Cl)CN(C(=O)c1ccc(F)cc1OCC(O)c1ccsc1)C3] |
| 265 | 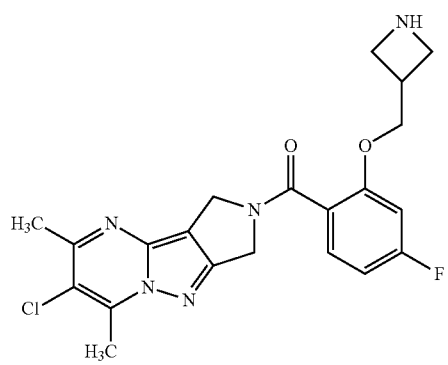 [SMILES: Cc1nc2c3c(nn2c(C)c1Cl)CN(C(=O)c1ccc(F)cc1OCC1CNC1)C3] |
| 266 and | 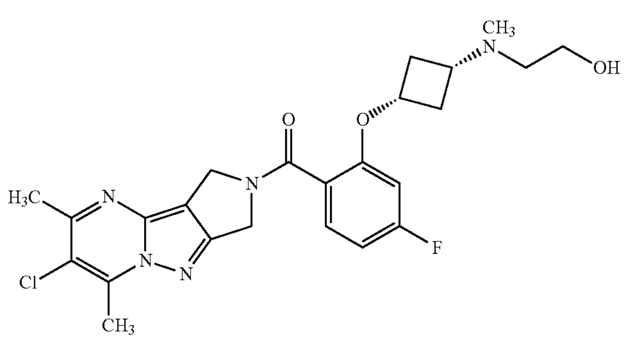 |
| 267 | 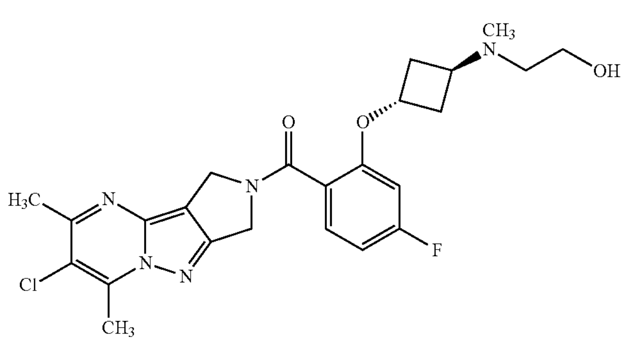 |

| Ex | Structure |
|---|---|
| 268a | 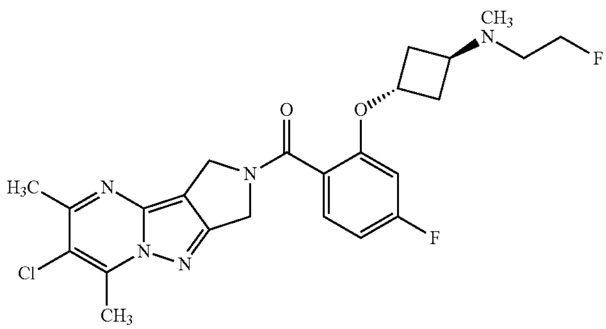 |
| 268b | 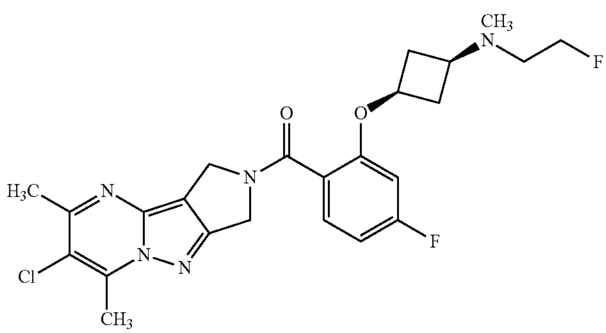 |
| 269 | 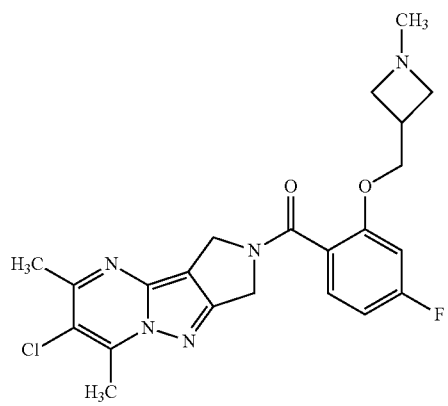 [SMILES: Cc1nc2c3c(nn2c(C)c1Cl)CN(C(=O)c1ccc(F)cc1OCC1CN(C)C1)C3] |
| 270 and | 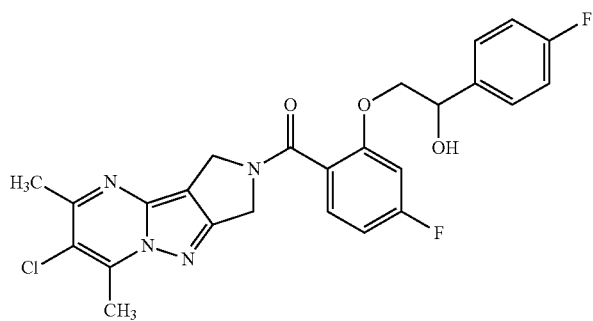 [SMILES: Cc1nc2c3c(nn2c(C)c1Cl)CN(C(=O)c1ccc(F)cc1OCC(O)c1ccc(F)cc1)C3] |

| Ex | Structure |
|---|---|
| 271 | 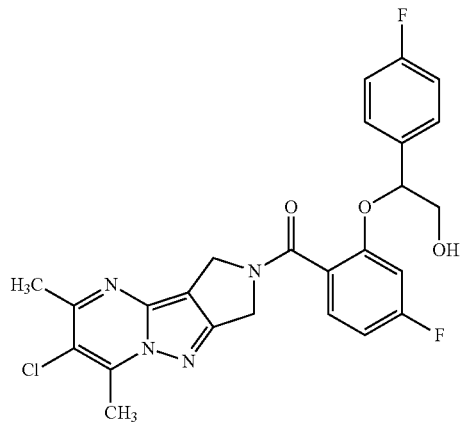 [SMILES: Cc1nc2c3c(nn2c(C)c1Cl)CN(C(=O)c1ccc(F)cc1OC(CO)c1ccc(F)cc1)C3] |
| 272a | 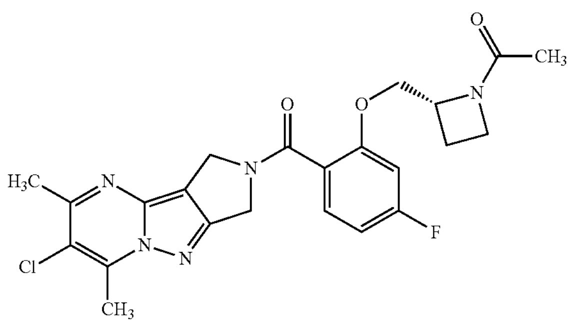 [SMILES: CC(=O)N1CC[C@@H]1COc1cc(F)ccc1C(=O)N1Cc2nn3c(C)c(Cl)c(C)nc3c2C1] |
| 272b | 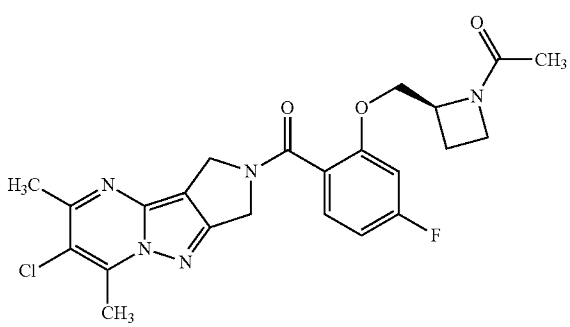 [SMILES: CC(=O)N1CC[C@H]1COc1cc(F)ccc1C(=O)N1Cc2nn3c(C)c(Cl)c(C)nc3c2C1] |
| 273a | 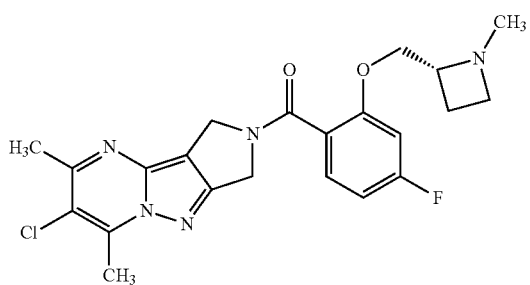 [SMILES: Cc1nc2c3c(nn2c(C)c1Cl)CN(C(=O)c1ccc(F)cc1OC[C@H]1CCN1C)C3] |

-continued

| Ex | Structure |
|---|---|
| 273b | 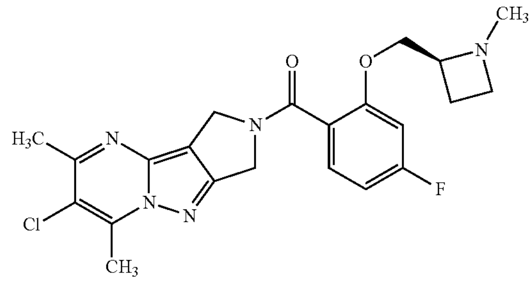 [SMILES: Cc1nc2c3c(nn2c(C)c1Cl)CN(C(=O)c1ccc(F)cc1OC[C@@H]1CCN1C)C3] |
| 274 | 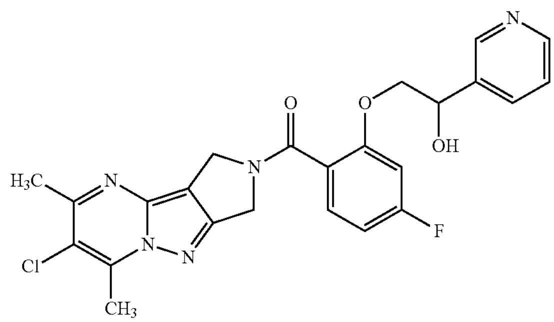 [SMILES: Cc1nc2c3c(nn2c(C)c1Cl)CN(C(=O)c1ccc(F)cc1OCC(O)c1cccnc1)C3] |
| 275 | 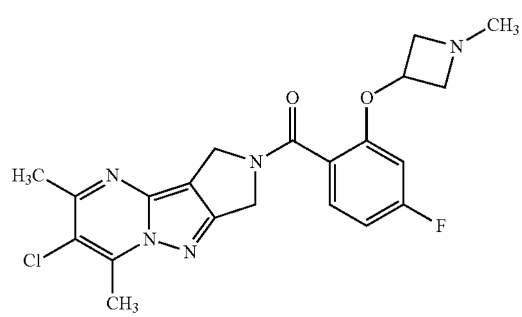 [SMILES: Cc1nc2c3c(nn2c(C)c1Cl)CN(C(=O)c1ccc(F)cc1OC1CN(C)C1)C3] |
| 276 | 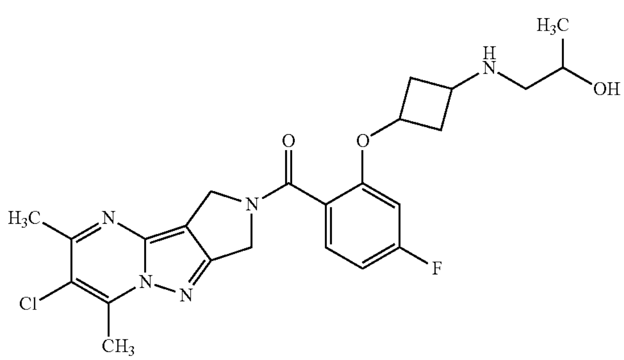 [SMILES: Cc1nc2c3c(nn2c(C)c1Cl)CN(C(=O)c1ccc(F)cc1OC1CC(NCC(C)O)C1)C3] |
| 277 | 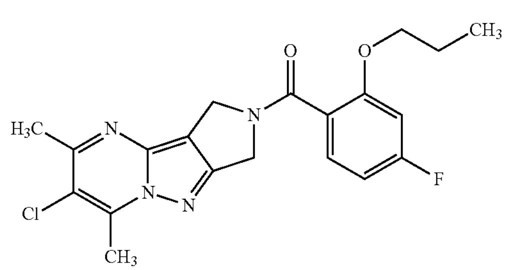 [SMILES: CCCOc1cc(F)ccc1C(=O)N1Cc2nn3c(C)c(Cl)c(C)nc3c2C1] |

-continued

| Ex | Structure |
|---|---|
| 278 | 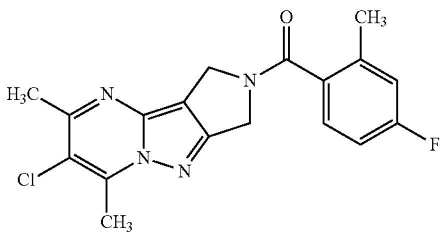 [SMILES: Cc1cc(F)ccc1C(=O)N1Cc2nn3c(C)c(Cl)c(C)nc3c2C1] |
| 279a | 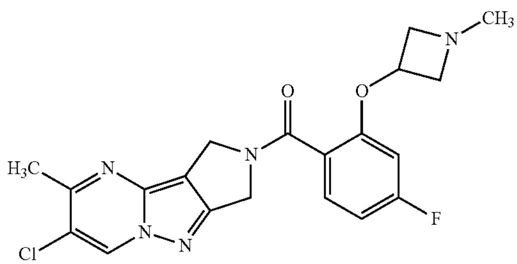 [SMILES: Cc1nc2c3c(nn2cc1Cl)CN(C(=O)c1ccc(F)cc1OC1CN(C)C1)C3] |
| 279b | 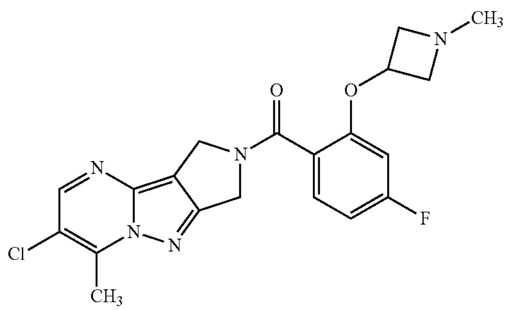 [SMILES: Cc1c(Cl)cnc2c3c(nn12)CN(C(=O)c1ccc(F)cc1OC1CN(C)C1)C3] |
| 280 | 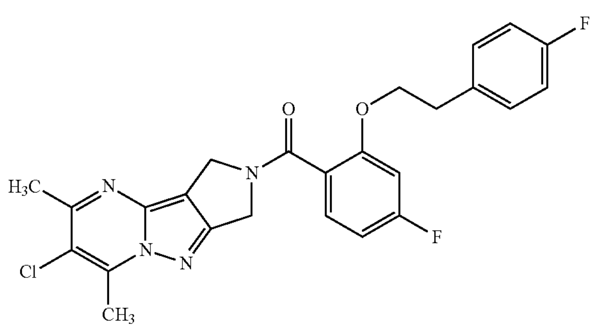 [SMILES: Cc1nc2c3c(nn2c(C)c1Cl)CN(C(=O)c1ccc(F)cc1OCCc1ccc(F)cc1)C3] |
| 281 | 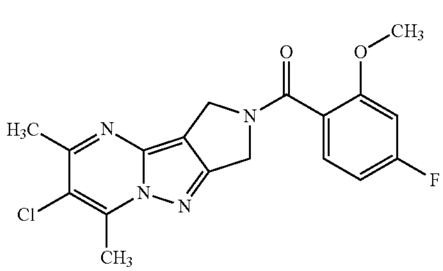 [SMILES: COc1cc(F)ccc1C(=O)N1Cc2nn3c(C)c(Cl)c(C)nc3c2C1] |

The following abbreviations refer to the abbreviations used below: ACN (acetonitrile), AcOH (acetic acid), aq. (aqueous), dba (dibenzylideneacetone), DBAD (di-tert-butylazodicarboxylate), DCC (dicyclohexylcarbodiimide), DCM (dichloromethane), DEAD (diethylazodicarboxylate), DIAD (diisopropylazodicarboxylate), DIC (diisopropylcarbodiimide), DIEA (di-isopropyl ethylamine), DMSO (dimethyl sulfoxide), DMF (N,N-dimethylformamide), DMP (Dess-Martin periodinane : acetic acid 1,1-diacetoxy-3-oxo-1λ5-ioda-2-oxa-indan-1-yl ester), EA (ethyl acetate), EDC (1-ethyl-3-(3-dimethylaminopropyl)carbodiimide hydrochloride), eq. (equivalent), EtOH (ethanol), g (gram), HATU (2-(1H-7-azabenzotriazol-1-yl)-1,1,3,3-tetramethyl uronium hexafluorophosphate methanaminium), cHex (cyclohexane), HPLC (high performance liquid chromatography), LG (leaving group), MeOH (methanol), MHz (Megahertz), MIBK (methyl isobutyl ketone), min (minute), mL (milliliter), mmol (millimole), MS (mass spectrometry), MTBE (tert-butyl methyl ether), MW (microwave), NMR (nuclear magnetic resonance), ppm (part per million), sat. (saturated), SFC (supercritical fluid chromatography), T3P (2,4,6-Tripropyl-[1,3,5,2,4,6]trioxatriphosphinane 2,4,6-trioxide), TEA (triethylamine), TFA (trifluoroacetic acid), THF (tetrahydrofurane), UV (ultraviolet).

In general, the compounds according to Formula (I) and related formulae of this invention can be prepared from readily available starting materials. If such starting materials are not commercially available, they may be prepared by standard synthetic techniques. In general, the synthesis pathways for any individual compound of Formula (I) and related formulae will depend on the specific substituent of each molecule, such factors being appreciated by those of ordinary skilled in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

A "leaving group" denotes a chemical moiety which can be removed or replaced by another chemical group.

Throughout the specification, the term leaving group preferably denotes Cl, Br, I or a reactively modified OH group, such as, for example, an activated ester, an imidazolide or alkylsulfonyloxy having 1 to 6 carbon atoms (preferably methylsulfonyloxy or trifluoromethylsulfonyloxy) or arylsulfonyloxy having 6 to 10 carbon atoms (preferably phenyl- or p tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example through addition of HOBt or N hydroxysuccinimide.

Depending on the nature of $R^1$, $R^2$, $R^3$, $R^4$ and $R^5$, different synthetic strategies may be selected for the synthesis of compounds of Formula (I). In the process illustrated in the following schemes, $R^1$, $R^2$, $R^3$, $R^4$ and $R^5$ are as above defined in the description unless otherwise mentioned.

Generally, tetraaza-cyclopenta[a]indenyl compounds of Formula (I) wherein $R^1$, $R^2$, $R^3$, $R^4$, and $R^5$ are defined as above can be prepared following the synthetic pathway described in the general scheme 1.

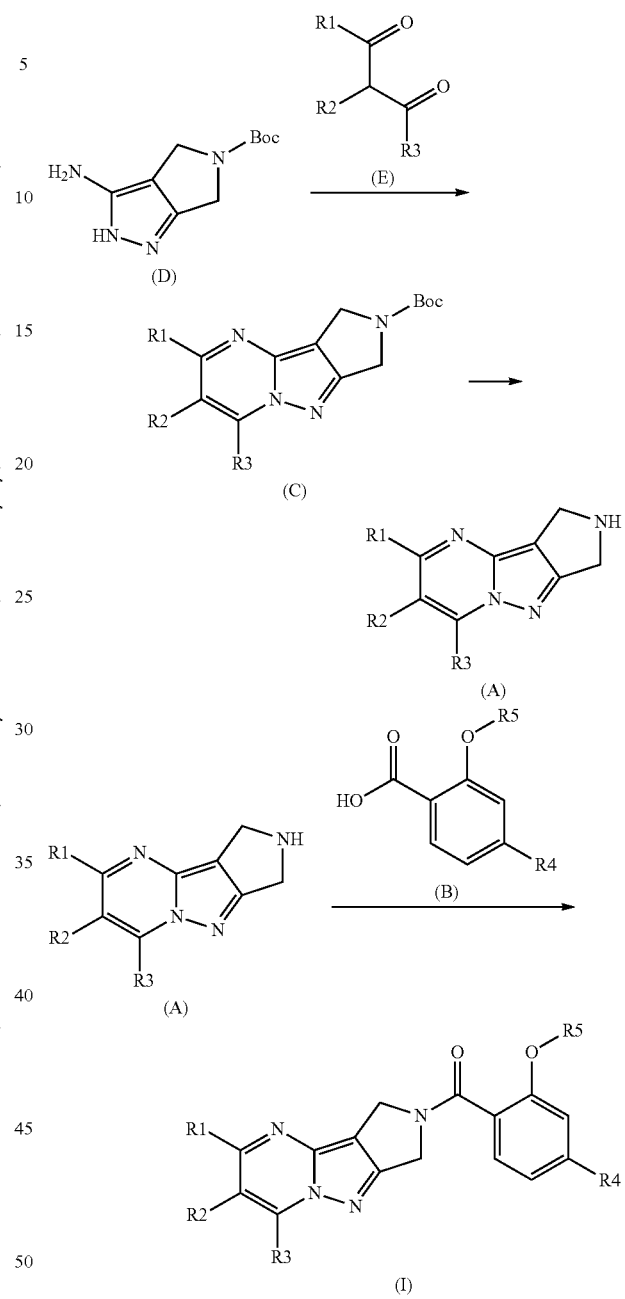

General scheme 1

According to a preferred synthetic pathway, compounds of Formula (I) wherein $R^1$, $R^2$, $R^3$, $R^4$ and $R^5$ are as above defined, may be prepared by reaction between an amine of Formula (A) and a carboxylic acid of Formula (B) following usual conditions for the formation of an amide starting from a carboxylic acid and an amine by using coupling agents such as EDC, HATU, DCC, DIC or via the formation of an acid chloride or an activated ester. Preferred conditions consist in the treatment of compounds of Formula (A) wherein $R^1$, $R^2$ and $R^3$ are as above defined with HATU or EDC followed by the addition of the amine of Formula (B) wherein $R^4$ and $R^5$ are as above defined, in the presence of a base such as TEA or DIEA in a suitable solvent such as DMF or DCM at room temperature.

Compounds of Formula (A) wherein $R^1$, $R^2$ and $R^3$ are as above defined may be prepared from the corresponding Boc protected amines of Formula (C), by treatment with an acid such TFA in DCM or HCl in dioxane or HCl in AcOH.

The method for preparing amine derivatives of Formula (A) selected below:
6-chloro-5,7-dimethyl-2,3-dihydro-1H-2,4,7a,8-tetraaza-cyclopenta[a]indene
6-chloro-2,3-dihydro-1H-2,4,7a,8-tetraaza-cyclopenta[a]indene
6-Chloro-5-methyl-2,3-dihydro-1H-2,4,7a,8-tetraaza-cyclopenta[a]indene hydrochloride
6-Chloro-7-methyl-2,3-dihydro-1H-2,4,7a,8-tetraaza-cyclopenta[a]indene hydrochloride is more particularly described in the examples.

Compounds of Formula (C) wherein $R^1$, $R^2$ and $R^3$ are as above defined may be prepared by reacting compounds of Formula (D) and compounds of Formula (E) in a suitable solvent such as AcOH at a temperature ranging from 25° C. to 75° C., for 30 minutes to 48 hours.

The method for preparing compounds of Formula (C) selected below:
6-chloro-5,7-dimethyl-1H,3H-2,4,7a,8-tetraaza-cyclopenta[a]indene-2-carboxylic acid tert-butyl ester
6-chloro-1H,3H-2,4,7a,8-tetraaza-cyclopenta[a]indene-2-carboxylic acid tert-butyl ester
6-Chloro-5-methyl-1H,3H-2,4,7a,8-tetraaza-cyclopenta[a]indene-2-carboxylic acid tert-butyl ester
6-Chloro-7-methyl-1H,3H-2,4,7a,8-tetraaza-cyclopenta[a]indene-2-carboxylic acid tert-butyl ester
is more particularly described in the examples.

Compound of Formula (D) may be prepared as described in Bioorg. Med. Chem. Lett. 2010, 20(14), 4273-4278.

Alternatively, compounds of general Formula (I) wherein $R^1$, $R^2$, $R^3$, $R^4$ and $R^5$, are as above defined, may be prepared as depicted in general scheme 2.

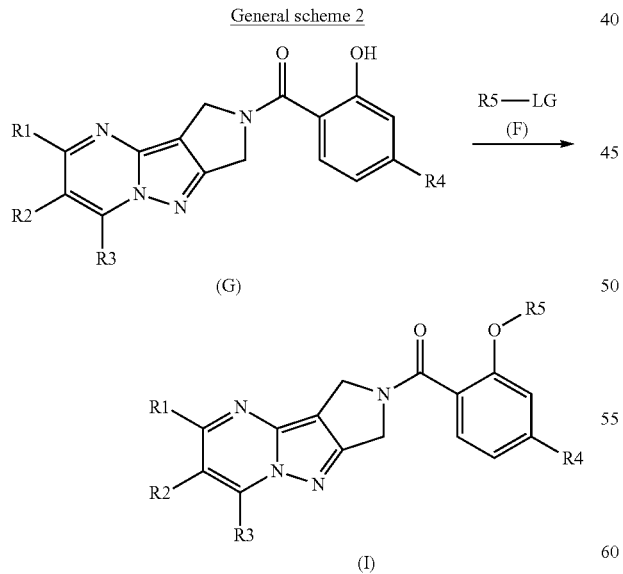

Compounds of Formula (I) wherein $R^1$, $R^2$, $R^3$, $R^4$ and $R^5$ are as above defined, may be prepared by reaction between a compound of Formula (G) wherein $R^1$, $R^2$, $R^3$ and $R^4$ are as above defined and a compound of Formula (F) wherein LG is a leaving group, preferably selected from Hal or an activated ester, in the presence of a base such as $K_2CO_3$, $Cs_2CO_3$, $Na_2CO_3$, NaH, in a solvent such as DMF, DMA, THF, 1,4-dioxane, acetone, ACN at a temperature ranging from 20° C. to 200° C. for few minutes to several hours. Preferred conditions consist in the treatment compound of Formula (G) by a compound of Formula (F) in the presence of $K_2CO_3$, in a solvent such as DMF at a temperature of about 150° C. using microwave heating for 10 minutes to 1 hour.

Alternatively, compound of Formula (G) wherein $R^1$, $R^2$, $R^3$ and $R^4$ are as above defined, may be added to an epoxide, in the presence of a base such as CsF, $K_2CO_3$, $Cs_2CO_3$, $Na_2CO_3$, NaH, in a solvent such as DMF, DMA, THF, 1,4-dioxane, acetone, ACN at a temperature ranging from 20° C. to 200° C. for few minutes to several hours, yielding compounds of Formula (I) bearing an alcohol functionality in alpha position to the phenoxy ether linkage.

Alternatively, compounds of general Formula (I) wherein $R^1$, $R^2$, $R^3$, $R^4$ and $R^5$ are as above defined, may be prepared as depicted in general scheme 3.

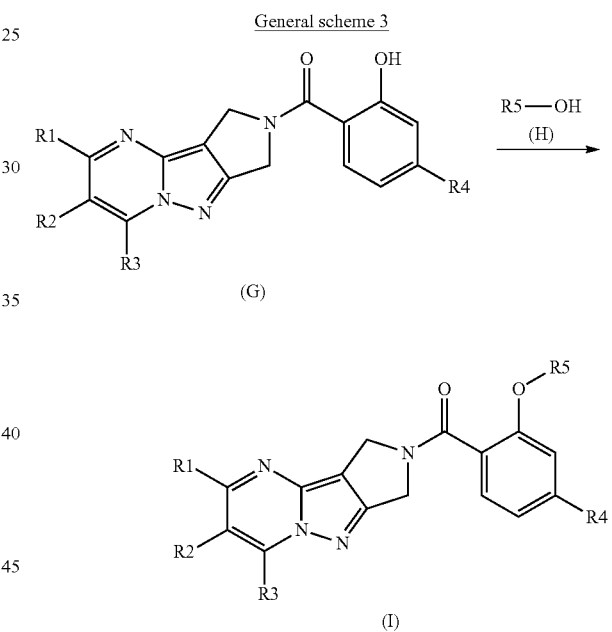

Compounds of Formula (I) wherein $R^1$, $R^2$, $R^3$, $R^4$ and $R^5$ are as above defined, may be prepared by a Mitsunobu type reaction between a compound of Formula (G) wherein $R^1$, $R^2$, $R^3$ and $R^4$ are as above defined, and an alcohol of Formula (H) wherein $R^5$ is as above defined, in the presence of a phosphine such as triphenylphosphine or tributylphosphine and an azodicarboxylate such as DEAD, DIAD, DBAD in a solvent such as THF, 1,4-dioxane, at a temperature ranging from 20° C. to 100° C. for few minutes to several hours. Preferred conditions consist in the treatment compound of Formula (G) by an alcohol of Formula (H) in the presence of tributylphosphine and DBAD in a solvent such as 1,4-dioxane or THF at a temperature between 0° C. to 40° C. for several hours.

Compounds of Formula (G) wherein $R^1$, $R^2$, $R^3$ and $R^4$ are as above defined may be prepared as depicted in general scheme 4.

General scheme 4

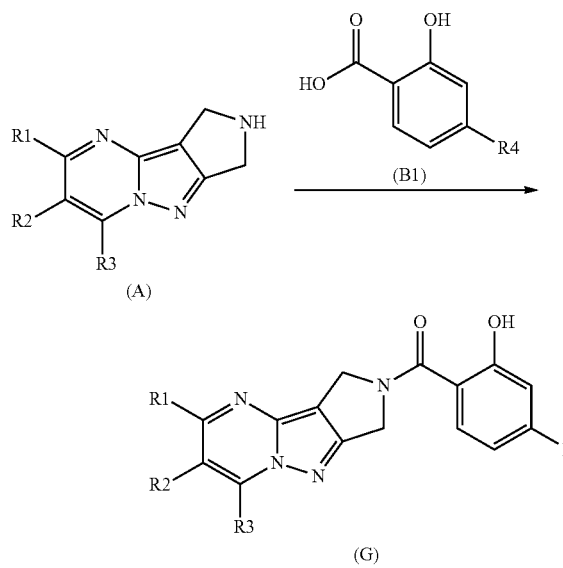

According to a preferred synthetic pathway, compounds of Formula (G) wherein $R^1$, $R^2$, $R^3$ and $R^4$ are as above defined, may be prepared by reaction between an amine of Formula (A) and a carboxylic acid of Formula (B1) following usual conditions for the formation of an amide starting from a carboxylic acid and an amine by using coupling agents such as EDC, HATU, DCC, DIC or via the formation of an acid chloride or an activated ester. Preferred conditions consist in the treatment of compounds of Formula (A) wherein $R^1$, $R^2$ and $R^3$ are as above defined with HATU or EDC followed by the addition of the amine of Formula (B1) wherein $R^4$ is as above defined, in the presence of a base such as TEA or DIEA in a suitable solvent such as DMF or DCM at room temperature.

The method for preparing compounds of Formula (G) selected below:

(3-chloro-2,4-dimethyl-7H-pyrrolo[3',4':3,4]pyrazolo[1,5-a]pyrimidin-8(9H)-yl)(4-fluoro-2-hydroxyphenyl)methanone (3-chloro-2,4-dimethyl-7H-pyrrolo[3',4':3,4]pyrazolo[1,5-a]pyrimidin-8(9H)-yl)(2-hydroxyphenyl)methanone (3-chloro-7H-pyrrolo[3',4':3,4]pyrazolo[1,5-a]pyrimidin-8(9H)-yl)(4-fluoro-2-hydroxyphenyl)methanone is more particularly described in the examples.

Compounds of Formula (B) wherein $R^4$ and $R^5$ are as above defined may be prepared according to general scheme 5.

General scheme 5

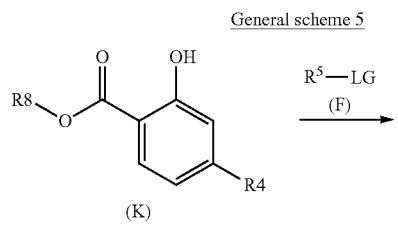

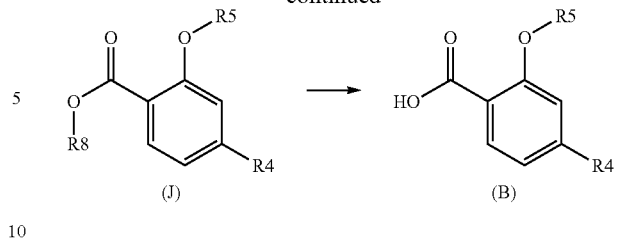

Compounds of Formula (B) may be prepared by saponification of esters of Formula (J) wherein $R^4$ and $R^5$ are as above defined and $R^8$ is a small alkyl group, such as but not limited to methyl, ethyl or tert-butyl, using LiOH, NaOH or KOH in water, water/THF, water/THF/ethanol or water/1,4-dioxane, at temperatures between 0 and 100° C.

Furthermore, ester can be hydrolyzed, for example, using acetic acid, TFA or HCl.

Compounds of Formula (J) wherein $R^4$, $R^5$ and $R^8$ are as above defined, may be prepared by reacting compounds of Formula (K) with compounds of Formula (F), wherein LG corresponds to a leaving group as defined above, in the presence of a base such as $K_2CO_3$, $Cs_2CO_3$, $Na_2CO_3$, NaH, in a solvent such as DMF, DMA, THF, 1,4-dioxane, acetone, ACN or mixtures thereof at a temperature ranging from 20° C. to 200° C. for few minutes to several hours.

Alternatively, compound of Formula (K) wherein $R^4$ and $R^8$ are as above defined, may be added to an epoxyde, in the presence of a base such as CsF, $K_2CO_3$, $Cs_2CO_3$, $Na_2CO_3$, NaH, in a solvent such as DMF, DMA, THF, 1,4-dioxane, acetone, ACN at a temperature ranging from 20° C. to 200° C. for few minutes to several hours, yielding compounds of Formula (J) bearing an alcohol functionality in alpha position to the phenoxy ether linkage.

Alternatively, compounds of general Formula (B) wherein $R^4$ and $R^5$ are as above defined, may be prepared as depicted in general scheme 6.

General scheme 6

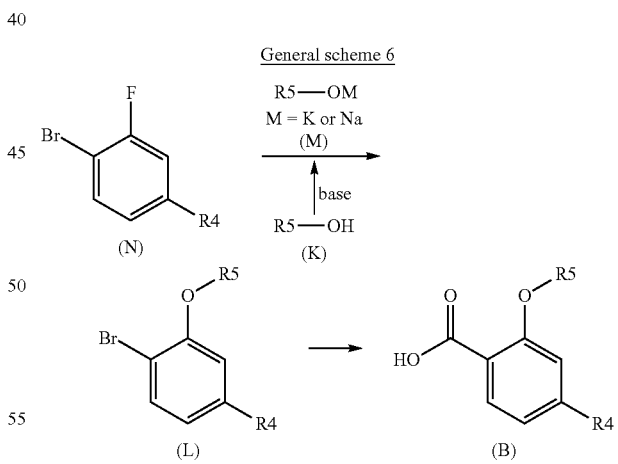

Compounds of Formula (B) may be prepared from compound of Formula (L) wherein $R^4$ and $R^5$ are as above defined. Compound of Formula (L) may be submitted to a halogen metal exchange step, performed with a base such as n-BuLi and in a solvent such as THF and at low temperature around −78° C. The resulting aryl lithium intermediate may be quenched with an electrophile such as carbon dioxide in gaseous or solid state. Alternatively, ethyl chloroformate may be added, yielding the corresponding ethyl ester that can be hydrolysed under basic or acidic conditions, as described for compound of Formula (J) or in the examples below.

As alternative procedure, compounds of Formula (B) may be prepared by palladium-catalyzed hydroxycarbonylation of compounds of Formula (L). Preferred conditions consist in the treatment of compound of Formula (L) with a palladium catalysis, such as but not limited to $Pd_2(dpba)_3$, $PdCl_2(dppp)$, $Pd(OAc)_2$, in the presence of acetic anhydride and lithium formate as a condensed source of carbon monoxide (see also *Organic Lett.* 2003, 5, 4269-4272).

The method for preparing carboxylic acid derivatives of Formula (B) selected below:

(syn)-3-(2-Carboxy-phenoxy)-4-fluoro-pyrrolidine-1-carboxylic acid tert-butyl ester 2-{[(3-endo)-8-(tert-butoxycarbonyl)-8-azabicyclo[3.2.1]oct-3-yl]oxy}-4-fluorobenzoic acid 2-{[(3-endo)-6-(6-endo)-fluoro-8-methyl-8-azabicyclo[3.2.1]oct-3-yl]oxy}-4-fluorobenzoic acid 2-{[(3-endo)-6-(6-exo)-6-(methoxymethyl)-8-methyl-8-azabicyclo[3.2.1]oct-3-yl]oxy}-4-fluorobenzoic acid 4-fluoro-2-{[(3-endo)-8-methyl-8-azabicyclo[3.2.1]oct-3-yl]oxy}benzoic acid 4-fluoro-2-{[(3-endo)-9-methyl-9-azabicyclo[3.3.1]non-3-yl]oxy}benzoic acid 2-(((3S,4S)-1-(tert-butoxycarbonyl)-3-hydroxypiperidin-4-yl)oxy)-4-fluorobenzoic acid 2-(((3R,4R)-1-(tert-butoxycarbonyl)-3-hydroxypiperidin-4-yl)oxy)-4-fluorobenzoic acid (2-endo)-2-(2-Carboxy-5-fluoro-phenoxy)-7-aza-bicyclo[2.2.1]heptane-7-carboxylic acid tert-butyl ester is more particularly described in the examples.

Compound of Formula (L) can be prepared by aromatic nucleophilic substitution from substituted 1-bromo-2-fluoro-benzene (N) and a suitable sodium or potassium alcoholate (M) in a solvent such as THF, 1,4-dioxane, DMF, at a temperature ranging from 20° C. to 150° C. for one to several hours. Sodium or potassium alcoholate (M) may be prepared from the corresponding alcohol (K) by addition of a base such as but not limited to 2-methyl-propan-2-ol potassium, potassium tertbutoxide, sodium hydride.

The method for preparing compounds of Formula (L) selected below:

(anti)-3-(2-bromo-phenoxy)-4-hydroxy-pyrrolidine-1-carboxylic acid tert-butyl ester (syn)-3-(2-bromo-phenoxy)-4-fluoro-pyrrolidine-1-carboxylic acid tert-butyl ester tert-butyl (3-endo)-3-(2-bromo-5-fluorophenoxy)-8-azabicyclo[3.2.1]octane-8-carboxylate (3-endo)-3-(2-bromo-5-fluorophenoxy)-(6-exo)-8-methyl-8-azabicyclo[3.2.1]octan-6-ol (3-endo)-3-(2-bromo-5-fluorophenoxy)-(6-endo)-6-fluoro-8-methyl-8-azabicyclo[3.2.1]octane (3-endo)-3-(2-bromo-5-fluorophenoxy)-(6-exo)-6-(methoxymethyl)-8-methyl-8-azabicyclo[3.2.1]octane (3-endo)-3-(2-bromo-5-fluorophenoxy)-8-methyl-8-azabicyclo[3.2.1]octane (3-endo)-3-(2-bromo-5-fluorophenoxy)-9-methyl-9-azabicyclo[3.3.1]nonane (3S,4S)-4-(2-bromo-5-fluorophenoxy)-3-hydroxypiperidine-1-carboxylic acid tert-butyl ester (3R,4R)-4-(2-bromo-5-fluorophenoxy)-3-hydroxypiperidine-1-carboxylic acid tert-butyl ester (2-endo)-2-(2-bromo-5-fluoro-phenoxy)-7-aza-bicyclo[2.2.1]heptane-7-carboxylic acid tert-butyl ester is more particularly described in the examples.

Compounds of Formulae (A) to (N), wherein $R^1$, $R^2$, $R^3$, $R^4$ and $R^5$ are as above defined, may be obtained either from commercial sources or they may be prepared from known compounds using procedures such as those described hereinafter in the examples, or conventional procedures, well known by one skilled in the art.

Compounds of Formulae (A) to (N), wherein $R^1$, $R^2$, $R^3$, $R^4$ and $R^5$ are as above defined, may be converted to alternative compounds of Formulae (A) to (N), respectively, using suitable interconversion procedures such as those described hereinafter in the examples, or conventional interconversion procedures well known by one skilled in the art.

As illustration, compounds of Formulae (A) to (N) bearing an alcohol functionality may be converted to the corresponding fluorine substituted analogue by reaction with a nucleophilic source of fluorine, such as but not limited to DAST, MOST or Deoxofluor (*Current Opinion in Drug Discovery & Development* 2008, 11, 803-819).

When compounds of Formulae (I), (B), (F), (H), (J) and (L) are obtained as mixture of enantiomers, they can be separated by chiral HPLC column, such as but not limited to the methods described below in the examples.

If the above set of general synthetic methods is not applicable to obtain compounds according to Formula (I) and/or necessary intermediates for the synthesis of compounds of Formula (I), suitable methods of preparation known by a person skilled in the art should be used.

Compounds of this invention can be isolated in association with solvent molecules by crystallization from an appropriate solvent or by evaporation of an appropriate solvent. The pharmaceutically acceptable anionic salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent.

The pharmaceutically acceptable cationic salts of the compounds of Formula (I), which contain an acidic center, may be prepared in a conventional manner. For example, a solution of the free acid may be treated with a suitable base, either neat or in a suitable solution, and the resulting salt isolated either by filtration or by evaporation under vacuum of the reaction solvent. In some cases, salts can be prepared by mixing a solution of the acid with a solution of an alkali or earth alkali salt (such as sodium ethylhexanoate, magnesium oleate), employing a solvent in which the desired alkali or earth alkali salt of the compounds of Formula (I) precipitates, or can be otherwise isolated by concentration and addition of a non-solvent.

Both types of salts may be formed or interconverted using ion-exchange resin techniques.

Depending on the conditions used, the reaction times are generally between a few minutes and 14 days. The reaction temperature is between about −30° C. and about 140° C., normally between −10° C. and 90° C., in particular between about 0° C. and 70° C. Compounds of the Formula (I) and related formulae can furthermore be obtained by liberating compounds of the Formula (I) from one of their functional derivatives by treatment with a solvolysing or hydrogenolysing agent.

Preferred starting materials for the solvolysis or hydrogenolysis are those which conform to the Formula I and related formulae, but contain corresponding protected amino and/or hydroxyl groups instead of one or more free amino and/or hydroxyl groups, preferably those which carry an amino-protecting group instead of an H atom bonded to an N atom, in particular those which carry an R*-N group, in which R* denotes an amino-protecting group, instead of an HN group, and/or those which carry a hydroxyl-protecting group instead of the H atom of a hydroxyl group, for example those which conform to the Formula I, but carry a —COOR group, in which R denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxycarbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxpcarbonyl, ethoxycarbonyl, 2,2,2- trichloroethoxycarbonyl, BOC (tert-butoxycarbonyl) and 2-iodoethoxycarbonyl; aralkoxycarbonyl, such as CBZ ("carbobenzoxy"), 4-methoxybenzyloxycarbonyl and FMOC; and aryl-sulfonyl, such as Mtr. Preferred amino-protecting groups are BOC and Mtr, furthermore CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the Formula I and related formulae are liberated from their functional derivatives—depending on the protecting group used—for example strong inorganic acids, such as hydrochloric acid, perchloric acid or sulfuric acid, strong organic carboxylic acids, such as trichloroacetic acid, TFA or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OtBut and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C. Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethyl-formamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be hydrolysed, for example, using HCl, $H_2SO_4$, or using LiOH, NaOH or KOH in water, water/THF, water/THF/ethanol or water/dioxane, at temperatures between 0 and 100° C.

Free amino groups can furthermore be acylated in a conventional manner using an acyl chloride or anhydride or alkylated using an unsubstituted or substituted alkyl halide, advantageously in an inert solvent, such as dichloromethane or THF and/or in the presence of a base, such as triethylamine or pyridine, at temperatures between −60° C. and +30° C.

Linear or branched $C_1$-$C_6$-alkyl denotes preferably methyl, ethyl, n-propyl, iso-propyl, n-butyl or tert-butyl and most preferably methyl.

$C_3$-$C_7$ cycloalkyl denotes preferably, cyclopropyl, cyclobutyl, cyclopentyl, cyclohexyl, cycloheptyl, methylcyclopropyl, dimethyl-cyclopropyl, methyl-cyclopentyl, dimethyl-cyclopentyl, methyl-cyclohexyl, preferably cyclopropyl, cyclopentyl or cyclohexyl.

The Formula (I) and related formulae also encompasses the optically active forms (stereoisomers), the enantiomers, the racemates, the diastereomers and the hydrates and solvates of these compounds. The term "solvates of the compounds" is taken to mean adductions of inert solvent molecules onto the compounds which form owing to their mutual attractive force. Solvates are, for example, mono- or dihydrates or alcoholates.

The term "pharmaceutically usable derivatives" is taken to mean, for example, the salts of the compounds of the Formula I and so-called pro-drug compounds.

The term "prodrug derivatives" is taken to mean compounds of the Formula I which have been modified with, for example, alkyl or acyl groups, sugars or oligopeptides and which are rapidly cleaved in the organism to form the active compounds. Preferably "prodrug", as of the compounds of Formula I, refers to derivative compounds that are rapidly transformed in vivo to yield the parent compound of the Formula I, as for example by hydrolysis in blood. T. Higuchi and V. Stella provide a thorough discussion of the prodrug concept in "Pro-drugs as Novel Delivery Systems", Vol 14 of the A.C.S. Symposium Series, American Chemical Society (1975). Examples of esters useful as prodrugs for compounds containing carboxyl groups can be found on pages 14-21 of "Bioreversible Carriers in Drug Design: Theory and Application", edited by E. B. Roche, Pergamon Press: New York (1987). It is intended that these references, and any others cited throughout this specification, are incorporated herein by reference.

These also include biodegradable polymer derivatives of the compounds according to the invention, as described, for example, in Int. J. Pharm. 115, 61-67 (1995).

The Formula (I) and related formulae also encompasses mixtures of the compounds of the Formula I, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

Pharmaceutical formulations can be administered in the form of dosage units, which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the disease condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process, which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medica-ment after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acacia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be formulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the Formula (I), and related formulae and salts, solvates and physiologically functional derivatives thereof and the other active ingredients can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the Formula (I), and related formulae and the salts, solvates and physiologically functional derivatives thereof and the other active ingredients can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamido-phenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, poly-orthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or sus-pended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insuf-flators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the Formula (I), and related formulae and of the other active ingredient depends on a number of factors, including, for example, the age and weight of the animal, the precise disease condition which requires treatment, and its severity, the nature of the formulation and the method of administration, and is ultimately determined by the treating doctor or vet. However, an effective amount of a compound is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as an individual dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound per se.

The present invention further relates to a compound of Formula (I) as set out above, for use as a medicament.

The present invention further relates to a pharmaceutical composition comprising at least one compound of Formula (I) as set out above and/or a pharmaceutically usable derivative, tautomer, salt, solvate or stereoisomer thereof, including mixtures thereof in all ratios, and optionally an excipient and/or an adjuvant.

The present invention further relates to a pharmaceutical composition comprising at least one compound of Formula (I) as set out above and/or a pharmaceutically usable derivative, tautomer, salt, solvate or stereoisomer thereof, including mixtures thereof in all ratios, and at least one further active ingredient.

The present invention further relates to a kit comprising separate packs of
(a) an effective amount of a compound of Formula (I) according to one or more of claims 1 to 6 and/or a pharmaceutically usable derivative, tautomer, salt, solvate or stereoisomer thereof, including mixtures thereof in all ratios; and
(b) an effective amount of a further medicament active ingredient.

The present invention further relates to a method for treating a subject suffering from cognitive impairment or decline and/or cholinergic dysfunction, comprising administering to said subject an effective amount of a compound of formula (I) and/or related formulae or a pharmaceutically usable derivative, salt, tautomer, solvate or stereoisomer thereof, including mixtures thereof in all ratios, to a patient in need thereof.

The invention further relates to a method of treatment and/or prophylaxis of a muscarinic M1 receptor associated disorder, said method comprising administering an effective amount of a compound of formula (I) and/or related formulae or a pharmaceutically usable derivative, salt, tautomer, solvate or stereoisomer thereof, including mixtures thereof in all ratios, to a patient in need thereof. In one embodiment the muscarinic M1 receptor associated disorder is selected from central nervous system disorders.

In a further embodiment of any of the above methods of treatment, the cognitive impairment or decline, cholinergic dysfunction, muscarinic M1 receptor associated disorder and/or central nervous system disorder is chosen from the group consisting of Alzheimer's disease and other degenerative diseases of nervous system, Parkinson disease, schizophrenia, other diseases which are associated with an impairment or decline in cognitive function or cholinergic dysfunction like movement disorders and memory disorders, chronic and neuropathic pain, sleep disorders, epilepsy, other degenerative diseases of basal ganglia, dementia in Alzheimer's disease, vascular dementia, dementia in other diseases, unspecified dementia, organic amnesic syndrome not induced by alcohol and other psychoactive substances, other mental disorders due to brain damage and dysfunction and to physical disease, personality and behavioral disorders due to brain disease, damage and dysfunction, schizotypal disorder, schizoaffective disorder, nociception disorder, dementia, hallucination, delusion and paranoia.

The invention further relates to a compound of formula (I) and/or related formulae or a pharmaceutically usable derivative, salt, tautomer, solvate or stereoisomer thereof, including mixtures thereof in all ratios, for use in a method of treatment of cognitive impairment or decline and/or cholinergic dysfunction.

The invention further relates to a compound of formula (I) and/or related formulae or a pharmaceutically usable derivative, salt, tautomer, solvate or stereoisomer thereof, including mixtures thereof in all ratios, for use in a method of treatment and/or prophylaxis of a muscarinic M1 receptor associated disorder. In one embodiment the muscarinic M1 receptor associated disorder is selected from central nervous system disorders.

In a further embodiment of any of the above compounds for use, the cognitive impairment or decline, cholinergic dysfunction, muscarinic M1 receptor associated disorder and/or central nervous system disorder is chosen from the group consisting of Alzheimer's disease and other degenerative diseases of nervous system, Parkinson disease, schizophrenia, other diseases which are associated with an impairment or decline in cognitive function or cholinergic dysfunction like movement disorders and memory disorders, chronic and neuropathic pain, sleep disorders, epilepsy, other degenerative diseases of basal ganglia, dementia in Alzheimer's disease, vascular dementia, dementia in other diseases, unspecified dementia, organic amnesic syndrome not induced by alcohol and other psychoactive substances, other mental disorders due to brain damage and dysfunction and to physical disease, personality and behavioral disorders due to brain disease, damage and dysfunction, schizotypal disorder, schizoaffective disorder, nociception disorder, dementia, hallucination, delusion and paranoia.

EXPERIMENTAL PART

The compounds of invention have been named according to the standards used in the program AutoNom 2000 or ACD Lab Version 12.01.

The determination of the stereochemistry (S) or (R) is performed using standard rules of the nomenclature well known by one skilled in the art.

The compounds according to Formula (I) can be prepared from readily available starting materials by several synthetic approaches, using both solution-phase and solid-phase chemistry protocols or mixed solution and solid phase protocols. Examples of synthetic pathways are described below in the examples. All reported yields are non optimized yields.

The commercially available starting materials used in the following experimental description were purchased from Aldrich, Sigma, ACROS or ABCR unless otherwise reported.

Preparation of Compounds of Formula (I)

$^1$H NMR analyses were carried out using BRUKER NMR, model AV-II and AV-III 400 MHz FT-NMR. Residual signal of deuterated solvent was used as internal reference. Chemical shifts ($\delta$) are reported in ppm in relative to the residual solvent signal ($\delta$=2.50 for $^1$H NMR in DMSO-d$_6$, and 7.26 in CDCl$_3$). s (singlet), d (doublet), t (triplet), q (quadruplet), br (broad), quint (quintuplet). Some compounds in the experimental part exist as mixture of rotamers in different ratios as described in the $^1$H NMR descriptions. The MS data provided in the examples described below were obtained as followed:

Mass spectrum: LC/MS Agilent (ESI/APCI).

LCMS Methods:

Method A: Method: A-0.1% TFA in H$_2$O, B-0.1% TFA in ACN: Flow-2.0 mL/min. Column: XBridge C8 (50×4.6 mm, 3.5 µm), +ve mode Method B: Method: A-10 mM NH$_4$HCO$_3$ in H$_2$O, B-ACN: Flow −1.0 mL/min. Column: XBridge C8 (50×4.6 mm, 3.5 µm), +ve mode Method C: Method: A-10 mM NH$_4$HCO$_3$ in H$_2$O, B-ACN: Flow −1.0 mL/min. Column: XBridge C8 (50×4.6 mm, 3.5 µm), −ve mode HPLC analyses were obtained as followed using % with UV detection (maxplot).

Method A: Method: A-0.1% TFA in H$_2$O, B-0.1% TFA in ACN: Flow −2.0 mL/min. Column: XBridge C8 (50×4.6 mm, 3.5 µm).

Method B: Method: A-10 mM NH$_4$HCO$_3$ in H$_2$O, B-ACN: Flow −1.0 mL/min. Column: XBridge C8 (50×4.6 mm, 3.5 µm).

Method C: Method: Gradient from 70% H₂O (10 mM K₂HPO₄): 30% MeCN to 70% MeCN over 15 minutes, Flow: 1 mL/min. Column: XTERRA RP18 (250×4.6) mm, 5 μm Method D: Chiral analytical method: Mobile Phase: 0.1% DEA in n-HEXANE: IPA:60:40; COLUMN: CHIRALPAK AD-H (250×4.6) mm, 5 μm, FLOW:1.0 mL/min The SFC purifications were performed with a Prep SFC, THAR-SFC 80.

Prep-HPLC Conditions

Method A: A-0.1% TFA in H₂O, B-MeOH or ACN. Column: Sunfire C8 (19 mm×250 mm) 5 μm or Sunfire C18 (30 mm x 250 mm) 10pm.

Method B: A-10 mM NH₄HCO₃ in H₂O, B-MeOH or ACN, Column: Sunfire C8 (19 mm x 250 mm) 5pm or Sunfire 018 (30 mm×250 mm) 10 μm.

Method C: Chiral preparative method: A-Hexane:IPA; Column: Chiral pak ADH (20×250) mm, 5 micron, Flow: 12 mL/min Method D: A-Hexane:IPA: 60:40, Column: Sunfire Silica (19×150) mm, 5 μm, Flow: 15 mL/min The mass directed preparative HPLC purifications were performed with a mass directed autopurification Fractionlynx from Waters.

MD Auto-Prep Conditions:

Method A: 0.1% HCOOH in H₂O, B-MeOH or ACN, Column: Symmetry C8 (300 mm×19 mm), 7 μm Method B: 0.1% TFA in H₂O, B-MeOH or ACN, Column: Symmetry C8 (300 mm×19 mm), 7 μm Method C: 10 mM NH₄HCO₃ in H₂O, B-MeOH or ACN, Column: Symmetry C8 (300 mm×19 mm), 7 μm Method D: 10 mM NH₄OAC in H₂O, B-MeOH or ACN, Column: Symmetry C8 (300 mm×19 mm), 7 μm The microwave chemistry was performed on a single mode microwave reactor Initiator™ Sixty from Biotage.

Intermediate A1

6-chloro-5,7-dimethyl-2,3-dihydro-1H-2,4,7a,8-tetraaza-cyclopenta[a]indene hydrochloride

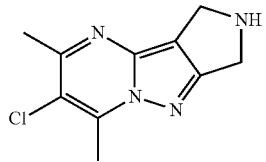

Step 1: 6-chloro-5,7-dimethyl-1H,3H-2,4,7a,8-tetraaza-cyclopenta[a]indene-2-carboxylic acid tert-butyl ester A solution of 3-amino-2,6-dihydro-4H-pyrrolo[3,4-c]pyrazole-5-carboxylic acid tert-butyl ester (1 g; 4.46 mmol; 1 eq.) and 3-chloroacetylacetone (0.71 mL; 6.24 mmol; 1.4 eq.) in AcOH (10 mL) was stirred at room temperature for 18 hours. The reaction was poured into water (100 mL) under vigorous stirring and the precipitate filtered off, washed with water (3×) and dried to afford the title compound (1298 mg, 90%) as an off-white solid. ¹H NMR (400 MHz, DMSO-d₆): δ 4.60-4.52 (m, 4H), 2.81 (m, 3H), 2.60-2.57 (m, 3H), 1.48 (s, 9H). HPLC (max plot) 98.4%; Rt 3.96 min. UPLC/MS: (MS+) 323 ([M+H]⁺).

Step 2: 6-chloro-5,7-dimethyl-2,3-dihydro-1H-2,4,7a,8-tetraaza-cyclopenta[a]indene hydrochloride Aq. 32% HCl (1.14 mL; 11.62 mmol; 3 eq.) was added to a suspension of 6-chloro-5,7-dimethyl-1H,3H-2,4,7a,8-tetraaza-cyclopenta[a]indene-2-carboxylic acid tert-butyl ester (1.25 g; 3.87 mmol; 1 eq.) in AcOH (6.25 mL) and the resulting mixture was stirred at room temperature for 2 hours then poured into MTBE (40 mL). The precipitate was filtered off, washed with MTBE (3×) and dried to afford the title compound (1 g, 100%) as an off-white solid. ¹H NMR (400 MHz, DMSO-d₆): δ 10.55 (s, 2H), 4.57-4.52 (m, 4H), 2.83 (s, 3H), 2.61 (s, 3H). HPLC (max plot) 100.0%; Rt 1.38 min. UPLC/MS: (MS+) 222.9 ([M+H]⁺).

Intermediate A2

6-chloro-2,3-dihydro-1H-2,4,7a,8-tetraaza-cyclopenta[a]indene hydrochloride

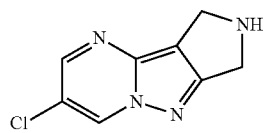 [SMILES: Clc1cnc2c3c(nn2c1)CNC3]

Step 1: 6-chloro-1H,3H-2,4,7a,8-tetraaza-cyclopenta[a]indene-2-carboxylic acid tert-butyl ester A mixture of 3-amino-2,6-dihydro-4H-pyrrolo[3,4-c]pyrazole-5-carboxylic acid tert-butyl ester (2 g; 8.92 mmol; 1 eq.) and 2-chloromalonaldehyde (1.04 g; 9.81 mmol; 1.1 eq.) in AcOH was stirred at room temperature for 18 hours then diluted with water (30 mL). The precipitate was filtered off and purified by column chromatography (DCM/EA, from 95/5 to 80/20) to afford the title compound (1.24 g, 47%) as a white solid. ¹H NMR (400 MHz, DMSO-d₆): δ 9.57 (d, J=2.3 Hz, 1H), 8.59 (d, J=2.3 Hz, 1H), 4.63-4.57 (m, 4H), 1.47 (s, 9H). HPLC (max plot) 99.1%; Rt 3.75 min.

Step 2: 6-chloro-2,3-dihydro-1H-2,4,7a,8-tetraaza-cyclopenta[a]indene hydrochloride Aq. 32% HCl (1.2 mL; 12.2 mmol; 3 eq.) was added to a suspension 6-chloro-1H,3H-2,4,7a,8-tetraaza-cyclopenta[a]indene-2-carboxylic acid tert-butyl ester (1.2 g; 4.07 mmol; 1 eq.) in AcOH (6 mL) and the resulting mixture was stirred at room temperature for 2 hours then poured dropwise into ACN (40 mL) under vigorous stirring. The precipitate was filtered off, washed with ACN (2×) and dried to afford the title compound (0.85 g, 78%) as a white solid. ¹H NMR (400 MHz, DMSO): δ 10.49 (s, 2H), 9.65 (d, J=2.3 Hz, 1H), 8.68 (d, J=2.3 Hz, 1H), 4.58 (s, 4H). HPLC (max plot) 100.0%; Rt 3.76 min. UPLC/MS: (MS+) 195 ([M+H]⁺).

Intermediate A3

6-Chloro-5-methyl-2,3-dihydro-1H-2,4,7a,8-tetraaza-cyclopenta[a]indene hydrochloride or 6-Chloro-7-methyl-2,3-dihydro-1H-2,4,7a,8-tetraaza-cyclopenta[a]indene hydrochloride

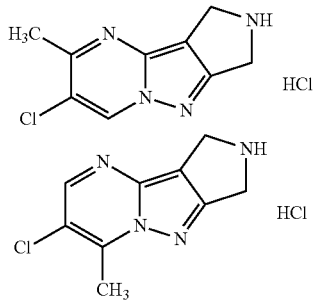

Step 1: 3-Chloro-4,4-diethoxy-butan-2-one

To a stirred solution of diethoxymethoxy ethane (17.9 mL, 108 mmol, Aldrich), borontrifluoride diethyl ether complex (9.34 mL, 108 mmol, Fluka) in dry DCM (100 mL) was added drop wise over a period of 50 min at −30° C. under N₂ atmosphere. The reaction mass was allowed to stir at −30° C. for 40 min then at RT for 1 h. Chloroacetone (4.31 mL, 54.0 mmol, Merck) was added rapidly at −78° C. followed by DIPEA (27.9 mL, 162.1 mmol) drop wise for 40 min. Then the reaction mixture was allowed to stir at −78° C. for 1 h. The completion of the reaction was confirmed by TLC. The reaction mass was added to saturated sodium bicarbonate solution and stirred for 15 min and the layer was separated. The crude was extracted in DCM (2×250 mL). The combined organic layer was washed with H₂SO₄:chilled water (1:10) ratio followed by water (2×100 mL). The organic layer was dried over anhydrous sodium sulphate and the solvent was evaporated to yield the required product as brown oil (5.2 g, 49.5%). ¹H NMR (400 MHz, DMSO-d₆): δ 4.80 (d, J=6.0 Hz, 1H), 4.63 (d, J=6.0 Hz, 1H), 3.68-3.49 (m, 4H), 2.24 (s, 3H), 1.15-1.06 (m, 6H).

Step 2: 6-Chloro-5-methyl-1H,3H-2,4,7a 8-tetraaza-cyclopenta[a]indene-2-carboxylic acid tert-butyl ester and 6-Chloro-7-methyl-1H,3H-2,4,7a,8-tetraaza-cyclopenta[a]indene-2-carboxylic acid tert-butyl ester To a stirred solution of tert-butyl 3-amino-2,6-dihydropyrrolo[3,4-c]pyrazole-5(4H)-carboxylate (5 g, 22.29 mmol, Activate Scientific GmbH) in glacial acetic acid (25 mL), 3-chloro-4,4-diethoxybutan-2-one (4.8 g, 22.2 mmol) was added and allowed to stir at RT for 14 h. The reaction completion was confirmed by LCMS. The acetic acid was evaporated and poured into saturated sodium bicarbonate solution; yellow solid formed was filtered off, washed with water and dried. The crude was purified by flash column chromatography using Silica gel (230-400 mesh) and n-hexane: Ethyl acetate as eluant. First eluting compound was obtained with 12% EtOAc as off-white solid. The second eluting compound was obtained with 14% EtOAc as off-white solid. First eluting compound: ¹H NMR (400 MHz, DMSO-d₆): δ 8.56 (s, 1H), 4.62-4.58 (m, 4H), 2.80 (s, 3H), 1.47 (s, 9H). LCMS: (Method A) 253.0 (M-ᵗBu+H)⁺, Rt. 4.5 min, 96.4% (Max). Second eluting compound: ¹H NMR (400 MHz, DMSO-d₆): δ 9.46 (s, 1H), 4.58-4.54 (m, 4H), 2.57-2.49 (m, 3H), 1.48 (s, 9H). LCMS: (Method A) 253.0 (M-ᵗBu+H)⁺, Rt. 4.3 min, 98.5% (Max).

Step 3: 6-Chloro-5-methyl-2,3-dihydro-1H-2,4,7a,8-tetraaza-cyclopenta[a]indene hydrochloride or 6-Chloro-7-methyl-2,3-dihydro-1H-2,4,7a,8-tetraaza-cyclopenta[a]indene hydrochloride To a stirred solution of the second eluting compound from step 2 (1.4 g, 4.53 mmol) in acetic acid (7.5 mL), HCl (2 mL, 11N) was added at 0° C. and allowed to stir for an hour. The reaction completion was confirmed by TLC. The reaction mixture was poured in to methyl tert-butyl ether with constant stirring. The solid was filtered off, given methyl tert-butyl ether wash and dried to afford an off-white solid (1.1 g, 99.0%). ¹H NMR (400 MHz, DMSO-d₆): δ 10.47 (brs, 2H), 9.53 (s, 1H), 4.51 (s, 4H), 2.58 (s, 3H). LCMS: (Method A) 209.0 (M+H)⁺, Rt. 1.5 min, 98.3% (Max).

Intermediate B1

(syn)-3-(2-Carboxy-phenox)-4-fluoro-pyrrolidine-1-carboxylic acid tert-butyl ester

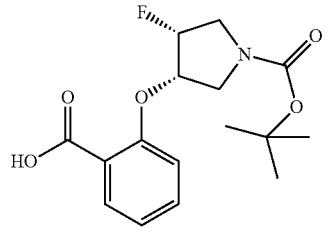 [SMILES: CC(C)(C)OC(=O)N1C[C@@H](F)[C@@H](Oc2ccccc2C(=O)O)C1]

Step 1: (anti)-3-(2-Bromo-phenoxy)-4-hydroxy-pyrrolidine-1-carboxylic acid tert-butyl ester To a stirred solution of 2-bromophenol (0.4 g, 0.23 mmol, Combiblock) in dry N,N-dimethylacetamide (15 mL) was added cesium carbonate (0.4 g, 2.3 mmol, Chempure) under N₂ atmosphere and the reaction mixture was stirred at 60° C. for 1 h. After 1 h, 6-Oxa-3-aza-bicyclo[3.1.0]hexane-3-carboxylic acid tert-butyl ester (0.855 g, 4.6 mmol) was added to the reaction mixture and allowed to stir at 80° C. for 16 h. After completion, the reaction mass was filtered through celite and concentrated under vacuum. Residue obtained was diluted with ethyl acetate (50 mL), washed with water, brine solution and dried over anhydrous Na₂SO₄. Organic phase was concentrated. The crude product was purified by flash chromatography (230-400 size mesh) (silica gel, pet ether/ethyl acetate as gradient elution), affording the title compound as colourless gum (450 mg, 55%). ¹H NMR (400 MHz, DMSO-d₆): δ 7.6 (d, J=7.8 Hz, 1H), 7.37-7.33 (m, 1H), 7.2 (d, J=8.2 Hz, 1H), 6.9 (t, J=7.6 Hz, 1H), 5.5 (d, J=3.3 Hz, 1H), 4,7 (s, 1H), 4.22-4.15 (m, 1H), 3.73-3.47 (m, 3H), 3.38-3.19 (m, 1H), 1.4 (s, 9H). LCMS: (Method A) 258.0 (M-Boc+H)⁺, Rt. 4.6 min, 83.5% (Max).

Step 2: (syn)-3-(2-Bromo-phenoxy)-4-fluoro-pyrrolidine-1-carboxylic acid tert-butyl ester To a stirred solution of (anti)-3-(2-bromo-phenoxy)-4-hydroxy-pyrrolidine-1-carboxylic acid tert-butyl ester (0.45 g, 1.25 mmol) in dry DCM (10 mL) was added (DAST) diethylaminosulphur trifluoride (0.304 g, 1.88 mmol) drop wise at 0° C. The reaction mixture was stirred at RT for 16 h. After completion, the reaction mass was filtered through celite and concentrated under vacuum. Residue obtained was diluted with ethyl acetate (50 mL), washed with water, brine solution and dried over anhydrous $Na_2SO_4$. Organic phase was concentrated. The crude product was purified by flash chromatography (230-400 size mesh) (silica gel, pet ether/ethyl acetate as gradient elution), affording the title product as colourless gum (270 mg, 59%). $^1$H NMR (400 MHz, DMSO-$d_6$): δ 7.6 (d, J=7.9 Hz, 1H), 7.38-7.31 (m, 1H), 7.20-7.17 (m, 1H), 6.99-6.93 (m, 1H), 5.39-5.28 (m, 1H), 5.25-5.15 (m, 1H), 5.02-4.96 (m, 1H), 3.90-3.84 (m, 1H), 3.74-3.62 (m, 2H), 1.5 (s, 9H). LCMS: (Method A) 360.0 (M+H)$^+$, Rt. 6.7 min, 96.0% (Max).

Step 3: (syn)-3-(2-Carboxy-phenoxy)-4-fluoro-pyrrolidine-1-carboxylic acid tert-butyl ester To a stirred solution of (syn)-3-(2-bromo-phenoxy)-4-fluoro-pyrrolidine-1-carboxylic acid tert-butyl ester (0.27 g, 0.75 mmol) in dry THF (10 mL) was added n-butyl lithium (1.6M, 0.46 mL) at −78° C. for 30 min. The reaction mixture was stirred at same temperature for 1 h. Then $CO_2$ gas was purged at −78° C. for 1 h. After completion, the reaction mass was quenched with a solution of 10% methanol in DCM and concentrated under vacuum. The crude product isolated as off white solid was used as such for next step. LCMS: (Method A) 324.0 (M−H)$^-$, Rt. 3.6 min, 35.5% (Max).

Intermediate B2

2-{[(3-endo)-8-(tert-butoxycarbonyl)-8-azabicyclo[3.2.1]oct-3-yl]oxy}-4-fluorobenzoic acid

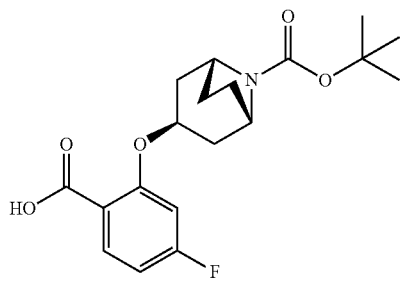 [SMILES: CC(C)(C)OC(=O)N1[C@@H]2CC[C@H]1C[C@@H](Oc1cc(F)ccc1C(=O)O)C2]

Step 1: tert-butyl (3-endo)-3-(2-bromo-5-fluorophenoxy)-8-azabicyclo[3.2.1]octane-8-carboxylate To a solution of tert-butyl (3-endo)-3-hydroxy-8-azabicyclo[3.2.1]octane-8-carboxylate (3 g, 13.20 mmol, combiblocks) in THF (30 mL) was added portion wise potassium tert butoxide (1.6 g, 14.5 mmol). The reaction was then refluxed for 1 h. The reaction was removed from the oil bath and 1-bromo-2,4-difluoro-benzene (1.6 mL, 14.52 mmol, Matrix) was added. The reaction was again refluxed for 1.5 h and cooled to RT. Ethyl acetate was added. The layers were separated and the organic layer was washed with water, brine, dried over sodium sulphate, filtered and concentrated in vacuo. The crude was purified by flash chromatography using 5% ethyl acetate in cyclohexane to give a colourless oil that crystallised upon standing (4.1 g, 79%). $^1$H NMR (400 MHz, DMSO-$d_6$): δ 7.63-7.59 (m, 1H), 6.98 (dd, J1=1140, J2=2.76 Hz, 1H), 6.76-6.71 (m, 1H), 4.81 (t, J=4.40 Hz, 1H), 4.06 (s, 2H), 2.15-2.05 (m, 4H), 1.87-1.84 (m, 4H), 1.41 (s, 9H). LCMS: (Method A) 344.0 (M-$^t$Bu+H)$^+$, Rt. 6.2 min, 84.9% (Max).

Step 2: 2-{[(3-endo)-8-(tert-butoxycarbonyl)-8-azabicyclo[3.2.1]oct-3-yl]oxy}-4-fluorobenzoic acid To a solution of tert-butyl (3-endo)-3-(2-bromo-5-fluorophenoxy)-8-azabicyclo[3.2.1]octane-8-carboxylate (1 g, 2.50 mmol) in THF (15 mL) at −78° C. was added butyl lithium 1.6 M solution in hexanes (1.7 mL, 2.75 mmol) over 15 min. The colourless solution was stirred at −78° C. for 30 min. Then, $CO_2$ (dried over $H_2SO_4$) was bubbled into the reaction. After 5 min, the cooling bath was removed, while maintaining the $CO_2$ bubbling. When the reaction was at RT, the bubbling was stopped and the reaction was cooled again at 0° C. Saturated aqueous $NH_4Cl$ was added followed by ethyl acetate. The aqueous phase was further extracted with ethyl acetate. The combined organics were dried over sodium sulphate, filtered and concentrated in vacuo. The oil was crystallised using n-heptane/EtOAc. The solid was filtered, washed with n-heptane and dried in vacuo to give the desired product as off white solid (600 mg, 56%). $^1$H NMR (400 MHz, DMSO-$d_6$): δ 12.72 (s, 1H), 7.75-7.71 (m, 1H), 6.93 (d, J=12.00 Hz, 1H), 6.85-6.77 (m, 1H), 4.85-4.79 (m, 1H), 4.28-4.04 (m, 2H), 2.15-2.04 (m, 4H), 1.82-1.64 (m, 4H), 1.42 (s, 9H). LCMS: (Method B) 364.0 (M−H)$^-$, Rt. 4.0 min, 81.8% (Max).

Intermediate B3

2-{[(3-endo)-6-(6-endo)-fluoro-8-methyl-8-azabicyclo[3.2.1]oct-3-yl]oxy}-4-fluorobenzoic acid

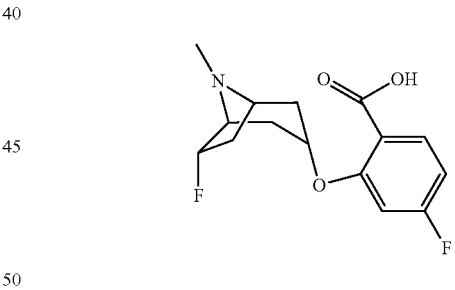

Step 1: (3-endo)-3-(2-bromo-5-fluorophenoxy)-(6-exo)-8-methyl-8-azabicyclo[3.2.1]octan-6-ol The title compound was prepared following the same protocol as described for Example 25, step 2, using using (3-endo)-3-(2-bromo-5-fluorophenoxy)-(6-exo)-6-(methoxymethyl)-8-methyl-8-azabicyclo[3.2.1]octane (Intermediate B4, step 1) as starting material. The crude product was purified by trituration with diethyl ether to get the title compound as brown oil (2.8 g, 82%). $^1$H NMR (400 MHz, DMSO-$d_6$): δ 7.64-7.60 (m, 1H), 6.93-6.90(m, 1H), 6.76-6.72 (m, 1H), 4.66-4.56 (m, 3H), 3.18-3.16 (m, 2H), 3.02-2.90 (m, 1H), 2.71 (s, 3H), 2.09-2.05 (m, 2H), 1.86-1.84 (m, 1H), 1.77-1.70 (m, 1H), 1.61-1.57 (m, 1H). LCMS: (Method A) 330.0 (M+H)$^+$, Rt. 2.8 min, 77.0% (Max).

Step 2: (3-endo)-3-(2-bromo-5-fluorophenoxy)-(6-endo)-6-fluoro-8-methyl-8-azabicyclo[3.2.1]octane The title compound was prepared following the same protocol as described for Intermediate B1, step 2, using (3-endo)-3-(2-bromo-5-fluorophenoxy)-(6-exo)-8-methyl-8-azabicyclo[3.2.1]octan-6-ol as starting material. The crude product was purified by flash chromatography and the title compound was isolated as brown solid. $^1$H NMR (400 MHz, DMSO-$d_6$): δ 7.66-7.61 (m, 1H), 7.13 (dd, J=10.96 Hz, 2.72, 1H), 6.81-6.76 (m, 1H), 5.09-5.05 (m, 2H), 3.71-3.58 (m, 1H), 3.34-3.28 (m, 1H), 2.67-2.64 (m, 1H), 2.40 (s, 2H), 2.24-2.03 (m, 2H), 1.89-1.83 (m, 3H), 1.41-1.24 (m, 1H). LCMS: (Method A) 332.0 (M+H)$^+$, RT. 3.3 min, 71.3% (Max).

Step 3: 2-{[(3-endo)-6-(6-endo)-fluoro-8-methyl-8-azabicyclo[3.2.1]oct-3-yl]oxy}-4-fluorobenzoic acid The title compound was prepared following the same protocol as described for Intermediate B2, step 2, starting from (3-endo)-3-(2-bromo-5-fluorophenoxy)-(6-endo)-6-fluoro-8-methyl-8-azabicyclo[3.2.1]octane. The crude product was purified by recrystallization, affording the title compound as brown solid. LCMS: (Method B) 298.0 (M+H)$^+$, Rt. 2.4 min, 29.2% (Max).

Intermediate B4

2-{[(3-endo)-6-(6-exo)-6-(methoxymethyl)-8-methyl-8-azabicyclo[3.2.1]oct-3-yl]oxy}-4-fluorobenzoic acid

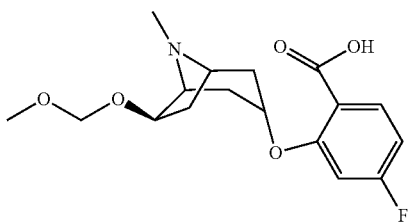 [SMILES: COCO[C@@H]1CC2CC(Oc3cc(F)ccc3C(=O)O)CC1N2C]

Step 1: (3-endo)-3-(2-bromo-5-fluorophenoxy)-(6-exo)-6-(methoxymethyl)-8-methyl-8-azabicyclo[3.2.1]octane The title compound was prepared following the same protocol as described for Intermediate B2, step 1, using (3-endo)-3-(hydroxy)-(6-exo)-6-(methoxymethyl)-8-methyl-8-azabicyclo[3.2.1]octane as starting material (synthesis described in *J. Med. Chem.* 2005, 48, 3337-3343). It was purified by trituration with diethyl ether to get the product as yellow liquid (5 g, 67%). $^1$H NMR (400 MHz, DMSO-$d_6$): δ 7.64-7.60 (m, 1H), 6.95 (dd, J=11.26, 2.40 Hz, 1H), 6.77-6.72 (m, 1H), 4.69-4.68 (m, 1H), 4.64-4.63 (m, 1H), 4.62-4.61 (m, 1H), 4.59-4.57 (m, 1H), 3.25-3.24 (m, 4H), 3.13-3.20 (m, 1H), 2.43 (s, 3H), 2.11-1.99 (m, 4H), 1.79-1.75 (m, 1H), 1.67-1.63 (m, 1H). LCMS: (Method A) 374.0 (M+H)$^+$, Rt. 3.4 min, 84.6% (Max).

Step 2: 2-{[(3-endo)-6-(6-exo)-6-(methoxymethyl)-8-methyl-8-azabicyclo[3.2.1]oct-3-yl]oxy}-4-fluorobenzoic acid The title compound was prepared following the same protocol as described for Intermediate B2, step 2, starting from (3-endo)-3-(2-bromo-5-fluorophenoxy)-(6-exo)-6-(methoxymethyl)-8-methyl-8-azabicyclo[3.2.1]octane. It was purified by trituration with diethyl ether to get the product as yellow liquid (800 mg, 53%). LCMS: (Method B) 340.2 (M+H)$^+$, Rt. 2.2 min, 53.6% (Max).

Intermediate B5

4-fluoro-2-{[(3-endo)-8-methyl-8-azabicyclo[3.2.1]oct-3-yl]oxy}benzoic acid

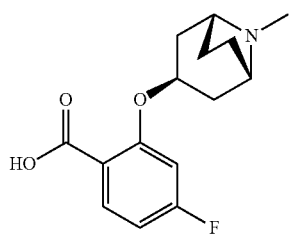 [SMILES: CN1[C@@H]2CC[C@H]1C[C@@H](Oc1cc(F)ccc1C(=O)O)C2]

Step 1: (3-endo)-3-(2-bromo-5-fluorophenoxy)-8-methyl-8-azabicyclo[3.2.1]octane To a solution of tropine (5 g, 354 mmol, Combiblock) in dry THF (50 mL) was added portion wised potassium tert butoxide (4.8 g, 42.4 mmol). Then the reaction was refluxed for 1 h. The reaction was removed from the oil bath and 1-bromo-2,4-difluoro-benzene (4.4 mL, 38.9 mmol, Matrix) in dry THF (20 mL) was added, while maintaining a gentle reflux. Then the reaction was again refluxed for 3 h. The reaction was cooled to RT. Ethyl acetate was added. The layers were separated and the organic layer was washed with water, brine, dried over sodium sulphate, filtered and concentrated in vacuo. The crude was stirred with 5% ethyl acetate in pet ether. The resulting solid was filtered off and the filtrate was evaporated and taken for next step without any further purification. The title compound was isolated as yellow solid (9 g, 81%). $^1$H NMR (400 MHz, CDCl$_3$): δ 7.51-7.47 (m, 1H), 6.59-6.48 (m, 2H), 4.55-4.53 (m, 1H), 3.32-3.15 (m, 2H), 2.50-2.29 (m, 7H), 2.10-2.00 (m, 4H). LCMS: (Method A) 314.0 (M+H)$^+$, Rt. 3.3 min, 82.0% (Max).

Step 2: 4-fluoro-2-{[(3-endo)-8-methyl-8-azabicyclo[3.2.1]oct-3-yl]oxy}benzoic acid To a solution of (3-endo)-3-(2-bromo-5-fluorophenoxy)-8-methyl-8-azabicyclo[3.2.1]octane (1 g, 3.19 mmol) in THF (25 mL) at −78° C. was added n-butyl lithium (1.6M solution in hexanes) (1.8 mL, 2.75 mmol) over 15 min. The colourless solution was stirred at −78° C. for 20 min. Then reaction mass was poured into crushed dry ice and stirred for 15 min. The reaction mass was evaporated in vacuo. The crude product was triturated with diethyl ether (50 mL), dried in vacuo. It was then azeotroped with toluene (3 times) and taken for next step without any further purification as pale brown solid (500 mg, 56%). LCMS: (Method A) 280.2 (M+H)$^+$, Rt. 2.2 min, 62.2% (Max).

Intermediate B6

4-fluoro-2-{[(3-endo)-9-methyl-9-azabicyclo[3.3.1]non-3-yl]oxy}benzoic acid

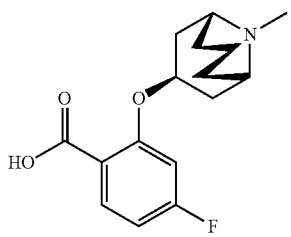

Steps 1: (3-endo)-9-methyl-9-azabicyclo[3.3.1]nonan-3-ol 9-methyl-9-azabicyclo[3.3.1]nonan-3-one as starting material (Arbor Chemicals, 1.226 g, 7.9 mmol) was diluted in THF (5 mL) and cooled to −78° C., followed by addition of L-Selectride (9.5 mL, 9.5 mmol) dropwise. After stirring for 1 h at −78° C., the reaction mixture was stirred in an ice-water bath for 2 h. The reaction was quenched by adding EtOH (5 mL). The mixture was concentrated under reduced pressure and re-dissolved in DCM (20 mL). The organic layer was washed with water (10 mL) and brine (10 mL). The combined aqueous phases were re-extracted with DCM (15 mL). Combined organic phases were dried over $Na_2SO_4$, and concentrated under reduced pressure. The crude product obtained was purified by flash column chromatography (230-400 size mesh), affording the title compound as brown solid (800 mg, 80%). $^1$H NMR (400 MHz, $CDCl_3$): δ 3.42-3.02 (m, 1H), 2.61 (s,3H), 2.31-1.90 (m, 1H), 1.61-1.48 (m, 4H), 1.40-1.25 (m, 2H), 1.24-1.15 (m, 2H), 1.12-0.85 (m, 4H). LCMS: (Method A) 156.2 (M+H)$^+$, Rt. 1.3 min, 98.6% (ELSD).

Step 2: (3-endo)-3-(2-bromo-5-fluorophenoxy)-9-methyl-9-azabicyclo[3.3.1]nonane The title compound was prepared following the same protocol as described for Intermediate B2, step 1, using (3-endo)-9-methyl-9-azabicyclo[3.3.1]nonan-3-ol as starting material. The crude product was purified by recrystallization, affording the title compound as yellow solid (1.2 g 75%). $^1$H NMR (400 MHz, DMSO-$d_6$): δ 7.60-7.54 (m, 1H), 7.08-6.96 (m, 1H), 6.75-6.71 (m, 1H), 4.73-4.72 (m, 2H), 2.89-2.71 (m, 2H), 2.26 (s, 3H), 1.97-1.81 (m, 2H), 1.61-1.58 (m, 1H), 1.46-1.42 (m, 1H), 1.35-1.18 (m, 2H), 1.02-0.95 (m, 1H), 0.90-0.85 (m, 2H). LCMS: (Method A) 328.0 (M+H)$^+$, Rt. 3.5 min, 50.7% (Max).

Step 3: 4-fluoro-2-{[(3-endo)-9-methyl-9-azabicyclo[3.3.1]non-3-yl]oxy}benzoic acid The title compound was prepared following the same protocol as described for Intermediate B2, step 2, using (3-endo)-3-(2-bromo-5-fluorophenoxy)-9-methyl-9-azabicyclo[3.3.1]nonane as starting material. The crude product was purified by recrystallization, affording the title compound as white solid (600 mg, 60%). LCMS: (Method B) 294.2 (M+H)$^+$, Rt. 1.8 min, 46.3% (Max).

Intermediates B8a and B8b 2-(((3S,4S)-1-(tert-butoxycarbonyl)-3-hydroxypiperidin-4-yl)oxy)-4-fluorobenzoic acid and 2-(((3R,4R)-1-(tert-butoxycarbonyl)-3-hydroxypiperdin-4-yl)oxy)-4-fluorobenzoic acid

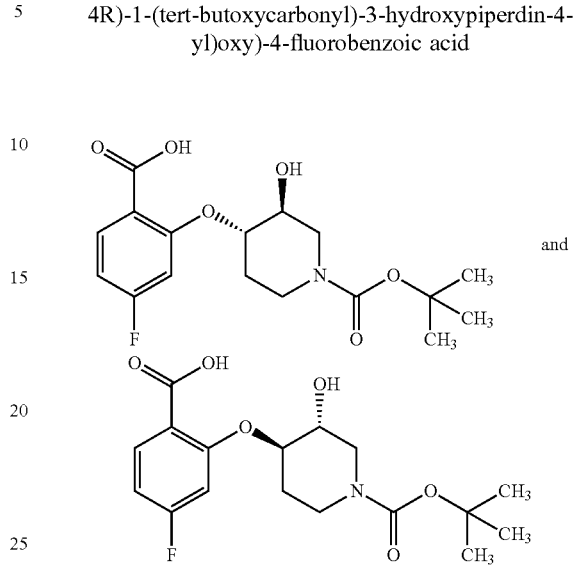

Step 1: Intermediates B7b1 and B7b2: (3S,4S)-4-(2-bromo-5-fluorophenoxy)-3-hydroxypiperidine-1-carboxylic acid tert-butyl ester and (3R,4R)-4-(2-bromo-5-fluorophenoxy)-3-hydroxypiperidine-1-carboxylic acid tert-butyl ester The title compounds were synthesized using the procedure as described for Example 5, step 1. LCMS report showed two peaks with the same product mass which indicated the mixture of two isomers. The isomeric mixture was purified by prep-HPLC (Method B). The first eluting isomer (minor isomer) and the second eluting isomer (major isomer) were isolated and characterized by $^1$H NMR experiments. The first eluting isomer was assigned to (anti)-3-(2-bromo-5-fluorophenoxy)-4-hydroxypiperidine-1-carboxylic acid tert-butyl ester and named Intermediate B7a (mixture of 2 enantiomers) and the second eluting isomer was assigned to (anti)-4-(2-bromo-5-fluorophenoxy)-3-hydroxypiperidine-1-carboxylic acid tert-butyl ester and named Intermediate B7b (mixture of 2 enantiomers). Intermediate B7b was submitted to chiral SFC separation (Method: Column: Chiral Pak IC (21×250) mm 5 μm Total Flow: 30.0 g/min, Mobile Phase: $CO_2$: Methanol (80:20), Run Time: 10 min, Loading: 100 mg /injection). The first eluting compound was concentrated and considered as Intermediate B7b1 and the second eluting compound was concentrated and considered as Intermediate B7b2. The structures of both enantiomers compounds were assigned arbitrarily. Intermediate B7b1 was isolated as white solid. $^1$H NMR (400 MHz, DMSO-$d_6$): δ 7.59-7.55 (m, 1H), 7.23 (dd, J=11.3, 2.8 Hz, 1H), 6.79-6.73 (m, 1H), 5.34 (d, J=4.8 Hz, 1H), 4.44-4.39 (m, 1H), 3.72-3.68 (m, 1H), 3.56-3.50 (m, 2H), 3.20-3.14 (m, 2H), 2.02-1.95 (m, 1H), 1.50-1.46 (m, 1H), 1.39 (s, 9H). HPLC: (Method A) Rt. 5.1, 95.7% (Max). Intermediate B7b2 was isolated as white solid. $^1$H NMR (400 MHz, DMSO-$d_6$): δ 7.59-7.55 (m, 1H), 7.23 (dd, J=11.3, 2.8 Hz, 1H), 6.79-6.73 (m, 1H), 5.34 (d, J=4.8 Hz, 1H), 4.44-4.39 (m, 1H), 3.72-3.68 (m, 1H), 3.56-3.50 (m, 2H), 3.20-3.14 (m, 2H), 2.02-

1.95 (m, 1H), 1.50-1.46 (m, 1H), 1.39 (s, 9H). HPLC: (Method A) Rt. 5.1, 99.9% (Max).

Step 2: Intermediate B8a and B8b: 2-(((3S,4S)-1-(tert-butoxycarbonyl)-3-hydroxypiperidin-4-yl)oxy)-4-fluorobenzoic acid and 2-(((3R,4R)-1-(tert-butoxycarbonyl)-3-hydroxypiperidin-4-yl)oxy)-4-fluorobenzoic acid The title compounds were prepared following the same protocol as described for Intermediate B2, step 2, starting from Intermediates B7b1 and B7b2 respectively. Intermediate B8a was obtained from Intermediate B7b1 and Intermediate B8b was obtained from Intermediate B7b2. Intermediate B8a was isolated as off white solid (250 mg, 47%). $^1$H NMR (400 MHz, DMSO-$d_6$): δ 7.99-7.93 (m, 1H), 7.08-7.02 (m, 1H), 6.84-6.76 (m, 1H), 6.68 (t, J=8.4 Hz, 1H), 4.02-3.88 (m, 2H), 3.80-3.74 (m, 2H), 3.33-3.25 (m, 2H), 2.88-2.72 (m, 2H), 2.13 (d, J=8.4 Hz, 1H), 1.39 (s, 9H). LCMS: (Method A) 256.0 (M-Boc+H)$^+$, Rt. 3.6 min, 30% (Max).

Intermediate B8b was isolated as off white solid (250 mg, 47%). $^1$H NMR (400 MHz, DMSO-$d_6$): δ 7.39-7.27 (m, 1H), 7.09 (t, J=6.9 Hz, 1H), 6.85-6.67 (m, 1H), 5.37 (s, 1H), 3.87-3.78 (m, 4H), 2.21-2.11 (m, 2H), 1.60-1.50 (m, 3H), 1.39 (s, 9H). LCMS: (Method A) 256.1 (M-Boc+H)$^+$, Rt. 3.6 min, 67.8% (Max).

Intermediate B9

(2-endo)-2-(2-Carboxy-5-fluoro-phenoxy)-7-aza-bicyclo[2.2.1]heptane-7-carboxylic acid tert-butyl ester

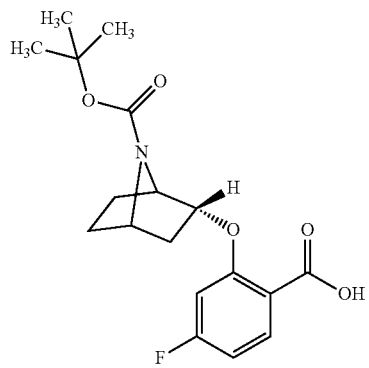 [SMILES: CC(C)(C)OC(=O)N1C2CCC1[C@H](Oc1cc(F)ccc1C(=O)O)C2]

Step 1: Bromo-propynoic acid methyl ester

To a stirred solution of methyl propiolate (50 g, 594 mmol, Spectrochem) in dry acetone (300 mL), silver nitrate (1.01 g, 5.94 mmol, Spectrochem) was added and cooled to 0° C. under N$_2$ atmosphere. N-bromo succinimide (116 g, 654 mmol, Spectrochem) was added in portions over 30 min and allowed to warm to room temperature. Reaction mixture was allowed to stir at RT for 4 h. The reaction mixture was concentrated and taken up in hexane and filtered through celite bed. The filtrate was concentrated in Rota-evaporator and residue obtained was purified by distillation to get the titled compound as colorless liquid (81 g, 83%). $^1$H NMR (400 MHz, CDCl$_3$): δ 3.78 (s, 3H).

Step 2: 3-Bromo-7-aza-bicyclo[2.2.1]hepta-2,5-diene-2,7-dicarboxylic acid 7-tert-butyl ester 2-methyl ester A mixture of bromo-propynoic acid methyl ester (81.2 g, 497 mmol) and t-butyl pyrrole-1-carboxylate (216.7 g, 1292 mmol, Combiblock) were combined and heated to 95° C. for 2 days. After completion of the reaction, the reaction mixture was concentrated in high vacuum and purified by flash column chromatography (230-400 size mesh silica gel) using gradient elution of ethyl acetate (7.5-8.0%) in n-hexane to afford the pure product as reddish brown gel. $^1$H NMR (400 MHz, DMSO-$d_6$): δ 7.25-7.22 (m, 2H), 5.30 (s, 1H), 5.15 (s, 1H), 3.72 (s, 3H), 1.34 (s, 9H). LCMS: (Method A) 232.0 (M-Boc+H)$^+$, Rt. 4.7 min, 95.6% (Max).

Step 3: 3-Oxo-7-aza-bicyclo[2.2.1]hept-5-ene-2,7-dicarboxylic acid 7-tert-butyl ester 2-methyl ester To a stirred solution of 3-bromo-7-aza-bicyclo[2.2.1]hepta-2,5-diene-2,7-dicarboxylic acid 7-tert-butyl ester 2-methyl ester (10 g, 30.3 mmol) in anhydrous acetonitrile (200 mL) triethylamine (15.4 g, 151 mmol) was added at RT. Reaction mass cooled to 0° C. under N$_2$ atmosphere and added a solution of diethyl amine (2.44 g, 33.4 mmol, Spectrochem) in acetonitrile (50 mL) slowly over a period of 45 min. Reaction mass allowed to stir at RT for 1 h. Starting material consumption was monitored by TLC. Upon completion of the reaction, reaction mixture was cooled to 0° C. and added a 10% solution of HCl (55.0 mL) in water slowly over a period of 45 min. Reaction mixture was allowed to stir at RT for 1 h. Progress of the reaction was monitored by LCMS analysis. Upon completion of the starting material, reaction mass was diluted with EtOAc (300 mL) and washed with water, followed by brine solution and dried over anhydrous Na$_2$SO$_4$. The crude product obtained was purified by flash column chromatography (230-400 size mesh) using 14-16% ethyl acetate in n-hexane to afford the pure product as pale yellow solid (4.5 g, 55%). $^1$H NMR (400 MHz, DMSO-$d_6$): δ 6.97-6.95 (m, 1H), 6.53-6.51 (m, 1H), 5.03-5.01 (m, 1H), 4.66-4.61 (m, 1H), 3.65 (s, 1H), 3.64 (s, 3H), 1.39 (s, 9H). LCMS: (Method A) 168.2 (M-Boc+H)$^+$, Rt. 3.7 & 3.9 min, 16.7 & 80.0% (Max).

Step 4: 3-Oxo-7-aza-bicyclo[2.2.1]heptane-2,7-dicarboxylic acid 7-tert-butyl ester 2-methyl ester To a stirred solution of 3-oxo-7-aza-bicyclo[2.2.1]hept-5-ene-2,7-dicarboxylic acid 7-tert-butyl ester 2-methyl ester (4.5 g, 16.8 mmol) in anhydrous methanol (84 mL) under N$_2$ atmosphere 10% Pd/C (0.62 g, Aldrich) was charged and hydrogenated at atmospheric pressure at RT for 16 h. Upon completion of the reaction as monitored by LCMS analysis, reaction mixture was filtered through celite bed. The solvent was removed in vacuo to provide the pure compound as colorless gel (4.5 g, 97%). $^1$H NMR (400 MHz, DMSO-$d_6$): δ 4.63-4.60 (m, 1H), 4.22-4.19 (m, 1H), 3.68-3.67 (m, 0.5H), 3.63 (s, 1.5H), 3.59 (s, 1.5H), 3.57-3.55 (m, 0.5H), 2.02-1.74 (m, 3H), 1.58-1.51 (m, 1H), 1.38 (s, 9H). LCMS: (Method A) 170.2 (M-Boc+H)$^+$, Rt. 3.8 & 4.0 min, 27 & 71% (ELSD).

Step 5: 2-Oxo-7-aza-bicyclo[2.2.1]heptane-7-carboxylic acid tert-butyl ester

A mixture of 3-oxo-7-aza-bicyclo[2.2.1]heptane-2,7-dicarboxylic acid 7-tert-butyl ester 2-methyl ester (5.0 g, 18.5 mmol) and 10% solution HCl in water (150 mL) was heated at 100° C. for 2 h. Progress of the reaction was monitored by LCMS analysis, upon completion of the starting material, solvent was removed in vacuo to provide a yellow residue. The residue obtained was taken up in dichloromethane (150 mL) triethylamine (11.2 g, 111 mmol) was added at 0° C. under $N_2$ atmosphere followed by Di-tert-butyldicarbonate (8.1 g, 37.1 mmol). Reaction mixture was allowed to stir at RT for 16 h. After the completion of the reaction as monitored by the LCMS analysis, reaction mass was diluted with dichloromethane (100 mL) and washed with water, brine solution and dried over anhydrous $Na_2SO_4$. The crude product obtained was purified by the flash column chromatography (230-400 size mesh) using 15-16% ethyl acetate in pet ether to afford the pure product as off white solid (2.4 g, 61%). $^1$H NMR (400 MHz, DMSO-$d_6$): δ 4.41-4.38 (m, 1H), 4.06-4.02 (m, 1H), 2.39-2.34 (m, 1H), 2.10 (s, 0.5H), 2.05 (s, 0.5H), 1.92-1.86 (m, 1H), 1.83-1.76 (m, 1H), 1.65-1.49 (m, 2H), 1.38 (s, 9H). LCMS: (Method A) 112.2 (M-Boc+H)$^+$, Rt. 3.5 min, 97.8% (Max).

Step 6: (2-endo)-2-Hydroxy-7-aza-bicyclo[2.2.1]heptanes-7-carboxylic acid tert-butyl ester and (2-exo)-2-Hydroxy-7-aza-bicyclo[2.2.1]heptane-7-carboxylic acid tert-butylester To a stirred solution of 2-oxo-7-aza-bicyclo[2.2.1]heptane-7-carboxylic acid tert-butyl ester (2.4 g, 11.3 mmol) in ethanol (48 mL) was charged platinum oxide (0.140 g, Hindustan Platinum) followed by triethylamine (3.45 g, 34.1 mmol) at RT under $N_2$ atmosphere. Nitrogen atmosphere was replaced by hydrogen and allowed to stir at RT for 12 h. Progress of the reaction was monitored by TLC and LCMS analysis. Analytic showed that reaction was not complete. Platinum oxide (0.070 g) was charged again and continued the stirring for 12 h. Upon completion of the reaction, catalyst was removed by filtration. The solvent was evaporated under vacuo to get the crude product. The crude product obtained was purified by the flash column chromatography (230-400 size mesh) using 28-29% ethyl acetate in n-hexane to afford the first eluting fraction as pale yellow liquid (0.8 g, 33%), and 30-32% ethyl acetate in n-hexanes to afford the second eluting fraction as off white solid (1.0 g, 41%). Based on NMR experiment, the first eluting compound was attributed to the endo isomer and the second eluting compound to the exo isomer.

First eluting compound (endo): $^1$H NMR (400 MHz, DMSO-$d_6$): δ 5.03 (d, J=4.0 Hz, 1H), 4.05 (dd, J=9.2, 4.0 Hz, 1H), 3.93 (t, J=4.8 Hz, 1H), 3.87 (t, J=4.0 Hz, 1H), 2.09-1.97 (m, 2H), 1.62-1.52 (m, 1H), 1.49-1.39 (m, 2H), 1.37 (s, 9H), 0.93 (dd, J=12.4, 3.2 Hz, 1H). LCMS: (Method A) 114.3 (M-Boc+H)$^+$, Rt. 3.1 min, 98.2% (ELSD). Second eluting compound (exo): $^1$H NMR (400 MHz, DMSO-$d_6$): δ 4.77 (d, J=3.6 Hz, 1H), 4.01 (t, J=4.4 Hz, 1H), 3.84 (d, J=4.8 Hz, 1H), 3.71 (s, 1H), 1.71-1.66 (m, 1H), 1.61-1.47 (m, 2H), 1.37 (s, 9H), 1.36-1.32 (m, 1H), 1.19 (d, J=8.0 Hz, 2H). LCMS: (Method A) 114.3 (M-Boc+H)$^+$, Rt. 2.9 min, 99% (ELSD).

Step 7: (2-endo)-2-(2-Bromo-5-fluoro-phenoxy)-7-aza-bicyclo[2.2.1]heptane-7-carboxylic acid tert-butyl ester Synthesized following the same procedure as described for Intermediate B2 Step1 using the first eluting alcohol from step 6 and 1-bromo-2,4-difluorobenzene (Matrix Sci.) as starting material. Compound was purified by flash column chromatography (230-400 size mesh) using 3.5-4.0% gradient elution of ethyl acetate in pet ether to afford the pure compound as pale yellow solid (0.75 g, 73%). $^1$H NMR (400 MHz, DMSO-$d_6$): δ 7.61 (dd, J=8.8, 6.4 Hz, 1H), 7.07 (dd, J=10.8, 2.4 Hz, 1H), 6.82-6.77 (dt, J=8.4, 2.8 Hz, 1H), 4.85-4.83 (m, 1H), 4.35 (t, J=4.4 Hz, 1H), 4.11 (t, J=5.2 Hz, 1H), 2.42-2.32 (m, 1H), 2.23-2.17 (m, 1H), 1.73-1.68 (m, 1H), 1.62-1.49 (m, 2H), 1.40 (s, 9H), 1.15 (dd, J=12.0, 3.0 Hz, 1H). LCMS: (Method A) 288.0 (M-Boc+2H)$^+$, Rt. 6.1 min, 98.3% (Max).

Step 8: (2-endo)-2-(2-Carboxy-5-fluoro-phenoxy)-7-aza-bicyclo[2.2.1]heptane-7-carboxylic acid tert-butyl ester The title compound has been synthesized following the same procedure as described for Intermediate B2 step 2, staring from the product of Intermediate B9 step 7. Crude product was taken as such to next step without further purification (0.60 g). LCMS: (Method B) 350.0 (M−H)$^+$, Rt. 3.7 min, 16.4% (Max).

Intermediate C1

(3-chloro-2,4-dimethyl-7H-pyrrolo[3',4':3,4]pyrazolo[1,5-a]pyrimidin-8(9H)-yl)(4-fluoro-2-hydroxyphenyl)methanone

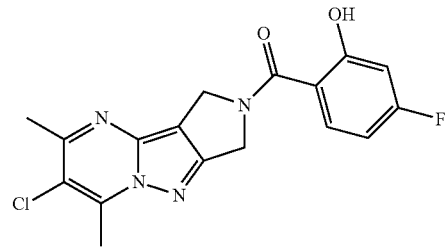 [SMILES: Cc1nc2c3c(nn2c(C)c1Cl)CN(C(=O)c1ccc(F)cc1O)C3]

To a solution of 4-fluoro-2-hydoxy benzoic acid (7.2 g, 46.3 mmol, Combiblock, USA) in DMF (100 mL) was added CDI (8.9 g, 55.5 mmol, Chempure, India). The reaction was stirred at RT for 2 h. Reaction was monitored by TLC. Intermediate A1 (8 g, 30.2 mmol) was added to the reaction mixture followed by DIPEA (10.6 mL, 61 mmol, Spectrochem, India) and the reaction was stirred at RT for 12 h. Reaction was quenched with ice cold water and the precipitated solid was filtered and dried to obtain the title compound as white solid (8 g, 73%). $^1$H NMR (400 MHz, DMSO-$d_6$): δ 10.64 (br s, 1H), 7.33 (s, 1H), 6.74 (t, J=5.32 Hz, 2H), 4.81 (d, J=11.72 Hz, 2H), 4.66 (m, 2H), 2.84 (s, 3H), 2.62 (s, 3H). LCMS: (Method A) 361.0 (M+H)$^+$, Rt. 3.7 min, 98.9% (Max).

Intermediate C2

(3-chloro-2,4-dimethyl-7H-pyrrolo[3',4':3,4]pyrazolo[1,5-a]pyrimidin-8(9H)-yl)(2-hydroxyphenyl)methanone

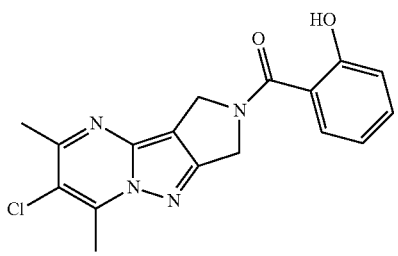 [SMILES: Cc1nc2c3c(nn2c(C)c1Cl)CN(C(=O)c1ccccc1O)C3]

To a mixture of Intermediate A1 (10 g, 38.59 mmol), salicylic acid (9.59 g, 69.46 mmol, Qualigens, India) and N,N-diisopropylethylamine (26.3 mL, 154.3 mmol, Spectrochem, India) in DMF (100 mL), HATU (22 g, 57.8 mmol, Chempure) was added portion-wise. The resulting mixture was stirred at RT for 12 h. After completion of the reaction, the mixture was concentrated under reduced pressure and diluted with ethyl acetate (600 mL). The organic phase was washed with 10% aqueous $NaHCO_3$ solution (50 mL×3), water and brine. The organic layer was dried over anhydrous sodium sulphate and evaporated. The crude product was recrystallized from ethyl acetate, filtered and dried affording the title compound as white solid (7.5 g, 57%). $^1$H NMR (400 MHz, DMSO-$d_6$): δ 10.05 (brs, 1H), 7.30-7.26 (m, 2H), 6.95-6.85 (m, 2H), 4.78 (br s, 2H), 4.59 (br s, 2H), 2.83, 2.79 (s, 3H), 2.61, 2.54 (s, 3H). LCMS: (Method A) 343.0 $(M+H)^+$, Rt. 4.7 min, 94.7% (Max).

Intermediate C3

(3-chloro-7H-pyrrolo[3',4':3,4]pyrazolo[1,5-a]pyrimidin-8(9H)-yl)4-flouro-2-hydroxyphenyl)methanone

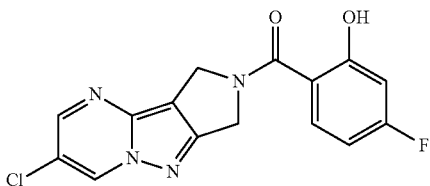 [SMILES: O=C(c1ccc(F)cc1O)N1Cc2nn3cc(Cl)cnc3c2C1]

To a stirred solution of 4-fluoro-2-hydoxy benzoic acid (1.0 g, 6.49 mmol, Combiblock) in DMF (20 mL) was added CDI (1.3 g, 1.2 mmol, Chempure). The reaction was stirred at RT for 2 h.

Intermediate A2 (1 g, 4.33 mmol) was added to the reaction mixture followed by DIPEA (2.3 mL, 13.0 mmol, Spectrochem) and the reaction was stirred at RT for 12 h. Reaction was quenched with ice cold water and the precipitated solid was filtered and dried to obtain the title compound as pale yellow solid (700 mg, 48%). $^1$H NMR (400 MHz, DMSO-$d_6$): δ 10.66-10.62 (m, 1H), 9.60 (d, J=4.8 Hz, 1H), 8.64-8.60 (m, 1H), 7.34 (s, 1H), 6.74 (d, J=9.8 Hz, 2H), 4.84 (s, 2H), 4.69-4.66 (m, 2H). LCMS: (Method A) 333.0 $(M+H)^+$, Rt. 3.2 min, 99.6% (Max).

Example 1

(anti)-(3-chloro-2,4-dimethyl-7H-pyrrolo[3',4':3,4]pyrazolo[1,5-a]pyrimidin-8(9H)-yl)(4-flouro-2-(-3-fluoropiperidin-4-yl)oxy)phenyl)methanone

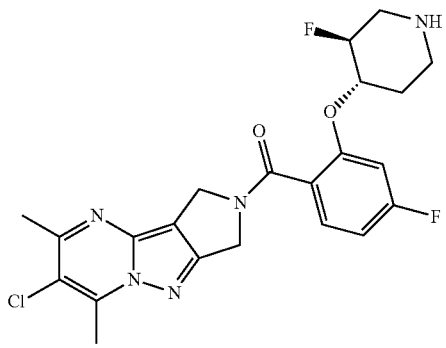 [SMILES: Cc1nc2c3c(nn2c(C)c1Cl)CN(C(=O)c1ccc(F)cc1O[C@H]1CCNC[C@@H]1F)C3]

Step 1: (anti)-3-fluoro-4-hydroxy-piperidine-1-carboxylic acid tert-butyl ester and (syn)-3-Fluoro-4-hydroxy-piperidine-1-carboxylic acid tert-butyl ester To a stirred solution of N-Boc-5-fluoro piperidine-4-one (2 g, 9.21 mmol, Combiblock, USA) in methanol (20 mL) at 0° C. was added sodium borohydride (696 mg, 18.41 mmol) portion wise. The reaction mixture was then stirred at RT for 4 h. The solvent was evaporated and the crude product was dissolved in DCM (20 mL). The organic layer was washed with water, brine solution and dried over anhydrous $Na_2SO_4$ and evaporated. The crude product was purified by silica gel (230-400) flash column chromatography to get two diastereomers with a gradient n-Hexane:Ethyl acetate (70:30 and then 60:40) as eluent. Based on the patent WO2010/128414 (2010), the first eluting product was assigned to anti isomer and the second eluting product was assigned to syn isomer. Both isomers were isolated as mixture of enantiomers.

(anti)-3-fluoro-4-hydroxy-piperidine-1-carboxylic acid tert-butyl ester: white solid (480 mg, 24%).
$^1$H NMR (400 MHz, $CDCl_3$): δ 4.37-4.14 (m, 2H), 3.94-3.91 (m, 1H), 3.87-3.78 (m, 1H), 2.97-2.90 (m, 2H), 2.06-1.98 (m, 1H), 1.59-1.50 (m, 2H), 1.47 (s, 9H). LCMS: (Method A) 120.3 $(M-Boc+H)^+$, Rt. 3.0 min, 99.6% (ELSD).

(syn)-3-fluoro-4-hydroxy-piperidine-1-carboxylic acid tert-butyl ester: white solid (1150 mg, 56%).
$^1$H NMR (400 MHz, $CDCl_3$): δ 4.68-4.54 (m, 1H), 3.93-3.91 (m, 2H), 3.85-3.58 (m, 1H), 3.52-3.31 (m, 1H), 3.28-3.08 (m, 1H), 1.89-1.77 (m, 2H), 1.47 (s, 9H). LCMS: (Method A) 120.3 $(M-Boc+H)^+$, Rt. 2.7 min, 99.5% (ELSD).

Step 2: (syn)-3-fluoro-4-((methylsulfonyl)oxy)piperidine-1-carboxylic acid tert-butyl ester To a stirred solution of (syn)-3-fluoro-4-hydroxy-piperidine-1-carboxylic acid tert-butyl ester (750 mg, 3.42 mmol)

in DCM (20 mL) at 0° C. was added triethyl amine (519 mg, 5.13 mmol, Spectrochem) and methane sulfonyl chloride (157 mg, 4.11 mmol, Spectrochem). Reaction mixture was brought to RT and stirred for 1 h. Reaction mixture was diluted with DCM (20 mL), washed with water, dried over anhydrous $Na_2SO_4$ and evaporated. The crude product was isolated as white solid and taken for next step without any further purification (970 mg, 95%). $^1$H NMR (400 MHz, $CDCl_3$): δ 4.93-4.80 (m, 1H), 4.65-4.63 (m, 1H), 3.67-3.38 (m, 4H), 3.15 (s, 3H), 2.19-2.11 (m, 1H), 1.90-1.68 (m, 1H), 1.47 (s, 9H). LCMS: (Method A) 198.2 (M-Boc+H)$^+$, Rt. 3.9 min, 99.1% (ELSD).

Step 3: (anti)-4-(2-(3-chloro-2,4-dimethyl-8,9-dihydro-7H-pyrrolo[3',4':3,4]pyrazolo[1,5-a]pyrimidine-8-carbonyl)-5-fluorophenoxy)-3-fluoropiperidine-1-carboxylic acid tert-butyl ester To stirred solution of Intermediate C1 (444 mg, 1.23 mmol) in DMF (10 mL) was added cesium carbonate (803 mg, 2.46 mmol) and (syn)-3-fluoro-4-((methylsulfonyl)oxy)piperidine-1-carboxylic acid tert-butyl ester from Step 2 (550 mg, 1.85 mmol). The reaction mixture was heated to 150° C. in MW for 6 h. The solvent was evaporated and the residue was dissolved in DCM (10 mL), washed with water, brine solution, dried over anhydrous $Na_2SO_4$ and evaporated. The crude product was isolated as brown semi solid and was taken for next step without any further purification (500 mg, 54%). LCMS: (Method A) 462.0 (M-Boc+H)$^+$, Rt. 5.2 min, 43% (Max).

Step 4: (anti)-(3-chloro-2,4-dimethyl-7H-pyrrolo[3',4':3,4]pyrazolo[1,5-a]pyrimidin-8(9H)-yl)(4-fluoro-2-(-3-fluoropiperidin-4-yl)oxy)phenyl)methanone To a stirred solution of 4-[2-(6-Chloro-5,7-dimethyl-1H,3H-2,4,7a,8-tetraaza-cyclopenta[a]indene-2-carbonyl)-5-fluoro-phenoxy]-3-fluoro-piperidine-1-carboxylic acid tert-butyl ester (500 mg, 0.09 mmol) in dioxane (10 mL) at 10° C. was added HCl in dioxane (1 M, 10 mL). Reaction mixture was then stirred at RT for 2 h. The solvent was evaporated. The crude product was dissolved in water, washed with ethyl acetate (3×50 ml). The aqueous layer was basified up to pH 8 with $NaHCO_3$, the product was extracted with DCM (20 mL×3), dried over anhydrous $Na_2SO_4$ and evaporated. The crude product was purified by silica gel (230-400) flash column chromatography using MeOH/DCM gradient as eluent to afford the title product as off white solid as mixture of two enantiomers. $^1$H NMR (400 MHz, DMSO-d$_6$): δ 7.38-7.33 (m, 1H), 7.24 (d, J=11.60 Hz, 1H), 6.89 (dd, J=8.40, 2.00 Hz, 1H), 4.83-4.80 (m, 2H), 4.66-4.43 (m, 5H), 3.17-3.16 (m, 1H), 3.09-3.08 (m, 1H), 2.84-2.76 (m, 4H), 2.67-2.50 (m, 4H), 2.15-2.05 (m, 1H), 1.36-1.33 (m, 1H). LCMS: (Method A) 462.0 (M+H)$^+$, Rt. 3.3 min, 98.2% (Max). HPLC: (Method A) Rt 3.3 min, 98.8% (Max).

Example 2

(anti)-(3-chloro-2,4-dimethyl-7H-pyrrolo[3',4':3,4]pyrazolo[1,5-a]pyrimidin-8(9H)-yl)(4-fluoro-2-((-3-fluoro-1-methylpiperidin-4-yl)oxy)phenyl)methanone

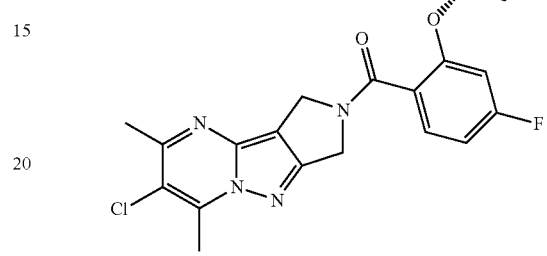

To a stirred solution of Example 1 (40 mg, 0.09 mmol) in dichloroethane (10 mL) at 0° C. was added paraformaldehyde (16 mg, 0.18 mmol, Spectrochem), triethyl amine (18 mg, 0.18 mmol, Spectrochem) and sodium triacetoxy borohydride (37 mg, 0.18 mmol). Trimethyl ortho formate (0.5 mL, Spectrochem) was added to the reaction mixture. The reaction mixture was stirred at RT for 24 h. The solvent was evaporated and the residue was dissolved in DCM (10 mL). The organic layer was washed with water, brine solution, dried over anhydrous $Na_2SO_4$ and evaporated. The crude product was triturated with diethyl ether to afford the title product as off white solid as mixture of two enantiomers. $^1$H NMR (400 MHz, DMSO-d$_6$): δ 7.40-7.35 (m, 1H), 7.27-7.24 (m, 1H), 6.93-6.89 (m, 1H), 4.84-4.82 (m, 2H), 4.60-4.45 (m, 4H), 2.85-2.81 (m, 4H), 2.63-2.51 (m, 4H), 2.19-2.10 (m, 6H), 1.52-1.48 (m, 1H). LCMS: (Method A) 476.2 (M+H)$^+$, Rt. 3.3 min, 99.2% (Max). HPLC: (Method A) Rt 3.3 min, 98.7% (Max).

Example 4

(anti)-(6-Chloro-5,7-dimethyl-1H,3H-2,4,7a,8-tetraaza-cyclopenta[a]inden-2-yl)-[2-(4-hydroxy-pyrrolidin-3-yloxy)-phenyl]-methanone

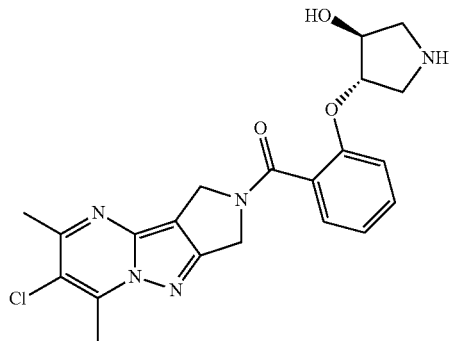 [SMILES: Cc1nc2c3c(nn2c(C)c1Cl)CN(C(=O)c1ccccc1O[C@H]1CNC[C@@H]1O)C3]

Step 1: (anti)-3-[2-(6-Chloro-5,7-dimethyl-1H,3H-2,4,7a,8-tetraaza-cyclopenta[a]indene-2-carbonyl)-phenoxy]-4-hydroxy-pyrrolidine-1-carboxylic acid tert-butyl ester To a stirred solution of Intermediate C2 (0.25 g, 0.73 mmol) in dry N,N-dimethylformamide (5 mL) was added cesium carbonate (0.95 g, 2.92 mmol, Chempure) under $N_2$ atmosphere and the reaction mixture was stirred at 60° C. for 1 h. After 1 h, tert-butyl 6-oxa-3-azabicyclo [3.1.0] hexane-3-carboxylate (0.14 g, 0.804 mmol) was added to the reaction mixture and allowed to stir at 80° C. for 18 h. After completion, the reaction mass was filtered through celite and concentrated under vacuum. Residue obtained was diluted with ethyl acetate (10 mL), washed with water, brine solution and dried over anhydrous $Na_2SO_4$. Organic phase was concentrated. The crude product was purified by flash column chromatography (230-400 size mesh) (silica gel, pet ether/ethyl acetate as gradient elution), affording the title product as brown gum as mixture of two enantiomers. $^1$H NMR 400 MHz, DMSO-$d_6$: δ 7.45 (t, J=4.00 Hz, 1H), 7.32 (t, J=4.00 Hz, 1H), 7.24 (d, J=8.00 Hz, 1H), 7.10 (t, J=8.00 Hz, 1H), 5.45 (d, J=12.00 Hz, 1H), 4.48-4.79 (m, 2H), 4.43-4.45 (m, 2H), 4.01-4.12 (m, 2H), 3.54-3.56 (m, 1H), 3.13-3.20 (m, 2H), 2.84 (s, 1.5H), 2.80 (s, 1.5H), 2.67 (s, 1.5H), 2.62 (s, 1.5H), 1.38 (s, 9H). LCMS: (Method A) 428.0 (M-Boc+H)$^+$, Rt. 5.51 min, 92.31%, (Max).

Step 2: (anti)-(6-Chloro-5,7-dimethyl-1H,3H-2,4,7a,8-tetraaza-cyclopenta[a]inden-2-yl)-[2-(4-hydroxy-pyrrolidin-3-yloxy)-phenyl]-methanone To a stirred solution of (anti)-3-[2-(6-Chloro-5,7-dimethyl-1H,3H-2,4,7a,8-tetraaza-cyclopenta[a]indene-2-carbonyl)-phenoxy]-4-hydroxy-pyrrolidine-1-carboxylic acid tert-butyl ester (0.13 g, 0.0246 mmol) in dioxane (2 mL) at 0° C. was added HCl in dioxane (1M, 5 mL). Reaction mass was brought to RT and stirred for 2 h. Reaction mass was concentrated and the crude product was purified by MD Auto-prep (Method A), yielding the title compound as brown solid as mixture of two enantiomers. $^1$H NMR 400 MHz, DMSO-$d_6$: δ 7.43 (t, J=12.00 Hz, 1H), 7.29 (t, J=8.00 Hz, 1H), 7.20 (d, J=8.00 Hz, 1H), 7.04 (t, J=12.00 Hz, 1H), 5.16 (s, 1H), 4.80 (d, J=12.00 Hz, 2H), 4.47-4.54 (m, 3H), 3.99 (s, 1H), 3.18-3.24 (m, 1H), 2.88-2.93 (m, 1H), 2.82 (s, 1.5H), 2.79 (s, 1.5H), 2.72 (s, 1H), 2.64 (s, 1H), 2.54-2.60 (m, 4H). LCMS: (Method A) 428.0 (M+H)$^+$, Rt. 2.97 min, 95.12% (Max). HPLC: (Method A) Rt 3.00 min, 96.00% (Max).

Example 5

(anti) (6-Chloro-5,7-dimethyl-1H,3H-2,4,7a8-tetraaza-cyclopenta[a]inden-2-yl)-[2-((3S,4S)-3-hydroxy-piperidin-4-yloxy)-phenyl]-methanone

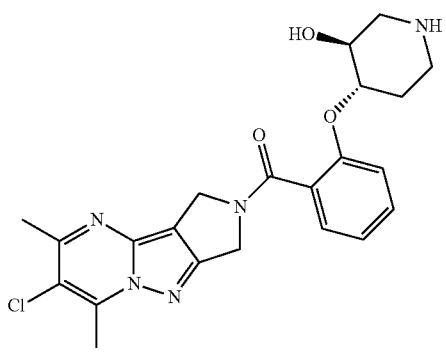 [SMILES: Cc1nc2c3c(nn2c(C)c1Cl)CN(C(=O)c1ccccc1O[C@H]1CCNC[C@@H]1O)C3]

Step 1: (anti)-4-[2-(6-Chloro-5,7-dimethyl-1H,3H-2,4,7a,8-tetraaza-cyclopenta[a]indene-2-carbonyl)-phenoxy]-3-hydroxy-piperidine-1-carboxylic acid tert-butyl ester A 20 mL microwave vial was charged with Intermediate C2 (1 g, 2.93 mmol), tert-butyl 7-oxa-3-azabicyclo[4.1.0]heptane-3-carboxylate (1.16 g, 5.84 mmol) and CsF (44.4 mg, 0.292 mmol) in DMF (10 mL). The capped vial was irradiated in a microwave reactor at 150° C. for 2 h. After completion of the reaction, the mixture was concentrated under reduced pressure and diluted with ethyl acetate (30 mL). The organic phase was washed with water and brine. The organic layer was dried over anhydrous sodium sulphate and evaporated. The crude product was purified by column chromatography (neutral alumina, ethyl acetate/pet ether gradient elution). The mixtures of isomers formed were separated by SFC preparative HPLC (Column: Lux C1, Solvent: 20% MeOH, Flow rate: MeOH 10 mL/min, $CO_2$ 40 mL/min). The title product corresponds to the second eluting product in SFC separation and was isolated as off white solid. The compound is a single isomer as mixture of two enantiomers. $^1$H NMR (400 MHz, DMSO-$d_6$): δ 7.42 (t, J=12 Hz, 1H), 7.31 (d, J=3.4 Hz, 1H), 7.26 (d, J=8.4 Hz, 1H), 7.04 (t, J=12 Hz, 1H), 5.28 (s, 1H), 4.84-4.68 (m, 3H), 4.50-4.32 (m, 2H), 3.59 (br s, 1H), 3.47 (br s, 1H), 3.40 (br s, 1H), 3.11-3.06 (m, 1H), 2.93-2.91 (m, 1H), 2.83 (s, 1.7H), 2.79 (s, 1.3H), 2.61 (s, 1.5H), 2.54 (s, 1.5H), 2.01-1.99 (m, 1H), 1.40-1.36 (m, 1H), 1.32 (s, 9H). LCMS: (Method A) 542.2 (M+H)$^+$, Rt. 4.5 min, 95.9% (Max).

Step 2: (anti) (6-Chloro-5,7-dimethyl-1H,3H-2,4,7a,8-tetraaza-cyclopenta[a]inden-2-yl)-[2-((3S,4S)-3-hydroxy-piperidin-4-yloxy)-phenyl]-methanone To (anti)-4-[2-(6-Chloro-5,7-dimethyl-1H,3H-2,4,7a,8-tetraaza-cyclopenta[a]indene-2-carbonyl)-phenoxy]-3-hydroxy-piperidine-1-carboxylic acid tert-butyl ester from Step 1 (80 mg, 0.1478 mmol), HCl solution in 1,4-dioxane (1M, 3 mL) was added drop-wise at 0° C. The resulting mixture was stirred at RT for 4 h. After completion of the reaction, the mixture was concentrated under reduced pressure to afford product as hydrochloride salt. It was dissolved in dichloromethane-methanol (98:2) mixture (6 mL) and neutralized with solid NaHCO$_3$(250 mg). The mixture was then filtered through celite bed. The solvent was evaporated under reduced pressure to afford the title product as off white solid (41.9 mg; 64.4%). The compound is a single isomer as a mixture of two enantiomers. $^1$H NMR (400 MHz, DMSO-d$_6$): δ 7.43-7.39 (m, 1H), 7.30 (s, 1H), 7.24 (d, J=8.4 Hz, 1H), 7.02 (t, J=12 Hz, 1H), 4.95 (s, 1H), 4.89-4.77 (m, 3H), 4.45 (s, 1H), 4.17-4.11 (m, 1H), 2.90-2.74 (m, 5H), 2.62 (s, 1.4H), 2.61 (s, 1.6H), 2.45-2.42 (m, 1H), 2.30-2.28 (m, 1H), 2.00-1.97 (m, 2H), 1.41-1.35 (m, 1H). LCMS: (Method A) 442.0 (M+H)$^+$, Rt. 3.0 min, 99.5% (Max). HPLC: (Method A) Rt 3.1 min, 99.6% (Max).

Example 6

(3-chloro-2,4-dimethyl-7H-pyrrolo[3',4':3,4]pyrazolo[1,5-a]pyrimidin-8(9H)-yl)(2-(1-(piperazin-1-yl)ethyl)phenyl)methanone

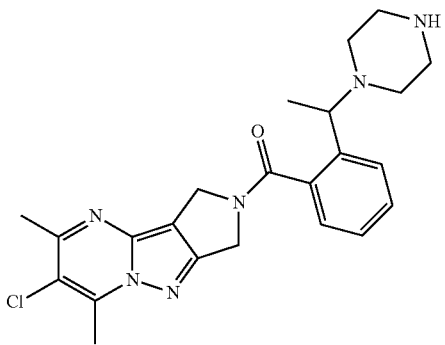 [SMILES: Cc1nc2c3c(nn2c(C)c1Cl)CN(C(=O)c1ccccc1C(C)N1CCNCC1)C3]

Step 1: 1-(2-(3-chloro-2,4-dimethyl-8,9-dihydro-7H-pyrrolo[3',4':3,4]pyrazolo[1,5-a]pyrimidine-8-carbonyl)phenyl)ethan-1-one To a stirred solution of Intermediate A1 (1.0 g, 3.85 mmol) and 2-acetylbenzoic acid (0.7 g, 4.24 mmol, Alfa Acer) in DCM (20 mL) was added tri ethylamine (1.7 mL, 11.5 mmol, Spectrochem) followed by T$_3$P (3.7 mL, 5.78 mmol) at 0° C. The reaction mixture was stirred at RT for 2 h. Reaction completion was monitored by LCMS. DCM was evaporated under vacuum. The resulting solid was washed with water. The crude product was triturated with n-hexanes and dried under vacuum, affording the title product as white solid (1 g, 79%). $^1$H NMR (400 MHz, DMSO-d$_6$): δ 8.05 (d, J=10.2 Hz, 1H), 7.72-7.58 (m, 2H), 7.49-7.46 (m, 1H), 4.84 (s, 1H), 4.82 (s, 1H), 4.42 (s, 1H), 4.37 (s, 1H) 2.85 (s, 1.5H), 2.80 (s, 1.5H), 2.63 (s, 1.5H), 2.57 (m, 4.5H). LCMS: (Method A) 369.0 (M+H)$^+$, Rt. 3.5 min, 99.2% (Max).

Step 2: (3-chloro-2,4-dimethyl-7H-pyrrolo[3',4':3,4]pyrazolo[1,5-a]pyrimidin-8(9H)-yl)(2-(1-hydroxyethyl)phenyl)methanone To a stirred solution of 1-(2-(3-chloro-2,4-dimethyl-8,9-dihydro-7H-pyrrolo [3',4':3,4]pyrazolo[1,5-a]pyrimidine-8-carbonyl)phenyl)ethan-1-one (0.4 g, 1.08 mmol) in THF/MeOH (3:1, 20 mL) was added sodium borohydride (0.04 g, 1.08 mmol) slowly at 0° C. The reaction mixture was stirred at 0° C. for 2 h. Reaction completion was monitored by TLC. The reaction was quenched by addition of saturated ammonium chloride solution (10 mL). The solvents were evaporated under vacuum and the residue obtained was diluted with water and extracted with dichloromethane (2×50 mL). The combined extract was washed with water, brine solution and dried over anhydrous Na$_2$SO$_4$ and evaporated. The crude product obtained as white solid was used as such for next step without further purification (0.3 g, 87%). $^1$H NMR (400 MHz, DMSO-d$_6$): δ 7.62 (dd, J$_1$=8.0 Hz, J$_2$=3.6 Hz, 1H), 7.47-7.44 (m, 1H), 7.34 (t, J=6.8 Hz, 2H), 5.17 (d, J=2.0 Hz, 1H), 4.88-4.49 (m, 3H), 4.61-4.40 (m, 2H), 2.84 (m, 3H), 2.62 (s, 3H), 1.30-1.37 (m, 3H). LCMS: (Method A) 371.0 (M+H)$^+$, Rt. 3.4 min, 77.2% (Max).

Step 3: (3-chloro-2,4-dimethyl-7H-pyrrolo[3',4':3,4]pyrazolo[1,5-a]pyrimidin-8(9H)-yl)(2-(1-chloroethyl)phenyl)methanone To a stirred solution of (3-chloro-2,4-dimethyl-7H-pyrrolo[3',4':3,4]pyrazolo[1,5-a]pyrimidin-8(9H)-yl)(2-(1-hydroxyethyl)phenyl)methanone (0.35 g, 0.94 mmol) in DCM (20 mL) was added thionyl chloride (0.1 mL, 4.71 mmol, Spectrochem) at 0° C. The reaction mixture was stirred at 0° C. for 1 h. Reaction completion was monitored by TLC. Reaction solvent was removed under vacuum at RT and the residue obtained was (2×5 mL), washed with ether. The crude product isolated as orange solid was used as such for next step without further purification (0.3 g, 97%). $^1$H NMR (400 MHz, DMSO-d$_6$): δ 7.70 (d, J=7.8 Hz, 1H), 7.58-7.46 (m, 3H), 4.95-4.86 (m, 2H), 4.61-4.28 (m, 3H), 2.85, 2.80 (s, 3H), 2.63 (s, 3H), 1.83-1.81 (m, 3H). LCMS: (Method A) 389.0 (M+H)$^+$, Rt. 4.7 min, 85.8% (Max).

Step 4: tert-butyl4-(1-(2-(3-chloro-2,4-dimethyl-8,9-dihydro-7H-pyrrolo[3',4':3,4]pyrazolo[1,5-a]pyrimidine-8-carbonyl)phenyl)ethyl)piperazine-1-carboxylate To a stirred solution of (3-chloro-2,4-dimethyl-7H-pyrrolo[3',4':3,4]pyrazolo[1,5-a]pyrimidin-8(9H)-yl) (2-(1-chloroethyl)phenyl)methanone (0.35 g, 0.89 mmol) in ACN (20 mL) was added N-boc-piperazine (0.33 g, 1.79 mmol, Combiblock) and dry potassium carbonate (0.37 g, 2.69 mmol, Ranchem). The reaction mixture was refluxed at 85° C. for 4 h. Reaction completion was monitored by TLC. Reaction solvent was removed under vacuum and the residue obtained was diluted with water (10 mL) and extracted in dichloromethane (2×50 mL). The combined extract was washed with water, brine solution and dried over anhydrous Na$_2$SO$_4$. The crude product isolated as brown fum was used as such for next step without further purification (0.3 mg, 72%). LCMS: (Method A) 539.0 (M+H)$^+$, Rt. 3.9 min, 66.6% (Max).

Step 5: (3-chloro-2,4-dimethyl-7H-pyrrolo[3',4':3,4]pyrazolo[1,5-a]pyrimidin-8(9H)-yl)(2-(1-(piperazin-1-yl)ethyl)phenyl)methanone To a stirred solution of tert-butyl4-(1-(2-(3-chloro-2,4-dimethyl-8,9-dihydro-7H-pyrrolo[3',4':3,4]pyrazolo[1,5-a]pyrimidine-8-carbonyl)phenyl)ethyl)piperazine-1-carboxylate (0.35 g, 0.89 mmol), HCl in dioxane (2 N, 5 mL) was added at 0° C. Reaction was stirred at RT for 1 h. Reaction completion was monitored by TLC. Reaction solvent was removed under vacuum and the residue obtained was washed with ether, purified by MD Auto-prep, affording the title compound as pale yellow solid. $^1$H NMR (400 MHz, DMSO-d$_6$): δ 7.47 (m, 3H), 7.36 (d, J=6.8 Hz, 1H), 4.93-4.89 (m, 1H), 4.83-4.74 (m, 1H), 4.69-4.61 (m, 1H), 4.46-

4.37 (m, 1H), 3.88 (s, 1H), 2.86 (s, 1.5H), 2.81 (s, 1.5H), 2.63 (s, 1.5H), 2.51 (s, 1.5H), 2.33-2.37 (m, 4H), 2.26 (d, J=9.2 Hz, 4H), 1.26 (d, J=6.8 Hz, 3H). LCMS: (Method A) 439.2 (M+H)$^+$, Rt. 2.7 min, 98.2% (Max). HPLC: (Method A) Rt. 2.7 min, 98.6% (Max).

Example 7

(3-chloro-2,4-dimethyl-7H-pyrrolo[3',4':3,4]pyrazolo[1,5-a]pyrimidin-8(9H)-yl)(2-(1-(4-methylpiperazin-1-yl)ethyl)phenyl)methanone

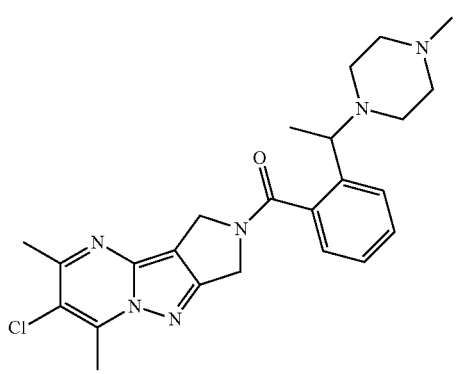

To a stirred solution of (3-chloro-2,4-dimethyl-7H-pyrrolo[3',4':3,4]pyrazolo[1,5-a]pyrimidin-8(9H)-yl) (2-(1-chloroethyl)phenyl)methanone (0.5 g, 1.28 mmol) in ACN (20 mL) was added N-methyl-piperazine (0.25 g, 2.56 mmol, Spectrochem) and dry potassium carbonate (0.6 g, 3.85 mmol, Ranchem). The reaction mixture was refluxed at 85° C. for 4 h. Reaction completion was monitored by TLC. Reaction solvent was removed under vacuum the residue obtained was diluted with water and extracted in dichloromethane (2×50 mL). The combined extract was washed with water, brine solution and dried over anhydrous Na$_2$SO$_4$, purified by Prep-HPLC (Method), affording the title compound as yellow solid. $^1$H NMR (400 MHz, DMSO-d$_6$): δ 7.45-7.35 (m, 4H), 4.97 (d, J=11.8 Hz, 1H), 4.81-4.77 (m, 1H), 4.68-4.63 (m, 1H), 4.38 (s, 1H), 3.88 (s, 1H), 2.86 (s, 1.6H), 2.81 (s, 1.4H), 2.63 (s, 1.6H), 2.55 (s, 1.4H), 2.33-2.28 (m, 5H), 2.00-1.96 (m, 3H), 1.64-1.71 (m, 3H), 1.25 (d, J=6.4 Hz, 3H). LCMS: (Method A) 453.2 (M+H)$^+$, Rt. 2.8 min, 98.3% (Max). HPLC: (Method A) Rt. 2.9 min, 97.17% (Max).

Example 8

(anti)-(6-Chloro-5,7-dimethyl-1H,3H-2,4,7a,8-tetraaza-cyclopenta[a]inden-2-yl)-[2-(2-hydroxy-cyclopentyloxy)-phenyl]-methanone

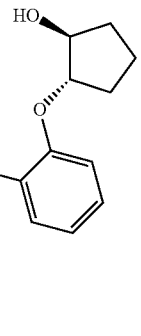

To a stirred solution of Intermediate C2 (0.25 g, 0.73 mmol) in dry N,N-dimethylformamide (5 mL) was added cesium carbonate (0.95 g, 2.92 mmol) under N$_2$ atmosphere and the reaction mixture was stirred at 60° C. for 1 h. After 1 h, 6-oxa-bicyclo[3.1.0]hexane (0.12 g, 1.46 mmol) was added to the reaction mixture and allowed to stir at 80° C. for 18 h. After completion of the reaction, the reaction mass was filtered through water, brine solution and dried over anhydrous Na$_2$SO$_4$. Organic phase was concentrated and the crude celite and concentrated under vacuum. Residue obtained was diluted with ethyl acetate (10 mL), washed with product was purified by MD Auto-prep (Method A), affording the title compound as mixture of enantiomers as white solid. $^1$H NMR (400 MHz, DMSO-d$_6$): δ 7.45-7.40 (m, 1H), 7.29-7.26 (m, 1H), 7.19 (d, J=12.00 Hz, 1H), 7.02 (t, J=12.00 Hz, 1H), 4.95-4.92 (m, 1H), 4.79 (d, J=8.00 Hz, 2H), 4.57-4.41 (m, 3H), 3.96 (s, 1H), 2.81 (s, 1.4H) 2.79 (s, 1.6H), 2.60 (s, 1.4H), 2.54 (s, 1.6H), 2.06-2.00 (m, 1H), 1.69-1.59 (m, 2H), 1.56-1.42 (m, 3H). LCMS: (Method A) 427.0 (M+H)$^+$, Rt. 3.87 min, 99.51% (Max). HPLC: (Method A) Rt. 3.81 min, 98.81% (Max).

Example 9

(anti)-(6-Chloro-5-ethyl-7-methyl-1H,3H-2,4,7a,8-tetraaza-cyclopenta[a]inden-2-yl)-[2-(2-hydroxy-cyclopentyloxy)-phenyl]-methanone or (anti)-(6-Chloro-5-methyl-7-ethyl-1H,3H-2,4,7a,8-tetraaza-cyclopenta[a]inden-2-yl)-[2-(2-hydroxy-cyclopentyloxy)-phenyl]-methanone

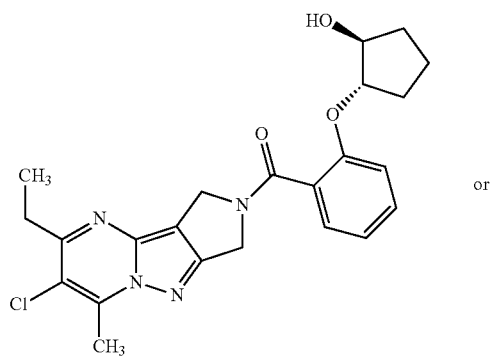 or

-continued

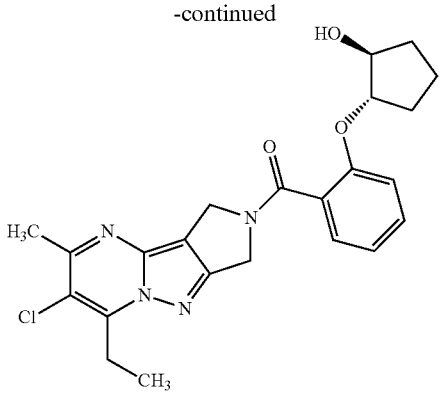

To a stirred solution of Example 8 (0.1 g, 0.23 mmol) in dry N,N-dimethylformamide (5 mL) was added sodium hydride (0.095 g, 0.704 mmol) under $N_2$ atmosphere and the reaction mixture was stirred at 0° C. for 30 min. After 30 min, methyl iodide (0.066 g, 0.46 mmol) was added to the reaction mixture and allowed to stir at RT for 2 h. After completion, the reaction mass was quenched with ice and concentrated the reaction mixture. The residue obtained was diluted with ethyl acetate (10 mL), washed with water, brine solution and dried over anhydrous $Na_2SO_4$. Organic phase was concentrated. The crude product was purified by MD Auto-Prep (Method A), affording the title compound as off white solid. The final structure was confirmed by NOE study and position of ethyl group was assigned to the position 5 or 7 of the pyrimidine ring. $^1$H NMR (400 MHz, DMSO-$d_6$): δ 7.43 (t, J=8.0 Hz, 1H), 7.29-7.26 (m, 1H), 7.19 (d, J=8.0 Hz, 1H), 7.03 (t, J=12.0 Hz, 1H), 4.94 (s, 1H), 4.80 (d, J=12.0 Hz, 2H), 4.53-4.49 (m, 3H), 3.97 (s, 1H), 3.29-3.27 (m, 2H), 2.61-2.55 (m, 3H), 3.04 (d, J=8.0 Hz, 1H), 1.67-1.61 (m, 2H), 1.54-1.51 (m, 2H), 1.44-1.40 (m, 1H), 1.30-1.22 (m, 3H). LCMS: (Method A) 441.2 (M+H)$^+$, Rt. 4.26 min, 98.3% (Max). HPLC: (Method A) Rt. 3.27 min, 95.7% (Max).

Example 10

(anti)-(6-Chloro-5-ethyl-7-methyl-1H,3H-2,4,7a,8-tetraaza-cyclopenta[a]inden-2-yl)-[2-(4-hydroxy-pyrrolidin-3-yl oxy)-phenyl]-methanone or (anti)-(6-Chloro-5-methyl-7-ethyl-1H,3H-2,4,7a,8-tetraaza-cyclopenta[a]inden-2-yl)-[2-(4-hydroxy-pyrrolidin-3-yl oxy)-phenyl]-methanone

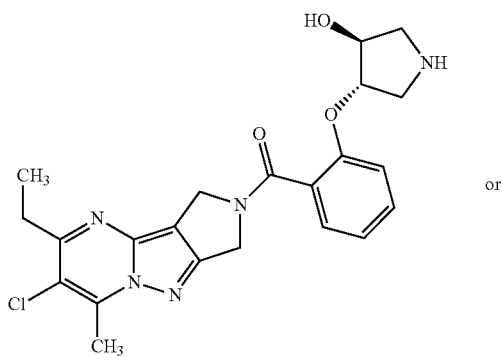

or

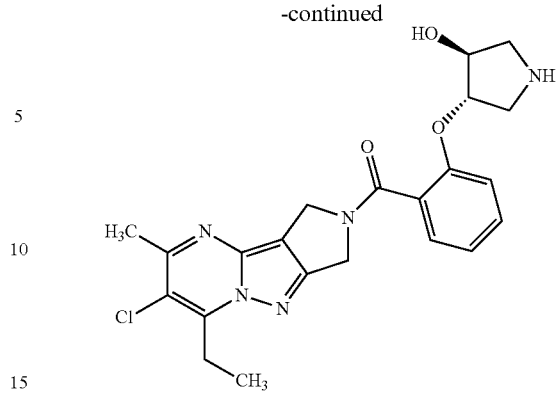

Step 1: (anti)-3-[2-(6-Chloro-5-ethyl-7-methyl-1H,3H-2,4,7a,8-tetraaza-cyclopenta[a]indene-2-carbonyl)-phenoxy]-4-hydroxy-pyrrolidine-1-carboxylicacid tert-butyl ester or (anti)-3-[2-(6-Chloro-5-methyl-7-ethyl-1H,3H-2,4,7a,8-tetraaza-cyclopenta[a]indene-2-carbonyl)-phenoxy]-4-hydroxy-pyrrolidine-1-carboxylicacid tert-butyl ester The title compound was prepared accrodong to the protocol described for Example 9, starting from the product of Example 4, step 1. It was isolated as brown solid. The structure of the final compound was confirmed by NMR studies and the position of ethyl group was assigned to the position 5 or 7 of the pyrimidine ring. $^1$H NMR (400 MHz, DMSO-$d_6$): δ 7.46 (t, J=8.0 Hz, 1H), 7.31 (t, J=12.0 Hz, 1H), 7.23 (d, J=12.0 Hz, 1H), 7.09 (t, J=8.0 Hz, 1H), 5.45 (s, 1H), 4.79-4.71 (m, 3H), 4.45 (d, J=12.0 Hz, 1H), 4.01 (t, J=8.0 Hz, 3H), 3.65-3.62 (m, 1H), 3.263.23 (m, 3H), 2.60-2.53 (m, 4H), 1.38 (m, 12H). LCMS: (Method A) 442.2 (M-Boc+H)$^+$, Rt. 4.59 min, 90.5% (Max).

Step 2: (anti-(6-Chloro-5-ethyl-7-methyl-1H,3H-2,4,7a,8-tetraaza-cyclopenta[a]inden-2-yl)-[2-(4-hydroxy-pyrrolidin-3-yl oxy)-phenyl]-methanone or (anti)-(6-Chloro-5-methyl-7-ethyl-1H,3H-2,4,7a,8-tetraaza-cyclopenta[a]inden-2-yl)-[2-(4-hydroxy-pyrrolidin-3-yl oxy)-phenyl]-methanone To a stirred solution of (anti)-3-[2-(6-Chloro-5-ethyl-7-methyl-1H,3H-2,4,7a,8-tetraaza-cyclopenta[a]indene-2-carbonyl)-phenoxy]-4-hydroxy-pyrrolidine-1-carboxylicacid tert-butyl ester or (anti)-3[2-(6-Chloro-5-methyl-7-ethyl-1H,3H-2,4,7a,8-tetraaza-cyclopenta[a]indene-2-carbonyl)-phenoxy]-4-hydroxy-pyrrolidine-1-carboxylicacid tert-butyl ester (0.26 g, 0.048 mmol), HCl in dioxane (2N, 5 mL) was added at 0° C. The reaction mixture was stirred at RT for 2 h. Reaction completion was monitored by TLC. The reaction mixture was concentrated completely and extracted with ethyl acetate, washed with 10% aqueous sodium bicarbonate (2×5 mL) and water (2×5 mL). Combined organic layers were dried over anhydrous $Na_2SO_4$, filtered, concentrated and the crude product was purified by MD Auto-Prep (Method A) to get the title product as off white solid. The final structure was confirmed by NOE study and the position of ethyl group was assigned to the position 5 or 7 of the pyrimidine ring. $^1$H NMR (400 MHz, DMSO-$d_6$): δ 7.45-7.41 (m, 1H), 7.31-7.27 (m, 1H), 7.21 (d, J=4.0 Hz, 1H), 7.04 (t, J=8.0 Hz, 1H), 5.15 (s, 1H), 4.81 (d, J=12.0 Hz, 2H), 4.55 (t, J=8.0 Hz, 2H), 4.47 (s, 1H), 4.00 (s, 1H), 3.21-3.19

(m, 3H), 2.82-2.77 (m, 1H), 2.67-2.64 (m, 1H), 2.61-2.54 (m, 4H), 1.301.22 (m, 4H). LCMS: (Method A) 442.0 (M+H)+, Rt. 3.30 min, 97.6% (Max). HPLC: (Method A) Rt. 3.27 min, 95.7% (Max).

Example 11

(R)-3-(2-(3-chloro-2,4-dimethyl-8,9-dihydro-7H-pyrrolo[3',4':3,4]pyrazolo[1,5-a]pyrimidine-8-carbonyl)-5-fluorophenoxy)pyrrolidin-2-one

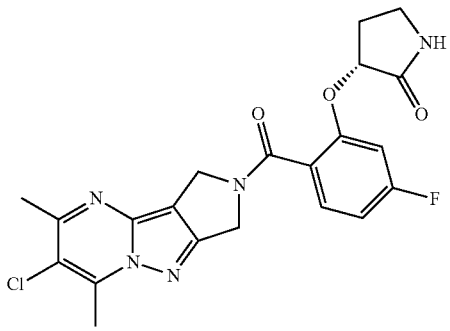 [SMILES: Cc1nc2c3c(nn2c(C)c1Cl)CN(C(=O)c1ccc(F)cc1O[C@@H]1CCNC1=O)C3]

Step 1: (S)-2-oxopyrrolidin-3-yl methanesulfonate

To a stirred solution of (S)-3-hydroxy-pyrollidin-2-one (250 mg, 2.5 mmol, ARK pharma) in dichloromethane (5 mL) at 0° C. was added triethyl amine (375 mg, 3.7 mmol, Spectrochem) and methane sulfonyl chloride (340 mg, 2.9 mmol, Spectrochem). Reaction mass was brought to RT and stirred for 2 h. Reaction mass diluted with DCM, washed with water, saturated aqueous sodium bicarbonate solution, brine solution. The organic layer was dried over anhydrous sodium sulfate and evaporated. The crude product was isolated as off white semi solid and was taken for next step without any further purification (400 mg, 90%). $^1$H NMR (400 MHz, DMSO-$d_6$): δ 6.14 (br s, 1H), 5.18 (t, J=7.60 Hz, 1H), 3.70-3.51 (m, 1H), 3.46-3.40 (m, 1H), 3.29 (s, 3H), 2.71-2.67 (m, 1H), 2.46-2.38 (m, 1H). LCMS: (Method A) 180.0 (M+H)+, Rt. 0.7 min, 97.9% (ELSD).

Step 2: (R)-3-(2-(3-chloro-2,4-dimethyl-8,9-dihydro-7H-pyrrolo[3',4':3,4]pyrazolo[1,5-a]pyrimidine-8-carbonyl)-5-fluorophenoxy)pyrrolidin-2-one To a stirred solution of Intermediate C1 (150 mg, 0.42 mmol) in DMF (10 mL) was added cesium carbonate (274 mg, 0.84 mmol). Reaction mass was heated at 60° C. for 1 h. Reaction mass was brought to RT and added (S)-2-oxopyrrolidin-3-yl methanesulfonate (112 mg, 0.62 mmol) in DMF (5 mL). Reaction mass was heated at 80° C. for 3 h. The reaction mixture was evaporated under vacuum. The crude product was dissolved in DCM, washed with water, brine solution, dried over anhydrous sodium sulfate and evaporated. The crude product was purified by flash chromatography using hexane/ethylacetate with gradient elution to get the title product as off white solid, $^1$H NMR (400 MHz, DMSO-$d_6$): δ 8.09 (d, J=5.60 Hz, 1H), 7.39-7.34 (m, 1H), 7.26-7.23 (m, 1H), 6.92 (dt, J=8.20, 2.40 Hz, 1H), 5.15-5.11 (m, 1H), 4.88-4.74 (m, 3H), 4.50-4.42 (m, 1H), 3.24-3.17 (m, 2H), 2.84 (s, 1.5H), 2.82 (s, 1.5H), 2.62 (s, 1.5H), 2.57 (s, 1.5H), 2.4-2.5 (m, 1H), 2.05-1.87 (m, 1H), LCMS: (Method A) 444.0 (M+H)+, Rt. 3.4 min, 98.9% (Max). HPLC: (Method A) Rt. 3.3 min, 99.5% (Max).

Example 13

(anti)-(6-Chloro-5,7-dimethyl-1H,3H-2,4,7a,8-tetraaza-cyclopenta[a]inden-2-yl)-[2-(4-hydroxy-1-methyl-pyrrolidin-3-yloxy)-phenyl]-methanone

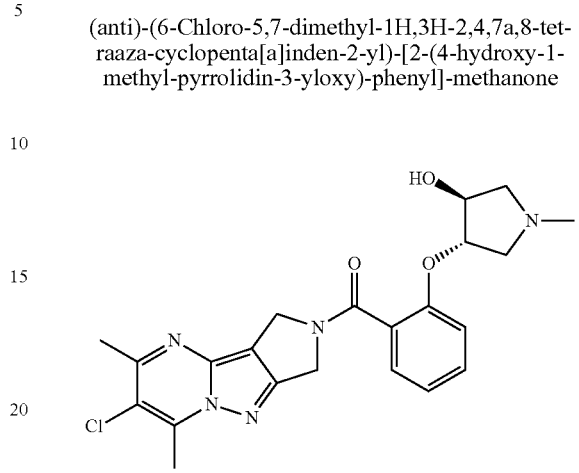

To a stirred solution of Example 4 (0.1 g, 0.233 mmol) in 1,2-dichloroethane (5 mL) and trimethyl orthoformate (1 mL) at 0° C. was added triethylamine (0.047 g, 0.467 mmol, Spectrochem), paraformaldehyde (0.042 g, 0.467 mmol, Spectrochem) and sodium triacetoxy borohydride (0.99 g, 0.467 mmol). Reaction mass was brought to RT and stirred for 12 h. Reaction mass was concentrated and the crude product was purified by MD Auto-Prep (Method A), affording the title product as brown solid as mixture of two enantiomers. $^1$H NMR (400 MHz, DMSO-$d_6$): δ 7.42 (t, J=12.00 Hz, 1H), 7.30 (t, J=12.00 Hz, 1H), 7.17 (d, J=8.00 Hz, 1H), 7.04 (t, J=12.00 Hz, 1H), 5.36 (s, 1H), 4.82 (d, J=12.00 Hz, 2H), 4.56-4.51 (m, 3H), 4.03 (s, 1H), 2.83-2.78 (m, 5H), 2.61-2.54 (m, 4H), 2.19 (s, 1H), 2.13 (m 3H). LCMS: (Method B) 442.0 (M+H)+, Rt. 3.0 min, 97.4% (Max). HPLC: (Method A) Rt. 3.0 min, 98.6% (Max).

Example 15

(3-Chloro-2,4-dimethyl-7H-pyrrolo[3',4':3,4]pyrazolo[1,5-a]pyrimidin-8(9H)-yl)(4-fluoro-2-(2-morpholinoethoxy)phenyl)methanone

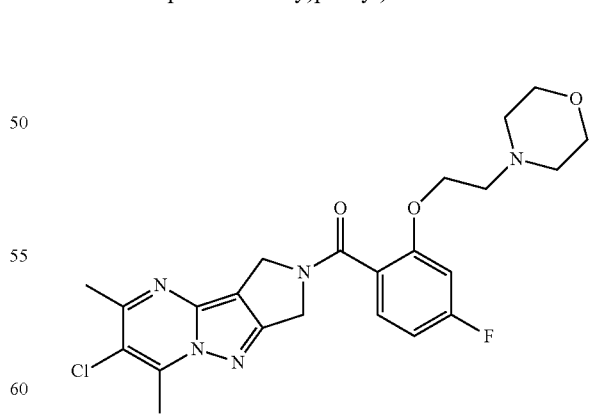

Step 1: 2-Morpholinoethan-1-ol

To a stirred solution of morpholine (2 g, 22.9 mmol, Spectrochem) in dry tetrahydrofuran (20 mL) was added potassium carbonate (6.3 g, 45.9 mmol, Ranchem) and 2-bromoethanol (2.4 mL, 34.4 mmol) and heated to 75° C. for 3 h. Reaction completion was monitored by TLC. The reaction mixture was concentrated under reduced pressure and water (20 mL) was added and extracted in ethyl acetate (3×50 mL). Combined extract was washed with water, brine solution and dried over anhydrous $Na_2SO_4$. The crude product was isolated as brown liquid and was used for next step without further purification (2 g, 65%). $^1$H NMR (400 MHz, DMSO-$d_6$): δ 4.40 (s, 1H), 3.64-3.54 (m, 6H), 2.48-2.33 (m, 6H). LCMS: (Method A) 132 (M+H)$^+$, Rt. 1.2 min, 99.6% (Max)

Step 2: 2-Morpholinoethyl methanesulfonate

To a stirred solution of 2-morpholinoethan-1-ol (0.5 g, 3.81 mmol) in dichloromethane (5 mL) at 0° C. was added triethylamine (0.8 mL, 5.72 mmol, Spectrochem) and methane sulphonylchloride (680 mg, 5.8 mmol, Spectrochem) was added dropwise at 0° C. The reaction mixture was stirred at RT for 30 minutes. Reaction completion was monitored by TLC. The reaction mixture was quenched with 10% aqueous sodium bicarbonate solution (25 mL) and extracted with dichloromethane (2×10 mL). Combined extract was washed with water, brine solution and dried over anhydrous $Na_2SO_4$. The crude product was isolated as brown liquid and used for next step without further purification (0.65 g, 81%). $^1$H NMR (400 MHz, DMSO-$d_6$): δ 4.43 (t, J=4 Hz, 2H), 3.95-3.73 (m, 4H), 3.59-3.33 (m, 2H), 2.36 (s, 3H), 2.48-2.47 (m, 4H).

Step 3: (3-Chloro-2,4-dimethyl-7H-pyrrolo[3',4':3,4]pyrazolo[1,5-a]pyrimidin-8(9H)-yl)(4-fluoro-2-(2-morpholinoethoxy)phenyl)methanone To a stirred solution of Intermediate C1 (0.2 g, 0.54 mmol) in dimethyl formamide (10 mL) was added cesium carbonate (0.36 g, 1.18 mmol) and heated the reaction mixture to 65° C. for 30 minutes. Then the reaction mixture was cooled to RT and 2-morpholinoethyl methanesulfonate (0.174 g, 0.41 mmol), was added dropwise and the reaction mixture was heated to 80° C. for 4 h. Reaction completion was monitored by TLC. The reaction mixture was concentrated under reduced pressure and water (10 mL) was added, extracted with dichloromethane (3×50 mL). Combined extract was washed with water, brine solution and dried over anhydrous $Na_2SO_4$. The crude product obtained was purified by the column chromatography using neutral alumina (dichloromethane/methanol gradient elution) to afford the titled product as white solid. $^1$H NMR (400 MHz, DMSO-$d_6$): δ 7.38-7.33 (m, 1H), 7.1-7.07 (m, 1H), 6.87 (dt, J=8.4, 2.4 Hz, 1H), 4.80 (s, 1H), 4.78 (s, 1H), 4.69-4.59 (m, 2H), 4.19 (t, J=4.8 Hz, 2H), 3.26-3.21 (m, 4H), 2.85 (s, 1.5H), 2.81 (s, 1.5H), 2.62 (s, 1.4H), 2.60 (t, J=5.2Hz, 2H), 2.56 (s, 1.6H), 2.32 (s, 4H). LCMS: (Method A) 474 (M+H)$^+$, Rt. 3.2 min, 98.8% (Max). HPLC: (Method A) Rt. 3.2 min, 99.4% (Max).

Example 16

(3-Chloro-2,4-dimethyl-7H-pyrrolo[3',4':3,4]pyrazolo[1,5-a]pyrimidin-8(9H)-yl)(4-fluoro-2-(2-pyrrolidinoethoxy)phenyl)methanone

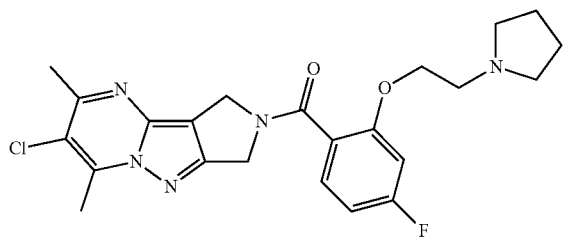 [SMILES: Cc1nc2c3c(nn2c(C)c1Cl)CN(C(=O)c1ccc(F)cc1OCCN1CCCC1)C3]

The title product was prepared according to the procedure described for Example 15, replacing morpholine with pyrrolidine. It was purified by MD-auto prep (Method A) and was isolated as off white solid. $^1$H NMR (400 MHz, DMSO-$d_6$): δ 7.37-7.32 (m, 1H), 7.08 (m, 1H), 6.89-6.84 (dt, J=8.4, 2 Hz, 1H), 4.8 (s, 1H), 4.7 (s, 1H), 4.64-4.57 (m, 2H), 4.16 (t, J=4.0 Hz, 2H), 2.85 (s, 1.6H), 2.81 (s, 1.4H) 2.69 (t, J=8.0 Hz, 2H), 2.62 (m, 2.5H), 2.56 (s, 1.5H), 2.34 (m, 4H), 1.39-1.35 (m, 4H). LCMS: (Method A) 458 (M+H)$^+$, Rt. 3.2 min, 99.6% (Max). HPLC: (Method A) Rt. 3.2 min, 99.7% (Max).

Example 17

(anti)-(3-chloro-2,4-dimethyl-7H-pyrrolo[3',4':3,4]pyrazolo[1,5-a]pyrimidin-8(9H)-yl)(2-((2-hydroxycyclohexyl)oxy)phenyl)methanone

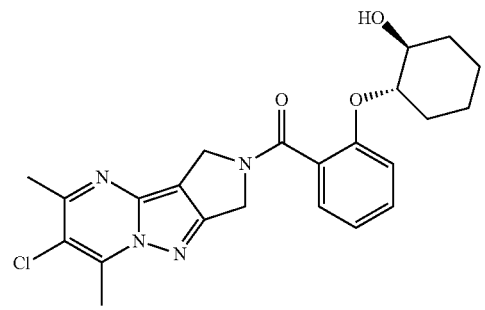 [SMILES: Cc1nc2c3c(nn2c(C)c1Cl)CN(C(=O)c1ccccc1O[C@H]1CCCC[C@@H]1O)C3]

To a solution of Intermediate C2 (100 mg, 0.29 mmol) in DMA (5 mL) were added dry cesium carbonate (190 mg, 0.58 mmol), and heated to 80° C. for 1 h. Cyclohexene epoxide (57 mg, 0.58 mmol) was added and heated to 100° C. for 12 hour. After completion of the reaction, reaction mass was filtered through celite pad and evaporated. The crude product was purified by MD-auto prep (Method A), affording the title compound as white solid as mixture of two enantiomers. $^1$H NMR (400 MHz, DMSO-$d_6$): δ 7.4 (t, J=12.0 Hz, 1H), 7.35-7.29 (m, 1H), 7.2 (d, J=8.4 Hz, 1H), 7.0 (t, J=12.0 Hz, 1H), 4.89-4.77 (m, 3H), 4.45-4.42 (m, 1H), 4.11-4.07 (m, 1H), 3.44-3.40 (m, 2H), 2.85 (s, 1.6H), 2.81 (s, 1.4H) 2.62 (s, 1.6H), 2.55 (s, 1.4H) 2.03-1.99 (m, 1H), 1.80-1.75 (m, 1H), 1.59-1.55 (m, 2H), 1.29-1.19 (m, 4H). LCMS: (Method A) 441.1 (M+H)$^+$, Rt. 4.3 min, 98.8% (Max). HPLC: (Method A) Rt. 4.3 min, 98.8% (Max).

Example 18

(syn)-(3-chloro-2,4-dimethyl-7H-pyrrolo[3',4':3,4]pyrazolo[1,5-a]pyrimidin-8(9H)-yl)(4-fluoro-2-(-3-fluoropiperidin-4-yl)oxy)phenyl)methanone

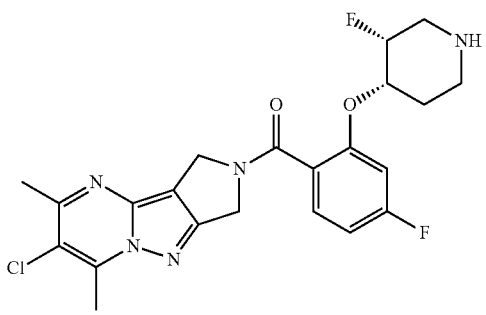 [SMILES: Cc1nc2c3c(nn2c(C)c1Cl)CN(C(=O)c1ccc(F)cc1O[C@H]1CCNC[C@H]1F)C3]

Step 1: (anti)-3-fluoro-4-methanesulfonyloxy-piperidine-1-carboxylic acid tert-butyl ester To a stirred solution of (anti)-3-fluoro-4-hydroxy-piperidine-1-carboxylic acid tert-butyl ester, obtained as described in step 1 of Example 1 as first eluting compound (anti isomer, 230 mg, 1.05 mmol) in DCM (10 mL) at 0° C. was added triethyl amine (213 mg, 2.10 mmol, Spectrochem) and methane sulfonyl chloride (180 mg, 1.57 mmol, Spectrochem). Reaction mixture was brought to RT and stirred for 1 h. Reaction mixture was diluted with DCM (50 mL), washed with water, dried over anhydrous $Na_2SO_4$ and dried. The crude product was isolated as off white solid and was taken for next step without any further purification (300 mg, 96%). $^1$H NMR (400 MHz, $CDCl_3$): δ 4.77-4.59 (m, 2H), 4.56-4.40 (m, 1H), 4.22-4.01 (m, 1H), 3.92-3.87 (m, 1H), 3.15-2.97 (m, 4H), 2.25-2.20 (m, 1H), 1.95-1.72 (m, 1H), 1.47 (s, 9H). LCMS: (Method A) 198.0 (M-Boc+H)$^+$, Rt. 4.0 min, 96.3% (ELSD).

Step 2: (syn)-4-(2-(3-chloro-2,4-dimethyl-8,9-dihydro-7H-pyrrolo[3',4':3,4]pyrazolo[1,5-a]pyrimidine-8-carbonyl)-5-fluorophenoxy)-3-fluoropiperidine-1-carboxylic acid tert-butyl ester To stirred solution of Intermediate C1 (240 mg, 0.67 mmol) in DMF (10 mL) was added cesium carbonate (437 mg, 1.34 mmol, GLR scientific) and (anti)-3-fluoro-4-methanesulfonyloxy-piperidine-1-carboxylic acid tert-butyl ester from step 1 (300 mg, 1.01 mmol). The reaction mixture was heated to 150° C. in MW for 5 h. The solvent was evaporated and the residue was dissolved in DCM (100 mL), washed with water, brine solution, dried over anhydrous $Na_2SO_4$ and evaporated. The crude product was isolated as brown semi solid and was taken for next step without any further purification. The LCMS analysis shows formation of required product and the product from step 3 of example 1. LCMS: (Method A) 462.0 (M-Boc+H)$^+$, Rt. 5.1, 5.2 min, 50%, 9.17% (Max).

Step 3: (syn)-(3-chloro-2,4-dimethyl-7H-pyrrolo[3',4':3,4]pyrazolo[1,5-a]pyrimidin-8(9H)-yl)(4-fluoro-2-(-3-fluoropiperidin-4-yl)oxy)phenyl)methanone To a stirred solution of product of step 2 (150 mg, 0.3 mmol) in dioxane (5 mL) at 10° C. was added HCl in dioxane (2N, 5 mL). Reaction mixture was stirred at RT for 2 h. The solvent was evaporated. The crude product was purified by prep HPLC (Method A) to get title product as a 75:21 mixture of the title compound and Example 1 as an off white solid. $^1$H NMR (400 MHz, DMSO-$d_6$): δ 7.39-7.36 (m, 1H), 7.24-7.21 (m, 1H), 6.91-6.87 (m, 1H), 4.83-4.68 (m, 3H), 4.65-4.48 (m, 3H), 2.95-2.81 (m, 4H), 2.73-2.62 (m, 5H), 1.70-1.64 (m, 2H), 1.39-1.37 (m, 2H). LCMS: (Method A) 462.0 (M+H)$^+$, Rt. 3.2, 3.3 min, 75.3, 21.1% (Max). HPLC: (Method A) Rt. 3.2, 3.3 min, 79.3, 17.0% (Max).

Example 20

(2-(3-1H-1,2,4-triazol-1-yl)propoxy)-4-fluorophenyl)(3-chloro-2,4-dimethyl-7H-pyrrolo[3',4':3,4]pyrazolo[1,5-a]pyrimidin-8(9H)-yl)methanone

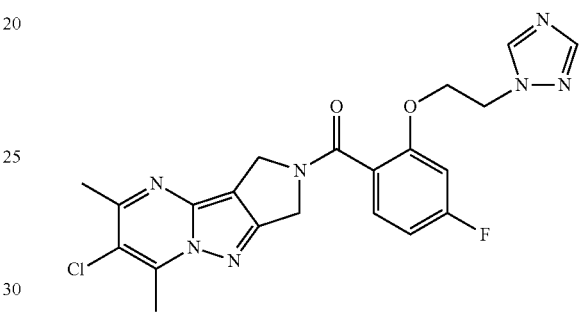

Step 1: 2-(1H-1,2,4-triazol-1-yl)ethan-1-ol

To a stirred solution of 1H-1,2,4-triazole (1 g, 14.4 mmol, Spectrochem) in dry DMF (15 mL) was added 2-bromo ethanol (3.6 g, 28.9 mmol, Spectrochem) and dry potassium carbonate (5.9 g, 43.4 mmol, Ranchem). The reaction mixture was heated in a sealed tube at 80° C. for 6 h. Reaction completion was monitored by TLC. The reaction mass was filtered through celite, washed with dichloromethane/methanol and the filtrate was evaporated. The crude mass was purified by flash column chromatography to get pure title product as colorless oil (0.9 g, 55%). $^1$H NMR (400 MHz, DMSO-$d_6$): δ 8.43 (s, 1H), 7.94 (s, 1H), 4.95 (t, J=5.3 Hz, 1H), 4.21-4.18 (m, 2H) 3.73-3.69 (m, 2H). LCMS: (Method A) 114 (M+H)$^+$, Rt. 3.14 min, 89.7% (ELSD).

Step 2: 1-(2-chloroethyl)-1H-1,2,4-triazole

To a stirred solution of 2-(1H-1,2,4-triazol-1-yl)ethan-1-ol (0.25 g, 2.21 mmol), obtained in step 1, in DCM (10 mL) was added thionyl chloride (0.8 mL, 11.1 mmol, Chempure) at 0° C. The reaction mixture was stirred at 50° C. for 1 h. Reaction completion was monitored by TLC. Reaction mixture was concentrated under vacuum and the residue obtained was azeotroped with dichloromethane (2×5 mL). The crude product was isolated as white solid and was used as such for next step without further purification. $^1$H NMR (400 MHz, DMSO-$d_6$): δ 4.01 (t, J=7.5 Hz, 2H), 4.56 (t, J=7.3 Hz, 2H), 8.15 (s, 1H), 8.76 (3. 1H).

Step 3: (2-(3-(1H-1,2,4-triazol-1-yl)propoxy)-4-fluorophenyl)(3-chloro-2,4-dimethyl-7H-pyrrolo[3',4':3,4]pyrazolo[1,5-a]pyrimidin-8(9H)-yl)methanone To a stirred solution of Intemediate C1 (0.15 g, 0.41 mmol) in dry DMA (15 mL) was added 1-(2-chloroethyl)-

1H-1,2,4-triazole (0.109 g, 0.83 mmol), obtained in step 2, and dry cesium carbonate (0.41 g, 1.24 mmol). The reaction mixture was heated in a sealed tube at 80° C. for 8 h. Reaction completion was monitored by TLC. The reaction mass was filtered through celite, washed with dichloromethane/methanol and the filtrate was evaporated. The crude mass was purified by MD-auto prep (Method A) to get title product as pale yellow solid. $^1$H NMR (400 MHz, DMSO-$d_6$): δ 8.30 (d, J=1.6 Hz, 1H), 7.54 (s, 0.5H), 7.46 (s, 0.5H), 7.34-7.29 (m, 1H), 7.10 (dd, J=11.3, 2.2 Hz, 1H), 6.90-6.85 (m, 1H), 4.74 (s, 1H), 4.71 (s, 1H), 4.52 (t, J=4.6 Hz, 2H), 4.42 (t, J=4.4 Hz, 2H), 4.16 (s, 1H), 4.10 (s, 1H), 2.86 (s, 1.5H), 2.82 (s, 1.5H), 2.62 (s, 1.4H), 2.56 (s, 1.6H). LCMS: (Method A) 456.0 (M+H)$^+$, Rt. 3.4 min, 99.6% (Max). HPLC: (Method A) Rt. 3.4 min, 99.6% (Max).

Example 21

(anti)-(3-chloro-2,4-dimethyl-7H-pyrrolo[3',4':3,4] pyrazolo[1,5-a]pyrimidin-8(9H)-yl)(2-((4-hydroxytetrahydrofuran-3-yl)oxy)phenyl)methanone SGN010041-01

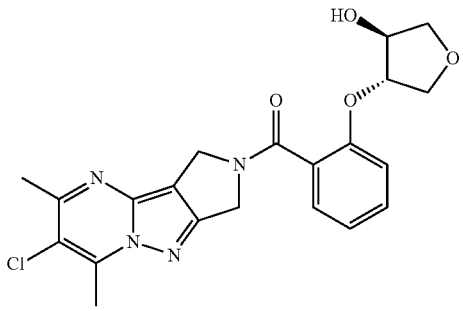 [SMILES: Cc1nc2c3c(nn2c(C)c1Cl)CN(C(=O)c1ccccc1O[C@H]1COC[C@@H]1O)C3]

A 8 mL microwave vial was charged with Intermediate C2 (100 mg, 0.2923 mmol), 3,4-epoxy tetrahydrofuran (50.3 mg, 0.5846 mmol, Combi blocks) and CsF (26.6 mg, 0.0292 mmol) in DMF (2 mL). The capped vial was irradiated in a microwave reactor at 150° C. for 1 h. After completion of the reaction, the mixture was concentrated under reduced pressure and diluted with ethyl acetate (5 mL). The organic phase was washed with water and brine. The organic layer was dried over anhydrous sodium sulphate and evaporated. The crude product was purified by MD Auto-Prep HPLC (method A) to get the pure title product as off white solid as mixture of enantiomers. $^1$H NMR (400 MHz, DMSO-$d_6$): δ 7.49-7.44 (m, 1H), 7.35-7.31 (m, 1H), 7.23 (d, J=8.4 Hz, 1H), 7.09 (t, J=12.0 Hz, 1H), 5.49-5.47 (m, 1H), 4.83 (s, 1H), 4.80 (s, 1H), 4.76 (d, J=3.6 Hz, 1H), 4.54-4.47 (m, 2H), 4.18 (br s, 1H), 4.03-3.99 (m, 1H), 3.74-3.69 (m, 2H), 3.53-3.49 (m, 1H), 2.84 (s, 1.6H), 2.80 (s, 1.4H), 2.62 (s, 1.5H), 2.56 (s, 1.5H). LCMS: (Method A) 429.0 (M+H)$^+$, Rt. 3.3 min, 92.8% (Max). HPLC: (Method A) Rt. 3.3 min, 94.8% (Max).

Example 25

(syn)-(6-Chloro-5,7-dimethyl-1H,3H-2,4,7a,8-tetraaza-cyclopenta[a]inden-2-yl)-[2-(4-fluoro-pyrrolidin-3-yloxy)-phenyl]-methanone

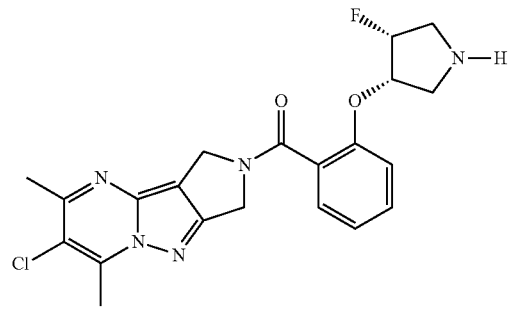 [SMILES: Cc1nc2c3c(nn2c(C)c1Cl)CN(C(=O)c1ccccc1O[C@H]1CNC[C@H]1F)C3]

Step 1: (syn)-(3-[2-(6-Chloro-5,7-dimethyl-1H,3H-2,4,7a,8-tetraaza-cyclopenta[a]indene-2-carbonyl)-phenoxy]-4-fluoro-pyrrolidine-1-carboxylic acid tert-butyl ester To a stirred solution of Intermediate A1 and Intermediate B1 (0.1 g, 0.32 mmol) in N,N-dimethylformamide (15 mL) was added HATU (123 mg, 0.32 mmol, Combiblock) followed by N,N-Diisopropylethylamine (0.15 mL, 0.86 mmol, Spectrochem). The reaction mixture was stirred at RT for 14 h. Reaction completion was monitored by TLC. The reaction mixture was concentrated and the residue obtained was diluted with water (50 mL). The aqueous layer was extracted in dichloromethane (3×25 mL). The combined extract was washed with brine solution (25 mL) and dried over anhydrous Na$_2$SO$_4$. Solvent was evaporated to dryness to afford the crude product. The crude product was purified by flash chromatography (230-400 size mesh) (silica gel, dichloromethane/methanol as gradient elution). LCMS: (Method A) 430.0 (M-Boc+H)$^+$, Rt. 4.9 min, 55.1% (Max).

Step 2: (syn)-(6-Chloro-5,7-dimethyl-1H,3H-2,4,7a,8-tetraaza-cyclopenta[a]inden-2-yl)-[2-(4-fluoro-pyrrolidin-3-yloxy)-phenyl]-methanone To a stirred solution of (syn)-3-[2-(6-Chloro-5,7-dimethyl-1H,3H-2,4,7a,8-tetraaza-cyclopenta[a]indene-2-carbonyl)-phenoxy]-4-fluoro-pyrrolidine-1-carboxylic acid tert-butyl ester (0.08 g, 0.15 mmol), HCl in dioxane (2 N, 5 mL) was added at 0° C. The reaction mixture was stirred at RT for 2 h. Reaction completion was monitored by TLC. The reaction mixture was concentrated and extracted with ethyl acetate, washed with 10% aqueous sodium bicarbonate (2×5 mL) and water (2×5 mL). Combined organic layers were dried over anhydrous Na$_2$SO$_4$, filtered, concentrated and the crude product was purified by MD Auto-Prep (Method C) to get the title product as off white solid and as mixture of 2 enantiomers. $^1$H NMR (400 MHz, DMSO-$d_6$): δ 7.50-7.46 (m, 1H), 7.37-7.34 (m, 1H), 7.32-7.20 (m, 1H), 7.13-7.07 (m, 1H), 5.16-5.04 (m, 1H), 4.97-4.81 (m, 3H), 4.58-4.49 (m, 2H), 3.30-3.17 (m, 2H), 2.99-2.90 (m, 2H), 2.85-2.81 (m, 3H), 2.75-2.71 (m, 1H), 2.63-2.56 (m, 3H). LCMS: (Method A) 430.0 (M+H)$^+$, Rt. 3.1 min, 96.8% (Max). HPLC: (Method A) Rt. 3.1 min, 96.7% (Max).

Example 26

(anti)-(3-chloro-2,4-dimethyl-7H-pyrrolo[3',4':3,4]
pyrazolo[1,5-a]pyrimidin-8(9H)-yl)(4-fluoro-2-((4-
hydroxytetrahydrofuran-3-yl)oxy)phenyl)methanone

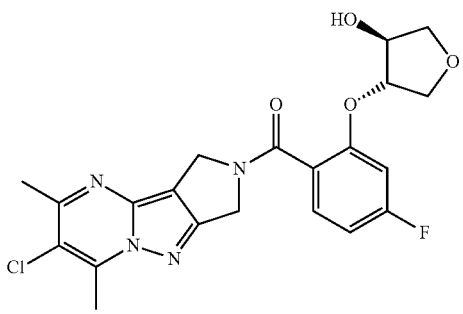

A 8 mL microwave vial was charged with Intermediate C1 (100 mg, 0.27 mmol), 3,4-epoxy tetrahydrofuran (47.8 mg, 0.55 mmol, Combi blocks) and CsF (4.22 mg, 0.03 mmol) in DMF (2 mL). The capped vial was irradiated in a microwave reactor at 150° C. for 1 h. After completion of the reaction, the mixture was concentrated under reduced pressure and diluted with ethyl acetate (5 mL). The organic phase was washed with water (3 mL) and brine (3 mL). The organic layer was dried over anhydrous sodium sulphate and evaporated. The crude product was purified by MD Auto-Prep (Method A) to get the title product as white solid as mixture of two enantiomers. $^1$H NMR (400 MHz, DMSO-$d_6$): δ 7.37 (d, J=7.2 Hz, 1H), 7.19 (d, J=11.2 Hz, 1H), 6.92 (t, J=12.0 Hz, 1H), 5.54 (s, 1H), 4.83-4.79 (m, 3H), 4.55-4.49 (m, 2H), 4.19 (s, 1H), 4.00 (d, J=10.0 Hz, 1H), 3.72 (d, J=8.8 Hz, 2H), 3.52 (br s, 1H), 2.85 (s, 1.7H), 2.82 (s, 1.3H), 2.63 (s, 1.4H), 2.57 (s, 1.6H). LCMS: (Method A) 447.0 (M+H)$^+$, Rt. 3.4 min, 97.7% (Max). HPLC: (Method A) Rt. 3.5 min, 99.5% (Max).

Example 27

(anti)-(6-Chloro-5,7-dimethyl-1H,3H-2,4,7a,8-tet-
raaza-cyclopenta[a]inden-2-yl)-[4-fluoro-2-(4-hy-
droxy-pyrrolidin-3-yloxy)-phenyl]-methanone

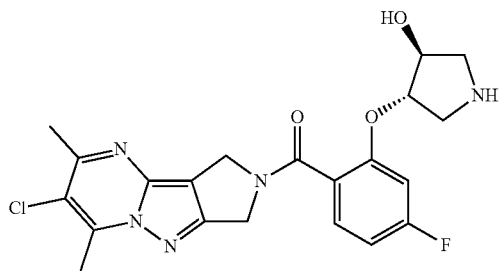 [SMILES: Cc1nc2c3c(nn2c(C)c1Cl)CN(C(=O)c1ccc(F)cc1O[C@H]1CNC[C@@H]1O)C3]

Step 1: (anti)-3-[2-(6-Chloro-5,7-dimethyl-1H,3H-2, 4,7a,8-tetraaza-cyclopenta[a]indene-2-carbonyl)-5-fluoro-phenoxy]-4-hydroxy-pyrrolidine-1-carboxylic acid tert-butyl ester To a stirred solution of Intermediate C1 (1 g, 9.4 mmol) in dry N,N-dimethylformamide (15 mL) was added cesium carbonate (2.1 g, 6.66 mmol, Chempure) under N$_2$ atmosphere and the reaction mixture was stirred at 60° C. for 1 h. After 1 h, 6-Oxa-3-aza-bicyclo[3.1.0]hexane-3-carboxylic acid tert-butyl ester (0.82 g, 4.44 mmol) was added to the reaction mixture and allowed to stir at 80° C. for 16 h. After completion, the reaction mass was filtered through celite and concentrated under vacuum. Residue obtained was diluted with ethyl acetate (50 mL), washed with water, brine solution and dried over anhydrous Na$_2$SO$_4$. Organic phase was concentrated. The crude product was purified by flash column chromatography (230-400 size mesh) (silica gel, pet ether/ethyl acetate as gradient elution), affording the title product as brown solid and as mixture of enantiomers. $^1$H NMR (400 MHz, DMSO-$d_6$): δ 7.39-7.35 (m, 1H), 7.22 (t, J=12.0 Hz, 1H), 6.94 (t, J=12.0 Hz, 1H), 5.50 (s, 1H), 4.78-4.75 (m, 3H), 4.49-4.43 (m, 2H), 4.13-4.09 (m, 1H), 3.56 (d, J=8.00 Hz, 1H), 3.24-3.21 (m, 3H), 3.14-3.11 (m, 1H), 2.83-2.79 (m, 2H), 2.61-2.54 (m, 3H) 1.29 (s, 9H). LCMS: (Method A) 446.0 (M-Boc+H)$^+$, Rt. 4.38 min, 81.4% (Max).

Step 2: (anti)-(6-Chloro-5,7-dimethyl-1H,3H-2,4,7a, 8-tetraaza-cyclopenta[a]inden-2-yl)-[4-fluoro-2-(4-hydroxy-pyrrolidin-3-yloxy)-phenyl]-methanone The protocol was the same as the one described for Example 10, step 2, starting from (anti)-3-[2-(6-Chloro-5,7-dimethyl-1H,3H-2,4,7a,8-tetraaza-cyclopenta[a]indene-2-carbonyl)-5-fluoro-phenoxy]-4-hydroxy-pyrrolidine-1-carboxylic acid tert-butyl ester. The crude product was purified by MD Auto-Prep (Method A) to get the pure title product as brown solid as mixture of two enantiomers. $^1$H NMR (400 MHz, DMSO-$d_6$): δ 7.37-7.32 (m, 1H), 7.13 (d, J=8.0 Hz, 1H), 6.90-6.86 (m, 1H), 5.23 (s, 1H), 4.82 (s, 1H), 4.79 (s, 1H), 4.54-4.58 (m, 2H), 4.49 (s, 1H), 3.99 (s, 1H), 3.22-3.16 (m, 1H), 2.84 (s, 1.6H), 2.80 (s, 1.4H), 2.78 (m, 1H), 2.67 (m, 1H), 2.61 (s, 1.5H), 2.58 (m, 1H), 2.56 (s, 1.5H). LCMS: (Method A) 446.2 (M+H)$^+$, Rt. 3.08 min, 99.0% (Max). HPLC: (Method A) Rt. 3.10 min, 99.3% (Max).

Example 29

(6-Chloro-5,7-dimethyl-1H,3H-2,4,7a8-tetraaza-
cyclopenta[a]inden-2-y )-{4-fluoro-2-[1-(2-hydroxy-
1-hydroxymethyl-ethyl)-piperidin-4-yloxy]-phenyl}-
methanone

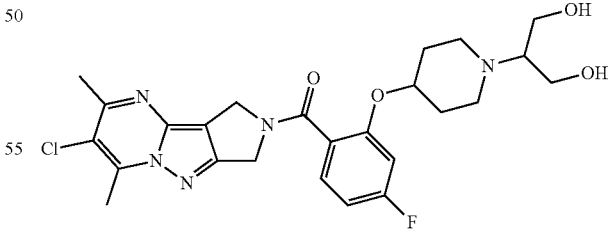

Step 1: (6-Chloro-5,7-dimethyl-1H,3H-2,4,7a,8-tetraaza-cyclopenta[a]inden-2-yl)-{2-[1-(2,2-dimethyl-[1,3]dioxan-5-yl)-piperidin-4-yloxy]-4-fluoro-phenyl}-methanone To a stirred solution of (6-Chloro-5,7-dimethyl-1H,3H-2, 4,7a,8-tetraaza-cyclopenta[a]inden-2-yl)-[4-fluoro-2-(piperidin-4-yloxy)-phenyl]-methanone hydrochloride obtained as in Example 32, step 3, (0.4 g, 0.902 mmol) in 1,2-dichloroethane (10 mL) and TMOF (1 mL) at 0° C. was added 2,2-dimethyl-[1,3]dioxan-5-one (0.054 g, 1.8 mmol, Combiblock) and sodium triacetoxyborohydride (0.95 g, 4.51 mmol). Reaction mass was brought to RT and stirred for 12 h. Residue obtained was diluted with ethyl acetate (50 mL), washed with water, brine solution and dried over anhydrous Na$_2$SO$_4$. Organic phase was concentrated. The crude product was isolated as pale brown solid and was taken for next step without any further purification (0.36 g, 84%). LCMS: (Method B) 558.2 (M+H)$^+$, Rt. 3.71 min, 66.3% (Max).

Step 2: (6-Chloro-5,7-dimethyl-1H,3H-2,4,7a,8-tetraaza-cyclopenta[a]inden-2-yl)-{4-fluoro-2-[1-(2-hydroxy-1-hydroxymethyl-ethyl)-piperidin-4-yloxy]-phenyl}-methanone To a stirred solution of (6-chloro-5,7-dimethyl-1H,3H-2,4,7a,8-tetraaza-cyclopenta[a]inden-2-yl)-{2-[1-(2,2-dimethyl-[1,3]dioxan-5-yl)-piperidin-4-yloxy]-4-fluoro-phenyl}-methanone (0.26 g, 0.048 mmol), dioxane in HCl (2 N, 5 mL) was added at 0° C. The reaction mixture was stirred at RT for 8 h. Reaction completion was monitored by TLC. The reaction mixture was concentrated and the crude product was purified by MD Auto-Prep (Method C) to get the title product as brown solid. $^1$H NMR (400 MHz, DMSO-d$_6$): δ 7.37-7.32 (m, 1H), 6.83-6.79 (m, 1H), 6.77-6.73 (m, 1H), 5.01 (d, J=8.00 Hz, 2H), 4.69-4.68 (m, 3H), 3.65-3.61 (m, 4H), 3.23-3.21 (m, 2H), 3.01-2.99 (m, 1H), 2.92 (s, 2H), 2.87 (s, 1H), 2.79-2.77 (m, 1H), 2.70 (s, 1.4H), 2.64 (s, 1.6H) 2.04-2.00 (m, 5H). LCMS: (Method A) 518.2 (M+H)$^+$, Rt. 3.24 min, 97.1% (Max). HPLC: (Method A) Rt. 3.22 min, 97.5% (Max).

Example 30

(3-chloro-2,4-dimethyl-7H-pyrrolo[3',4':3,4]pyrazolo[1,5-a]pyrimidin-8(9H)-yl)(4-fluoro-2-((1-(2-hydroxyethyl)azetidin-3-yl)oxy)phenyl)methanone

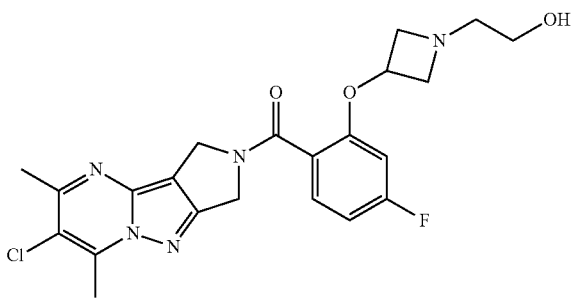 [SMILES: Cc1nc2c3c(nn2c(C)c1Cl)CN(C(=O)c1ccc(F)cc1OC1CN(CCO)C1)C3]

The title compound was prepared following the same protocol as described for Example 46, replacing 1-bromo-2-fluoro ethane with 2-bromoethanol (Spectrochem). The crude product was purified by MD-auto prep (Method A) and the title compound was isolated as off white solid, $^1$H NMR (400 MHz, DMSO-d$_6$): δ 7.41-7.36 (m, 1H), 6.92-6.88 (m, 1H), 6.82-6.79 (m, 1H), 4.91 (t, J=5.2 Hz, 1H), 4.85 (d, J=12.0 Hz, 2H), 4.61 (s, 1H), 4.56 (s, 1H), 4.38 (t, J=7.2 Hz, 1H), 3.74-3.71 (m, 2H), 3.31-3.38 (m, 2H), 2.99 (d, J=6.4 Hz, 2H), 2.85-2.81 (m, 3H), 2.62-2.56 (m, 4H), 2.46 (d, J=8 Hz, 1H). LCMS: (Method A) 460.0 (M+H)$^+$, Rt. 3.04 min, 99.8% (Max). HPLC: (Method A) Rt. 3.02 min, 99.6% (Max).

Example 32

(6-Chloro-5,7-dimethyl-1H,3H-2,4,7a,8-tetraaza-cyclopenta[a]inden-2-yl)-{4-fluoro-2-[1-(2-hydroxy-ethyl)-piperidin-4-yloxy]-phenyl}-methanone

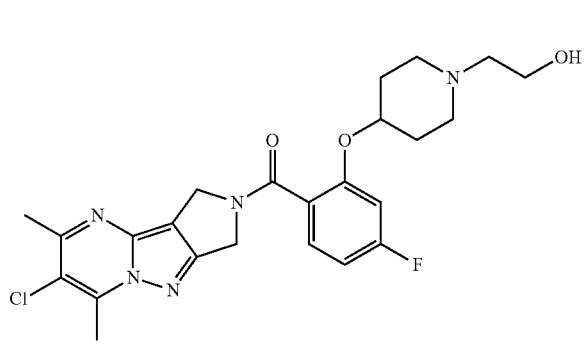 [SMILES: Cc1nc2c3c(nn2c(C)c1Cl)CN(C(=O)c1ccc(F)cc1OC1CCN(CCO)CC1)C3]

Step 1:
4-Methanesulfonyloxy-piperidine-1-carboxylic acid tert-butyl ester

To a stirred solution of 4-hydroxy-N-boc piperidine (1 g, 5.0 mmol, ABCR Ltd.) in DCM (25 mL) at 0° C. was added triethyl amine (754 mg, 7.5 mmol, Spectrochem) and methane sulfonyl chloride (683 mg, 6.0 mmol, Spectrochem). Reaction mass was brought to RT and stirred for 2 h. Reaction mass diluted with DCM, washed with water, saturated aqueous sodium bicarbonate solution, brine solution. The organic layer was dried over anhydrous sodium sulfate and evaporated. The crude product was isolated as off white solid and was taken for next step without any further purification (1.1 g, 79%). $^1$H NMR (400 MHz, CDCl$_3$): δ 4.93-4.85 (m, 1H), 3.75-3.67 (m, 2H), 3.35-3.26 (m, 2H), 3.04 (s, 3H), 2.02-1.95 (m, 2H), 1.92-1.85 (m, 2H), 1.46 (s, 9H). LCMS: (Method A) 180.0 (M-Boc+H)$^+$, Rt. 0.7 min, 99.7% (ELSD).

Step 2: 4-[2-(6-Chloro-5,7-dimethyl-1H,3H-2,4,7a,8-tetraaza-cyclopenta[a]indene-2-carbonyl)-5-fluoro-phenoxy]-piperidine-1-carboxylic acid tert-butyl ester To a stirred solution of Intermediate C1 (250 mg, 0.69 mmol) in DMF (10 mL) was added cesium carbonate (450 mg, 1.40 mmol, GLR scientific). Reaction mass was heated at 60° C. for 1 h. Reaction mass was brought to RT and added 4-methanesulfonyloxy-piperidine-1-carboxylic acid tert-butyl ester from step 1 (272 mg, 1.03 mmol) in DMF (5 mL). Reaction mass was heated at 80° C. for 12 h. The reaction mixture was evaporated under vacuum. The crude product was dissolved in DCM (50 mL), washed with water, brine solution, dried over anhydrous sodium sulfate and evaporated. The crude product was purified by Biotage flash column chromatography using dichloro methane/methanol with gradient elution to get the title product as off white solid (240 mg, 64%). $^1$H NMR (400 MHz, DMSO-d$_6$): δ 7.37 (t, J=6.7 Hz, 1H), 7.21-7.18 (m, 1H), 6.89 (t, J=8.2 Hz, 1H), 4.82 (d, J=12.1 Hz, 2H), 4.80-4.67 (m, 1H), 4.57-4.53 (m, 2H), 3.55-3.38 (m, 2H), 3.28-3.12 (m, 2H), 2.85-2.81 (m, 3H), 2.63-2.57 (m, 3H), 1.98-1.83 (m, 2H), 1.48-1.40 (m, 2H), 1.34 (s, 9H). LCMS: (Method A) 444.0 (M-Boc+H)$^+$, Rt. 5.2 min, 97.5% (Max).

Step 3: (6-Chloro-5,7-dimethyl-1H,3H-2,4,7a,8-tetraaza-cyclopenta[a]inden-2-yl)-[4-fluoro-2-(piperidin-4-yloxy)-phenyl]-methanone hydrochloride To a stirred solution of 4-[2-(6-Chloro-5,7-dimethyl-1H,3H-2,4,7a,8-tetraaza-cyclopenta[a]indene-2-carbonyl)-5-fluoro-phenoxy]-piperidine-1-carboxylic acid tert-butyl ester, from step 2 (240 mg, 0.44 mmol) in dioxane (5 mL) at 0° C. was added HCl in dioxane (2 N, 5 mL). Reaction mass was brought to RT and stirred for 2 h. The reaction mixture was evaporated under vacuum. The title product was isolated as pale yellow solid and was taken for next step without any further purification (200 mg, 94%). $^1$H NMR (400 MHz, DMSO-d$_6$): δ 8.75-8.62 (m, 1H), 8.55-8.46 (m, 1H), 7.55-7.35 (m, 1H), 7.24-7.21 (m, 1H), 6.94-6.88 (m, 1H), 4.85-4.82 (m, 3H), 4.57-4.52 (m, 2H), 3.82 (s, 3H), 3.15-2.95 (m, 2H), 2.83 (s, 1.3H), 2.79 (s, 1.7H), 2.61 (s, 1.5H), −2.59 (s, 1.5H) 2.16-1.99 (m, 2H), 1.79-1.65 (m, 1H). LCMS: (Method A) 444.2 (M+H)$^+$, Rt. 3.3 min, 96.6% (Max).

Step 4: (6-Chloro-5,7-dimethyl-1H,3H-2,4,7a,8-tetraaza-cyclopenta[a]inden-2-yl)-{4-fluoro-2-[1-(2-hydroxy-ethyl)-piperidin-4-yloxy]phenyl}-methanone To a stirred solution of (6-Chloro-5,7-dimethyl-1H,3H-2,4,7a,8-tetraaza-cyclopenta[a]inden-2-yl)-[4-fluoro-2-(piperidin-4-yloxy)-phenyl]-methanone hydrochloride, from step 3 (200 mg, 0.42 mmol) in DMF (5 mL) was added potassium carbonate (116 mg, 0.84 mmol, GLR scientific) and 2-bromo ethanol (78 mg, 0.62 mmol, Spectrochem). The reaction mixture was heated at 60° C. for 3.5 h, then evaporated under vacuum. The crude product was dissolved in DCM (50 mL), washed with water, brine solution, dried over anhydrous sodium sulfate and evaporated. The crude product was purified by Biotage flash column chromatography using dichloro methane/methanol with gradient elution to get the title product as pale yellow solid (96 mg, 47%). $^1$H NMR (400 MHz, D$_2$O): 7.34-7.30 (m, 1H), 6.98-6.93 (m, 1H), 6.85-6.79 (m, 1H), 4.83 (s, 1H), 4.77 (s, 1H), 4.56 (s, 1H), 4.49 (s, 1H), 3.68-3.64 (m, 2H), 3.01 (m, 2H), 2.82 (m, 4H), 2.57 (s, 1.6H), 2.52 (s, 1.4H), 2.43 (s, 1.6H), 2.37 (s, 1.4H) 2.02-1.96 (m, 4H). LCMS: (Method A) 488.2 (M+H)$^+$, Rt. 3.3 min, 97.4% (Max). HPLC: (Method A) Rt. 3.3 min, 97.4% (Max).

Example 33

(3-chloro-7H-pyrrolo[3',4':3,4]pyrazolo[1,5-a]pyrimidin-8(9H)-yl)(4-fluoro-2-(piperidin-4-yloxy)phenyl)methanone hydrochloride

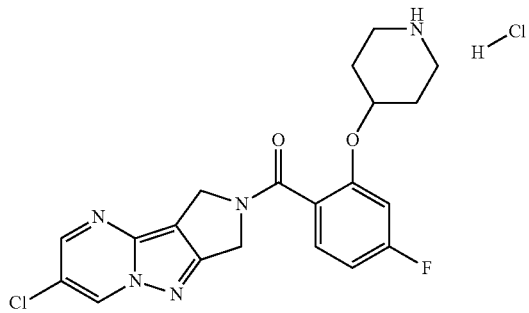

Step 1: 4-(2-(3-chloro-8,9-dihydro-7H-pyrrolo[3',4':3,4]pyrazolo[1,5-a]pyrimidine-8-carbonyl)-5-fluorophenoxy)piperidine-1-carboxylic acid tert-butyl ester To a solution of Intermediate C3 (535 mg, 1.4 mmol), 4-hydroxy-N-boc piperidine (583 mg, 2.9 mmol, ABCR Ltd.) and tributyl phosphine (0.7 mL, 2.9 mmol) in THF (20 mL) was added di-tert-butyl azodicarboxylate (671 mg, 2.9 mmol). The reaction was stirred at RT for 18 h. The reaction was concentrated in vacuo. The crude product was purified by column chromatography using 60-70% EtOAc in hexane to give the title compound as brown solid (412 mg, 71%). $^1$H NMR (400 MHz, DMSO-d$_6$): δ 9.60 (dd, J=2.36, 12.04 Hz, 1H), 8.62 (dd, J=2.28, 11.44 Hz, 1H), 7.38-7.37 (m, 1H), 7.20 (d, J=11.88 Hz, 1H), 6.89-6.87 (m, 1H), 4.84 (s, 1H), 4.71-4.70 (m, 1H), 4.57 (d, J=12.0 Hz, 2H), 3.60-3.59 (m, 2H), 3.21-3.19 (m, 2H), 2.95-2.90 (m, 1H), 1.93-1.83 (m, 1H), 1.69-1.66 (m, 1H), 1.50-1.48 (m, 2H), 1.34 (s, 9H). LCMS: (Method A) 416.0 (M-Boc+H)$^+$, Rt. 4.7 min, 98.1% (Max).

Step 2: (3-chloro-7H-pyrrolo[3',4':3,4]pyrazolo[1,5-a]pyrimidin-8(9H)-yl)(4-fluoro-2-(piperidin-4-yloxy)phenyl)methanone hydrochloride The title compound was prepared following the same protocol as described for example 32 step 3, starting with 4-(2-(3-chloro-8,9-dihydro-7H-pyrrolo[3',4':3,4]pyrazolo[1,5-a]pyrimidine-8-carbonyl)-5-fluorophenoxy)piperidine-1-carboxylic acid tert-butyl ester obtained in Step 1. It was purified by recrystallization and isolated as brown solid. $^1$H NMR (400 MHz, DMSO-d$_6$): δ 9.61 (d, J=8.80 Hz, 1H), 8.84 (s, 1H), 8.65-8.61 (m, 2H), 7.45-7.40 (m, 1H), 7.25 (d, J=11.20 Hz, 1H), 6.93 (t, J=8.40 Hz, 1H), 5.02-4.82 (m, 2H), 4.59 (d, J=12.40 Hz, 2H), 3.05-2.92 (m, 4H), 2.10-2.04 (m, 2H), 2.00-1.83 (m, 2H), 1.57-1.55 (m, 1H). LCMS: (Method A) 416.0 (M+H)$^+$, Rt. 2.7 min, 99.0% (Max). HPLC: (Method A) Rt. 2.7 min, 99.1% (Max).

Example 34

(3-chloro-7H-pyrrolo[3',4':3,4]pyrazolo[1,5-a]pyrimidin-8(9H)-yl)(4-fluoro-2-((1-2-fluoroethyl)piperidin-4-yl)oxy)phenyl)methanone

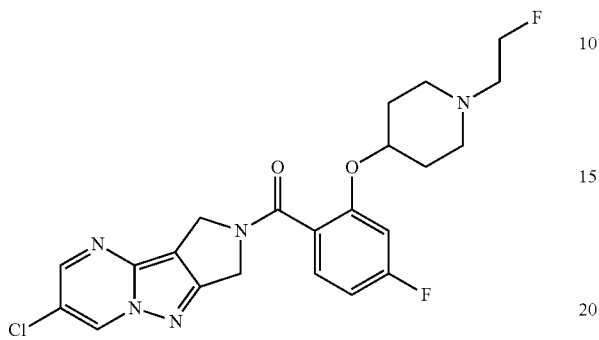

To a stirred solution of Example 33 (0.166 g, 0.4 mmol) in dry DMF (15 mL) was added 1-bromo-2-fluoro ethane (0.06 mL, 0.8 mmol, Combiblock) and dry cesium carbonate (0.4 g, 1.3 mmol). The reaction mixture was heated in a sealed tube at 80° C. for 4 h. Reaction completion was monitored by TLC. The reaction mass was filtered through celite, washed with dichloromethane/methanol and the filtrate was evaporated. The crude mass was purified by MD Auto-Prep (Method A) to get the title product as yellow solid. $^1$H NMR (400 MHz, DMSO-$d_6$): δ 9.59 (dd, $J_1$=11.6, 11.5 Hz, 1H), 8.64-8.58 (m, 1H), 7.39-7.34 (m, 1H), 7.15 (d, J=11.6 Hz, 1H), 6.90-6.87 (m, 1H), 4.85 (s, 2H), 4.59 (d, J=12.0 Hz, 3H), 4.49-4.45 (m, 1H), 4.37-4.33 (m, 1H), 2.52-2.41 (m, 4H), 2.34-2.31 (m, 2H), 1.86-1.84 (m, 2H), 1.59-1.57 (m, 2H). LCMS: (Method A) 462.0 (M+H)$^+$, Rt. 2.8 min, 96.6% (Max). HPLC: (Method A) Rt. 2.8 min, 97.3% (Max).

Example 35

(3-chloro-7H-pyrrolo[3',4':3,4]pyrazolo[1,5-a]pyrimidin-8(9H)-yl)(4-fluoro-2-((1-(2-hydroxyethyl)piperidin-4-yl)oxy)phenyl)methanone

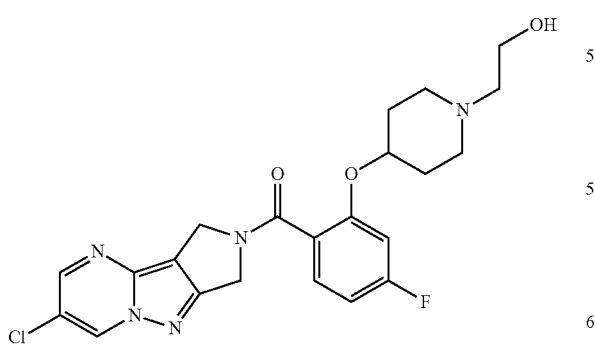

The title compound was prepared following the same protocol as described for Example 34, replacing 1-bromo-2-fluoro ethane with 2-bromo ethanol. The crude product was purified by flash chromatography using dichloromethane/methanol with gradient elution to get the title product as brown solid. $^1$H NMR (400 MHz, DMSO-$d_6$): δ 9.59 (dd, J=11.2, 11.2 Hz, 1H), 8.64-8.59 (m, 1H), 7.39-7.34 (m, 1H), 7.15 (d, J=12.00 Hz, 1H), 6.87 (t, J=8.40 Hz, 1H), 4.85 (s, 2H), 4.59 (d, J=12.00 Hz, 3H), 4.50-4.30 (m, 1H), 3.39-3.34 (m, 2H), 2.51-2.51 (m, 2H), 2.34-2.24 (m, 4H), 1.94-1.84 (m, 2H), 1.70-1.58 (m, 2H). LCMS: (Method A) 460.0 (M+H)$^+$, Rt. 2.7 min, 95.5% (Max). HPLC: (Method A) Rt. 2.7 min, 96.5% (Max).

Example 36

(3-chloro-2,4-dimethyl-7H-pyrrolo[3',4':3,4]pyrazolo[1,5-a]pyrimidin-8(9H)-yl)(4-fluoro-2-{[(3-endo)-8-(2-fluoroethyl)-8-azabicyclo[3.2.1]oct-3-yl]oxy}phenyl)methanone

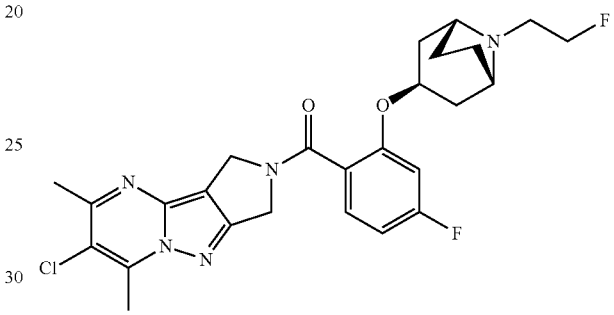

Step 1: {2-[(3-endo)-8-azabicyclo[3.2.1]oct-3-yloxy]-4-fluorophenyl}(3-chloro-2,4-dimethyl-7H-pyrrolo[3',4':3,4]pyrazolo[1,5-a]pyrimidin-8(9H)-yl)methanone hydrochloride The title compound was prepared following the same protocol as described for Example 25, step 1 and 2, using Intermediate A1 and Intermediate B2 as starting material. It was purified by recrystallization and isolated as hydrochloride salt and as brown solid (200 mg, 50% over two steps). It was taken further for the next step. LCMS: (Method A) 470.2 (M+H)$^+$, Rt. 3.2 min, 53.1% (Max).

Step 2: (3-chloro-2,4-dimethyl-7H-pyrrolo[3',4':3,4]pyrazolo[1,5-a]pyrimidin-8(9H)-yl)(4-fluoro-2-{[(3-endo)-8-(2-fluoroethyl)-8-azabicyclo[3.2.1]oct-3-yl]oxy}phenyl)methanone The title compound was prepared following the same protocol as described for Example 34, using {2-[(3-endo)-8-azabicyclo[3.2.1]oct-3-yloxy]-4-fluorophenyl}(3-chloro-2,4-dimethyl-7H-pyrrolo[3',4':3,4]pyrazolo[1,5-a]pyrimidin-8(9H)-yl)methanone hydrochloride as starting material. The crude product was purified by MD Auto-Prep (Method B), affording the title product as white solid. $^1$H NMR (400 MHz, DMSO-$d_6$): δ 7.38-7.33 (m, 1H), 6.98-6.93 (m, 1H), 6.85-6.80 (m, 1H), 4.69 (s, 2H), 4.60 (s, 1H), 4.55 (s, 2H), 4.47 (t, J=5.2 Hz, 1H), 4.35 (t, J=5.2 Hz, 1H), 3.06 (s, 2H), 2.84-2.80 (m, 3H), 2.61 (s, 3H), 2.55 (s, 2H), 2.01-1.98 (m, 2H), 1.66-1.59 (m, 6H). LCMS: (Method B) 516.1 (M+H)$^+$, Rt. 5.6 min, 98.1% (Max). HPLC: (Method B) Rt. 5.6 min, 97.8% (Max).

Example 37

(3-chloro-2,4-dimethyl-7H-pyrrolo[3',4':3,4]pyrazolo[1,5-a]pyrimidin-8(9H)-yl)(4-fluoro-2-{[(3-endo)-8-(2-hydroxyethyl)-8-azabicyclo[3.2.1]oct-3-yl]oxy}phenyl)methanone

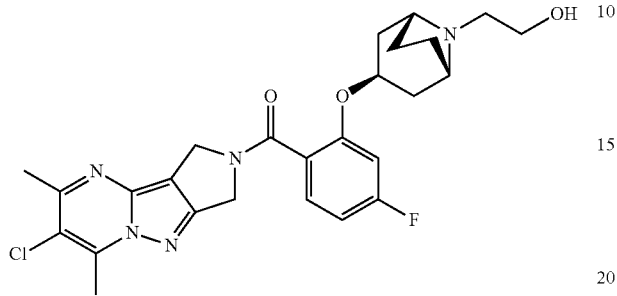

The title compound was prepared following the same protocol as described for Example 34, using {2-[(3-endo)-8-azabicyclo[3.2.1]oct-3-yloxy]-4-fluorophenyl}(3-chloro-2,4-dimethyl-7H-pyrrolo[3',4':3,4]pyrazolo[1,5-a]pyrimidin-8(9H)-yl)methanone hydrochloride (Example 36, step 1) and 2-bromo ethanol as starting materials. The crude product was purified by MD Auto-Prep (Method C) to get the title product as pale brown solid. $^1$H NMR (400 MHz, DMSO-d6): δ 7.39-7.30 (m,1H), 6.99 (d, J=10.8 Hz, 1H), 6.86-6.82 (m, 1H), 4.82 (d, J=8.0 Hz, 2H), 4.71 (d, J=4.4 Hz, 1H), 4.62-4.57 (m, 2H), 4.36 (s, 1H), 3.41 (d, J=6.8 Hz, 3H), 3.03-2.98 (m, 3H), 2.85-2.81 (m, 3H), 2.61 (s, 3H), 2.05-2.02 (m, 2H), 1.75-1.65 (m, 6H). LCMS: (Method A) 514.0 (M+H)$^+$, Rt. 3.3 min, 99.0% (Max). HPLC: (Method A) Rt. 3.4 min, 99.3% (Max).

Example 38

(3-chloro-2,4-dimethyl-7H-pyrrolo[3',4':3,4]pyrazolo[1,5-a]pyrimidin-8(9H)-yl)(4-fluoro-2-(((3-endo)-(6-endo)-6-fluoro-8-methyl-8-azabicyclo[3.2.1]octan-3-yl)oxy)phenyl)methanone

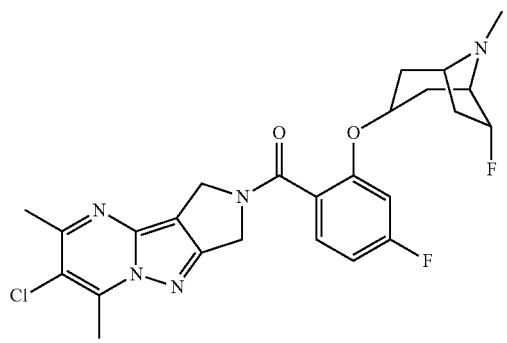

The title compound was prepared following the same protocol as described for Example 25, step 1, using Intermediate A1 and Intermediate B3 as starting material. The crude product was purified by MD Auto-Prep (Method B) to get the title product. This product is isolated as off white solid as racemic mixture. $^1$H NMR (400 MHz, DMSO-d$_6$): δ 7.42-7.38 (m, 1H), 7.13 (d, J=10.40 Hz, 1H), 6.90 (t, J=7.60 Hz, 1H), 5.20-5.04 (m, 1H), 4.87-4.77 (m, 3H), 4.59-4.50 (m, 2H), 3.43-3.39 (m, 2H), 3.18-3.16 (m, 2H), 2.85 (s, 1.6H), 2.81 (s, 1.4H), 2.62 (s, 2H), 2.56 (s, 1H), 2.32-2.33 (m, 3H), 1.90-1.73 (m, 3H), 1.31-1.24 (m, 1H). LCMS: (Method A) 502.0 (M+H)$^+$, Rt. 3.3 min, 97.0% (Max). HPLC: (Method A) Rt. 3.4 min, 97.3% (Max).

Example 39

(3-chloro-2,4-dimethyl-7H-pyrrolo[3',4':3,4]pyrazolo[1,5-a]pyrimidin-8(9H)-yl)(4-fluoro-2-(((3-endo)-(6-exo)-6-hydroxy-8-methyl-8-azabicyclo[3.2.1]octan-3-yl)oxy)phenyl)methanone

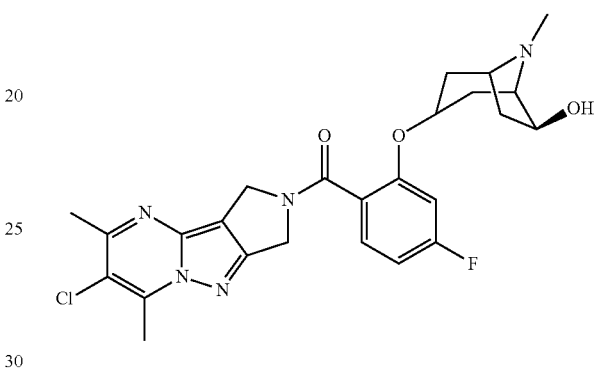

The title compound was prepared following the same protocol as described for Example 25, step 1 and 2, using Intermediate A1 and Intermediate B4 as starting material. The crude product was purified by MD Auto-Prep (Method B) to get the title product as off white solid as racemic mixture. $^1$H NMR (400 MHz, DMSO-d$_6$): δ 7.39-7.35 (m, 1H), 6.96-6.93 (m, 1H), 6.86 (t, J=8.0 Hz, 1H), 4.87 (d, J=9.2 Hz, 2H), 4.68-4.50 (m, 4H), 4.32-4.28 (m, 1H), 3.09-3.04 (m, 1H), 2.85 (s, 3H), 2.81-2.78 (m, 1H), 2.62-2.56 (m, 3H), 2.37-2.33 (m, 3H), 2.20-2.12 (m, 1H), 2.05-1.94 (m, 2H), 1.64-1.56 (m, 2H), 1.47-1.43 (m, 1H), LCMS: (Method A) 500.0 (M+H)$^+$, Rt. 3.1 min, 98.5% (Max). HPLC: (Method A) Rt. 3.1 min, 99.1% (Max).

Example 40

(3-chloro-2,4-dimethyl-7H-pyrrolo[3',4':3,4]pyrazolo[1,5-a]pyrimidin-8(9H)-yl)(4-fluoro-2-(2-(2-methyl-1H-imidazol-1-yl)ethoxy)phenyl)methanone

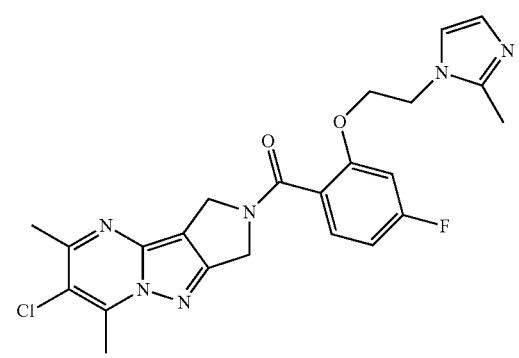 [SMILES: Cc1nc2c3c(nn2c(C)c1Cl)CN(C(=O)c1ccc(F)cc1OCCn1ccnc1C)C3]

Step 1: 1-(2-chloroethyl)-2-methyl-1H-imidazole

To a stirred solution of 2-methyl-1H-imidazole (2 g, 24.3 mmol, Combiblock) in dry DMF (20 mL) was added 1-bromo-2-chloroethane (6.9 g, 48.7 mmol) and dry potassium carbonate (10 g, 73.1 mmol, Spectrochem). The reaction mixture was heated in a sealed tube at 80° C. for 6 h. Reaction completion was monitored by TLC. The reaction mass was filtered through celite, washed with dichloromethane/methanol and the filtrate was evaporated. The crude mass was purified by flash column chromatography to get the title product as yellow liquid (1.5 g, 43%). $^1$H NMR (400 MHz, DMSO-$d_6$): δ 7.12-7.11 (m, 1H), 6.74 (d, J=1.2 Hz, 1H), 4.23 (t, J=5.7 Hz, 2H), 3.92 (t, J=5.6 Hz, 2H), 2.30 (s, 3H). LCMS: (Method B) 145 (M+H)$^+$, Rt. 2.9 min, 70.0% (Max).

Step 2: (3-chloro-2,4-dimethyl-7H-pyrrolo[3',4':3,4]pyrazolo[1,5-a]pyrimidin-8(9H)-yl)(4-fluoro-2-(2-(2-methyl-1H-imidazol-1-yl)ethoxy)phenyl)methanone To a stirred solution of Intermediate C1 (0.3 g, 0.83 mmol) in dry DMF (15 mL) was added 1-(2-chloroethyl)-2-methyl-1H-imidazole (0.24 g, 1.66 mmol) and dry cesium carbonate (0.81 g, 2.5 mmol, Spectrochem). The reaction mixture was heated in a sealed tube at 80° C. for 8 h. Reaction completion was monitored by TLC. The reaction mass was filtered through celite, washed with dichloromethane/methanol and the filtrate was evaporated. The crude mass was purified by flash column chromatography to get the title product as off white solid (206 mg, 53%). $^1$H NMR (400 MHz, DMSO-$d_6$): δ 7.36-7.31 (m, 1H), 7.07 (dd, J=6.6, 2.0 Hz, 1H), 6.91-6.87 (m, 2H), 6.25 (s, 0.5H), 6.18 (s, 0.5H), 4.79 (s, 1H), 4.77 (s, 1H), 4.31 (t, J=4.4 Hz, 2H), 4.25-4.19 (m, 4H), 2.87 (s, 1.5H), 2.82 (s, 1.5H), 2.64 (s, 1.4H), 2.56 (s, 1.6H), 2.19 (s, 1.5H), 2.18 (s, 1.5H). LCMS: (Method A) 469.0 (M+H)$^+$, Rt. 3.2 min, 98.1% (Max). HPLC: (Method A) Rt. 3.2 min, 99.4% (Max).

Example 41 and Example 49

(anti)-(6-Chloro-5,7-dimethyl-1H,3H-2,4,7a8-tetraaza-cyclopenta[a]inden-2-yl)-[4-fluoro-2-(4-hydroxy-cyclohexyloxy)-phenyl]-methanone and (syn)-(6-Chloro-5,7-dimethyl-1H,3H-2,4,7a,8-tetraaza-cvclopenta[a]inden-2-yl)-[4-fluoro-2-(4-hydroxy-cyclohexyloxy)-phenyl]-methanone

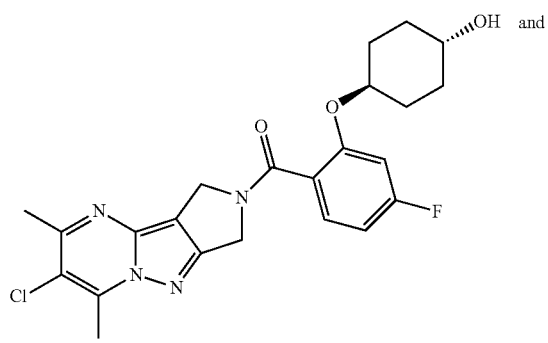

and

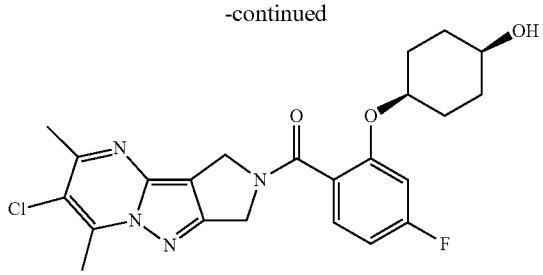

Step 1: 1,4-dioxaspiro[4.5]decan-8-ol

To a stirred solution of 1,4-dioxaspiro[4.5]decan-8-one (5 g, 32.0 mmol, Lobochem) in dry MeOH (50 mL) was added Sodium borohydride (1.8 g, 48.0 mmol) portion wise at 0° C. The reaction mixture was stirred at RT for 2 h. Reaction completion was monitored by TLC. Reaction mixture was quenched with ice. The reaction mixture was concentrated completely and extracted with dichloromethane, washed with water (2×30 mL) and brine solution (2×20 mL). Combined organic layers were dried over anhydrous Na$_2$SO$_4$, filtered, concentrated and the crude mass obtained as brown liquid was used as such for next step without further purification (3 g, 59%). $^1$H NMR (400 MHz, DMSO-$d_6$): δ 4.47 (d, J=4.0 Hz, 1H), 3.85-3.80 (m, 4H), 3.55 (s, 1H), 1.66-1.64 (m, 4H), 1.48-1.42 (m, 4H).

Step 2: 1,4-dioxaspiro[4.5]decan-8-yl methanesulfonate

To a stirred solution of 1,4-dioxaspiro[4.5]decan-8-ol (1 g, 6.32 mmol) in dry DCM (20 mL) at 0° C. was added triethyl amine (2.6 mL, 18.9 mmol, Spectrochem) followed by addition of methane sulfonyl chloride (0.7 mL, 9.4 mmol, Spectrochem). Reaction mass was brought to RT and stirred for 1 h. Reaction completion was monitored by TLC. Reaction mass was diluted with DCM, washed with water, dried over Na$_2$SO$_4$ and evaporated. The crude was isolated as pale brown solid and was taken for next step without any further purification (1.4 g, 93%). $^1$H NMR (400 MHz, DMSO-$d_6$): δ 4.77 (t, J=3.6 Hz, 1H), 3.88-3.86 (m, 4H), 3.19 (s, 3H), 2.00-1.84 (m, 4H), 1.83-1.77 (m, 4H).

Step 3: (6-Chloro-5,7-dimethyl-1H,3H-2,4,7a,8-tetraaza-cyclopenta[a]inden-2-yl)-[2-(1,4-dioxaspiro[4.5]dec-8-yloxy)-4-fluoro-phenyl]-methanone To a stirred solution of Intermediate C1 (1 g, 2.7 mmol) in dry DMF (15 mL) was added 1,4-dioxaspiro[4.5]decan-8-yl methanesulfonate (1.3 g, 0.83 mmol) and dry cesium-carbonate (2.7 g, 8.32 mmol). The reaction mixture was heated in a sealed tube at 80° C. for 8 h. Reaction completion was monitored by TLC. The reaction mass was filtered through celite, washed with dichloromethane/methanol and the filtrate was evaporated. The crude mass was purified by flash chromatography to get the title product as yellow solid (1 g, 72%). $^1$H NMR (400 MHz, DMSO-$d_6$): δ 7.37-7.32 (m, 1H), 7.17-7.17 (m, 1H), 6.88-6.83 (m, 1H), 4.76 (s, 2H), 4.75 (s, 2H), 3.86-3.82 (m, 4H), 3.82-3.77 (m, 1H), 2.88 (s, 3H), 2.61 (s, 3H), 1.88-1.85 (m, 4H), 1.60-1.56 (m, 4H). LCMS: (Method A) 501.0 (M+H)$^+$, Rt. 4.6 min, 98.7% (Max).

211

Step 4: 4-[2-(6-Chloro-5,7-dimethyl-1H,3H-2,4,7a,
8-tetraaza-cyclopenta[a]indene-2-carbonyl)-5-fluoro-
phenoxy]-cyclohexanone To a stirred solution of (6-Chloro-5,7-dimethyl-1H,3H-2,
4,7a,8-tetraaza-cyclopenta[a]inden-2-yl)-[2-(1,4-dioxa-
spiro[4.5]dec-8-yloxy)-4-fluoro-phenyl]-methanone (0.5
mg, 0.99 mmol), from step 3. HCl in dioxane (2N, 5 mL)
was added followed by water (1 mL). The reaction mixture
was stirred at RT for 12 h. Reaction completion was moni-
tored by LCMS. The reaction mixture was concentrated,
neutralized with sodium bicarbonate and washed with
dichloromethane. Combined organic layers were concen-
trated and the crude mass obtained was isolated as pale
yellow solid and was taken for next step without further
purification (400 mg, 89%). $^1$H NMR (400 MHz, DMSO-
$d_6$): δ 7.42-7.40 (m, 1H), 7.39-7.26 (m, 1H), 6.92-6.86 (m,
1H), 4.93 (s, 1H), 4.80 (d, J=12.0 Hz, 2H), 4.62-4.52 (m,
2H), 2.83,2.79 (s, 3H), 2.66,2.60 (s, 3H), 2.35-2.30 (m, 2H),
2.22-2.19 (m, 2H), 2.02-1.98 (m, 2H), 1.66-1.49 (m, 2H).
LCMS: (Method A) 457.0 (M+H)$^+$, Rt. 4.1 min, 62.2%
(Max).

Step 5: (anti)-(6-Chloro-5,7-dimethyl-1H,3H-2,4,7a,
8-tetraaza-cyclopenta[a]inden-2-yl)-[4-fluoro-2-(4-
hydroxy-cyclohexyloxy)-phenyl]-methanone and
(syn)-(6-Chloro-5,7-dimethyl-1H,3H-2,4,7a,8-tet-
raaza-cyclopenta[a]inden-2-yl)-[4-fluoro-2-(4-hy-
droxy-cyclohexyloxy)-phenyl]-methanone To a stirred solution of 4-(2-(3-chloro-2,4-dimethyl-8,9-
dihydro-7H-pyrrolo[3',4':3,4]pyrazolo[1,5-a]pyrimidine-8-
carbonyl)-5-fluorophenoxy)cyclohexan-1-one, (0.4 g, 0.875
mmol) in dry MeOH (50 mL) was added sodium borohy-
dride (0.66 g, 1.75 mmol) portion wise at 0° C. The reaction
mixture was stirred at RT for 1 h. Reaction completion was
monitored by TLC. The reaction mixture was concentrated
completely and the crude LCMS report showed two peaks
with the same product mass which indicated the mixture of
two diastereomers. The diastereomeric mixture was purified
by Prep-HPLC (Method B). First eluting compound (minor
isomer) was concentrated and considered as Example 49.
Second eluting compound (major isomer) was concentrated
and considered as Example 41.

Example 49 (first eluting compound): off-white solid. $^1$H
NMR (400 MHz, DMSO-$d_6$): δ 7.35-7.30 (m, 1H), 7.12 (d,
J=12.0 Hz, 1H), 6.86-6.81 (m, 1H), 4.80 (s, 1H), 4.77 (s,
1H), 4.55-4.49 (m, 4H), 3.45 (t, J=4.0 Hz, 1H), 2.83 (s,
1.5H), 2.80 (s, 1.5H), 2.61 (s, 1.4H), 2.55 (s, 1.6H) 1.94-1.92
(m, 2H), 1.73-1.71 (m, 2H), 1.35-1.32 (m, 4H). LCMS:
(Method A) 459.0 (M+H)$^+$, Rt. 3.90 min, 95.4% (Max).
HPLC: (Method A) Rt. 3.88 min, 97.2% (Max).

Example 41 (second eluting compound): off white solid.
$^1$H NMR (400 MHz, DMSO-$d_6$): δ 7.38-7.33 (m, 1H), 7.12
(d, J=11.6 Hz, 1H), 6.86 (t, J=8.4 Hz, 1H), 4.84 (s, 1H), 4.81
(s, 1H), 4.60-4.43 (m, 3H), 4.43 (s, 1H), 3.51 (s, 1H), 2.84
(s, 1.5H), 2.81 (s, 1H), 2.62 (s, 1.5H), 2.56 (s, 1.5H)
1.74-1.73 (m, 2H), 1.58-1.56 (m, 2H), 1.49-1.43 (m, 4H).
LCMS: (Method A) 459.0 (M+H)$^+$, Rt. 4.1 min, 98.5%
(Max). HPLC: (Method A) Rt. 4.2 min, 99.8% (Max).

Example 42

(3-chloro-2,4-dimethyl-7H-pyrrolo[3',4':3,4]pyrazolo
[1,5-a]pyrimidin-8(9H)-yl)(4-fluoro-2-(2-(6-methyl-
pyridin-3-yl)ethoxy)phenyl)methanone

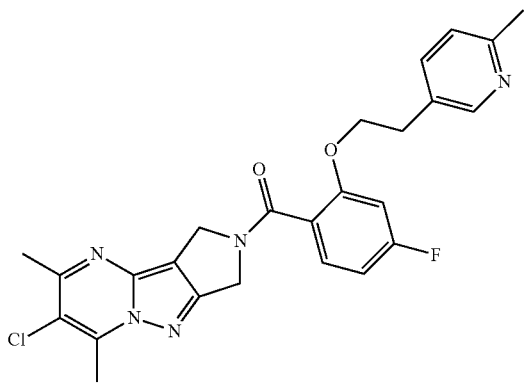

Step 1: Diethyl 2-(6-methylpyridin-3-yl)malonate

To a stirred solution of 5-bromo -2-methylpyridine (5 g,
29.06 mmol, Flurochem) in dry Toluene (50 mL), diethyl-
malonate (11 mL, 72.6 mmol, Spectrochem), palladium
acetate (0.65 g, 2.90 mmol), dry potassium phosphate (18.5
g, 87.2 mmol) and 2-Di(tert-butylphosphino) biphenyl (0.86
g, 2.9 mmol) were added and degasify under argon for 20
minutes. The reaction mixture was heated in a sealed tube at
100° C. for 48 h. Reaction completion was monitored by
TLC. The reaction mass was filtered through celite, washed
with dichloromethane/methanol and the filtrate was evapo-
rated. The crude mass was purified by flash column chro-
matography to get the title product as yellow oil (3.5 g,
48%). $^1$H NMR (400 MHz, DMSO-$d_6$): δ 8.41 (d, J=2.0 Hz,
1H), 7.67 (dd, J=8.0, 2.2 Hz, 1H), 7.26 (d, J=8.0 Hz, 1H),
5.01 (s, 1H), 4.19-4.10 (m, 4H), 2.43 (s, 3H), 1.18-1.15 (m,
6H). LCMS: (Method A) 252 (M+H)$^+$, Rt. 2.2 min, 58.9%
(Max).

Step 2: 2-(6-methylpyridin-3-yl) acetic acid

Diethyl 2-(6-methylpyridin-3-yl) malonate (3 g, 11.9
mmol) was taken in HCl (6N, 30 mL) and heated at 100° C.
for 6 h. Reaction completion was monitored by TLC. The
reaction mass was completely concentrated using high
vacuum. The residue obtained was neutralized with solid
sodium bicarbonate. The crude mass was purified by recrys-
tallisation to get the title product as yellow solid (1.5 g,
83%). $^1$H NMR (400 MHz, DMSO-$d_6$): δ 8.28 (s, 1H),
7.55-7.51 (m, 1H), 7.18-7.15 (m, 1H), 3.53 (s, 2H), 2.41 (s,
3H). LCMS: (Method B) 152.0 (M+H)$^+$, Rt. 0.9 min, 87.2%
(Max).

Step 3: 2-(6-methylpyridin-3-yl) ethan-1-ol

To a stirred solution of 2-(6-methylpyridin-3-yl) acetic
acid (1.5 g, 9.9 mmol) in dry THF (20 mL) was added
Borane-DMS (2 mL, 19.8 mmol) drop wise at 0° C. The reaction mixture was stirred at RT for 1 h. Reaction completion was monitored by TLC. Reaction mixture was quenched with methanol at 0° C. The reaction mixture was concentrated completely and extracted with ethyl acetate, washed with water (2×10 mL), sodium bicarbonate (2×10 mL) and brine solution (2×10 mL). Combined organic layers were dried over anhydrous $Na_2SO_4$, filtered, concentrated and the crude mass obtained was purified by flash column chromatography to get the title product as pale yellow liquid. $^1$H NMR (400 MHz, DMSO-$d_6$): δ 8.55 (s, 1H), 7.93 (dd, J=8.0, 1.9 Hz, 1H), 7.56 (d, J=8.0 Hz, 1H), 4.74 (s, 1H), 3.65-3.60 (m, 2H), 2.77 (t, J=6.2 Hz, 2H), 2.59 (s, 3H). LCMS: (Method B) 138.2 (M+H)$^+$, Rt. 3.5 min, 91.6% (Max).

Step 4: 2-(6-methylpyridin-3-yl) ethyl methanesulfonate

To a stirred solution of 2-(6-methylpyridin-3-yl)ethan-1-ol (0.5 g, 3.6 mmol) in dry DCM (10 mL) at 0° C. was added triethyl amine (1.5 mL, 10.8 mmol, Spectrochem) followed by addition of methane sulfonyl chloride (0.4 mL, 5.4 mmol, Spectrochem). Reaction mass was brought to RT and stirred for 1 h. Reaction completion was monitored by TLC. Reaction mass was diluted with DCM, washed with water, dried over $Na_2SO_4$ and evaporated. The crude was isolated as pale brown liquid and was taken for next step without any further purification (0.36 g, 46%). $^1$H NMR (400 MHz, DMSO-$d_6$): δ 8.63 (s, 1H), 8.00 (dd, J=8.0, 1.8 Hz, 1H), 7.62-7.58 (m, 1H), 4.45 (t, J=6.4 Hz, 2H), 3.14 (s, 3H), 3.07 (d, J=6.4 Hz, 2H), 2.59 (s, 3H). LCMS: (Method A) 216.0 (M+H)$^+$, Rt. 3.3 min, 50.2% (Max).

Step 5: (3-chloro-2,4-dimethyl-7H-pyrrolo[3',4':3,4]pyrazolo[1,5-a]pyrimidin-8(9H)-yl)(4-fluoro-2-(2-(6-methylpyridin-3-yl)ethoxy)phenyl)methanone To a stirred solution of Intermediate C1 (0.3 g, 0.83 mmol) in dry DMF (15 mL) was added 2-(6-methylpyridin-3-yl)ethyl methanesulfonate (0.36 g, 1.66 mmol) and dry cesium carbonate (0.81 g, 2.5 mmol, Spectrochem). The reaction mixture was heated in a sealed tube at 80° C. for 8 h. Reaction completion was monitored by TLC. The reaction mass was filtered through celite, washed with dichloromethane/methanol and the filtrate was evaporated. The crude mass obtained was purified by MD auto-prep (Method B) to get the title product as pale yellow solid. $^1$H NMR (400 MHz, DMSO-$d_6$): δ 8.22 (s, 1H), 7.46-7.41 (m, 1H), 7.31-7.26 (m, 1H), 7.06 (d, J=2.4 Hz, 1H), 6.86-6.82 (m, 1H), 6.68 (d, J=8.0 Hz, 0.5H), 6.56 (d, J=8.0 Hz, 0.5H), 4.77 (s, 1H), 4.74 (s, 1H), 4.27 (s, 2H), 4.05 (s, 1H), 4.00 (s, 1H) 2.91-2.88 (m, 2H), 2.87 (s, 1.6H), 2.81 (s, 1.4H) 2.65 (s, 1,4H), 2.56 (s, 1.6H), 1.86 (s, 1.4H), 1.76 (s, 1.6H) LCMS: (Method A) 480.0 (M+H)$^+$, Rt. 3.3 min, 99.5% (Max). HPLC: (Method A) Rt. 3.3 min, 99.6% (Max).

Example 43

(3-chloro-2,4-dimethyl-7H-pyrrolo[3',4':3,4]pyrazolo[1,5-a]pyrimidin-8(9H)-yl)(4-fluoro-2-(2-(5-fluoropyridin-3-yl)ethoxy)phenyl)methanone

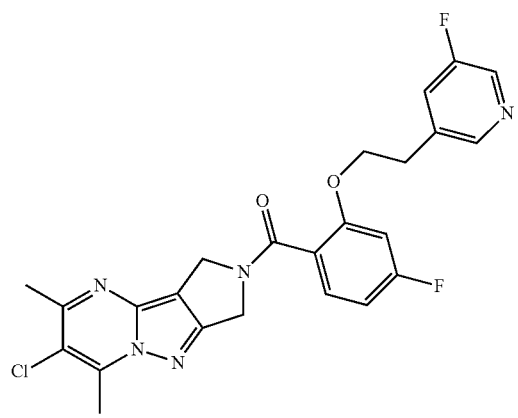 [SMILES: Cc1nc2c3c(nn2c(C)c1Cl)CN(C(=O)c1ccc(F)cc1OCCc1cncc(F)c1)C3]

The title compound was prepared following the same protocol as described for Example 42, using 5-bromo-3-fluoropyridine as starting material. It was isolated as off white solid (230 mg, 57%). $^1$H NMR (400 MHz, DMSO-$d_6$): δ 8.23 (s, 1H), 7.81-7.74 (m, 1H), 7.56-7.53 (m, 1H), 7.32-7.27 (m, 1H), 7.09 (dd, J1=11.4, J2=2.0 Hz, 1H), 6.88-6.83 (m, 1H), 4.69 (s, 2H), 4.35 (t, J=5.6 Hz, 2H), 4.13 (s, 1H), 4.08 (s, 1H) 3.01 (t, J=5.2 Hz, 2H), 2.88 (s, 1.5H), 2.82 (s, 1.5H), 2.64 (s, 1.5H), 2.56 (s, 1.5H). LCMS: (Method A) 484.0 (M+H)$^+$, Rt. 3.8 min, 98.8% (Max). HPLC: (Method A) Rt. 3.7 min, 98.1% (Max).

Example 44

(R)-(3-chloro-2,4-dimethyl-7H-pyrrolo[3',4':3,4]pyrazolo[1,5-a]pyrimidin-8(9H)-yl)(4-fluoro-2-(2-(2-methylpyrrolidin-1-yl)ethoxy)phenyl)methanone

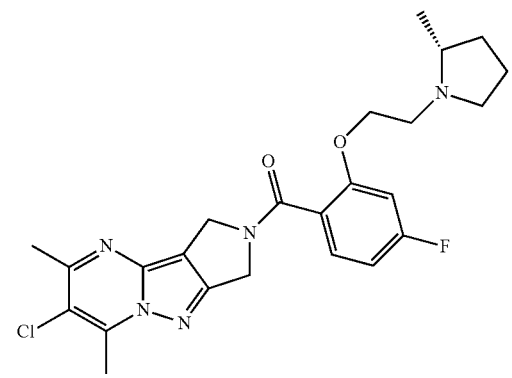 [SMILES: Cc1nc2c3c(nn2c(C)c1Cl)CN(C(=O)c1ccc(F)cc1OCCN1CCC[C@H]1C)C3]

The title compound was prepared following the same protocol as described for Example 15, using (R)-2-methylpyrrolidine as starting material. The crude product was purified by MD Auto-prep. (Method A). The title compound was isolated as brown solid and as a single enantiomer. $^1$H NMR (400 MHz, DMSO-$d_6$): δ 7.37-7.32 (m, 1H), 6.78-6.70 (m, 2H), 4.99 (d, J=5.6 Hz, 2H), 7.71-4.63 (m, 2H), 4.27-4.21 (m, 2H), 3.22 (s, 2H), 2.92 (s, 1.5H), 2.86 (s, 1.5H), 2.70 (s, 1.5H), 2.68 (s, 1.5H), 2.35 (s, 2H), 1.87 (s, 1H), 1.44-1.34 (m, 3H), 1.33-1.10 (m, 2H), 0.91 (d, J=8.0 Hz, 2H). LCMS: (Method A) 472 (M+H)$^+$, Rt. 3.3 min, 95.7% (Max). HPLC: (Method A) Rt. 3.3 min, 96.1% (Max).

Example 45

(anti)-(6-Chloro-5,7-dimethyl-1H,3H-2,4,7a,8-tetraaza-cyclopenta[a]inden-2-yl)-[4-fluoro-2-(4-hydroxy-1-methyl-pyrrolidin-3-yloxy)-phenyl]-methanone

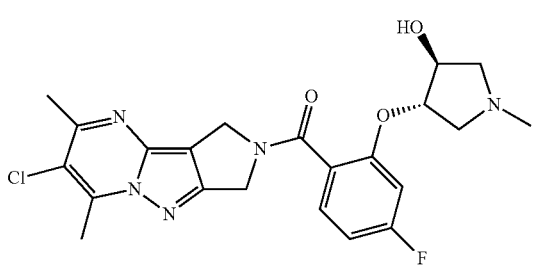 [SMILES: Cc1nc2c3c(nn2c(C)c1Cl)CN(C(=O)c1ccc(F)cc1O[C@H]1CN(C)C[C@@H]1O)C3]

To a stirred solution of Example 27 (0.3 g, 0.67 mmol) in 1,2-dichloroethane (10 mL) and trimethyl orthoformate (1 mL, Spectrochem) at 0° C. was added triethylamine (0.18 g, 13.4 mmol, Spectrochem), paraformaldehyde (0.12 g, 13.4 mmol) and sodium triacetoxyborohydride (0.28 g, 13.4 mmol). Reaction mass was brought to RT and stirred for 12 h. Reaction mass was concentrated and the crude product was purified by MD auto-prep (Method A). The title product was isolated as pale yellow solid as mixture of two enantiomers. $^1$H NMR (400 MHz, DMSO-d$_6$): δ 7.38-7.33 (m, 1H), 7.12 (d, J=12.0 Hz, 1H), 6.89 (t, J=8.0 Hz, 1H), 5.47-5.44 (m, 1H), 4.82 (d, J=12.0 Hz, 2H), 4.58-4.53 (m, 3H), 4.06 (s, 1H), 2.84-2.80 (m, 5H), 2.61-2.56 (m, 4H), 2.21-2.19 (m, 1H), 2.14-2.13 (m, 3H). LCMS: (Method B) 460.0 (M+H)$^+$, Rt. 3.10 min, 97.9% (Max). HPLC: (Method A) Rt. 3.12 min, 96.5% (Max).

Example 46

(3-chloro-2,4-dimethyl-7H-pyrrolo[3',4':3,4]pyrazolo[1,5-a]pyrimidin-8(9H)-yl)(4-fluoro-2-((1-(2-fluoroethyl)azetidin-3-yl)oxy)phenyl)methanone

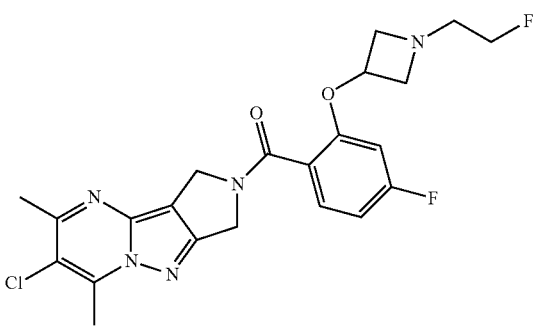 [SMILES: Cc1nc2c3c(nn2c(C)c1Cl)CN(C(=O)c1ccc(F)cc1OC1CN(CCF)C1)C3]

Step 1: tert-butyl 3-((methylsulfonyl)oxy)azetidine-1-carboxylate

To a stirred solution of tert-butyl 3-hydroxyazetidine-1-carboxylate (1.2 g, 6.92 mmol) in DCM (20 mL) was added TEA (2.0 mL, 13.8 mmol) followed by methane sulfonyl chloride (0.80 mL, 10.3 mmol, spectrochem) at 0° C. The reaction mixture was stirred at RT for 1 h. Reaction completion was monitored by TLC. Reaction mixture was diluted with water and extracted in dichloromethane (2×50 mL). The combined extract was washed with water, brine solution and dried over anhydrous Na$_2$SO$_4$ and concentrated. The crude product was isolated as pale yellow gum and was used as such for next step without further purification (1.2 g, 70%). $^1$H NMR (400 MHz, DMSO-d$_6$): δ 5.26-5.23 (m, 1H), 4.23 (t, J=9.6 Hz, 2H), 3.92 (d, J=6.8 Hz, 2H), 3.24 (s, 3H) 1.37 (s, 9H). LCMS: (Method A) 152.0 (M-Boc+H)$^+$, Rt. 3.48 min, 99.7% (Max).

Step 2: 3-(2-(3-chloro-2,4-dimethyl-8,9-dihydro-7H-pyrrolo[3',4':3,4]pyrazolo[1,5-a]pyrimidine-8-carbonyl)-5-fluorophenoxy)azetidine-1-carboxylic acid tert-butyl ester To a stirred solution of Intermediate C1 (0.6 g, 1.66 mmol) in DMF (degassed) in a sealed tube was added tert-butyl 3-((methyl sulfonyl)oxy)azetidine-1-carboxylate (1.2 g, 4.99 mmol) followed by cesium carbonate (1.08 g, 3.33 mmol). The reaction mixture was stirred at 70° C. for 20 h. Reaction completion was monitored by TLC. Reaction mixture was filtered through celite. DMF was removed under high vacuum the residue obtained was diluted with water and extracted in dichloromethane (2×50 mL). The combined extract was washed with water, brine solution and dried over anhydrous Na$_2$SO$_4$ and concentrated. The title product was isolated as brown gum and was taken as such to next step without further purification (0.7 g, 82%). $^1$H NMR (400 MHz, DMSO-d$_6$): δ 7.37-7.32 (m, 1H), 7.12-7.08 (m, 1H), 6.88 (t, J=8.6 Hz, 1H), 4.82-4.73 (m, 2H), 4.65-4.49 (m, 2H), 4.24 (t, J=8.9 Hz, 1H), 3.93 (d, J=8.3 Hz, 2H), 3.34-3.25 (m, 3H), 2.89-2.80 (m, 1H), 2.32-2.28 (m, 4H) 1.39 (s, 9H). LCMS: (Method A) 416.0 (M-Boc+H)$^+$, Rt. 4.87 min, 59.5% (Max).

Step 3: (2-(azetidin-3-yloxy)-4-fluorophenyl)(3-chloro-2,4-dimethyl-7H-pyrrolo[3',4':3,4]pyrazolo[1,5-a]pyrimidin-8(9H)-yl)methanone hydrochloride The title compound was prepared following the same protocol as described for Example 32 step 3, starting with 3-(2-(3-chloro-2,4-dimethyl-8,9-dihydro-7H-pyrrolo[3',4':3,4]pyrazolo[1,5-a]pyrimidine-8-carbonyl)-5-fluorophenoxy)azetidine-1-carboxylic acid tert-butyl ester obtained in step 2. It was isolated as brown solid (0.6 g, 98%). $^1$H NMR (400 MHz, DMSO-d$_6$): δ 9.50 (s, 2H), 7.93 (s, 1H), 7.26 (m 1H), 6.96-6.93 (m, 1H), 4.30-4.27 (m, 2H), 4.08-3.99 (m, 6H), 3.54 (s, 3H), 3.28 (s, 3H). LCMS: (Method A) 416.0 (M+H)$^+$, Rt. 3.06 min, 75.1% (Max).

Step 4: (3-chloro-2,4-dimethyl-7H-pyrrolo[3',4':3,4]pyrazolo[1,5-a]pyrimidin-8(9H)-yl)(4-fluoro-2-((1-(2-fluoroethyl)azetidin-3-yl)oxy)phenyl)methanone To a stirred solution of (2-(azetidin-3-yloxy)-4-fluorophenyl)(3-chloro-2,4-dimethyl-7H-pyrrolo[3',4':3,4]pyrazolo[1,5-a]pyrimidin-8(9H)-yl)methanone hydrochloride (0.3 g, 0.66 mmol) in DMF was added 1-bromo-2-fluoroethane (1

M solution in DMF) (1.5 mL, 0.99 mmol) followed by TEA (0.3 mL, 1.99 mmol). The reaction mixture was stirred at RT for 20 h. Reaction completion was monitored by TLC. DMF was removed under high vacuum. The residue obtained was washed with ether, purified by MD-auto prep, (Method A), affording the title compound as off white solid (40 mg, 13%). $^1$H NMR (400 MHz, DMSO-d$_6$): δ 7.40-7.37 (m, 1H), 6.93-6.89 (m, 1H), 6.84-6.81 (m, 1H), 4.95-4.90 (m, 1H), 4.86 (s, 1H), 4.82 (s, 1H), 4.61 (s, 1H), 4.56 (s, 1H), 4.44 (m 1H), 4.32 (m, 1H), 3.77-3.73 (m, 2H), 3.05-3.01 (m, 2H), 2.85 (s, 1.5H), 2.81 (s, 1.5H), 2.72-2.67 (m, 2H), 2.62 (s, 1.5H), 2.56 (s, 1.5H). LCMS: (Method A) 462.0 (M+H)$^+$, Rt. 3.20 min, 97.9% (Max). HPLC: (Method A) Rt. 3.16 min, 98.5% (Max).

Example 47

(3-chloro-2,4-dimethyl-7H-pyrrolo[3',4':3,4]pyrazolo [1,5-a]pyrimidin-8(9H)-yl)(2-((4,4-difluorocyclohexyl)oxy)-4-fluorophenyl)methanone

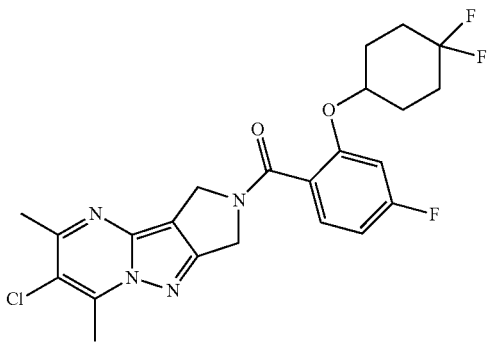 [SMILES: Cc1nc2c3c(nn2c(C)c1Cl)CN(C(=O)c1ccc(F)cc1OC1CCC(F)(F)CC1)C3]

To a stirred solution of 4-(2-(3-chloro-2,4-dimethyl-8,9-dihydro-7H-pyrrolo[3',4':3,4]pyrazolo[1,5-a]pyrimidine-8-carbonyl)-5-fluorophenoxy)cyclohexan-1-one (Example 41 and 49, step 4, 0.2 g, 0.43 mmol) in dry DCM (10 mL) was added (DAST) diethylaminosulphur trifluoride (0.16 g, 1.0 mmol) portion wise at 0° C. The reaction mixture was stirred at RT for 16 h. Reaction completion was monitored by TLC. The reaction mixture was concentrated and the crude mass obtained was purified by MD auto-prep (Method A) to get the title product as white solid. $^1$H NMR (400 MHz, DMSO-d$_6$): δ 7.42-7.37 (m, 1H), 7.23 (d, J=11.6 Hz, 1H), 6.93 (t, J=1.6 Hz, 1H), 4.81 (s, 1H), 4.79 (s, 1H), 4.76 (m, 1H), 4.59 (s, 1H), 4.54 (s, 1H), 2.85 (s, 1.6H), 2.81 (s, 1.4H), 2.62 (s, 1.5H), 2.56 (s, 1.5H), 1.92-1.81 (m, 8H). LCMS: (Method A) 479.0 (M+H)$^+$, Rt. 5.0 min, 99.4% (Max). HPLC: (Method A) Rt. 5.2 min, 99.9% (Max).

Example 50

(3-chloro-7H-pyrrolo[3',4':3,4]pyrazolo[1,5-a]pyrimidin-8(9H)-yl)(4-fluoro-2-{[(3-endo)-8-(2-hydroxyethyl)-8-azabicyclo[3.2.1]oct-3-yl]oxy}phenyl)methanone

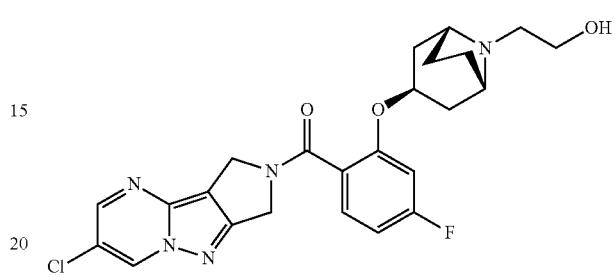

Step 1: {2-[(3-endo)-8-azabicyclo[3.2.1]oct-3-yloxy]-4-fluorophenyl}(3-chloro-7H-pyrrolo[3',4':3,4]pyrazolo[1,5-a]pyrimidin-8(9H)-yl)methanone hydrochloride The title compound was prepared following the same protocol as described for Example 25, step 1 and 2, using Intermediate A2 and Intermediate B2 as starting material. It was purified by recrystallization and isolated as hydrochloride salt and as brown solid as single isomer (300 mg, 61% over two steps). $^1$H NMR (400 MHz, DMSO-d$_6$): δ 9.58 (s, 1H), 8.88-8.78 (m, 2H), 8.62-8.58 (m, 1H), 7.78-7.70 (m, 1H), 7.41-7.37 (m, 1H), 7.22-7.12 (m, 1H), 4.81 (s, 2H), 4.61-4.58 (m, 2H), 4.05-3.97 (m, 2H), 3.55-3.09 (m, 2H), 2.25-2.21 (m, 3H), 2.14-2.06 (m, 1H), 1.97-1.95 (m, 1H), 1.34-1.28 (m, 1H). LCMS: (Method A) 442.0 (M+H)$^+$, Rt. 2.9 min, (90.3) % (Max).

Step 2: (3-chloro-7H-pyrrolo[3',4':3,4]pyrazolo[1,5-a]pyrimidin-8(9H)-yl)(4-fluoro-2-{[(3-endo)-8-(2-hydroxyethyl)-8-azabicyclo[3.2.1]oct-3-yl]oxy}phenyl)methanone The title compound was prepared following the same protocol as described for Example 34, using {2-[(3-endo)-8-azabicyclo[3.2.1]oct-3-yloxy]-4-fluorophenyl}(3-chloro-7H-pyrrolo[3',4':3,4]pyrazolo[1,5-a]pyrimidin-8(9H)-yl) methanone hydrochloride as starting material and replacing 1-bromo-2-fluoro ethane with 2-bromo ethanol. The crude product was purified by MD Auto-Prep (Method C) to get the title product as off white solid as single isomer. $^1$H NMR (400 MHz, DMSO-d$_6$): δ 9.60 (dd, J=8.0, 7.6 Hz, 1H), 8.65-8.59 (m, 1H), 7.39-7.35 (m, 1H), 6.99 (d, J=11.2 Hz, 1H), 6.89-6.86 (m, 1H), 4.83 (s, 2H), 4.71 (s, 1H), 4.63 (s, 1H), 4.63-4.60 (m, 2H), 4.29-4.26 (m, 1H), 3.40-3.35 (m, 2H), 3.07 (d, J=4.8 Hz, 2H), 2.51 (s, 2H), 2.04 (d, J=11.2 Hz, 2H), 1.68 (s, 6H). LCMS: (Method B) 486.0 (M+H)$^+$, Rt. 4.4 min, 96.9% (Max). HPLC: (Method B) Rt. 4.5 min, 98.2% (Max).

Example 51

(3-chloro-7H-pyrrolo[3',4':3,4]pyrazolo[1,5-a]pyrimidin-8(9H)-yl)(4-fluoro-2-{[(3-endo)-8-(2-fluoroethyl)-8-azabicyclo[3.2.1]oct-3-yl]oxy}phenyl)methanone

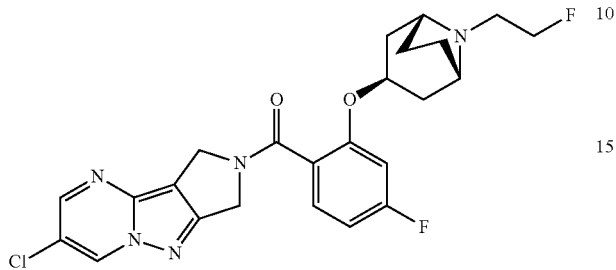

The title compound was prepared following the same protocol as described for Example 34, using {2-[(3-endo)-8-azabicyclo[3.2.1]oct-3-yloxy]-4-fluorophenyl}(3-chloro-7H-pyrrolo[3',4':3,4]pyrazolo[1,5-a]pyrimidin-8(9H)-yl) methanone hydrochloride (Example 50, step 1) as starting material. The crude product was purified by MD Auto-Prep (Method B) to get the title product as off white solid as single isomer. $^1$H NMR (400 MHz, DMSO-d$_6$): δ 9.59-9.56 (m, 1H), 8.63-8.58 (m, 1H), 7.36 (s, 1H), 6.97 (d, J=11.6 Hz, 1H), 6.85 (t, J=6.8 Hz, 1H), 4.82-4.70 (m, 2H), 4.69 (s, 1H), 4.62 (d, J=12 Hz, 2H), 4.47 (t, J=4.4 Hz, 1H), 4.35 (d, J=5.6 Hz, 1H), 3.06-2.94 (m, 3H), 2.02-1.98 (m, 3H), 1.67-1.60 (m, 6H). LCMS: (Method A) 488.3 (M+H)$^+$, Rt. 2.9 min, 96.1% (Max). HPLC: (Method A) Rt. 2.8 min, 96.5% (Max).

Example 52

(3-chloro-7H-pyrrolo[3',4':3,4]pyrazolo[1,5-a]pyrimidin-8(9H)-yl)(4-fluoro-2-{[(3-endo)-8-(2-methoxyethyl)-8-azabicyclo[3.2.1]oct-3-yl]oxy}phenyl)methanone

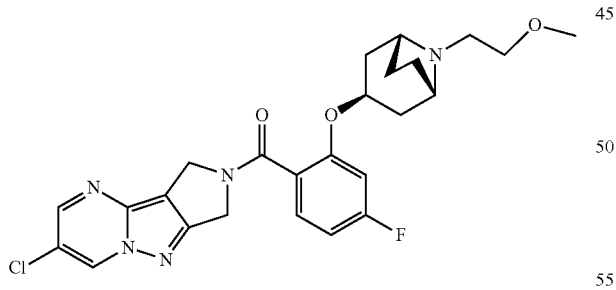

The title compound was prepared following the same protocol as described for Example 34, using {2-[(3-endo)-8-azabicyclo[3.2.1]oct-3-yloxy]-4-fluorophenyl}(3-chloro-7H-pyrrolo[3',4':3,4]pyrazolo[1,5-a]pyrimidin-8(9H)-yl) methanone hydrochloride (Example 50, step 1) as starting material and replacing 1-bromo-2-fluoro ethane with 1-bromo-2-methoxy ethane. The crude product was purified by Prep HPLC (Method B) to get the title product as pale yellow solid. $^1$H NMR (400 MHz, DMSO-d$_6$): δ 9.59 (dd, J=7.6, 7.2 Hz, 1H), 8.63-8.58 (m, 1H), 7.41-7.37 (m, 1H), 7.10-6.96 (m, 1H), 6.90-6.84 (m, 1H), 4.81 (s, 2H), 4.75-4.71 (m, 1H), 4.61-4.58 (m, 2H), 3.68-3.50 (m, 1H), 3.26-3.22 (m, 3H), 3.10-3.02 (m, 2H), 2.41-2.37 (m, 2H), 2.08-1.96 (m, 4H), 1.70-1.66 (m, 5H). LCMS: (Method B) 500.0 (M+H)$^+$, Rt. 4.9 min, 97.0% (Max). HPLC: (Method A) Rt. 2.9 min, 98.2% (Max).

Example 53

(3-chloro-7H-pyrrolo[3',4':3,4]pyrazolo[1,5-a]pyrimidin-8(9H)-yl)(4-fluoro-2-{[(3-endo)-8-methyl-8-azabicyclo[3.2.1]oct-3-yl]oxy}phenyl)methanone

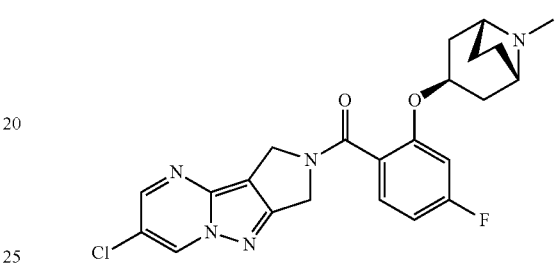

The title compound was prepared following the same protocol as described for Example 25, step 1, using Intermediate A2 and Intermediate B5 as starting material. It was purified by MD auto-prep (Method B) to get the title product as off white solid. $^1$H NMR (400 MHz, DMSO-d$_6$): δ 9.58 (dd, J=7.80, 2.00 Hz, 1H), 8.63-8.58 (m, 1H), 7.39-7.34 (m, 1H), 6.99-6.96 (m, 1H), 6.84 (dt, J=8.40, 2.00 Hz, 1H), 4.82 (s, 2H), 4.70-4.59 (m, 3H), 2.88-3.06 (m, 2H), 2.13-2.00 (m, 5H), 1.72-1.63 (m, 6H). LCMS: (Method A, Column Temperature: 50° C.) 456.0 (M+H)$^+$, Rt. 2.7 min, 99.3% (Max). HPLC: (Method A, Column Temperature: 50° C.) Rt. 2.7 min, 99.5% (Max).

Example 54

(syn)-(6-Chloro-5,7-dimethyl-1H,3H-2,4,7a,8-tetraaza-cyclopenta[a]inden-2-yl)-[4-fluoro-2-(4-fluoro-cyclohexyloxy)-phenyl]-methanone or (anti)-(6-Chloro-5,7-dimethyl-1H,3H-2,4,7a,8-tetraaza-cyclopenta[a]inden-2-yl)-[4-fluoro-2-(4-fluoro-cyclohexyloxy)-phenyl]-methanone

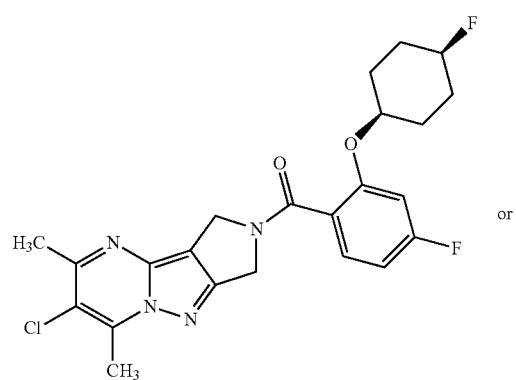

or

-continued

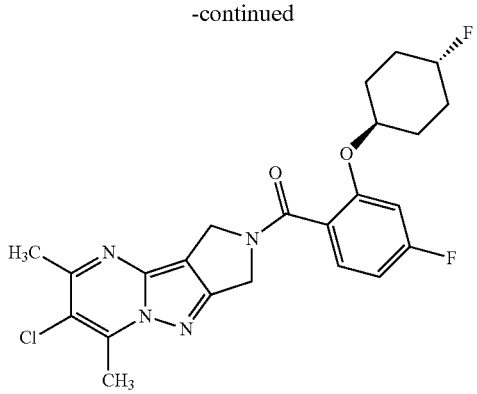

To a stirred solution of Example 41 (0.08 g, 0.174 mmol) in dry DCM (5 mL) was added (DAST) diethylaminosulphur trifluoride (0.042 g, 0.262 mmol) portion wise at 0° C. The reaction mixture was stirred at RT for 16 h. Reaction completion was monitored by TLC. The reaction mixture was concentrated completely and the crude mass obtained was purified by MD auto-prep (Method A) to get the title product as brown solid as single isomer. $^1$H NMR (400 MHz, DMSO-$d_6$): δ 7.38-7.35 (m, 1H), 7.18 (d, J=12.0 Hz, 1H), 6.89-6.85 (m, 1H), 4.81 (d, J=12.0 Hz, 2H), 4.66-4.61 (m, 2H), 4.57-4.52 (m, 2H), 2.83 (d, J=12.0 Hz, 3H), 2.62-2.56 (m, 3H), 1.88-1.80 (m, 4H), 1.57-1.53 (m, 4H). LCMS: (Method A) 461.0 (M+H), Rt. 4.98 min, 93.6% (Max). HPLC: (Method A) Rt. 4.94 min, 94.6% (Max).

Example 58

(3-chloro-2,4-dimethyl-7H-pyrrolo[3',4':3,4]pyrazolo[1,5-a]pyrimidin-8(9H)-yl)(4-fluoro-2-{[(3-endo)-9-methyl-9-azabicyclo[3.2.1]nonan-3-yl]oxy}phenyl)methanone

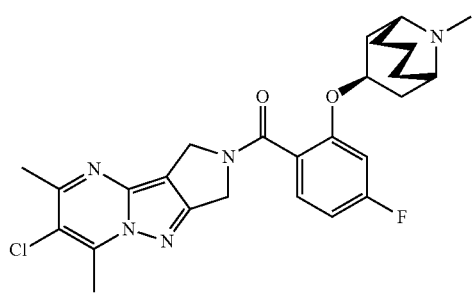

The title compound was prepared following the same protocol as described for Example 25, step 1, using Intermediate A1 and Intermediate B6 as starting material. It was purified by MD auto-prep (Method B) to get the title product as off white solid as single isomer. $^1$H NMR (400 MHz, DMSO-$d_6$): δ 7.36-7.32 (m, 1H), 7.01 (d, J=11.6 Hz, 1H), 6.87-6.83 (m, 1H), 4.77 (m, 3H), 4.55 (s, 1H), 4.49 (s, 1H), 2.83 (s, 1.5H), 2.80 (s, 1.5H), 2.79 (m, 1H), 2.61 (s, 1.6H), 2.55 (s, 1.4H), 2.43-2.38 (m, 3H), 2.30 (s, 3H), 2.12 (t, J=6.0 Hz, 1H), 1.70 (d, J=5.2 Hz, 2H), 1.37-1.34 (m, 2H), 1.10-0.98 (m, 3H). LCMS: (Method A) 498.2 (M+H)$^+$, Rt. 3.3 min, 97.2% (Max). HPLC: (Method A) Rt. 3.3 min, 98.2% (Max).

Example 59

(3-chloro-7H-pyrrolo[3',4':3,4]pyrazolo[1,5-a]pyrimidin-8(9H)-yl)(2-{[(3-endo)-8-(cyclopropylmethyl)-8-azabicyclo[3.2.1]oct-3-yl]oxy}-4-fluorophenyl)methanone

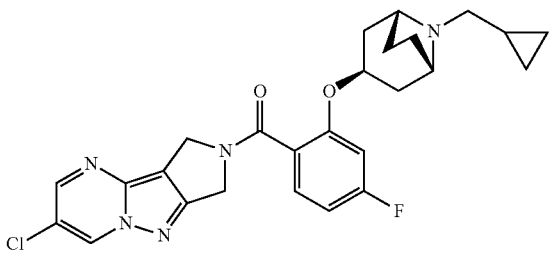 [SMILES: O=C(c1ccc(F)cc1O[C@H]1C[C@H]2CC[C@@H](C1)N2CC1CC1)N1Cc2nn3cc(Cl)cnc3c2C1]

To a stirred solution of {2-[(3-endo)-8-azabicyclo[3.2.1]oct-3-yloxy]-4-fluorophenyl}(3-chloro-7H-pyrrolo[3',4':3,4]pyrazolo[1,5-a]pyrimidin-8(9H)-yl)methanone hydrochloride (Example 50, step 1, 0177 g, 0.4 mmol) in dichloroethane (10 mL) at 0° C. was added cyclopropane carboxaldehyde (56 mg, 0.8 mmol, Spectrochem), triethyl amine (0.1 mL, 1.2 mmol, Spectrochem) and sodium triacetoxy borohydride (179 mg, 0.8 mmol). Trimethyl ortho formate (0.5 mL, catalytic, Spectrochem) was added to the reaction mass. Reaction mass was brought to RT and stirred for 24 h. Reaction mass was concentrated and the residue was dissolved in DCM, washed with water (30 mL), brine solution (30 mL), dried over Na$_2$SO$_4$ and evaporated. The crude was purified by preparative HPLC (Method C) affording the title product as off white solid. $^1$H NMR (400 MHz, CDCl$_3$): δ 8.74-8.71 (m, 1H), 8.46-8.39 (m, 1H), 7.37-7.33 (m, 1H), 6.78-6.76 (m, 1H), 6.75-6.73 (m, 1H), 5.0 (d, J=10.4 Hz, 2H), 4.72-4.63 (m, 3H), 3.50-3.35 (m, 2H), 2.40-2.20 (m, 3H), 2.00-1.30 (m, 7H), 1.00-0.81 (m, 1H), 0.58-0.42 (m, 2H), 0.20-0.05 (m, 2H). LCMS: (Method A) 496.0 (M+H)$^+$, Rt. 3.3 min, 97.8% (Max). HPLC: (Method A) Rt. 2.9 min, 99.0% (Max).

Example 61

[2-(3-Amino-cyclobutoxy)-4-fluoro-phenyl]-(6-chloro-5,7-dimethyl-1H,3H-2,4,7a,8-tetraaza-cyclopenta[a]inden-2-yl)-methanone, hydrochloride

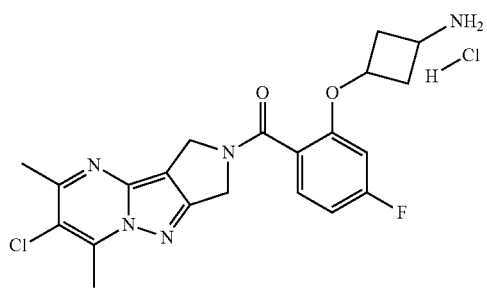

The title compound was prepared following the same protocol as described for Example 41, steps 1 to 4, using 3-Boc-amino-cyclobutanone (Combiblock) as starting material. The product was as purified by recrystallization to get the title product as pale yellow solid. $^1$H NMR (400 MHz, DMSO-d$_6$): δ 8.17-8.11 (m, 3H), 7.43-7.36 (m, 1H), 6.94-6.89 (m, 1H), 6.81-6.80 (m, 1H), 5.08-5.06 (m, 0.6H), 4.85 (s, 1H), 6.64-4.62 (m, 0.4H), 4.82 (s, 1H), 4.58 (s, 1H), 4.52 (s, 1H), 3.74 (s, 1H), 2.88 (s, 1.6H), 2.81 (s, 1.4H), 2.62 (s, 1.8H), 2.59 (m, 1H), 2.56 (s, 1.2H), 2.41-2.37 (m, 3H). LCMS: (Method A) 430.0 (M+H)$^+$, Rt. 3.07 min, 98.3% (Max). HPLC: (Method A) Rt. 3.15 min, 98.6% (Max).

Example 63

(3-chloro-7H-pyrrolo[3',4':3,4]pyrazolo[1,5-a]pyrimidin-8(9H)-yl)(2-{[(3-endo)-8-ethyl-8-azabicyclo[3.2.1]oct-3-yl]oxy}-4-fluorophenyl)methanone

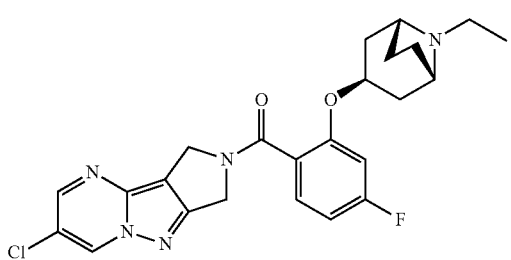 [SMILES: CCN1[C@@H]2CC[C@H]1C[C@@H](Oc1cc(F)ccc1C(=O)N1Cc3nn4cc(Cl)cnc4c3C1)C2]

The title compound was prepared following the same protocol as described for Example 59, replacing cyclopropane carboxaldehyde with acetaldehyde. The crude product was purified by MD Auto-Prep (Method C) to get the title product as white solid. $^1$H NMR (400 MHz, DMSO-d$_6$): δ 9.60-9.58 (m, 1H), 8.64-8.59 (m, 1H), 7.40-7.35 (m, 1H), 6.98-6.94 (m, 1H), 6.9 (t, J=2.0 Hz, 1H), 4.87-4.80 (m, 2H), 4.73-4.69 (m, 1H), 4.6 (d, J=10.8 Hz, 2H), 3.10-3.00 (m, 2H), 2.27-2.22 (m, 2H), 2.00-1.97 (m, 2H), 1.69-1.61 (m, 6H), 0.9 (t, J=6.8 Hz, 3H). LCMS: (Method A) 470.0 (M+H)$^+$, Rt. 2.8 min, 99.3% (Max). HPLC: (Method A) Rt. 2.8 min, 98.6% (Max).

Example 64

(3-chloro-7H-pyrrolo[3',4':3,4]pyrazolo[1,5-a]pyrimidin-8(9H)-yl)(4-fluoro-2-{[(3-endo)-8-propyl-8-azabicyclo[3.2.1]oct-3-yl]oxy}phenyl)methanone

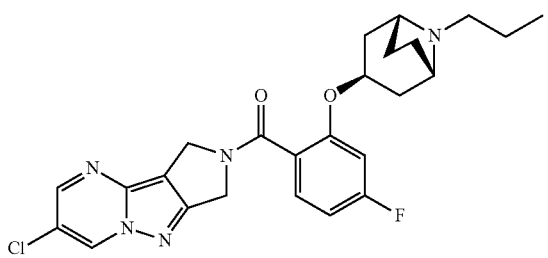 [SMILES: CCCN1[C@@H]2CC[C@H]1C[C@@H](Oc1cc(F)ccc1C(=O)N1Cc3nn4cc(Cl)cnc4c3C1)C2]

The title compound was prepared following the same protocol as described for Example 59, replacing cyclopropane carboxaldehyde with propaldehyde. The crude product was purified by MD Auto-Prep (Method B) to get the title product as off white solid. $^1$H NMR (400 MHz, DMSO-d$_6$): δ 9.60-9.58 (dd, J=8.0, 2.0 Hz, 1H), 8.64-8.59 (m, 1H), 7.39-7.34 (m, 1H), 6.98-6.93 (m, 1H), 6.86-6.81 (m, 1H), 4.82 (s, 2H), 4.72-4.68 (m, 1H), 4.62, 4.59 (s, 2H), 3.01 (s, 2H), 2.16 (t, J=7.20 Hz, 2H), 2.00-1.97 (m, 2H), 1.66-1.59 (m, 6H), 1.36-1.31 (m, 2H), 0.82 (t, J=7.20 Hz, 3H). LCMS: (Method B) 484.0 (M+H)$^+$, Rt. 5.0 min, 96.4% (Max). HPLC: (Method B) Rt. 5.0 min, 98.5% (Max).

Example 65

(3-chloro-7H-pyrrolo[3',4':3,4]pyrazolo[1,5-a]pyrimidin-8(9H)-yl)(2-{[(3-endo)-8-(2,2-difluoroethyl)-8-azabicyclo[3.2.1]oct-3-yl]oxy}-4-fluorophenyl)methanone

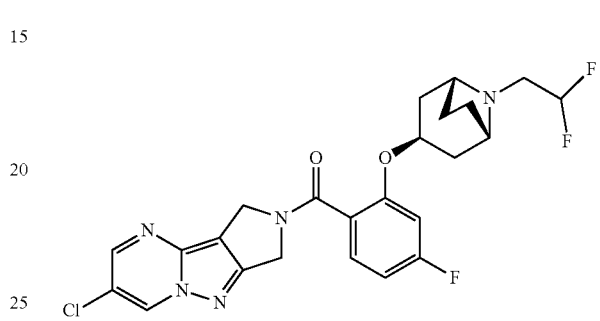

The title compound was prepared following the same protocol as described for Example 51, replacing 1-bromo-2-fluoroethane with 2-bromo-1,1-difluoroethane (Combiblock). The crude product was purified by Prep-HPLC (Method C), affording the title product as white solid. $^1$H NMR (400 MHz, CDCl$_3$): δ 8.74-8.71 (m, 1H), 8.46-8.39 (m, 1H), 7.38-7.33 (m, 1H), 6.77-6.72 (m, 1H), 6.61-6.57 (m, 1H), 5.94-5.68 (m, 1H), 5.0 (d, J=10.4 Hz, 2H), 4.72-4.57 (m, 3H), 3.30-3.10 (m, 2H), 2.72-2.51 (m, 2H), 2.30-2.05 (m, 2H), 2.00-1.70 (m, 6H). LCMS: (Method A) 506.0 (M+H)$^+$, Rt. 2.8 min, 99.6% (Max). HPLC: (Method A) Rt. 2.8 min, 98.2% (Max).

Example 66

[(3endo)-3-{2[(3-chloro-7H-pyrrolo[3',4':3,4]pyrazolo[1,5-a]pyrimidin-8(9H)-yl)carbonyl]-5-fluorophenoxy}-8-azabicyclo[3.2.1]oct-8-yl]acetonitrile

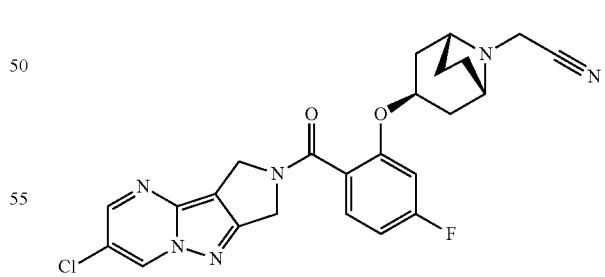

The title compound was prepared following the same protocol as described for Example 51, replacing 1-bromo-2-fluoroethane with bromo acetonitrile. The crude product was purified by flash column chromatography to get the title product as off white solid. $^1$H NMR (400 MHz, DMSO-d$_6$): δ 8.74-8.71 (m, 1H), 8.47-8.39 (m, 1H), 7.39-7.33 (m, 1H), 6.78-6.74 (m, 1H), 6.61-6.59 (m, 1H), 5.0 (d, J=10.0 Hz, 2H), 4.71-4.58 (m, 3H), 3.30-3.20 (m, 4H), 2.30-2.10 (m, 2H), 1.98-1.87 (m, 6H). LCMS: (Method A) 481.0 (M+H)+, Rt. 3.3 min, 95.30% (Max). HPLC: (Method A) Rt. 3.4 min, 98.5% (Max).

Example 67

(3-chloro-2,4-dimethyl-7H-pyrrolo[3',4':3,4]pyrazolo [1,5-a]pyrimidin-8(9H)-yl)(4-fluoro-2-(2-(5-methyl-pyridin-3-yl)ethoxy)phenyl)methanone

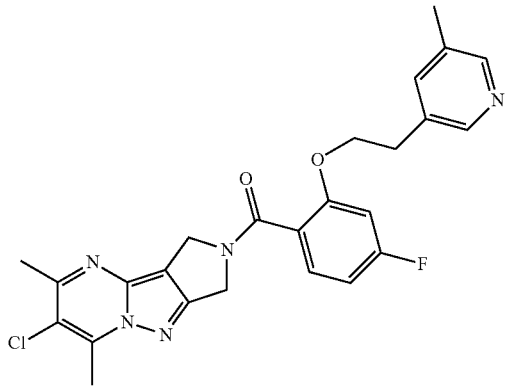 [SMILES: Cc1cncc(CCOc2cc(F)ccc2C(=O)N2Cc3nn4c(C)c(Cl)c(C)nc4c3C2)c1]

The title compound was prepared following the same protocol as described for Example 42, using 3-bromo-5-methyl pyridine (Combiblock) as starting material. It was isolated as off white solid. $^1$H NMR (400 MHz, DMSO-d$_6$): δ 8.13 (d, J=4.8 Hz, 1H), 7.66 (s, 0.5H), 7.56 (s, 0.5H), 7.45-7.41 (m, 1H), 7.31-7.26 (m, 1H), 7.08 (d, J=11.8 Hz, 1H), 6.86-6.82 (m, 1H), 4.71 (d, J=6.2 Hz, 2H), 4.32 (t, J=5.6 Hz, 2H), 4.12 (s, 1H), 4.03 (s, 1H), 2.94-2.89 (m, 2H), 2.88 (s, 1.5H), 2.82 (s, 1.5H), 2.64 (s, 1.5H), 2.55 (s, 1.5H), 1.98 (s, 1.5H), 1.90 (s, 1.5H). LCMS: (Method A) 480.0 (M+H)+, Rt. 3.4 min, 97.7% (Max). HPLC: (Method A) Rt. 3.3 min, 98.9% (Max).

Example 68

(3-chloro-7H-pyrrolo[3',4':3,4]pyrazolo[1,5-a]pyrimidin-8(9H)-yl)(4-fluoro-2-(((3-endo)-(6-exo)-6-hydroxy-8-methyl-8-azabicyclo[3.2.1]octan-3-yl)oxy)phenyl)methanone

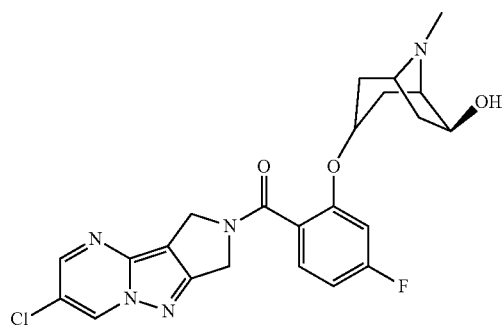 [SMILES: CN1C2CC(Oc3cc(F)ccc3C(=O)N3Cc4nn5cc(Cl)cnc5c4C3)CC1[C@@H](O)C2]

The title compound was prepared following the same protocol as described for Example 25, step 1 and 2, using Intermediate A2 and Intermediate B4 as starting material. The crude product was purified by MD Auto-Prep (Method B) to get the title product as off white solid as racemic mixture. $^1$H NMR (400 MHz, DMSO-d$_6$): δ 9.58 (dd, J=9.8, 2.40 Hz, 1H), 8.63-8.58 (m, 1H), 7.39-7.35 (m, 1H), 6.98-6.95 (m, 1H), 6.84 (dt, J=8.4, 2.4 Hz, 1H), 4.88 (s, 2H), 4.68-4.66 (m, 1H), 4.62-4.58 (m, 3H), 4.30-4.20 (m, 1H), 3.32-3.16 (m, 1H), 2.95-2.89 (m, 1H), 2.43 (s, 3H), 2.20-2.10 (m, 1H), 2.04-1.92 (m, 2H), 1.75-1.67 (m, 2H), 1.54-1.48 (m, 1H). LCMS: (Method A) 472.0 (M+H)+, Rt. 2.5 min, 99.0% (Max). HPLC: (Method A) Rt. 2.5 min, 99.5% (Max).

Example 70

(3-chloro-2,4-dimethyl-7H-pyrrolo[3',4':3,4]pyrazolo [1,5-a]pyrimidin-8(9H)-yl)(4-fluoro-2-(((3S,4S)-3-hydroxypiperidin-4-yl)oxy)phenyl)methanone hydrochloride or (3-chloro-2,4-dimethyl-7H-pyrrolo [3',4':3,4]pyrazolo[1,5-a]pyrimidin-8(9H)-yl)(4-fluoro-2-(((3R,4R)-3-hydroxypiperidin-4-yl)oxy) phenyl)methanone hydrochloride

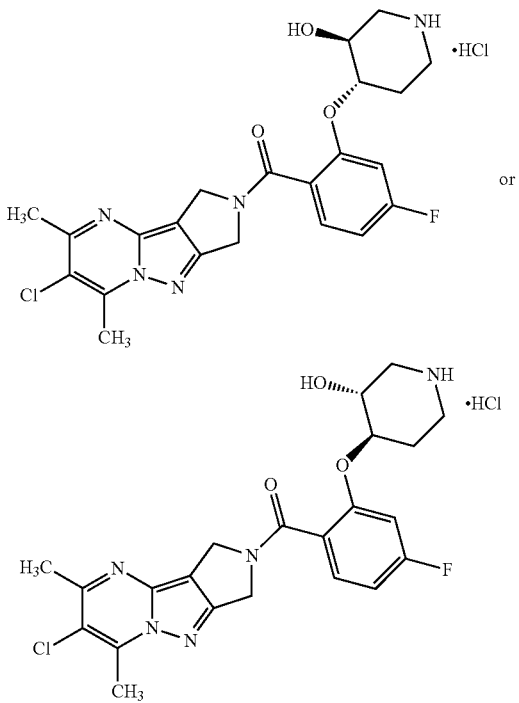

The title compound was prepared following the same protocol as described for Example 25, using Intermediate A1 and Intermediate B8a as starting material. It was purified by recrystallization and isolated as pale yellow solid (70 mg, 70%). The title compound is a single enantiomer. $^1$H NMR (400 MHz, DMSO-d$_6$): δ 8.90-8.85 (m, 1H), 8.68-8.59 (m, 1H), 7.55-7.42 (m, 1H), 7.29-7.15 (m, 1H), 7.03-6.93 (m, 1H), 6.03-5.89 (m, 1H), 4.91-4.83 (m, 2H), 4.74-4.58 (m, 3H), 3.82 (s, 1H), 3.09 (m 3H), 2.85 (m, 2.6H), 2.81 (s, 1.4H) 2.63 (s, 1.5H), 2.56 ((S, 1.5H), 2.17 (m, 1H), 1.81 (m, 1H). LCMS: (Method B) 460.0 (M+H)+, Rt. 47 min, 96.9% (Max). HPLC: (Method B) Rt. 4.8 min, 97.3% (Max).

Example 71

(6-Chloro-5,7-dimethyl-1H,3H-2,4,7a,8-tetraaza-cyclopenta[a]inden-2-yl)-[2-(3-dimethylamino-cyclobutoxy)-4-fluoro-phenyl]-methanone

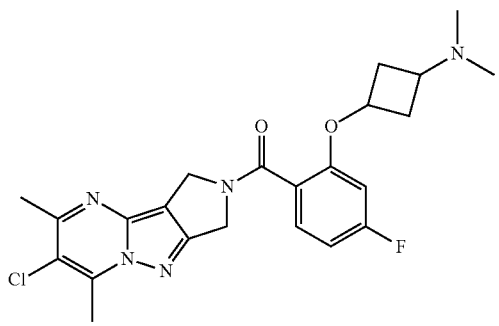

The title compound was prepared following the same protocol as described for Example 2, starting from Example 61. The crude product was purified by Prep-HPLC (Method B) to get the title product as pale brown solid. $^1$H NMR (400 MHz, DMSO-d$_6$): δ 7.35-7.38 (m, 1H), 6.85-6.90 (m, 1H), 6.77-6.81 (m, 1H), 4.81-4.85 (m, 2H), 4.52-4.58 (m, 2H), 2.85 (s, 1.6H), 2.81 (s, 1.4H), 2.65 (m, 1H), 2.62 (m, 2.2H), 2.56 (s, 1.8H), 2.25-2.31 (m, 2H), 2.05-2.10 (m, 1H), 1.94-2.00 (m, 6H), 1.88-1.90 (m, 1H). LCMS: (Method A) 458.0 (M+H)$^+$, Rt. 3.28 min, 94.6% (Max). HPLC: (Method A) Rt. 3.27 min, 95.8% (Max).

Example 72

(3-chloro-2,4-dimethyl-7H-pyrrolo[3',4':3,4]pyrazolo[1,5-a]pyrimidin-8(9H)-yl)(4-fluoro-2-(2-(5-methyl-pyridin-3-yl)ethoxy)phenyl)methanone

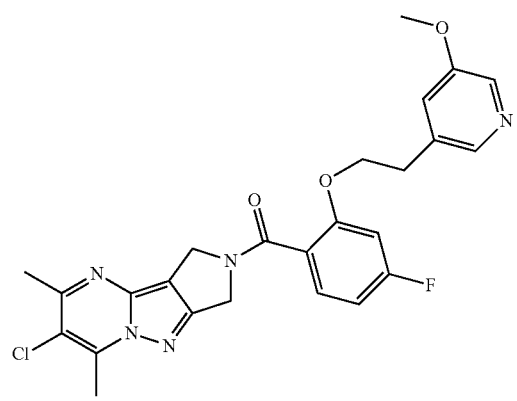 [SMILES: COc1cncc(CCOc2cc(F)ccc2C(=O)N2Cc3nn4c(C)c(Cl)c(C)nc4c3C2)c1]

The title compound was prepared following the same protocol as described for Example 42, using 3-bromo-5-methoxypyridine (ARK Pharma) as starting material. The crude product was purified by MD Auto-Prep (Method C) to get the title product as off white solid. $^1$H NMR (400 MHz, DMSO-d$_6$): δ 7.94 (dd, J=7.6, 1.2 Hz, 1H), 7.58-7.46 (m, 1H), 7.33-7.27 (m, 1H), 7.21-7.19 (m, 1H), 7.10 (dd, J=11.4, 2.0 Hz, 1H), 6.88-6.84 (m, 1H), 4.68 (s, 2H), 4.36 (t, J=6.0 Hz, 2H), 4.13 (s, 1H), 4.04 (s, 1H), 3.57 (s, 1.5H), 3.50 (s, 1.5H) 2.96-2.95 (m, 2H), 2.89 (s, 1.5H), 2.83 (s, 1.5H) 2.65 (s, 1.5H), 2.58 (s, 1.5H). LCMS: (Method A) 496.0 (M+H)$^+$, Rt. 3.3 min, 97.8% (Max). HPLC: (Method A) Rt. 3.3 min, 99.8% (Max).

Example 78

(2-endo)-(R)-[2-(7-Aza-bicyclo[2.2.1]hept-2-yloxy)-4-fluoro-phenyl]-(6-chloro-5,7-dimethyl-1H,3H-2,4,7a,8-tetraaza-cyclopenta[a]inden-2-yl)-methanone hydrochloride or (2-endo)-(S)-[2-(7-Aza-bicyclo[2.2.1]hept-2-yloxy)-4-fluoro-phenyl]-(6-chloro-5,7-dimethyl-1H,3H-2,4,7a,8-tetraaza-cyclopenta[a]inden-2-yl)-methanone hydrochloride

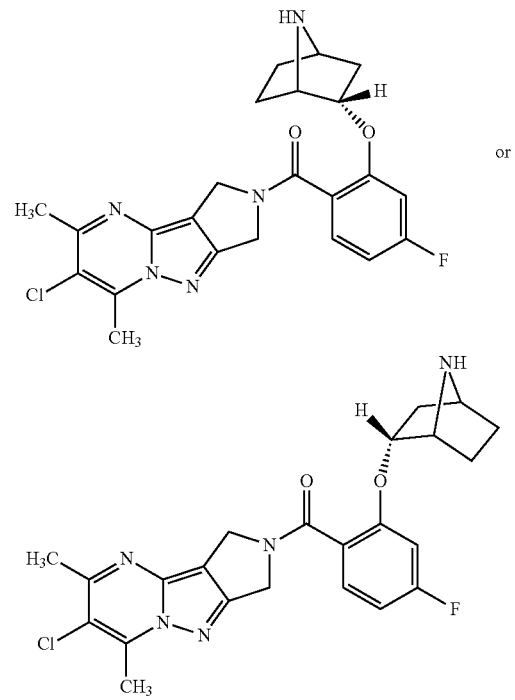

Step 1: (2-endo)-2-[2-(6-Chloro-5,7-dimethyl-1H,3H-2,4,7a,8-tetraaza-cyclopenta[a]indene-2-carbonyl)-5-fluoro-phenoxy]-7-aza-bicyclo[2.2.1]heptane-7-carboxylic acid tert-butyl ester Synthesized following the same procedure as described for synthesis of Intermediate C2 using Intermediate A1 and Intermediate B9 as the starting material. Crude product was purified by flash column chromatography (230-400 size mesh) using 7.5-8.0% gradient elution of ethyl acetate in n-hexane to afford the pure product as off white solid. $^1$H NMR (400 MHz, DMSO-d$_6$): δ 7.39-7.35 (m, 1H), 7.02 (dd, J=11.2, 2.4 Hz, 1H), 6.97-6.87 (m, 1H), 4.88 (s, 1.7H), 4.80 (s, 1.3H), 4.54 (s, 1.08H), 4.50 (s, 0.87H), 4.25-4.22 (m, 1H), 4.05 (s, 1H), 2.84 (s, 1.6H), 2.80 (s, 1.4H), 2.61 (s, 1.7H), 2.56 (s, 1.3H), 2.49-2.46 (m, 2H), 1.83-1.81 (m, 1H), 1.55-1.52 (m, 1H), 1.40-1.37 (m, 1H), 1.36 (s, 9H), 1.25-1.20 (m, 1H). LCMS: (Method A) 500.0 (M-tBu+H)$^+$, Rt. 5.4 min, 99.0% (Max).

Step 2: (2-endo)-(R)-[2-(7-Aza-bicyclo[2.2.1]hept-2-yloxy)-4-fluoro-phenyl]-(6-chloro-5,7-dimethyl-1H,3H-2,4,7a,8-tetraaza-cyclopenta[a]inden-2-yl)-methanone hydrochloride or (2-endo)-(S)-[2-(7-Aza-bicyclo[2.2.1]hept-2-yloxy)-4-fluoro-phenyl]-(6-chloro-5,7-dimethyl-1H,3H-2,4,7a,8-tetraaza-cyclopenta[a]inden-2-yl)-methanone hydrochloride Synthesized using the procedure as described for Example 1 Step 4. The crude hydrochloride salt was purified by prep-HPLC (Method C) without further processing to get the title product as off white solid as second eluting compound and as single enantiomer. $^1$H NMR (400 MHz, DMSO-$d_6$): δ 8.23 (brs, 1H), 7.44-7.39 (m, 1H), 6.97-6.92 (m, 2H), 4.89-4.81 (m, 3H), 4.55 (s, 1H), 4.51 (s, 1H), 4.24 (s, 1H), 3.98 (s, 1H), 2.84 (s, 1.6H), 2.80 (s, 1.4H), 2.61 (s, 1.6H), 2.54 (s, 1.4H), 2.35-2.29 (m, 1H), 1.98-1.86 (m, 1H), 1.70-1.64 (m, 1H), 1.55-1.31 (m, 3H). LCMS: (Method A) 456.0 (M+H)$^+$, Rt. 3.1 min, 99.4% (Max). HPLC: (Method A) Rt. 3.1 min, 99.4% (Max). HPLC: (Method D) Rt. 15.9 min, 100% (242 nm).

The examples below were synthesized according to procedures described in the previous examples.

Example 3

(3-chloro-2,4-dimethyl-7H-pyrrolo[3',4':3,4]pyrazolo[1,5-a]pyrimidin-8(9H)-yl)(3-((1-methylpiperidin-4-yl)oxy)pyridin-4-yl)methanone

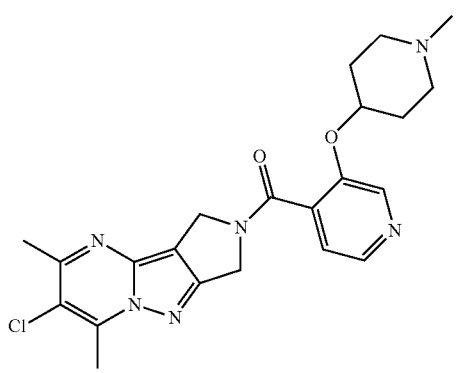

The crude product was purified by MD Auto-Prep (Method A) affording the title product as white solid. $^1$H NMR (400 MHz, DMSO-$d_6$): δ 8.57 (d, J=2.5 Hz, 1H), 8.30 (d, J=4.6 Hz, 1H), 7.36 (t, J=4.1 Hz, 1H), 4.84 (d, J=10.9 Hz, 2H), 4.64-4.55 (m, 3H), 2.83,2.80 (s, 3H), 2.61 (s, 3H), 2.37-2.32 (m, 2H), 2.17-2.14 (m, 2H), 2.02,2.0 (s, 3H), 1.86 (s, 2H), 1.60-1.58 (m, 2H). LCMS: (Method A) 441.2 (M+H), Rt. 2.4 min, 97.6% (Max). HPLC: (Method A) Rt. 2.4 min, 98.7% (Max).

Example 12

(3-chloro-7H-pyrrolo[3',4':3,4]pyrazolo[1,5-a]pyrimidin-8(9H)-yl)(4-fluoro-2-((1-methylpiperidin-4-yl)oxy)phenyl)methanone

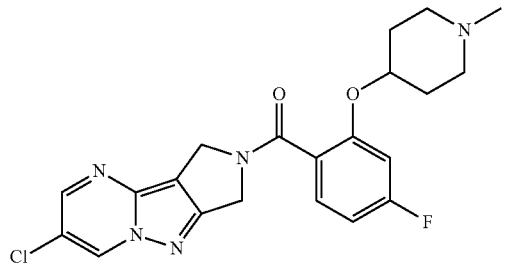 [SMILES: CN1CCC(Oc2cc(F)ccc2C(=O)N2Cc3nn4cc(Cl)cnc4c3C2)CC1]

The crude product was purified by MD auto-prep (Method B) affording the title product as off white solid. $^1$H NMR (400 MHz, DMSO-$d_6$): δ 9.58 (dd, J=10.40, 2.00 Hz, 1H), 8.62-8.58 (m, 1H), 7.38-7.33 (m, 1H), 7.13 (d, J=11.20 Hz, 1H), 6.86 (dt, J=8.40, 2.00 Hz, 1H), 4.84 (s, 2H), 4.60-4.53 (m, 3H), 2.38-2.25 (m, 2H), 2.22-2.08 (m, 2H), 1.99 (d, J=12.00 Hz, 3H), 1.89-1.78 (m, 2H), 1.63-1.51 (m, 2H). LCMS: (Method A, Column Temperature: 50° C.) 430.0 (M+H), Rt. 2.7 min, 98.9% (Max). HPLC: (Method A, Column Temperature: 50° C.) Rt. 2.7 min, 99.3% (Max).

Example 14

4-(3-chloro-2,4-dimethyl-8,9-dihydro-7H-pyrrolo[3',4':3,4]pyrazolo[1,5-a]pyrimidine-8-carbonyl)-3-(2-(dimethylamino)ethoxy)benzonitrile

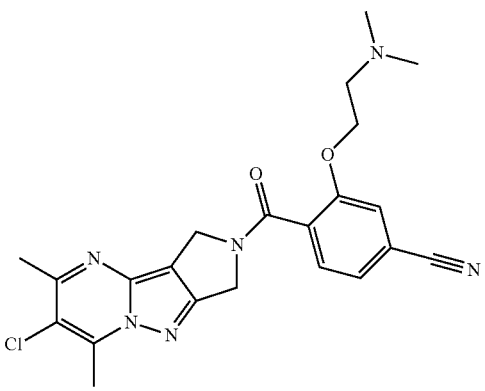 [SMILES: Cc1nc2c3c(nn2c(C)c1Cl)CN(C(=O)c1ccc(C#N)cc1OCCN(C)C)C3]

The crude product was purified by MD Auto-Prep (Method A), affording the title compound as white solid. $^1$H NMR (400 MHz, DMSO-$d_6$): δ 7.69 (s, 1H), 7.54-7.49 (m, 2H), 4.83 (d, J=10.8 Hz, 2H), 4.61-4.56 (m, 2H), 4.23 (t, J=5.2 Hz, 2H), 2.85, 2.81 (s, 3H), 2.62-2.56 (m, 5H), 2.05 (s, 6H). LCMS: (Method A) 439.2 (M+H), Rt. 3.1 min, 99.1% (Max). HPLC: (Method A) Rt. 3.1 min, 98.3% (Max).

Example 19

(6-Chloro-5,7-dimethyl-1H,3H-2,4,7a,8-tetraaza-cyclopenta[a]inden-2-yl)-[4-fluoro-2-(pyridin-3-ylmethoxy)-phenyl]-methanone

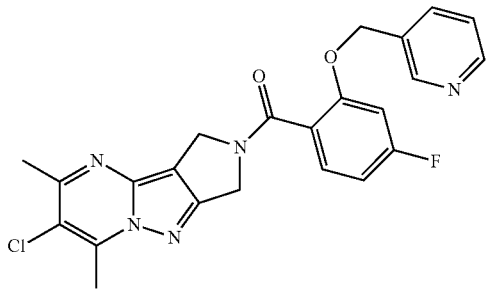 [SMILES: Cc1nc2c3c(nn2c(C)c1Cl)CN(C(=O)c1ccc(F)cc1OCc1cccnc1)C3]

The crude sample was purified by the flash column chromatography (230-400 size mesh) using a gradient elution of 2-2.25% methanol in dichloromethane to afford the title product as off white solid. $^1$H NMR (400 MHz, DMSO-d$_6$): δ 8.56 (t, J=2.0 Hz, 1H), 8.45-8.43 (m, 1H), 7.74-7.72 (m, 1H), 7.44-7.39 (m, 1H), 7.32-7.28 (m, 1H), 7.25-7.22 (dd, J=11.6, 2.4 Hz, 1H), 6.95-6.91 (m, 1H), 5.29 (s, 2H), 4.82, 4.79 (s, 2H), 4.57, 4.51 (s, 2H), 2.84, 2.80 (s, 3H), 2.62, 2.56 (s, 3H). LCMS: (Method A) 452.0 (M+H), Rt. 3.2 min, 95.9% (max). HPLC: (Method A) Rt. 3.2 min, 96.4% (max).

Example 22

(3-chloro-4-ethyl-2-methyl-7H-pyrrolo[3',4':3,4]pyrazolo[1,5-a]pyrimidin-8(9H)-yl)(2-((4-hydroxytetrahydrofuran-3-yl)oxy)phenyl)methanone or (3-chloro-2-ethyl-4-methyl-7H-pyrrolo[3',4':3,4]pyrazolo[1,5-a]pyrimidin-8(9H)-yl)(2-((4-hydroxytetrahydrofuran-3-yl)oxy)phenyl)methanone

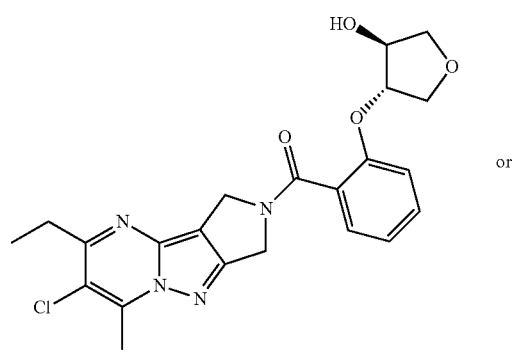

or

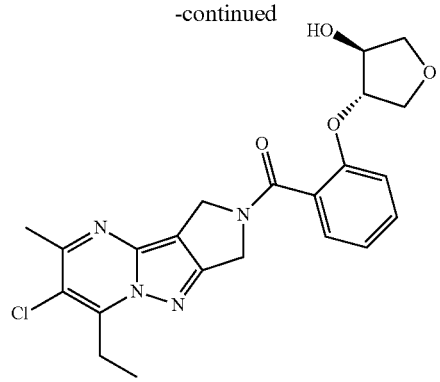

The crude product was purified by MD Auto-Prep (Method A), affording the title compound as off white solid. $^1$H NMR (400 MHz, DMSO-d$_6$): δ 7.48-7.44 (m, 1H), 7.34-7.31 (m, 1H), 7.23(d, J=8.4 Hz, 1H), 7.09 (t, J=12.0 Hz, 1H), 5.48 (t, J=6.8 Hz, 1H), 4.82 (d, J=14.0 Hz, 2H), 4.76 (d, J=3.6 Hz, 1H), 4.54-4.47 (m, 2H), 4.18 (br s, 1H), 4.03-4.00 (m, 1H), 3.75-3.69 (m, 2H), 3.52-3.50 (m, 1H), 3.30-3.26 (m, 2H), 2.62,2.55 (s, 3H), 1.31-1.24 (m, 3H). LCMS: (Method A) 443.2 (M+H), Rt. 3.7 min, 97.8% (Max). HPLC: (Method A) Rt. 3.7 min, 97.5% (Max).

Example 23

(6-Chloro-1-hydroxymethyl-5,7-dimethyl-1H,3H-2,4,7a,8-tetraaza-cyclopenta[a]inden-2yl)-[2-(1-methyl-piperidin-4-yloxy)-phenyl]-methanone

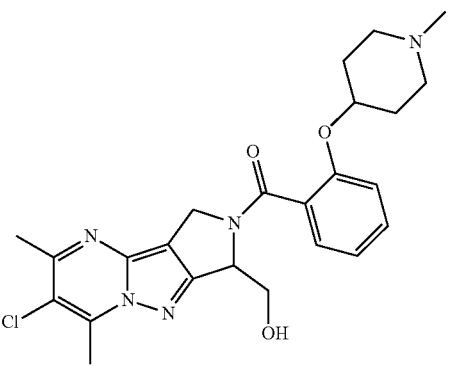

Step 1:
3-tert-Butoxy-2-(2-cyanoethylamino)propionic acid

To a stirred solution of sodium hydroxide (5.58 g, 139 mmol, S.D. Fine Chemicals) in water was added 2-amino-3-tert-butoxy propionic acid (15 g, 93.05 mmol, Fluka Chemica) in portions at 0° C. Once the suspension was turned to a clear solution, acrylonitrile (5.93 g, 111 mmol, Sigma Aldrich) was added in drops over a period of 45 min. Reaction mixture was allowed to stir at RT overnight. After the completion of the reaction as monitored by the TLC, reaction mass was acidified with citric acid (≈pH=3-4). The resulting precipitate was filtered, washed with water (3×75 mL), diethyl ether (50 mL) and dried under vacuo to afford the title product as white solid (12 g, 60%). $^1$H NMR (300 MHz, DMSO-d$_6$): δ 3.51-3.47 (m, 2H), 3.23 (t, J=4.7 Hz, 2H), 2.90-2.86 (m, 1H), 2.72-2.66 (m, 1H), 2.62-2.60 (m, 2H), 1.12, 1.09 (s, 9H). LCMS: (Method A) 215.3 (M+H)$^+$, Rt=1.5 min, 98.6% (ELSD).

Step 2: 3-tert-Butoxy-2-[tert-butoxycarbonyl-(2-cyanoethyl)amino]-propionic acid To a stirred solution of 3-tert-butoxy-2-(2-cyanoethyl-amino)propionic acid (12 g, 56 mmol) in methanol (280 mL) was added triethylamine (17.0 g, 168 mmol, Spectrochem) followed by di-tert-butyl dicarbonate (18.3 g, 84.0 mmol, Spectrochem) at 0° C. under N$_2$ atmosphere. Reaction mixture was allowed to stir at RT for 16 h. The progress of the reaction was monitored by TLC. Upon completion of the reaction, reaction mass was diluted with dichloromethane (100 mL). The organic phase was washed with water, brine solution and dried over anhydrous Na$_2$SO$_4$. The crude product was isolated as yellow gum and was taken to next step without further purification (15 g, 85%). $^1$H NMR (400 MHz, DMSO-d$_6$): δ 4.21-4.09 (m, 2H), 3.75-3.73 (m, 1H), 3.56-3.52 (m, 2H), 3.42-3.38 (m, 2H), 1.42, 1.38 (s, 9H), 1.13, 1.08 (s, 9H). LCMS: (Method A) 215.0 (M-BOC+H)$^+$, Rt. 4.1 min, 97.6% (ELSD).

Step 3: 3-tert-Butoxy-2-[tert-butoxycarbonyl-(2-cyanoethyl)amino]propionic acid methyl ester To a stirred solution of 3-tert-butoxy-2-[tert-butoxycarbonyl-(2-cyanoethyl)amino]-propionic acid (15 g, 47.7 mmol) in anhydrous DMF (235 mL) was added anhydrous potassium carbonate (16.5 g, 119 mmol, Loba Chemie) at RT under N$_2$ atmosphere and allowed to stir at the same temperature for 30 min. A solution of iodomethane (13.5 g, 95.4 mmol, Aldrich) in DMF (10 mL) was added in drops at 0° C. and allowed to stir at RT for 3 h. The progress of the reaction was monitored by the TLC. Upon completion of the reaction solvent was removed under vacuo. Residue obtained was dissolved in water (50 mL) and extracted in dichloromethane (3×150 mL). Combined extract was washed with water, brine solution and dried over anhydrous Na$_2$SO$_4$. The crude product obtained was purified by flash column chromatography (230-400 size mesh) using gradient elution of ethyl acetate (25-28%) in pet ether to afford the title product as colorless gum (10.1 g, 64%). $^1$H NMR (300 MHz, DMSO-d$_6$): δ 4.35-4.32 (m, 1H), 3.80-3.67 (m, 2H), 3.59, 3.56 (s, 3H), 3.49-3.39 (m, 2H), 2.70-2.64 (m, 2H), 1.41, 1.32 (s, 9H), 1.12, 1.09 (s, 9H). LCMS: (Method A) 229.3 (M-BOC+H)$^+$, Rt. 3.8 min, 99.5% (ELSD).

Step 4: 2-tert-Butoxymethyl-4-cyano-3-oxo-pyrrolidine-1-carboxylic acid tert-butyl ester To a pre-cooled (-78° C.) solution of diisopropylamine (3.6 g, 35.6 mmol, Spectrochem) in anhydrous THF (100 mL) was added n-butyl lithium (2.28 g, 14.3 mL, 2.5 M in THF, FMC Chemicals) in drops under N$_2$ atmosphere. Reaction mass was allowed to stir at the same temperature for 1 h and at 0° C. for 30 min. A solution of 3-tert-butoxy-2-[tert-butoxycarbonyl-(2-cyanoethyl)-amino]-propionic acid methyl ester (9 g, 27.4 mmol) in anhydrous THF (15 mL) was added at -78° C. in drops over a period of 45 min. Reaction mass was allowed to stir at the same temperature for 45 min. The progress of the reaction was monitored by the TLC and LCMS analysis. Upon completion of the reaction, reaction mass was quenched with ice-water and citric acid at 0° C. Reaction mass was extracted in ethyl acetate (3×100 mL). Combined extract was washed with water, brine solution and dried over anhydrous Na$_2$SO$_4$. The crude product obtained was taken to next step without further purification (12 g; yellow gum). LCMS: (Method B) 295.2 (M-H)$^+$, Rt 4.3 min, 38.8% (Max).

Step 5: 3-Amino-6-tert-butoxymethyl-4,6-dihydro-1H-pyrrolo[3,4-c]pyrazole-5-carboxylicacid tert-butyl ester A mixture of 2-tert-butoxymethyl-4-cyano-3-oxo-pyrrolidine-1-carboxylic acid tert-butyl ester (2.0 g, 44% purity by LCMS, 6.7 mmol) and hydrazine monohydrochloride (0.69 g, 10.1 mmol, Sigma Aldrich) in ethanol (67 mL) were heated to reflux under N$_2$ atmosphere for 6 h. The progress of the reaction was monitored by LCMS analysis. After the completion of the reaction, solvent was evaporated to dryness. Residue obtained was taken to next step without further purification (2.5 g; reddish brown gum). LCMS: (Method C) 309.2 (M-H)$^+$, Rt. 4.8 min, 10.5% (Max).

Step 6: 1-tert-Butoxymethyl-6-chloro-5,7-dimethyl-1H,3H-2,4,7a,8-tetraaza-cyclopenta[a]indene-2-carboxylic acid tert-butyl ester A mixture of 3-amino-6-tert-butoxymethyl-4,6-dihydro-1H-pyrrolo[3,4-c]pyrazole-5-carboxylicacid tert-butyl ester (2.5 g, 10.5% purity by LCMS, 8.0 mmol) and 3-chloro acetyl acetone (0.81 g, 6.04 mmol, Sigma Aldrich) in glacial acetic acid (20 mL) was allowed to stir at RT in a sealed tube for 3 h. The progress of the reaction was monitored by LCMS analysis. After the completion of the reaction, solvent was evaporated to dryness. Residue obtained was diluted with water (20 ml) and basified with 10% solution of NaHCO$_3$ in water. Aqueous layer was extracted in dichloromethane (3×50 mL). Combined extract was washed with water, brine solution and dried over anhydrous Na$_2$SO$_4$. The crude product obtained was purified by flash column chromatography (230-400 size mesh) using gradient elution of ethyl acetate (20-22%) in pet ether to afford the title compound as yellow oil (0.4 g, 96%). $^1$H NMR (400 MHz, DMSO-d$_6$): δ 5.00-4.97 (m, 1H), 4.62, 4.59 (s, 1H), 4.46, 4.32 (s, 1H), 3.92-3.79 (m, 2H), 2.82 (s, 3H), 2.58 (s, 3H), 1.46 (s, 9H), 1.01 (s, 9H). LCMS: (Method C) 409.2 (M+H)$^+$, Rt. 4.8 min, 89.2% (Max).

Step 7: (6-Chloro-5,7-dimethyl-2,3-dihydro-1H-2,4,7a,8-tetraaza-cyclopenta[a]inden-1-yl)methanol To a stirred solution of 1-tert-butoxymethyl-6-chloro-5,7-dimethyl-1H,3H-2,4,7a,8-tetraaza-cyclopenta[a]indene-2-carboxylic acid tert-butyl ester (400 mg, 0.97 mmol) in anhydrous methanol (2 mL) was added HCl in dioxane (2N, 10 mL) drop wise at 0° C. under N$_2$ atmosphere. Reaction mixture was allowed to stir at RT for 12 h. Upon completion of the reaction as monitored by the TLC and LCMS analysis, solvent was removed in vacuo. Residue obtained was washed with diethyl ether (2×25 mL) to get the title product, which was taken to next step without further purification (0.34 g; reddish brown gel). LCMS: (Method C) 253.0 (M+H)$^+$, Rt. 1.9 min, 94.7% (Max).

Step 8: 4-(2-Methoxycarbonyl-phenoxy)-piperidine-1-carboxylic acid tert-butyl ester To a stirred solution of methyl salicylate (5.0 g, 32.8 mmol, Alfa Aesar) in anhydrous dichloromethane (160 mL) was added 4-hydroxy-N-boc-piperidine (9.9 g, 49.2 mmol, Spectrochem), triphenyl phosphine (10.3 g, 39.4 mmol) at 0° C. under N₂ atmosphere followed by di-tert-butyl azodicarboxylate (9.8 g, 42.7 mmol, Spectrochem). Reaction mixture was allowed to stir at RT for 2 h. Starting material consumption was monitored by the TLC. Upon completion of the reaction, reaction mass was evaporated to dryness. Residue obtained was purified by the flash column chromatography (230-400 size mesh) using gradient elution of ethyl acetate (24-26%) in pet ether to afford the title compound as off white solid (10.5 g, 93%). ¹H NMR (400 MHz, DMSO-d₆): δ 7.65-7.62 (dd, J=7.7, 1.7 Hz, 1H), 7.52-7.47 (m, 1H), 7.20 (d, J=8.2 Hz, 1H), 7.00 (t, J=7.6 Hz, 1H), 4.72-4.70 (m, 1H), 3.77 (s, 3H), 3.47 (brs, 2H), 3.37 (brs, 2H), 1.80-1.77 (m, 2H), 1.63-1.60 (m, 2H), 1.40 (s, 9H). LCMS: (Method C) 236.2 (M-BOC+H)⁺, Rt. 6.4 min, 94.7% (Max).

Step 9: 2-(Piperidin-4-yloxy)-benzoic acid methyl ester hydrochloride

To a stirred solution of 4-(2-methoxycarbonylphenoxy)-piperidine-1-carboxylic acid tert-butyl ester (4.0 g, 11.9 mmol) in anhydrous dioxane (5 mL) was added HCl in dioxane (2N, 58 mL) at 0° C. under N₂ atmosphere. Reaction mass was allowed to stir at RT for 2 h. Upon completion of the reaction as monitored by the TLC, solvent was removed under vacuo. Residue obtained was triturated and washed with diethyl ether (3×50mL) to afford the title product as off white solid (3.1 g, 96%). ¹H NMR (300 MHz, DMSO-d₆): δ 7.65 (d, J=7.6 Hz, 1H), 7.53-7.48 (m, 1H), 7.23 (d, J=8.4 Hz, 1H), 7.01 (t, J=7.6 Hz, 1H), 4.85 brs, 2H), 3.81 (s, 3H), 3.12-3.07 (m, 4H), 2.11-2.03 (m, 2H), 1.93-1.88 (m, 2H). LCMS: (Method C) 236.2 (M+H)⁺, Rt. 3.8 min, 96.4% (Max).

Step 10: 2-(1-Methyl-piperidin-4-yloxy)-benzoic acid methyl ester

To a stirred solution of 2-(piperidin-4-yloxy)-benzoic acid methyl ester hydrochloride (3.1 g, 11.4 mmol) in dichloroethane (57 mL) was added triethylamine (5.7 g, 57 mmol, Spectrochem) at 0° C. under N₂ atmosphere followed by paraformaldehyde (1.54 g, 17.1 mmol, Loba Chemie). Reaction mass was allowed to stir at RT for 15 min. Sodium triacetoxy borohydride (4.84 g, 22.8 mmol, Sigma Aldrich) was added in portions at 0° C. and allowed to stir at RT for 16 h. Starting material consumption was monitored by the TLC. After the completion of the reaction, reaction mass was quenched with ice water and extracted in dichloromethane (3×100 mL). Combined extract was washed with water (2×50 mL), brine solution (50 mL) and dried over anhydrous Na₂SO₄. The crude product obtained was purified by flash column chromatography (230-400 size mesh) using gradient elution of methanol (4-4.25%) in dichloromethane to afford the title compound as off white solid. ¹H NMR (400 MHz, DMSO-d₆): δ 7.65-7.62 (dd, J=7.6, 1.6 Hz, 1H), 7.52-7.48 (m, 1H), 7.20 (d, J=8.4 Hz, 1H), 7.01 (t, J=7.5 Hz, 1H), 4.63 brs, 1H), 3.80 (s, 3H), 2.80 (brs, 2H), 2.64 (brs, 2H), 2.40 (s, 3H), 2.00-1.95 (m, 2H), 1.82-1.80 (m, 2H). LCMS: (Method A) 250.2 (M+H)⁺, Rt. 2.4 min, 93.3% (Max).

Step 11: 2-(1-Methyl-piperidin-4-yloxy)-benzoic acid lithium salt

To a pre-cooled (0° C.) stirred solution of 2-(1-methyl-piperidin-4-yloxy)-benzoic acid methyl ester (0.59 g, 2.10 mmol) in THF/MeOH/water (21 mL, 3:2:1 by volume) was added lithium hydroxide monohydrate (0.17 g, 4.2 mmol) and allowed to stir at 60° C. for 12 h. After the completion of the reaction, solvent was removed under vacuo. Residue obtained was azeotroped with toluene (3×25 mL) to afford free flowing solid of lithium salt of acid as the required product. Lithium salt was isolated as off white solid and was taken to next step without further purification (0.52 g, 91%). ¹H NMR (400 MHz, DMSO-d₆): δ 7.20-7.18 (dd, J=7.3, 1.5 Hz, 1H), 7.06-7.02 (m, 1H), 6.84-6.77 (m, 2H), 4.24-4.19 (m, 1H), 2.65-2.62 (m, 2H), 2.13 (s, 3H), 2.00 (t, J=9.5 Hz, 2H), 1.84-1.81 (m, 2H), 1.63-1.57 (m, 2H). LCMS: (Method A) 236.2 (M+H)⁺, Rt 1.9 min, 90.0% (Max).

Step 12: (6-Chloro-1-hydroxymethyl-5,7-dimethyl-1H,3H-2,4,7a,8-tetraaza-cyclopenta[a]inden-2yl)-[2-(1-methyl-piperidin-4-yloxy)-phenyl]-methanone To a stirred solution of (6-chloro-5,7-dimethyl-2,3-dihydro-1H-2,4,7a,8-tetraaza-cyclopenta[a]inden-1-yl)methanol (Step 7, 0.32 g, 1.10 mmol) and lithium salt of 2-(1-methyl-piperidin-4-yloxy)-benzoic acid (Step 11, 0.26 g, 1.10 mmol) in anhydrous dichloromethane (11 mL) was added triethylamine (0.34 g, 3.31 mmol, Spectrochem) at 0° C. under N₂ atmosphere followed by 2-(1H-7-azabenzotriazol-1-yl)-1,1,3,3-tetramethyl uronium hexafluorophosphate (0.46 g, 1.21 mmol). Reaction mass was allowed to stir at RT for 4 h. The progress of the reaction was monitored by the LCMS analysis. After the completion of the reaction, solvent was removed under vacuo. Residue obtained was purified by the flash column chromatography (230-400 size mesh) using a gradient elution of 8-8.5% methanol in dichloromethane to afford the impure fraction, which was purified again by flash column chromatography (230-400 size mesh) using a gradient elution of 9-9.25% methanol in dichloromethane to afford the title product as pale brown solid. ¹H NMR (400 MHz, DMSO-d₆): δ 7.46-7.36 (m, 2H), 7.24, 7.20 (d, J=8.4 Hz, 1H), 7.08 (t, J=7.4 Hz, 1H), 5.40 (s, 1H), 4.98-4.90 (m, 2H), 4.70, 4.67, 4.56, 4.53 (brs, 2H), 4.38, 4.34 (s, 1H), 4.13, 3.96 (brs, 2H), 3.50 (brs, 1H), 2.99-2.90 (m, 3H), 2.85, 2.82 (s, 3H), 2.63, 2.55 (s, 3H), 2.00-1.67 (m, 6H). LCMS: (Method A) 470.2 (M+H)⁺, Rt. 2.8 min, 96.9% (max). HPLC: (Method C) Rt. 8.0 min, 94.6% (max).

Example 24

(3-chloro-2,4-dimethyl-7H-pyrrolo[3',4':3,4]pyrazolo[1,5-a]pyrimidin-8(9H)-yl)(4-fluoro-2-((2-methylpiperidin-4-yl)oxy)phenyl)methanone hydrochloride

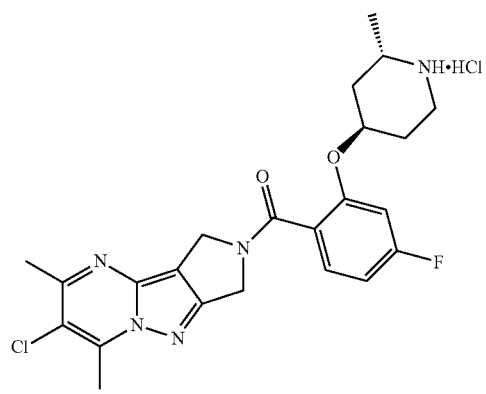

The title product was isolated as momo-hydrochloride salt as off white solid. $^1$H NMR (400 MHz, DMSO-$d_6$): δ 9.07 (s, 1H), 8.52 (s, 1H), 7.39-7.34 (m, 1H), 7.26 (d,d, $J_1$=11.6 Hz, $J_2$=11.2 Hz, 1H), 6.92-6.88 (m, 1H), 4.82 (d, J=12 Hz, 2H), 4.67 (t, J=3.2 Hz, 1H), 4.54-4.49 (m, 2H), 3.33-3.27 (m, 2H), 2.96 (d, J=11.2 Hz, 1H), 2.83-2.80 (m, 3H), 2.61-2.55 (m, 3H), 2.25-2.15 (m, 2H), 1.59 (d, J=5.2 Hz, 1H), 1.46-1.42 (m, 1H), 1.23-1.20 (m, 3H). LCMS: (Method A) 458.0 (M+H), RT. 3.32 min, 99.2% (Max). HPLC: (Method A) Rt. 3.43 min, 99.2% (Max).

Example 28

4-[2-(6-Chloro-5,7-dimethyl-1H,3H-2,4,7a,8-tetraaza-cyclopenta[a]indene-2-carbonynl)-5-fluoro-phenoxy]-piperidine-1-carboxylic acid ethyl ester

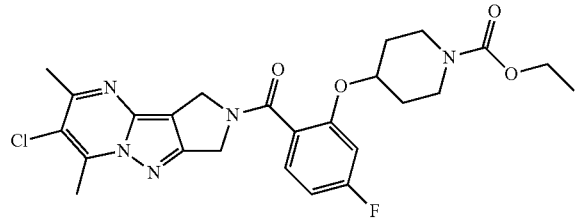 [SMILES: CCOC(=O)N1CCC(Oc2cc(F)ccc2C(=O)N2Cc3nn4c(C)c(Cl)c(C)nc4c3C2)CC1]

The crude product was purified by MD Auto-Prep (Method A) to get the title product as off white solid. $^1$H NMR (400 MHz, DMSO-$d_6$): δ 7.35-7.40 (m, 1H), 7.20 (d, J=8.0 Hz, 1H), 6.86-6.91 (m, 1H), 4.82 (d, J=12.0 Hz, 2H), 4.74 (s, 1H), 4.52-4.57 (m, 2H), 3.96-3.99 (m, 2H), 3.43-3.46 (m, 2H), 3.24-3.27 (m, 2H), 3.80 (s, 3H), 2.56-2.61 (m, 3H), 1.83-1.84 (m, 2H), 1.50-1.53 (m, 2H), 1.13 (t, J=8.0 Hz, 3H). LCMS: (Method A) 516.2 (M+H), Rt. 4.63 min, 98.3% (Max). HPLC: (Method A) RT 4.65 min, 99.2% (Max).

Example 31

(4-bromo-2-(2-(dimethylamino)ethoxy)phenyl)(3-chloro-2,4-dimethyl-7H-pyrrolo[3',4':3,4]pyrazolo[1,5-a]pyrimidin-8(9H)-yl)methanone

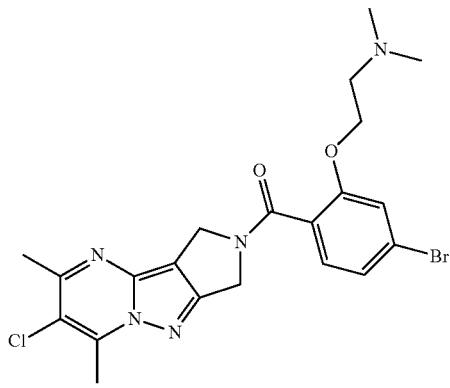 [SMILES: Cc1nc2c3c(nn2c(C)c1Cl)CN(C(=O)c1ccc(Br)cc1OCCN(C)C)C3]

The crude product was purified by MD Auto-Prep (Method B) to get the title product as white solid. $^1$H NMR (400 MHz, DMSO-$d_6$): δ 7.39 (s, 1H), 7.28-7.23 (m, 2H), 4.80 (d, J=10.8 Hz, 2H), 4.62-4.58 (m, 2H), 4.18 (t, $J_1$=5.2 Hz, $J_2$=5.6 Hz, 2H), 2.84-2.81 (m, 3H), 2.62 (s, 3H), 2.56 (s, 2H), 2.04 (s, 6H). LCMS: (Method A) 492.0 (M+H), Rt. 3.52 min, 99.5% (Max). HPLC: (Method A) Rt. 3.52 min, 99.1% (Max).

Example 48

(3-chloro-2,4-dimethyl-7H-pyrrolo[3',4':3,4]pyrazolo[1,5-a]pyrimidin-8(9H)-yl)(4-fluoro-2-((2-methylpiperidin-4-yl)oxy)phenyl)methanone hydrochloride

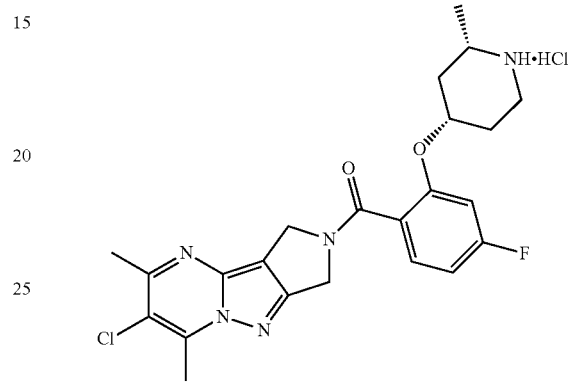

The title compound was isolated as mono-hydrochloride salt as orange yellow solid. $^1$H NMR (400 MHz, DMSO-$d_6$): δ 8.71 (s, 2H), 7.47-7.42 (m, 1H), 7.26 (d,d, $J_1$=11.6 Hz, $J_2$=11.2 Hz, 1H), 6.96-6.93 (m, 1H), 4.95 (s, 1H), 4.87 (d, J=10.4 Hz, 2H), 4.59-4.55 (m, 2H), 3.24-3.19 (m, 1H), 3.13-3.10 (m, 1H), 2.92 (s, 1H), 2.85 (d, J=14.4 Hz, 3H), 2.63-2.57 (m, 3H), 2.03-1.85 (m, 3H), 1.75-1.69 (m, 1H), 1.13 (d, J=1.2 Hz, 3H). LCMS: (Method A) 458.2 (M+H), Rt. 3.39 min, 99.8% (Max). HPLC: (Method A) Rt. 3.38 min, 99.2% (Max).

Example 55

(6-Chloro-5,7-dimethyl-1H,3H-2,4,7a,8-tetraaza-cyclopenta[a]inden-2-yl)-[4-fluoro-2-((2R,4S)-4-fluoro-pyrrolidin-2-ylmethoxy)-phenyl]-methanone

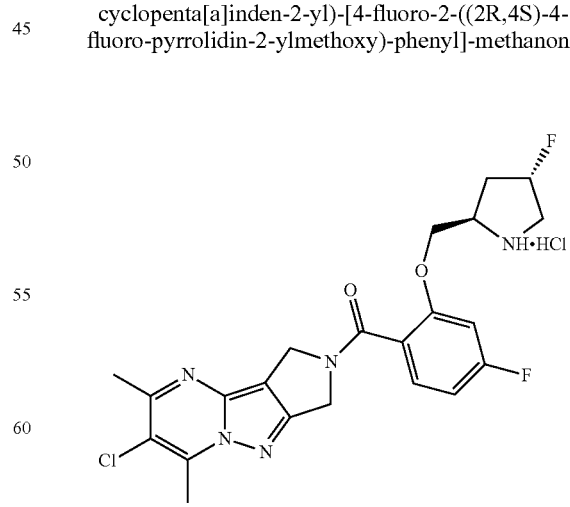

The title compound was purified by recrystallization and isolated as off white solid. $^1$H NMR (400 MHz, DMSO-$d_6$): δ 9.87-9.75 (m, 1H), 9.61-9.55 (m, 1H), 7.45-7.40 (m, 1H), 7.14 (d, J=12.0 Hz, 1H), 6.95 (t, J=8.0 Hz, 1H), 5.51-5.35 (m, 1H), 4.87 (d, J=12.0 Hz, 2H), 4.68-4.54 (m, 2H), 4.43 (d, J=8.0 Hz, 1H), 4.28-4.25 (m, 1H), 4.13 (br s, 1H), 3.75-3.51 (m, 2H), 2.85, 2.82 (s, 3H), 2.62, 2.56 (s, 3H), 2.36-2.25 (m, 1H), 2.14-2.07 (m, 1H). LCMS: (Method A) 462.0 (M+H), Rt. 3.2 min, 98.9% (Max). HPLC: (Method A) Rt. 3.25 min, 99.5% (Max).

Example 56

(6-Chloro-5,7-dimethyl-1H,3H-2,4,7a,8-tetraaza-cyclopenta[a]inden-2-yl)-[2-((R)-4,4-difluoro-pyrrolidin-2-ylmethoxy)-4-fluoro-phenyl]-methanone

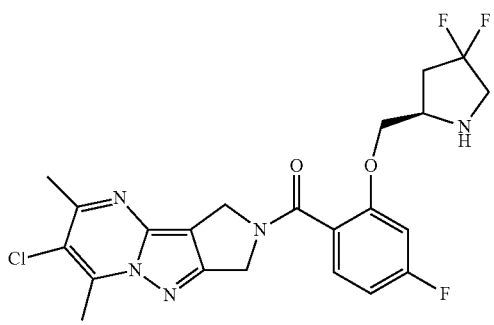 [SMILES: Cc1nc2c3c(nn2c(C)c1Cl)CN(C(=O)c1ccc(F)cc1OC[C@H]1CC(F)(F)CN1)C3]

The title product was purified by Auto MD prep (Method C) and was isolated as off white solid. ¹H NMR (400 MHz, DMSO-d₆): δ 7.35-7.40 (m, 1H), 6.83-6.86 (m, 1H), 6.74-6.77 (m, 1H), 4.99-5.02 (m, 2H), 4.67-4.73 (m, 2H), 4.15-4.22 (m, 2H), 3.83-3.86 (m, 1H), 3.26-3.35 (m, 2H), 2.88-2.93 (m, 3H), 2.64-2.71 (m, 3H), 2.33-2.38 (m, 1H), 2.22-2.24 (m, 1H). LCMS: (Method A) 480.0 (M+H), Rt. 3.39 min, 98.9% (Max). HPLC: (Method A) Rt. 3.38 min, 99.7% (Max).

Example 60

(6-Chloro-5,7-dimethyl-1H,3H-2,4,7a,8-tetraaza-cyclopenta[a]inden-2-yl)-[4-fluoro-2-((2R,4R)-4-fluoro-pyrrolidin-2-ylmethoxy)-phenyl]-methanone

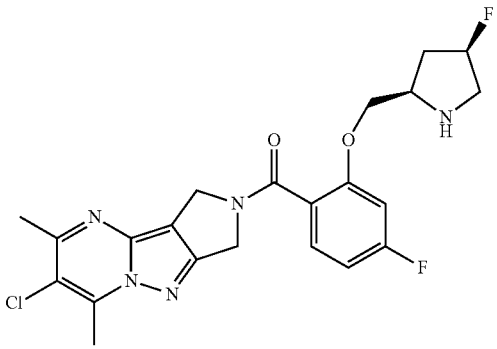 [SMILES: Cc1nc2c3c(nn2c(C)c1Cl)CN(C(=O)c1ccc(F)cc1OC[C@H]1C[C@@H](F)CN1)C3]

The title compound was purified by recrystallization and was isolated as white solid. ¹H NMR (400 MHz, DMSO-d₆): δ 7.33-7.38 (m, 1H), 7.09 (d, J=12.0 Hz, 1H), 6.86-6.90 (m, 1H), 5.02-5.16 (m, 1H), 4.81 (d, J=8.0 Hz, 2H), 4.51-4.60 (m, 2H), 4.02 (d, J=8.0 Hz, 2H), 3.31-3.32 (m, 1H), 2.92-2.95 (m, 1H), 2.86 (d, J=8.0 Hz, 3H), 2.72-2.74 (m, 1H), 2.56-2.62 (m, 3H), 2.00-2.14 (m, 1H), 1.81-1.84 (m, 1H). LCMS: (Method A) 462.0 (M+H), Rt. 3.29 min, 98.3% (Max). HPLC: (Method A) Rt. 3.26 min, 98.8% (Max).

Example 62

(6-Chloro-5,7-dimethyl-1H,3H-2,4,7a,8-tetraaza-cyclopenta[a]inden-2-yl)-{4-fluoro-2-[2-((R)-3-fluoro-pyrrolidin-1-yl)-ethoxy]-phenyl}-methanone

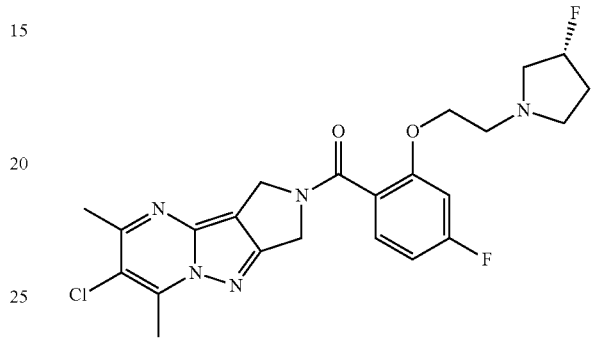

The crude product was purified by MD Auto-Prep (Method A) to get the title product as brown gum. ¹H NMR (400 MHz, DMSO-d₆): δ 7.39-7.34 (m, 1H), 7.11 (s, 0.5H), 7.08 (s, 0.5H), 6.91-6.86 (dt, J=8.4, 2.4 Hz, 1H), 5.01-4.87 (m, 1H), 4.80 (s, 1H), 4.78 (s, 1H), 4.61 (s, 0.9H), 4.55 (s, 1.1H), 4.19 (s, 2H), 2.84 (s, 1.7H), 2.80 (s, 1.3H), 2.78-2.67 (m, 4H), 2.62 (s, 1.6H), 2.56 (s, 1.4H), 2.51-2.50 (m, 1H), 2.39-2.33 (m, 1H), 1.99-1.86 (m, 1H), 1.72-1.61 (m, 1H). LCMS: (Method A) 476.0 (M+H)⁺, Rt. 3.2 min, 99.3% (Max). HPLC: (Method A) Rt. 3.2 min, 99.6% (Max).

Example 68

(2-((1-aminocyclopropyl)methoxy)-4-fluorophenyl)(3-chloro-2,4-dimethyl-7H-pyrrolo[3',4':3,4]pyrazolo[1,5-a]pyrimidin-8(9H)-yl)methanone

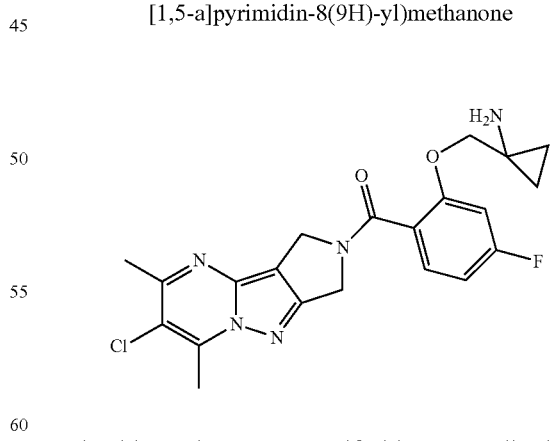

The title product was as purified by recrystalization and was isolated as off white solid. ¹H NMR (400 MHz, DMSO-d₆): δ 7.39-7.35 (m, 1H), 7.04 (d, J=11.6 Hz, 1H), 6.90-6.85 (m, 1H), 4.86-4.83 (m, 2H), 4.62-4.57 (m, 2H), 3.98 (s, 2H), 2.85-2.81 (m, 3H), 2.62-2.56 (m, 3H), 1.95 (s, 2H), 0.47-0.40 (m, 4H). LCMS: (Method A) 430.0 (M+H), Rt. 3.3 min, 98.9% (Max). HPLC: (Method A) Rt. 3.3 min, 99.6% (Max).

Example 73

(3-chloro-7H-pyrrolo[3',4':3,4]pyrazolo[1,5-a]pyrimidin-8(9H)-yl)(4-fluoro-2-{[(3-endo)-8-(2-hydroxypropyl)-8-azabicyclo[3.2.1]oct-3-yl]oxy}phenyl)methanone

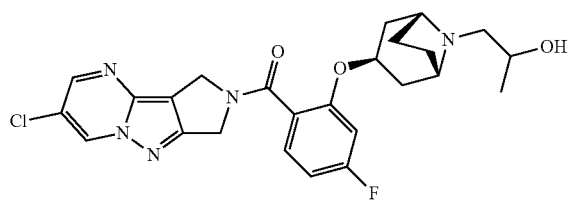 [SMILES: CC(O)CN1[C@@H]2CC[C@H]1C[C@@H](Oc1cc(F)ccc1C(=O)N1Cc3nn4cc(Cl)cnc4c3C1)C2]

The crude product was purified by MD Auto-Prep (Method B) to get the title product as white solid. $^1$H NMR (400 MHz, DMSO-$d_6$): δ 9.60 (d, J=7.6 Hz, 1H), 8.64 (dd, J=2.4, 2.0 Hz, 1H), 7.39-7.35 (m, 1H), 7.00 (s, 0.5H), 6.97 (s, 0.5H), 6.87-6.82 (m, 1H), 4.83 (s, 2H), 4.71 (d, J=4.00 Hz, 1H), 4.63 (s, 1H), 4.59 (s, 1H), 4.24 (s, 1H), 3.57 (s, 1H), 3.08 (s, 2H), 2.16-2.10 (m, 2H), 2.07-2.03 (m, 2H), 1.66-1.63 (m, 6H), 1.01 (d, J=4.00 Hz, 3H). LCMS: (Method A) 500.0 (M+H)$^+$, Rt. 2.7 min, 98.8% (Max). HPLC: (Method A) Rt. 2.7 min, 99.3% (Max).

Example 74

(3-cyclopropyl-7H-pyrrolo[3',4':3,4]pyrazolo[1,5-a]pyrimidin-8(9H)-yl)(4-fluoro-2-{[(3-endo)-8-methyl-8-azabicyclo[3.2.1]oct-3-yl]oxy}phenyl)methanone

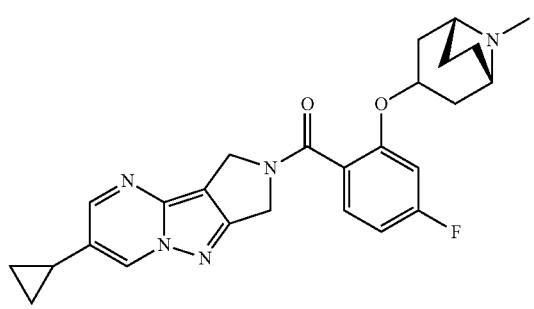 [SMILES: CN1[C@@H]2CC[C@H]1CC(Oc1cc(F)ccc1C(=O)N1Cc3nn4cc(C5CC5)cnc4c3C1)C2]

To a stirred solution of Example 53 (0.3 g, 0.66 mmol) in toluene (9 mL) and water (1 ml) was added cyclopropyl boronic acid (66 mg, 0.78 mmol, Avacado), palladium acetate (12 mg, 0.03 mmol), tricyclohexyl phosphine tetra fluoro borate (24 mg, 0.06 mmol) and potassium phosphate (420 mg, 1.98 mmol). Reaction mass irradiated with microwave at 160° C. for 1 h. Reaction mass filtered through celite and evaporated. The crude product was purified by MD Auto-Prep (Method B) to get the title product as pale brown solid. $^1$H NMR (400 MHz, DMSO-$d_6$): δ 8.93-8.91 (m, 1H), 8.45 (s, 0.5H), 8.40 (s, 0.5H), 7.43-7.38 (m, 1H), 7.11-7.08 (m, 1H), 6.90-6.88 (m, 1H), 4.82-4.75 (m, 3H), 4.59-4.57 (m, 2H), 3.67-3.42 (m, 2H), 2.50-2.38 (m, 3H), 2.28-2.12 (m, 2H), 2.07-2.00 (m, 1H), 1.95-1.84 (m, 6H), 1.01-1.00 (m, 2H), 0.88-0.78 (m, 2H). LCMS: (Method A) 462.2 (M+H)$^+$, Rt. 2.9 min, 96.9% (Max). HPLC: (Method A) Rt. 3.0 min, 97.4% (Max).

Example 75

(6-Chloro-5,7-dimethyl-1H,3H-2,4,7a,8-tetraazacyclopenta[a]inden-2-yl)-{4-fluoro-2-[1-(3,3,3-trifluoro-2-hydroxy-propyl)-piperidin-4-yloxy]-phenyl}-methanone

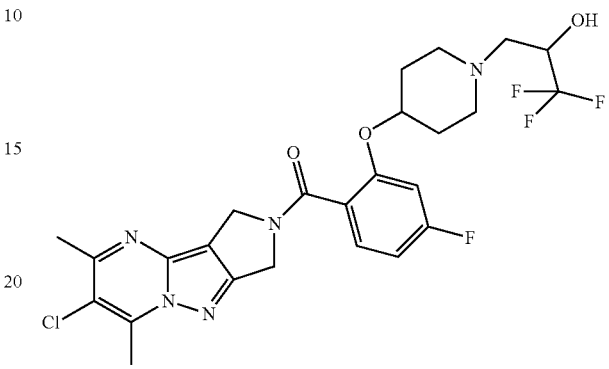

The crude product was purified by MD Auto-Prep (Method B) to get the pure title product as brown solid. $^1$H NMR (400 MHz, DMSO-$d_6$): δ 7.39-7.34 (m, 1H), 7.14 (d, J=11.20 Hz, 1H), 6.89-6.85 (m, 1H), 6.02 (s, 1H), 4.84 (s, 1H), 4.81 (s, 1H), 4.59 (m, 2H), 4.54 (s, 1H), 3.97-3.96 (m, 1H), 2.83 (s, 1.5H), 2.80 (s, 1.5H), 2.67 (s, 1.5H), 2.61 (s, 1.5H), 2.51-2.36 (m, 4H), 2.23-2.18 (m, 2H), 1.83-1.73 (m, 2H), 1.60-1.07 (m, 2H). LCMS: (Method A) 556.0 (M+H)$^+$, RT. 3.6 min, 96.2% (Max). HPLC: (Method A) RT 3.5 min, 96.6% (Max).

Example 76

(6-Chloro-5,7-dimethyl-1H,3H-2,4,7a,8-tetraazacyclopenta[a]inden-2-yl)-[2-(1-ethyl-piperidin-4-yloxy)-4-fluoro-phenyl]-methanone

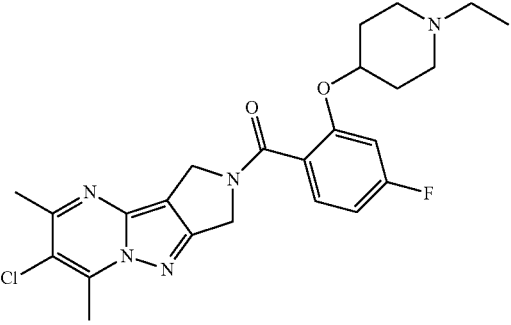 [SMILES: CCN1CCC(Oc2cc(F)ccc2C(=O)N2Cc3nn4c(C)c(Cl)c(C)nc4c3C2)CC1]

The crude product was purified by flash column chromatography to get the pure title product as brown solid. $^1$H NMR (400 MHz, DMSO-$d_6$): δ 7.41-7.39 (m, 1H), 7.23 (d, J=10.00 Hz, 1H), 6.94-6.92 (m, 1H), 4.87-4.84 (m, 2H), 4.78-4.54 (m, 3H), 3.01-2.93 (m, 2H), 2.95 (m, 2.5H), 2.93 (m, 2.5H), 2.67 (m, 2H), 2.62 (m, 2H), 2.30-1.73 (m, 4H), 1.36-1.10 (m, 4H). LCMS: (Method A) 472.0 (M+H)$^+$, RT. 3.3 min, 97.5% (Max). HPLC: (Method A) RT 3.3 min, 98.0% (Max).

Example 77

(6-Chloro-5,7-dimethyl-1H,3H-2,4,7a,8-tetraaza-cyclopenta[a]inden-2-yl)-[4-fluoro-2-(1-propyl-piperidin-4-yloxy)-phenyl]-methanone

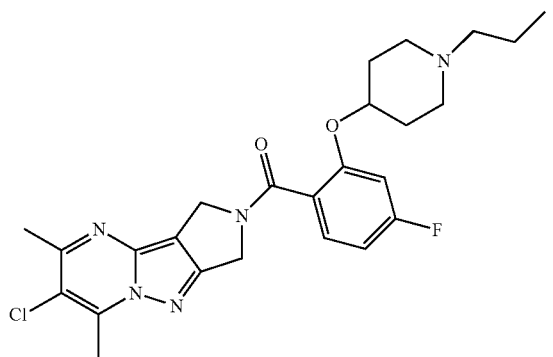 [SMILES: CCCN1CCC(Oc2cc(F)ccc2C(=O)N2Cc3nn4c(C)c(Cl)c(C)nc4c3C2)CC1]

The crude product was purified by flash column chromatography to get the pure title product as brown solid. $^1$H NMR (400 MHz, DMSO-d$_6$): δ 7.39-7.34 (m, 1H), 7.14 (d, J=10.80 Hz, 1H), 6.87 (t, J=8.40 Hz, 1H), 4.83 (s, 1H), 4.81 (s, 1H), 4.59-4.54 (m, 3H), 2.84 (s, 1.5H), 2.81 (s, 1.5H), 2.56 (s, 1.5H), 2.52 (s, 1.5H), 2.40-2.34 (m, 2H), 2.33-2.19 (m, 2H), 1.99-1.96 (m, 2H), 1.84-1.75 (m, 2H), 1.58-1.49 (m, 2H), 1.32-1.24 (m, 2H), 0.83-0.71 (m, 3H). LCMS: (Method A) 486.0 (M+H)$^+$, RT. 3.4 min, 97.5% (Max). HPLC: (Method A) RT 3.4 min, 98.1% (Max).

Example 79

(6-Chloro-5,7-dimethyl-1H,3H-2,4,7a,8-tetraaza-cyclopenta[a]inden-2-yl)-{4-fluoro-2-[2-((S)-3-fluoro-pyrrolidin-1-yl)-ethoxy]-phenyl}-methanone

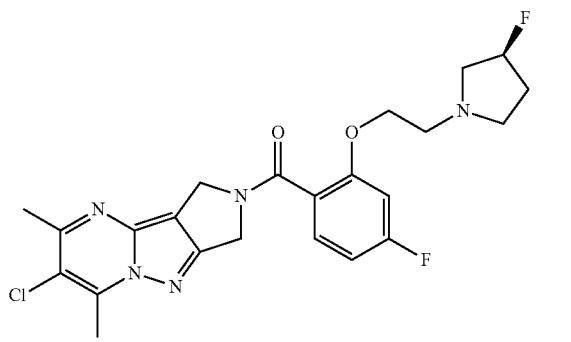 [SMILES: Cc1nc2c3c(nn2c(C)c1Cl)CN(C(=O)c1ccc(F)cc1OCCN1CC[C@H](F)C1)C3]

The crude product was purified by MD Auto-Prep (Method A) to get the title product as pale brown gum. $^1$H NMR (400 MHz, DMSO-d$_6$): δ 7.38-7.33 (m, 1H), 7.07 (t, J=8.0 Hz, 1H), 6.90-6.85 (dt, J=8.0, 2.4 Hz, 1H), 4.99 (m, 1H), 4.80 (s, 1H), 4.78 (s, 1H), 4.61-4.55 (m, 2H), 4.17-4.12 (m, 2H), 2.85 (s, 1.5H), 2.81 (s, 1.5H) 2.72-2.67 (m, 3H), 2.62 (s, 2H), 2.56 (s, 1H), 2.51-2.50 (m, 2H), 2.28 (m, 1H), 1.90-1.78 (m, 1H), 1.67-1.65 (m, 1H). LCMS: (Method A) 476.0 (M+H)$^+$, Rt. 3.3 min, 94.8% (Max). HPLC: (Method A) Rt. 3.2 min, 94.0% (Max).

Example 80

(6-Chloro-5,7-dimethyl-1H,3H-2,4,7a,8-tetraaza-cyclopenta[a]inden-2-yl)-[4-fluoro-2-(3-[1,2,4]triazol-4-yl-propoxy)-phenyl]-methanone

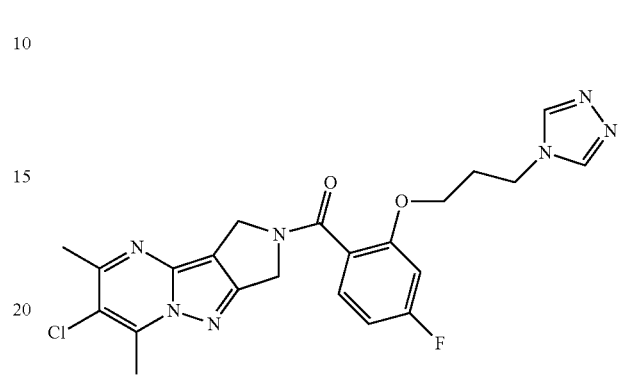

The crude product was purified by MD Auto-Prep (Method A) to get the title product as brown gum. $^1$H NMR (400 MHz, DMSO-d$_6$): δ 8.38 (d, J=6.4 Hz, 1H), 7.87 (d, J=2.4 Hz, 1H), 7.42-7.37 (m, 1H), 7.08 (d, J=11.2 Hz, 1H), 6.92-6.88 (m, 1H), 4.88 (s, 1H), 4.85 (s, 1H), 4.59 (s, 1H), 4.54 (s, 1H), 4.17 (t, J=6.4 Hz, 2H), 4.06 (t, J=5.6 Hz, 2H), 2.84 (s, 1.6H), 2.79 (s, 1.4H), 2.62 (s, 1.4H), 2.51 (s, 1.6H), 2.14 (t, J=6.80 Hz, 2H). LCMS: (Method A) 470.0 (M+H)$^+$, Rt. 3.6 min, 97.9% (Max). HPLC: (Method A) Rt.3.6 min, 98.3% (Max).

Example 81

(6-Chloro-5,7-dimethyl-1H,3H-2,4,7a,8-tetraaza-cyclopenta[a]inden-2-yl)-[4-fluoro-2-(2-hydroxy-ethoxy)-phenyl]-methanone

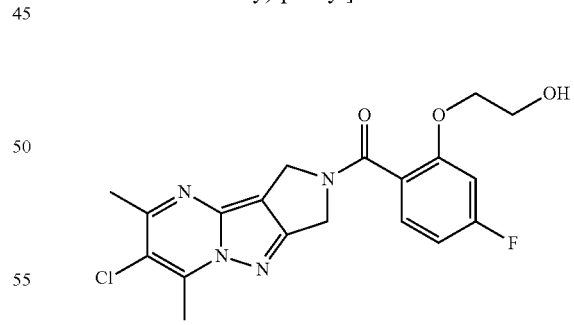

The title product was purified by flash column chromatography (silica gel 230-400 size mesh, DCM/MeOH as gradient elution) and isolated as off white solid. $^1$H NMR (400 MHz, DMSO-d$_6$): δ 7.37-7.32 (m, 1H), 7.10-7.07 (dd, J=12.0, 8.0 Hz, 1H), 6.88-6.83 (dt, J=8.8, 2.4 Hz, 1H), 4.82-4.77 (m, 3H), 4.63-4.57 (m, 2H), 4.12-4.09 (m, 2H), 3.69-3.61 (m, 2H), 2.83, 2.80 (s, 3H), 2.61, 2.55 (s, 3H). LCMS: (Method A) 405.0 (M+H), Rt. 3.6 min, 98.5% (Max). HPLC: (Method A) Rt. 3.5 min, 99.7% (Max).

Example 82

(6-Chloro-5,7-dimethyl-1H,3H-2,4,7a,8-tetraaza-cyclopenta[a]inden-2-yl)-{4-fluoro-2-[2-(5-pyrrolidin-1-yl-pyridin-3yl)-ethoxy]-phenyl}-methanone

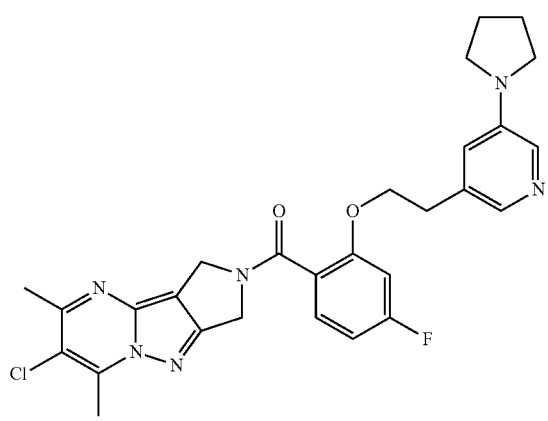 [SMILES: Cc1nc2c3c(nn2c(C)c1Cl)CN(C(=O)c1ccc(F)cc1OCCc1cncc(N2CCCC2)c1)C3]

The crude product was purified by MD Auto-Prep (Method C) to get the title product as pale brown gum. $^1$H NMR (400 MHz, DMSO-d$_6$): δ 7.65 (s, 0.5H), 7.62 (s, 0.5H), 7.31-7.07 (m, 3H), 6.87-6.83 (m, 1H), 6.71 (s, 1H), 4.74-4.64 (m, 2H), 4.35-4.28 (m, 2H), 4.16-4.08 (m, 1H), 4.05-3.95 (s, 1H), 2.96-2.92 (m, 2H), 2.88-2.82 (m, 7H) 2.64 (s, 1.2H), 2.56 (s, 1.8H), 1.81-1.80 (m, 4H). LCMS: (Method A) 535.2 (M+H)$^+$, Rt. 3.7 min, 98.4% (Max). HPLC: (Method A) Rt. 3.7 min, 98.9% (Max).

Example 83

(6-Chloro-5,7-dimethyl-1H,3H-2,4,7a,8-tetraaza-cyclopenta[a]inden-2-yl)-[4-fluoro-2-(3-hydroxy-ethoxy)-phenyl]-methanone

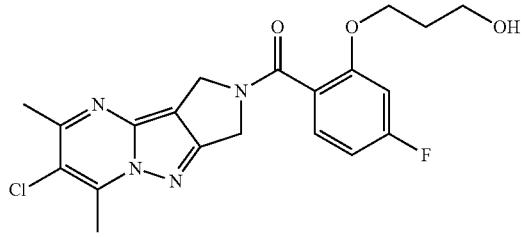 [SMILES: Cc1nc2c3c(nn2c(C)c1Cl)CN(C(=O)c1ccc(F)cc1OCCCO)C3]

The title product was purified by MD-auto prep (Method A) off white solid. $^1$H NMR (400 MHz, CDCl$_3$): δ 7.37-7.34 (m, 1H), 6.80-6.74 (m, 2H), 5.02 (d, J=4.0 Hz, 2H), 4.66 (d, J=8.0 Hz, 2H), 4.21-4.17 (m, 2H), 3.76-3.71 (m, 2H), 2.93, 2.87 (s, 3H), 2.71, 2.64 (s, 3H), 2.02-1.96 (m, 2H). LCMS: (Method A) 419.0 (M+H), Rt. 3.7 min, 98.4% (Max). HPLC: (Method A) Rt. 3.6 min, 99.1% (Max).

Example 84

(syn)-(6-Chloro-5,7-dimethyl-1H,3H-2,4,7a,8-tetraaza-cyclopenta[a]inden-2-yl)-[4-fluoro-2-(3-hydroxy-cyclopentyloxy)-phenyl]-methanone or (anti)-(6-Chloro-5,7-dimethyl-1H,3H-2,4,7a,8-tetraaza-cyclopenta[a]inden-2-yl)-[4-fluoro-2-(3-hydroxy-cyclopentyloxy)-phenyl]-methanone

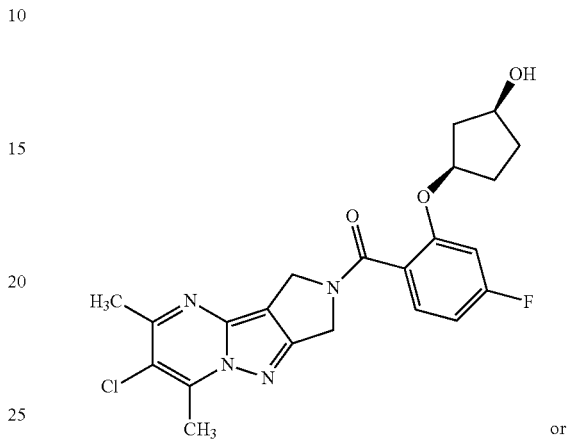

or

The crude product was purified by flash column chromatography to get the title product as off white solid. $^1$H NMR (400 MHz, DMSO-d$_6$): δ 7.37-7.32 (m, 1H), 6.99-6.96 (dd, J=11.6, 1.6 Hz, 1H), 6.87-6.82 (dt, J=8.4, 2 Hz, 1H), 4.82-4.80 (d, J=10.4, Hz, 3H), 4.63-4.51 (m, 3H), 4.06-4.02 (m, 1H), 2.84 (s, 1.4H), 2.80 (s, 1.6H), 2.61 (s, 1.5H), 2.56 (s, 1.5H), 2.33-2.28 (m, 1H), 1.96-1.90 (m, 1H) 1.78-1.65 (m, 2H), 1.54-1.50 (m, 2H). LCMS: (Method A) 445.0 (M+H)$^+$, Rt. 3.9 min, 99.4% (Max). HPLC: (Method A) Rt. 3.9 min, 99.8% (Max).

Example 85

(6-Chloro-5,7-dimethyl-1H,3H-2,4,7a,8-tetraaza-cyclopenta[a]inden-2-yl)-{4-fluoro-2-[2-(6-hydroxy-pyridin-3-yl)-ethoxy]-phenyl}-methanone

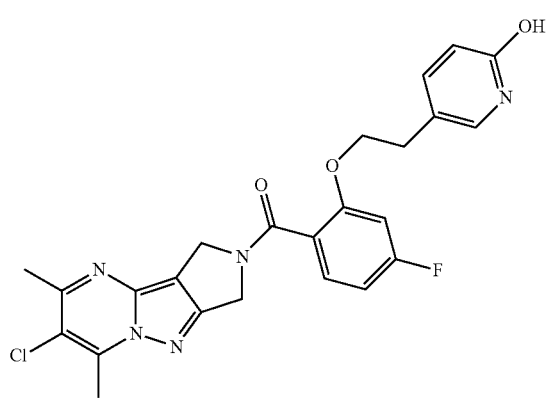 [SMILES: Cc1nc2c3c(nn2c(C)c1Cl)CN(C(=O)c1ccc(F)cc1OCCc1ccc(O)nc1)C3]

The crude product was purified by flash column chromatography to get the title product as off white solid. ¹H NMR (400 MHz, DMSO-d₆): δ 10.99 (s, 1H), 7.34-7.29 (m, 1H), 7.25-7.23 (m, 1H), 7.06 (d, J=9.2 Hz, 2H), 6.89-6.84 (dt, J=8.4, 2.0 Hz, 1H), 5.80-5.71 (m, 1H), 4.78 (d, J=6.8 Hz, 2H), 4.26-4.19 (m, 4H), 2.85 (s, 1.5H), 2.80 (s, 1.5H), 2.67 (d, J=1.5 Hz, 2H), 2.63 (s, 1.5H), 2.55 (s, 1.5H). LCMS: (Method A) 482.0 (M+H)⁺, RT. 3.3 min, 99.2% (Max). HPLC: (Method A) RT 3.3 min, 99.3% (Max).

Example 86

(6-Chloro-5-methyl-1H,3H-2,4,7a,8-tetraaza-cyclopenta[a]inden-2-yl)-[4-fluoro-2-(1-methyl-piperidin-4-yloxy)-phenyl]-methanone or (6-Chloro-7-methyl-1H,3H-2,4,7a,8-tetraaza-cyclopenta[a]inden-2-yl)-[4-fluoro-2-(1-methyl-piperidin-4-yloxy)-phenyl]-methanone

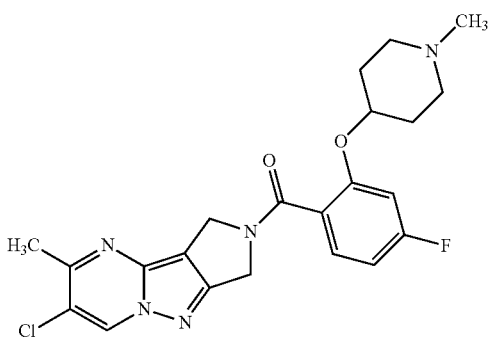

or

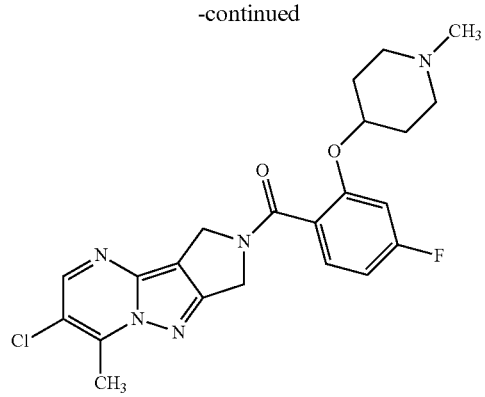

The crude product was purified by MD Auto-Prep (Method B) to get the title product as yellow solid. ¹H NMR (400 MHz, DMSO-d₆): δ 9.49-9.47 (d, J=9.6 Hz, 1H), 7.37-7.32 (m, 1H), 7.15 (s, 0.5H), 7.12 (s, 0.5H), 6.88-6.84 (t, J=8.4, 2.1 Hz, 1H), 4.81-4.80 (d, J=5,4 Hz, 2H), 4.57 (m, 1.4H), 4.54 (m, 1.6H), 2.60 (s, 1.5H), 2.54 (s, 1.5H), 2.33-2.32 (m, 2H), 2.16-2.15 m, 2H) 2.00-1.99 (d, J=5.6 Hz 3H), 1.86-1.81 (m, 2H), 1.59-1.58 (m, 2H). LCMS: (Method A) 444.0 (M+H)⁺, Rt. 2.9 min, 99.5% (Max). HPLC: (Method A) Rt. 3.0 min, 99.5% (Max).

Example 87

(syn)-[2-(4-Amino-cyclohexyloxy)-4-fluoro-phenyl]-(6-chloro-5,7-dimethyl-1H,3H-2,4,7a,8-tetraaza-cyclopenta[a]inden-2-yl)-methanone hydrochloride

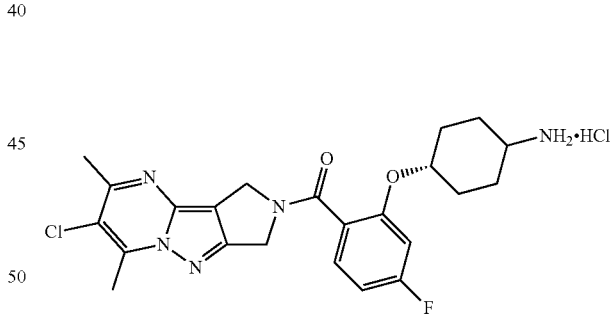

The crude product was purified by triturating to get the title product as pale brown solid. ¹H NMR (400 MHz, DMSO-d₆): δ 7.91 (s, 3H), 7.39-7.34 (m, 1H), 7.17 (d, J=11.6, 2.0 Hz, 1H), 6.90-6.86 (m, 1H), 4.91 (s, 1H), 4.89 (s, 1H), 4.72 (s, 1H), 4.59 (s, 1H), 4.55 (s, 1H), 3.06 (t, J=8.0 Hz, 1H), 2.85 (s, 1.6H), 2.81 (s, 1.4H), 2.62 (s, 1.4H), 2.56 (s, 1.6H), 1.86-1.84 (m, 2H), 1.65-1.55 (m, 4H), 1.51-1.45 (m, 2H). LCMS: (Method A) 458.0 (M+H)⁺, Rt. 3.5 min, 97.7% (Max). HPLC: (Method A) Rt. 3.5 min, 98.3% (Max).

Example 88

(2-{[(3-endo)-8-butyl-8-azabicyclo[3.2.1]oct-3-yl]oxy}-4-fluorophenyl)(3-chloro-7H-pyrrolo[3',4':3,4]pyrazolo[1,5-a]pyrimidin-8(9H)-yl)methanone

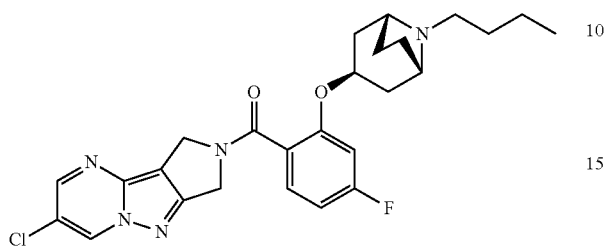

The crude product was purified by silica gel chromatography to get the title product as orange solid. ¹H NMR (400 MHz, DMSO-$d_6$): δ 9.60-9.58 (m, 1H), 8.64 (s, 0.6H), 8.60 (s, 0.4H), 7.39-7.35 (m, 1H), 6.98-6.95 (m, 1H), 6.86-6.82 (m, 1H), 4.85-4.79 (m, 2H), 4.73-4.65 (m, 1H), 4.63-4.60 (m, 2H), 3.11-2.92 (m, 2H), 2.25-2.17 (m, 2H), 2.08-1.99 (m, 2H), 1.66-1.61 (m, 6H), 1.34-1.24 (m, 4H), 0.88-0.78 (m, 3H). LCMS: (Method A) 498.0 (M+H)⁺, Rt. 3.3 min, 99.0% (Max). HPLC: (Method A) Rt. 3.3 min, 98.5% (Max).

Example 89

(3-chloro-7H-pyrrolo[3',4':3,4]pyrazolo[1,5-a]pyrimidin-8(9H)-yl)(4-fluoro-2-{[(3-endo)-8-(2-methylpropyl)-8-azabicyclo[3.2.1]oct-3-yl]oxy}phenyl)methanone

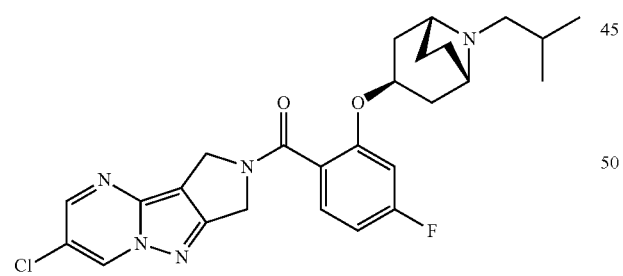 [SMILES: CCCCN1[C@@H]2CC[C@H]1C[C@@H](Oc1cc(F)ccc1C(=O)N1Cc3nn4cc(Cl)cnc4c3C1)C2]

The crude product was purified by MD Auto-Prep (Method C) to get the title product as off white solid. ¹H NMR (400 MHz, DMSO-$d_6$): δ 9.60-9.56 (m, 1H), 8.64 (s, 0.5H), 8.60 (s, 0.5H), 7.40-7.35 (m, 1H), 6.98-6.95 (m, 1H), 6.84 (t, J=8 Hz, 1H), 4.85-4.80 (m, 2H), 4.73-4.65 (m, 1H), 4.63-4.60 (m, 2H), 3.01-2.93 (m, 2H), 2.02-1.94 (m, 4H), 1.64-1.55 (m, 7H), 0.83 (d, J=8 Hz, 6H). LCMS: (Method A) 498.0 (M+H), Rt. 3.1 min, 94.7% (Max). HPLC: (Method A) Rt. 3.3 min, 95.8% (Max).

Example 90

(6-Chloro-5,7-dimethyl-1H,3H-2,4,7a,8-tetraaza-cyclopenta[a]inden-2-yl)-[4-fluoro-2-((3R,4R)-3-fluoro-piperidin-4-yloxy)-phenyl]-methanone hydrochloride or (6-Chloro-5,7-dimethyl-1H,3H-2,4,7a,8-tetraaza-cyclopenta[a]inden-2-yl)-[4-fluoro-2-((3S,4S)-3-fluoro-piperidin-4-yloxy)-phenyl]-methanone hydrochloride

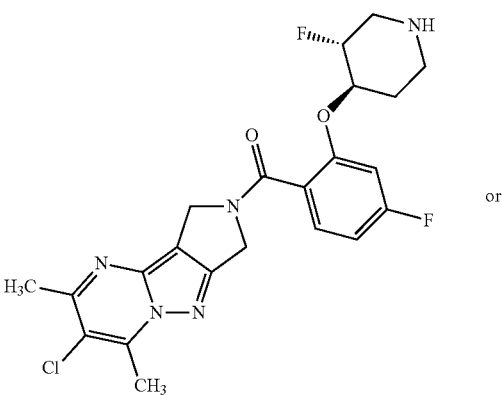

or

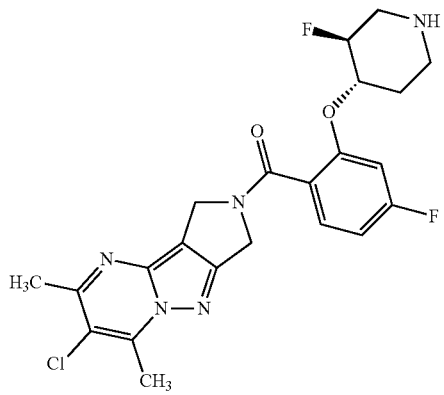

The crude product was purified by Prep HPLC (Method A) to get the title product as pale yellow solid. ¹H NMR (400 MHz, DMSO-$d_6$): δ 8.69 (br s, 2H), 7.48-7.43 (m, 1H), 7.37-7.34 (m, 1H), 7.01-6.96 (m, 1H), 4.95-4.91 (m, 2H), 4.87 (s, 1H), 4.85 (s, 1H), 4.63-4.49 (m, 2H), 3.26-3.20 (m, 2H), 3.05-2.95 (m, 2H), 2.85 (s, 1.6H), 2.82 (s, 1.4H), 2.63 (s, 1.4H), 2.57 (s, 1.6H), 2.16-2.11 (m, 1H), 1.86-1.84 (m, 1H). LCMS: (Method A) 462.0 (M+H)⁺, Rt. 3.3 min, 95.6% (Max). HPLC: (Method A) Rt. 3.3 min, 97.1% (Max).

Example 91

6-Chloro-5-methyl-1H,3H-2,4,7a,8-tetraaza-cyclopenta[a]inden-2-yl)-[4-fluoro-2-(1-propyl-piperdin-4-yloxy)-phenyl]-methanone or (6-Chloro-7-methyl-1H,3H-2,4,7a,8-tetraaza-cyclopenta[a]inden-2-yl)-[4-fluoro-2-(1-propyl-piperidin-4-yloxy)-phenyl]-methanone

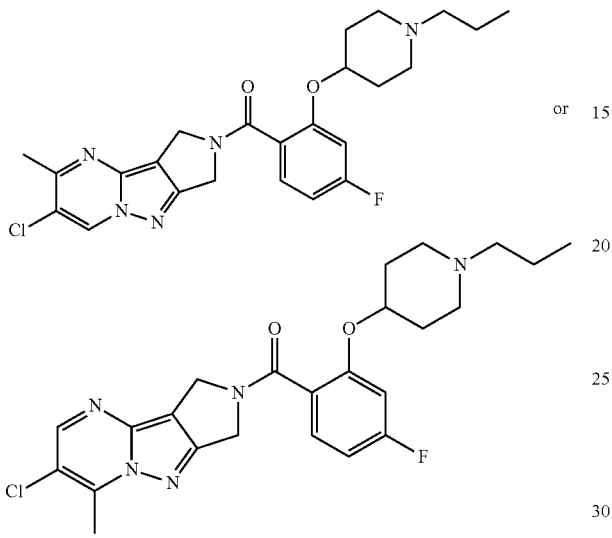

The crude product was purified by flash column chromatography to get the title product as pale yellow solid. $^1$H NMR (400 MHz, DMSO-d$_6$): δ 9.52 (s, 0.5H), 9.48 (s, 0.5H), 7.38-7.33 (m, 1H), 7.14-7.11 (dd, J=11.2, 3.2 Hz, 1H), 6.88-6.84 (m, 1H), 4.81 (d, J=5.2 Hz, 2H), 4.56 (s, 2H), 4.53 (s, 1H), 2.67 (s, 1.6H), 2.60 (s, 1.4H), 2.33 (m, 2H), 2.20 (m, 2H), 2.00-2.95 (m, 2H), 1.82 (m, 2H), 1.59 (m, 2H), 1.25 (t, J=6.4 Hz, 2H), 0.74-0.69 (m, 3H). LCMS: (Method A) 472.0 (M+H)$^+$, Rt. 3.1 min, 97.2% (Max). HPLC: (Method A) Rt. 3.3 min, 99.2% (Max).

Example 92

{4-[2-(6-Chloro-5,7-dimethyl-1H,3H-2,4,7a,8-tetraaza-cyclopenta[a]indene-2-carbonyl)-5-fluoro-phenoxy]-piperidin-1-yl}-acetic acid hydrochloride

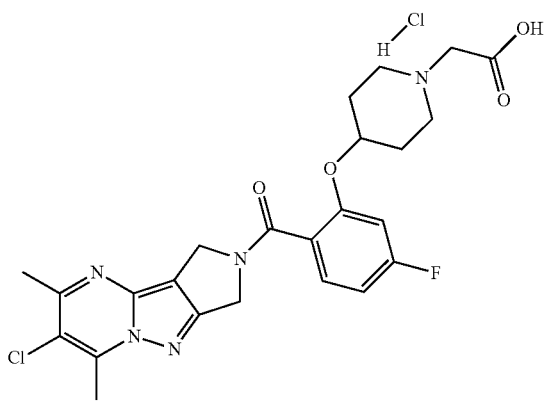

The crude product was purified by flash column chromatography to get the title product as pale yellow solid. $^1$H NMR (400 MHz, DMSO-d$_6$): δ 14.01 (s, 1H), 9.87 (brs, 1H), 7.42-7.39 (m, 1H), 7.29-7.26 (m, 1H), 6.96-6.92 (m, 1H), 4.88 (m, 3H), 4.58 (s, 1H), 4.53 (s, 1H), 4.03 (m, 2H), 3.30-3.27 (m, 4H), 2.85 (s, 1.5H), 2.81 (s, 1.5H), 2.62 (s, 1.8H), 2.56 (s, 1.2H), 2.14 (m, 2H), 1.91 (m, 2H). LCMS: (Method A) 502.0 (M+H), Rt. 3.3 min, 96.7% (Max). HPLC: (Method A) Rt. 3.3 min, 97.8% (Max).

Example 93

(2-{[(3-endo)-8-butyl-8-azabicyclo[3.2.1]oct-3-yl]oxy}-4-fluorophenyl)(3-chloro-2-methyl-7H-pyrrolo[3',4':3,4]pyrazolo[1,5-a]pyrimidin-8(9H)-yl)methanone or (2-{[(3-endo)-8-butyl-8-azabicyclo[3.2.1]oct-3-yl]oxy}-4-fluorophenyl)(3-chloro-4-methyl-7H-pyrrolo[3',4':3,4]pyrazolo[1,5-a]pyrimidin-8(9H)-yl)methanone

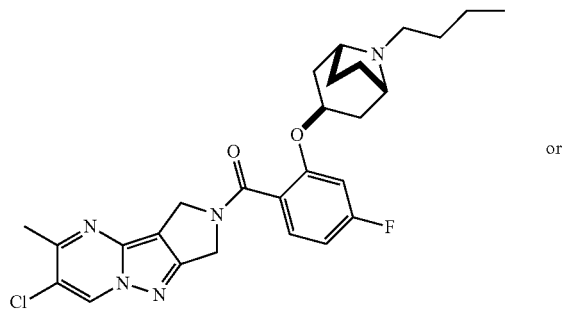

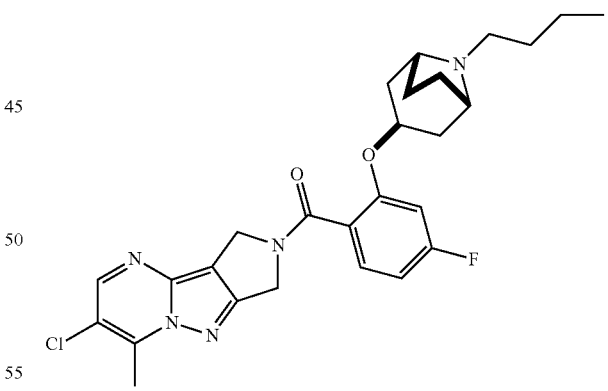

The crude product was purified by flash column chromatography to get the pure title product as yellow solid. $^1$H NMR (400 MHz, DMSO-d$_6$): δ 9.50 (d, J=6.40 Hz, 1H), 7.42-7.37 (m, 1H), 7.29-7.11 (m, 1H), 6.90-6.86 (m, 1H), 4.79-4.70 (m, 3H), 4.60 (s, 1H), 4.56 (s, 1H), 3.96-3.68 (m, 2H), 3.15-2.76 (m, 2H), 2.75 (s, 1.5H), 2.61 (s, 1.5H), 2.40-2.33 (m, 2H), 1.91-1.71 (m, 6H), 1.62-1.52 (m, 2H), 1.32-1.24 (m, 2H), 0.87 (t, J=7.20 Hz, 3H). LCMS: (Method A) 512.2 (M+H)$^+$, Rt. 3.3 min, 98.0% (Max). HPLC: (Method A) Rt. 3.5 min, 99.1% (Max).

Example 94

(2((8-azabicyclo[3.2.1]octan-3-yl)oxy)-4-fluorophenyl)(3-chloro-2-methyl-7H-pyrrolo[3',4':3,4]pyrazolo[1,5-a]pyrimidin-8(9H)-yl)methanonehydrochloride or (2-((8-azabicyclo[3.2.1]octan-3-yl)oxy)-4-fluorophenyl)(3-chloro-4-methyl-7H-pyrrolo[3',4':3,4]pyrazolo[1,5-a]pyrimidin-8(9H)-yl)methanonehydrochloride

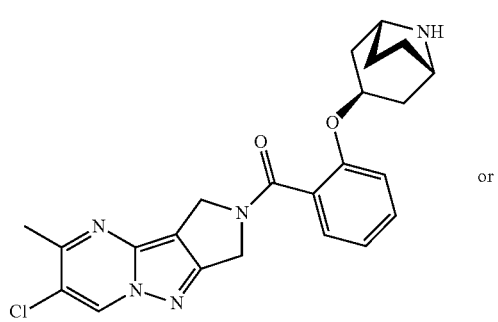

or

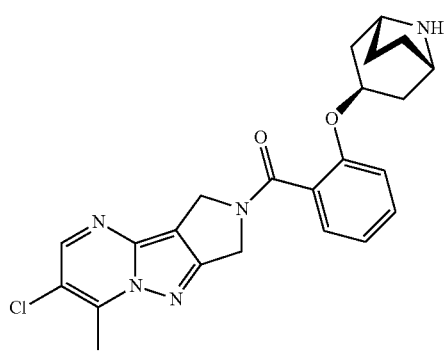

The crude product was washed with Hexane and diethyl ether to get the pure title product as yellow solid. $^1$H NMR (400 MHz, DMSO-$d_6$): δ 9.51 (d, J=6.80 Hz, 1H), 8.75-8.52 (m, 2H), 7.43-7.38 (m, 1H), 7.17-7.14 (m, 1H), 6.92-6.89 (m, 1H), 4.85-4.79 (m, 3H), 4.60-4.56 (m, 2H), 3.87-3.80 (m, 2H), 2.61 (s, 3H), 2.33-2.23 (m, 2H), 2.01-2.01 (m, 4H), 1.81-1.80 (m, 2H). LCMS: (Method A) 456.0 (M+H), Rt. 2.9 min, 95.8% (Max). HPLC: (Method A) Rt. 2.8 min, 96.2% (Max).

Example 95

(2S,4S)-4-[2-(6-Chloro-5,7-dimethyl-1H,3H-2,4,7a,8-tetraaza-cyclopenta[a]indene-2-carbonyl)-5-fluoro-phenoxy]-pyrrolidine-2-carboxylic acid, hydrochloride

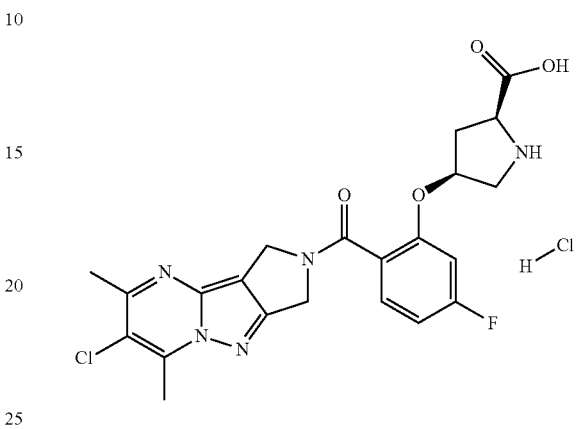

The crude product was purified by recrystallization to get the title product as brown solid. $^1$H NMR (400 MHz, DMSO-$d_6$): δ 10.54 (s, 1H), 8.78 (t, J=4.0 Hz, 1H), 7.42-7.37 (m, 1H), 7.19 (d, J=12.0 Hz, 1H), 6.97-6.93 (m, 1H), 5.21 (s, 1H), 4.86 (s, 1H), 4.84 (s, 1H), 4.60-4.44 (m, 3H), 3.46-3.45 (m, 1H), 2.85 (s, 1.5H), 2.81 (s, 1.5H), 2.74-2.67 (m, 2H), 2.62 (s, 2H), 2.56 (s, 1H), 2.33-2.27 (m, 1H). LCMS: (Method A) 474.0 (M+H)$^+$, Rt. 3.0 min, 95.6% (Max). HPLC: (Method A) Rt. 3.0 min, 96.0% (Max).

Example 96

(3-chloro-2,4-dimethyl-7H-pyrrolo[3',4':3,4]pyrazolo[1,5-a]pyrimidin-8(9H)-yl)(4-fluoro-2-{[(3-endo)-2-exo-fluoro-8-azabicyclo[3.2.1]octan-3-yl]oxy}phenyl) methanone or (3-chloro-2,4-dimethyl-7H-pyrrolo[3',4':3,4]pyrazolo[1,5-a]pyrimidin-8(9H)-yl)(4-fluoro-2-{[(3-endo)-2-endo-fluoro-8-azabicyclo[3.2.1]octan-3-yl]oxy}phenyl) methanone

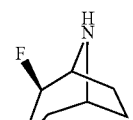

OR

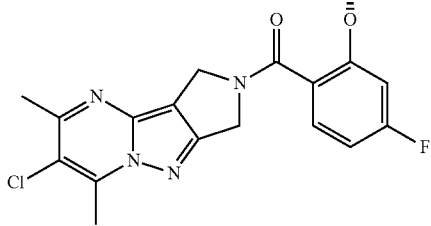

-continued

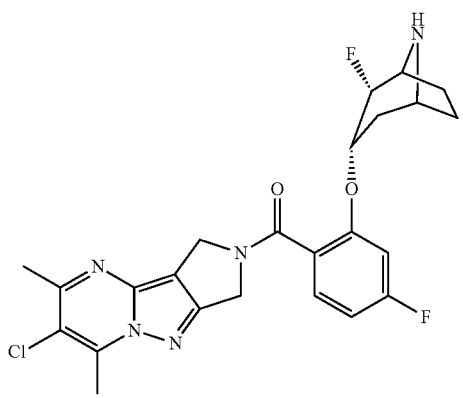

The crude product was purified by trituration with diethyl ether to get the title product as off white solid (90 mg, 67%). $^1$H NMR (400 MHz, DMSO-d$_6$): δ 9.48 (br s, 2H), 7.43-7.38 (m, 1H), 7.26 (d, J=11.60 Hz, 1H), 6.91 (dt, J=8.40, 2.00 Hz, 1H), 5.26 (s, 1H), 5.20 (s, 0.5H), 5.09 (s, 0.5H), 4.91-4.76 (m, 2H), 4.61-4.54 (m, 2H), 4.08 (s, 1H), 3.95 (s, 1H), 2.85 (s, 1.5H), 2.81 (s, 1.5H), 2.68 (s, 1.5H), 2.62 (s, 1.5H), 2.33-2.26 (m, 2H), 2.06-2.02 (m, 1H), 1.87-1.86 (m, 2H), 1.74-1.71 (m, 1H). LCMS: (Method B) 488.0 (M+H)$^+$, Rt. 4.9 min, 93.1% (Max). HPLC: (Method B) Rt. 5.1 min, 93.6% (Max).

Example 98

(3-chloro-2,4-dimethyl-7H-pyrrolo[3',4':3,4]pyrazolo[1,5-a]pyrimidin-8(9H)-yl)(4-fluoro-2-(2-(pyrimidin-5-yl)ethoxy)phenyl)methanone

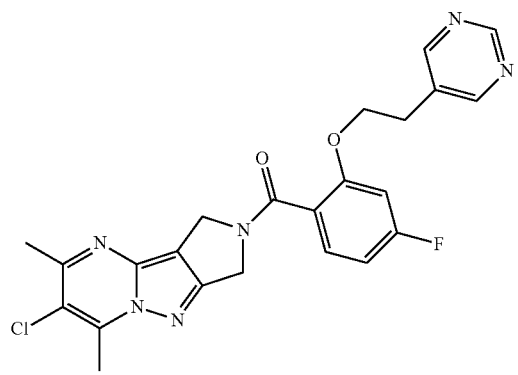 [SMILES: Cc1nc2c3c(nn2c(C)c1Cl)CN(C(=O)c1ccc(F)cc1OCCc1cncnc1)C3]

The crude product was purified by MD-Auto prep (Method B) to get the title product as off white solid. $^1$H NMR (400 MHz, DMSO-d$_6$): δ 8.59 (d, J=2.4 Hz, 2H), 8.52 (s, 0.5H), 8.43 (s, 0.5H), 7.34-7.28 (m, 1H), 7.11-7.08 (m, 1H), 6.87 (t, J=8.0 Hz, 1H), 4.79-4.76 (m, 2H), 4.34 (t, J=5.6 Hz, 2H), 4.19-4.12 (m, 2H), 3.12 (t, J=8.4 Hz, 2H), 2.89 (s, 1.5H), 2.83 (s, 1.5H), 2.65 (s, 1.5 H), 2.57 (s, 1.5H). LCMS: (Method A) 467.0 (M+H)$^+$, Rt. 3.5 min, 98.6% (Max). HPLC: (Method A) Rt. 3.6 min, 98.1% (Max).

Example 101

(Syn)-(3-chloro-2,4-dimethyl-7H-pyrrolo[3',4':3,4]pyrazolo[1,5-a]pyrimidin-8(9H)-yl)(2((4-(ethylamino)cyclohexyl)oxy)-4-fluorophenyl)methanone

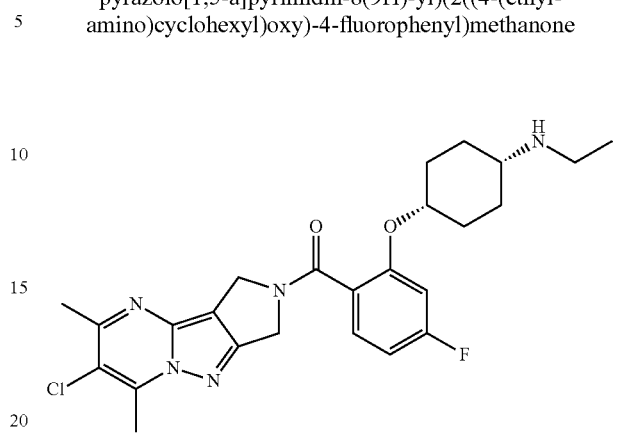

The crude product was purified by silica gel column chromatography to get the title product as pale brown solid. $^1$H NMR (400 MHz, DMSO-d$_6$): δ 7.33-7.38 (m, 1 H), 7.20 (dd, J=11.6, 2.0 Hz, 1H), 6.84-6.89 (m, 1H), 4.89-4.86 (m, 2H), 4.70 (s, 1H), 4.59 (s, 1H), 4.54 (s, 1H), 2.93-2.92 (m, 1H), 2.83 (s, 1.5H), 2.80 (s, 1.5H), 2.77-2.76 (m, 2H), 2.61 (s, 1.5H), 2.55 (s, 1.5H), 1.89-1.85 (m, 2H), 1.71-1.69 (m, 2H), 1.61-1.55 (m, 2H), 1.47-1.49 (m, 2H), 1.11 (t, J=8.2 Hz, 3H). LCMS: (Method A) 486.0 (M+H)$^+$, Rt. 3.74 min, 95.5% (Max). HPLC: (Method A) Rt. 3.69 min, 98.1% (Max).

Example 102

(syn)-(3-chloro-2,4-dimethyl-7H-pyrrolo[3',4':3,4]pyrazolo[1,5-a]pyrimidin-8(9H)-yl)(2-((4-(dimethylamino)cyclohexyl)oxy)-4-fluorophenyl)methanone

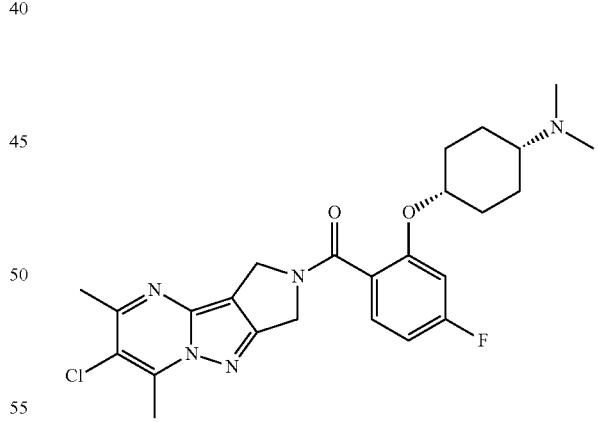

The crude product was purified by silica gel column chromatography to get the title product as off white solid. $^1$H NMR (400 MHz, DMSO-d$_6$): δ 7.33-7.37 (m, 1H), 7.12-7.08 (m, 1H), 6.87-6.82 (m, 1H), 4.81 (d, J=12.0, 2H), 4.66 (s, 1H), 4.60 (s, 1H), 4.54 (s, 1H), 2.83 (s, 1.5H), 2.80 (s, 1.5H), 2.61 (s, 1.5H), 2.55 (s, 1.5H), 2.10 (s, 1H), 1.93-1.92 (m, 6H), 1.87-1.84 (m, 2H), 1.51-1.45 (m, 2H), 1.38-1.34 (m, 4H). LCMS: (Method A) 486.0 (M+H)$^+$, Rt. 3.57 min, 99.3% (Max). HPLC: (Method A) Rt. 3.55 min, 99.3% (Max).

Example 114

(3-chloro-2,4-dimethyl-7H-pyrrolo[3',4':3,4]pyrazolo[1,5-a]pyrimidin-8(9H)-yl)(4-fluoro-2-(((3-(endo)-(6exo)-6-hydroxy-8-(2-fluoroethyl)-8azabicyclo[3.2.1]octan-3-yl)oxy)phenyl)methanone

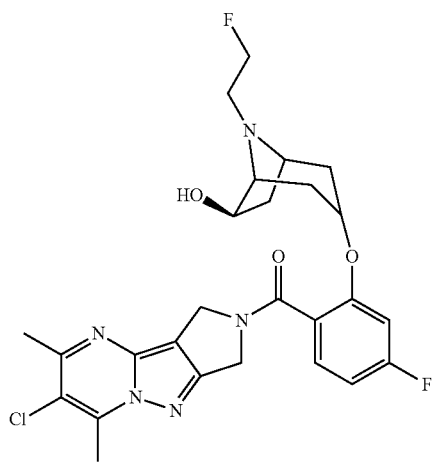 [SMILES: Cc1nc2c3c(nn2c(C)c1Cl)CN(C(=O)c1ccc(F)cc1OC1CC2C[C@@H](O)C(C1)N2CCF)C3]

The crude product was purified by MD Auto-Prep (Method B) to get the title product as white solid (130 mg, 70%). $^1$H NMR (400 MHz, DMSO-d$_6$): δ 7.38-7.35 (m, 1H), 6.94 (d, J=10.8 Hz, 1H), 6.84 (t, J=8.4 Hz, 1H), 4.86 (d, J=9.2 Hz, 2H), 4.68-4.48 (m, 5H), 4.34-4.31 (m, 2H), 3.26-3.21 (m, 1H), 2.97-2.91 (m, 2H), 2.84 (s, 1.5H), 2.84-2.81 (m, 1H), 2.81 (s, 1.5H), 2.62 (s, 1.5H), 2.56 (s, 1.5H), 2.32-2.15 (m, 1H), 1.97-1.64 (m, 2H), 1.60-1.47 (m, 3H). LCMS: (Method A) 532.0 (M+H)$^+$, Rt. 3.2 min, 97.5% (Max). HPLC: (Method A) Rt. 3.2 min, 98.3% (Max).

Example 116

(anti)-(3-chloro-2,4-dimethyl-7H-pyrrolo[3',4':3,4]pyrazolo[1,5-a]pyrimidin-8(9H)-yl)(4-fluoro-2-((3-fluoro-1-propylpiperidin-4-yl)oxy)phenyl)methanone

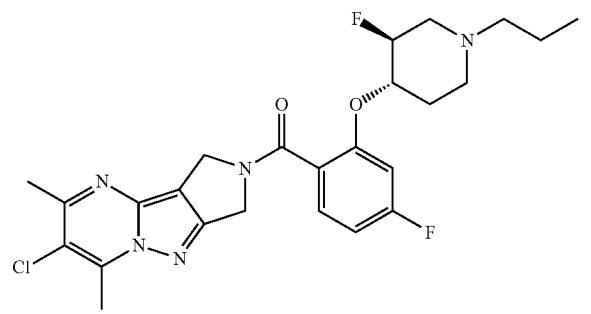 [SMILES: CCCN1CC[C@H](Oc2cc(F)ccc2C(=O)N2Cc3nn4c(C)c(Cl)c(C)nc4c3C2)[C@@H](F)C1]

The crude product was purified by Prep HPLC (Method A) to get the title product as white solid. $^1$H NMR (400 MHz, DMSO-d$_6$): δ 7.38-7.34 (m, 1H), 7.26-7.22 (m, 1H), 6.92-6.87 (m, 1H), 4.83 (s, 1H), 4.80 (s, 1H), 4.62-4.53 (m, 3H), 4.48-4.45 (m, 2H), 2.90-2.89 (m, 1H), 2.84 (s, 1.5H), 2.80 (s, 1.5H), 2.61 (s, 1.5H), 2.60-2.58 (m, 1H), 2.55 (s, 1.5H), 2.20-2.07 (m, 5H), 1.50-1.43 (m, 1H), 1.35-1.29 (m, 2H), 0.78-0.74 (m, 3H). LCMS: (Method A) 504.0 (M+H)$^+$, Rt. 3.4 min, 99.6% (Max). HPLC: (Method A) Rt. 3.5 min, 99.5% (Max).

Example 117

(anti)-(3-chloro-2,4-dimethyl-7H-pyrrolo[3',4':3,4]pyrazolo[1,5-a]pyrimidin-8(9H)-yl)(4-fluoro-2-((3-fluoro-1-(2-hydroxyethyl)piperidin-4-yl)oxy)phenyl)methanone

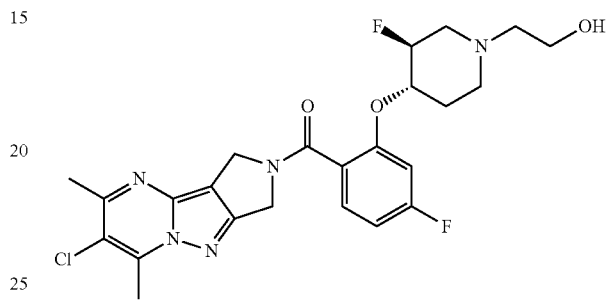

The crude product was purified by MD Auto-Prep (Method B) to get the title product as off white solid. $^1$H NMR (400 MHz, DMSO-d$^6$): δ 7.38-7.33 (m, 1H), 7.24 (d, J=11.6 Hz, 1H), 6.92-6.87 (m, 1H), 4.83 (s, 1H), 4.80 (s, 1H), 4.62-4.53 (m, 3H), 4.47-4.38 (m, 2H), 3.41-3.33 (m, 2H), 3.01-3.00 (m, 1H), 2.83 (s, 1.5H), 2.80 (s, 1.5H), 2.67-2.63 (m, 1H), 2.61 (s, 1.5H), 2.55 (s, 1.5H), 2.40-2.32 (m, 2H), 2.24-2.22 (m, 2H), 2.10-2.06 (m, 1H), 1.47-1.44 (m, 1H). LCMS: (Method A) 506.0 (M+H)$^+$, Rt. 3.2 min, 98.6% (Max). HPLC: (Method A) Rt. 3.2 min, 99.6% (Max).

Example 119

(3-chloro-7H-pyrrolo[3',4':3,4]pyrazolo[1,5-a]pyrimidin-8(9H)-yl)(4-fluoro-2-(((3-endo)-2-exo-fluoro-8-azabicyclo[3.2.1]octan-3-yl)oxy)phenyl)methanone or (3-chloro-7H-pyrrolo[3',4':3,4]pyrazolo[1,5-a]pyrimidin-8(9H)-yl)(4-fluoro-2-(((3-endo)-2-endo-fluoro-8-azabicyclo[3.2.1]octan-3-yl)oxy)phenyl)methanone

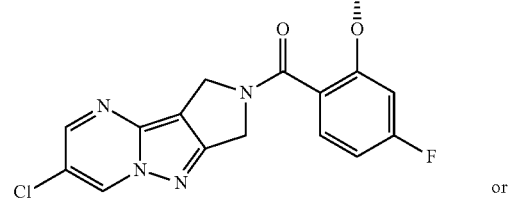

or

-continued

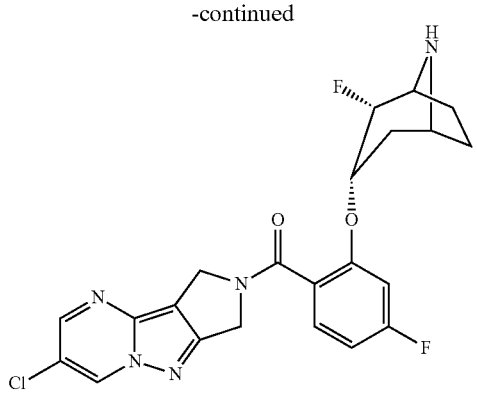

The crude product was purified by trituration with diethyl ether to get the title product as brown solid. ¹H NMR (400 MHz, DMSO-d$_6$): δ 9.60-9.44 (m, 3H), 8.64-8.60 (m, 1H), 7.40 (s, 1H), 7.26 (d, J=10.8 Hz, 1H), 6.91 (t, J=8.0 Hz, 1H), 5.25-5.05 (m, 2H), 4.83-4.80 (m, 2H), 4.60-4.57 (m, 2H), 4.04 (s, 1H), 3.87 (s, 1H), 2.33-2.27 (m, 2H), 2.06-2.02 (m, 2H), 1.89-1.73 (m, 2H). LCMS: (Method B) 460.0 (M+H)⁺, Rt. 4.5 min, 94.9% (Max). HPLC: (Method A) Rt. 2.8 min, 98.8% (Max).

Examples 135 and 136

(3-chloro-2,4-dimethyl-7H-pyrrolo[3',4':3,4]pyrazolo [1,5-a]pyrimidin-8(9H)-yl)(4-fluoro-2-(((3S,4S)-4-hydroxypyrrolidin-3-yl)oxy)phenyl)methanone hydrochloride and (3-chloro-2,4-dimethyl-7H-pyrrolo[3',4':3,4]pyrazolo[1,5-a]pyrimidin-8(9H)-yl)(4-fluoro-2-(((3R,4R)-4-hydroxypyrrolidin-3-yl)oxy)phenyl)methanone hydrochloride

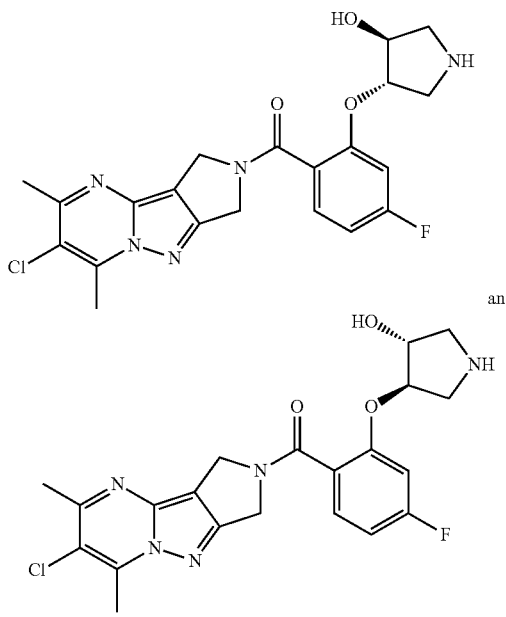

Tert-butyl 3-(2-bromo-5-fluorophenoxy)-4-hydroxypyrrolidine-1-carboxylate was prepared following the procedure described for Intermediate B1, step 1, using tert-butyl 6-oxa-3-azabicyclo[3.1.0]hexane-3-carboxylate (Aldrich) and 2-bromo-5-fluorophenol (Aldrich) as starting materials. The enantiomeric mixture was purified by Prep-HPLC (Method C). Elution-1 was concentrated and used for the synthesis of Example 135. Example 135 was isolated after recrystallization as orange solid. ¹H NMR (400 MHz, DMSO-d$_6$): δ 9.38 (s, 2H), 7.46-7.41 (m, 1H), 7.46 (d, J=10.0 Hz, 1H), 7.01-6.97 (m, 1H), 6.02 (m, 1H), 4.95 (s, 1H), 4.86 (s, 1H), 4.83 (s, 1H), 4.55-4.45 (m, 2H), 4.30 (s, 1H), 3.29-3.26 (m, 1H), 3.16-3.15 (m, 2H), 2.85 (s, 1.5H), 2.82 (s, 1.5H), 2.62 (s, 1.5H), 2.61 (s, 1.5H). MS: 446 (M+H)⁺. HPLC: (Method A) Rt. 3.06 min, 99.2% (Max).

Elution-2 was concentrated and used for the synthesis of Example 136. Example 136 was isolated after recrystallization as brown solid. ¹H NMR (400 MHz, DMSO-d$_6$): δ 9.40 (s, 2H), 7.46-7.41 (m, 1H), 7.33-7.30 (m, 1H), 7.01-6.97 (m, 1H), 6.03 (s, 1H), 4.95 (s, 1H), 4.86 (s, 1H), 4.83 (s, 2H), 4.55-4.49 (m, 2H), 4.30 (s, 1H), 3.29-3.26 (m, 1H), 3.17-3.15 (s, 2H), 2.85 (s, 1.6H), 2.82 (s, 1.4H), 2.62 (s, 1.5H), 2.56 (s, 1.5H) MS: 446 (M+H)⁺. HPLC: (Method A) Rt. 3.08 min, 98.8% (Max).

Examples 137 and 138

(3-chloro-2,4-dimethyl-7H-pyrrolo[3',4':3,4]pyrazolo [1,5-a]pyrimidin-8(9H)-yl)(4-fluoro-2-(((3S,4S)-4-fluoropyrrolidin-3-yl)oxy)phenyl)methanone hydrochloride and (3-chloro-2,4-dimethyl-7H-pyrrolo[3',4':3,4]pyrazolo[1,5-a]pyrimidin-8(9H)-yl)(4-fluoro-2-(((3R,4R)-4-fluoropyrrolidin-3-yl)oxy)phenyl)methanone

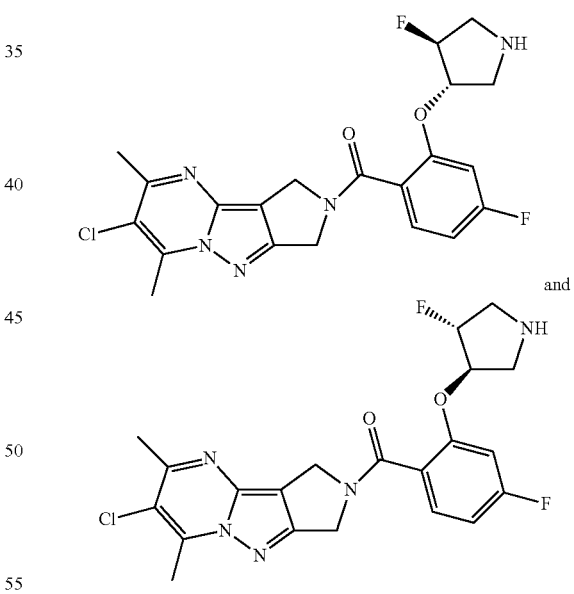

Tert-butyl 3-(2-bromo-5-fluorophenoxy)-4-hydroxypyrrolidine-1-carboxylate was prepared following the procedure described for Intermediate B1, step 1, using tert-butyl 6-oxa-3-azabicyclo[3.1.0]hexane-3-carboxylate (Aldrich) and 2-bromo-5-fluorophenol (Aldrich) as starting materials. The enantiomeric mixture was purified by Prep-HPLC (Method C).

Elution-1 was concentrated and used for the synthesis of Example 137. Example 137 was isolated after recrystallization as orange solid. ¹H NMR (400 MHz, DMSO-d$_6$): δ 9.94 (s, 1H), 9.78 (s, 1H), 7.50-7.45 (m, 1H), 7.38-7.35 (m, 1H), 7.05-7.00 (m, 1H), 5.45 (s, 1H), 5.38-5.33 (m, 1H), 4.88-4.84 (m, 2H), 4.56 (s, 1H), 4.51 (s, 1H), 3.60-3.58 (m, 2H), 3.47-3.45 (m, 2H), 2.85 (s, 1.5H), 2.81 (s, 1.5H), 2.62 (s, 1.4H), 2.56 (s, 1.6H). MS: 448 (M+H)$^+$. HPLC: (Method A) Rt. 3.3 min, 98.52% (Max).

Elution-2 was concentrated and used for the synthesis of Example 138. Example 138 was isolated after recrystallization as brown solid.$^1$H NMR (400 MHz, DMSO-d$_6$): δ 9.68-9.60 (m, 2H), 7.49-7.44 (m, 1H), 7.37-7.33 (m, 1H), 7.05-7.00 (m, 1H), 5.46 (s, 1H), 5.38-5.34 (m, 1H), 4.86-4.83 (m, 2H), 4.55 (s, 1H), 4.51 ((d, J=3.2 Hz, 1H), 3.62-3.59 (m, 2H), 3.47-3.44 (m, 2H), 2.84 (s, 1.7H), 2.81 (s, 1.3H), 2.61 (s, 1.4H), 2.55 (s, 1.6H). MS: 448 (M+H)$^+$. HPLC: (Method A) Rt. 3.24 min, 98.08% (Max).

Examples 167 and 168

(3-chloro-2,4-dimethyl-7H-pyrrolo[3',4':3,4]pyrazolo[1,5-a]pyrimidin-8(9H)-yl)(4-fluoro-2-(((1,4-syn)-4-hydroxy-4-methylcyclohexyl)oxy)phenyl)methanone and (3-chloro-2,4-dimethyl-7H-pyrrolo[3',4':3,4]pyrazolo[1,5-a]pyrimidin-8(9H)-yl)(4-fluoro-2-((1,4-anti)-4-hydroxy-4-methylcyclohexyl)oxy)phenyl)methanone

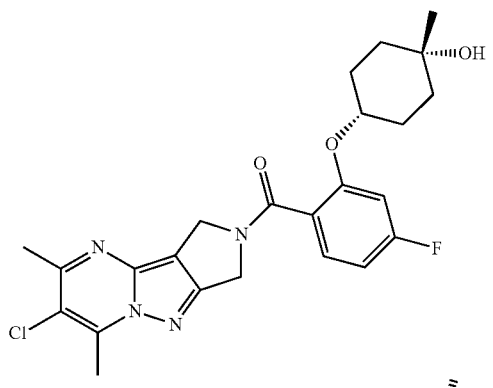

and

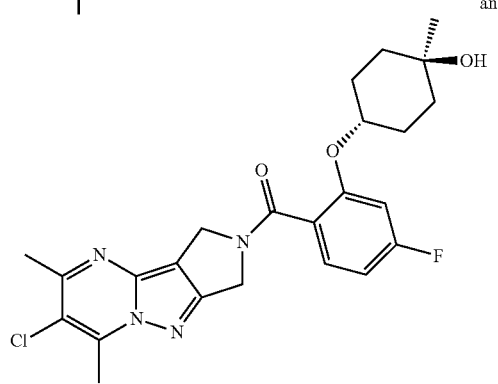

The title compounds were purified by MD Auto Prep, Method C.

The 1$^{st}$ eluting compound and was isolated as white solid. $^1$H NMR (400 MHz, DMSO-d$_6$): δ 7.37-7.32 (m, 1H), 7.12 (s, 0.5H), 7.09 (s, 0.5H), 6.86-6.83 (dt, J=8.40, 2.4 Hz, 1H), 4.8 (d, J=9.6 Hz, 2H), 4.66 (s, 1H), 4.59 (s, 1H), 4.53 (s, 1H), 4.05 (d, J=5.2 Hz, 1H), 2.84 (s, 1.5H), 2.80 (s, 1.5H), 2.62 (s, 1.5H), 2.56 (s, 1.5H), 1.83-1.77 (m, 2H), 1.56-1.53 (m, 2H),1.39-1.32 (m, 2H), 1.25-1.23 (m, 2H), 0.88 (s, 1.5H), 0.79 (s, 1.5 H). MS: 473 (M+H)$^+$. HPLC: (Method A) Rt. 4.0 min, 97.95% (Max).

The 2nd eluting compound and was isolated as off white solid. $^1$H NMR (400 MHz, DMSO-d$_6$): δ 7.36-7.31 (m, 1H), 7.13 (dd, J=10.0 Hz, 2.0 Hz 1H), 6.86-6.82 (dt, J=8.40, 2.0 Hz, 1H), 4.83 (d, J=11.6 Hz, 2H), 4.58 (s, 1H), 4.55 (s, 1H), 4.44-4.38 (m, 1H), 4.13 (d, J=2.8 Hz 1H), 2.83 (s, 1.5H), 2.81 (s, 1.5H), 2.62 (s, 1.5H), 2.56 (s, 1.5H), 1.74-1.71 (m, 2H), 1.67-1.58 (m, 2H), 1.54-1.51 (m, 2H), 1.42-1.23 (m, 2H), 1.08 (s, 3H). MS: 473 (M+H)$^+$. HPLC: (Method A) Rt. 4.33 min, 98.36% (Max).

Examples 222 and 223

(3-chloro-2,4-dimethyl-7H-pyrrolo[3',4':3,4]pyrazolo[1,5-a]pyrimidin-8(9H)-yl)(2-(((1,3-anti)-3-(dimethylamino)cyclopentyl)oxy)-4-fluorophenyl)methanone and (3-chloro-2,4-dimethyl-7H-pyrrolo[3',4':3,4]pyrazolo[1,5-a]pyrimidin-8(9H)-yl)(2-(((1,3-syn)-3-(dimethylamino)cyclopentyl)oxy)-4-fluorophenyl)methanone

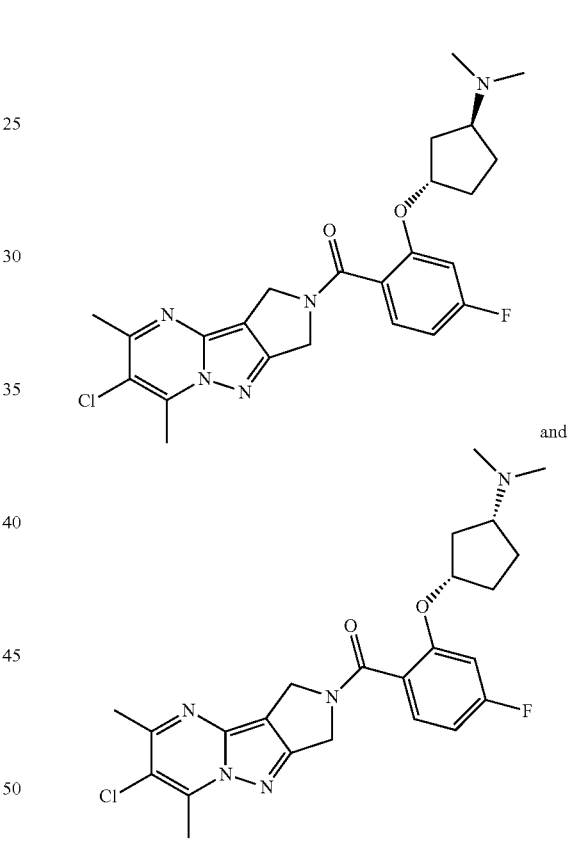

tert-butyl (3-hydroxycyclopentyl)carbamate (Aurora) was purified by silica gel column chromatography.

Elution-1 was concentrated and used for the synthesis of Example 222. Example 222 was isolated after purification by MD-Autoprep (Method B) as pale yellow gum. $^1$H NMR (400 MHz, DMSO-d$_6$): δ 7.35 (q, J=7.20 Hz, 1H), 7.00 (d, J=11.60 Hz, 1H), 6.86 (t, J=8.40 Hz, 1H), 4.96-4.86 (m, 1H), 4.80 (d, J=11.20 Hz, 2H), 4.63-4.47 (m, 2H), 2.85 (s, 1.5H), 2.81 (s, 1.5H), 2.62 (s, 1.5H), 2.57 (s, 1.5H), 2.33-2.25 (m, 1H), 1.98 (s, 3H), 1.95 (s, 3H), 1.91-1.57 (m, 4H), 1.55-1.35 (m, 2H). MS: 472 (M+H)$^+$. HPLC: (Method A) Rt. 3.37 min, 98.53% (Max).

Elution-2 was concentrated and used for the synthesis of Example 223. Example 223 was isolated after purification by silicagel column chromatography as pale yellow gum. ¹H NMR (400 MHz, DMSO-d₆): δ 7.35 (q, J=7.20 Hz, 1H), 7.00 (d, J=11.60 Hz, 1H), 6.86 (t, J=8.40 Hz, 1H), 4.96-4.86 (m, 1H), 4.80 (d, J=11.20 Hz, 2H), 4.63-4.47 (m, 2H), 2.85 (s, 1.5H), 2.81 (s, 1.5H), 2.62 (s, 1.5H), 2.57 (s, 1.5H), 2.33-2.25 (m, 1H), 1.98 (s, 3H), 1.95 (s, 3H), 1.91-1.57 (m, 4H), 1.55-1.35 (m, 2H) MS: 472 (M+H)⁺. HPLC: (Method A) Rt. 3.47 min, 96.74% (Max).

Example 225 and 226

N-((1,3-syn)-3-(2-(3-chloro-2,4-dimethyl-8,9-di-hydro-7H-pyrrolo[3',4':3,4]pyrazolo[1,5-a]pyrimi-dine-8-carbonyl)-5-fluorophenoxy)cyclobutyl)acet-amide and N-((1,3-anti)-3-(2-(3-chloro-2,4-dimethyl-8,9-dihydro-7H-pyrrolo[3',4':3,4]pyrazolo[1,5-a]pyrimidine-8-carbonyl)-5-fluorophenoxy)cyclobutyl)acetamide

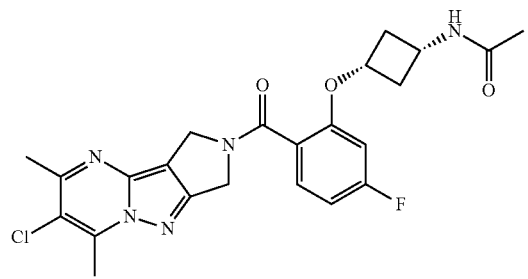

and

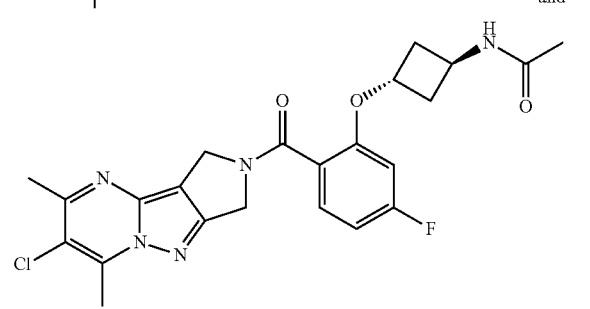

The title compounds were purified by Silicagel column chromatography.

The eluting compound (under non polar conditions) was isolated as white solid. ¹H NMR (400 MHz, DMSO-d₆): δ 8.15 (d, J=7.6 Hz, 1H), 7.39-7.34 (m, 1H), 6.91-6.86 (m, 2H), 4.84 (s, 1H), 4.81 (s, 1H), 4.57-4.51 (m, 3H), 3.90-3.88 (m, 1H), 2.85 (s, 1.5H), 2.81 (s, 1.5H), 2.79-2.78 (m, 2H), 2.62 (s, 1.5H), 2.56 (s, 1.5H), 1.89-1.87 (m, 2H), 1.73 (d, J=5.2 Hz, 3H). MS: 472 (M+H)⁺. HPLC: (Method A) Rt. 3.67 min, 99.73% (Max).

The 2ⁿᵈ eluting compound (under polar conditions) was isolated as off white solid. ¹H NMR (400 MHz, DMSO-d₆): δ 8.21-8.20 (m, 1H), 7.40-7.35 (m, 1H), 6.91-6.86 (m, 1H), 6.80-6.78 (m, 1H), 4.91-4.90 (m, 1H), 4.86 (s, 1H), 4.83 (s, 1H), 4.58 (s, 1H), 4.52 (s, 1H), 4.17-4.16 (m, 1H), 2.84 (s, 1.5H), 2.81 (s, 1.5H), 2.62 (s, 1.5H), 2.56 (s, 1.5H), 2.35-2.29 (m, 4H), 1.77 (d, J=3.2 Hz, 3H). MS: 472 (M+H)⁺. HPLC: (Method A) Rt. 3.62 min, 99.7% (Max).

Example 229 and 230

(3-chloro-2,4-dimethyl-7H-pyrrolo[3',4':3,4]pyrazolo[1,5-a]pyrimidin-8(9H)-yl)(2-((1,3-syn)-3-(dimethylamino)cyclobutoxy)-4-fluorophenyl) methanone and (3-chloro-2,4-dimethyl-7H-pyrrolo[3',4':3,4]pyrazolo[1,5-a]pyrimidin-8(9H)-yl)(2-((1,3-anti)-3-(dimethylamino)cyclobutoxy)-4-fluorophenyl)methanone

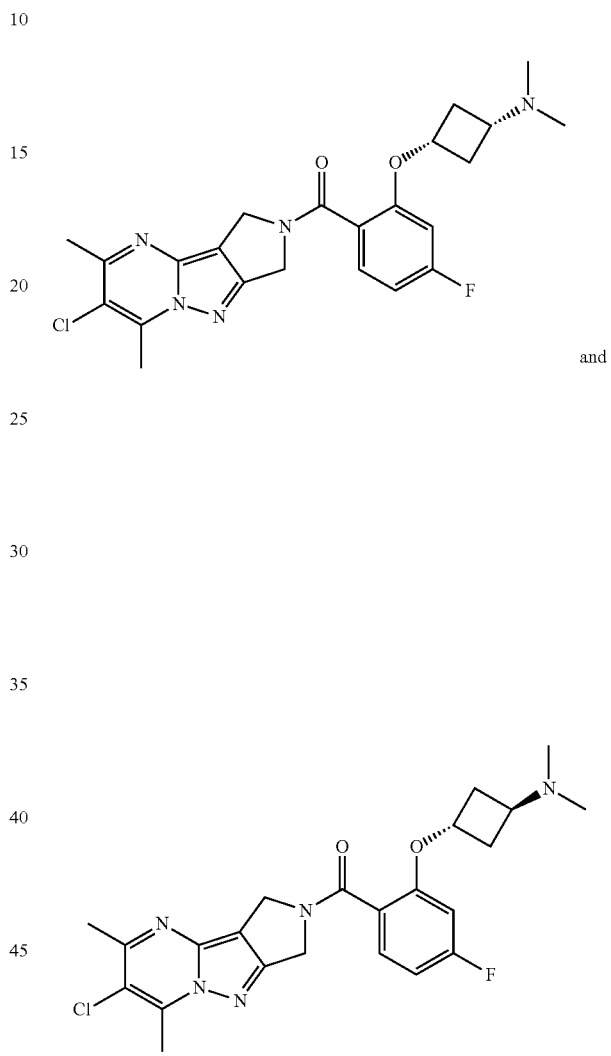

The title compounds were purified by preparative HPLC (Method D).

The 1ˢᵗ eluting compound was isolated as off white solid. ¹H NMR (400 MHz, DMSO-d₆): δ 7.39-7.36 (m, 1H), 6.91-6.86 (m, 2H), 4.84 (s, 1H), 4.81 (s, 1H), 4.58-4.52 (m, 3H), 2.85 (s, 1.6H), 2.81 (s, 1.4H), 2.67-2.65 (m, 2H), 2.62 (m, 1.4H), 2.56 (s, 1.6H), 2.08-2.04 (m, 7H), 1.80-1.78 (m, 2H). MS: 458 (M+H)⁺. HPLC: (Method A) Rt. 3.29 min, 99.31% (Max).

The 2ⁿᵈ eluting compound was isolated as off white solid. ¹H NMR (400 MHz, DMSO-d₆): δ 7.39-7.35 (m, 1H), 6.90-6.85 (m, 1H), 6.81-6.77 (m, 1H), 4.85-4.82 (m, 3H), 4.58 (s, 1H), 4.54 (s, 1H), 2.84 (s, 1.6H), 2.81 (s, 1.4H), 2.68-2.87 (m, 1H), 2.62 (s, 1.3H), 2.56 (s, 1.7H), 2.35-2.31 (m, 2H), 2.07-2.06 (m, 2H), 2.00 (s, 3H), 1.97 (s, 3H). MS: 458 (M+H)⁺. HPLC: (Method A) Rt. 3.28 min, 99.24% (Max).

Examples 242 and 243

N-((1,3-syn)-3-(2-(3-chloro-2,4-dimethyl-8,9-dihydro-7H-pyrrolo[3',4':3,4]pyrazolo[1,5-a]pyrimidine-8-carbonyl)-5-fluorophenoxy) cyclobutyl)propionamide and N-((1,3-anti)-3-(2-(3-chloro-2,4-dimethyl-8,9-dihydro-7H-pyrrolo[3',4':3,4]pyrazolo[1,5-a]pyrimidine-8-carbonyl)-5-fluorophenoxy) cyclobutyl)propionamide

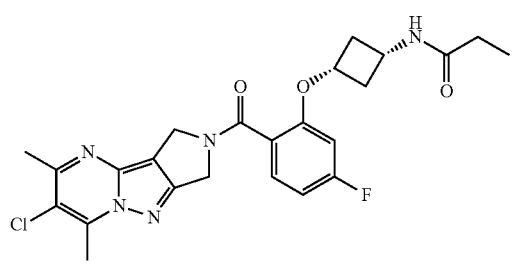

and

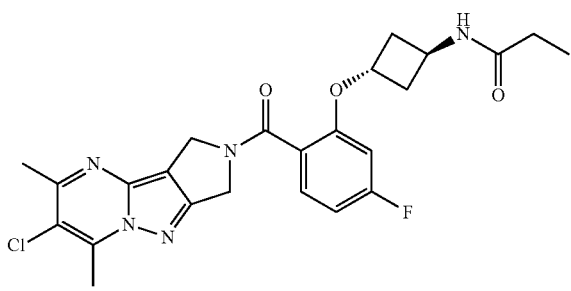

The title compounds were purified by preparative HPLC (Method D).

The 1$^{st}$ eluting compound was isolated as white solid. $^1$H NMR (400 MHz, DMSO-d$_6$): δ 8.03 (t, J=8.0 Hz, 1H), 7.38-7.33 (m, 1H), 6.90-6.85 (m, 2H), 4.82 (d, J=10.8 Hz, 2H), 4.56-4.50 (m, 3H), 3.92-3.85 (m, 1H), 2.84 (s, 1.5H), 2.81 (s, 1.5H), 2.78-2.66 (m, 2H), 2.62 (s, 1.5H), 2.56 (s, 1.5H), 1.99-1.95 (m, 2H), 1.90-1.88 (m, 2H), 0.94-0.89 (m, 3H). MS: 486 (M+H)$^+$. HPLC: (Method A) Rt. 3.89 min, 99.44% (Max).

The 2$^{nd}$ eluting compound was isolated as white solid. $^1$H NMR (400 MHz, DMSO-d$_6$): δ 8.10 (t, J=4.8 Hz, 1H), 7.39-7.34 (m, 1H), 6.88 (dt, J=8.2, 2.4 Hz, 1H), 6.79 (td, J=4.8, 2.8 Hz, 1H), 4.95-4.90 (m, 1H), 4.85 (s, 1H), 4.82 (s, 1H), 4.57 (s, 1H), 4.51 (s, 1H), 4.23-4.27 (m, 1H), 2.84 (s, 1.5H), 2.80 (s, 1.5H), 2.61 (s, 1.5H), 2.55 (s, 1.5H), 2.36-2.38 (m, 4H), 2.04-1.99 (m, 2H), 0.97-0.92 (m, 3H). MS: 486 (M+H)$^+$. HPLC: (Method A) Rt. 3.87 min, 98.62% (Max).

Examples 252 and 253

(3-chloro-2,4-dimethyl-7H-pyrrolo[3',4':3,4]pyrazolo[1,5-a]pyrimidin-8(9H)-yl)(4-fluoro-2-((1,3-syn)-3-(propylamino)cyclobutoxy) phenyl) methanone and (3-chloro-2,4-dimethyl-7H-pyrrolo[3',4':3,4]pyrazolo[1,5-a]pyrimidin-8(9H)-yl)(4-fluoro-2-((1,3-anti)-3-(propylamino)cyclobutoxy)phenyl)methanone

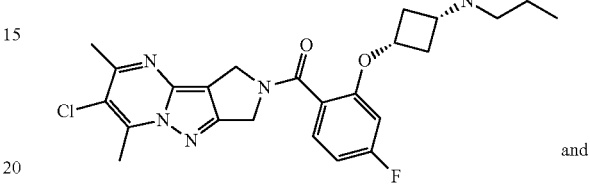

and

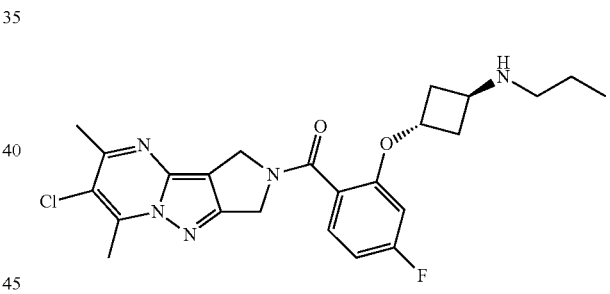

The title compounds were purified by preparative HPLC (Method D).

The 1$^{st}$ eluting compound was isolated as pale yellow solid. $^1$H NMR (400 MHz, DMSO-d$_6$): δ 7.39-7.34 (m, 1H), 6.89 (d, J=9.20 Hz, 2H), 4.83 (d, J=10.80 Hz, 2H), 4.58-4.52 (m, 3H), 3.01-2.91 (m, 1H), 2.85 (s, 1.5H), 2.82 (s, 1.5H), 2.78-2.71 (m, 2H), 2.63 (s, 1.5H), 2.56 (s, 1.5H), 2.46-2.33 (m, 2H), 1.89-1.77 (m, 2H), 1.40-1.34 (m, 2H), 0.86-0.79 (m, 3H). MS: 472 (M+H)$^+$. HPLC: (Method A) Rt. 3.5 min, 95.89% (Max).

The 2$^{nd}$ eluting compound was isolated as white solid. $^1$H NMR (400 MHz, DMSO-d$_6$): δ 7.39-7.34 (m, 1H), 6.89-6.85 (dt, J=8.4, 2.4 Hz, 1H), 6.78-6.75 (dd, J=11.2, 1.6 Hz, 1H), 4.91-4.88 (m, 1H), 4.84 (d, J=12.0 Hz, 2H), 4.58 (s, 1H), 4.53 (s, 1H), 3.23-3.21 (m, 1H), 2.85 (s, 1.5H), 2.81 (s, 1.5H), 2.62 (s, 1.5H), 2.56 (s, 1.5H), 2.52-2.51 (m, 1H), 2.34-2.25 (m, 2H), 2.22-2.10 (m, 4H), 1.36-1.27 (m, 2H), 0.84-0.77 (m, 3H). MS: 472 (M+H)$^+$. HPLC: (Method A) Rt. 3.43 min, 98.51% (Max).

Examples 262 and 263

(S)-(3-chloro-2,4-dimethyl-7H-pyrrolo[3',4':3,4]pyrazolo[1,5-a]pyrimidin-8(9H)-yl)(4-fluoro-2-(3,3,3-trifluoro-2-hydroxypropoxy)phenyl)methanone and (R)-(3-chloro-2,4-dimethyl-7H-pyrrolo[3',4':3,4]pyrazolo[1,5-a]pyrimidin-8(9H)-yl)(4-fluoro-2-(3,3,3-trifluoro-2-hydroxypropoxy)phenyl)methanone

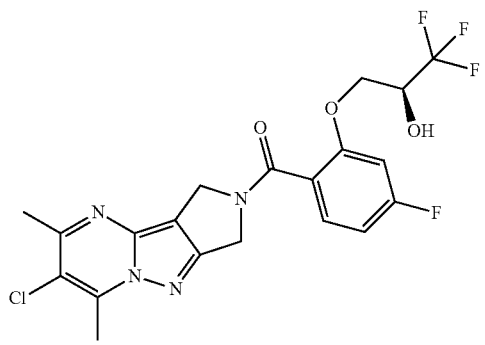

and

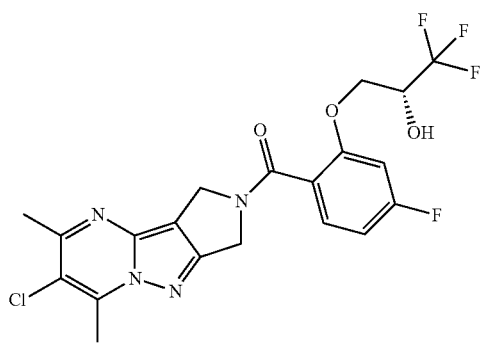

The title compounds were purified by preparative HPLC (Method C).

The 1$^{st}$ eluting compound was isolated as white solid. $^1$H NMR (400 MHz, DMSO-d$_6$): δ 7.39-7.34 (m, 1H), 7.17 (d, J=11.2 Hz, 1H), 6.94-6.89 (m, 1H), 6.61-6.58 (m, 1H), 4.79 (d, J=8.8 Hz, 2H), 4.58-4.54 (m, 2H), 4.34-4.27 (m, 2H), 4.20-4.16 (m, 1H), 2.85 (s, 1.6H), 2.81 (s, 1.4H), 2.62 (s, 1.4H), 2.56 (s, 1.6H). MS: 473 (M+H)$^+$. HPLC: (Method A) Rt. 4.37 min, 99.47% (Max).

The 2$^{nd}$ eluting compound was isolated as off white solid. $^1$H NMR (400 MHz, DMSO-d$_6$): δ 7.39-7.34 (m, 1H), 7.17 (d, J=10.4 Hz, 1H), 6.94-6.89 (m, 1H), 6.61-6.58 (m, 1H), 4.79 (d, J=8.8 Hz, 2H), 4.58-4.53 (m, 2H), 4.20-4.16 (m, 1H), 2.85 (s, 1.6H), 2.81 (s, 1.4H), 2.62 (s, 1.4H), 2.56 (s, 1.6H). MS: 473 (M+H)$^+$. HPLC: (Method A) Rt. 4.37 min, 99.68% (Max).

Examples 266 and 267

(3-chloro-2,4-dimethyl-7H-pyrrolo[3',4':3,4]pyrazolo[1,5-a]pyrimidin-8(9H)-yl)(4-fluoro-2-((1,3-syn)-3-((2-hydroxyethyl)(methyl)amino)cyclobutoxy)phenyl)methanone and (3-chloro-2,4-dimethyl-7H-pyrrolo[3',4':3,4]pyrazolo[1,5-a]pyrimidin-8(9H)-yl)(4-fluoro-2-(1,3-anti)-3-((2-hydroxyethyl)(methyl)amino)cyclobutoxy)phenyl)methanone

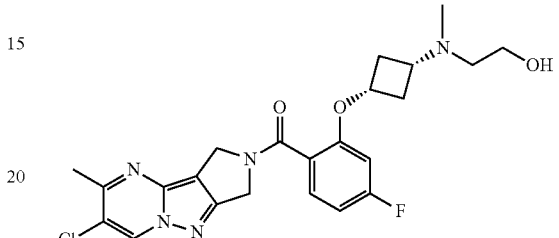

and

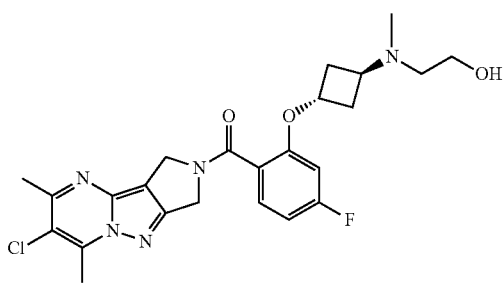

The title compounds were purified by preparative HPLC (Method D).

The 1$^{st}$ eluting compound was isolated as pale brown solid. $^1$H NMR (400 MHz, DMSO-d$_6$): δ 7.36-7.34 (m, 1H), 6.90-6.85 (m, 2H), 4.84 (s, 1H), 4.81 (s, 1H), 4.57-4.52 (m, 3H), 4.30-4.29 (m, 1H), 3.39-3.36 (m, 2H), 2.84 (s, 1.5H), 2.81 (s, 1.5H), 2.67-2.62 (m, 2H), 2.62 (s, 1.5H), 2.56 (s, 1.5H), 2.24-2.23 (m, 2H), 2.01-1.99 (m, 3H), 1.73-1.71 (m, 2H). MS: 488 (M+H)$^+$. HPLC: (Method A) Rt. 3.28 min, 99.35% (Max).

The 2$^{nd}$ eluting compound was isolated as pale brown solid. $^1$H NMR (400 MHz, DMSO-d$_6$): δ 7.39-7.34 (m, 1H), 6.89-6.84 (m, 1H), 6.80-6.77 (m, 1H), 4.84-4.81 (m, 3H), 4.58 (s, 1H), 4.53 (s, 1H), 4.32-4.30 (m, 1H), 3.39-3.37 (m, 2H), 2.87-2.86 (m, 1H), 2.84 (s, 1.5H), 2.80 (s, 1.5H), 2.62 (s, 1.5H), 2.55 (s, 1.5H), 2.32-2.31 (m, 1H), 2.23-2.21 (m, 2H), 2.02-1.99 (m, 5H). MS: 488 (M+H)$^+$. HPLC: (Method A) Rt. 3.38 min, 98.5% (Max).

Examples 270 and 271

(3-Chloro-2,4-dimethyl-7H-pyrrolo[3',4':3,4]pyrazolo[1,5-a]pyrimidin-8(9H)-yl)(4-fluoro-2-(2-(4-fluorophenyl)-2-hydroxyethoxy)phenyl)methanone and (3-Chloro-2,4-dimethyl-7H-pyrrolo[3',4':3,4]pyrazolo[1,5-a]pyrimidin-8(9H)-yl)(4-fluoro-2-(1-(4-fluorophenyl)-2-hydroxyethoxy)phenyl)methanone

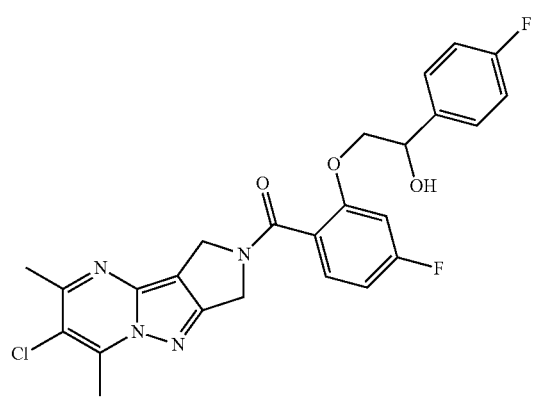

and

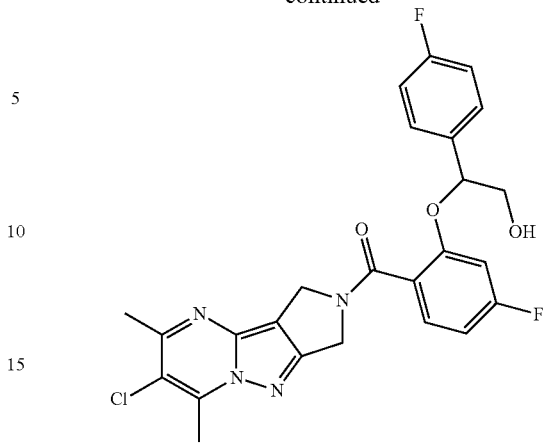

The title compounds were purified by preparative HPLC (Method B).

The 1$^{st}$ eluting compound was isolated as off white solid. $^1$H NMR (400 MHz, DMSO-d$_6$): δ 7.33-7.26 (m, 3H), 7.08-7.04 (m, 1H), 6.85 (dt, J=8.4, 2.0 Hz, 1H), 6.75-6.70 (m, 1H), 6.68-6.63 (m, 1H), 5.67-5.64 (m, 1H), 4.86-4.81 (m, 1H), 4.75 (s, 1H), 4.72 (s, 1H), 4.23-4.20 (m, 1H), 4.17-3.94 (m, 3H), 2.87 (s, 1.54H), 2.82 (s, 1.46H), 2.65 (s, 1.4H), 2.57 (s, 1.6H). MS: 499 (M+H)$^+$. HPLC: (Method A) Rt. 4.36 min, 98.47% (Max).

The 2$^{nd}$ eluting compound was isolated as of pale yellow solid. $^1$H NMR (400 MHz, DMSO-d$_6$): δ 7.40-7.32 (m, 3H), 7.09-6.92 (m, 3H), 6.87-6.82 (m, 1H), 5.50-5.48 (m, 1H), 5.17-5.12 (m, 1H), 4.91-4.74 (m, 2H), 4.71-4.55 (m, 1H), 4.32-4.12 (m, 1H), 3.68-3.60 (m, 1H), 3.57-3.51 (m, 1H), 2.86 (s, 1.6H), 2.81 (s, 1.4H), 2.63 (s, 1.4H), 2.56 (s, 1.6H). MS: 499 (M+H)$^+$. HPLC: (Method A) Rt. 4.55 min, 98.62% (Max).

The examples below were synthesized according to procedures described in the previous examples.

| No | Isolated Form | Appearance | Purification mode | HPLC Method; Rt (min) | Purity | Mass found [M$^+$] | $^1$H NMR |
|---|---|---|---|---|---|---|---|
| 133 | Parent | Off white solid | MD Auto Prep, Method B | Method A; Rt: 4.77 min | 98.03 | 459 | $^1$H NMR (400 MHz, DMSO-d$_6$): δ 7.39-7.35(m, 1H), 7.09-7.13(m, 1H), 6.82-6.91(m, 1H) 4.74-4.82 (m, 3H), 4.59-4.44 (m, 2H), 3.67 (s, 1H), 3.16 (s, 3H), 2.83 (s, 3H), 2.59 (s, 3H), 2.06-2.02 (m, 1H), 1.75-1.74 (m, 1H), 1.55-1.50 (m, 4H). |
| 134 | Parent | White solid | MD Auto Prep, Method B | Method A; Rt: 2.75 min | 98.82 | 470 | $^1$H NMR (400 MHz, DMSO-d$_6$): δ 9.59-9.56 (m, 1H), 8.62-8.57 (m, 1H), 7.37-7.32 (m, 1H), 7.02 (d, d J$_1$ = 11.6 Hz, J$_2$ = 11.6 Hz, 1H), 6.87-6.83 (m, 1H), 4.79-4.75 (m, 3H), 4.56-4.52 (m, 2H), 2.76-2.72 (m, 2H), 2.41-2.37 (m, 2H), 2.33-2.29 (m, 3H), 2.10 (t, J = 5.2 Hz, 1H), 1.70-1.66 (m, 2H), 1.36-1.33 (m, 2H), 1.10-0.98 (m, 3H). |
| 139 | Parent | Off white solid | MD Auto Prep, Method B | Method A; Rt: 3.37 min | 98.24 | 444 | $^1$H NMR (400 MHz, DMSO-d$_6$): δ 7.42-7.37 (m, 1H), 7.19-7.17(m, 1H), 6.93-6.88 (m, 1H), 4.84 (d, J = 10.0 Hz, 2H), 4.67-4.48 (m, 3H), 3.12 (d, J = 11.2 Hz, 1H), 2.84-2.73 (m, 5H), 2.66 (t, J = 1.6 Hz, 1H), 2.61 (s, 3H), 2.50-2.48 (m, 1H), 1.94-1.89 (m, 1H), 1.48-1.46 (m, 3H). |
| 140 | Parent | Off white solid | Silicagel column chromatography | Method A; Rt: 3.78 min | 99.65 | 419 | $^1$H NMR (400 MHz, DMSO-d$_6$): δ 7.38-7.33 (m, 1H), 7.09 (t, J = 10.80 Hz, 1H), 6.90-6.85 (dt, J = 8.40, 2.40 Hz, 1H), 4.84 (s, 1.5H), 4.81 (s, 1.5H), 4.63 (s, 1H), 4.57 (s, 1H), 3.94-3.86 (m, 2H), 3.87 (s, 1H), 2.84 (s, 1.5H), 2.81 (s, 1.5H), 2.62 (s, 1.5H), 2.56 (s, 1.5H), 1.03 (d, J = 4.80 Hz, 1.5H), 1.01 (d, J = 4.40 Hz, 1.5H). |

-continued

| No | Isolated Form | Appearance | Purification mode | HPLC Method; Rt (min) | Purity | Mass found [M+] | 1H NMR |
|---|---|---|---|---|---|---|---|
| 141 | Hydrochoride (1) | Off white solid | Prep HPLC, Method C: 1st eluting compound | Method A; Rt: 3.16 min | 98.53 | 456 | 1H NMR (400 MHz, DMSO-d6): δ 8.78 (brs, 2H), 7.45-7.40 (m, 1H), 6.98-6.94 (m, 2H), 4.95-4.92 (m, 1H), 4.84 (s, 1.05 H), 4.81 (s, 0.96H), 4.55 (s, 0.96H), 4.51 (s, 1.05H), 4.38-4.36 (m, 1H), 4.12-4.09 (m, 1H), 2.84 (s, 1.54H), 2.80 (s, 1.42H), 2.61 (s, 1.4H), 2.55 (s, 1.6H), 2.43-2.36 (m, 1H), 2.01-1.94 (m, 1H), 1.78-1.72 (m, 1H), 1.63-1.49 (m, 3H). |
| 142 | Parent | White solid | Silicagel column chromatography | Method A; Rt: 3.33 min | 97.79 | 510 | 1H NMR (400 MHz, DMSO-d6): δ 9.59-7.33 (m, 1H), 8.63(dd, J = 17.2, 2.4 Hz, 1H), 7.38-7.34 (m, 1H), 6.9(d, J = 11.60 Hz, 1H), 6.86-6.81 (m, 1H), 4.82. (brs, 2H), 4.69-4.59 (m, 3H), 2.9 (brs, 2H), 2.35-2.28 (m, 1H), 2.24(d, J = 6.8 Hz, 2H), 2.0-1.9 (m, 4H), 1.8-1.7 (m, 2H), 1.7-1.5 (m, 8H). |
| 144 | Parent | Pale brown solid | MD Auto Prep, Method A | Method A, Column Tempature: 50° C.; Rt: 2.88 min | 99.02 | 470 | 1H NMR (400 MHz, DMSO-d6): δ 9.51 (d, J = 6.40 Hz, 1H), 7.44-7.39 (m, 1H), 7.15 (d, J = 10.40 Hz, 1H), 6.90 (t, J = 8.40 Hz, 1H), 4.80-4.75 (m, 3H), 4.60 (s, 1H), 4.56 (s, 1H), 3.79-3.69 (m, 2H), 2.61 (s, 2H), 2.58 (s, 2H), 2.55 (s, 2H), 2.29-2.26 (m, 2H), 2.10-2.00 (m, 6H). |
| 145 | Parent | Off white solid | MD Auto Prep, Method A | Method A, Column Tempature: 50° C.; Rt: 3.22 min | 97.9 | 498 | 1H NMR (400 MHz, DMSO-d6): δ 9.49 (d, J = 6.00 Hz, 1H), 7.38 (s, 1H), 6.98 (s, 1H), 6.85 (s, 1H), 4.79-4.72 (m, 3H), 4.60 (s, 1H), 4.56 (s, 1H), 3.12-3.05 (m, 2H), 2.67 (s, 1.5H), 2.61 (s, 1.5H), 2.33-2.02 (m, 4H), 1.79-1.69 (m, 6H), 1.38-1.24 (m, 2H), 0.83 (s, 3H) |
| 146 | Parent | Off white solid | MD Auto Prep, Method A | Method A, Column Tempature: 50° C.; Rt: 2.94 min | 99.55 | 500 | 1H NMR (400 MHz, DMSO-d6): δ 9.48 (d, J = 8.0 Hz, 1H), 7.39-7.34 (m, 1H), 6.99-6.94 (m, 1H), 6.86-6.81 (m, 1H), 4.81-4.79 (m, 2H), 4.70-4.69 (m, 1H), 4.60 (s, 1H), 4.55 (s, 1H), 4.32 (s, 1H), 3.41-3.39 (m, 2H), 3.10-3.06 (m, 2H), 2.61 (s, 1.5H), 2.54 (s, 1.5H), 2.33-2.30 (m, 2H), 2.03-2.00 (m, 2H), 1.67-1.59 (m, 6H). |
| 147 | Parent | Pale brown solid | MD Auto Prep, Method A | Method A; Rt: 3.14 min | 99.47 | 460 | 1H NMR (400 MHz, DMSO-d6): δ 7.45-7.34 (m, 1H), 7.13-6.87 (m, 2H), 5.01-4.79 (m, 2H), 4.64-4.50 (m, 3H), 3.67-3.34 (m, 1H), 3.21-3.01 (m, 4H), 2.84 (s, 1.5H), 2.81 (s, 1.5H), 2.63 (s, 1.5H), 2.60 (s, 1.5H), 2.50-2.27 (m, 3H), 1.69-1.65 (m, 1H). |
| 148 | Parent | Pale brown solid | MD Auto Prep, Method B | Method A, Column Tempature: 50° C.; Rt: 2.85 min | 96.2 | 484 | 1H NMR (400 MHz, DMSO-d6): δ 9.62-9.60 (m, 1H), 8.62-8.61 (m, 1H), 7.45-7.43 (m, 1H), 7.24-7.21 (m, 1H), 6.93-6.91 (m, 1H), 4.85-4.79 (m, 3H), 4.64 (s, 1H), 4.61 (s, 1H), 4.12-4.05 (m, 2H), 3.95-3.92 (m, 1H), 3.16-3.08 (m, 1H), 2.33-2.30 (m, 1H), 2.09-1.99 (m, 6H), 1.24-1.23 (m, 6H). |
| 150 | Parent | White solid | Silicagel column chromatography | Method A; Rt: 3.29 min | 96.46 | 528.2 | 1H NMR (400 MHz, DMSO-d6): δ 5 7.38-7.33 (m, 1H), 6.97-6.94 (m, 1H), 6.85-6.80 (m, 1H), 4.80-4.78 (m, 2H), 4.69-4.68 (m, 1H), 4.60 (s, 1H), 4.55 (s, 1H), 4.19 (s, 1H), 3.56-3.54 (m, 1H), 3.10-3.05 (m, 2H), 2.84 (s, 1.6H), 2.80 (s, 1.4H), 2.61 (s, 1.5H), 2.55 (s, 1.5H), 2.12-2.10 (m, 2H), 2.02-1.99 (m, 2H), 1.63-1.59 (m, 6H), 1.00 (d, J = 6.0 Hz, 3H). |
| 151 | Parent | Off white solid | Silicagel column chromatography | Method A; Rt: 3.27 min | 96.68 | 458 | 1H NMR (400 MHz, DMSO-d6): δ 7.41-7.36 (m, 1H), 6.92-6.78 (m, 2H), 4.96 (s, 1H), 4.85-4.82 (m, 2H), 4.58-4.53 (m, 2H), 3.49-3.47 (m, 1H), 3.16-3.12 (m, 1H), 2.85 (s, 1.5H), 2.81 (s, 1.5H), 2.67-2.63 (m, 4H), 2.59-2.53 (m, 2H), 2.45-2.43 (m, 2H), 1.97-1.95 (m, 1H), 1.06-1.02 (m, 3H). |
| 152 | Parent | White solid | Silicagel column chromatography | Method A, Column Tempature: 50° C.; Rt: 2.98 min | 99.54 | 458 | 1H NMR (400 MHz, DMSO-d6): δ 9.62-9.59 (m, 1H), 8.64-8.59 (m, 1H), 7.45-7.36 (m, 1H), 7.13 (d, J = 10.8 Hz, 1H), 6.87 (t, J = 8 Hz, 1H), 4.90-4.85 (m, 2H), 4.59 (s, 1.4H), 4.57 (s, 1.6H), 2.98-2.93 (m, 2H), 2.29-2.19 (m, 2H), 1.99-1.93 (m, 2H), 1.82-1.75 (m, 2H), 1.60-1.56 (m, 2H), 1.26-1.98 (m, 2H), 0.79-0.72 (m, 3H). |
| 153 | Parent | White solid | Silicagel column chromatography | Method A; Rt: 3.52 min | 99.06 | 512.2 | 1H NMR (400 MHz, DMSO-d6): δ 7.39-7.3 (m, 1H), 6.97-6.94 (m, 1H), 6.85-6.81 (m, 1H), 4.81-4.79 (m, 2H), 4.71-4.69 (m, 1H), 4.61 (s, 1H), 4.56 (s, 1H), 3.08-3.01 (m, 2H), 2.85 (s, 1.6H), 2.81 (s, 1.4H), 2.62 (s, 1.3H), 2.56 (s, 1.7H), 2.17-2.14 (m, 2H), 1.99-1.96 (m, 2H), 1.65-1.58 (m, 6H), 1.36-1.31 (m, 2H), 0.87-0.80 (m, 3H). |

| No | Isolated Form | Appearance | Purification mode | HPLC Method; Rt (min) | Purity | Mass found [M+] | 1H NMR |
|---|---|---|---|---|---|---|---|
| 154 | Parent | Orange solid | Silicagel column chromatography | Method A, Column Tempature: 50° C.; Rt: 2.69 min | 95.96 | 500 | 1H NMR (400 MHz, DMSO-$d_6$): δ 9.60-9.58 (dd, J = 7.2, 2 Hz, 1H), 8.64-8.59 (m, 1H), 7.41-7.36 (m, 1H), 7.0 (d, J = 11.6 Hz, 1H), 6.88-6.84 (m, 1H), 4.82 (s, 2H), 4.8 (d, J = 4.4 Hz, 1H), 4.6 (d, J = 12.4 Hz, 2H), 3.5 (t, J = 2.84 Hz, 2H), 3.38 (d, J = 7.2 Hz, 2H), 2.12-2.08 (m, 2H), 1.7-1.5 (m, 9H), 1.28-1.02 (m, 2H). |
| 155 | Parent | Pale yellow solid | Silicagel column chromatography | Method A; Rt: 3.11 min | 99.1 | 472 | 1H NMR (400 MHz, DMSO-$d_6$): δ 9.62 (d, J = 11.6 Hz, 1H), 8.65-8.60 (m, 1H), 7.41-7.37 (m, 1H), 7.22-7.15 (m, 2H), 6.91-6.86 (m, 1H), 4.91-4.85 (m, 1H), 4.60-4.57 (m, 3H), 2.99-2.86 (m, 4H), 2.08-1.91 (m, 3H), 1.68-1.50 (m, 3H), 1.33-1.19 (m, 4H), 0.91-0.84 (m, 3H). |
| 156 | Parent | Pale yellow solid | MD Auto Prep, Method C | Method A; Rt: 3.31 min | 99.63 | 502 | 1H NMR (400 MHz, DMSO-$d_6$): δ 7.37-7.32 (m, 1H), 7.12 (d, J = 11.6 Hz, 1H), 6.86 (dt, J = 8.0, 1.6 Hz, 1H), 4.81 (d, J = 10.4 Hz, 2H), 4.57 (s, 1.5H), 4.53 (s, 1.5H), 4.19-4.13 (m, 1H), 3.59 (d, J = 7.2 Hz, 1H), 2.83 (s, 1.5H), 2.80 (s, 1.5H), 2.62 (s, 1.5H), 2.55 (s, 1.5H), 2.31-2.22 (m, 3H), 2.06-1.79 (m, 4H), 1.60-1.49 (m, 3H), 0.91 (d, J = 6.0 Hz, 3H). |
| 157 | Parent | Yellow solid | MD Auto Prep, Method B | Method A, Column Tempature: 50° C.; Rt: 2.94 min | 98.54 | 514 | 1H NMR (400 MHz, DMSO-$d_6$): δ 9.49 (d, J = 8.0 Hz, 1H), 7.39-7.34 (m, 1H), 6.97 (d, J = 10.4 Hz, 1H), 6.86-6.81 (m, 1H), 4.79-4.69 (m, 3H), 4.60-4.56 (m, 2H), 4.29-4.19 (m, 1H), 3.56-3.51 (m, 1H), 3.13-3.03 (m, 2H), 2.61 (s, 1.5H), 2.55 (s, 1.5H), 2.11-2.00 (m, 4H), 1.68-1.61 (m, 6H), 1.01 (d, J = 6.0 Hz, 3H). |
| 158 | Parent | Pale yellow solid | Silicagel column chromatography | Method A; Rt: 3.26 min | 97.11 | 502 | 1H NMR (400 MHz, DMSO-$d_6$): δ 7.43-7.38 (m, 1H), 7.22 (d, J = 10.2 Hz, 1H), 6.93 (t, J = 8.4 Hz, 1H), 4.85 (d, J = 10.8 Hz, 2H), 4.76-4.72 (m, 1H), 4.58 (s, 1H), 4.54 (s, 1H), 3.43-3.39 (m, 3H), 3.32-3.22 (m, 2H), 3.11-2.84 (m, 2H), 2.85 (s, 1.5H), 2.81 (s, 1.4H), 2.62 (s, 1.4H), 2.56 (s, 1.7H), 2.12-2.64 (m, 7H). |
| 159 | Hydrochoride (1) | White solid | Suspention in diethyl ether | Method B Column Tempature: 50° C.; Rt: 98.17 min | 98.17 | 474 | 1H NMR (400 MHz, DMSO-$d_6$): δ 10.85-9.85 (m, 2H), 9.49 (d, J = 9.2 Hz, 1H), 7.42-7.37 (m, 1H), 7.26-7.23 (m, 1H), 6.91 (t, J = 7.6 Hz, 1H), 5.25-5.06 (m, 2H), 4.80-4.75 (m, 2H), 4.60-4.52 (m, 2H), 4.11-4.01 (m, 1H), 3.86-3.80 (m, 1H), 2.61 (s, 1.5H), 2.55 (s, 1.5H), 2.24-2.00 (m, 2H), 1.83-1.69 (m, 4H). |
| 160 | Parent | Pale brown gum | MD Auto Prep, Method B | Method A; Rt: 3.16 min | 97.52 | 474 | 1H NMR (400 MHz, DMSO-$d_6$): δ 7.36-7.32 (m, 1H), 7.0 (d, J = 12.0 Hz, 1H), 6.88-6.83 (dt, J = 8.0, 2.0 Hz, 1H), 4.93 (s, 1H), 4.81 (d, J = 8.0 Hz, 2H), 4.71 (brs, 1H), 4.51 (d, J = 12.0 Hz, 1H), 4.31 (s, 1H), 3.20-3.19 (m, 1H), 3.12-3.04 (m, 2H), 2.85 (s, 1.5H), 2.81 (s, 1.5H), 2.62 (s, 1.5H), 2.54 (s, 1.5H), 2.44-2.39 (m, 2H), 2.22-2.20 (m, 1H), 2.18 (s, 1.5H), 2.14 (s, 1.5H), 1.64-1.58 (m, 1H). |
| 161 | Parent | Off white solid | MD Auto Prep, Method B | Method A, Column Tempature: 50° C.; Rt: 3.08 min | 97.56 | 464 | 1H NMR (400 MHz, DMSO-$d_6$): δ 8.53-8.47 (m, 1H), 7.40-7.35 (m, 1H), 7.01-6.97 (m, 2H), 6.85 (t, J = 8.4 Hz 1H), 4.88-4.69 (m, 2H), 4.75-4.68 (m, 1H), 4.66-4.58 (m, 2H), 3.81-3.69 (m, 1H), 3.09-2.92 (m, 2H), 2.22-2.11 (m, 3H), 2.08-1.95 (m, 2H), 1.81-1.61 (m, 6H), 1.39-1.35 (m, 6H). |
| 162 | Hydrochoride (1) | Yellow solid | Recrystallization | Method A; Rt: 3.27 min | 96.43 | 528 | 1H NMR (400 MHz, DMSO-$d_6$): δ 14.03 (s, 1H), 9.87 (brs, 1H), 7.44-7.40 (m, 1H), 7.16 (d, J = 9.6 Hz, 1H), 6.92 (dt, J = 8.4, 2.4 Hz, 1H), 4.85-4.79 (m, 3H), 4.61 (s, 1H), 4.56 (s, 1H), 3.94-3.87 (m, 4H), 2.85 (s, 1.7H), 2.81 (s, 1.5H), 2.62 (s, 1.4H), 2.56 (s, 1.7H), 2.50-2.42 (m, 2H), 2.10-2.03 (m, 6H). |
| 163 | Hydrochoride (1) | White solid | Recrystallization | Method A, Column Tempature: 50° C.; Rt: 2.67 min | 94.18 | 500 | 1H NMR (400 MHz, DMSO-$d_6$): δ 13.89 (s, 1H), 9.6 (d, J = 4.4 Hz, 1H), 8.64-8.60 (m, 1H), 7.43-7.4 (m, 1H), 7.1 (d, J = 10.8 Hz, 1H), 6.9 (t, J = 6.8 Hz, 1H) 4.82 (s, 3H), 4.6 (d, J = 11.6 Hz, 2H), 3.87-3.82 (m, 4H), 2.5 (s, 2H), 2.06-2.02 (m, 6H). |
| 164 | Parent | Pale yellow solid | MD Auto Prep, Method B | Method A, Column Tempature: 50° C.; Rt: 2.75 min | 99.23 | 474 | 1H NMR (400 MHz, DMSO-$d_6$): δ 9.60 (dd, J = 12.0, 2.4 Hz, 1H), 8.64-8.59 (m, 1H), 7.38-7.33 (m, 1H), 7.17 (d, J = 5.6 Hz, 1H), 6.88-6.82 (m, 1H), 4.91-4.85 (m, 3H), 4.58 (d, J = 10.8 Hz, 4H), 4.19-4.12 (m, 1H), 3.79-3.74 (m, 3H), 1.91-1.86 (m, 3H), 1.74-1.60 (m, 4H), 0.95-0.85 (m, 4H). |
| 165 | Parent | White solid | Silicagel column chromatography | Method A, Column Tempature: 50° C.; | 97.29 | 514 | 1H NMR (400 MHz, DMSO-$d_6$): δ 9.61-9.59 (m, 1H), 8.64-8.60 (m, 1H), 7.48-7.38 (m, 1H), 7.01-6.98 (m, 1H), 6.85 (t, J = 8.8 Hz, 1H), 5.15-5.02 (m, 1H), 4.90-4.83 (m, 2H), 4.80-4.73 (m, 1H), 4.63-4.60 (m, |

| No | Isolated Form | Appearance | Purification mode | HPLC Method; Rt (min) | Purity | Mass found [M+] | 1H NMR |
|---|---|---|---|---|---|---|---|
| | | | | Rt: 2.83 min | | | 2H), 3.07-2.90 (m, 3H), 2.51-2.50 (m, 2H), 2.20-2.18 (m, 1H), 2.00-1.99 (m, 2H), 1.70-1.61 (m, 7H), 0.77 (d, J = 6.0 Hz, 3H). |
| 166 | Parent | White solid | Silicagel column chromatography | Method A, Column Tempature: 50° C.; Rt: 2.82 min | 96.88 | 514 | 1H NMR (400 MHz, DMSO-d6): δ 9.59-9.57 (dd, J = 7.6, 2 Hz, 1H), 8.63 (m, 1H), 7.38-7.33 (m, 1H), 6.9 (d, J = 12.0 Hz, 1H), 6.85-6.81 (m, 1H), 5.0 (s, 1H), 4.81 (s, 2H), 4.7 (d, J = 4.8 Hz, 1H), 4.6 (d, J = 12.8 Hz, 2H), 3.29-3.28 (m, 2H), 3.06-3.0 (m, 2H), 2.2-2.1 (m, 2H), 2.0-1.9 (m, 2H), 1.7-1.52 (m, 7H), 0.75 (d, J = 6.8 Hz, 3H). |
| 169 | Parent | Off white solid | MD Auto Prep, Method C | Method A, Column Tempature: 50° C.; Rt: 3.17 min | 97.02 | 476.2 | 1H NMR (400 MHz, DMSO-d6): δ 8.54 (d, J = 4.40, 0.5H), 8.50 (d, J = 4.40, 0.5H), 7.36 (t, J = 6.40 Hz, 1H), 7.04 (s, 1H), 6.97 (d, J = 11.60 Hz, 1H), 6.86-6.82 (m, 1H), 4.90-4.78 (m, 2H), 4.72-4.66 (m, 1H), 4.64-4.53 (m, 2H), 4.21-4.14 (m, 1H), 2.98-2.91 (m, 2H), 2.50-2.43 (m, 2H), 2.33-2.24 (m, 2H), 2.18-2.08 (m, 4H), 2.06-1.97 (m, 2H), 1.93-1.86 (m, 1H), 1.78-1.67 (m, 4H), 1.65-1.62 (m, 2H). |
| 170 | Parent | White solid | MD Auto Prep, Method B | Method B; Rt: 5.06 min | 96.22 | 532 | 1H NMR (400 MHz, DMSO-d6): δ 7.38-7.33 (m, 1H), 7.11-7.08 (m, 1H), 6.86 (t, J = 8.4 Hz, 1H), 5.02-5.01 (m, 1H), 4.80-4.78 (m, 3H), 4.68-4.67 (m, 1H), 4.55-4.49 (m, 1H), 4.35 (t, J = 5.2 Hz, 1H), 3.42-3.39 (m, 2H), 3.34-3.24 (m, 1H), 3.11-3.07 (m, 1H), 2.85 (s, 1.5H), 2.82 (s, 1.5H), 2.62 (s, 1.5H), 2.56 (s, 1.5H), 2.33-2.30 (m, 2H), 1.95-1.92 (m, 2H), 1.75-1.69 (m, 3H), 1.61-1.55 (m, 1H). |
| 171 | Parent | Yellow solid | MD Auto Prep, Method B | Method A, Column Tempature: 50° C.; Rt: 2.96 min | 99.16 | 518 | 1H NMR (400 MHz, DMSO-d6): δ 9.48 (d, J = 9.6 Hz, 1H), 7.37-7.32 (m, 1H), 7.09 (d, J = 11.6 Hz, 1H), 6.86 (t, J = 8.4 Hz, 1H), 5.12-5.02 (m, 1H), 4.79-4.68 (m, 3H), 4.64-4.50 (m, 2H), 4.35 (t, J = 5.60 Hz, 1H), 3.44-3.41 (m, 2H), 3.34-3.24 (m, 1H), 3.07-3.01 (m, 1H), 2.68 (s, 1.5H), 2.61 (s, 1.5H), 2.33-2.29 (m, 2H), 1.95-1.91 (m, 2H), 1.72-1.69 (m, 3H), 1.55-1.54 (m, 1H). |
| 172 | Parent | Yellow solid | MD Auto Prep, Method B | Method A, Column Tempature: 50° C.; Rt: 2.9 min | 97.63 | 514 | 1H NMR (400 MHz, DMSO-d6): δ 9.49 (d, J = 7.6 Hz, 1H), 7.39-7.34 (m, 1H), 6.97 (d, J = 11.6 Hz, 1H), 6.84 (t, J = 8.4 Hz, 1H), 4.85-4.79 (m, 2H), 4.71-4.70 (m, 1H), 4.60-4.56 (m, 2H), 3.44 (t, J = 6.0 Hz, 3H), 3.15-3.06 (m, 2H), 2.67 (s, 1.5H), 2.55 (s, 1.5H), 2.33-2.28 (m, 2H), 1.99-1.96 (m, 2H), 1.66-1.62 (m, 6H), 1.52-1.47 (m, 2H). |
| 173 | Parent | Pale yellow solid | MD Auto Prep, Method B | Method A; Rt: 3.12 min | 99.4 | 460 | 1H NMR (400 MHz, DMSO-d6): δ 7.42-7.37 (m, 1H), 7.10 (d, J = 11.6 Hz, 1H), 6.93 (t, J = 8.0 Hz, 1H), 5.16 (s, 1H), 4.84 (d, J = 10.8 Hz, 2H), 4.64-4.56 (m, 2H), 4.27 (d, J = 10.4 Hz, 2H), 4.10 (t, J = 10.0 Hz, 1H), 3.89 (s, 1H), 2.96 (d, J = 9.6 Hz, 2H), 2.89 (s, 1H), 2.86 (s, 1.6H), 2.82 (s, 1.4H), 2.63 (s, 1.5H), 2.57 (s, 1.5H), 1.91-1.86 (m, 1H), 1.76-1.74 (m, 1H). |
| 174 | Parent | Off white solid | Prep HPLC, Method D | Method B; Rt: 4.04 min | 99.32 | 462 | 1H NMR (400 MHz, DMSO-d6): δ 7.42-7.37 (m, 1H), 7.11 (dd, J = 11.2, 2.0 Hz, 1H), 6.91 (dt, J = 8.5, 2.0 Hz, 1H), 4.86-4.83 (m, 2H), 4.58 (s, 1H), 4.53 (s, 1H), 4.25 (t, J = 5.2 Hz, 2H), 3.31-3.27 (m, 3H), 3.19-3.11 (m, 2H), 2.83 (s, 1.5H), 2.79 (s, 1.5H), 2.61 (s, 1.5H), 2.54 (s, 1.5H). |
| 175 | Parent | Off white solid | Prep HPLC, Method B | Method A; Rt: 3.11 min | 99.52 | 476 | 1H NMR (400 MHz, DMSO-d6): δ 7.42-7.37 (m, 1H), 7.11 (dd, J = 11.2, 2.0 Hz, 1H), 6.89 (dt, J = 8.5, 2.0 Hz, 1H), 4.82-4.79 (m, 2H), 4.61 (s, 1H), 4.58 (s, 1H), 4.22 (t, J = 5.2 Hz, 2H), 3.31-3.28 (m, 2H), 3.06-2.98 (m, 2H), 2.84 (s, 1.5H), 2.81 (s, 1.5H), 2.62 (s, 1.5H), 2.56 (s, 1.5H), 2.34 (s, 3H). |
| 176 | Parent | Off white solid | Silicagel column chromatography | Method A; Rt: 3.72 min | 99.4 | 514 | 1H NMR (400 MHz, DMSO-d6): δ 7.38-7.35 (m, 1H), 7.12-7.09 (m, 1H), 6.88-6.86 (m, 1H), 4.81 (d, J = 8.0 Hz, 2H), 4.68 (s, 1H), 4.61 (s, 1H), 4.57 (s, 1H), 2.84 (s, 1.6H), 2.81 (s, 1.4H), 2.62 (s, 1.5H), 2.56 (s, 1.5H), 2.49-2.47 (m, 1H), 4.13-4.08 (m, 4H), 1.91-1.88 (m, 2H), 1.48-1.46 (m, 2H), 1.33-1.32 (m, 4H), 0.68-0.67 (m, 6H). |
| 177 | Parent | Off white solid | MD Auto Prep, Method C | Method B; Rt: 5.39 min | 98.13 | 520 | 1H NMR (400 MHz, DMSO-d6): δ 7.37-7.33 (m, 1H), 7.24 (d, J = 11.6 Hz, 1H), 6.92-6.87 (m, 1H), 4.83-4.81 (m, 2H), 4.62-4.59 (m, 3H), 4.54-4.50 (m, 1H), 4.28-4.27 (m, 1H), 3.75-3.66 (m, 1H), 3.10-3.00 (m, 1H), 2.83 (s, 1.5H), 2.80 (s, 1.5H), 2.70-2.67 (m, 1H), 2.66 (s, 1.5H), 2.61 (s, 1.5H), 2.25-2.06 (m, 5H), 1.49-1.46 (m, 1H), 0.96 (d, J = 6.00 Hz, 3H). |

-continued

| No | Isolated Form | Appearance | Purification mode | HPLC Method; Rt (min) | Purity | Mass found [M+] | 1H NMR |
|---|---|---|---|---|---|---|---|
| 178 | Parent | White solid | Silicagel column chromatography | Method A; Rt: 3.94 min | 99.46 | 433 | $^1$H NMR (400 MHz, DMSO-d$_6$): δ 7.38-7.33 (m, 1H), 7.06 (d, J = 11.6 Hz, 1H), 6.87 (t, J = 8.4 Hz, 1H), 4.83-4.80 (m, 2H), 4.55-4.48 (m, 3H), 4.00-3.94 (m, 2H), 3.27-3.25 (m, 2H), 2.85 (s, 1.5H), 2.82 (s, 1.5H), 2.63 (s, 1.5H), 2.57 (s, 1.5H), 1.89-1.75 (m, 1H), 0.80 (dd, J = 6.6, 2.8 Hz, 3H). |
| 179 | Parent | Off white solid | Prep HPLC, Method A | Method A; Rt: 3.28 min | 99.33 | 520 | $^1$H NMR (400 MHz, DMSO-d$_6$): δ 7.40-7.35 (m, 1H), 7.26 (d, J = 11.2 Hz, 1H), 6.91 (t, J = 8.4 Hz, 1H), 4.84-4.82 (m, 2H), 4.63-4.49 (m, 4H), 4.46-4.37 (m, 1H), 3.47-3.41 (m, 1H), 2.92-2.85 (m, 1H), 2.90 (s, 1.5H), 2.85 (s, 1.5H), 2.68 (s, 1.5H), 2.63 (s, 1.5H), 2.33-2.29 (m, 2H), 2.26-2.01 (m, 4H), 1.52-1.48 (m, 4H). |
| 180 | Parent | Pale yellow solid | MD Auto Prep, Method B | Method A; Rt: 3.44 min | 97.36 | 502 | $^1$H NMR (400 MHz, DMSO-d$_6$): δ 7.40-7.35 (m, 1H), 7.26 (d, J = 11.2 Hz, 1H), 6.91 (t, J = 8.4 Hz, 1H), 4.84-4.82 (m, 2H), 4.63-4.49 (m, 4H), 4.46-4.37 (m, 1H), 3.47-3.41 (m, 1H), 2.92-2.85 (m, 1H), 2.90 (s, 1.5H), 2.85 (s, 1.5H), 2.68 (s, 1.5H), 2.63 (s, 1.5H), 2.33-2.29 (m, 2H), 2.26-2.01 (m, 4H), 1.52-1.48 (m, 4H). |
| 181 | Parent | Yellow solid | Silicagel column chromatography | Method A; Rt: 3.3 min | 99.71 | 458 | $^1$H NMR (400 MHz, DMSO-d$_6$): δ 7.40-7.35 (m, 1H), 6.91-6.80 (dt, J = 8.4, 2.4 Hz, 1H), 6.83 (d, J = 11.2 Hz, 1H), 4.89 (t, J = 5.2 Hz, 1H), 4.84 (s, 1H), 4.81 (s, 1H), 4.60 (s, 1H), 4.55 (s, 1H), 3.66 (t, J = 6.2 Hz, 2H), 2.90-2.87 (m, 2H), 2.83 (s, 1.6H), 2.79 (s, 1.4H), 2.61 (s, 1.4H), 2.54 (s, 1.6H), 2.32-2.25 (m, 2H), 1.25-1.13 (m, 2H), 0.79-0.77 (m, 3H). |
| 182 | Parent | Off white solid | Prep HPLC, Method B | Method A; Rt: 3.12 min | 99.81 | 474 | $^1$H NMR (400 MHz, DMSO-d$_6$): δ 7.41-7.37 (m, 1H), 6.90 (t, J = 8.0 Hz, 1H), 6.81-6.79 (m, 1H), 4.92-4.83 (m, 3H), 4.63 (s, 1H), 4.31 (br s, 1H), 3.72 (t, J = 6.4 Hz, 2H), 3.52-3.51 (m, 1H), 3.02-2.91 (m, 2H), 2.85 (s, 1.5H), 2.81 (s, 1.5H), 2.68 (s, 1.5H), 2.63 (s, 1.5H), 2.32-2.28 (m, 2H), 0.96-0.92 (m, 3H). |
| 183 | Hydrochoride (1) | Orange solid | Recrystallization | Method A; Rt: 3.62 min | 99.51 | 472 | $^1$H NMR (400 MHz, DMSO-d$_6$): δ 8.50 (s, 2H), 7.38-7.37 (m, 1H), 7.18 (dd, J = 11.6, 2.4 Hz, 1H), 6.89-6.82 (m, 1H), 4.90 (s, 1H), 4.88 (s, 1H), 4.74 (s, 1H), 4.59 (s, 1H), 4.55 (s, 1H), 2.98-2.96 (m, 1H), 2.85 (s, 1.6H), 2.82 (s, 1.4H), 2.62 (s, 1.4H), 2.57 (s, 1.6H), 2.46 (s, 3H), 1.91-1.88 (m, 2H), 1.75-1.70 (m, 2H), 1.66-1.59 (m, 2H), 1.56-1.42 (m, 2H). |
| 184 | Parent | Pale yellow solid | Silicagel column chromatography | Method A; Rt: 3.79 min | 98.78 | 514 | $^1$H NMR (400 MHz, DMSO-d$_6$): δ 7.39-7.34 (m, 1H), 7.13 (d, J = 11.6 Hz, 1H), 6.88 (t, J = 8.4 Hz, 1H), 4.82 (s, 1H), 4.80 (s, 1H), 4.69 (s, 1H), 4.61 (s, 1H), 4.57 (s, 1H), 3.39-3.37 (m, 1H), 2.84 (s, 1.5H), 2.81 (s, 1.5H), 2.62 (s, 1.5H), 2.56 (s, 1.5H), 2.10-2.09 (m, 2H), 2.02-1.87 (m, 2H), 1.47-1.45 (m, 2H), 1.35-1.28 (m, 3H), 1.23-1.21 (m, 2H), 1.12-1.08 (m, 2H), 0.56-0.54 (m, 3H). |
| 185 | Parent | Pale yellow solid | Prep HPLC, Method A or Silicagel column chromatography: see experiment SGN010249-01-10294-075 | Method A; Rt: 3.64 min | 99.24 | 518 | $^1$H NMR (400 MHz, DMSO-d$_6$): δ 7.39-7.34 (m, 1H), 7.13-7.10 (m, 1H), 6.88-6.84 (m, 1H), 4.82 (s, 1H), 4.80 (s, 1H), 4.69 (s, 1H), 4.62 (s, 1H), 4.56 (s, 1H), 4.30-4.26 (m, 1H), 4.18-4.13 (m, 1H), 2.84 (s, 1.4H), 2.81 (s, 1.6H), 2.62 (s, 1.4H), 2.56 (s, 1.6H), 2.46-2.42 (m, 1H), 2.39-2.33 (m, 2H), 1.94-1.93 (m, 3H), 1.88-1.82 (m, 2H), 1.48-1.45 (m, 2H), 1.35-1.32 (m, 4H). |
| 186 | Parent | Pale yellow solid | MD Auto Prep Method-C or B? see SGN010250-01-10232-074 | Method A, Column Tempature: 50° C.; Rt: 2.91 min | 97.91 | 436 | $^1$H NMR (400 MHz, DMSO-d$_6$): δ 8.91 (dd, J = 11.4, 4.0 HZ, 1H), 8.45 (d, J = 2.4 Hz, 0.5H), 8.39 (d, J = 2.4 Hz, 0.5H), 7.43-7.31 (m, 1H), 7.15 (d, J = 10.0 Hz, 1H), 6.91-6.82 (m, 1H), 4.88-4.79 (m, 2H), 4.64-4.48 (m, 3H), 2.31-2.11 (m, 2H), 2.10-1.98 (m, 4H), 1.92-1.77 (m, 3H), 1.68-1.55 (m, 3H), 1.01-0.97 (m, 2H), 0.87-0.85 (m, 2H). |
| 187 | Parent | White solid | MD Auto Prep, Method B | Method A; Rt: 3.39 min | 99.87 | 528.2 | $^1$H NMR (400 MHz, DMSO-d$_6$): δ 7.40-7.35 (m, 1H), 6.95-6.92 (m, 1H), 6.84 (t, J = 8.4 Hz, 1H), 4.88-4.85 (m, 2H), 4.69-4.55 (m, 3H), 4.41-4.40 (m, 1H), 4.28-4.13 (m, 1H), 3.35-3.14 (m, 1H), 2.86 (s, 1.5H), 2.82-2.81 (m, 1H), 2.72 (s, 1.5H), 2.68-2.64 (m, 1H), 2.63 (s, 1.5H), 2.57 (s, 1.5H), 2.29-2.25 (m, 1H), 2.12-1.91 (m, 2H), 1.76-1.60 (m, 2H), 1.57-1.44 (m, 1H), 1.39-1.33 (m, 3H), 0.96-0.68 (m, 3H). |
| 188 | Parent | Brown gum | Silicagel column | Method A; Rt: 3.22 min | 98.1 | 488 | $^1$H NMR (400 MHz, DMSO-d$_6$): δ7.38-7.36 (m, 1H), 7.0 (d, J = 11.2 Hz, 1H), 6.9 (t, J = 8.8 Hz, 1H), |

| No | Isolated Form | Appearance | Purification mode | HPLC Method; Rt (min) | Purity | Mass found [M+] | ¹H NMR |
|---|---|---|---|---|---|---|---|
| | | | chromatography | | | | 5.05-4.94 (m, 1H), 4.8 (d, J = 11.6 Hz, 2H), 4.61-4.54 (m, 2H), 4.45-4.15 (m, 1H), 3.45-3.44 (m, 2H), 2.85 (s, 1.5H), 2.81 (s, 1.5H), 2.67-2.63 (m, 1H), 2.62 (s, 1.4H), 2.56 (s, 1.6H), 2.54-2.4 (m, 2H), 2.33-2.24 (m, 3H), 1.9-1.62 (m, 1H), 0.9-0.8 (m, 3H). |
| 189 | Parent | White solid | MD Auto Prep, Method B | Method A; Rt: 3.19 min | 99.05 | 544 | ¹H NMR (400 MHz, DMSO-d₆): δ 7.41-7.38 (m, 1H), 6.94-6.85 (m, 2H), 5.61-5.12 (m, 1H), 4.85 (d, J = 9.2 Hz, 2H), 4.69-4.65 (m, 1H), 4.60-4.55 (m, 2H), 4.51-4.44 (m, 1H), 4.24-4.09 (m, 2H), 3.58-3.55 (m, 1H), 3.17-3.16 (m, 1H), 2.85 (s, 1.5H), 2.81 (s, 1.5H), 2.67-2.63 (m, 1H), 2.62 (s, 1.5H), 2.56 (s, 1.5H), 2.40-2.32 (m, 1H), 2.17-1.97 (m, 3H), 1.55-1.23 (m, 3H), 1.01 (s, 3H). |
| 190 | Parent | White solid | MD Auto Prep, Method B | Method A; Rt: 3.14 min | 98.48 | 486 | ¹H NMR (400 MHz, DMSO-d₆): δ 7.39-7.34 (m, 1H), 6.94 (d, J = 12.4 Hz, 1H), 6.83 (t, J = 8.4 Hz, 1H), 4.85 (d, J = 8.0 Hz, 2H), 4.67-4.65 (m, 1H), 4.60-4.55 (m, 2H), 4.45-4.31 (m, 1H), 4.18-4.15 (m, 1H), 3.37-3.33 (m, 1H), 2.88-2.85 (m, 1H), 2.85 (s, 1.5H), 2.81 (s, 1.5H), 2.62 (s, 1.5H), 2.56 (s, 1.5H), 2.32-2.23 (m, 1H), 1.89-1.81 (m, 2H), 1.69-1.65 (m, 1H), 1.56-1.53 (m, 1H), 1.36-1.23 (m, 2H). |
| 191 | Parent | Pale brown gum | Silicagel column chromatography | Method A; Rt: 3.16 min | 99.62 | 474 | ¹H NMR (400 MHz, DMSO-d₆): δ 7.38-7.33 (m, 1H), 7.0 (d, J = 11.6 Hz, 1H), 6.87 (dt, J = 10.4, 2.0 Hz, 1H), 5.0-4.93 (m, 1H), 4.8 (d, J = 11.6 Hz, 2H), 4.65-4.51 (m, 2H), 4.42-4.35 (m, 1H), 3.41-3.39 (m, 2H), 2.84 (s, 2H), 2.81 (s, 2H), 2.7-2.6 (m, 3H), 2.56 (s, 2H), 2.4-2.33 (m, 3H), 2.24-2.19 (m, 1H), 1.72-1.70 (m, 1H). |
| 192 | Parent | Yellow solid | MD Auto Prep, Method C | Method A; Rt: 3.18 min | 98.43 | 488 | ¹H NMR (400 MHz, DMSO-d₆): δ 7.37-7.32 (m, 1H), 7.0 (dd, J = 11.4, 2.4 Hz, 1H), 6.86 (dt, J = 11.87, 2 Hz, 1H), 5.01-4.94 (m, 1H), 4.82 (s, 1H), 4.79 (s, 1H), 4.65-4.49 (m, 2H), 4.36-4.22 (m, 1H), 3.28-3.2 (m, 3H), 2.83 (s, 1.5H), 2.80 (s, 1.5H), 2.74 (s, 1H), 2.66 (s, 2H), 2.55-2.5 (m, 2H), 2.32-2.2 (m, 4H), 1.77-1.65 (m, 1H), 1.46-1.44 (m, 2H). |
| 193 | Parent | White solid | MD Auto Prep, Method C | Method A; Rt: 3.48 min | 99.54 | 516.2 | ¹H NMR (400 MHz, DMSO-d₆): δ 7.36-7.34 (m, 1H), 7.12-7.09 (m, 1H), 6.87-6.82 (m, 1H), 4.81 (s, 1H), 4.79 (s, 1H), 4.68 (s, 1H), 4.61 (s, 1H), 4.55 (s, 1H), 4.10-4.09 (m, 1H), 3.21-3.20 (m, 2H), 2.83 (s, 1.5H), 2.80 (s, 1.5H), 2.61 (s, 1.4H), 2.55 (s, 1.6H), 2.32-2.31 (m, 1H), 2.22-2.20 (m, 2H), 1.86-1.84 (m, 5H), 1.46-1.44 (m, 2H), 1.34-1.32 (m, 4H). |
| 194 | Parent | Off white solid | MD Auto Prep, Method C | Method A; Rt: 3.58 min | 98.19 | 530.1 | ¹H NMR (400 MHz, DMSO-d₆): δ 7.37-7.33 (m, 1H), 7.12-7.09 (m, 1H), 6.87-6.82 (m, 1H), 4.81(s, 1H), 4.79 (s, 1H), 4.68 (s, 1H), 4.61 (s, 1H), 4.56 (s, 1H), 3.96-3.94 (m, 1H), 3.49-3.33 (m, 1H), 2.82 (s, 1.4H), 2.79 (m, 1.6H), 2.60 (s, 1.4H), 2.55 (s, 1.6H), 2.32-2.31 (m, 1H), 2.06-2.00 (m, 2H), 1.91-1.86 (m, 4H), 1.46-1.43 (m, 2H), 1.34-1.32 (m, 4H), 0.83 (d, J = 6.00 Hz, 3H). |
| 195 | Parent | Pale yellow solid | Prep HPLC, Method B | Method A; Rt: 3.21 min | 99.2 | 498 | ¹H NMR (400 MHz, DMSO-d₆): δ 7.37-7.32 (m, 1H), 6.99-6.95 (m, 1H), 6.84 (t, J = 8.4 Hz, 1H), 4.82-4.73 (m, 3H), 4.72-4.66 (m, 1H), 4.58 (s, 1H), 4.53 (s, 1H), 3.00 (s, 2H), 2.85 (s, 1.5H), 2.81 (s, 1.5H), 2.62 (s, 1.5H), 2.56 (s, 1.5H), 2.35 (s, 3H), 2.33-2.31 (m, 1H), 2.00-1.96 (m, 2H), 1.62-1.54 (m, 2H). |
| 196 | Parent | Pale yellow solid | MD Auto Prep, Method B | Method A; Rt: 3.61 min | 95.26 | 528 | ¹H NMR (400 MHz, DMSO-d₆): δ 7.48-7.42 (m, 1H), 6.99 (d, J = 12.0 Hz, 1H), 6.89 (t, J = 8.0 Hz, 1H), 4.92-4.76 (m, 3H), 4.70-4.65 (m, 1H), 4.54-4.44 (m, 1H), 3.63-3.60 (m, 1H), 3.34-3.30 (m, 2H), 2.95-2.85 (m, 1H), 2.68 (s, 1.5H), 2.63 (s, 1.5H), 2.33-2.27 (m, 3H), 2.22-2.17 (m, 2H), 1.84-1.68 (m, 3H), 1.32-1.27 (m, 5H), 1.26-1.25 (m, 3H). |
| 197 | Parent | White solid | MD Auto Prep, Method B | Method A; Rt: 3.55 min | 98.97 | 542.3 | ¹H NMR (400 MHz, DMSO-d₆): δ 7.43-7.40 (m, 1H), 7.24-6.87 (m, 2H), 4.88-4.86 (m, 2H), 4.71-4.52 (m, 4H), 4.35-4.31 (m, 2H), 4.13-3.65 (m, 1H), 3.26-3.11 (m, 1H), 2.86 (s, 1.5H), 2.82 (s, 1.5H), 2.63 (s, 1.5H), 2.61-2.58 (m, 1H), 2.57 (s, 1.5H), 2.10-1.76 (m, 3H), 1.59-1.44 (m, 4H), 1.30-1.15 (m, 3H), 0.87 (t, J = 6.40 Hz, 3H). |
| 198 | Parent | Pale yellow solid | Silicagel column chromatography | Method A; Rt: 3.37 min | 97.73 | 528 | ¹H NMR (400 MHz, DMSO-d₆): δ 7.45-7.35 (m, 1H), 7.16-7.11 (m, 1H), 6.92-6.86 (m, 1H), 4.93-4.81 (m, 1H), 4.83-4.81 (m, 1H), 4.58-4.56 (m, 1H), 4.55-4.53 (m, 2H), 4.39-4.38 (m, 1H), 3.74-3.71 (m, 1H), |

-continued

| No | Isolated Form | Appearance | Purification mode | HPLC Method; Rt (min) | Purity | Mass found [M⁺] | ¹H NMR |
|---|---|---|---|---|---|---|---|
| | | | | | | | 3.32-3.10 (m, 2H), 2.84 (s, 1.5H), 2.67 (s, 1.5H), 2.56 (s, 1.5H), 2.53-2.50 (m, 2H), 2.50 (s, 1.5H), 2.33-2.32 (m, 2H), 2.24-2.06 (m, 1H), 1.90-1.82 (m, 1H), 1.56-1.48 (m, 4H), 1.35-1.14 (m, 2H), 0.87-0.85 (m, 1H). |
| 199 | Hydrochoride (1) | Brown gum | Recrystallization | Method A; Rt: 3.33 min | 99.54 | 474 | ¹H NMR (400 MHz, DMSO-d₆): δ 9.71 (s, 1H), 8.90 (s, 1H), 7.46-7.41 (m, 1H), 7.18 (d, J = 11.2 Hz, 1H), 6.98-6.94 (dt, J = 8.4, 2.0 Hz, 1H), 5.22 (s, 1H), 4.85 (d, J = 10.4 Hz, 2H), 4.66-4.48 (m, 2H), 3.81-3.77 (m, 1H), 3.55-3.39 (m, 5H), 3.11 (d, J = 4.4 Hz, 3H), 2.85 (s, 1.5H), 2.82 (s, 1.5H), 2.63 (s, 1.5H), 2.57 (s, 1.5H), 1.81-1.77 (m, 1H). |
| 200 | Parent | Brown solid | Silicagel column chromatography | Method A, Column Temparature: 50° C.; Rt: 3.12 min | 97.88 | 490 | ¹H NMR (400 MHz, DMSO-d₆): δ 9.61-9.57 (m, 1H), 8.64-8.58 (m, 1H), 7.39-7.35 (m, 1H), 7.14-7.11 (m, 1H), 6.88-6.84 (m, 1H), 4.91-4.79 (m, 2H), 4.75-4.65 (m, 1H), 4.62 (d, J = 10.0 Hz, 2H), 4.30-4.25 (m, 1H), 4.18-4.14 (m, 1H), 2.45-2.43 (m, 1H), 2.37-2.36 (m, 2H), 1.93-1.88 (m, 5H), 1.56-1.45 (m, 2H), 1.41-1.29 (m, 4H). |
| 201 | Parent | Pale yellow solid | Recrystallization | Method A; Rt: 3.32 min | 98.23 | 474 | ¹H NMR (400 MHz, DMSO-d₆): δ 7.37-7.33 (m, 1H), 7.07-7.04 (dd, J = 11.60, 2.00 Hz, 1H), 6.90-6.89 (dt, J = 8.40, 2.00 Hz, 1H), 4.83 (s, 1H), 4.81 (s, 1H), 4.60-4.50 (m, 2H), 4.05-4.03 (m, 1H), 3.95 (d, J = 4.80 Hz, 2H), 3.68-3.65 (m, 1H), 3.46-3.41 (m, 1H), 3.01 (d, J = 1.20 Hz, 3H), 2.85 (s, 1.5H), 2.81 (s, 1.5H), 2.75-2.65 (m, 2H), 2.62 (s, 1.5H), 2.56 (s, 1.5H), 1.75-1.72 (m, 1H), 1.53-1.47 (m, 1H). |
| 202 | Parent | Off white solid | MD Auto Prep, Method B | Method A; Rt: 3.82 min | 99.49 | 433 | ¹H NMR (400 MHz, DMSO-d₆): δ 7.36-7.31 (m, 1H), 7.1 (d, J = 11.2 Hz, 1H), 6.86 (dt, J = 11.87, 2.0 Hz, 1H), 4.82 (s, 1H), 4.79 (s, 1H), 4.54 (s, 1H) 4.49 (s, 1H), 4.34-4.31 (m, 1H), 4.08-4.05 (m, 2H), 3.29-3.25 (m, 2H), 2.83 (s, 2H), 2.80 (s, 1H), 2.61 (s, 1H), 2.55 (s, 2H), 1.7-1.6 (m, 2H), 1.45-1.35 (m, 2H). |
| 203 | Parent | Pale yellow solid | MD Auto Prep Method C | Method A; Rt: 3.27 min | 98.3 | 444 | ¹H NMR(400 MHz, DMSO-d₆): δ 7.39-7.35 (m, 1H), 7.11-7.07 (dd, J = 11.6, 2.0 Hz, 1H), 6.92-6.87 (dt, J = 8.4, 2.0 Hz, 1H), 4.83 (d, J = 12.0 Hz, 2H), 4.63-4.56 (m, 2H), 4.09-4.06 (m, 1H), 4.03-3.99 (m, 1H), 3.51 (s, 1H), 2.85 (s, 1.5H), 2.82 (s, 1.5H), 2.78-2.73 (m, 2H), 2.63 (s, 1.5H), 2.56 (s, 1.5H), 1.82-1.76 (m, 1H), 1.67-1.56 (m, 2H), 1.55-1.42 (m, 1H). |
| 204 | Parent | White solid | MD Auto Prep Method B | Method A, Column Tempature: 50° C.; Rt: 3.05 min | 99.03 | 391 | ¹H NMR (400 MHz, DMSO-d₆): δ 9.59 (dd, J = 8.4, 2.0 Hz, 1H), 8.63-8.58 (m, 1H), 7.37-7.33 (m, 1H), 7.08 (dd, J = 11.6, 2.0 Hz, 1H), 6.89 (t, J = 2.4 Hz, 1H), 4.83 (d, J = 3.4 Hz, 2H), 4.57-4.54 (m, 2H), 4.47-4.42 (m, 1H), 4.15-4.12 (m, 2H), 3.41-3.93 (m, 2H), 1.79-1.75 (m, 2H). |
| 205 | Hydrochoride (1) | Orange solid | Recrystallization | Method A; Rt: 3.33 min | 96.68 | 458 | ¹H NMR (400 MHz, DMSO-d₆): δ 7.97 (s, 3H), 7.37-7.32 (m, 1H), 7.24-7.21 (m, 1H), 6.89-6.84 (m, 1H), 4.82 (s, 1H), 4.79 (s, 1H), 4.55 (s, 1H), 4.50 (s, 1H), 4.42 (s, 1H), 3.01-2.99 (m, 1H), 2.84 (s, 1.6H), 2.81 (s, 1.4H), 2.62 (s, 1.4H), 2.56 (s, 1.6H), 2.05-2.03 (m, 2H), 1.93-1.90 (m, 2H), 1.49-1.36 (m, 4H). |
| 206 | Parent | White solid | Prep-HPLC, Method A | Method A; Rt: 3.41 min | 99.07 | 486 | ¹H NMR (400 MHz, DMSO-d₆): δ 7.37-7.32 (m, 1H), 7.17-7.14 (m, 1H), 6.88-6.84 (m, 1H), 4.82 (s, 1H), 4.79 (s, 1H), 4.56 (s, 1H), 4.50 (s, 1H), 4.42-4.38 (m, 1H), 2.84 (s, 1.6H), 2.81 (s, 1.4H), 2.62 (s, 1.5H), 2.56 (s, 1.5H), 2.37-2.34 (m, 6H), 2.09-2.06 (m, 2H), 1.85-1.82 (m, 2H), 1.46-1.40 (m, 2H), 1.35-1.29 (m 3H). |
| 207 | Parent | Orange solid | Prep-HPLC, Method D | Method A; Rt: 4.3 min | 96.22 | 487 | ¹H NMR (400 MHz, DMSO-d₆): δ 12.14 (brs, 1H), 7.36-7.31 (m, 1H), 7.16 (d, J = 11.60 Hz, 1H), 6.87-6.83 (dt, J = 8.40, 2.00 Hz, 1H), 4.81 (d, J = 11.60 Hz, 2H), 4.56-4.51 (m, 2H), 4.50-4.35 (m, 1H), 2.89 (s, 1.5H), 2.84 (s, 1.5H), 2.63 (s, 1.5H), 2.56 (s, 1.5H), 2.20-2.17 (m, 1H), 2.02-1.98 (m, 2H), 1.87-1.84 (m, 2H), 1.54-1.45 (m, 2H), 1.36-1.28 (m, 2H). |
| 208 | Parent | Yellow solid | Silicagel column chromatography | Method A, Column Tempature: 50° C.; Rt: 3.44 min | 97.5 | 379 | ¹HNMR (400 MHz, DMSO-d₆): δ 9.60-9.57 (m, 1H), 8.64-8.58 (m, 1H), 7.41-7.36 (m, 1H), 7.14 (dd, J = 11.6, 2.0 Hz, 1H), 6.92 (dt, J = 8.4, 2.4 Hz, 1H), 4.85 (d, J = 3.6 Hz, 2H), 4.74 (dd, J = 7.2, 3.7 Hz, 1H), 4.63-4.57 (m, 3H), 4.43-4.41 (m, 1H), 4.34-4.36 (m, 1H). |
| 209 | Parent | Off white solid | Silicagel column chromatography | Method A, Column Tempature: | 97.77 | 401 | ¹HNMR (400 MHz, DMSO-d₆): δ 9.60-9.58 (m, 1H), 8.63-8.59 (m, 1H), 7.36 (t, J = 1.6 Hz, 1H), 7.07 (d, J = 11.6 Hz, 1H), 6.88-6.78 (m, 1H), 4.84-4.80 (m, |

| No | Isolated Form | Appearance | Purification mode | HPLC Method; Rt (min) | Purity | Mass found [M+] | 1H NMR |
|---|---|---|---|---|---|---|---|
| | | | | 50° C.; Rt: 4.54 min | | | 2H), 4.59-4.55 (m, 2H), 4.04 (d, J = 6.0 Hz, 2H), 2.67-2.61 (m, 2H), 1.89-1.87 (m, 2H), 1.75-1.70 (m, 3H). |
| 210 | Parent | White solid | Prep-HPLC, Method A | Method A, Column Tempature: 50° C.; Rt: 3.99 min | 99.53 | 459 | 1H NMR (400 MHz, DMSO-d6): δ 7.36-7.31 (m, 1H), 7.04-7.01 (m, 1H), 6.88-6.83 (m, 1H), 4.93-4.92 (m, 1H), 4.82 (s, 1H), 4.79 (s, 1H), 4.54 (s, 1H), 4.49-4.45 (m, 2H), 3.24-3.21 (m, 1H), 3.20-3.18 (s, 1H), 2.84 (s, 1.5H), 2.81 (s, 1.5H), 2.62 (s, 2H), 2.51 (s, 2H), 2.06-1.96 (m, 2H), 1.79-1.61 (m, 4H). |
| 211 | Parent | White solid | MD Auto Prep Method B | Method A, Column Tempature: 50° C.; Rt: 2.65 min | 99.63 | 430 | 1H NMR (400 MHz, DMSO-d6): δ 9.62-9.60 (m, 1H), 8.6 (dd, J = 14, 2.4 Hz, 1H), 7.38-7.34 (m, 1H), 7.1 (d, J = 10.0 Hz, 1H), 6.9 (t, J = 8.0 Hz, 1H), 4.82-4.77 (m, 2H), 4.7-4.55 (m, 2H), 4.22-4.13 (m, 2H), 2.8-2.7 (m, 2H), 2.4-2.3 (m, 3H), 1.42-1.36 (m, 5H). |
| 212 | Parent | Pale yellow solid | Silicagel column chromatography | Method A; Rt: 3.62 min | 98.31 | 472 | 1H NMR (400 MHz, DMSO-d6): δ 8.23-8.20 (m, 1H), 7.40-7.35 (m, 1H), 6.91-6.87 (m, 1H), 6.81-6.77 (m, 1H), 4.92-4.90 (m, 1H), 4.86 (s, 1H), 4.83 (s, 1H), 4.58 (s, 1H), 4.52 (s, 1H), 4.19-4.10 (m, 1H), 2.84 (s, 1.6H), 2.81 (s, 1.4H), 2.62 (s, 1.5H), 2.56 (s, 1.5H), 2.36-2.28 (m, 4H), 1.787 (d, J = 3.2 Hz, 3H). |
| 213 | Parent | Pale brown solid | Silicagel column chromatography | Method A, Column Tempature: 50° C.; Rt: 2.81 min | 99.7 | 500 | 1H NMR (400 MHz, DMSO-d6): δ 9.61-9.58 (m, 1H), 8.64-8.59 (m, 1H), 7.45-7.35 (m, 1H), 7.29-7.14 (m, 1H), 6.89-6.84 (m, 1H), 4.89-4.84 (m, 2H), 4.58 (d, J = 10.4 Hz, 3H), 4.45-4.39 (m, 1H), 3.79-3.73 (s, 1H), 3.10-2.90 (m, 2H), 2.61-2.58 (m, 1H), 2.25-2.21 (m, 2H), 1.91-1.83 (m, 2H), 1.63-1.50 (m, 4H), 1.42-1.35 (m, 3H), 1.16-1.14 (m, 1H). |
| 214 | Parent | Off white solid | Silicagel column chromatography | Method A; Rt: 4.25 min | 95.19 | 473 | 1H NMR (400 MHz, DMSO-d6): δ 7.38-7.33 (m, 1H), 7.11 (d, J = 11.60 Hz, 1H), 6.88-6.84 (m, 1H), 4.81 (d, J = 8.80 Hz, 2H), 4.74 (s, 1H), 4.63 (s, 1H), 4.56 (s, 1H), 4.27 (t, J = 3.60 Hz, 1H), 2.93 (t, J = 5.20 Hz, 2H), 2.85 (s, 1.5H), 2.82 (s, 1.5H), 2.63 (s, 1.5H), 2.57 (s, 1.5H), 1.83-1.79 (m, 2H), 1.50-1.34 (m, 5H), 1.06-1.00 (m, 2H). |
| 215 | Parent | Pale yellow solid | Silicagel column chromatography | Method A; Rt: 3.57 min | 97.99 | 500 | 1H NMR (400 MHz, DMSO-d6): δ 7.39-7.31 (m, 1H), 7.10 (t, J = 12.00 Hz, 1H), 6.87-6.82 (m, 1H), 4.82-4.73 (m, 2H), 4.62-4.51 (m, 2H), 4.30-4.45 (m, 1H), 2.84 (s, 1.5H), 2.81 (s, 1.5H), 2.68 (s, 1.5H), 2.62 (s, 1.5H), 2.15-2.05 (m, 3H), 2.04-1.95 (m, 2H), 1.93-1.85 (m, 2H), 1.83-1.73 (m, 2H), 1.62-1.45 (m, 2H), 1.39-1.37 (m, 2H), 1.31-1.22 (m, 2H), 1.18-0.98 (m, 2H). |
| 216 | Parent | Brown solid | Recrystallization | Method A, Column Tempature: 50° C.; Rt: 2.62 min | 98.53 | 402 | 1H NMR (400 MHz, DMSO-d6): δ 9.6 (dd, J = 10.6, 2.4 Hz, 1H), 8.64-8.59 (m, 1H), 7.38-7.33 (m, 1H), 7.1 (d, J = 11.2 Hz, 1H), 6.8 (dt, J = 11.8, 2.0 Hz 1H), 5.0-4.95 (m, 1H), 4.84-4.83 (m, 2H), 4.58-4.53 (m, 2H), 3.1-3.0 (m, 2H), 2.82-2.7 (m, 3H), 2.0-1.9 (m, 1H), 1.75-1.65 (m, 1H). |
| 217 | Parent | Yellow solid | MD Auto Prep, Method B | Method A; Rt: 3.34 min | 99.08 | 444 | 1H NMR (400 MHz, DMSO-d6): δ 7.36-7.31 (m, 1H), 7.04-7.01 (m, 1H), 6.87 (dt, J = 8.4, 2.0 Hz, 1H), 4.84 (s, 1H), 4.81 (s, 1H), 4.55 (s, 1H), 4.51 (s, 1H), 3.98-3.96 (m, 2H), 3.15-3.02 (m, 1H), 2.83 (s, 1.5H), 2.80 (s, 1.5H), 2.66 (s, 1H), 2.61 (s, 2H), 2.12-2.06 (m, 3H), 1.77-1.53 (m, 2H), 1.35-1.25 (m, 2H). |
| 218 | Parent | Off white solid | MD Auto Prep Method B | Method A, Column Tempature: 50° C.; Rt: 2.57 min | 97.35 | 402 | 1H NMR (400 MHz, DMSO-d6): δ 9.57 (dd, J = 8.0, 2.0 Hz, 1H), 8.62-8.57 (m, 1H), 7.37-7.32 (m, 1H), 7.10 (d, J = 11.4 Hz, 1H), 6.86 (t, J = 1.6 Hz, 1H), 4.84-4.81 (m, 3H), 4.63-4.60 (m, 2H), 4.04-4.02 (s, 4H), 3.10-6.05 (s, 1H), 2.12-2.08 (m, 1H), 2.04-2.00 (m, 1H). |
| 219 | Parent | Off white solid | MD Auto Prep Method B | Method A; Rt: 3.19 min | 99.26 | 430 | 1H NMR (400 MHz, DMSO-d6): δ 7.38-7.33 (m, 1H), 7.10 (d, J = 10.0 Hz, 1H), 6.88 (dt, J = 8.60, 2.00 Hz, 1H), 4.81 (s, 1H), 4.81 (s, 1H), 4.62 (s, 1H), 4.57 (s, 1H), 4.05-4.04 (m, 1H), 3.16-3.06 (m, 1H), 2.85 (s, 1.5H), 2.81 (s, 1.5H), 2.62 (s, 1.5H), 2.56 (s, 1.5H), 2.12-2.05 (m, 1H), 2.00-1.95 (m, 1H), 1.59-1.36 (m, 2H), 0.92-0.82 (m, 2H). |
| 220 | Parent | White solid | MD Auto Prep Method C | Method A, Column Tempature: 50° C.; Rt: 2.93 min | 97.83 | 514 | 1H NMR (400 MHz, DMSO-d6): δ 9.64-9.60 (m, 1H), 8.65-8.60 (m, 1H), 7.35 (t, J = 3.4 Hz, 1H), 7.14-7.12 (m, 1H), 6.89-6.84 (m, 1H), 4.86-4.82 (m, 2H), 4.60-4.58 (m, 3H), 3.92-3.87 (m, 1H), 3.21-3.17 (m, 1H), 2.67-2.61 (m, 1H), 2.33-2.28 (m, 1H), 2.01-1.97 (m, 1H), 1.89-1.83 (m, 3H), 1.71-1.66 (m, 2H), 1.52-1.49 (m, 2H), 1.16-1.14 (m, 2H), 1.01-0.95 (m, 4H), 0.84-0.77 (m, 1H). |

-continued

| No | Isolated Form | Appearance | Purification mode | HPLC Method; Rt (min) | Purity | Mass found [M+] | 1H NMR |
|---|---|---|---|---|---|---|---|
| 221 | Parent | Pale yellow solid | Silicagel column chromatography | Method A; Rt: 3.43 min | 97.57 | 472.2 | 1H NMR (400 MHz, DMSO-d6): δ 7.40-7.35 (m, 1H), 6.90-6.76 (m, 2H), 4.91 (d, J = 2.0 Hz, 1H), 4.85-4.82 (m, 2H), 4.58-4.53 (m, 2H), 3.29-3.25 (m, 1H), 2.85 (s, 1.5H), 2.81 (s, 1.5H), 2.75-2.74 (m, 1H), 2.62 (s, 1.5H), 2.56 (s, 1.5H), 2.40-2.29 (m, 2H), 2.25-2.14 (m, 3H), 1.80-1.65 (m, 1H), 1.36-1.29 (m, 2H), 0.84-0.77 (m, 3H). |
| 224 | Parent | White solid | Silicagel column chromatography | Method A; Rt: 3.89 min | 99.76 | 508 | 1H NMR (400 MHz, DMSO-d6): δ 7.50-7.45 (m, 1H), 7.39-7.36 (m, 1H), 6.91-6.78 (m, 2H), 4.89-4.82 (m, 2H), 4.58-4.55 (m, 1H), 4.52-4.48 (m, 1H), 3.88-3.85 (m, 1H), 2.99-2.96 (m, 1H), 2.91-2.90 (m, 1H), 2.85-2.80 (m, 6H), 2.67 (s, 1.5H), 2.57 (s, 1.5H), 2.50-2.48 (m, 2H), 1.99-1.96 (m, 1H). |
| 227 | Parent | Pale yellow solid | Silicagel column chromatography | Method A; Rt: 3.56 min | 99.73 | 486.2 | 1H NMR (400 MHz, DMSO-d6): δ 7.39-7.36 (m, 1H), 6.90-6.79 (m, 2H), 4.86-4.83 (m, 3H), 4.58-4.53 (m, 2H), 2.85 (s, 1.5H), 2.81 (s, 1.5H), 2.68-2.65 (m, 1H), 2.62 (s, 1.5H), 2.56 (s, 1.5H), 2.39-2.30 (m, 2H), 2.20-1.92 (m, 6H), 1.95-1.65 (m, 1H), 1.42-1.30 (m, 2H), 0.82-0.75 (m, 3H). |
| 228 | Parent | Off white solid | Silicagel column chromatography (230-400 mesh silica gel, pet ether/ethyl acetate as gradient elution) | Method A; Rt: 4.37 min | 98.53 | 473 | 1H NMR (400 MHz, DMSO-d6): δ 7.39-7.34 (m, 1H), 7.19-7.16 (m, 1H), 6.94-6.89 (m, 1H), 6.62-6.58 (m, 1H), 4.80 (s, 1H), 4.78 (s, 1H), 4.58-4.53 (m, 2H), 4.35-4.27 (m, 2H), 4.21-4.16 (m, 1H), 2.85 (s, 1.5H), 2.81 (s, 1.5H), 2.62 (s, 1.5H), 2.56 (s, 1.5H). |
| 231 | Parent | Off white solid | Silicagel column chromatography | Method A; Rt: 3.98 min | 99.56 | 500 | 1H NMR (400 MHz, DMSO-d6): δ 7.71 (t, J = 4.4 Hz, 1H), 7.38-7.33 (m, 1H), 7.14-7.11 (m, 1H), 6.88-6.84 (m, 1H), 4.89 (s, 1H), 4.86 (s, 1H), 4.64-4.56 (m, 3H), 3.55-3.53 (m, 1H), 2.84 (s, 1.5H), 2.81 (s, 1.5H), 2.62 (s, 1.4H), 2.56 (s, 1.6H), 1.78-1.71 (m, 5H), 1.63-1.57 (m, 2H), 1.51-1.48 (m, 2H), 1.38-1.32 (m, 2H). |
| 232 | Parent | White solid | MD Auto Prep Method B | Method A; Rt: 3.2 min | 99.62 | 430 | 1H NMR (400 MHz, DMSO-d6): δ 7.38-7.33 (m, 1H), 7.12-7.09 (m, 1H), 6.88 (dt, J = 8.4, 2.0 Hz, 1H), 4.83 (s, 1H), 4.80 (s, 1H), 4.62 (s, 1H), 4.58 (s, 1H), 4.07-4.00 (m, 3H), 3.12-3.05 (m, 2H), 2.85 (s, 1.5H), 2.81 (s, 1.5H), 2.62 (s, 1.5H), 2.56 (s, 1.5H), 2.46 (s, 1H), 2.12-2.11 (m, 1H), 2.04-2.01 (m, 1H). |
| 233 | Parent | Pale brown solid | Silicagel column chromatography | Method A; Rt: 3.52 min | 97.67 | 486.2 | 1H NMR (400 MHz, DMSO-d6): δ 7.37-7.32 (m, 1H), 7.03 (dd, J = 11.6, 2.0 Hz, 1H), 6.86 (dt, J = 8.4, 2.0 Hz, 1H), 4.99-4.94 (m, 1H), 4.81 (s, 1H), 4.79 (s, 1H), 4.54 (s, 1H), 4.49 (s, 1H), 2.84 (s, 1.5H), 2.80 (s, 1.5H), 2.62 (s, 1.5H), 2.56 (s, 1.5H), 2.02-1.97 (m, 4H), 1.96-1.92 (m, 4H), 1.83-1.80 (m, 2H), 1.65-1.63 (m, 2H), 1.47-1.45 (m, 1H), 1.23-1.15 (m, 2H). |
| 234 | Parent | Off white solid | Silicagel column chromatography | Method A; Rt: 3.34 min | 99.25 | 514.1 | 1H NMR (400 MHz, DMSO-d6): δ 7.40-7.35 (m, 1H), 6.88-6.85 (m, 1H), 6.80-6.77 (m, 1H), 4.95-4.90 (m, 1H), 4.85-4.82 (m, 2H), 4.58-4.52 (m, 2H), 3.76-3.73 (m, 2H), 3.49-3.40 (m, 2H), 3.22-3.16 (m, 2H), 3.03-2.95 (m, 1H), 2.85 (s, 1.5H), 2.81 (s, 1.5H), 2.80-2.75 (m, 1H), 2.62 (s, 1.5H), 2.56 (s, 1.5H), 2.28-2.20 (m, 2H), 1.83-1.79 (m, 1H), 1.62-1.54 (m, 2H), 1.23-1.19 (m, 2H). |
| 235 | Parent | Off white solid | MD Auto Prep Method B | Method A; Rt: 3.35 min | 99.38 | 472 | 1H NMR (400 MHz, DMSO-d6): δ 7.39-7.34 (m, 1H), 6.87 (dt, J = 8.4, 2.0 Hz, 1H), 6.79 (dd, J = 11.6, 2.4 Hz, 1H), 4.91 (t, J = 6.0 Hz, 1H), 4.85 (s, 1H), 4.82 (s, 1H), 4.59 (s, 1H), 4.54 (s, 1H), 2.84 (s, 1.5H), 2.80 (s, 1.5H), 2.62 (s, 1.5H), 2.56 (s, 1.5H), 2.36-2.27 (m, 3H), 2.19-2.15 (m, 2H), 2.09-2.05 (m, 8H). |
| 236 | Parent | White solid | Silicagel column chromatography | Method A; Rt: 3.44 min | 99.73 | 446 | 1H NMR (400 MHz, DMSO-d6): δ 7.91 (t, J = 5.2 Hz, 1H), 7.38-7.35 (m, 1H), 7.11 (td, J = 10.9, 2.0 Hz, 1H), 6.88 (dt, J = 8.40, 2.0 Hz, 1H), 4.84 (s, 1H), 4.81 (s, 1H), 4.55 (s, 1H), 4.50 (s, 1H), 4.10-4.07 (m, 2H), 3.34-3.33 (m, 2H), 2.85 (s, 1.5H), 2.81 (s, 1.5H), 2.63 (s, 1.5H), 2.56 (s, 1.5H), 1.50 (s, 1.5H), 1.45 (s, 1.5H). |
| 237 | Parent | White solid | Silicagel column chromatography | Method A; Rt: 3.58 min | 99.12 | 490 | 1H NMR (400 MHz, DMSO-d6): δ 7.90 (t, J = 5.2 Hz, 1H), 7.38-7.33 (m, 1H), 7.33-7.09 (m, 1H), 6.89 (dt, J = 8.40, 2.0 Hz, 1H), 4.84 (s, 1H), 4.81 (s, 1H), 4.55 (s, 1H), 4.50 (s, 1H), 4.11-4.07 (m, 2H), 3.36- |

| No | Isolated Form | Appearance | Purification mode | HPLC Method; Rt (min) | Purity | Mass found [M+] | 1H NMR |
|---|---|---|---|---|---|---|---|
| | | | | | | | 3.36 (m, 2H), 3.26-3.21 (m, 2H), 3.04 (s, 3H), 2.85 (s, 1.5H), 2.81 (s, 1.5H), 2.68 (s, 1.5H), 2.56 (s, 1.5H), 2.00-1.92 (m, 2H). |
| 238 | Parent | White solid | Silicagel column chromatography | Method A; Rt: 3.77 min | 99.68 | 482 | 1H NMR (400 MHz, DMSO-d6): δ 7.39-7.35 (m, 1H), 7.20 (d, J = 5.2 Hz, 1H), 7.12-7.09 (m, 1H), 6.92-6.87 (m, 1H), 4.82 (s, 1H), 4.79 (s, 1H), 4.59 (s, 1H), 4.54 (s, 1H), 4.16-4.12 (m, 2H), 3.27-3.26 (m, 2H), 2.85-2.80 (m, 6H), 2.65 (s, 1.5H), 2.55 (s, 1.5H). |
| 239 | Parent | Off white solid | Silicagel column chromatography | Method A; Rt: 3.48 min | 98.07 | 458 | 1H NMR (400 MHz, DMSO-d6): δ 7.41-7.36 (m, 1H), 7.11-7.08 (m, 1H), 6.88 (t, J = 8.4 Hz, 1H), 4.85 (s, 1H), 4.82 (s, 1H), 4.64 (s, 1H), 4.59 (s, 1H), 4.12 (t, J = 4.8 Hz, 2H), 3.22-3.19 (m, 1H), 2.84 (s, 1.5H), 2.81 (s, 1.5H), 2.80-2.79 (m, 2H), 2.62 (s, 1.5H), 2.56 (s, 1.5H), 2.49 (s, 1H), 1.89-1.87 (m, 2H), 1.49-1.40 (m, 4H). |
| 240 | Parent | Yellow solid | Silicagel column chromatography (pet ether/ethyl acetate gradient) | Method A, Column Tempature: 50° C.; Rt: 3.92 min | 98.95 | 459 | 1H NMR (400 MHz, DMSO-d6): δ 9.5 (d, J = 8.4 Hz, 1H), 7.39-7.34 (m, 1H), 7.2 (dd, J = 11.4, 2.0 Hz, 1H), 6.92 (td, J = 11.8, 2 Hz, 1H), 6.6 (t, J = 6 Hz, 1H), 4.8 (d, J = 4.8 Hz, 2H), 4.57-4.52 (m, 2H), 4.35-31 (m, 2H), 4.21-4.16 (m, 1H), 2.6 (s, 1.5H), 2.54 (s, 1.5H). |
| 241 | Parent | Yellow solid | Silicagel column chromatography (pet ether/ethyl acetate gradient) | Method A, Column Tempature: 50° C.; Rt: 3.32 min | 97.47 | 445 | 1H NMR (400 MHz, DMSO-d6): δ 9.58 (d, J = 8.40 Hz, 1H), 8.62-8.58 (m, 1H), 7.40-7.35 (m, 1H), 7.18 (d, J = 11.6 Hz, 1H), 6.94-6.90 (m, 1H), 6.62-6.55 (m, 1H), 4.81 (s, 2H), 4.60-4.56 (m, 2H), 4.34-4.28 (m, 2H), 4.20-4.19 (m, 1H). |
| 244 | Parent | Off white solid | MD Auto Prep Method B | Method A, Column Tempature: 50° C.; Rt: 2.69 min | 97.6 | 430 | 1H NMR (400 MHz, DMSO-d6): δ 9.6 (d, J = 8.8 Hz, 1H), 8.63-8.59 (m, 1H), 7.4-7.35 (m 1H), 6.9 (t, J = 7.2 Hz, 1H), 6.8 (d J = 11.6 Hz 1H), 4.89-4.84 (m, 3H), 4.6 (d, J = 12. Hz 2H), 3.68-3.66 (m, 2H), 2.89-2.84 (m, 2H), 2.32-2.25 (m, 2H), 1.25.-1.18 (m, 2H), 0.79-0.72 (m, 3H). |
| 245 | Parent | Off white solid | Silicagel column chromatography | Method A, Column Tempature: 50° C.; Rt: 2.42 min | 99.61 | 416 | 1H NMR (400 MHz, DMSO-d6): δ 9.6 (d, J = 7.6 Hz, 1H), 8.64-8.6 (m, 1H), 7.39 (dt, J = 11.0, 3.2 Hz, 1H), 6.9 (t, J = 8.8 Hz, 1H), 6.8 (d J = 12 Hz, 1H), 4.91-4.86 (m, 3H) 4.6 (d, J = 12.0 Hz, 2H), 3.72-3.65 (m, 2H), 2.93-2.85 (m, 2H), 2.4-2.3 (m, 2H), 0.83-0.80 (m, 3H). |
| 246 | Parent | Off white solid | Silicagel column chromatography | Method A; Rt: 4.25 min | 98.87 | 514 | 1H NMR (400 MHz, DMSO-d6): δ 7.39 (s, 1H), 6.93-6.77 (m, 2H), 4.87-4.82 (m, 3H), 4.60-4.53 (m, 3H), 3.20-3.16 (m, 2H), 2.84 (s, 2H), 2.81 (s, 2H), 2.68-2.67 (m, 2H), 2.59-2.55 (m, 2H), 2.39-2.37 (m, 1H), 2.32-2.25 (m, 1H), 2.01-1.93 (m, 2H), 1.75-1.71 (m, 1H), 1.37-1.35 (m, 2H), 0.82-0.77 (m, 2H), 0.68-0.53 (m, 1H). |
| 247 | Parent | White solid | Prep-HPLC Method D | Method A; Rt: 3.74 min | 98.77 | 516 | 1H NMR (400 MHz, DMSO-d6): δ 8.24-8.22 (m, 1H), 7.40-7.35 (m, 1H), 6.89 (dt, J = 8.4, 2.4 Hz, 1H), 6.79 (dd, J = 11.2, 2.0 Hz, 1H), 4.91-4.90 (m, 1H), 4.86-4.83 (m, 2H), 4.58 (s, 1H), 4.52 (s, 1H), 4.25-4.18 (m, 1H), 3.50-3.46 (m, 2H), 3.18 (s, 3H), 2.84 (s, 1.5H), 2.81 (s, 1.5H), 2.62 (s, 1.5H), 2.55 (s, 1.5H), 2.36-2.32 (m, 4H), 2.30-2.26 (m, 2H). |
| 248 | Parent | White solid | Prep-HPLC Method D: 2nd eluting compound | Method A; Rt: 4.14 min | 99.33 | 500 | 1H NMR (400 MHz, DMSO-d6): δ 8.07 (t, J = 6.0 Hz, 1H), 7.40-7.35 (m, 1H), 6.90-6.85 (m, 1H), 6.80-6.77 (m, 1H), 4.91-4.90 (m, 1H), 4.85 (s, 1H), 4.82 (s, 1H), 4.57 (s, 1H), 4.51 (s, 1H), 4.17-4.46 (m, 1H), 2.84 (s, 1.5H), 2.80 (s, 1.5H), 2.61 (s, 1.5H), 2.60 (s, 1.5H), 2.36-2.25 (m, 5H), 0.98-0.94 (m, 6H). |
| 249 | Parent | Off white solid | Prep-HPLC Method D: 2nd eluting compound | Method A; Rt: 4.25 min | 96.31 | 514 | 1H NMR (400 MHz, DMSO-d6): δ 7.37 (s, 1H), 6.92-6.89 (m, 2H), 4.84-4.82 (m, 2H), 4.59-4.55 (m, 3H), 4.21 (s, 0.5H), 4.01 (s, 0.5H), 3.19-3.07 (m, 2H), 2.88-2.81 (m, 5H), 2.67-2.66 (m, 1H), 2.55-2.52 (m, 2H), 2.02-1.92 (m, 4H), 1.33-1.23 (m, 2H), 0.91-0.89 (m, 2H), 0.67-0.59 (m, 3H). |
| 250 | Parent | Yellow solid | MD Auto Prep Method B | Method A, Column Temparature: 50° C.; Rt: 13.00 min | 99.04 | 458 | 1H NMR (400 MHz, DMSO-d6): δ 9.61-9.58 (m, 1H), 7.40-7.35 (m, 1H), 7.39-7.34 (m, 1H), 7.13-7.09 (m, 1H), 6.88-6.83 (m, 1H), 4.83 (s, 2H), 4.67 (s, 1H), 4.61 (s, 1H), 4.59 (s, 1H), 2.12-2.10 (m, 1H), 1.90-1.89 (m, 8H), 1.52-1.46 (m, 2H), 1.37-1.31 (m, 4H). |

| No | Isolated Form | Appearance | Purification mode | HPLC Method; Rt (min) | Purity | Mass found [M⁺] | ¹H NMR |
|---|---|---|---|---|---|---|---|
| 251 | Parent | Pale yellow solid | Silicagel column chromatography | Method A, Column Temparature: 50° C.; Rt: 3.3 min | 99.64 | 486 | ¹H NMR (400 MHz, DMSO-$d_6$): δ 9.62-9.59 (m, 1H), 8.64-8.60 (m, 1H), 7.39-7.34 (m, 1H), 7.14-7.09 (m, 1H), 6.88-6.84 (m, 1H), 4.83 (s, 2H), 4.70 (s, 1H), 4.62 (s, 1H), 4.60 (s, 1H), 2.59-2.58 (m, 1H), 2.05-2.02 (m, 2H), 1.91-1.88 (m, 5H), 1.52-1.48 (m, 2H), 1.35-1.32 (m, 4H), 1.14-1.12 (m, 2H), 0.64 (d, J = 6.4 Hz, 3H). |
| 254 | Parent | Pale yellow solid | Silicagel column chromatography | Method A, Column Temparature: 50° C.; Rt: 3.43 min | 98.51 | 486 | ¹H NMR (400 MHz, DMSO-$d_6$): δ 9.62-9.58 (m, 1H), 8.64-8.60 (m, 1H), 7.41-7.37 (m, 1H), 7.16-7.14 (m, 1H), 6.89-6.85 (m, 1H), 4.90 (s, 2H), 4.75 (s, 1H), 4.61 (s, 1H), 4.57 (s, 1H), 4.29-4.24 (m, 0.5H), 3.61-3.60 (m, 0.5H), 2.52-2.51 (m, 2H), 2.26-2.24 (m, 1H), 1.96-1.91 (m, 3H), 1.88-1.87 (m, 2H), 1.65-1.53 (m, 4H), 1.33-1.32 (m, 2H), 1.17-1.16 (m, 1H). |
| 255 | Parent | Pale yellow solid | Prep-HPLC Method A | Method A; Rt: 3.29 min | 99.22 | 488 | ¹H NMR (400 MHz, DMSO-$d_6$): δ 7.39-7.34 (m, 1H), 6.89-6.84 (m, 1H), 6.78-6.76 (m, 1H), 4.89 (s, 1H), 4.85 (s, 1H), 4.82 (s, 1H), 4.58 (s, 1H), 4.53 (s, 1H), 3.36-3.35 (m, 1H), 3.31-3.29 (m, 3H), 3.20-3.16 (m, 4H), 2.85 (s, 1.5H), 2.81 (s, 1.5H), 2.62 (s, 1.4H), 2.56 (s, 1.6H), 2.19-2.12 (m, 4H). |
| 256 | Parent | White solid | Silicagel column chromatography (pet ether/ethyl acetate gradient) | Method A; Rt: 3.81 min | 98.33 | 437 | ¹H NMR (400 MHz, DMSO-$d_6$): δ 7.39-7.34 (m, 1H), 7.11 (d, J = 11.2 Hz, 1H), 6.91 (t, J = 8.4 Hz, 1H), 5.43-5.40 (m, 1H), 4.82 (d, J = 11.2 Hz, 2H), 4.59-4.54 (m, 2H), 4.42-4.23 (m, 2H), 4.18-4.08 (m, 2H), 4.02-3.92 (m, 1H), 2.85 (s, 1.5H), 2.81 (s, 1.5H), 2.62 (s, 1.5H), 2.56 (s, 1.5H). |
| 257 | Parent | Brown solid | Silicagel column chromatography | Method A, Column Temparature: 50° C.; Rt: 2.6 min | 98.59 | 515 | ¹H NMR (400 MHz, DMSO-$d_6$): δ 9.59 (dd, J = 11.0, 2.4 Hz, 1H), 8.64-8.59 (m, 1H), 7.39-7.34 (m, 1H), 7.15 (d, J = 11.20 Hz, 1H), 6.90-6.87 (m, 1H), 4.91-4.85 (m, 3H), 4.60-4.57 (m, 3H), 4.01-3.93 (m, 1H), 2.81-2.74 (m, 1H), 2.68-2.54 (m, 3H), 2.43-2.40 (m, 4H), 2.38-2.22 (m, 4H), 1.85-1.84 (m, 2H), 1.69-1.59 (m, 2H). |
| 258 | Parent | Brown solid | Silicagel column chromatography | Method A; Rt: 3.2 min | 98.17 | 486 | ¹H NMR (400 MHz, DMSO-$d_6$): δ 7.39-7.34 (m, 1H), 6.90-6.85 (m, 1H), 6.77 (d, J = 11.2 Hz, 1H), 4.93-4.80 (m, 3H), 4.57-4.44 (m, 4H), 4.30-4.22 (m, 2H), 3.81-3.71 (m, 1H), 3.28-3.22 (m, 1H), 2.85 (s, 1.5H), 2.82 (s, 1.5H), 2.81-2.81 (m, 1H), 2.63 (s, 1.5H), 2.57 (s, 1.5H), 2.51-2.51 (m, 1H), 2.18-2.10 (m, 3H). |
| 259 | Parent | Off white solid | MD Auto Prep Method B | Method A; Rt: 3.22 min | 98.37 | 500 | ¹H NMR (400 MHz, DMSO-$d_6$): δ 7.39-7.35 (m, 1H), 6.90-6.76 (m, 2H), 4.85-4.82 (m, 3H), 4.58-4.54 (m, 2H), 3.65-3.55 (m, 3H), 3.26-3.18 (m, 3H), 2.85 (s, 1.5H), 2.81 (s, 1.5H), 2.62 (s, 1H), 2.56 (s, 2H), 2.45-2.10 (m, 4H), 1.90-1.67 (m, 2H), 1.62-1.40 (m, 1H). |
| 260 | Parent | Yellow solid | Silicagel column chromatography | Method A; Rt: 3.79 min | 98.27 | 472 | ¹H NMR (400 MHz, DMSO-$d_6$): δ 8.1 (br s, 1H), 7.38-7.33 (m, 1H), 7.12 (d, J = 10.8 Hz, 1H), 6.88 (t, J = 8.4 Hz, 1H), 4.85 (s, 1H), 4.81 (s, 1H), 4.56 (s, 1H), 4.52 (s, 1H), 4.10 (d, J = 4.8 Hz, 2H), 2.85 (s, 1.5H), 2.81 (s, 1.5H), 2.63 (s, 1.5H), 2.56 (s, 1.5H), 2.51-2.50 (m, 2H), 1.31-1.24 (m, 1H), 0.50-0.47 (m, 2H), 0.39 (d, J = 4.00 Hz, 1H), 0.32 (d, J = 5.20 Hz, 1H). |
| 261 | Parent | White solid | Silicagel column chromatography | Method A; Rt: 3.89 min | 96.62 | 482 | ¹H NMR (400 MHz, DMSO-$d_6$): δ 8.84-8.82 (m, 1H), 7.39-7.34 (m, 1H), 7.13-7.10 (m, 1H), 6.92-6.87 (m, 1H), 6.13-5.82 (m, 1H), 4.82 (s, 1H), 4.79 (s, 1H), 4.55 (s, 1H), 4.50 (s, 1H), 4.18-4.14 (m, 2H), 3.47-3.46 (m, 2H), 2.85 (s, 1.5H), 2.82 (s, 1.5H), 2.63 (s, 1.5H), 2.56 (s, 1.5H). |
| 264 | Parent | Off white solid | Prep-HPLC Method D | Method A; Rt: 4.3 min | 97.8 | 487 | ¹H NMR (400 MHz, DMSO-$d_6$): δ 7.35-7.29 (m, 2H), 7.23-7.15 (m, 1H), 7.11-7.05 (m, 2H), 6.86 (dt, J = 8.4, 2.4 Hz, 1H), 5.58-5.55 (m, 1H), 4.92-4.88 (m, 1H), 4.80 (s, 1H), 4.78 (s, 1H), 4.47-4.30 (m, 2H), 4.19 (s, 1H), 4.17 (s, 1H), 2.86 (s, 1.6H), 2.82 (s, 1.4H), 2.63 (s, 1.4H), 2.57 (s, 1.6H). |
| 265 | Parent | White solid | Prep-HPLC Method C | Method A; Rt: 3.21 min | 99.18 | 430 | ¹H NMR (400 MHz, DMSO-$d_6$): δ 7.38-7.33 (m, 1H), 7.1 (d, J = 11.6 Hz, 1H), 6.9 (t, J = 8.8 Hz, 1H), 4.831-4.8 (m, 2H), 4.541-4.493 (m, 2H), 4.2 (d, J = 6.4 Hz, 2H), 3.38-3.36 (m, 1H), 3.21-3.19 (m 2H), 2.92-2.86 (m, 1H), 2.84 (s, 1.5H), 2.81 (s, 1.5H), 2.62 (s, 1H), 2.56 (s, 2H), 2.507-2.503 (m, 2H). |
| 268 | Parent | Off white solid | Prep-HPLC Method D: 2nd | Method A; Rt: 3.38 min | 99.42 | 490 | ¹H NMR (400 MHz, DMSO-$d_6$): δ 7.40-7.35 (m, 1H), 6.90-6.85 (m, 1H), 6.81-6.78 (m, 1H), 4.85-4.82 (m, |

| No | Isolated Form | Appearance | Purification mode | HPLC Method; Rt (min) | Purity | Mass found [M+] | 1H NMR |
|---|---|---|---|---|---|---|---|
| | | | eluting compound | | | | 3H), 4.58 (s, 1H), 4.54 (s, 1H), 4.52-4.47 (m, 1H), 4.38-4.35 (m, 1H), 3.00-2.94 (m, 1H), 2.85 (s, 1.5H), 2.81 (s, 1.5H), 2.62 (s, 1.5H), 2.56 (s, 1.5H), 2.41-2.39 (m, 2H), 2.33-2.27 (m, 2H), 2.07-2.04 (m, 5H). |
| 269 | Parent | White solid | Prep-HPLC Method D | Method A; Rt: 3.22 min | 99.72 | 444 | 1H NMR (400 MHz, DMSO-d6): δ 7.36-7.33 (m, 1H), 7.09-7.06 (m, 1H), 6.9 (dt, J = 8.4, 2.4 Hz, 1H), 4.8 (d, J = 10.4 Hz, 2H), 4.57-4.52 (m, 2H), 4.1 (d, J = 5.6 Hz, 2H), 3.12-3.09 (m, 2H), 2.84 (s, 1H), 2.81 (s, 2H), 2.77-2.76 (m, 2H), 2.62 (s, 2H), 2.56 (s, 2H), 1.97 (s, 3H). |
| 272 | Parent | White solid | Silicagel column chromatography | Method A; Rt: 3.5 min | 99.87 | 472 | 1H NMR (400 MHz, DMSO-d6): δ 7.40-7.35 (m, 1H), 7.13-7.11 (m, 1H), 6.94-6.87 (m, 1H), 4.87-4.84 (m, 2H), 4.64-4.47 (m, 3H), 4.35-4.29 (m, 1H), 4.09-4.06 (m, 1H), 3.64-3.52 (m, 1H), 2.85 (s, 1.5H), 2.80 (s, 1.5H), 2.62 (s, 1.5H), 2.56 (s, 1.5H), 2.33-2.19 (m, 1H), 2.03-1.90 (m, 1H), 1.68 (d, J = 5.2 Hz, 1H), 1.32-1.24 (m, 2H). |
| 273 | Parent | White solid | MD Auto Prep Method B | Method A; Rt: 3.19 min | 98.3 | 444 | 1H NMR (400 MHz, DMSO-d6): δ 7.37-7.32 (m, 1H), 7.07-7.04 (m, 1H), 6.88 (td, J = 8.8, 2.4 Hz, 1H), 4.79 (s, 1H), 4.77 (s, 1H), 4.58-4.53 (m, 2H), 4.14-4.10 (m, 1H), 3.99-3.55 (m, 1H), 3.17-3.14 (m, 1H), 3.12-3.06 (m, 1H), 2.84 (s, 1.5H), 2.81 (s, 1.5H), 2.67-2.63 (m, 1H), 2.61 (s, 1.5H), 2.58 (s, 1.5H), 2.01 (s, 3H), 1.84-1.80 (m, 2H). |
| 274 | Parent | Pale yellow solid | Silicagel column chromatography (2.5% methanol in DCM) | Method A; Rt: 3.09 min | 98.66 | 482 | 1H NMR (400 MHz, DMSO-d6): δ 8.48 (s, 1H), 8.03-7.95 (m, 1H), 7.70-7.67 (m, 1H), 7.33-7.27 (m, 1H), 7.10 (d, J = 11.6 Hz, 1H), 7.05-6.96 (m, 1H), 6.90-6.82 (m, 1H), 5.77-5.75 (m, 1H), 4.91 (t, J = 4.4 Hz, 1H), 4.76 (d, J = 6.0 Hz, 2H), 4.31-4.17 (m, 4H), 2.88 (s, 1.6H), 2.83 (s, 1.4H), 2.65 (s, 1.4H), 2.57 (s, 1.6H). |
| 275 | Parent | White solid | MD Auto Prep Method B | Method A; Rt: 3.08 min | 95.31 | 430 | 1H NMR (400 MHz, DMSO-d6): δ 7.43-7.36 (m, 1H), 6.9 (t, J = 8.4 Hz, 1H), 6.8 (d, J = 11.2 Hz, 1H), 4.95-4.9 (m, 1H), 4.8 (d, J = 11.2 Hz, 2H), 4.6-4.54 (m, 2H), 3.9-3.83 (m, 2H), 3.2-3.1 (m, 2H), 2.84 (s, 2H), 2.80 (s, 1H), 2.66 (s, 2H), 2.55 (s, 1H), 2.34 (s, 3H). |
| 276 | Parent | White solid | MD Auto Prep Method B | Method A, Column Temperature: 50° C.; Rt: 3.11 min | 99.79 | 488 | 1H NMR (400 MHz, DMSO-d6): δ 7.4-7.32 (m, 1H), 6.89-6.87 (m, 1H), 6.8 (d, J = 10.8 Hz, 1H), 4.931-4.89 (m, 1H), 4.85-4.82 (m, 2H), 4.58-4.53 (m, 2H), 4.45-4.35 (m, 1H), 3.6-3.5 (m, 2H), 3.3-3.1(m, 2H), 2.84 (s, 2H), 2.81 (s, 1H), 2.8-2.7 (m, 1H), 2.67 (s, 1H), 2.56 (s, 2H), 2.35-2.1(m, 5H), 1.72-1.61(m, 1H), 1.1-.91(m, 2H). |
| 277 | Parent | Off white solid | Silicagel column chromatography (pet ether/ethyl acetate gradient) | Method A; Rt: 4.75 min | 99.77 | 403 | 1HNMR (400 MHz, DMSO-d6): δ 7.34 (t, J = 4.4 Hz, 1H), 7.07-7.05 (d, J = 10.4 Hz, 1H), 6.87 (t, J = 8.4 Hz, 1H), 4.83-4.80 (d, J = 11.2 Hz, 2H), 4.56-4.51 (m, 2H), 4.03 (t, J = 6.4 Hz, 2H), 2.85 (s, 2H), 2.81 (s, 1H), 2.62 (s, 2H), 2.56 (s, 2H), 1.64-1.62 (d, J = 7.2 Hz, 1H), 0.85-0.80 (q, J = 4.0 Hz, 3H). |
| 278 | Parent | White solid | Silicagel column chromatography | Method A; Rt: 4.23 min | 99.49 | 359 | 1H NMR (400 MHz, DMSO-d6): δ 7.45-7.43 (m, 1H), 7.2 (d, J = 9.2 Hz 1H), 7.1(t, J = 8.4 Hz, 1H), 4.9 (d, J = 11.2, 2H), 4.52-4.46 (m, 2H), 2.85 (s, 2H), 2.81 (s, 1H), 2.62 (s, 2H), 2.55 (s, 1H), 2.29(s, 3H). |
| 279 | Parent | White solid | Silicagel column chromatography | Method A, Column Temperature: 50° C.; Rt: 2.68 min | 97 | 416 | 1H NMR (400 MHz, DMSO-d6): δ 9.5 (d, J = 8.8 Hz, 1H), 7.4 (d, J = 6.4 Hz, 1H), 6.9 (t, J = 8.4 Hz, 1H), 6.8 (d, J = 10.8 Hz, 1H), 4.9-4.86 (m, 1H), 4.8(d, J = 6.4 Hz, 2H), 4.59-4.54 (m, 2H), 3.75-3.68 (m, 2H), 3-2.93 (m, 2H), 2.61 (s, 1H), 2.55 (s, 2H), 2.23 (s, 3H). |
| 280 | Parent | Pale yellow solid | Silicagel column chromatography | Method A; Rt: 4.98 min | 98.9 | 483 | 1H NMR (400 MHz, DMSO-d6): δ 7.29-7.26 (m, 1H), 7.17-7.13 (m, 2H), 7.07-7.03 (m, 1H), 6.87-6.82 (m, 1H), 6.60-6.56 (m, 1H), 6.53-6.49 (m, 1H), 4.74 (s, 1H), 4.71 (s, 1H), 4.28-4.26 (m, 2H), 3.94-3.91 (m, 2H), 2.93-2.92 (m, 2H), 2.88 (s, 1.6H), 2.81 (s, 1.4H), 2.65 (s, 1.5H), 2.57 (s, 1.5H). |
| 281 | Parent | White solid | Silicagel column chromatography | Method A; Rt: 4.07 min | 96.89 | 375 | 1H NMR (400 MHz, DMSO-d6): δ 7.37-7.31 (m, 1H), 6.77-6.69 (m, 2H), 5.02-5.01 (d, J = 4.0 Hz, 2H), 4.65-4.63 (d, J = 8.8 Hz, 2H), 3.86, 3.85 (d, J = 3.6 Hz, 3H), 2.92 (s, 1.7H), 2.89-2.87 (m, 1.3H), 2.70 (s, 1.3H), 2.64 (s, 1.7H). |

Example 282

M1 PAM Assay

M1-CHO cells are plated in culture medium (HAM's-F12, P/S, 10% FCS) on the day before the experiment with 10 000 cells/well in a 384 well plate (3750 Corning White 384 w plate with lid). On the day of experiment, cells are washed with PBS and IPone buffer is added (Glucose 5.5 mM, NaCl 146 mM, $MgCl_2$ 0.5 mM, HEPES 10 mM, LiCl 50 mM, $CaCl_2$ 1 mM, KCl 4.2 mM). Then diluted compounds (0.6% DMSO final concentration) are added together with $EC_{20}$ of acetylcholine and incubated with the cells for 30 min at 37° C., 5% CO2. The intracellular concentration of IP1 is then measured using the IP-One HTRF assay from Cisbio (cat.no 621PAPEJ).

CHO-K1 cells stably transfected with human muscarinic acetylcholine M1 receptor are cultured in Ham's F12 medium containing 10% heat inactivated fetal calf serum, 2 mM L-glutamine and Penicillin-Streptomycin grown in a humidified atmosphere at 5% $CO_2$/95% air at 37° C. Cells are seeded in white 384 well plates (Corning cat.no 3750) at a density at 10,000 cells/well and incubated in medium overnight. Prior to the treatment with compounds, medium is discarded and cells are washed twice with PBS and IP-One buffer (Glucose 5.5 mM, NaCl 146 mM, $MgCl_2$ 0.5 mM, HEPES 10 mM, LiCl 50 mM, $CaCl_2$ 1 mM, KCl 4.2 mM) is added. Various concentrations of compounds (0.6% DMSO final concentration) are added in absence or prescence of 25 nM of acetylcholine ($EC_{20}$) and incubated for 30 minutes. $IP_1$ levels are measured using the IP-One HTRF® assay (Cisbio cat.no 621PAPEJ).

Activity range of the compounds of Formula (I) is the following:

| Ex | Structure | M1 PAM EC50 (nM) |
|---|---|---|
| 1 | 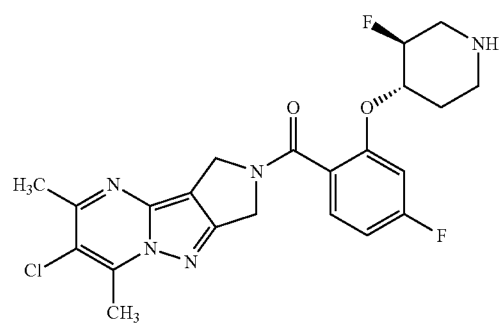 [SMILES: Cc1nc2c3c(nn2c(C)c1Cl)CN(C(=O)c1ccc(F)cc1O[C@H]1CCNC[C@@H]1F)C3] | *** |
| 2 | 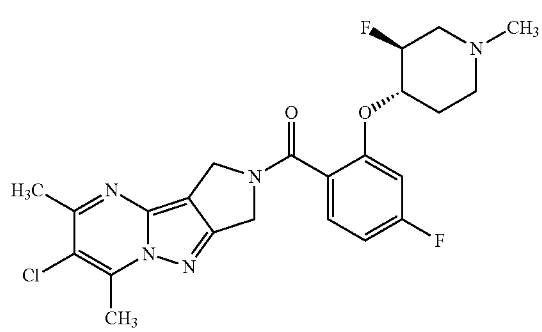 | ** |
| 3 | 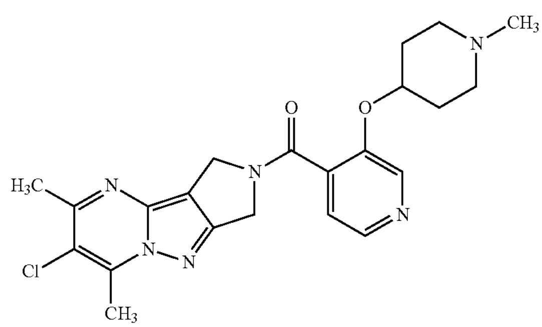 | * |

-continued

| Ex | Structure | M1 PAM EC50 (nM) |
|---|---|---|
| 4 | 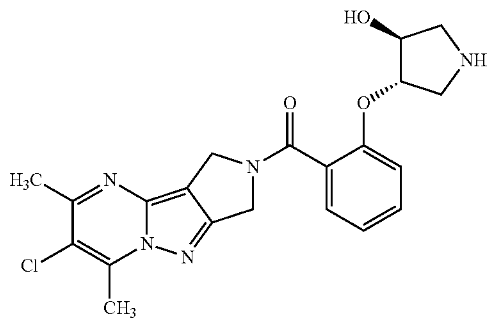 [SMILES: Cc1nc2c3c(nn2c(C)c1Cl)CN(C(=O)c1ccccc1O[C@H]1CNC[C@@H]1O)C3] | ** |
| 5 | 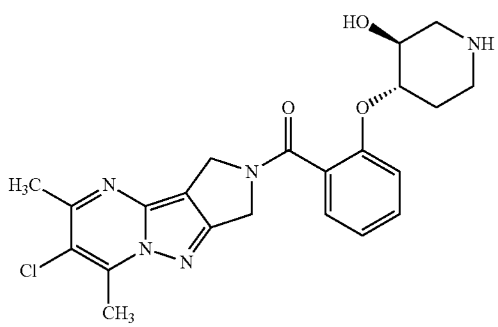 [SMILES: Cc1nc2c3c(nn2c(C)c1Cl)CN(C(=O)c1ccccc1O[C@H]1CCNC[C@@H]1O)C3] | ** |
| 6 | 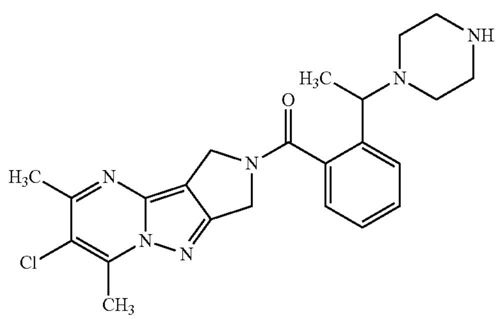 [SMILES: Cc1nc2c3c(nn2c(C)c1Cl)CN(C(=O)c1ccccc1C(C)N1CCNCC1)C3] | * |
| 7 | 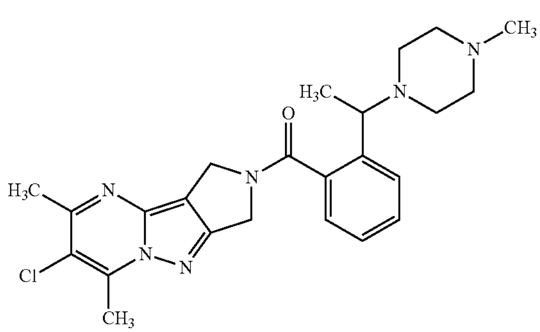 | * |

-continued

| Ex | Structure | M1 PAM EC50 (nM) |
|---|---|---|
| 8 | 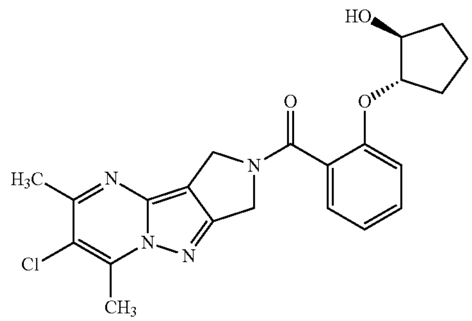 [SMILES: Cc1nc2c3c(nn2c(C)c1Cl)CN(C(=O)c1ccccc1O[C@H]1CCC[C@@H]1O)C3] | ** |
| 9 | | * |
| 10 | | ** |
| 11 | 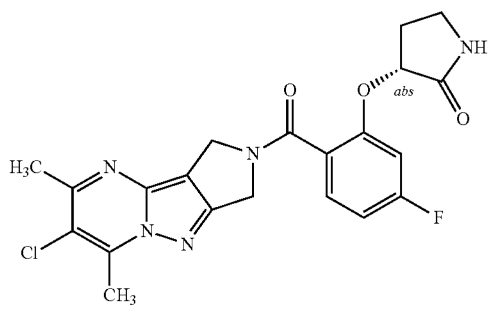 [SMILES: Cc1nc2c3c(nn2c(C)c1Cl)CN(C(=O)c1ccc(F)cc1O[C@@H]1CCNC1=O)C3] | ** |
| 12 | 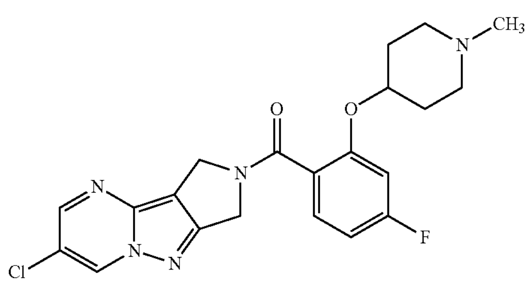 [SMILES: CN1CCC(Oc2cc(F)ccc2C(=O)N2Cc3nn4cc(Cl)cnc4c3C2)CC1] | ** |
| 13 | 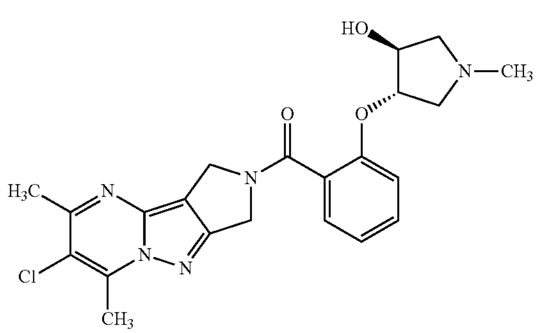 | * |

| Ex | Structure | M1 PAM EC50 (nM) |
|---|---|---|
| 14 | 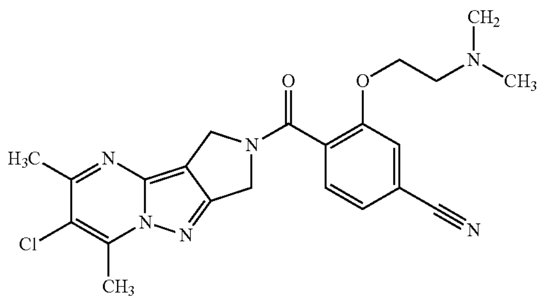 | ** |
| 15 | 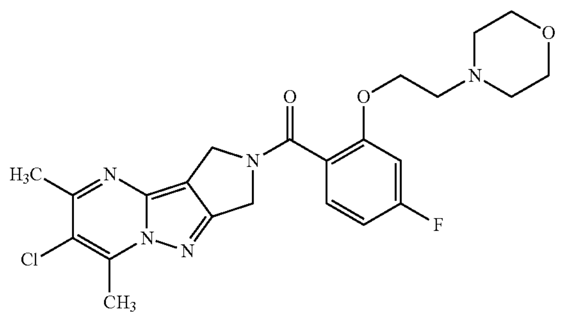 | * |
| 16 | 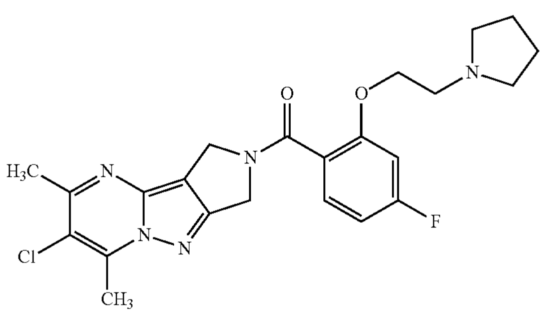 [SMILES: Cc1nc2c3c(nn2c(C)c1Cl)CN(C(=O)c1ccc(F)cc1OCCN1CCCC1)C3] | *** |
| 17 | 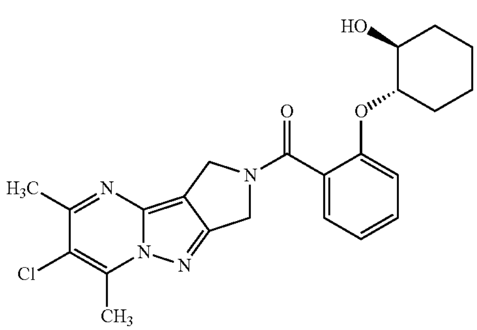 [SMILES: Cc1nc2c3c(nn2c(C)c1Cl)CN(C(=O)c1ccccc1O[C@H]1CCCC[C@@H]1O)C3] | * |

| Ex | Structure | M1 PAM EC50 (nM) |
|---|---|---|
| 18 | 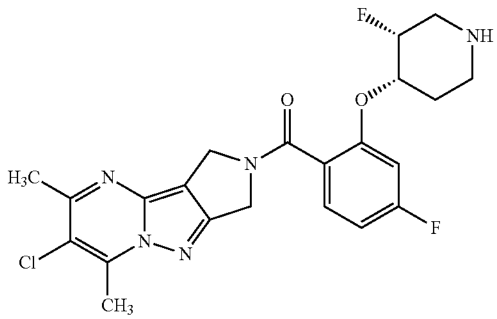 [SMILES: Cc1nc2c3c(nn2c(C)c1Cl)CN(C(=O)c1ccc(F)cc1O[C@H]1CCNC[C@H]1F)C3] | ** |
| 19 | 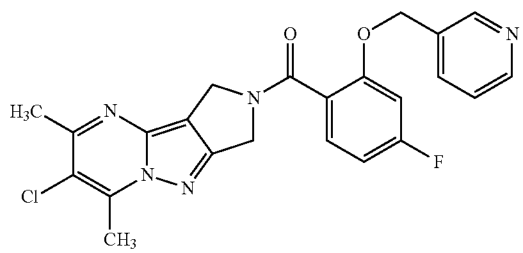 [SMILES: Cc1nc2c3c(nn2c(C)c1Cl)CN(C(=O)c1ccc(F)cc1OCc1cccnc1)C3] | * |
| 20 | 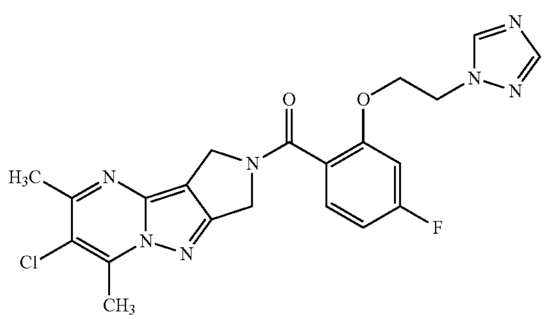 [SMILES: Cc1nc2c3c(nn2c(C)c1Cl)CN(C(=O)c1ccc(F)cc1OCCn1cncn1)C3] | ** |
| 21 | 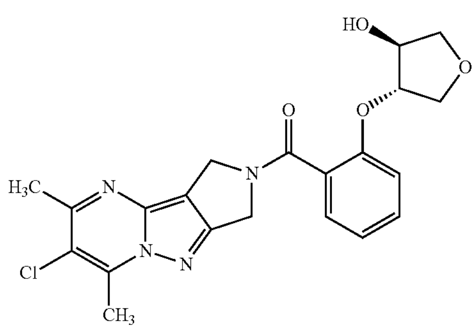 [SMILES: Cc1nc2c3c(nn2c(C)c1Cl)CN(C(=O)c1ccccc1O[C@H]1COC[C@@H]1O)C3] | * |
| 22 | | * |
| 23 | 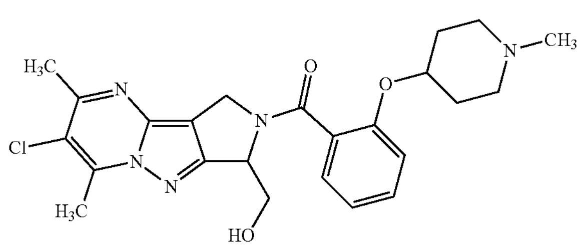 [SMILES: Cc1nc2c3c(nn2c(C)c1Cl)C(CO)N(C(=O)c1ccccc1OC1CCN(C)CC1)C3] | * |

-continued

| Ex | Structure | M1 PAM EC50 (nM) |
|---|---|---|
| 24 | 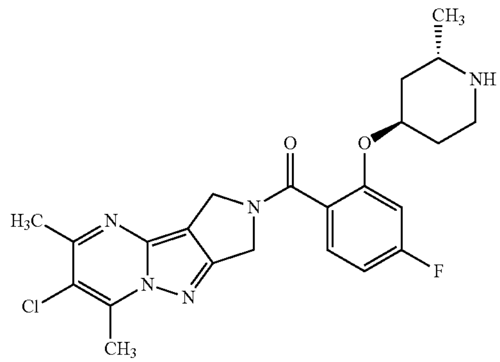 | ** |
| 25 | 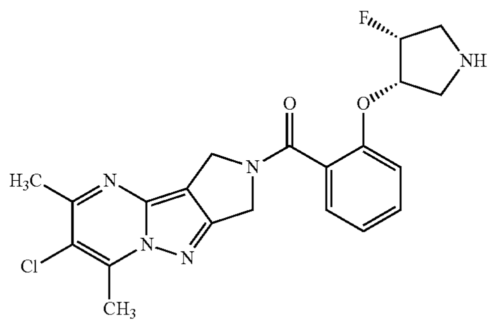 [SMILES: Cc1nc2c3c(nn2c(C)c1Cl)CN(C(=O)c1ccccc1O[C@H]1CNC[C@H]1F)C3] | ** |
| 26 | 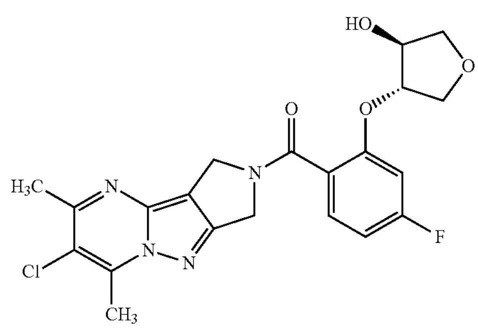 [SMILES: Cc1nc2c3c(nn2c(C)c1Cl)CN(C(=O)c1ccc(F)cc1O[C@H]1COC[C@@H]1O)C3] | * |
| 27 | 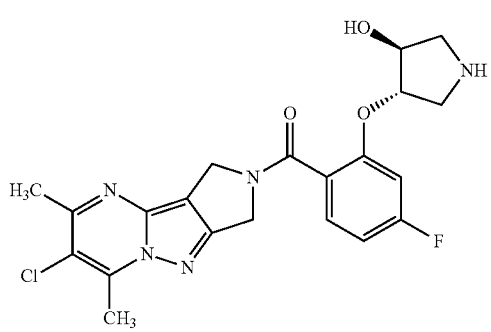 [SMILES: Cc1nc2c3c(nn2c(C)c1Cl)CN(C(=O)c1ccc(F)cc1O[C@H]1CNC[C@@H]1O)C3] | ** |

-continued
| Ex | Structure | M1 PAM EC50 (nM) |
|---|---|---|
| 28 | 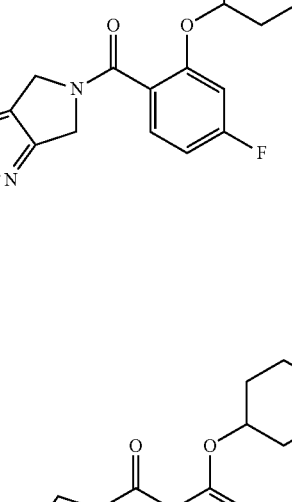 | * |
| 29 | 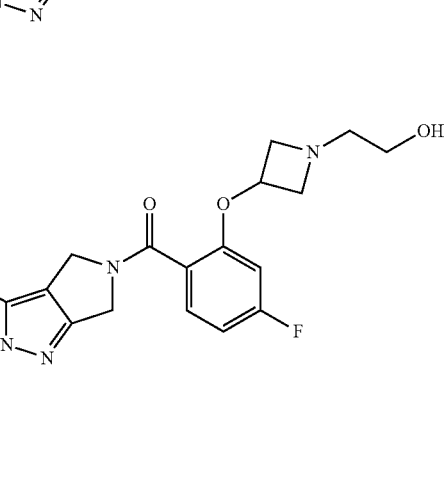 | *** |
| 30 | 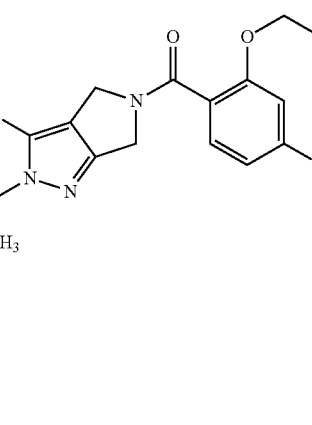 | ** |
| 31 | 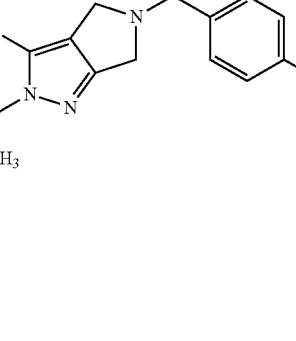 | ** |

| Ex | Structure | M1 PAM EC50 (nM) |
|---|---|---|
| 32 | 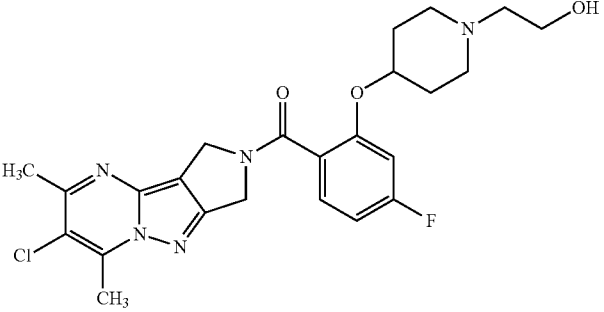 | *** |
| 33 | 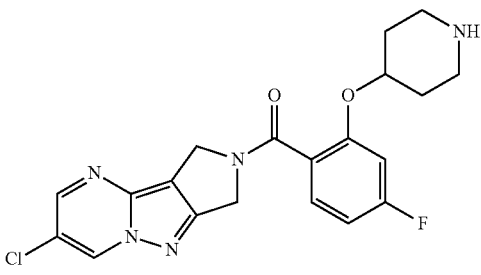 [SMILES: O=C(c1ccc(F)cc1OC1CCNCC1)N1Cc2nn3cc(Cl)cnc3c2C1] | ** |
| 34 | 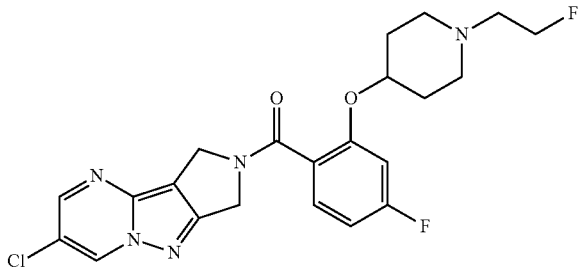 [SMILES: O=C(c1ccc(F)cc1OC1CCN(CCF)CC1)N1Cc2nn3cc(Cl)cnc3c2C1] | ** |
| 35 | 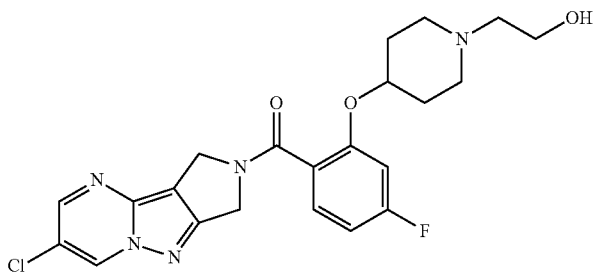 [SMILES: O=C(c1ccc(F)cc1OC1CCN(CCO)CC1)N1Cc2nn3cc(Cl)cnc3c2C1] | ** |
| 36 | 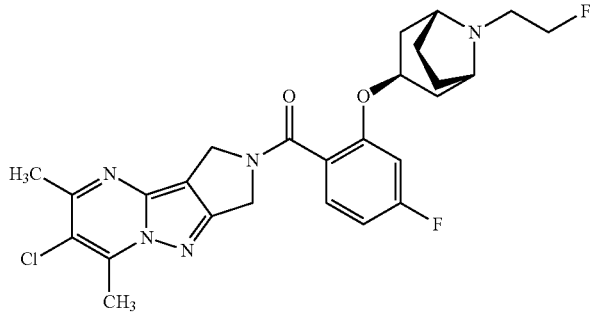 | *** |

| Ex | Structure | M1 PAM EC50 (nM) |
|---|---|---|
| 37 | 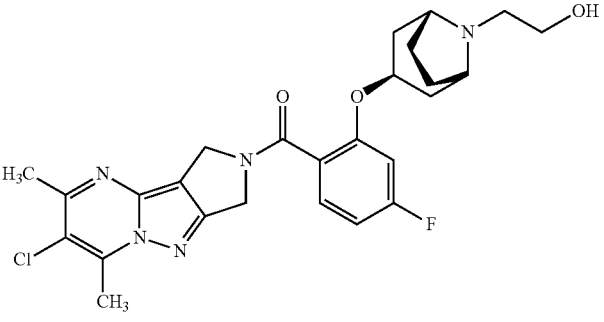 | *** |
| 38 | 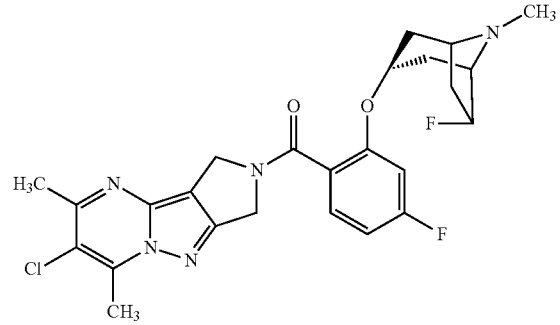 [SMILES: Cc1nc2c3c(nn2c(C)c1Cl)CN(C(=O)c1ccc(F)cc1O[C@H]1CC2CC(F)C(C1)N2C)C3] | *** |
| 39 | 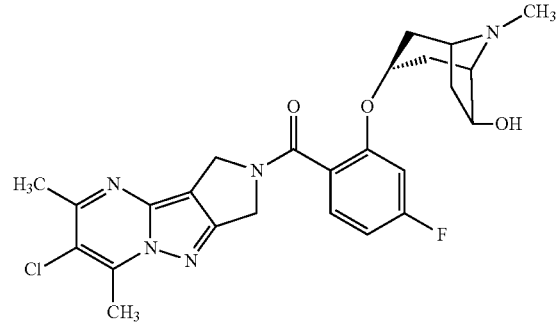 [SMILES: Cc1nc2c3c(nn2c(C)c1Cl)CN(C(=O)c1ccc(F)cc1O[C@H]1CC2CC(O)C(C1)N2C)C3] | *** |
| 40 | 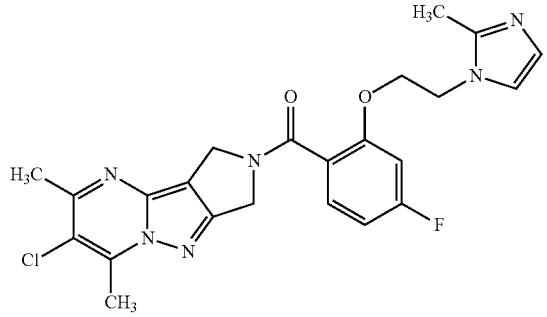 [SMILES: Cc1nc2c3c(nn2c(C)c1Cl)CN(C(=O)c1ccc(F)cc1OCCn1ccnc1C)C3] | * |

-continued
| Ex | Structure | M1 PAM EC50 (nM) |
|---|---|---|
| 41 | | *** |
| 42 | 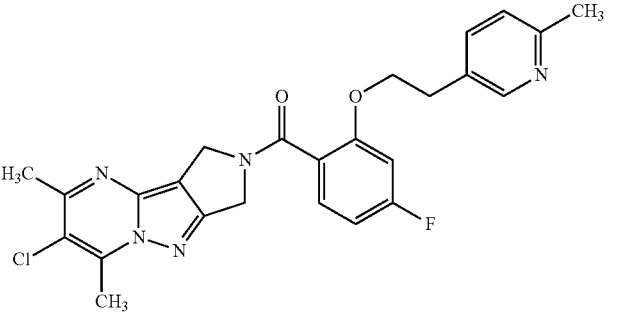 [SMILES: Cc1ccc(CCOc2cc(F)ccc2C(=O)N2Cc3nn4c(C)c(Cl)c(C)nc4c3C2)cn1] | ** |
| 43 | 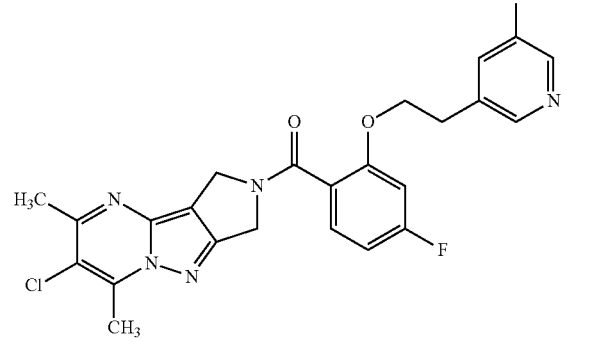 | *** |
| 44 | 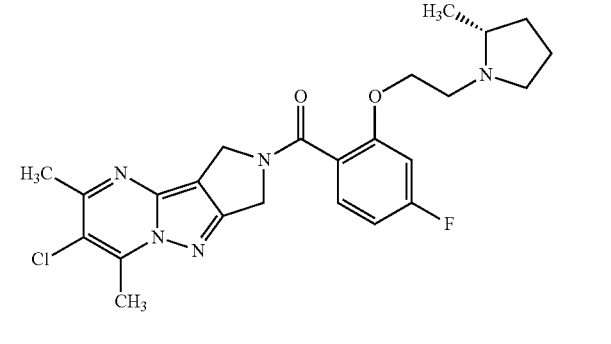 | * |
| 45 | 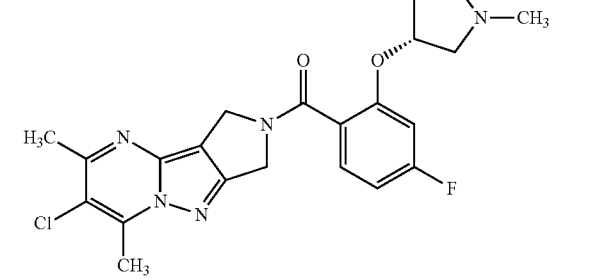 | ** |

-continued

| Ex | Structure | M1 PAM EC50 (nM) |
|---|---|---|
| 46 | 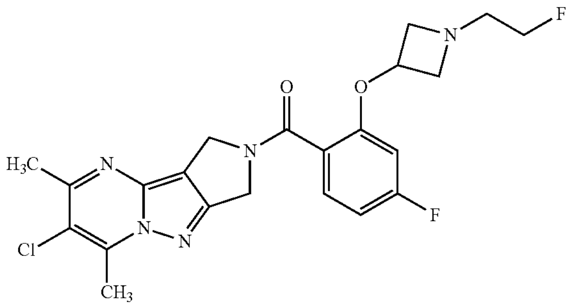 [SMILES: Cc1nc2c3c(nn2c(C)c1Cl)CN(C(=O)c1ccc(F)cc1OC1CN(CCF)C1)C3] | * |
| 47 | 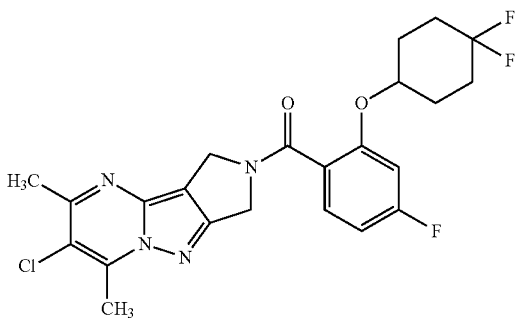 | * |
| 48 | 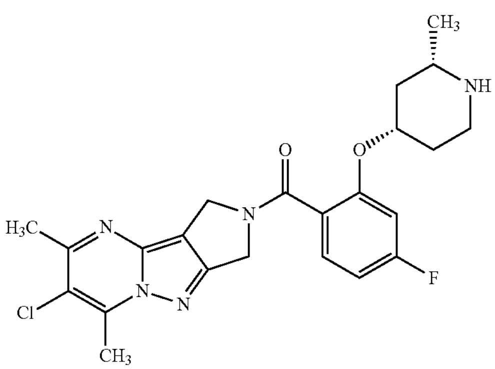 [SMILES: Cc1nc2c3c(nn2c(C)c1Cl)CN(C(=O)c1ccc(F)cc1O[C@H]1CCN[C@@H](C)C1)C3] | ** |
| 49 | | ** |
| 50 | 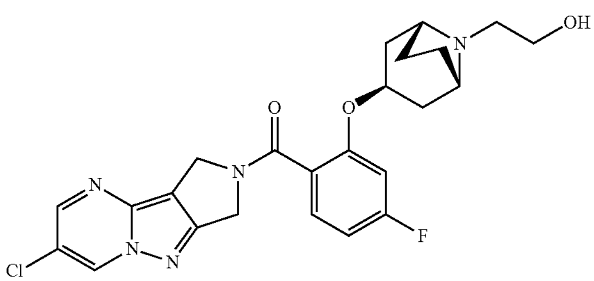 [SMILES: O=C(c1ccc(F)cc1O[C@H]1C[C@H]2CC[C@@H](C1)N2CCO)N1Cc2nn3cc(Cl)cnc3c2C1] | ** |

-continued

| Ex | Structure | M1 PAM EC50 (nM) |
|---|---|---|
| 51 | 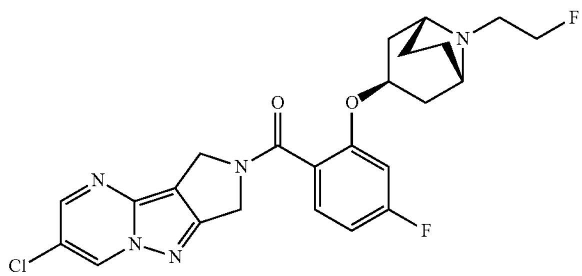 [SMILES: O=C(c1ccc(F)cc1O[C@H]1C[C@H]2CC[C@@H](C1)N2CCF)N1Cc2nn3cc(Cl)cnc3c2C1] | *** |
| 52 | 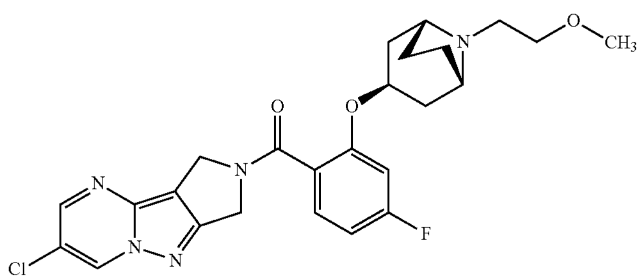 [SMILES: COCCN1[C@@H]2CC[C@H]1C[C@@H](Oc1cc(F)ccc1C(=O)N1Cc3nn4cc(Cl)cnc4c3C1)C2] | ** |
| 53 | 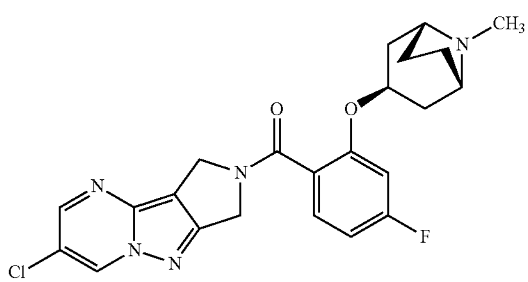 [SMILES: CN1[C@@H]2CC[C@H]1C[C@@H](Oc1cc(F)ccc1C(=O)N1Cc3nn4cc(Cl)cnc4c3C1)C2] | *** |
| 54 | | * |
| 55 | 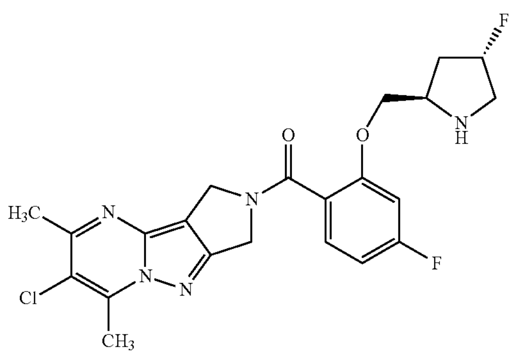 [SMILES: Cc1nc2c3c(nn2c(C)c1Cl)CN(C(=O)c1ccc(F)cc1OC[C@H]1C[C@H](F)CN1)C3] | ** |

-continued
| Ex | Structure | M1 PAM EC50 (nM) |
|---|---|---|
| 56 | 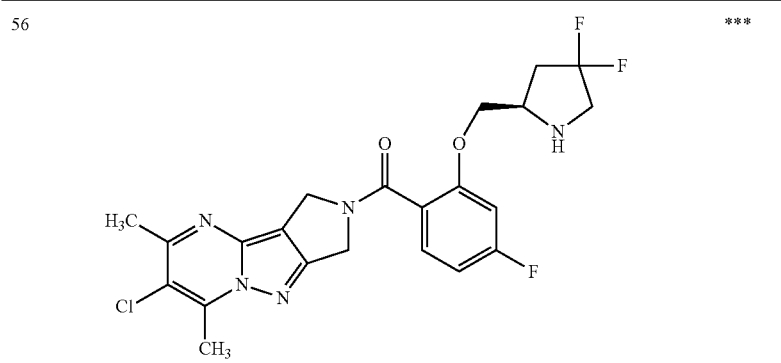 | *** |
| 58 | 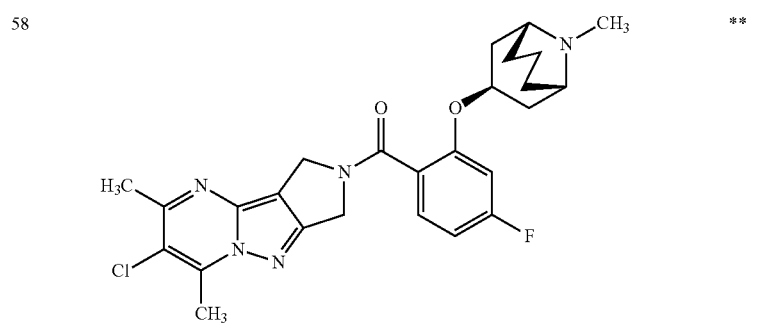 | ** |
| 59 | 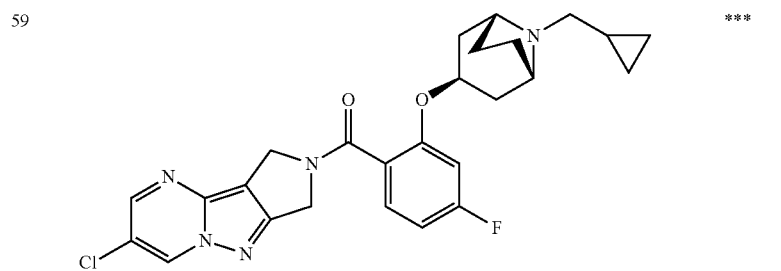 | *** |
| 60 | 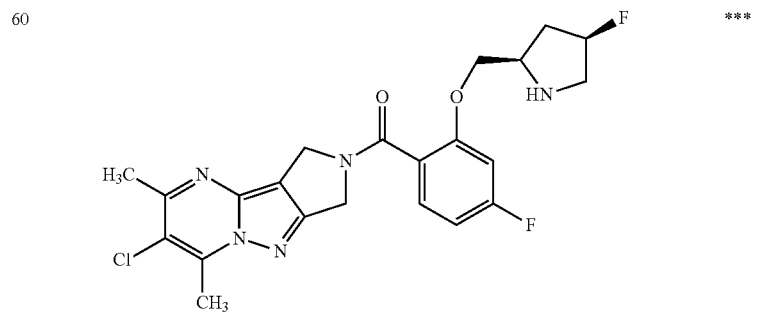 | *** |

-continued

| Ex | Structure | M1 PAM EC50 (nM) |
|---|---|---|
| 61 | 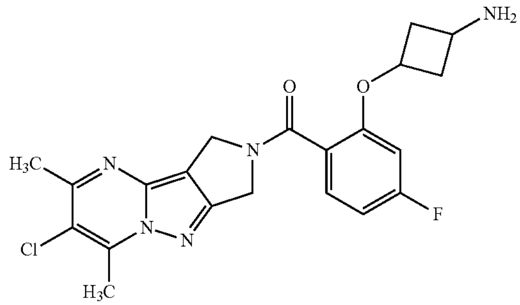 [SMILES: Cc1nc2c3c(nn2c(C)c1Cl)CN(C(=O)c1ccc(F)cc1OC1CC(N)C1)C3] | *** |
| 62 | 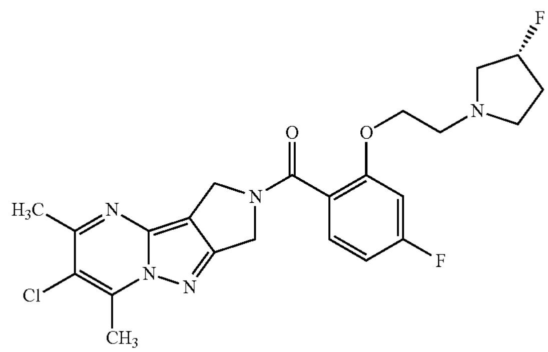 [SMILES: Cc1nc2c3c(nn2c(C)c1Cl)CN(C(=O)c1ccc(F)cc1OCCN1CC[C@@H](F)C1)C3] | ** |
| 63 | 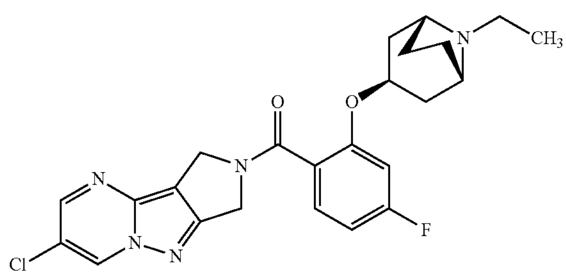 [SMILES: CCN1[C@@H]2CC[C@H]1C[C@@H](Oc1cc(F)ccc1C(=O)N1Cc3nn4cc(Cl)cnc4c3C1)C2] | *** |
| 64 | 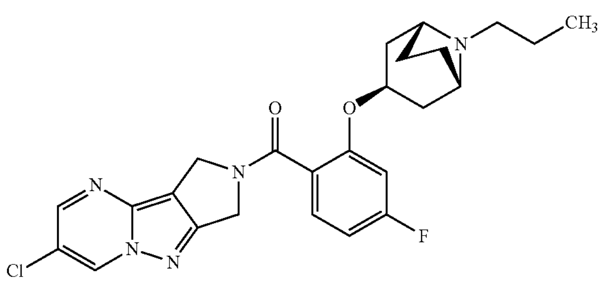 [SMILES: CCCN1[C@@H]2CC[C@H]1C[C@@H](Oc1cc(F)ccc1C(=O)N1Cc3nn4cc(Cl)cnc4c3C1)C2] | *** |
| 65 | 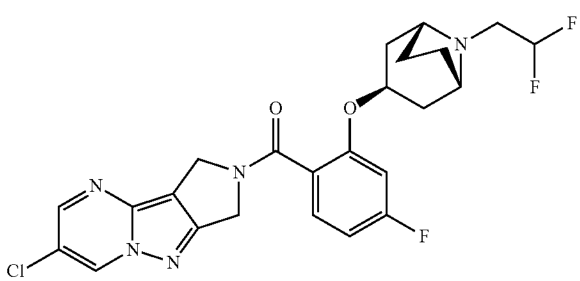 [SMILES: O=C(c1ccc(F)cc1O[C@H]1C[C@H]2CC[C@@H](C1)N2CC(F)F)N1Cc2nn3cc(Cl)cnc3c2C1] | ** |

-continued

| Ex | Structure | M1 PAM EC50 (nM) |
|---|---|---|
| 66 | 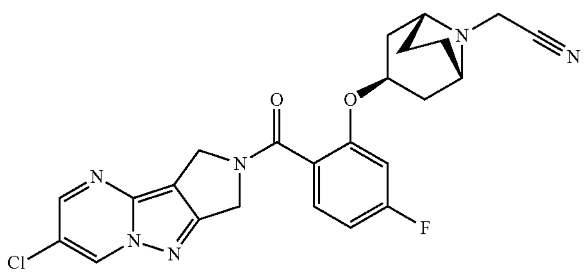 [SMILES: N#CCN1[C@@H]2CC[C@H]1C[C@@H](Oc1cc(F)ccc1C(=O)N1Cc3nn4cc(Cl)cnc4c3C1)C2] | ** |
| 67 | 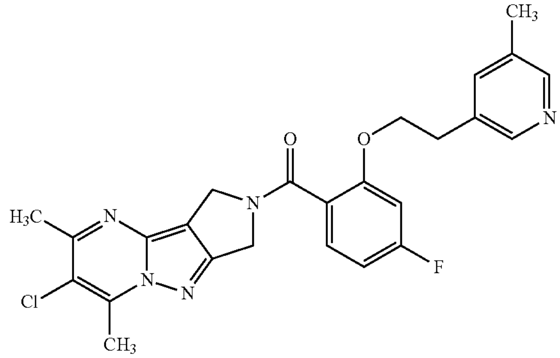 [SMILES: Cc1cncc(CCOc2cc(F)ccc2C(=O)N2Cc3nn4c(C)c(Cl)c(C)nc4c3C2)c1] | ** |
| 68 | 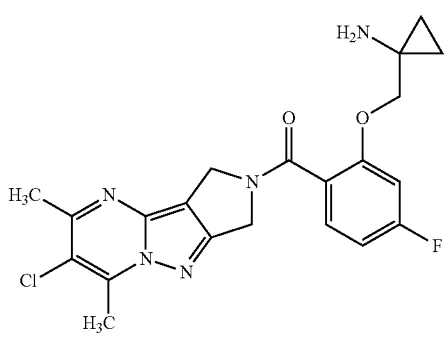 [SMILES: Cc1nc2c3c(nn2c(C)c1Cl)CN(C(=O)c1ccc(F)cc1OCC1(N)CC1)C3] | * |
| 69 | 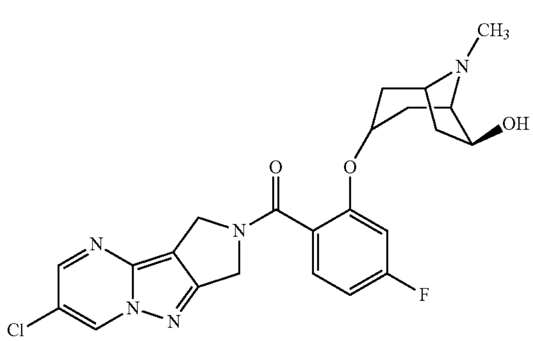 [SMILES: CN1C2CC(Oc3cc(F)ccc3C(=O)N3Cc4nn5cc(Cl)cnc5c4C3)CC1[C@@H](O)C2] | *** |

-continued
| Ex | Structure | M1 PAM EC50 (nM) |
|---|---|---|
| 70 | | ** |
| 71 | 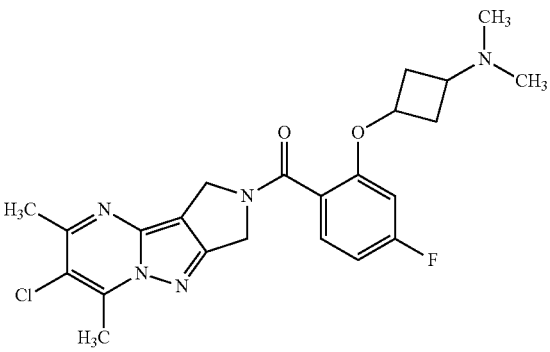 [SMILES: Cc1nc2c3c(nn2c(C)c1Cl)CN(C(=O)c1ccc(F)cc1OC1CC(N(C)C)C1)C3] | ** |
| 72 | 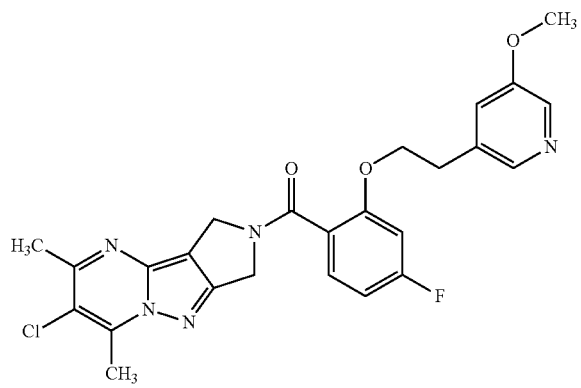 [SMILES: COc1cncc(CCOc2cc(F)ccc2C(=O)N2Cc3nn4c(C)c(Cl)c(C)nc4c3C2)c1] | * |
| 73 | 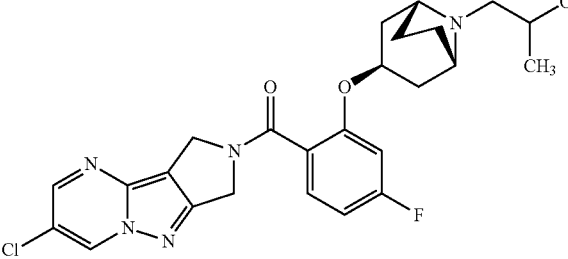 | ** |
| 74 | 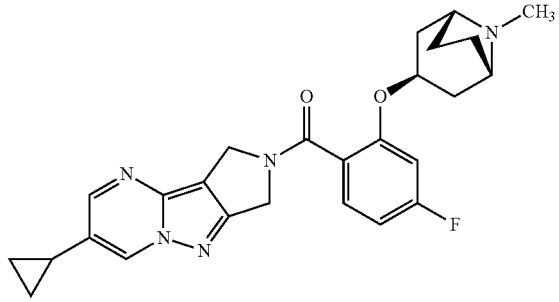 [SMILES: CN1[C@@H]2CC[C@H]1C[C@@H](Oc1cc(F)ccc1C(=O)N1Cc3nn4cc(C5CC5)cnc4c3C1)C2] | *** |

| Ex | Structure | M1 PAM EC50 (nM) |
|---|---|---|
| 75 | 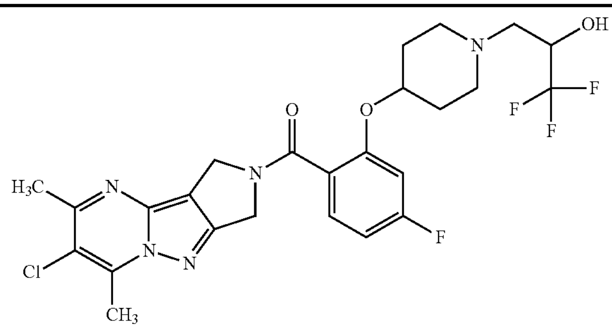 | ** |
| 76 | 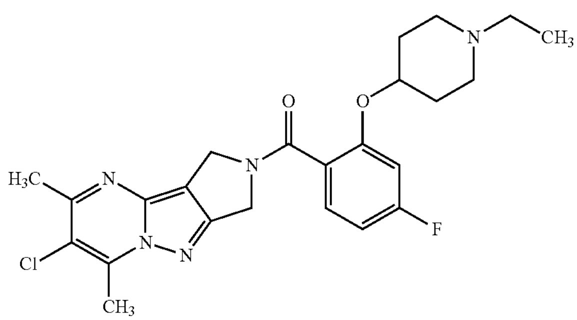 [SMILES: CCN1CCC(Oc2cc(F)ccc2C(=O)N2Cc3nn4c(C)c(Cl)c(C)nc4c3C2)CC1] | *** |
| 77 | 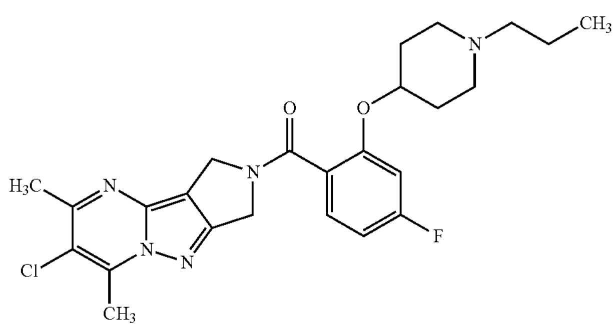 [SMILES: CCCN1CCC(Oc2cc(F)ccc2C(=O)N2Cc3nn4c(C)c(Cl)c(C)nc4c3C2)CC1] | *** |

\* 1 to 3 μM
\*\* 0.2 to 1 μM
\*\*\* below 0.2 μM

Example 283

Preparation of a Pharmaceutical Formulations

Formulation 1—Tablets

A compound of Formula (I) is admixed as a dry powder with a dry gelatin binder in an approximate 1:2 weight ratio. A minor amount of magnesium stearate is added as a lubricant. The mixture is formed into 240-270 mg tablets (80-90 mg of active compound according to the invention per tablet) in a tablet press.

Formulation 2—Capsules

A compound of Formula (I) is admixed as a dry powder with a starch diluent in an approximate 1:1 weight ratio. The mixture is filled into 250 mg capsules (125 mg of active compound according to the invention per capsule).

Formulation 3—Liquid

A compound of Formula (I) (1250 mg), sucrose (1.75 g) and xanthan gum (4 mg) are blended, passed through a No. 10 mesh U.S. sieve, and then mixed with a previously prepared solution of microcrystalline cellulose and sodium carboxymethyl cellulose (11:89, 50 mg) in water. Sodium benzoate (10 mg), flavor, and color are diluted with water and added with stirring. Sufficient water is then added to produce a total volume of 5 mL.

Formulation 4—Tablets

A compound of Formula (I) is admixed as a dry powder with a dry gelatin binder in an approximate 1:2 weight ratio. A minor amount of magnesium stearate is added as a lubricant. The mixture is formed into 450-900 mg tablets (150-300 mg of active compound according to the invention) in a tablet press.

Formulation 5—Injection

A compound of Formula (I) is dissolved in a buffered sterile saline injectable aqueous medium to a concentration of approximately 5 mg/mL.

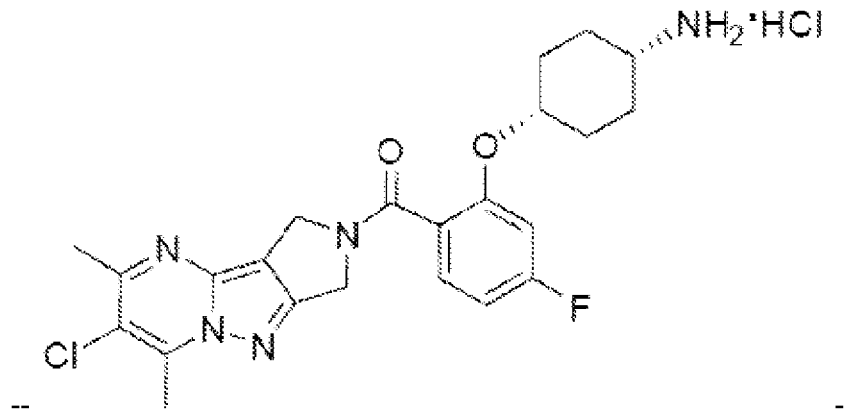

The invention claimed is:
1. A compound of Formula (I):

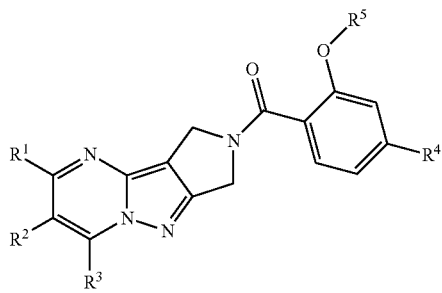

wherein
R¹ and R³ are independently from each other selected from the group consisting of H and linear or branched $C_1$-$C_6$-alkyl,
R² is selected from the group consisting of chloro, linear or branched $C_1$-$C_6$-alkyl and $C_3$-$C_7$ cycloalkyl,
R⁴ is selected from the group consisting of F and H, and
R⁵ is selected from the group consisting of A and $CH_2CH_2R^7$, wherein A is selected from the group consisting of:

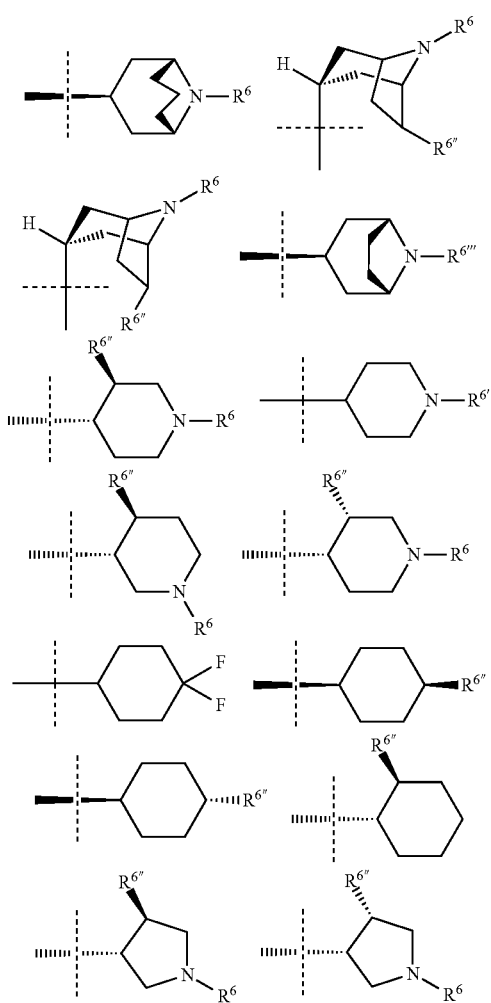

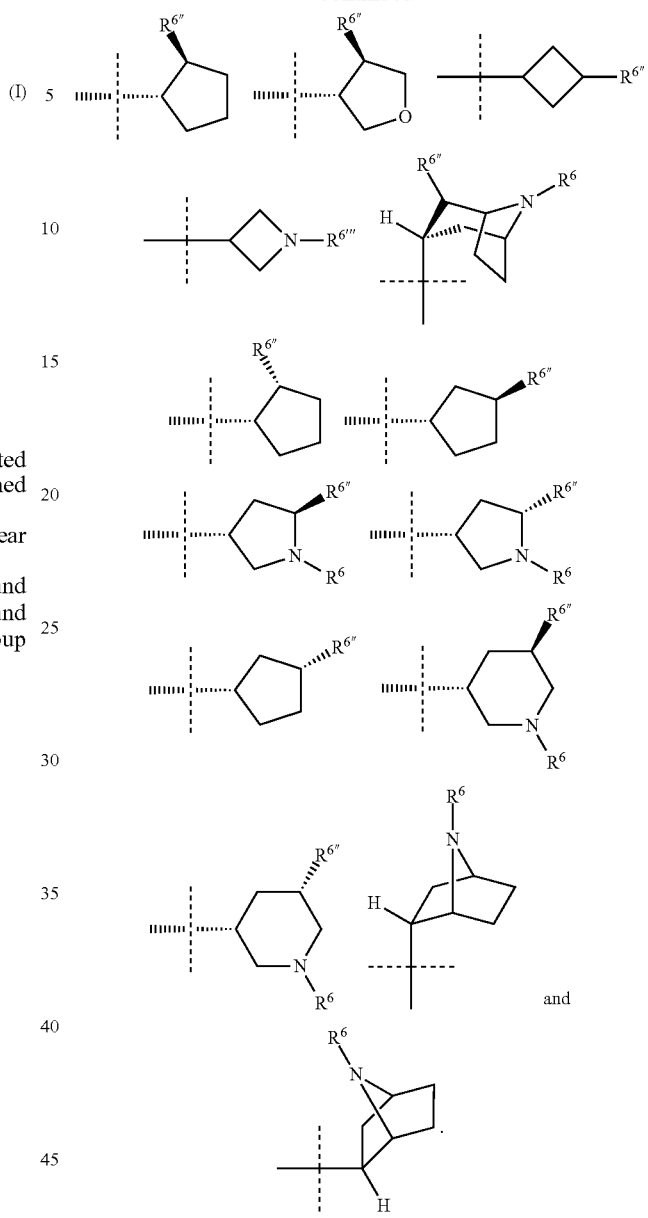

wherein
R⁶ is selected from the group consisting of H, $CH_3$, $CH_2CH_2R$, $CH(CH_2R)_2$, $CH_2CR_3$, $CH_2$-cyclopropyl, $CH_2CN$, and $CH_2CHF_2$,
R⁶' is selected from the group consisting of $CH_2CH_2R'$, $CH(CH_2R')_2$, $CH_2CR_3$, and $CH_2CO_2R^1$,
R⁶'' is selected from the group consisting of F, OH, $OCH_3$, $NH_2$, $N(CH_3)_2$, $N(R^1)_2$, and $CO_2R^1$,
R⁶''' is selected from the group consisting of $CH_2CH_2R$, $CH(CH_2R)_2$, $CH_2CR_3$, $CH_2$-cyclopropyl, $CH_2CN$, and $CH_2CHF_2$,
R is selected from the group consisting of H, CN, OH, $OCH_3$, Cl, F, $CHF_2$, $CH_3$, $CF_3$, $CH_2CH_3$ and cyclopropyl,
R' is selected from the group consisting of CN, OH, $OCH_3$, Cl, $CHF_2$, $CH_3$, $CF_3$ and cyclopropyl, and $R^7$ is selected from the group consisting of:

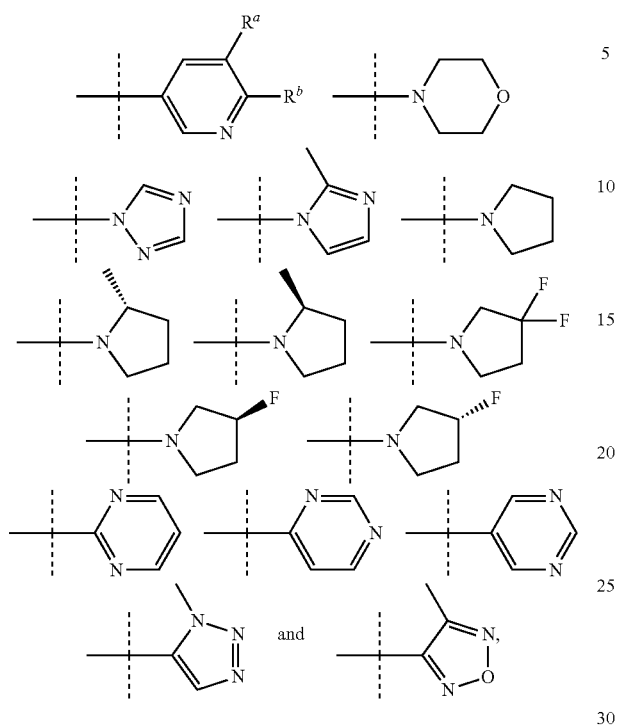

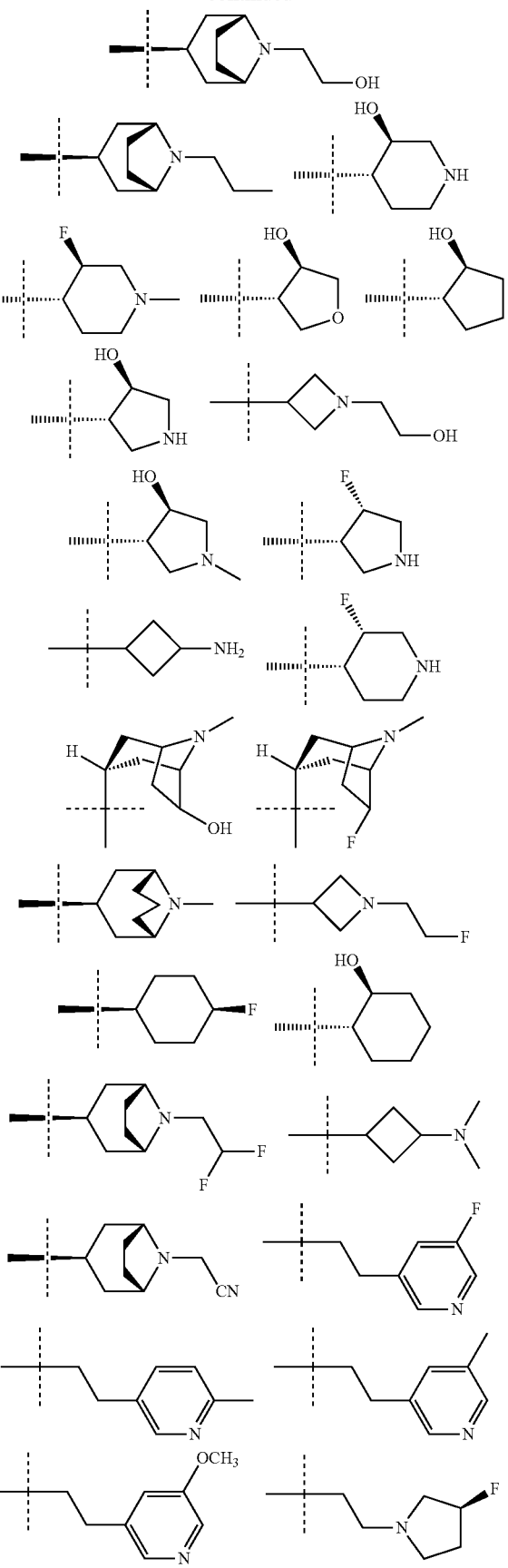

wherein $R^a$ and $R^b$ are each independently selected from the group consisting of H, F, CH$_3$, OCH$_3$, OH and 1-pyrrolidinyl and at least one of $R^a$ and $R^b$ is selected from the group consisting of F, CH$_3$, OCH$_3$, OH and 1-pyrrolidinyl, or tautomers, salts, solvates, stereoisomers, diastereomers and enantiomers thereof.

2. The compound of claim 1, wherein $R^1$ and $R^3$ are simultaneously either H or methyl.

3. The compound of claim 1, wherein $R^4$ is F.

4. The compound of claim 1, wherein $R^5$ is selected from the group consisting of:

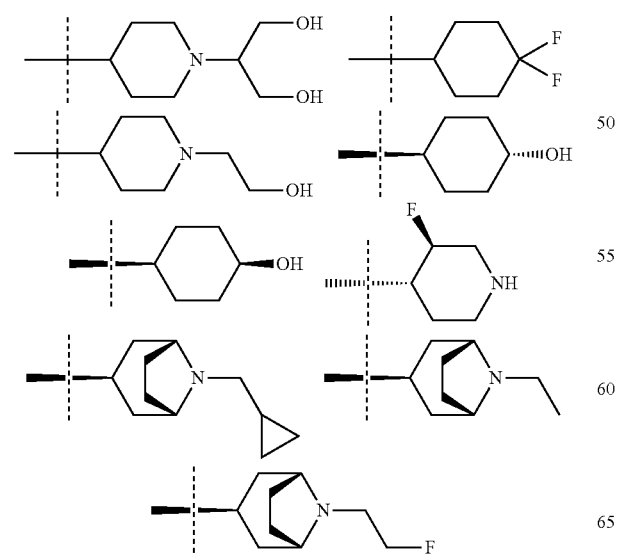

331
-continued
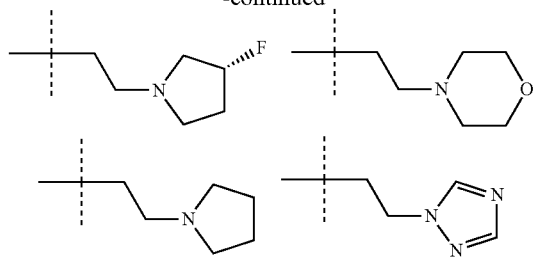
332
-continued
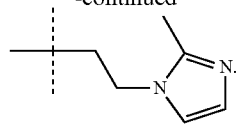
5. The compound of claim 1, wherein R⁵ is A.
6. The compound of claim 1, wherein the compound, or any diastereoisomer or enantiomer thereof, is selected from the group consisting of:
| Ex | Structure |
|---|---|
| 1 | 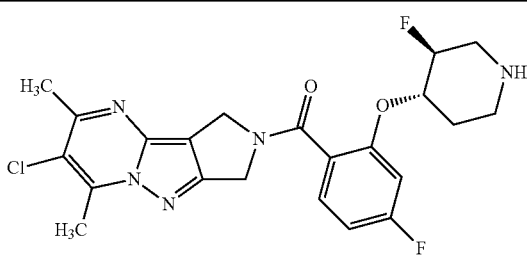 |
| 2 | 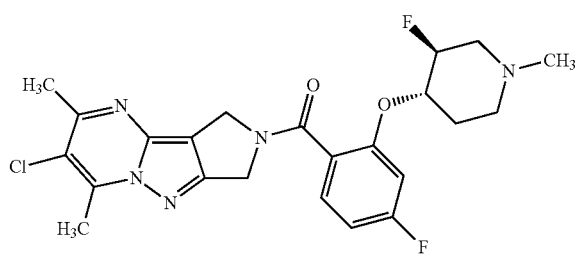 [SMILES: Cc1nc2c3c(nn2c(C)c1Cl)CN(C(=O)c1ccc(F)cc1O[C@H]1CCN(C)C[C@@H]1F)C3] |
| 4 | 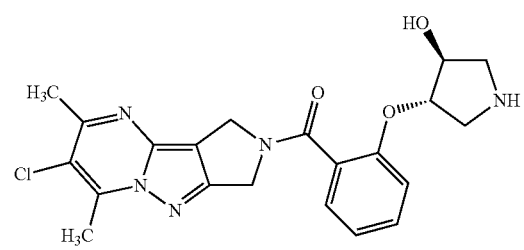 [SMILES: Cc1nc2c3c(nn2c(C)c1Cl)CN(C(=O)c1ccccc1O[C@H]1CNC[C@@H]1O)C3] |
| 5 | 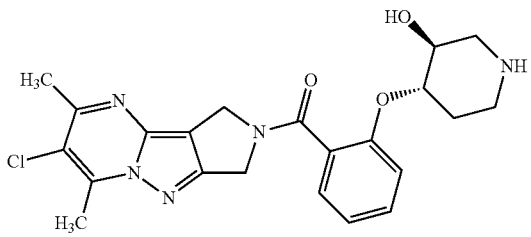 [SMILES: Cc1nc2c3c(nn2c(C)c1Cl)CN(C(=O)c1ccccc1O[C@H]1CCNC[C@@H]1O)C3] |
| 8 | 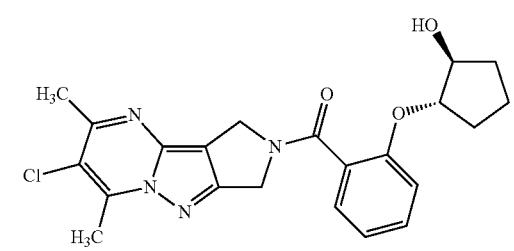 [SMILES: Cc1nc2c3c(nn2c(C)c1Cl)CN(C(=O)c1ccccc1O[C@H]1CCC[C@@H]1O)C3] |

-continued
| Ex | Structure |
|---|---|
| 13 | 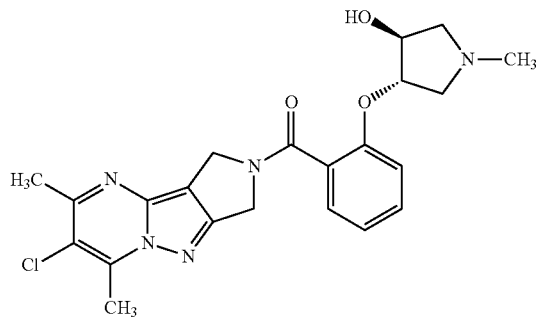 |
| 15 | 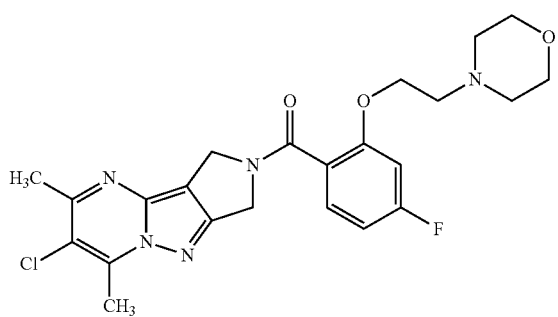 |
| 16 | 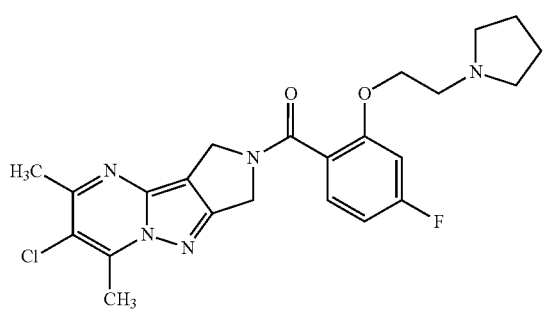 [SMILES: Cc1nc2c3c(nn2c(C)c1Cl)CN(C(=O)c1ccc(F)cc1OCCN1CCCC1)C3] |
| 17 | 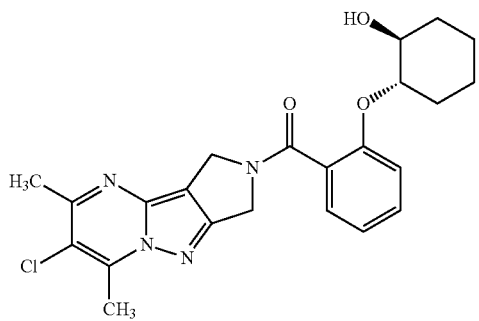 [SMILES: Cc1nc2c3c(nn2c(C)c1Cl)CN(C(=O)c1ccccc1O[C@H]1CCCC[C@@H]1O)C3] |

| Ex | Structure |
|---|---|
| 18 | 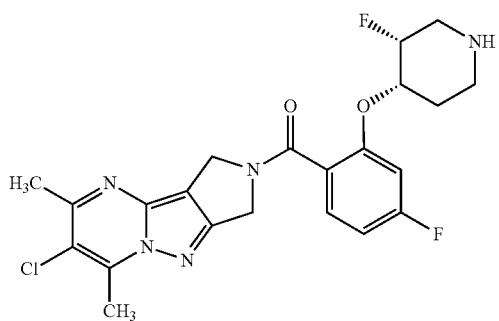 [SMILES: Cc1nc2c3c(nn2c(C)c1Cl)CN(C(=O)c1ccc(F)cc1O[C@H]1CCNC[C@H]1F)C3] |
| 20 | 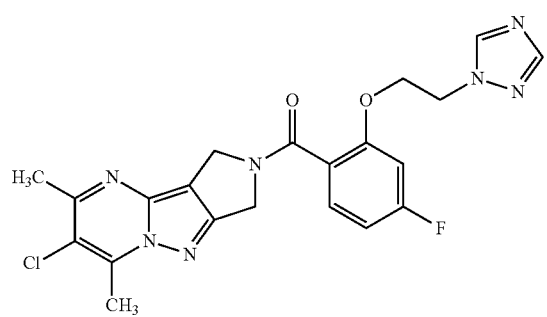 [SMILES: Cc1nc2c3c(nn2c(C)c1Cl)CN(C(=O)c1ccc(F)cc1OCCn1cncn1)C3] |
| 21 | 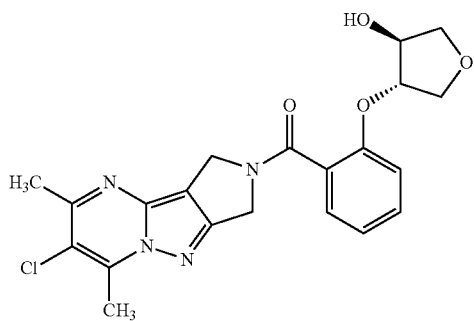 |
| 25 | 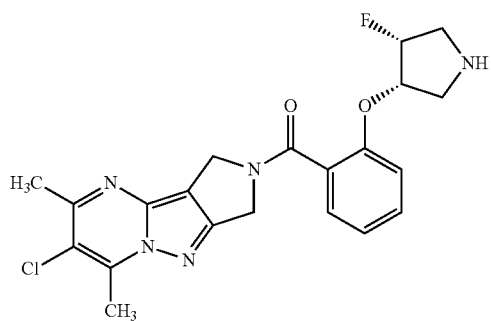 |

-continued
| Ex | Structure |
|---|---|
| 26 | 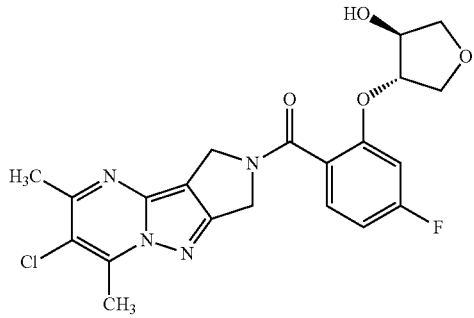 |
| 27 | 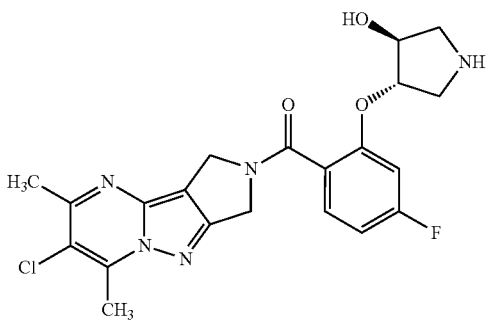 |
| 29 | 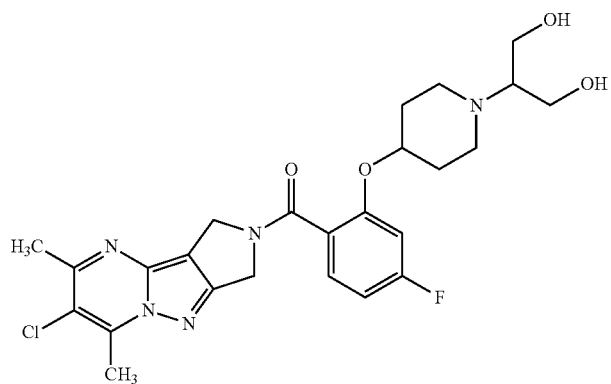 |
| 30 | 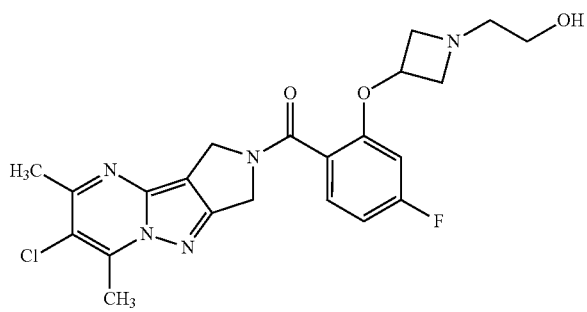 [SMILES: Cc1nc2c3c(nn2c(C)c1Cl)CN(C(=O)c1ccc(F)cc1OC1CN(CCO)C1)C3] |

| Ex | Structure |
|---|---|
| 32 | 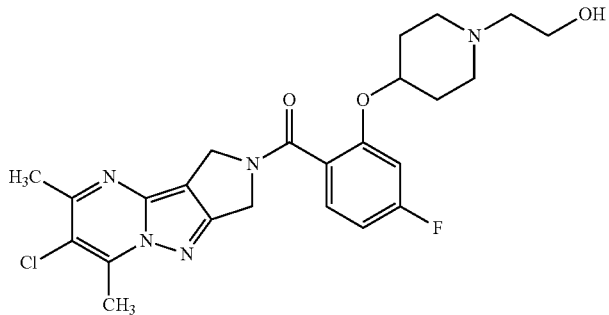 [SMILES: Cc1nc2c3c(nn2c(C)c1Cl)CN(C(=O)c1ccc(F)cc1OC1CCN(CCO)CC1)C3] |
| 35 | 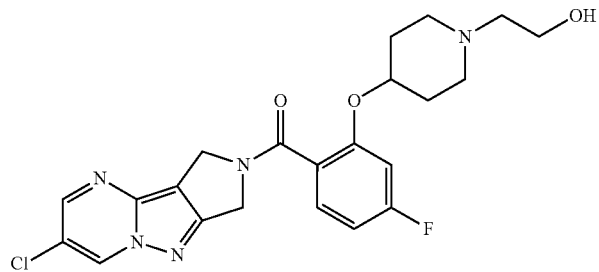 [SMILES: O=C(c1ccc(F)cc1OC1CCN(CCO)CC1)N1Cc2nn3cc(Cl)cnc3c2C1] |
| 36 | 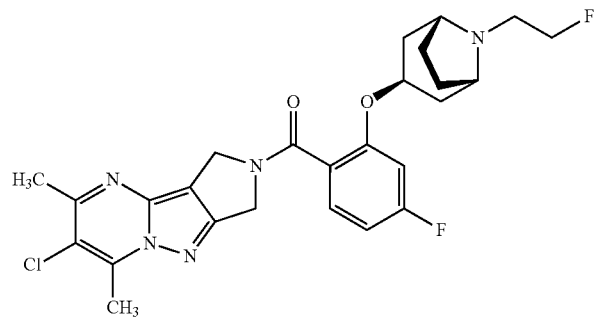 |
| 37 | 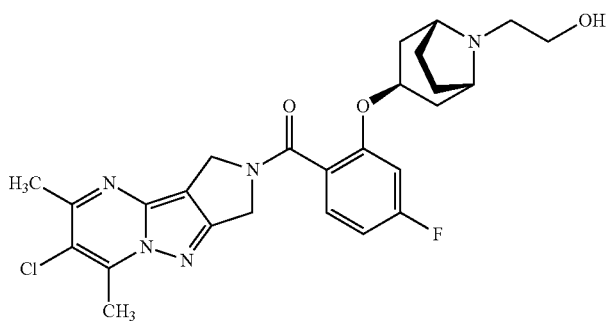 |

| Ex | Structure |
|---|---|
| 38 | 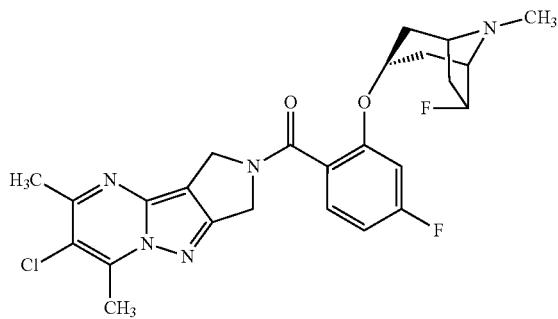 [SMILES: Cc1nc2c3c(nn2c(C)c1Cl)CN(C(=O)c1ccc(F)cc1O[C@H]1CC2CC(F)C(C1)N2C)C3] |
| 39 | 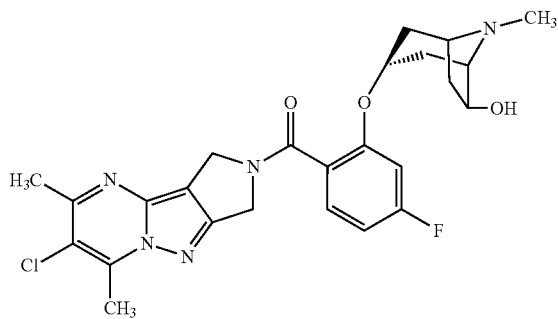 [SMILES: Cc1nc2c3c(nn2c(C)c1Cl)CN(C(=O)c1ccc(F)cc1O[C@H]1CC2CC(O)C(C1)N2C)C3] |
| 40 | 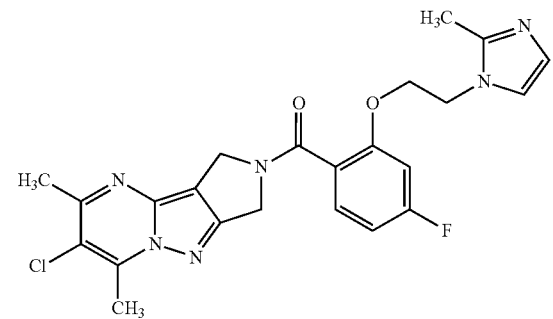 [SMILES: Cc1nc2c3c(nn2c(C)c1Cl)CN(C(=O)c1ccc(F)cc1OCCn1ccnc1C)C3] |
| 41 | 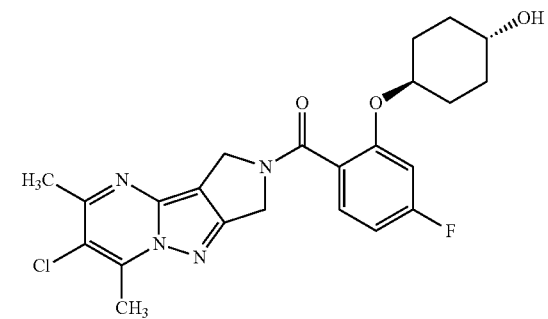 [SMILES: Cc1nc2c3c(nn2c(C)c1Cl)CN(C(=O)c1ccc(F)cc1O[C@H]1CC[C@H](O)CC1)C3] |

| Ex | Structure |
|---|---|
| 42 | 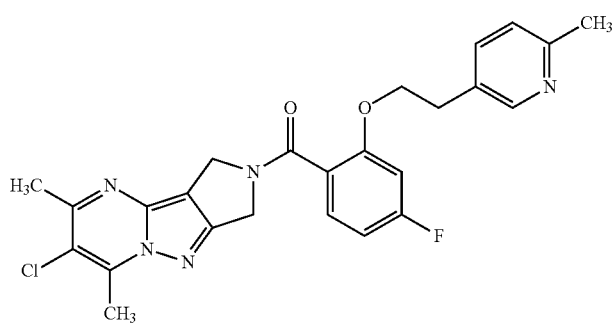 |
| 43 | 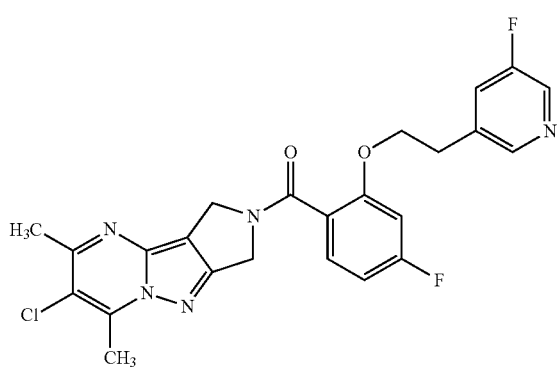 |
| 44 | 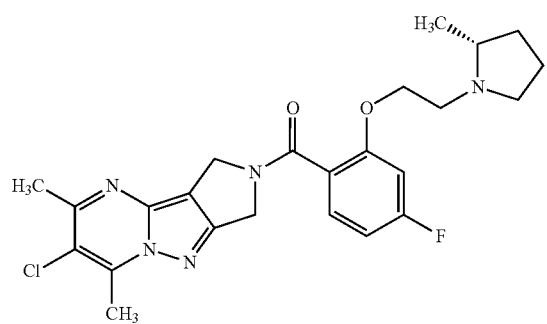 |
| 45 | 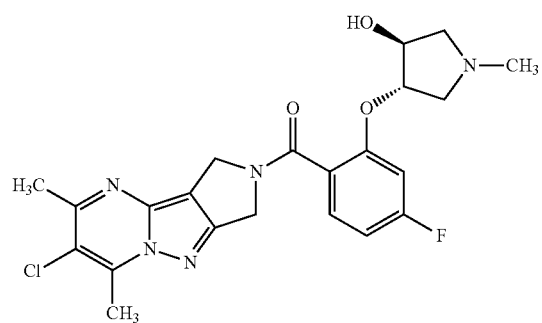 |

-continued

| Ex | Structure |
|---|---|
| 46 | 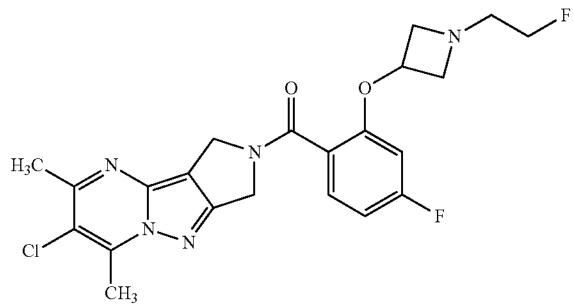 [SMILES: Cc1nc2c3c(nn2c(C)c1Cl)CN(C(=O)c1ccc(F)cc1OC1CN(CCF)C1)C3] |
| 47 | 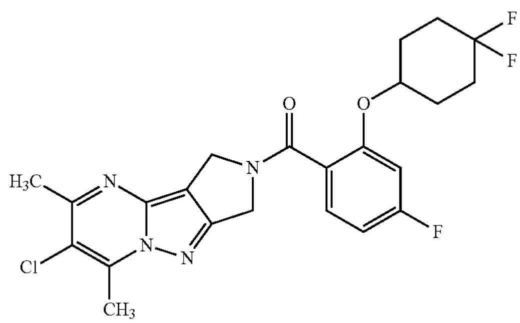 |
| 49 | 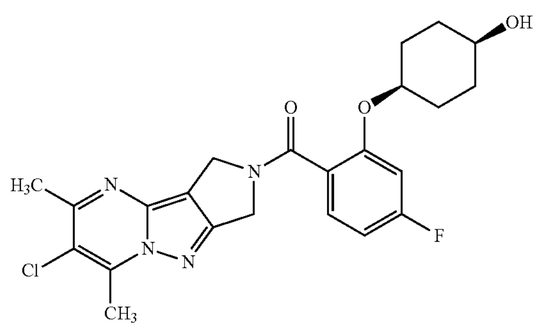 [SMILES: Cc1nc2c3c(nn2c(C)c1Cl)CN(C(=O)c1ccc(F)cc1O[C@H]1CC[C@@H](O)CC1)C3] |
| 50 | 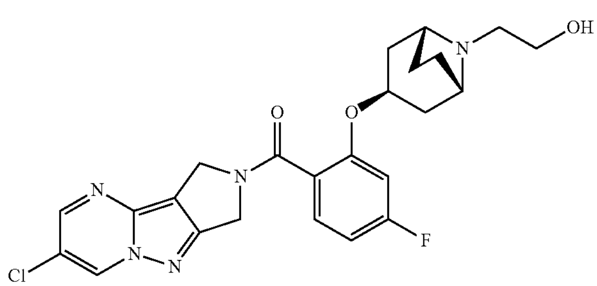 [SMILES: O=C(c1ccc(F)cc1O[C@H]1C[C@H]2CC[C@@H](C1)N2CCO)N1Cc2nn3cc(Cl)cnc3c2C1] |
| 51 | 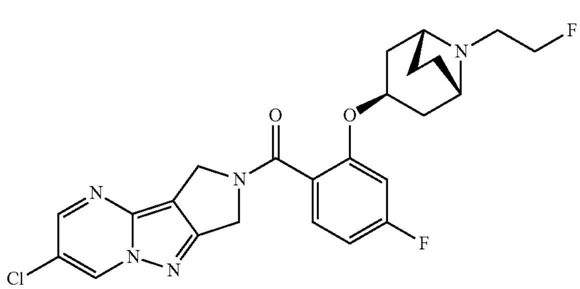 [SMILES: O=C(c1ccc(F)cc1O[C@H]1C[C@H]2CC[C@@H](C1)N2CCF)N1Cc2nn3cc(Cl)cnc3c2C1] |

| Ex | Structure |
|---|---|
| 52 | 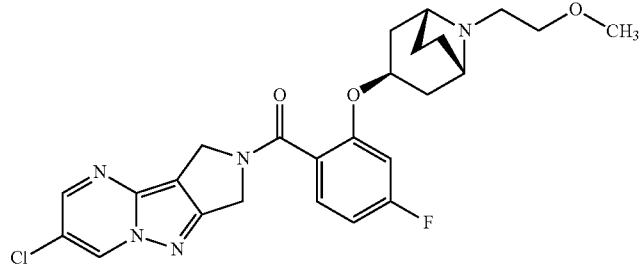 [SMILES: COCCN1[C@@H]2CC[C@H]1C[C@@H](Oc1cc(F)ccc1C(=O)N1Cc3nn4cc(Cl)cnc4c3C1)C2] |
| 54a | 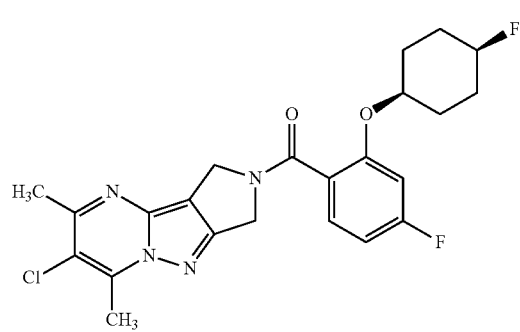 [SMILES: Cc1nc2c3c(nn2c(C)c1Cl)CN(C(=O)c1ccc(F)cc1O[C@H]1CC[C@@H](F)CC1)C3] |
| 54b | 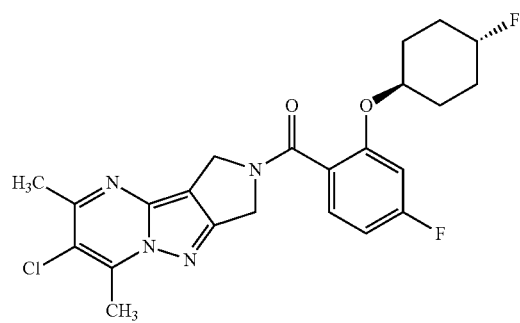 [SMILES: Cc1nc2c3c(nn2c(C)c1Cl)CN(C(=O)c1ccc(F)cc1O[C@H]1CC[C@H](F)CC1)C3] |
| 58 | 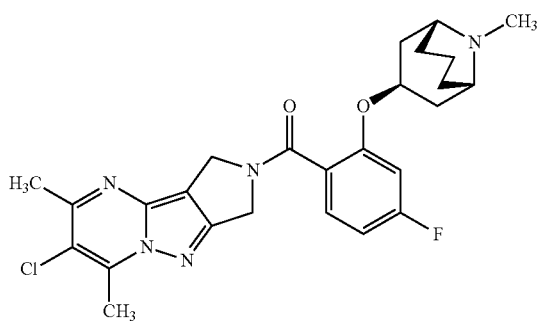 [SMILES: Cc1nc2c3c(nn2c(C)c1Cl)CN(C(=O)c1ccc(F)cc1O[C@H]1C[C@H]2CCC[C@@H](C1)N2C)C3] |
| 59 | 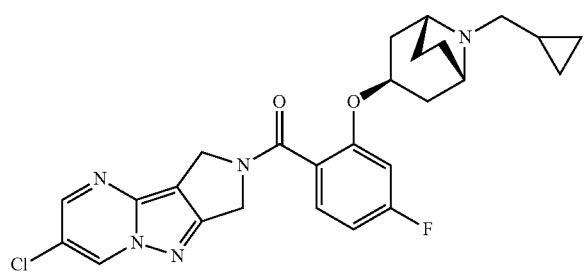 [SMILES: O=C(c1ccc(F)cc1O[C@H]1C[C@H]2CC[C@@H](C1)N2CC1CC1)N1Cc2nn3cc(Cl)cnc3c2C1] |

| Ex | Structure |
|---|---|
| 61 | 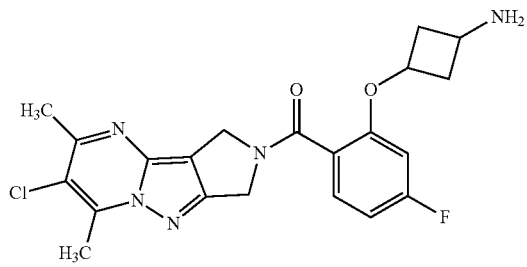 [SMILES: Cc1nc2c3c(nn2c(C)c1Cl)CN(C(=O)c1ccc(F)cc1OC1CC(N)C1)C3] |
| 62 | 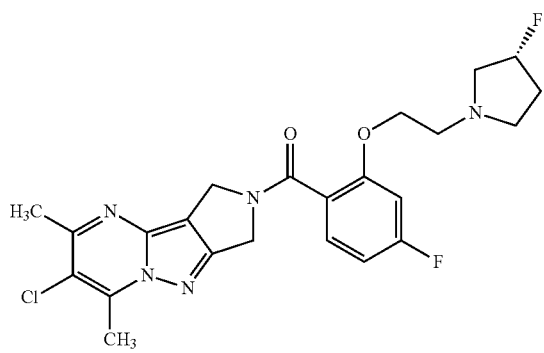 [SMILES: Cc1nc2c3c(nn2c(C)c1Cl)CN(C(=O)c1ccc(F)cc1OCCN1CC[C@@H](F)C1)C3] |
| 63 | 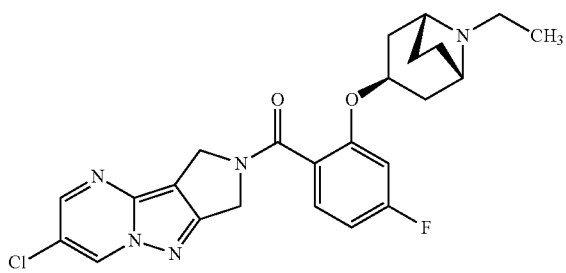 [SMILES: CCN1[C@@H]2CC[C@H]1C[C@@H](Oc1cc(F)ccc1C(=O)N1Cc3nn4cc(Cl)cnc4c3C1)C2] |
| 64 | 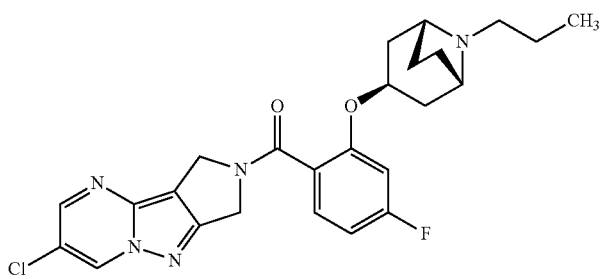 [SMILES: CCCN1[C@@H]2CC[C@H]1C[C@@H](Oc1cc(F)ccc1C(=O)N1Cc3nn4cc(Cl)cnc4c3C1)C2] |
| 65 | 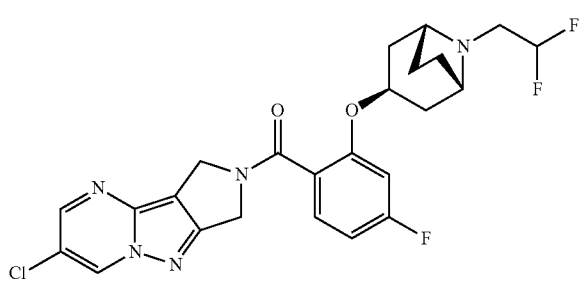 [SMILES: O=C(c1ccc(F)cc1O[C@H]1C[C@H]2CC[C@@H](C1)N2CC(F)F)N1Cc2nn3cc(Cl)cnc3c2C1] |

-continued
| Ex | Structure |
|---|---|
| 66 | 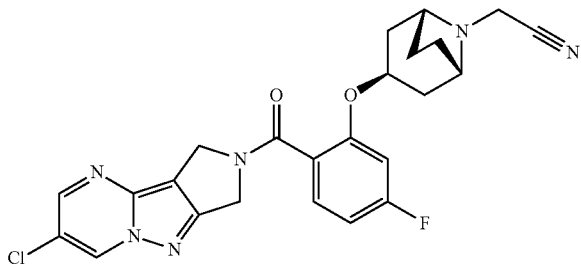 [SMILES: N#CCN1[C@@H]2CC[C@H]1C[C@@H](Oc1cc(F)ccc1C(=O)N1Cc3nn4cc(Cl)cnc4c3C1)C2] |
| 67 | 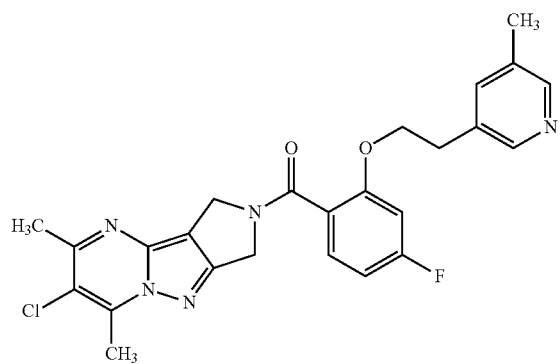 |
| 69 | 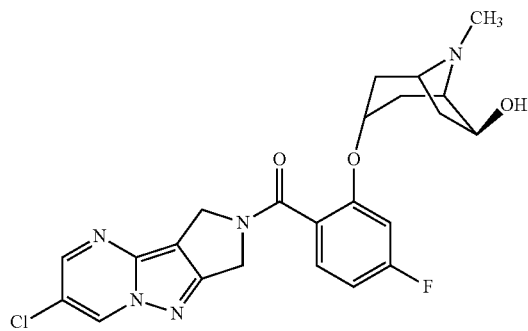 [SMILES: CN1C2CC(Oc3cc(F)ccc3C(=O)N3Cc4nn5cc(Cl)cnc5c4C3)CC1[C@@H](O)C2] |
| 70a | 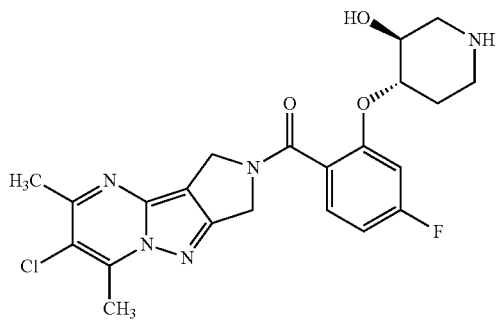 |

-continued
| Ex | Structure |
|---|---|
| 70b | 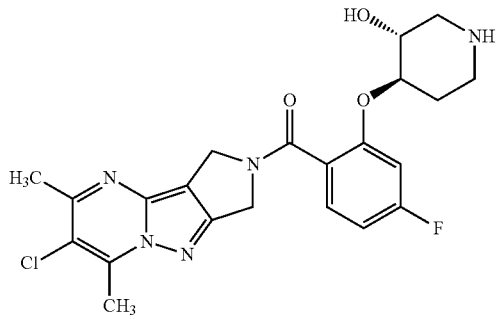 |
| 71 | 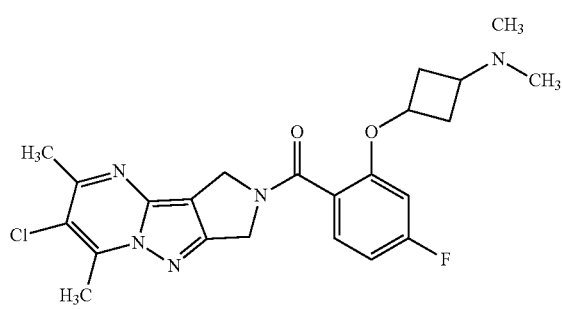 |
| 72 | 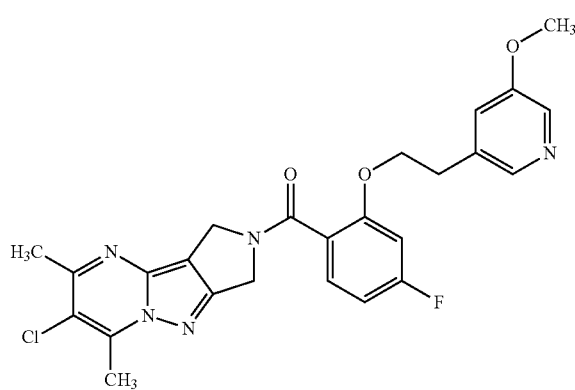 [SMILES: COc1cncc(CCOc2cc(F)ccc2C(=O)N2Cc3nn4c(C)c(Cl)c(C)nc4c3C2)c1] |
| 73 | 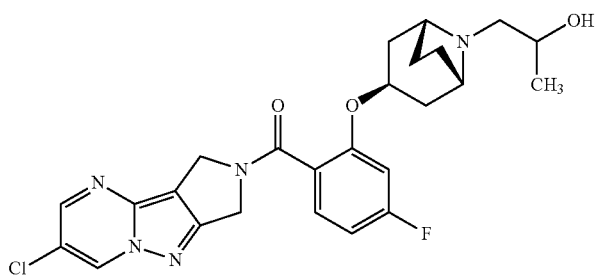 [SMILES: CC(O)CN1[C@@H]2CC[C@H]1C[C@@H](Oc1cc(F)ccc1C(=O)N1Cc3nn4cc(Cl)cnc4c3C1)C2] |
| 74 | 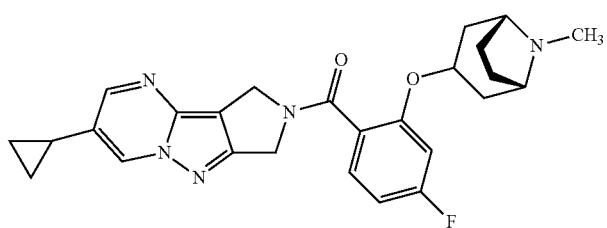 |

-continued
| Ex | Structure |
|---|---|
| 75 | 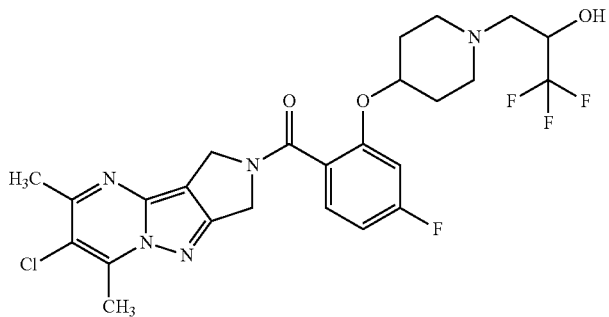 [SMILES: Cc1nc2c3c(nn2c(C)c1Cl)CN(C(=O)c1ccc(F)cc1OC1CCN(CC(O)C(F)(F)F)CC1)C3] |
| 76 | 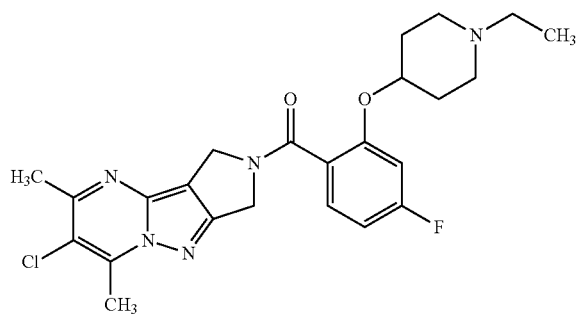 [SMILES: CCN1CCC(Oc2cc(F)ccc2C(=O)N2Cc3nn4c(C)c(Cl)c(C)nc4c3C2)CC1] |
| 77 | 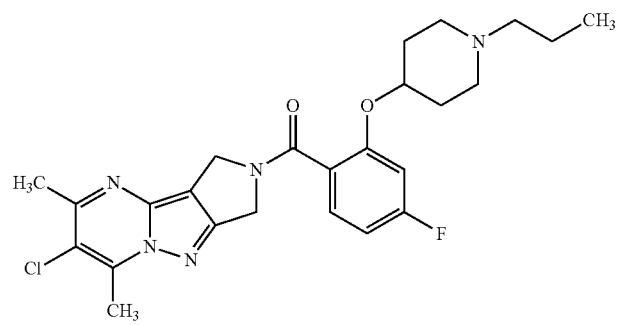 [SMILES: CCCN1CCC(Oc2cc(F)ccc2C(=O)N2Cc3nn4c(C)c(Cl)c(C)nc4c3C2)CC1] |
| 78a | 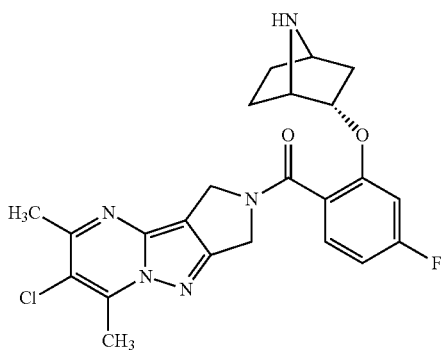 |

357
-continued
| Ex | Structure |
|---|---|
| 78b | 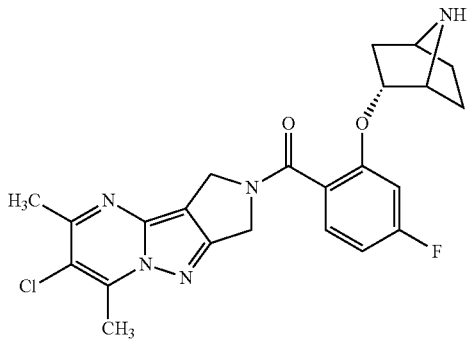 |
| 79 | 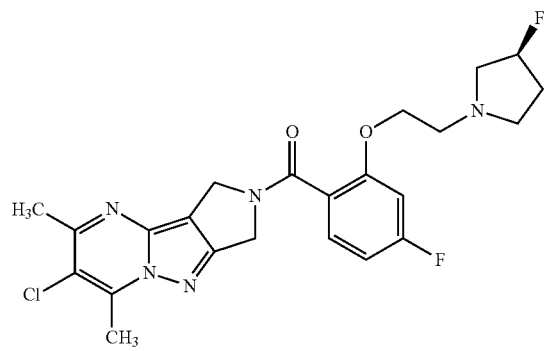 [SMILES: Cc1nc2c3c(nn2c(C)c1Cl)CN(C(=O)c1ccc(F)cc1OCCN1CC[C@H](F)C1)C3] |
| 82 | 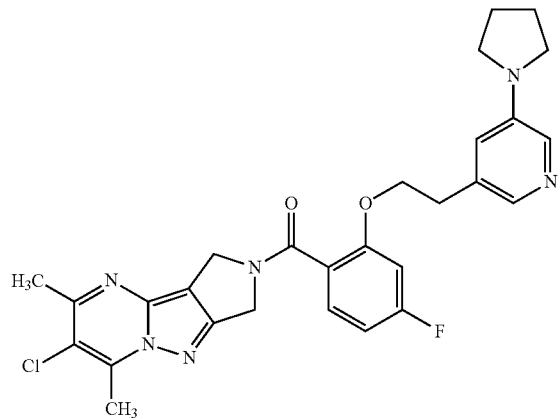 [SMILES: Cc1nc2c3c(nn2c(C)c1Cl)CN(C(=O)c1ccc(F)cc1OCCc1cncc(N2CCCC2)c1)C3] |
| 84a | 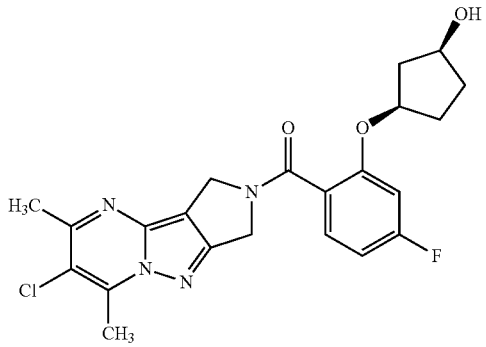 [SMILES: Cc1nc2c3c(nn2c(C)c1Cl)CN(C(=O)c1ccc(F)cc1O[C@@H]1CC[C@H](O)C1)C3] |

-continued
| Ex | Structure |
|---|---|
| 84b | 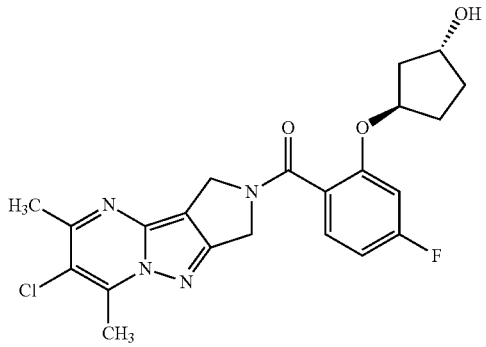 |
| 85 | 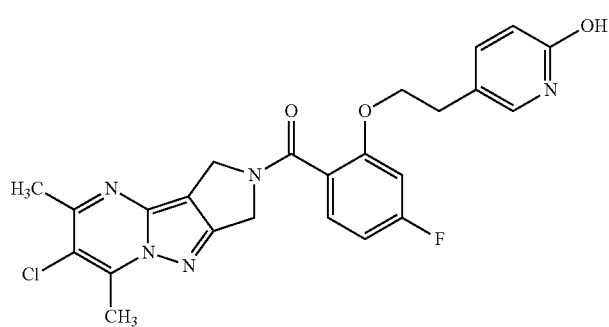 [SMILES: Cc1nc2c3c(nn2c(C)c1Cl)CN(C(=O)c1ccc(F)cc1OCCc1ccc(O)nc1)C3] |
| 87 | 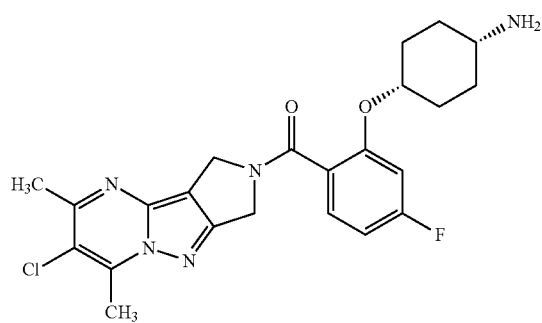 [SMILES: Cc1nc2c3c(nn2c(C)c1Cl)CN(C(=O)c1ccc(F)cc1O[C@H]1CC[C@@H](N)CC1)C3] |
| 88 | 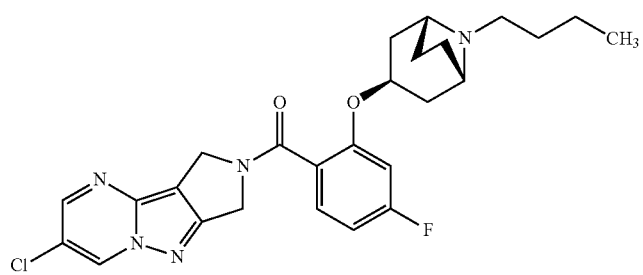 [SMILES: CCCCN1[C@@H]2CC[C@H]1C[C@@H](Oc1cc(F)ccc1C(=O)N1Cc3nn4cc(Cl)cnc4c3C1)C2] |
| 89 | 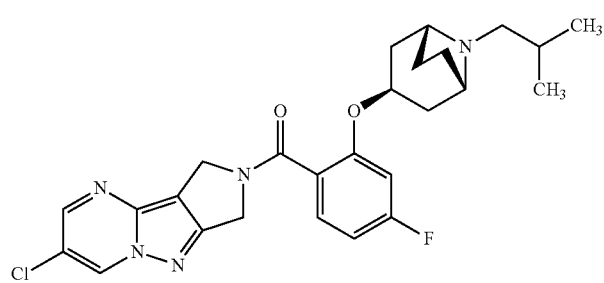 [SMILES: CC(C)CN1[C@@H]2CC[C@H]1C[C@@H](Oc1cc(F)ccc1C(=O)N1Cc3nn4cc(Cl)cnc4c3C1)C2] |

| Ex | Structure |
|---|---|
| 90a | 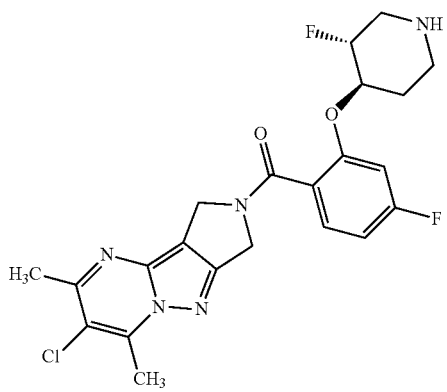 [SMILES: Cc1nc2c3c(nn2c(C)c1Cl)CN(C(=O)c1ccc(F)cc1O[C@@H]1CCNC[C@H]1F)C3] |
| 90b | 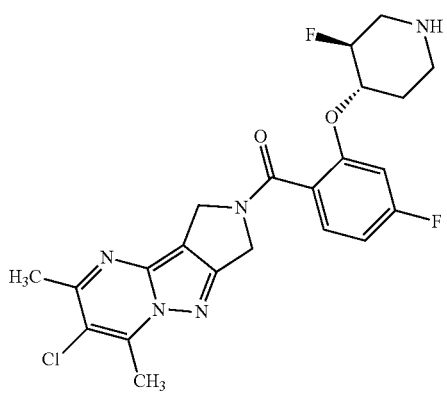 [SMILES: Cc1nc2c3c(nn2c(C)c1Cl)CN(C(=O)c1ccc(F)cc1O[C@H]1CCNC[C@@H]1F)C3] |
| 91a | 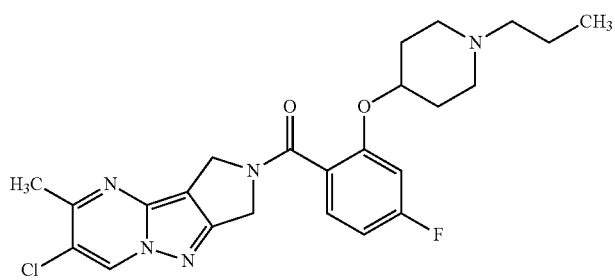 [SMILES: CCCN1CCC(Oc2cc(F)ccc2C(=O)N2Cc3nn4cc(Cl)c(C)nc4c3C2)CC1] |
| 91b | 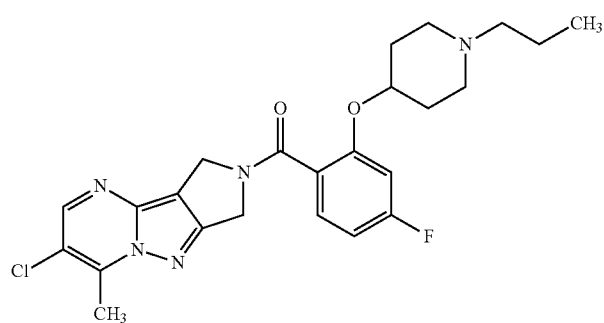 |

| Ex | Structure |
|---|---|
| 92 | 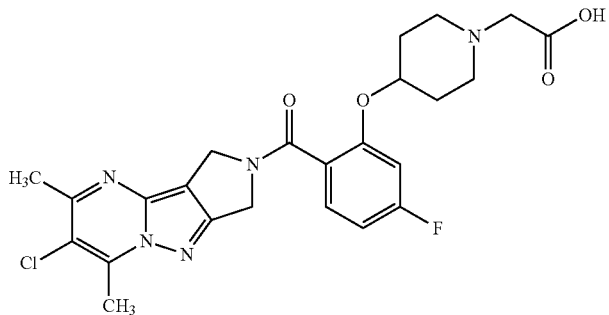 [SMILES: Cc1nc2c3c(nn2c(C)c1Cl)CN(C(=O)c1ccc(F)cc1OC1CCN(CC(=O)O)CC1)C3] |
| 93a | 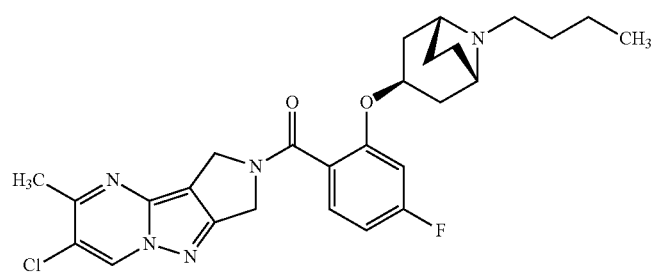 [SMILES: CCCCN1[C@@H]2CC[C@H]1C[C@@H](Oc1cc(F)ccc1C(=O)N1Cc3nn4cc(Cl)c(C)nc4c3C1)C2] |
| 93b | 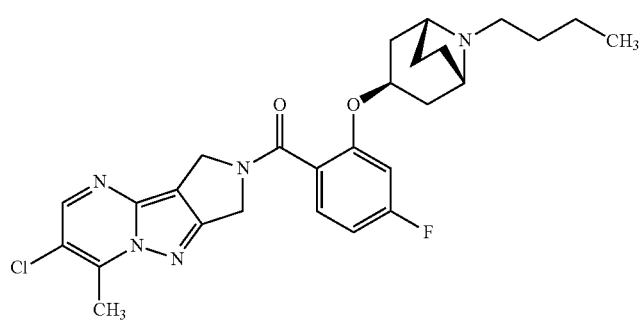 [SMILES: CCCCN1[C@@H]2CC[C@H]1C[C@@H](Oc1cc(F)ccc1C(=O)N1Cc3nn4c(C)c(Cl)cnc4c3C1)C2] |
| 95 | 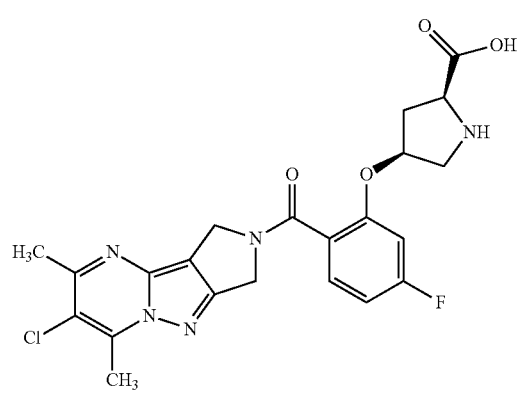 [SMILES: Cc1nc2c3c(nn2c(C)c1Cl)CN(C(=O)c1ccc(F)cc1O[C@@H]1CN[C@H](C(=O)O)C1)C3] |

-continued
| Ex | Structure |
|---|---|
| 96 | 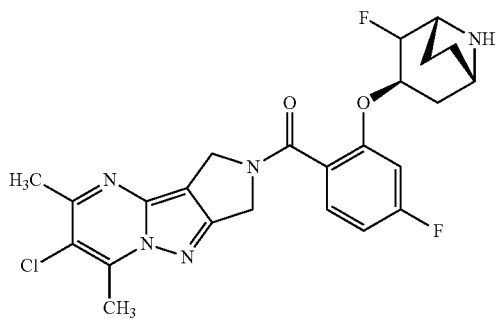 [SMILES: Cc1nc2c3c(nn2c(C)c1Cl)CN(C(=O)c1ccc(F)cc1O[C@@H]1C[C@@H]2CC[C@@H](N2)C1F)C3] |
| 97 | 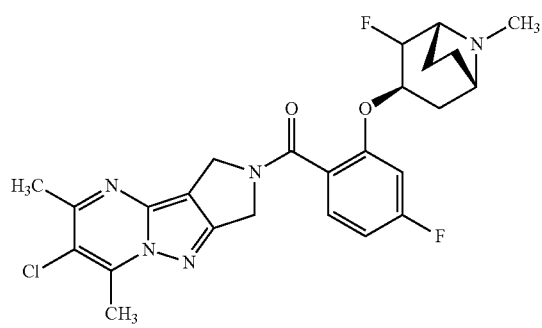 [SMILES: Cc1nc2c3c(nn2c(C)c1Cl)CN(C(=O)c1ccc(F)cc1O[C@@H]1C[C@@H]2CC[C@H](C1F)N2C)C3] |
| 98 | 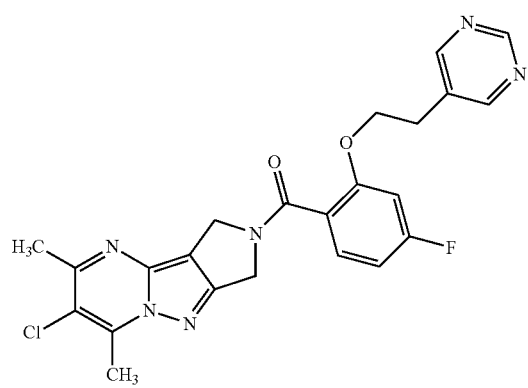 [SMILES: Cc1nc2c3c(nn2c(C)c1Cl)CN(C(=O)c1ccc(F)cc1OCCc1cncnc1)C3] |
| 99 | 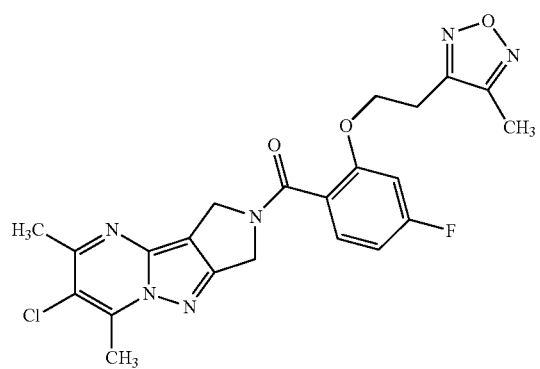 [SMILES: Cc1nonc1CCOc1cc(F)ccc1C(=O)N1Cc2nn3c(C)c(Cl)c(C)nc3c2C1] |

| Ex | Structure |
|---|---|
| 100 | 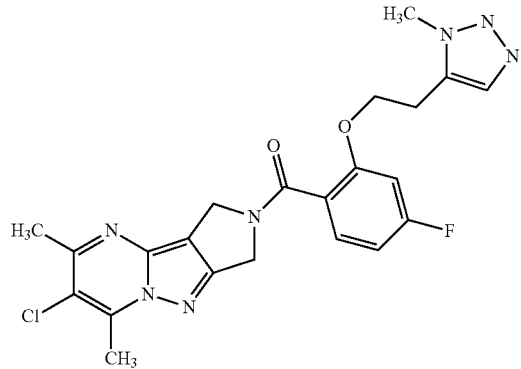 [SMILES: Cc1nc2c3c(nn2c(C)c1Cl)CN(C(=O)c1ccc(F)cc1OCCC1=CNNN1C)C3] |
| 101 | 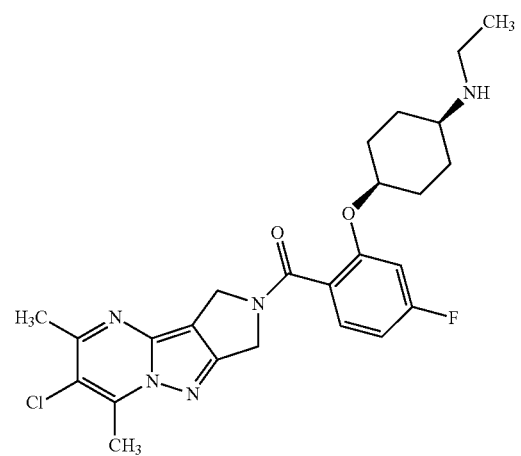 [SMILES: CCN[C@H]1CC[C@@H](Oc2cc(F)ccc2C(=O)N2Cc3nn4c(C)c(Cl)c(C)nc4c3C2)CC1] |
| 102 | 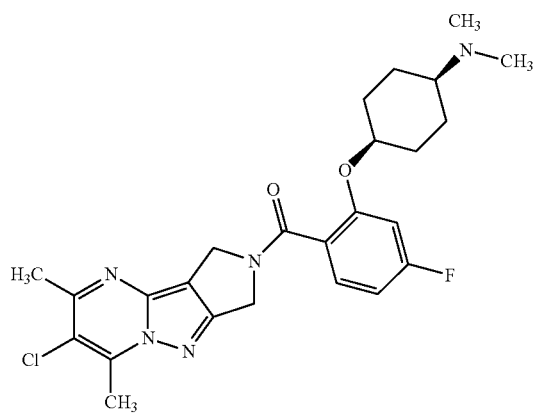 |

| Ex | Structure |
|---|---|
| 103 | 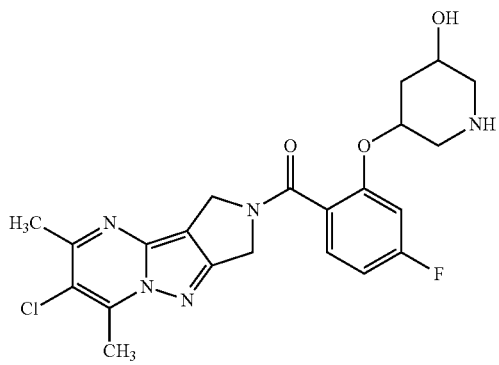 [SMILES: Cc1nc2c3c(nn2c(C)c1Cl)CN(C(=O)c1ccc(F)cc1OC1CNCC(F)C1)C3] |
| 104 | 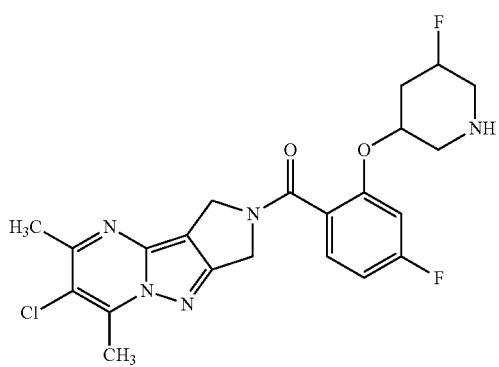 |
| 105 | 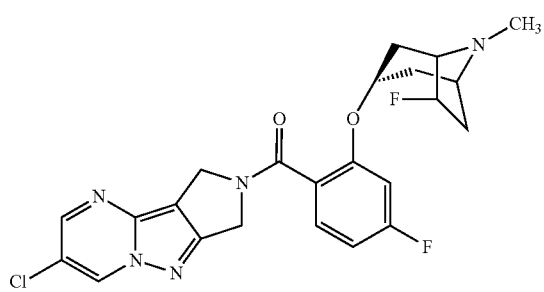 [SMILES: CN1C2CC(F)C1C[C@H](Oc1cc(F)ccc1C(=O)N1Cc3nn4cc(Cl)cnc4c3C1)C2] |
| 106 | 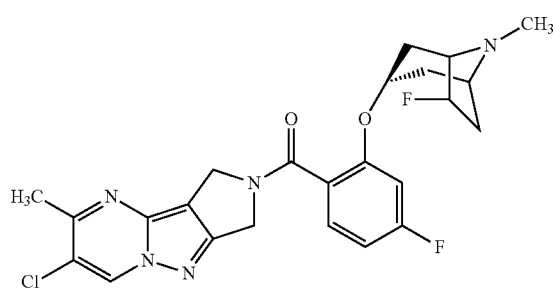 [SMILES: Cc1nc2c3c(nn2cc1Cl)CN(C(=O)c1ccc(F)cc1O[C@@H]1CC2CC(F)C(C1)N2C)C3] |

-continued

| Ex | Structure |
|---|---|
| 107 | 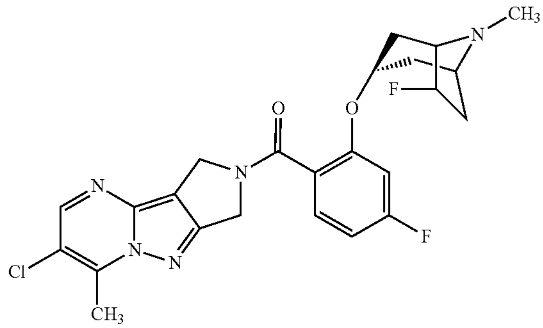 [SMILES: Cc1c(Cl)cnc2c3c(nn12)CN(C(=O)c1ccc(F)cc1O[C@@H]1CC2CC(F)C(C1)N2C)C3] |
| 108 | 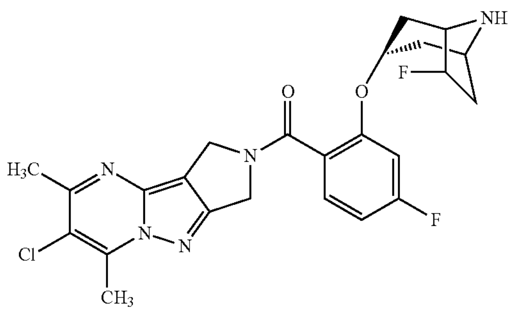 [SMILES: Cc1nc2c3c(nn2c(C)c1Cl)CN(C(=O)c1ccc(F)cc1O[C@@H]1CC2CC(F)C(C1)N2)C3] |
| 109 | 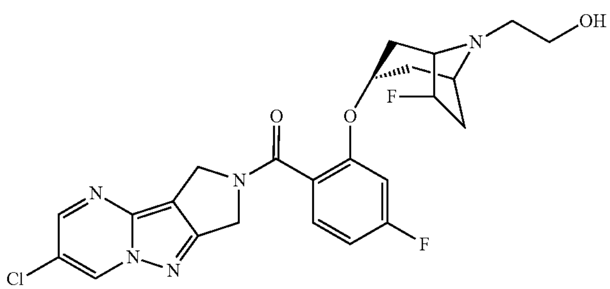 [SMILES: O=C(c1ccc(F)cc1O[C@@H]1CC2CC(F)C(C1)N2CCO)N1Cc2nn3cc(Cl)cnc3c2C1] |
| 110 | 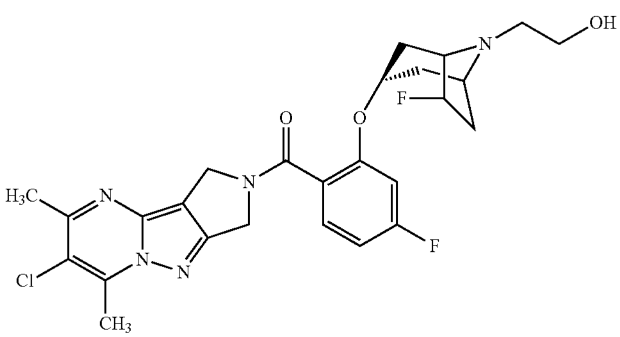 [SMILES: Cc1nc2c3c(nn2c(C)c1Cl)CN(C(=O)c1ccc(F)cc1O[C@@H]1CC2CC(F)C(C1)N2CCO)C3] |
| 111 | 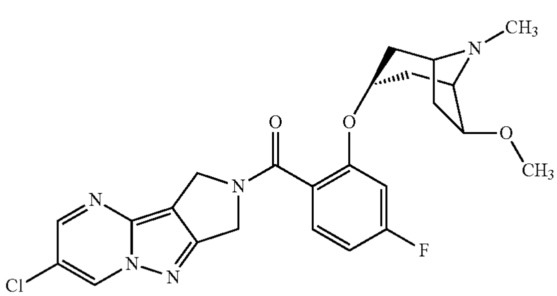 [SMILES: COC1CC2C[C@H](Oc3cc(F)ccc3C(=O)N3Cc4nn5cc(Cl)cnc5c4C3)CC1N2C] |

-continued
| Ex | Structure |
|---|---|
| 112 | 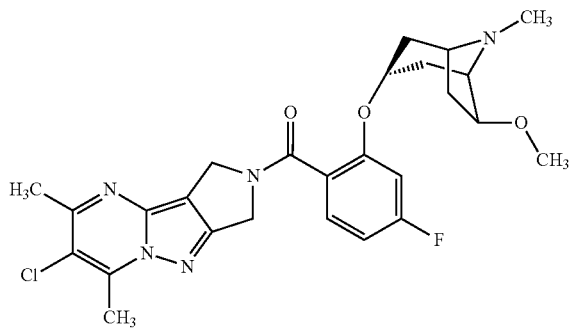 [SMILES: COC1CC2C[C@H](Oc3cc(F)ccc3C(=O)N3Cc4nn5c(C)c(Cl)c(C)nc5c4C3)CC1N2C] |
| 113 | 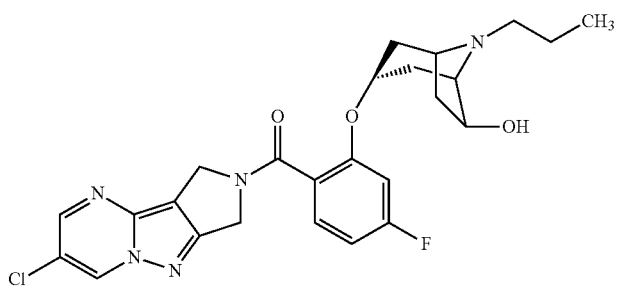 [SMILES: CCCN1C2CC(O)C1C[C@@H](Oc1cc(F)ccc1C(=O)N1Cc3nn4cc(Cl)cnc4c3C1)C2] |
| 114 | 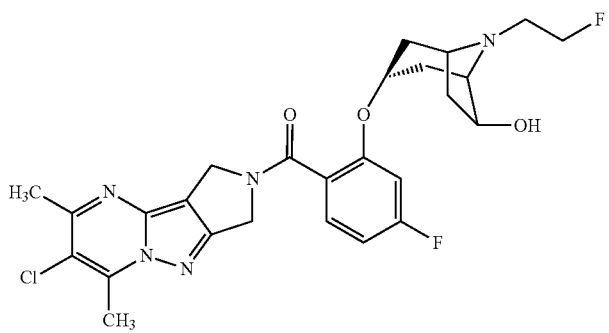 [SMILES: Cc1nc2c3c(nn2c(C)c1Cl)CN(C(=O)c1ccc(F)cc1O[C@H]1CC2CC(O)C(C1)N2CCF)C3] |
| 115 | 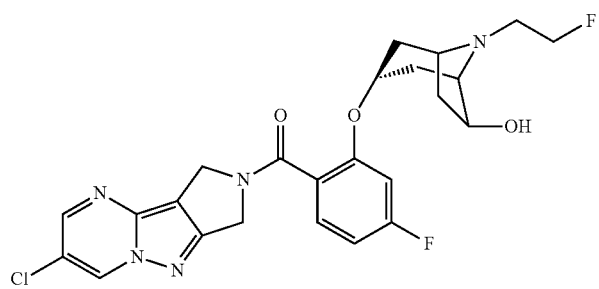 [SMILES: O=C(c1ccc(F)cc1O[C@H]1CC2CC(O)C(C1)N2CCF)N1Cc2nn3cc(Cl)cnc3c2C1] |

| Ex | Structure |
| --- | --- |
| 116 | 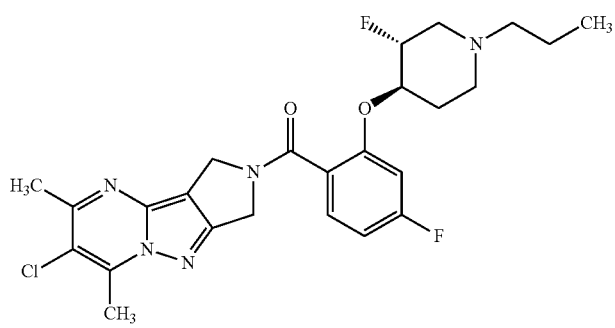 [SMILES: CCCN1CC[C@@H](Oc2cc(F)ccc2C(=O)N2Cc3nn4c(C)c(Cl)c(C)nc4c3C2)[C@H](F)C1] |
| 117 | 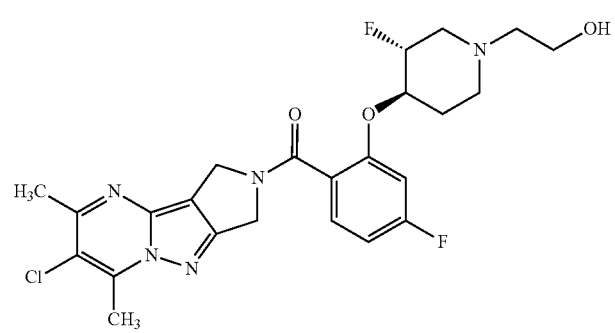 [SMILES: Cc1nc2c3c(nn2c(C)c1Cl)CN(C(=O)c1ccc(F)cc1O[C@@H]1CCN(CCO)C[C@H]1F)C3] |
| 118 | 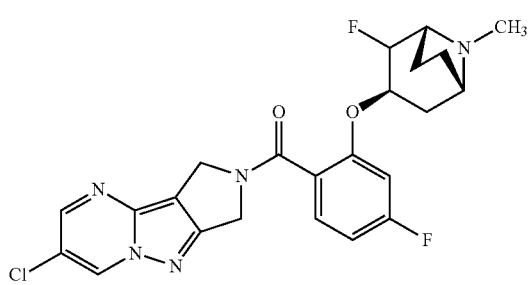 [SMILES: CN1[C@H]2CC[C@@H]1C(F)[C@H](Oc1cc(F)ccc1C(=O)N1Cc3nn4cc(Cl)cnc4c3C1)C2] |
| 119 | 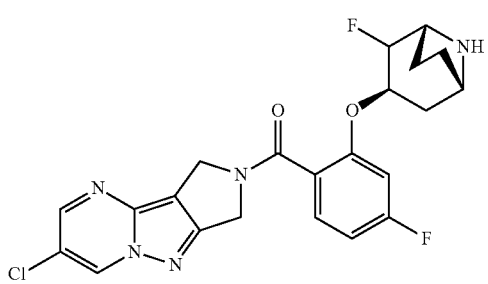 [SMILES: O=C(c1ccc(F)cc1O[C@@H]1C[C@@H]2CC[C@@H](N2)C1F)N1Cc2nn3cc(Cl)cnc3c2C1] |
| 120 | 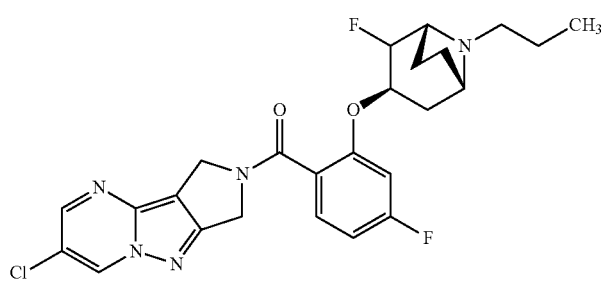 [SMILES: CCCN1[C@H]2CC[C@@H]1C(F)[C@H](Oc1cc(F)ccc1C(=O)N1Cc3nn4cc(Cl)cnc4c3C1)C2] |

-continued

| Ex | Structure |
|---|---|
| 121 | 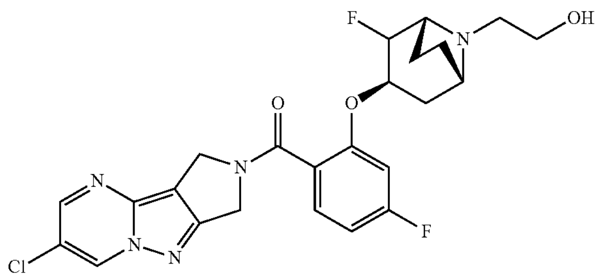 [SMILES: O=C(c1ccc(F)cc1O[C@@H]1C[C@@H]2CC[C@H](C1F)N2CCO)N1Cc2nn3cc(Cl)cnc3c2C1] |
| 122 | 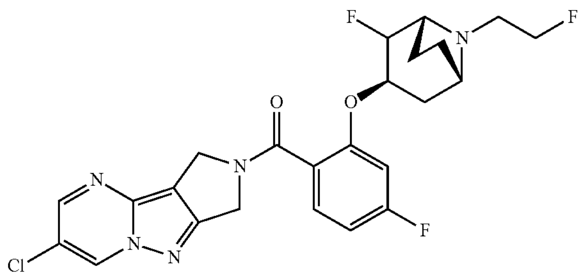 [SMILES: O=C(c1ccc(F)cc1O[C@@H]1C[C@@H]2CC[C@H](C1F)N2CCF)N1Cc2nn3cc(Cl)cnc3c2C1] |
| 123 | 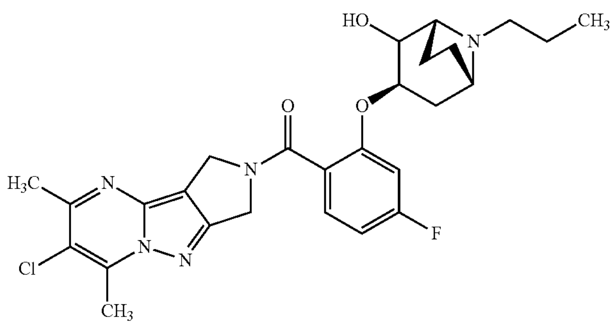 [SMILES: CCCN1[C@H]2CC[C@@H]1C(O)[C@H](Oc1cc(F)ccc1C(=O)N1Cc3nn4c(C)c(Cl)c(C)nc4c3C1)C2] |
| 124 | 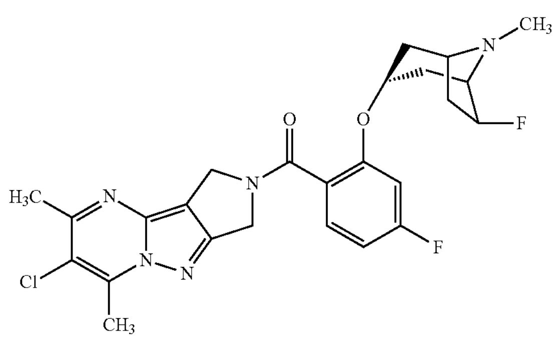 [SMILES: Cc1nc2c3c(nn2c(C)c1Cl)CN(C(=O)c1ccc(F)cc1O[C@H]1CC2CC(F)C(C1)N2C)C3] |
| 125 | 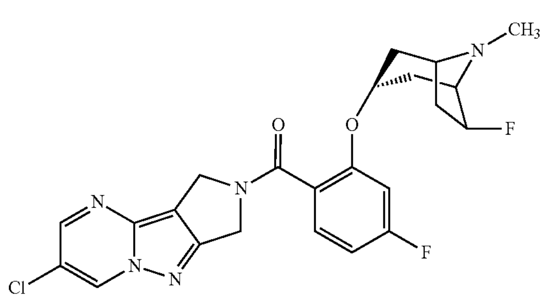 [SMILES: CN1C2CC(F)C1C[C@@H](Oc1cc(F)ccc1C(=O)N1Cc3nn4cc(Cl)cnc4c3C1)C2] |

| Ex | Structure |
|---|---|
| 126 | 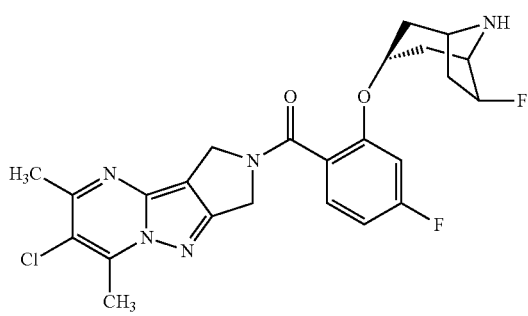 [SMILES: Cc1nc2c3c(nn2c(C)c1Cl)CN(C(=O)c1ccc(F)cc1O[C@H]1CC2CC(F)C(C1)N2)C3] |
| 127 | 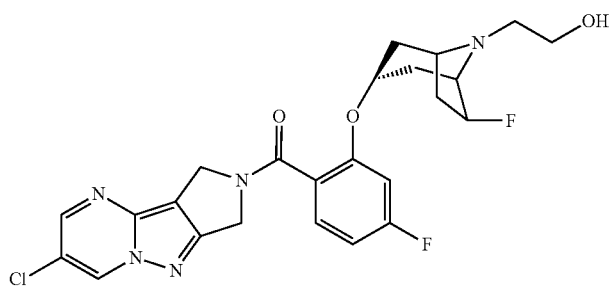 [SMILES: O=C(c1ccc(F)cc1O[C@H]1CC2CC(F)C(C1)N2CCO)N1Cc2nn3cc(Cl)cnc3c2C1] |
| 128 | 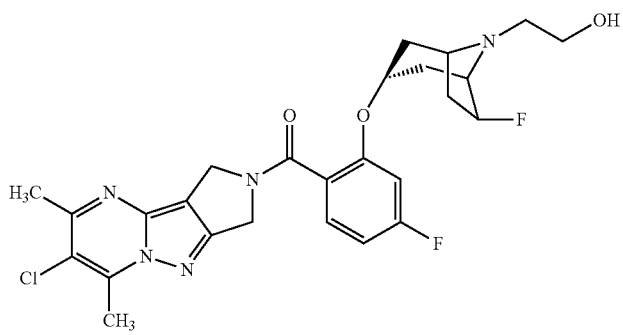 [SMILES: Cc1nc2c3c(nn2c(C)c1Cl)CN(C(=O)c1ccc(F)cc1O[C@H]1CC2CC(F)C(C1)N2CCO)C3] |
| 129 | 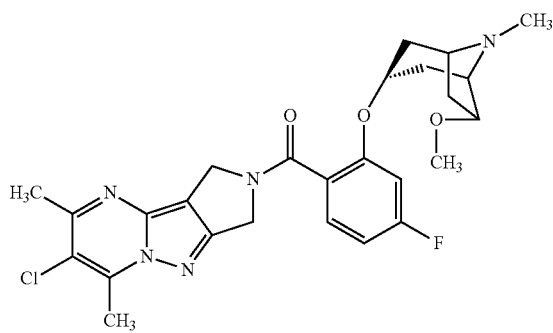 [SMILES: COC1CC2C[C@H](Oc3cc(F)ccc3C(=O)N3Cc4nn5c(C)c(Cl)c(C)nc5c4C3)CC1N2C] |

| Ex | Structure |
|---|---|
| 130 | 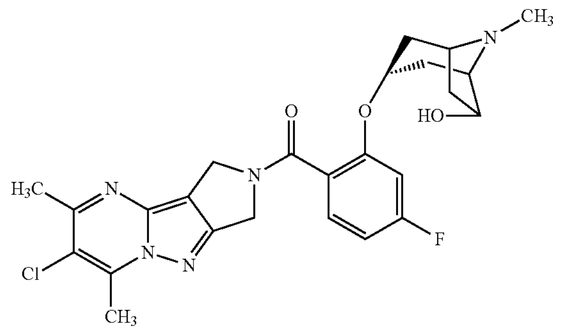 [SMILES: Cc1nc2c3c(nn2c(C)c1Cl)CN(C(=O)c1ccc(F)cc1O[C@H]1CC2CC(O)C(C1)N2C)C3] |
| 131 | 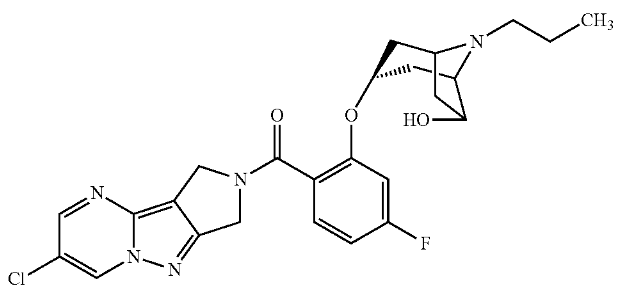 [SMILES: CCCN1C2CC(O)C1C[C@@H](Oc1cc(F)ccc1C(=O)N1Cc3nn4cc(Cl)cnc4c3C1)C2] |
| 132 | 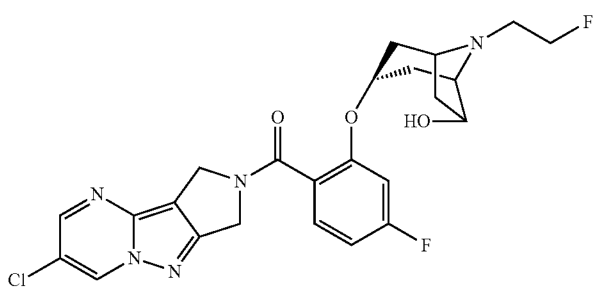 [SMILES: O=C(c1ccc(F)cc1O[C@H]1CC2CC(O)C(C1)N2CCF)N1Cc2nn3cc(Cl)cnc3c2C1] |

7. A pharmaceutical composition comprising at least one compound of claim 1, a tautomer, salt, solvate or stereoisomer thereof, or any mixtures thereof, and optionally at least one selected from the group consisting of an excipient and an adjuvant.

8. A pharmaceutical composition comprising at least one compound of claim 1, a tautomer, salt, solvate or stereoisomer thereof, or any mixtures thereof, and at least one further active ingredient.

9. A kit comprising separate packs of
(a) at least one compound of claim 1, a tautomer, salt, solvate or stereoisomer thereof, or any mixtures thereof; and
(b) a further medicament active ingredient.

10. A method of treating a muscarinic M1 receptor associated disorder in a subject, the method comprising administering to the subject in need thereof a therapeutically effective amount of at least one compound of claim 1, a tautomer, salt, solvate or stereoisomer thereof, or any mixtures thereof.

11. The method of claim 10, wherein the muscarinic M1 receptor associated disorder is at least one central nervous system disorder.

12. A method of treating a cognitive impairment or decline, or a cholinergic dysfunction, the method comprising administering to the subject in need thereof a therapeutically effective amount of at least one compound of claim 1, a tautomer, salt, solvate or stereoisomer thereof, or any mixtures thereof.

13. The method of claim 12, wherein the cognitive impairment or decline, or cholinergic dysfunction, is selected from the group consisting of Alzheimer's disease Parkinson disease, schizophrenia, chronic and neuropathic pain, sleep disorders, epilepsy, dementia in Alzheimer's disease, vascular dementia, unspecified dementia, organic amnesic syndrome not induced by alcohol and other psychoactive substances, schizotypal disorder, schizoaffective disorder, nociception disorder, dementia, hallucination, delusion and paranoia.

14. A method of preparing at least one compound of claim 1, the method comprising reacting a compound of Formula (A)

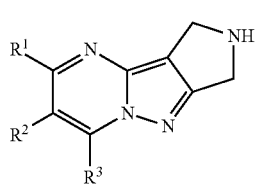
(A)
wherein R¹, R², R³ are as defined in claim 1, with a compound of Formula (B)
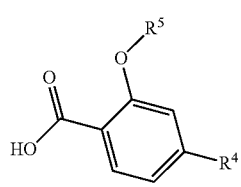
(B)
wherein R⁴ and R⁵ are as defined in claim 1, in the presence of a coupling agent, wherein the compound of Formula (I) is prepared.
* * * * *

UNITED STATES PATENT AND TRADEMARK OFFICE
CERTIFICATE OF CORRECTION

| | | |
|---|---|---|
| PATENT NO. | : 9,505,769 B2 | Page 1 of 4 |
| APPLICATION NO. | : 14/896757 | |
| DATED | : November 29, 2016 | |
| INVENTOR(S) | : Anna Quattropani et al. | |

It is certified that error appears in the above-identified patent and that said Letters Patent is hereby corrected as shown below:

In Column 85, structures for compounds 159a-159b should read:

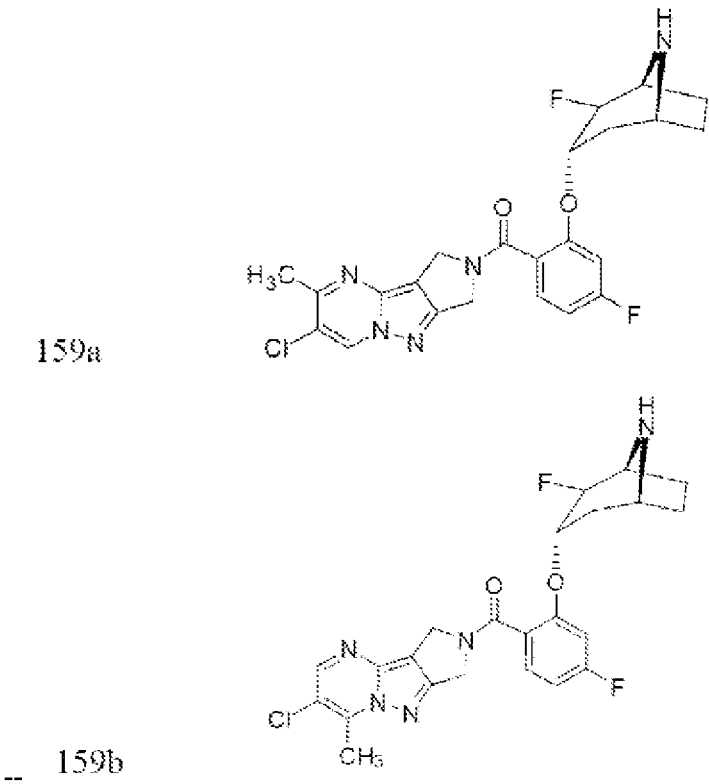

Signed and Sealed this
Fourth Day of April, 2017

Michelle K. Lee
*Director of the United States Patent and Trademark Office*

CERTIFICATE OF CORRECTION (continued)
U.S. Pat. No. 9,505,769 B2

Page 2 of 4

In Column 89, structures for compounds 167 and 168 should read:

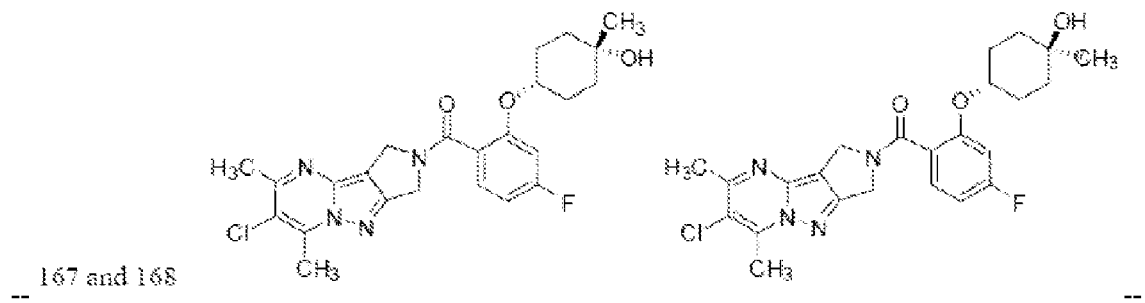

In Column 91, structures for compounds 171a-171b should read:

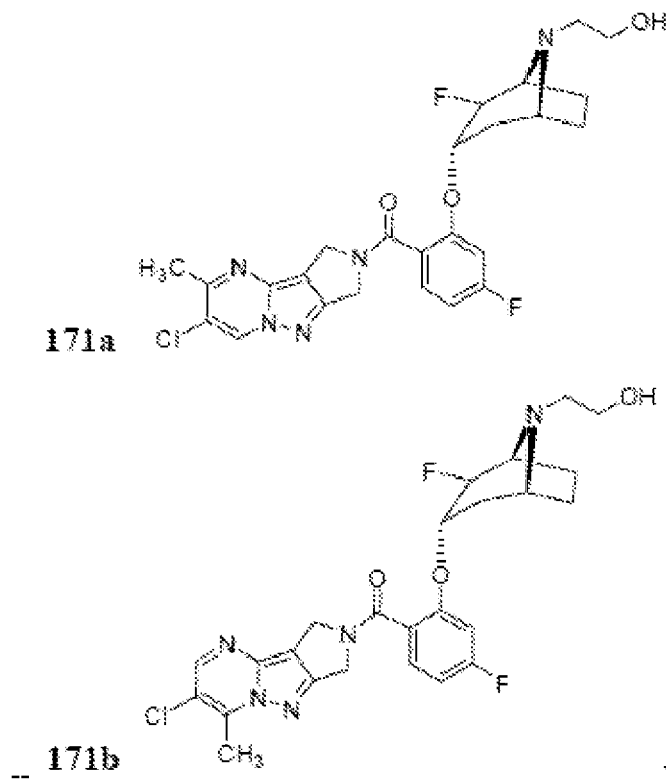

CERTIFICATE OF CORRECTION (continued)
U.S. Pat. No. 9,505,769 B2

In Column 93, the structure for compound 173 should read:

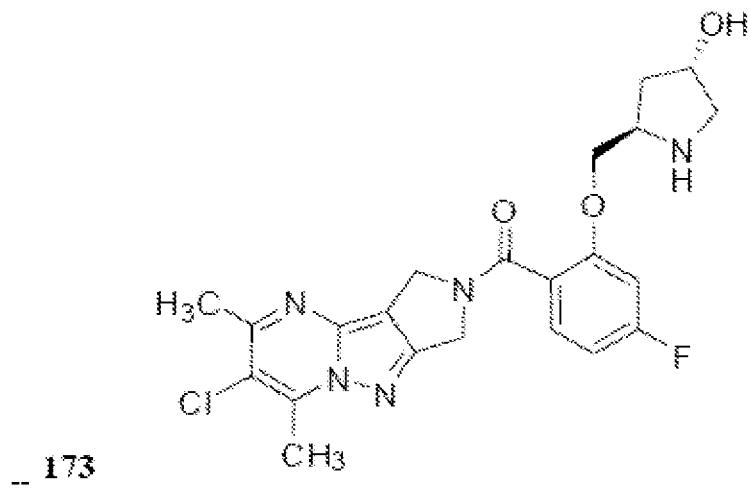

In Column 95, the compound of structure 179 should read:

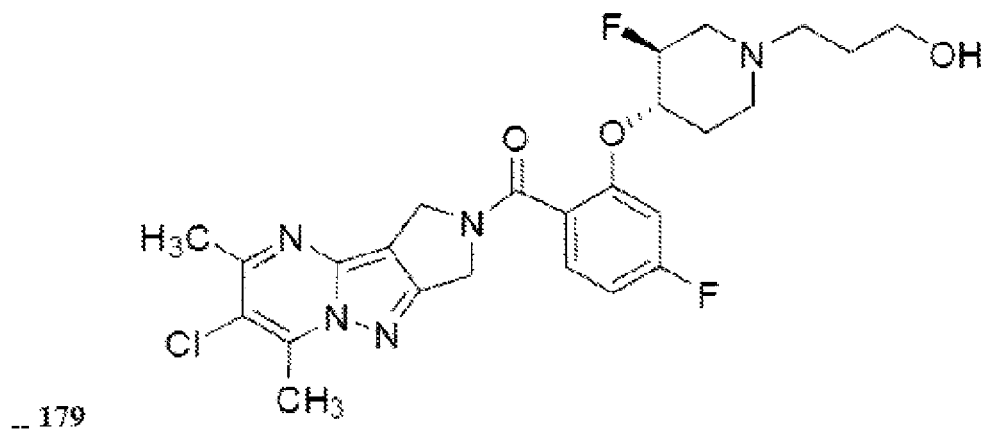

In Column 117, the structure for compound 224 should read:

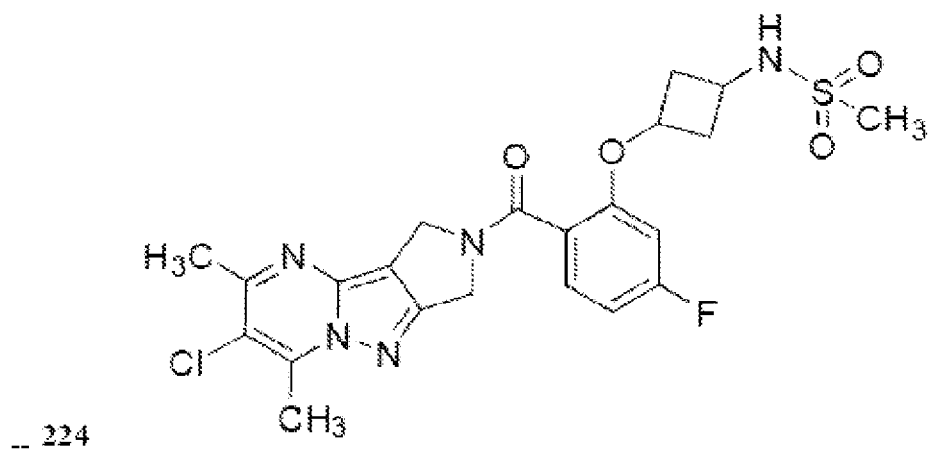

CERTIFICATE OF CORRECTION (continued)
U.S. Pat. No. 9,505,769 B2

Page 4 of 4

In Column 125, the structure of compound 238 should read:

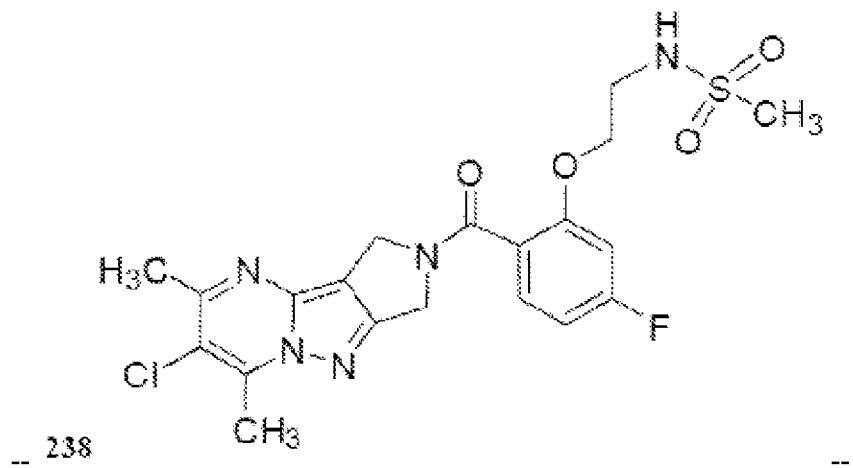

-- 238 --

In Column 248, the structure in Example 87 should read: